United States Patent
Li et al.

(10) Patent No.: US 10,442,810 B2
(45) Date of Patent: *Oct. 15, 2019

(54) PYRROLOTRIAZINE COMPOUNDS AS TAM INHIBITORS

(71) Applicant: Incyte Corporation, Wilmington, DE (US)

(72) Inventors: Yun-Long Li, Chadds Ford, PA (US); Xiaozhao Wang, Mt. Laurel, NJ (US); Chunhong He, Chadds Ford, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/971,017

(22) Filed: May 4, 2018

(65) Prior Publication Data

US 2018/0327412 A1 Nov. 15, 2018

Related U.S. Application Data

(63) Continuation of application No. 15/469,975, filed on Mar. 27, 2017, now Pat. No. 9,981,975.

(60) Provisional application No. 62/438,750, filed on Dec. 23, 2016, provisional application No. 62/362,934, filed on Jul. 15, 2016, provisional application No. 62/314,066, filed on Mar. 28, 2016.

(51) Int. Cl.
| | | |
|---|---|---|
| C07D 487/04 | (2006.01) | |
| C07D 403/04 | (2006.01) | |
| C07D 403/14 | (2006.01) | |
| A61K 31/53 | (2006.01) | |
| A61P 35/00 | (2006.01) | |

(52) U.S. Cl.
CPC ............ C07D 487/04 (2013.01); A61K 31/53 (2013.01); A61P 35/00 (2018.01); C07D 403/04 (2013.01); C07D 403/14 (2013.01)

(58) Field of Classification Search
CPC .. C07D 487/04; C07D 403/04; C07D 403/14; A61K 31/53; A61P 35/00
USPC .......................................... 544/184; 514/243
See application file for complete search history.

(56) References Cited

U.S. PATENT DOCUMENTS

| | | | |
|---|---|---|---|
| 9,708,333 B2 | 7/2017 | Li et al. | |
| 9,840,503 B2 | 12/2017 | Sun et al. | |
| 9,981,975 B2 * | 5/2018 | Li | C07D 487/04 |
| 2010/0298334 A1 | 11/2010 | Rodgers et al. | |
| 2011/0015212 A1 | 1/2011 | Li et al. | |
| 2011/0059951 A1 | 3/2011 | Rodgers et al. | |
| 2011/0183985 A1 | 7/2011 | Li et al. | |
| 2011/0224190 A1 | 9/2011 | Huang et al. | |
| 2012/0015937 A1 | 1/2012 | Ding et al. | |
| 2012/0088768 A1 | 4/2012 | Singh et al. | |
| 2012/0149681 A1 | 6/2012 | Rodgers et al. |
| 2012/0149682 A1 | 6/2012 | Rodgers et al. |
| 2012/0157430 A1 | 6/2012 | Li et al. |
| 2012/0184535 A1 | 7/2012 | Brzozka et al. |
| 2012/0219522 A1 | 8/2012 | Xi |
| 2012/0230993 A1 | 9/2012 | Graham et al. |
| 2012/0264740 A1 | 10/2012 | Goff et al. |
| 2012/0283261 A1 | 11/2012 | Bearss et al. |
| 2013/0018034 A1 | 1/2013 | Yao et al. |
| 2013/0018051 A1 | 1/2013 | Singh et al. |
| 2013/0045963 A1 | 2/2013 | Rodgers et al. |
| 2013/0059835 A1 | 3/2013 | Li et al. |
| 2013/0090330 A1 | 4/2013 | Ding et al. |
| 2013/0197070 A1 | 8/2013 | De Franciscis et al. |
| 2013/0281468 A1 | 10/2013 | Goff et al. |
| 2014/0005166 A1 | 1/2014 | Rodgers et al. |
| 2014/0018365 A1 | 1/2014 | Schultz-Fademrecht et al. |
| 2014/0121198 A1 | 5/2014 | Li et al. |
| 2014/0128390 A1 | 5/2014 | Lin |
| 2014/0128400 A1 | 5/2014 | Singh et al. |
| 2014/0275023 A1 | 9/2014 | Namdev et al. |
| 2016/0333008 A1 | 11/2016 | Sun et al. |
| 2017/0044164 A1 | 2/2017 | Li et al. |
| 2017/0057965 A1 | 3/2017 | Li et al. |
| 2017/0275290 A1 | 9/2017 | Li et al. |
| 2018/0009815 A1 | 1/2018 | Li et al. |
| 2019/0031663 A1 | 1/2019 | Li et al. |
| 2019/0112313 A1 | 4/2019 | Jia et al. |

FOREIGN PATENT DOCUMENTS

| | | |
|---|---|---|
| CN | 102408411 | 4/2012 |
| EP | 2465505 | 6/2012 |

(Continued)

OTHER PUBLICATIONS

"Urbonas et al., ""A Novel Highly Site-Selective Synthesis of 2,4,7-Triarylpyrrolo[2,3-d]pyrimidines by a Combination of Palladium(0)-, Nickel(0)-, and Copper(I)-Catalyzed Cross-Coupling Reactions,"" Synlett, 2013, 24(11):1383-1386".

(Continued)

*Primary Examiner* — Venkataraman Balasubramanian
(74) *Attorney, Agent, or Firm* — Fish & Richardson P.C.

(57) ABSTRACT

This application relates to compounds of Formula I:

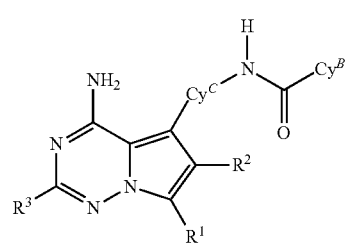

or pharmaceutically acceptable salts thereof, which are inhibitors of TAM kinases which are useful for the treatment of disorders such as cancer.

25 Claims, No Drawings

Specification includes a Sequence Listing.

(56) References Cited

FOREIGN PATENT DOCUMENTS

| | | |
|---|---|---|
| EP | 2484679 | 8/2012 |
| WO | WO 2004/035580 | 4/2004 |
| WO | WO 2005/025515 | 3/2005 |
| WO | WO 2006/046023 | 5/2006 |
| WO | WO 2007/061737 | 5/2007 |
| WO | WO 2007/070514 | 6/2007 |
| WO | WO 2007/120752 | 10/2007 |
| WO | WO 2007/125315 | 11/2007 |
| WO | WO 2008/076392 | 6/2008 |
| WO | WO 2009/023269 | 2/2009 |
| WO | WO 2009/047514 | 4/2009 |
| WO | WO 2009/053737 | 4/2009 |
| WO | WO 2009/054864 | 4/2009 |
| WO | WO 2009/085185 | 7/2009 |
| WO | WO 2009/087225 | 7/2009 |
| WO | WO 2009/127417 | 10/2009 |
| WO | WO 2010/005876 | 1/2010 |
| WO | WO 2010/005879 | 1/2010 |
| WO | WO 2010/008454 | 1/2010 |
| WO | WO 2010/014755 | 2/2010 |
| WO | WO 2010/025073 | 3/2010 |
| WO | WO 2010/071885 | 6/2010 |
| WO | WO 2010/090764 | 8/2010 |
| WO | WO 2011/038185 | 3/2011 |
| WO | WO 2011/045084 | 4/2011 |
| WO | WO 2011/139273 | 11/2011 |
| WO | WO 2012/028332 | 3/2012 |
| WO | WO 2012/048129 | 4/2012 |
| WO | WO 2012/129344 | 9/2012 |
| WO | WO 2012/135800 | 10/2012 |
| WO | WO 2013/052417 | 4/2013 |
| WO | WO 2013/074633 | 5/2013 |
| WO | WO 2013/085802 | 6/2013 |
| WO | WO 2013/115280 | 8/2013 |
| WO | WO 2013/162061 | 10/2013 |
| WO | WO 2014/062774 | 4/2014 |
| WO | WO 2014/079545 | 5/2014 |
| WO | WO 2014/109858 | 7/2014 |
| WO | WO 2014/164729 | 10/2014 |
| WO | WO 2015/012298 | 1/2015 |
| WO | WO 2015/068767 | 5/2015 |
| WO | WO 2016/097918 | 6/2016 |
| WO | WO 2017/027717 | 2/2017 |
| WO | WO 2017/062797 | 4/2017 |
| WO | WO 2017/083788 | 5/2017 |
| WO | WO 2017/083789 | 5/2017 |
| WO | WO 2017/172596 | 10/2017 |

OTHER PUBLICATIONS

Affouard et al., "Multi-Kilo Delivery of AMG 925 Featuring a Buchwald-Hartwig Amination and Processing with Insoluble Synthetic Intermediates," Organic Process Research & Development, 2015, 19: 476-485.
Angelillo-Scherrer et al., "Role of Gas6 in erythropoiesis and anemia in mice," J. Clin. Invest., 2008, 118: 583-596.
Baladi et al., "State-of-the-art of small molecule inhibitors of the TAM family: The point of view of the chemist," European Journal of Medicinal Chemistry, Oct. 2015, 105: 220-237.
Balupuri et al., "Molecular modeling study on Mer kinase inhibitors using 3D-QSAR and docking approaches," Medicinal Chemistry Research, Jul. 2015, 24(10): 3730-3742.
Berge, "Pharmaceutical Salts," Journal of Pharmaceutical Science, 66, 2 (1977).
Blom et al., "Optimizing Preparative LC/MS Configurations and Methods for Parallel Synthesis Purification," J. Comb. Chem., 2003, 5: 670-683.
Blom et al., "Preparative LC-MS Purification: Improved Compound-Specific Method Optimization," J. Comb. Chem., 2004, 6: 874-883.
Blom, "Two-Pump at-Column-Dilution Configuration for Preparative Liquid Chromatography-Mass Spectrometry," J. Comb. Chem., 2002, 4: 295-301.
Borovik et al., "Pyrimidines. XLIX. Synthesis of 9-phenylpyrimido[4,5-b] indoles," Izvestiya Sibirskogo Otdeleniya Akademii Nauk SSSR, Seriya Khimicheskikh Nauk , 1975, 137-41 (English abstract only).
Borovik et al., "Synthesis of 2-substituted pyrimido[4,5-b]indoles and N-phenyl-2,2-diethoxy-3-arylideneindolines," v sb., Khimiya i Farmakol. Indol'n. Soedinenii, 1975, 50 (English abstract only).
Burbridge et al., "S49076 Is a Novel Kinase Inhibitor of MET, AXL, and FGFR with Strong Preclinical Activity Alone and in Association with Bevacizumab," AACR Journals, 2013, 1749-1762.
Cecil Textbook of Medicine, edited by Bennet, J.C., and Plum F., 20th edition, vol. 1, 1004-1010, 1996.
Chambers et al., "Lymphoproliferation in CTLA-4-deficient mice is mediated by costimulation-dependent activation of CD4+ T cells," Immunity, Dec. 1997, 7(6): 885-95.
Chung et al., "Synthesis of certain [6:5:6] linear tricyclic nucleosides as potential antitumor agents," Journal of Medicinal Chemistry, Nov. 1980, 23(11): 1158-66.
Cohen., "The development and therapeutic potential of protein kinase inhibitors," Current Opinion in Chemical Biology, 1999, 3: 459-465, 1999.
Cook et al., "MerTK inhibition in tumor leukocytes decreases tumor growth and metastasis," J. Clin. Invest., Aug. 2013, 123(8): 3231-42.
Cosemans et al., "Potentiating role of Gas6 and Tryo3, Axl and Mer (TAM) receptors in human and murine platelet activation and thrombus stabilization," J. of Thrombosis and Haemostasis, 2010, 8: 1797-1808.
Demarest et al., "Evaluation of Tyro3 expression, Gas6-mediated Akt phosphorylation, and the impact of anti-Tyro3 antibodies in melanoma cell lines," Biochemistry, May 2013, 52(18): 3102-18.
Dermer et al., "Another Anniversary for the War on Cancer," Bio/Technology, Mar. 1994, 12: 320.
Dodonova et al., "Synthesis of 4-aryl-, 2, 4-diaryl-and 2, 4, 7-triarylpyrrolo [2, 3-d] pyrimidines by a combination of the Suzuki cross-coupling and N-arylation reactions," Tetrahedron, 2012, 68(1):329-339.
Feneyrolles et al., "Axl kinase as a key target for oncology: focus on small molecule inhibitors," Mol Cancer Therapy, Sep. 2014, 13(9): 2141-8.
Freshney et al., "Culture of Animal Cells," A Manual of Basic Technique, Alan R. Liss, Inc., 1983, New York, p. 4.
Ghosh, "Synthesis of 4-oxazolinephenylboronic acid and heterobiaryl oxazolines via a Suzuki reaction," Journal of Chemical Research, Apr. 2009, 4:205-207.
Golub et al., "Molecular Classification of Cancer: Class Discovery and Class Prediction by Gene Expression Monitoring," Science, 1999, 286: 531-537.
Graham et al., "Cloning and developmental expression analysis of the murine c-mer tyrosine kinase," Oncogene, Jun. 1995, 10(12): 2349-59.
Graham et al., "The TAM family: phosphatidylserine sensing receptor tyrosine kinases gone awry in cancer," Nat. Rev. Cancer, Dec. 2014, 14(12): 769-85.
Gustafsson et al., "Differential expression of Axl and Gas6 in renal cell carinoma reflecting tumor advancement and survival," Clin. Cancer Res., 2009, 15: 4742-4749.
Holland et al., "R428, a Selective Small Molecule Inhibitor of Axl Kinase, Blocks Tumor Spread and Prolongs Survival in Models of Metastatic Breast Cancer," Cancer Research, Feb. 2010, 70(4): 1544-1554.
Huang et al., "Structural insights into the inhibited states of the Mer receptor tyrosine kinase," Journal of Structural Biology, 2009, 165: 88-96.
International Search Report and Written Opinion in International Application No. PCT/US2016/031625, dated Jul. 7, 2016, 11 pages.
International Search Report and Written Opinion in International Application No. PCT/US2016/046574, dated Oct. 21, 2016, 14 pages.
International Search Report and Written Opinion in International Application No. PCT/US2016/048716, dated Nov. 2, 2016, 12 pages.

(56) References Cited

OTHER PUBLICATIONS

International Search Report and Written Opinion in International Application No. PCT/US2017/024270, dated Jun. 14, 2017, 18 pages.
International Preliminary Report on Patentability in International Application No. PCT/US2016/048716, dated Mar. 8, 2018, 7 pages.
Keegan et al., "Preclinical Evaluation of AMG 925, a FLT3/CDK4 Kinase Inhibitor for Treating Acute Myeloid Leukemia," Molecular Cancer Therapeutics, Apr. 2014, 13(4): 880-889.
Kerekes et al., "Aurora kinase inhibitors based on the imidazo [1,2-a]pyrazine core: fluorine and deuterium incorporation improve oral absorption and exposure," J. Med. Chem., 2011, 54: 201-210.
Klimke and Ludemann, "Further evidence for a S-syn correlation in the purine (β) ribosides: the solution conformation of two tricyclic analogs of adenosine and guanosine," Journal of Biosciences, 1979, 34C(9-10): 653-7.
Koorstra et al., "The Axl receptor tyrosine kinase confers an adverse prognostic influence in pancreatic cancer and represents a new threapeutic target," Cancer Biol. Ther., Apr. 2009, 8(7): 618-26.
Lai and Lemke, "An extended family of protein-tyrosine kinase genes differentially expressed in the vertebrate nervous system," Neuron, May 1991, 6(5): 691-704.
Lee-Sherick et al., "Aberrant Mer receptor tyrosine kinase expression contributes to leukemogenesis in acute myeloid leukemia," Oncogene, Nov. 2013, 32(46): 5359-68.
Lemke, "Biology of the TAM Receptors," Cold Spring Harb Perspect Biol., 2013, 5: 1-17.
Lew et al., "Differential TAM receptor-ligand-phospholipid interactions delimit differential TAM bioactivities," Elife, Sep. 2014, e03385.
Li et al., "Axl as a potential therapeutic target in cancer: role of Axl in tumor growth, metastasis and angiogenesis," Oncogene, Oct. 2009, 28(39): 3442-55.
Li et al., "Discovery of AMG 925, a FLT3 and CDK4 Dual Kinase Inhibitor with Preferential Affinity for the Activated State of FLT3," Journal of Medicinal Chemistry, 2014, 57(8): 3430-3449.
Linger et al., "Mer or Axl receptor tyrosine kinase inhibition promotes apoptosis, blocks growth and enhances chemosensitivity of human non-small cell lung cancer," Oncogene, Jul. 2013, 32(29): 3420-31.
Linger et al., "Taking aim at Mer and Axl receptor tyrosine kinases as novel therapeutic targets in solid tumors," Expert Opin. Ther. Targets, Oct. 2010, 14(10): 1073-1090.
Linger et al., "TAM Receptor Tyrosine Kinases. Biologic Functions, Signaling, and Potential Therapeutic Targeting in Human Cancer," Adv. Cancer Research, 2008, 100: 35-83.
Liu et al., "Discovery of Novel Small Molecule Mer Kinase Inhibitors for the Treatment of Pediatric Acute Lymphoblastic Leukemia," ACS Med. Chem. Lett., 2012, 3(2): 129-134.
Liu et al., "Discovery of Novel Small Molecule Mer Kinase Inhibitors for the Treatment of Pediatric Acute Lymphoblastic Leukemia," Supporting Information, 53 pages.
Liu et al., "Discovery of Small Molecule Mer Kinase Inhibitors for the Treatment of Pediatric Acute Lymphoblastic Leukemia," ACS Medicinal Chemistry Letters, 2012, 3: 129-134.
Liu et al., "UNC1062, a new and potent Mer inhibitor," European Journal of Medicinal Chemistry, 2013, 65: 83-93.
Lu and Lemke, "Homeostatic regulation of the immune system by receptor tyrosine kinases of the Tyro 3 family," Science, Jul. 2001, 293(5528): 306-11.
Mollard et al., "Design, Synthesis, and Biological Evaluation of a Series of Novel AXL Kinase Inhibitors," ACS Medicinal Chemistry Letters, 2011, 2: 907-912.
Mudduluru et al., "Myeloid zinc finger 1 induces migration, invasion, and in vivo metastasis through Axl gene expression in solid cancer," Mol. Cancer Res., Feb. 2010, 8(2): 159-169.
Myers et al., "AXL inhibitors in cancer: A medicinal chemistry perspective," Journal of Medicinal Chemistry, 2015, pp. 1-53.
Nishimura et al., "Autoimmune dilated cardiomyopathy in PD-1 receptor-deficient mice," Science, 2001, 291(5502): 319-22.

O'Bryan et al., "axl, a transforming gene isolated from primary human myeloid leukemia cells, encodes a novel receptor tyrosine kinase," Mol. Cell Biol., Oct. 1991, 11(10): 5016-31.
Okamoto et al., "Oligonucleotides containing 7-vinyl-7-deazaguanine as a facile strategy for expanding the functional diversity of DNA," Bioorganic & Medicinal Chemistry Letters, 2002, 12(15): 1895-1896.
Paolino et al., "The E3 ligase Cbl-b and TAM receptors regulate cancer metastasis via natural killer cells," Nature, 2014, 19 pages.
Pardoll, "The blockade of immune checkpoints in cancer immunotherapy," Nat. Rev. Cancer, Mar. 2012, 12(4): 252-64.
Powell et al., "Highly selective 2,4-diaminopyrimidine-5-carboxamide inhibitors of Sky kinase," Bioorganic & Medicinal Chemistry Letters, 2013, 23: 1046-1050.
Powell et al., "Novel and selective spiroindoline-based inhibitors of sky kinase," Bioorganic & Medicinal Chemistry Letters, 2012, 22: 190-193.
Remington's Pharmaceutical Sciences, 17th ed., Mack Publishing Company, Easton, Pa., 1985, p. 1418.
Rho et al., "MET and AXL Inhibitor NPS-1034 Exerts Efficacy against Lung Cancer Cells Resistant to EGFR Kinase Inhibitors Because of MET or AXL Activation," AARC Journals, 2013, 253-262.
Schlegel et al., "MERTK receptor tyrosine kinase is a therapeutic target in melanoma," The Journal of Clinical Investigation, May 2013, 123(5): 2257-2267.
Schroeder et al., "Discovery of N-(4-(2-Amino-3-chloropyridin-4-yloxy)-3-fluorophenyl)-4-ethoxy-1-(4-fluorophenyl)-2-oxo-1,2-dihydropyridine-3-carboxamide (BMS-777607), a Selective and Orally Efficacious Inhibitor of the Met Kinase Superfamily," J. Med. Chem., 2009, 52: 1251-1254.
Singer et al., "Photochromism of Diarylethene-Functionalized 7-Deazaguanosines," European Journal of Organic Chemistry, 2013, 14: 2766-2769.
Shibata et al., "Axl receptor blockade ameliorates pulmonary pathology resulting from primary viral infection and viral exacerbation of asthma," The Journal of Immunology, 2014, 192: 3569-3581.
Skardziute, "Optical study of the formation of pyrrolo[2,3-d]pyrimidine-based fluorescent nanoaggregates," Tetrahedron, 2013, 69(46):9566-9572.
Strassmaier and Karpen, "Novel N7- and N1-Substituted cGMP Derivatives Are Potent Activators of Cyclic Nucleotide-Gated Channels," Journal of Medicinal Chemistry, Aug. 2007, 50: 4186-4194.
Suarez et al., "Inhibitors of the TAM subfamily of tyrosine kinsases: Synthesis and biological evaluation," European Journal of Medicinal Chemistry, 2013, 61: 2-25.
Tai et al., "Axl promotes cell invasion by inducing MMP-9 activity through activation of NF-kappaB and Brg-1," Oncogene, Jul. 2008, 27(29): 4044-55.
Traore et al., "New aminopyrimidine derivatives as inhibitors of the TAM family," European Journal of Medicinal Chemistry, 2013, 70: 789-801.
Tumkevicius, "Pyrrolo [2, 3-d] pyrimidine-Core-Extended π-Systems: Synthesisof 2, 4, 7-Triarylpyrrolo [2, 3-d] pyrimidines," Synlett, 2011, 12:1705-1708.
Tumkevicius, "Synthesis and photophysical properties of oligoarylenes with a pyrrolo [2, 3-d] pyrimidine core," Tetrahedron Letters (2010), 51(30), 3902-3906.
Waizeneggar et al., "Role of Growth arrest-specific gene 6-Mer axis in multiple myeloma," Leukemia, 2015, 29: 696-704.
Wang et al., "Mer receptor tyrosine kinase promotes invasion and survival in glioblastoma multiforme," Oncogene, Feb. 2013, 32(7): 872-82.
Wu et al., "Multisubstituted quinoxalines and pyrido[2,3-d]pyrimidines: Synthesis and SAR study as tyrosine kinase c-Met inhibitors," Bioorganic & Medicinal Chemistry Letters, 2012, 22: 6368-6372.
Xu et al., "Design, synthesis and biological evaluation of deuterated nintedanib for improving pharmacokinetic properties," J. Label Compd. Radiopharm., 2015, 58: 308-312.
Yamazoe et al., "Mechanism of formation and structural characterization of DNA adducts derived from peroxidative activation of benzidine," Carcinogenesis, Sep. 1988, 9(9): 1635-41.

(56) References Cited

OTHER PUBLICATIONS

Zhang et al., "Activation of the AXL kinase causes resistance to EGFR-targeted therapy in lung cancer," Nat. Genet., 2012, 44(8): 852-60.

Zhang et al., "Discovery of Mer Specific Tyrosine Kinase Inhibitors for the Treatment and Prevention of Thrombosis," Journal of Medicinal Chemistry, 2013, 56: 9693-9700.

Zhang et al., "Discovery of novel type II c-Met inhibitors based on BMS-777607," European Journal of Medicinal Chemistry, 2014, 80: 254-266.

Zhang et al., "Pseudo-Cyclization through Intramolecular Hydrogen Bond Enables Discovery of Pyridine Substituted Pyrimidines as New Mer Kinase Inhibitors," Journal of Medicinal Chemistry, 2013, 56: 6983-9692.

Zhang et al., "UNC20205, a Potent and Orally Bioavailable MER/FLT3 Dual Inhibitor," Journal of Medicinal Chemistry, 2014, 57: 7031-7041.

Zhao, et al., "Discovery of novel Bruton's tyrosine kinase (BTK) inhibitors bearing a pyrrolo [2, 3-d] pyrimidine scaffold," Bioorganic & Medicinal Chemistry, Feb. 2015, 23(4):891-901.

Zhou et al., "Synthesis and evaluation of Janus type nucleosides as potential HCV NS5B polymerase inhibitors," Bioorganic & Medicinal Chemistry Letters, Jun. 2013, 23: 3385-3388.

International Search Report and Written Opinion in International Application No. PCT/US2018/052925, dated Nov. 5, 2018, 14 pages.

Johnson et al., "Relationships between drug activity in NCI preclinical in vitro and in vivo models and early clinical trials," British J. of Cancer., May 18, 2001, 84(10):1424-1431.

Sausville et al., "Contributions of human tumor xenografts to anticancer drug development," Cancer Research, Apr. 1, 2006, 66(7):3351-3354.

Brunton et al., "Chemotherapy of Neoplastic Diseases," Goodman & Gilman's: The Pharmacological Basis of Therapeutics, 2008, pp. 853-908.

\* cited by examiner

PYRROLOTRIAZINE COMPOUNDS AS TAM INHIBITORS

CROSS-REFERENCE TO RELATED APPLICATIONS

This application is a continuation of U.S. application Ser. No. 15/469,975, filed Mar. 27, 2017 which claims priority to U.S. Provisional Patent Application Nos. 62/314,066, filed on Mar. 28, 2016; 62/362,934, filed on Jul. 15, 2016; 62/438,750, filed on Dec. 23, 2016; the entireties of which are incorporated herein by reference.

TECHNICAL FIELD

This application relates to pyrrolotriazine inhibitors of TAM kinases, and in one embodiment inhibitors of AXL and MER kinases, which are useful in the treatment of disorders such as cancer, as well as pharmaceutical compositions related thereto.

BACKGROUND OF INVENTION

Receptor tyrosine kinases (RTKs) are cell surface proteins that transmit signals from the extracellular environment to the cell cytoplasm and nucleus to regulate cellular events such as survival, growth, proliferation, differentiation, adhesion and migration.

The TAM subfamily consists of three RTKs including Tyro3, AXL and Mer (Graham et al., 2014, Nature Reviews Cancer 14, 769-785; Linger et al., 2008, Advances in Cancer Research 100, 35-83). TAM kinases are characterized by an extracellular ligand binding domain consisting of two immunoglobulin-like domains and two fibronectin type III domains. Two ligands, growth arrest specific 6 (GAS6) and protein S (PROS1), have been identified for TAM kinases. GAS6 can bind to and activate all three TAM kinases, while PROS1 is a ligand for Mer and Tyro3 (Graham et al., 2014, Nature Reviews Cancer 14, 769-785).

AXL (also known as UFO, ARK, JTK11 and TYRO7) was originally identified as a transforming gene from DNA of patients with chronic myelogenous leukemia (O'Bryan et al., 1991, Mol Cell Biol 11, 5016-5031; Graham et al., 2014, Nature Reviews Cancer 14, 769-785; Linger et al., 2008, Advances in Cancer Research 100, 35-83). GAS6 binds to AXL and induces subsequent auto-phosphorylation and activation of AXL tyrosine kinase. AXL activates several downstream signaling pathways including PI3K-Akt, Raf-MAPK, PLC-PKC (Feneyrolles et al., 2014, Molecular Cancer Therapeutics 13, 2141-2148; Linger et al., 2008, Advances in Cancer Research 100, 35-83).

MER (also known as MERTK, EYK, RYK, RP38, NYK and TYRO12) was originally identified as a phospho-protein from a lymphoblastoid expression library (Graham et al., 1995, Oncogene 10, 2349-2359; Graham et al., 2014, Nature Reviews Cancer 14, 769-785; Linger et al., 2008, Advances in Cancer Research 100, 35-83). Both GAS6 and PROS1 can bind to Mer and induce the phosphorylation and activation of Mer kinase (Lew et al., 2014). Like AXL, MER activation also conveys downstream signaling pathways including PI3K-Akt and Raf-MAPK (Linger et al., 2008, Advances in Cancer Research 100, 35-83).

TYRO3 (also known as DTK, SKY, RSE, BRT, TIF, ETK2) was originally identified through a PCR-based cloning study (Lai et al., Neuron 6, 691-70, 1991; Graham et al., 2014, Nature Reviews Cancer 14, 769-785; Linger et al., 2008, Advances in Cancer Research 100, 35-83). Both ligands, GAS6 and PROS1, can bind to and activate TYRO3. Although the signaling pathways downstream of TYRO3 activation are the least studied among TAM RTKs, it appears that both PI3K-Akt and Raf-MAPK pathways are involved (Linger et al., 2008, Advances in Cancer Research 100, 35-83). AXL, MER and TYRO3 are found to be over-expressed in cancer cells.

Accordingly, there is a need for compounds and methods of use thereof for the modulation of TAM kinases in the treatment of cancer.

SUMMARY OF INVENTION

In one aspect, the present application relates to compounds having Formula I:

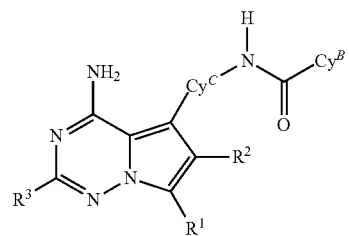

or a pharmaceutically acceptable salt thereof, wherein variables $R^1$, $R^2$, $R^3$, $Cy^C$ and $Cy^B$ are as described herein.

The present application further provides compositions comprising a compound described herein, or a pharmaceutically acceptable salt thereof, and at least one pharmaceutically acceptable carrier.

The present application also provides methods of inhibiting TAM kinases, and in one embodiment methods of inhibiting AXL and MER kinases, comprising contacting one or more TAM kinase with a compound described herein, or a pharmaceutically acceptable salt thereof.

The present application also provides a compound described herein, or a pharmaceutically acceptable salt thereof, for use in any of the methods described herein.

The present application further provides use of a compound described herein, or a pharmaceutically acceptable salt thereof, for manufacture of a medicament for use in any of the methods described herein.

DETAILED DESCRIPTION

The application provides, inter alia, a compound of Formula I:

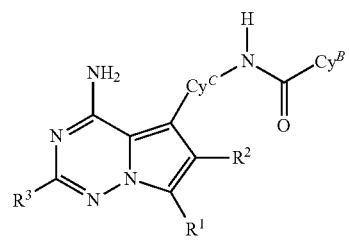

or a pharmaceutically acceptable salt thereof, wherein:
$R^1$ is $A^1$-$A^2$-$A^3$-$R^4$;
$R^2$ is H, halo, CN, $C_{1-4}$ alkyl, $C_{1-4}$ haloalkyl, $C_{1-4}$ alkoxy, $C_{1-4}$ haloalkoxy, cyano-$C_{1-3}$ alkyl or $C_{1-6}$ alkoxyalkyl;

R$^3$ is H, halo, CN, C$_{1-6}$ alkyl, C$_{1-6}$ haloalkyl, OR$^a$, SR$^a$, C(O)NR$^c$R$^d$, NR$^c$R$^d$, NR$^c$C(O)R$^b$, NR$^c$S(O)$_2$R$^b$ or S(O)$_2$R$^b$; wherein said C$_{1-6}$ alkyl and C$_{1-6}$ haloalkyl are optionally substituted with 1, 2 or 3 substituents independently selected from halo, CN, OR$^a$, SR$^a$, C(O)NR$^c$R$^d$, NR$^c$R$^d$, NR$^c$C(O)R$^b$, NR$^c$S(O)$_2$R$^b$, S(O)$_2$R$^b$, NR$^c$C(O)OR$^a$, NR$^c$C(O)NR$^c$R$^d$, NR$^c$S(O)$_2$NR$^c$R$^d$ and Cy$^{R3}$;

A$^1$ is selected from a bond, Cy$^{A1}$, —Y—, —C$_{1-3}$ alkylene-, —C$_{1-3}$ alkylene-Y—, —Y—C$_{1-3}$ alkylene-, and —C$_{1-2}$ alkylene-Y—C$_{1-2}$ alkylene-; wherein said alkylene groups are each optionally substituted with 1, 2, or 3 substituents independently selected from halo, CN, OH, C$_{1-3}$ alkyl, C$_{1-3}$ alkoxy, C$_{1-3}$ haloalkyl, C$_{1-3}$ haloalkoxy, amino, C$_{1-3}$ alkylamino, and di(C$_{1-3}$ alkyl)amino;

A$^2$ is selected from a bond, Cy$^{A2}$, —Y—, —C$_{1-3}$ alkylene-, —C$_{1-3}$ alkylene-Y—, —Y—C$_{1-3}$ alkylene-, and —C$_{1-2}$ alkylene-Y—C$_{1-2}$ alkylene-; wherein said alkylene groups are each optionally substituted with 1, 2, or 3 substituents independently selected from halo, CN, OH, C$_{1-3}$ alkyl, C$_{1-3}$ alkoxy, C$_{1-3}$ haloalkyl, C$_{1-3}$ haloalkoxy, amino, C$_{1-3}$ alkylamino, and di(C$_{1-3}$ alkyl)amino;

A$^3$ is selected from a bond, Cy$^{A3}$, —Y—, —C$_{1-3}$ alkylene-, —C$_{1-3}$ alkylene-Y—, —Y—C$_{1-3}$ alkylene-, and —C$_{1-2}$ alkylene-Y—C$_{1-2}$ alkylene-; wherein said alkylene groups are each optionally substituted with 1, 2, or 3 substituents independently selected from halo, CN, OH, C$_{1-3}$ alkyl, C$_{1-3}$ alkoxy, C$_{1-3}$ haloalkyl, C$_{1-3}$ haloalkoxy, amino, C$_{1-3}$ alkylamino, and di(C$_{1-3}$ alkyl)amino;

R$^A$ is H, C$_{1-6}$ alkyl, C$_{1-6}$ haloalkyl, halo, C$_{3-6}$ cycloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$OR$^{d1}$, NR$^{c1}$C(O)R$^{b1}$, NR$^{c1}$C(O)OR$^{a1}$, NR$^{c1}$C(O)NR$^{c1}$R$^{d1}$, C(=NR$^{e1}$)R$^{b1}$, C(=NR$^{e1}$)NR$^{c1}$R$^{d1}$, NR$^{c1}$C(NR$^{e1}$)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, or S(O)$_2$NR$^{c1}$R$^{d1}$; wherein said C$_{1-6}$ alkyl or C$_{1-6}$ haloalkyl is optionally substituted with 1, 2, 3 or 4 substituents independently selected from R$^{11}$;

Y is O, S, S(O), S(O)$_2$, C(O), C(O)NR$^f$, NR$^f$C(O), NR$^f$C(O)NR$^f$, NR$^f$S(O)$_2$NR$^f$, S(O)$_2$NR$^f$, NR$^f$S(O)$_2$, or NR$^f$;

each R$^f$ is independently selected from H and C$_{1-3}$ alkyl;

Cy$^{A1}$ is C$_{3-7}$ cycloalkyl, phenyl, 5-6 membered heteroaryl, or 4-7 membered heterocycloalkyl; wherein each 5-6 membered heteroaryl and 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of C$_{3-7}$ cycloalkyl and 4-7 membered heterocycloalkyl is optionally substituted by oxo to form a carbonyl group; and wherein the C$_{3-7}$ cycloalkyl, phenyl, 5-6 membered heteroaryl, and 4-7 membered heterocycloalkyl are each optionally substituted with 1, 2, 3 or 4 substituents independently selected from R$^{A1}$;

each R$^{A1}$ is independently selected from OH, NO$_2$, CN, halo, C$_{1-6}$ alkyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, H$_2$N—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

Cy$^{A2}$ is C$_{3-7}$ cycloalkyl, phenyl, 5-6 membered heteroaryl, or 4-7 membered heterocycloalkyl; wherein each 5-6 membered heteroaryl and 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of C$_{3-7}$ cycloalkyl and 4-7 membered heterocycloalkyl is optionally substituted by oxo to form a carbonyl group; and wherein the C$_{3-7}$ cycloalkyl, phenyl, 5-6 membered heteroaryl, and 4-7 membered heterocycloalkyl are each optionally substituted with 1, 2, 3 or 4 substituents independently selected from R$^{A2}$;

each R$^{A2}$ is independently selected from OH, NO$_2$, CN, halo, C$_{1-6}$ alkyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, H$_2$N—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

Cy$^{A3}$ is C$_{3-7}$ cycloalkyl, phenyl, 5-6 membered heteroaryl, or 4-7 membered heterocycloalkyl; wherein each 5-6 membered heteroaryl and 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of C$_{3-7}$ cycloalkyl and 4-7 membered heterocycloalkyl is optionally substituted by oxo to form a carbonyl group; and wherein the C$_{3-7}$ cycloalkyl, phenyl, 5-6 membered heteroaryl, and 4-7 membered heterocycloalkyl are each optionally substituted with 1, 2, 3 or 4 substituents independently selected from R$^{A3}$;

each R$^{A3}$ is independently selected from OH, NO$_2$, CN, halo, C$_{1-6}$ alkyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, H$_2$N—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

Cy$^{R3}$ is C$_{3-7}$ cycloalkyl, phenyl, 5-6 membered heteroaryl, or 4-7 membered heterocycloalkyl; wherein each 5-6 membered heteroaryl and 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of C$_{3-7}$ cycloalkyl and 4-7 membered heterocycloalkyl is optionally substituted by oxo to form a carbonyl group; and wherein the C$_{3-7}$ cycloalkyl, phenyl, 5-6 membered heteroaryl, and 4-7 membered heterocycloalkyl are each optionally substituted with 1, 2, 3 or 4 substituents independently selected from R$^g$;

Cy$^C$ is phenylene or 5-6 membered heteroarylene; wherein the 5-6 membered heteroarylene has at least one ring-forming carbon atom and 1 or 2 ring-forming heteroatoms independently selected from N, O, and S; and wherein the phenylene and 5-6 membered heteroarylene are each optionally substituted by 1, 2, 3, or 4 substituents independently selected from R$^C$;

each R$^C$ is independently selected from OH, CN, halo, C$_{1-4}$ alkyl, C$_{1-3}$ haloalkyl, C$_{1-4}$ alkoxy, C$_{1-3}$ haloalkoxy, cyano-C$_{1-3}$ alkyl, HO—C$_{1-3}$ alkyl, amino, C$_{1-4}$ alkylamino, di($C_{1-4}$ alkyl)amino, $C_{1-4}$ alkylsulfinyl, $C_{1-4}$ alkylsulfonyl, carbamyl, $C_{1-4}$ alkylcarbamyl, di($C_{1-4}$ alkyl)carbamyl, carboxy, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, and di($C_{1-4}$ alkyl)aminosulfonyl;

$Cy^B$ is $C_{3-10}$ cycloalkyl or 4-10 membered heterocycloalkyl; wherein at least one ring-forming carbon atom of $C_{3-10}$ cycloalkyl and 4-10 membered heterocycloalkyl is substituted by oxo to form a carbonyl group; wherein the 4-10 membered heterocycloalkyl has at least one ring-forming carbon atom and 1, 2, 3, or 4 ring-forming heteroatoms independently selected from N, O, and S; wherein the N and S are optionally oxidized; and wherein the $C_{3-10}$ cycloalkyl and 4-10 membered heterocycloalkyl are each optionally substituted with 1, 2, 3 or 4 substituents independently selected from $R^B$; or $Cy^B$ is 6-10 membered aryl or 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein: (a) at least one ring-forming carbon atom of the 5-10 membered heteroaryl is substituted by oxo to form a carbonyl group; or (b) the 6-10 membered aryl or 5-10 membered heteroaryl is substituted by halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}OR^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; and wherein the 6-10 membered aryl or 5-10 membered heteroaryl is further optionally substituted with 1, 2, 3 or 4 substituents independently selected from $R^B$;

each $R^B$ is independently selected from halo, $C_{1-6}$ alkyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$ $NR^{c2}OR^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkynyl, $C_{3-6}$ cycloalkyl, phenyl, 5-6 membered heteroaryl, and 4-7 membered heterocycloalkyl are each optionally substituted with 1, 2, 3, or 4 substituents independently selected from $R^{12}$;

each $R^{11}$ is independently selected from CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}OR^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $R^{12}$ is independently selected from halo, CN, $NO_2$, $C_{1-6}$ alkyl, $C_{1-6}$ haloalkyl, $C_{3-6}$ cycloalkyl, phenyl, 5-6 membered heteroaryl, 4-7 membered heterocycloalkyl, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}OR^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{3-6}$ cycloalkyl, phenyl, 5-6 membered heteroaryl, and 4-7 membered heterocycloalkyl are each optionally substituted with 1, 2, 3, or 4 substituents independently selected from $R^g$;

$R^a$ is selected from H, $C_{1-6}$ alkyl, and $C_{1-6}$ haloalkyl;

$R^b$ is selected from $C_{1-6}$ alkyl and $C_{1-6}$ haloalkyl;

$R^c$ and $R^d$ are each independently selected from H, $C_{1-6}$ alkyl, $C_{1-6}$ haloalkyl, $C_{3-6}$ cycloalkyl, phenyl, 5-6 membered heteroaryl, 4-6 membered heterocycloalkyl, $C_{3-6}$ cycloalkyl-$C_{1-3}$ alkylene, phenyl-$C_{1-3}$ alkylene, 5-6 membered heteroaryl-$C_{1-3}$ alkylene, and 4-6 membered heterocycloalkyl-$C_{1-3}$ alkylene; wherein said $C_{1-6}$ alkyl, $C_{1-6}$ haloalkyl, $C_{3-6}$ cycloalkyl, phenyl, 5-6 membered heteroaryl, 4-6 membered heterocycloalkyl, $C_{3-6}$ cycloalkyl-$C_{1-3}$ alkylene, phenyl-$C_{1-3}$ alkylene, 5-6 membered heteroaryl-$C_{1-3}$ alkylene, and 4-6 membered heterocycloalkyl-$C_{1-3}$ alkylene are each optionally substituted with 1, 2 or 3 substituents independently selected from $R^g$;

$R^{a1}$, $R^{c1}$ and $R^{d1}$ are each independently selected from H, $C_{1-6}$ alkyl, and $C_{1-6}$ haloalkyl; wherein said $C_{1-6}$ alkyl is optionally substituted with 1, 2, 3, or 4 substituents independently selected from $R^g$; or alternatively, $R^{c1}$ and $R^{d1}$ attached to the same N atom, together with the N atom to which they are attached, form a 4-, 5-, 6- or 7-membered heterocycloalkyl group optionally substituted with 1, 2 or 3 substituents independently selected from $R^g$;

$R^{b1}$ is selected from $C_{1-6}$ alkyl and $C_{1-6}$ haloalkyl, each of which is optionally substituted with 1, 2, 3, or 4 substituents independently selected from $R^g$;

$R^{e1}$ is selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^{a2}$, $R^{c2}$, and $R^{d2}$ is independently selected from H, $C_{1-6}$ alkyl, $C_{1-6}$ haloalkyl, $C_{3-6}$ cycloalkyl, phenyl, 5-6 membered heteroaryl, and 4-7 membered heterocycloalkyl; wherein said $C_{1-6}$ alkyl, $C_{3-6}$ cycloalkyl, phenyl, 5-6 membered heteroaryl, and 4-7 membered heterocycloalkyl are each optionally substituted with 1, 2, 3, or 4 substituents independently selected from $R^{12}$; or alternatively, any $R^{c2}$ and $R^{d2}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b2}$ is independently selected from $C_{1-6}$ alkyl, $C_{1-6}$ haloalkyl, $C_{3-6}$ cycloalkyl, phenyl, 5-6 membered heteroaryl, and 4-7 membered heterocycloalkyl, each of which is optionally substituted with 1, 2, 3, or 4 substituents independently selected from $R^{12}$;

each $R^{a3}$, $R^{c3}$ and $R^{d3}$ is independently selected from H, $C_{1-6}$ alkyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-4}$ alkylene, phenyl-$C_{1-4}$ alkylene, 5-6 membered heteroaryl-$C_{1-4}$ alkylene, and 4-7 membered heterocycloalkyl-$C_{1-4}$ alkylene; wherein said $C_{1-6}$ alkyl, $C_{3-6}$ cycloalkyl, phenyl, 5-6 membered heteroaryl, 4-7 membered heterocycloalkyl, $C_{3-6}$ cycloalkyl-$C_{1-4}$ alkylene, phenyl-$C_{1-4}$ alkylene, 5-6 membered heteroaryl-$C_{1-4}$ alkylene, and 4-7 membered heterocycloalkyl-$C_{1-4}$ alkylene are each optionally substituted with 1, 2, 3, or 4 substituents independently selected from $R^g$; or alternatively, any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b3}$ is independently selected from $C_{1-6}$ alkyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-4}$ alkylene, phenyl-$C_{1-4}$ alkylene, 5-6 membered heteroaryl-$C_{1-4}$ alkylene, and 4-7 membered heterocycloalkyl-$C_{1-4}$ alkylene, each of which is optionally substituted with 1, 2, 3, or 4 substituents independently selected from $R^g$;

each $R^{a4}$, $R^{c4}$ and $R^{d4}$, is independently selected from H, $C_{1-6}$ alkyl, and $C_{1-6}$ haloalkyl; wherein said $C_{1-6}$ alkyl is optionally substituted with 1, 2, 3, or 4 substituents independently selected from $R^g$; or alternatively, any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b4}$ is independently selected from $C_{1-6}$ alkyl and $C_{1-6}$ haloalkyl, each of which is optionally substituted with 1, 2, 3, or 4 substituents independently selected from $R^g$; and each $R^g$ is independently selected from OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

provided that:
1) $A^1$-$A^2$-$A^3$ is not Y—Y when one of $A^1$, $A^2$ or $A^3$ is a bond, or Y—Y—Y; and
2) when $A^3$ is —Y— or —$C_{1-3}$ alkylene-Y— then $R^A$ is H, $C_{1-6}$ alkyl, or $C_{1-6}$ haloalkyl, wherein said $C_{1-6}$ alkyl or $C_{1-6}$ haloalkyl is optionally substituted with 1, 2, 3 or 4 substituents independently selected from $R^1$.

In some embodiments, provided herein is a compound of Formula (I),
or a pharmaceutically acceptable salt thereof, wherein:
$R^1$ is $A^1$-$A^2$-$A^3$-$R^A$;
$R^2$ is H, halo, CN, $C_{1-4}$ alkyl, $C_{1-4}$ haloalkyl, $C_{1-4}$ alkoxy, $C_{1-4}$ haloalkoxy, cyano-$C_{1-3}$ alkyl or $C_{1-6}$ alkoxyalkyl;
$R^3$ is H, halo, CN, $C_{1-6}$ alkyl, $C_{1-6}$ haloalkyl, $OR^a$, $SR^a$, $C(O)NR^cR^d$, $NR^cR^d$, $NR^cC(O)R^b$, $NR^cS(O)_2R^b$ or $S(O)_2R^b$; wherein said $C_{1-6}$ alkyl and $C_{1-6}$ haloalkyl are optionally substituted with 1, 2 or 3 substituents independently selected from halo, CN, $OR^a$, $SR^a$, $C(O)NR^cR^d$, $NR^cR^d$, $NR^cC(O)R^{b1}$, $NR^cS(O)_2R^b$, $S(O)_2R^b$, $NR^cC(O)OR^a$, $NR^cC(O)NR^cR^d$, $NR^cS(O)_2NR^cR^d$ and $Cy^{R3}$;
$A^1$ is selected from a bond, $Cy^{41}$, —Y—, —$C_{1-3}$ alkylene-, —$C_{1-3}$ alkylene-Y—, —Y—$C_{1-3}$ alkylene-, and —$C_{1-2}$ alkylene-Y—$C_{1-2}$ alkylene-; wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino;
$A^2$ is selected from a bond, $Cy^{42}$, —Y—, —$C_{1-3}$ alkylene-, —$C_{1-3}$ alkylene-Y—, —Y—$C_{1-3}$ alkylene-, and —$C_{1-2}$ alkylene-Y—$C_{1-2}$ alkylene-; wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino;
$A^3$ is selected from a bond, $Cy^{43}$, —Y—, —$C_{1-3}$ alkylene-, —$C_{1-3}$ alkylene-Y—, —Y—$C_{1-3}$ alkylene-, and —$C_{1-2}$ alkylene-Y—$C_{1-2}$ alkylene-; wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino;
$R^A$ is H, $C_{1-6}$ alkyl, $C_{1-6}$ haloalkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^cOR^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, or $S(O)_2NR^{c1}R^{d1}$; wherein said $C_{1-6}$ alkyl or $C_{1-6}$ haloalkyl is optionally substituted with 1, 2, 3 or 4 substituents independently selected from $R^{11}$;

Y is O, S, S(O), $S(O)_2$, C(O), $C(O)NR^f$, $NR^fC(O)$, $NR^fC(O)NR^f$, $NR^fS(O)_2NR^f$, $S(O)_2NR^f$, $NR^fS(O)_2$, or $NR^f$;

each $R^f$ is independently selected from H and $C_{1-3}$ alkyl;

$Cy^{41}$ is $C_{3-7}$ cycloalkyl, phenyl, 5-6 membered heteroaryl, or 4-7 membered heterocycloalkyl; wherein each 5-6 membered heteroaryl and 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of $C_{3-7}$ cycloalkyl and 4-7 membered heterocycloalkyl is optionally substituted by oxo to form a carbonyl group; and wherein the $C_{3-7}$ cycloalkyl, phenyl, 5-6 membered heteroaryl, and 4-7 membered heterocycloalkyl are each optionally substituted with 1, 2, 3 or 4 substituents independently selected from $R^{41}$;

each $R^{41}$ is independently selected from OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$Cy^{42}$ is $C_{3-7}$ cycloalkyl, phenyl, 5-6 membered heteroaryl, or 4-7 membered heterocycloalkyl; wherein each 5-6 membered heteroaryl and 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of $C_{3-7}$ cycloalkyl and 4-7 membered heterocycloalkyl is optionally substituted by oxo to form a carbonyl group; and wherein the $C_{3-7}$ cycloalkyl, phenyl, 5-6 membered heteroaryl, and 4-7 membered heterocycloalkyl are each optionally substituted with 1, 2, 3 or 4 substituents independently selected from $R^{42}$;

each $R^{42}$ is independently selected from OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$Cy^{43}$ is $C_{3-7}$ cycloalkyl, phenyl, 5-6 membered heteroaryl, or 4-7 membered heterocycloalkyl; wherein each 5-6 membered heteroaryl and 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of $C_{3-7}$ cycloalkyl and 4-7 membered heterocycloalkyl is optionally substituted by oxo to form a carbonyl group; and wherein the $C_{3-7}$ cycloalkyl, phenyl, 5-6 membered heteroaryl, and 4-7 membered heterocycloalkyl are each optionally substituted with 1, 2, 3 or 4 substituents independently selected from $R^{43}$;

each $R^{43}$ is independently selected from OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$Cy^{R3}$ is $C_{3-7}$ cycloalkyl, phenyl, 5-6 membered heteroaryl, or 4-7 membered heterocycloalkyl; wherein each 5-6 membered heteroaryl and 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of $C_{3-7}$ cycloalkyl and 4-7 membered heterocycloalkyl is optionally substituted by oxo to form a carbonyl group; and wherein the $C_{3-7}$ cycloalkyl, phenyl, 5-6 membered heteroaryl, and 4-7 membered heterocycloalkyl are each optionally substituted with 1, 2, 3 or 4 substituents independently selected from $R^g$;

$Cy^C$ is phenylene or 5-6 membered heteroarylene; wherein the 5-6 membered heteroarylene has at least one ring-forming carbon atom and 1 or 2 ring-forming heteroatoms independently selected from N, O, and S; and wherein the phenylene and 5-6 membered heteroarylene are each optionally substituted by 1, 2, 3, or 4 substituents independently selected from $R^C$;

each $R^C$ is independently selected from OH, CN, halo, $C_{1-4}$ alkyl, $C_{1-3}$ haloalkyl, $C_{1-4}$ alkoxy, $C_{1-3}$ haloalkoxy, cyano-$C_{1-3}$ alkyl, HO—$C_{1-3}$ alkyl, amino, $C_{1-4}$ alkylamino, di($C_{1-4}$ alkyl)amino, $C_{1-4}$ alkylsulfinyl, $C_{1-4}$ alkylsulfonyl, carbamyl, $C_{1-4}$ alkylcarbamyl, di($C_{1-4}$ alkyl)carbamyl, carboxy, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, and di($C_{1-4}$ alkyl)aminosulfonyl;

$Cy^B$ is $C_{3-10}$ cycloalkyl or 4-10 membered heterocycloalkyl; wherein at least one ring-forming carbon atom of $C_{3-10}$ cycloalkyl and 4-10 membered heterocycloalkyl is substituted by oxo to form a carbonyl group; wherein the 4-10 membered heterocycloalkyl has at least one ring-forming carbon atom and 1, 2, 3, or 4 ring-forming heteroatoms independently selected from N, O, and S; wherein the N and S are optionally oxidized; and wherein the $C_{3-10}$ cycloalkyl and 4-10 membered heterocycloalkyl are each optionally substituted with 1, 2, 3 or 4 substituents independently selected from $R^B$; or $Cy^B$ is 6-10 membered aryl or 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein: (a) at least one ring-forming carbon atom of the 5-10 membered heteroaryl is substituted by oxo to form a carbonyl group; or (b) the 6-10 membered aryl or 5-10 membered heteroaryl is substituted by halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}OR^{d2}$, $NR^{c2}C(O)R^{b2}$, $NR^{c2}C(O)OR^{a2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; and wherein the 6-10 membered aryl or 5-10 membered heteroaryl is further optionally substituted with 1, 2, 3 or 4 substituents independently selected from $R^B$;

each $R^B$ is independently selected from halo, $C_{1-6}$ alkyl, $C_{1-6}$ haloalkyl, $C_{3-6}$ cycloalkyl, phenyl, 5-6 membered heteroaryl, 4-7 membered heterocycloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}OR^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{3-6}$ cycloalkyl, phenyl, 5-6 membered heteroaryl, and 4-7 membered heterocycloalkyl are each optionally substituted with 1, 2, 3, or 4 substituents independently selected from $R^{12}$;

each $R^{11}$ is independently selected from CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}$ $OR^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $R^{12}$ is independently selected from halo, CN, $NO_2$, $C_{1-6}$ alkyl, $C_{1-6}$ haloalkyl, $C_{3-6}$ cycloalkyl, phenyl, 5-6 membered heteroaryl, 4-7 membered heterocycloalkyl, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}OR^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{3-6}$ cycloalkyl, phenyl, 5-6 membered heteroaryl, and 4-7 membered heterocycloalkyl are each optionally substituted with 1, 2, 3, or 4 substituents independently selected from $R^g$;

$R^a$ is selected from H, $C_{1-6}$ alkyl, and $C_{1-6}$ haloalkyl;

$R^b$ is selected from $C_{1-6}$ alkyl and $C_{1-6}$ haloalkyl;

$R^c$ and $R^d$ are each independently selected from H, $C_{1-6}$ alkyl, $C_{1-6}$ haloalkyl, $C_{3-6}$ cycloalkyl, phenyl, 5-6 membered heteroaryl, 4-6 membered heterocycloalkyl, $C_{3-6}$ cycloalkyl-$C_{1-3}$ alkylene, phenyl-$C_{1-3}$ alkylene, 5-6 membered heteroaryl-$C_{1-3}$ alkylene, and 4-6 membered heterocycloalkyl-$C_{1-3}$ alkylene; wherein said $C_{1-6}$ alkyl, $C_{1-6}$ haloalkyl, $C_{3-6}$ cycloalkyl, phenyl, 5-6 membered heteroaryl, 4-6 membered heterocycloalkyl, $C_{3-6}$ cycloalkyl-$C_{1-3}$ alkylene, phenyl-$C_{1-3}$ alkylene, 5-6 membered heteroaryl-$C_{1-3}$ alkylene, and 4-6 membered heterocycloalkyl-$C_{1-3}$ alkylene are each optionally substituted with 1, 2 or 3 substituents independently selected from $R^g$;

$R^{a1}$, $R^{c1}$ and $R^{d1}$ are each independently selected from H, $C_{1-6}$ alkyl, and $C_{1-6}$ haloalkyl; wherein said $C_{1-6}$ alkyl is optionally substituted with 1, 2, 3, or 4 substituents independently selected from $R^g$; or alternatively, $R^{c1}$ and $R^{d1}$ attached to the same N atom, together with the N atom to which they are attached, form a 4-, 5-, 6- or 7-membered heterocycloalkyl group optionally substituted with 1, 2 or 3 substituents independently selected from $R^g$;

$R^{b1}$ is selected from $C_{1-6}$ alkyl and $C_{1-6}$ haloalkyl, each of which is optionally substituted with 1, 2, 3, or 4 substituents independently selected from $R^g$;

$R^{e1}$ is selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^{a2}$, $R^{c2}$, and $R^{d2}$ is independently selected from H, $C_{1-6}$ alkyl, $C_{1-6}$ haloalkyl, $C_{3-6}$ cycloalkyl, phenyl, 5-6 membered heteroaryl, and 4-7 membered heterocycloalkyl; wherein said $C_{1-6}$ alkyl, $C_{3-6}$ cycloalkyl, phenyl, 5-6 membered heteroaryl, and 4-7 membered heterocycloalkyl are each optionally substituted with 1, 2, 3, or 4 substituents independently selected from $R^{12}$; or alternatively, any $R^{c2}$ and $R^{d2}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b2}$ is independently selected from $C_{1-6}$ alkyl, $C_{1-6}$ haloalkyl, $C_{3-6}$ cycloalkyl, phenyl, 5-6 membered heteroaryl, and 4-7 membered heterocycloalkyl, each of which is optionally substituted with 1, 2, 3, or 4 substituents independently selected from $R^{12}$;

each $R^{a3}$, $R^{c3}$ and $R^{d3}$ is independently selected from H, $C_{1-6}$ alkyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-4}$ alkylene, phenyl-$C_{1-4}$ alkylene, 5-6 membered heteroaryl-$C_{1-4}$ alkylene, and 4-7 membered heterocycloalkyl-$C_{1-4}$ alkylene; wherein said $C_{1-6}$ alkyl, $C_{3-6}$ cycloalkyl, phenyl, 5-6 membered heteroaryl, 4-7 membered heterocycloalkyl, $C_{3-6}$ cycloalkyl-$C_{1-4}$ alkylene, phenyl-$C_{1-4}$ alkylene, 5-6 membered heteroaryl-$C_{1-4}$ alkylene, and 4-7 membered heterocycloalkyl-$C_{1-4}$ alkylene are each optionally substituted with 1, 2, 3, or 4 substituents independently selected from $R^g$; or alternatively, any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b3}$ is independently selected from $C_{1-6}$ alkyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-4}$ alkylene, phenyl-$C_{1-4}$ alkylene, 5-6 membered heteroaryl-$C_{1-4}$ alkylene, and 4-7 membered heterocycloalkyl-$C_{1-4}$ alkylene, each of which is optionally substituted with 1, 2, 3, or 4 substituents independently selected from $R^g$;

each $R^{a4}$, $R^{c4}$ and $R^{d4}$, is independently selected from H, $C_{1-6}$ alkyl, and $C_{1-6}$ haloalkyl; wherein said $C_{1-6}$ alkyl is optionally substituted with 1, 2, 3, or 4 substituents independently selected from $R^g$; or alternatively, any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b4}$ is independently selected from $C_{1-6}$ alkyl and $C_{1-6}$ haloalkyl, each of which is optionally substituted with 1, 2, 3, or 4 substituents independently selected from $R^g$; and each $R^g$ is independently selected from OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

provided that:
1) $A^1$-$A^2$-$A^3$ is not Y—Y when one of $A^1$, $A^2$ or $A^3$ is a bond, or Y—Y—Y; and
2) when $A^3$ is —Y— or —$C_{1-3}$ alkylene-Y— then $R^4$ is H, $C_{1-6}$ alkyl, or $C_{1-6}$ haloalkyl, wherein said $C_{1-6}$ alkyl or $C_{1-6}$ haloalkyl is optionally substituted with 1, 2, 3 or 4 substituents independently selected from $R^{11}$.

In some embodiments, $A^1$ is a bond.
In some embodiments, $A^2$ is a bond.
In some embodiments, $A^3$ is a bond.
In some embodiments, $R^4$ is H, halo, $C_{1-6}$ alkyl or $C_{1-6}$ haloalkyl.
In some embodiments, $R^4$ is $C_{1-6}$ alkyl.
In some embodiments, $R^4$ is methyl or ethyl.
In some embodiments, $A^1$ is a bond. For example, $R^1$ is $A^2$-$A^3$-$R^4$.
In some embodiments, $A^1$ is a bond, $A^2$ is a bond, and $A^3$ is $Cy^{43}$. For example, $R^1$ is $Cy^{43}$-$R^4$.
In some embodiments, one of $A^1$, $A^2$, and $A^3$ is not a bond.
In some embodiments, one of $A^1$, $A^2$, and $A^3$ is —$C_{1-3}$ alkylene-, —Y—, —$C_{1-3}$ alkylene-Y—, or —Y—$C_{1-3}$ alkylene-. In some embodiments, one of $A^1$, $A^2$, and $A^3$ is —$C_{1-6}$ alkylene- or —Y—. In some embodiments, one of $A^1$, $A^2$, and $A^3$ is —$C_{1-6}$ alkylene-. In some embodiments, one of $A^1$, $A^2$, and $A^3$ is methylene.
In some embodiments, $R^1$ is H, halo, $C_{1-6}$ alkyl or $C_{1-6}$ haloalkyl.
In some embodiments, $R^1$ is $C_{1-6}$ alkyl. In some embodiments, $R^1$ is methyl or ethyl.
In some embodiments, $R^1$ is $A^2$-$A^3$-$R^4$.
In some embodiments, $R^1$ is $Cy^{43}$-$R^4$.
In some embodiments, $Cy^{43}$ is $C_{3-7}$ cycloalkyl, 5-6 membered heteroaryl, or 4-7 membered heterocycloalkyl; each optionally substituted with 1, 2, 3 or 4 substituents independently selected from $R^{43}$.
In some embodiments, $Cy^{43}$ is $C_{3-6}$ cycloalkyl or 4-6 membered heterocycloalkyl, each optionally substituted with 1 or 2 substituents independently selected from $R^{43}$.
In some embodiments, $Cy^{43}$ is piperidinyl, cyclohexyl, or tetrahydropyranyl; each optionally substituted with 1 or 2 substituents independently selected from $R^{43}$.
In some embodiments, $Cy^{43}$ is $C_{3-6}$ cycloalkyl optionally substituted with 1, 2, 3 or 4 independently selected $R^{43}$ groups. In some embodiments, $Cy^{43}$ is cyclohexyl and cyclopropyl optionally substituted with 1, 2, 3 or 4 independently selected $R^{43}$ groups.
In some embodiments, $Cy^{43}$ is 4-6 membered heterocycloalkyl optionally substituted with 1, 2, 3 or 4 independently selected $R^{43}$ groups. In some embodiments, $Cy^{43}$ is piperidinyl or morpholinyl optionally substituted with 1, 2, 3 or 4 independently selected $R^{43}$ groups.
In some embodiments, $Cy^{43}$ is 5-10 membered heteroaryl optionally substituted with 1, 2, 3 or 4 independently selected $R^{43}$ groups. In some embodiments, $Cy^{43}$ is pyridyl optionally substituted with 1, 2, 3 or 4 independently selected $R^{43}$ groups.
In some embodiments, $Cy^{43}$ is piperidinyl, cyclohexyl, tetrahydropyranyl, pyrazolyl, pyridinyl, azetidinyl, cyclopropyl, or morpholinyl; each optionally substituted with 1 or 2 substituents independently selected from $R^{43}$.
In some embodiments, $Cy^{43}$ is piperidinyl, pyridyl, morpholinyl, cyclohexyl, or tetrahydropyranyl; each optionally substituted with 1, 2, 3 or 4 independently selected $R^{43}$ groups.
In some embodiments, $Cy^{43}$ is piperidinyl optionally substituted with 1, 2, 3 or 4 independently selected $R^{43}$ groups.
In some embodiments, $Cy^{43}$ is cyclohexyl optionally substituted with 1, 2, 3 or 4 independently selected $R^{43}$ groups.
In some embodiments, $Cy^{43}$ is morpholinyl optionally substituted with 1, 2, 3 or 4 independently selected $R^{43}$ groups.

In some embodiments, Cy$^{A3}$ is

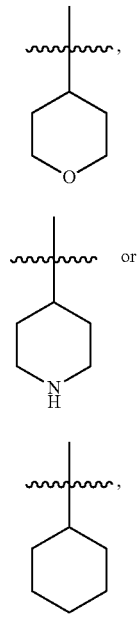

wherein Cy$^{A3}$-1, Cy$^{A3}$-2 and Cy$^{A3}$-3 are each optionally substituted with 1, 2 or 3 substituents independently selected from R$^{A3}$.

In some embodiments, A$^1$ is a bond, A$^2$ is a bond, A$^3$ is a bond, and R$^A$ is methyl or ethyl; or A$^1$ is a bond, A$^2$ is a bond, and A$^3$ is Cy$^{A3}$-R$^A$ selected from

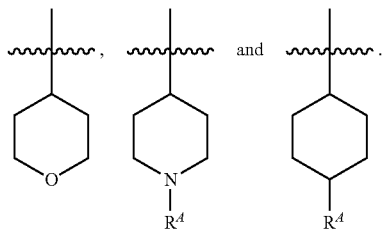

In some embodiments, R$^A$ is C$_{1-6}$ alkyl, CN, OR$^{a1}$, NR$^{c1}$R$^{d1}$, C(O)R$^{b1}$, C(O)NR$^{c1}$R$^{d1}$, C(O)OR$^{a1}$, S(O)R$^{b1}$, S(O)NR$^{c1}$R$^{d1}$, S(O)$_2$R$^{b1}$ or S(O)$_2$NR$^{c1}$R$^{d1}$; wherein said C$_{1-6}$ alkyl is optionally substituted with 1 or 2 substituents independently selected from R$^{11}$, provided that if R$^A$ is attached to a nitrogen atom, then R$^A$ is not CN, OR$^{a1}$, or NR$^{c1}$R$^{d1}$.

In some embodiments, R$^A$ is C$_{1-6}$ alkyl, CN, OR$^{a1}$, C(O)R$^{b1}$, C(O)NR$^{c1}$R$^{d1}$, C(O)OR$^{a1}$, and S(O)$_2$R$^{b1}$; wherein said C$_{1-6}$ alkyl is optionally substituted with 1 substituent selected from R$^{11}$, provided that if R$^A$ is attached to a nitrogen atom, then R$^A$ is not CN or OR$^{a1}$. In some embodiments, R$^{b1}$ is isopropyl.

In some embodiments, each R$^A$ is independently selected from C$_{1-3}$ alkyl, CN, OH, methylcarbonyl, methoxycarbonyl, N,N-dimethylaminocarbonyl, and methylsulfonyl, wherein said C$_{1-3}$ alkyl is optionally substituted with a OH or OCH$_3$ group, provided that if R$^A$ is attached to a nitrogen atom, then R$^A$ is not CN or OH.

In some embodiments, each R$^A$ is independently selected from CH$_3$, CH$_2$CH$_3$, CN, OH, CH$_2$CH$_2$OH, CH$_2$CH$_2$OCH$_3$, C(O)CH$_3$, C(O)CH$_2$OH, C(O)CH(OH)CH$_3$, S(O)$_2$CH$_3$, C(O)OCH$_3$, C(O)N(CH$_3$)$_2$, C(O)NHCH$_3$, C(O)N(CH$_2$CH$_3$)$_2$, and C(O)N(CH$_3$)(CH$_2$CH$_3$).

In some embodiments, each R$^A$ is independently selected from CH$_3$, CH$_2$CH$_3$, CH(CH$_3$)$_2$, CN, OH, CH$_2$CH$_2$OH, CH$_2$CH$_2$OCH$_3$, C(O)CH$_3$, C(O)CH$_2$CH$_3$, C(O)CH(CH$_3$)$_2$, C(O)CH$_2$OH, C(O)CH(OH)CH$_3$, S(O)$_2$CH$_3$, C(O)OCH$_3$, C(O)N(CH$_3$)$_2$, C(O)N(CH$_2$CH$_3$)$_2$, C(O)N(CH$_3$)(CH$_2$CH$_3$), C(O)NHCH$_3$, C(O)NH(CH$_2$CH$_3$) and C(O)[morpholin-4-yl].

In some embodiments, each R$^{11}$ is independently OR$^{a3}$.

In some embodiments, each R$^{11}$ is independently OH or OCH$_3$.

In some embodiments, Cy$^{A3}$ is piperidinyl, cyclohexyl, tetrahydropyranyl, pyrazolyl, pyridinyl, azetidinyl, cyclopropyl, or morpholinyl; each optionally substituted with R$^A$ independently selected from CH$_3$, CN, OH, CH$_2$CH$_2$OH, CH$_2$CH$_2$OCH$_3$, C(O)CH$_3$, C(O)CH$_2$CH$_3$, C(O)CH(CH$_3$)$_2$, C(O)CH$_2$OH, C(O)CH(CH$_3$)OH, S(O)$_2$CH$_3$, C(O)OCH$_3$, C(O)N(CH$_3$)$_2$, C(O)NH(CH$_3$), C(O)N(CH$_2$CH$_3$)$_2$, C(O)NH(CH$_2$CH$_3$), C(O)N(CH$_3$)(CH$_2$CH$_3$), CH$_2$C(O)N(CH$_3$)$_2$, 1-methyl-2-oxopyrrolidin-3-yl, C(O)(cyclopropyl), N(CH$_3$)$_2$, and C(O)(morpholin-4-yl).

In some embodiments, Cy$^{A3}$ is piperidinyl, cyclohexyl, or tetrahydropyranyl; each optionally substituted with R$^A$ independently selected from CH$_3$, CN, OH, CH$_2$CH$_2$OH, CH$_2$CH$_2$OCH$_3$, C(O)CH$_3$, C(O)CH$_2$OH, C(O)CH(CH$_3$)OH, S(O)$_2$CH$_3$, C(O)OCH$_3$, C(O)N(CH$_3$)$_2$, C(O)NH(CH$_3$), C(O)N(CH$_2$CH$_3$)$_2$, C(O)NH(CH$_2$CH$_3$) and C(O)N(CH$_3$)(CH$_2$CH$_3$).

In some embodiments, Cy$^{A3}$ is piperidinyl, cyclohexyl, or tetrahydropyranyl; each optionally substituted with R$^A$ independently selected from CH$_3$, CH$_2$CH$_3$, CH(CH$_3$)$_2$, CN, OH, CH$_2$CH$_2$OH, CH$_2$CH$_2$OCH$_3$, C(O)CH$_3$, C(O)CH$_2$CH$_3$, C(O)CH(CH$_3$)$_2$, C(O)CH$_2$OH, C(O)CH(OH)CH$_3$, S(O)$_2$CH$_3$, C(O)OCH$_3$, C(O)N(CH$_3$)$_2$, C(O)N(CH$_2$CH$_3$)$_2$, C(O)N(CH$_3$)(CH$_2$CH$_3$), C(O)NHCH$_3$, C(O)NH(CH$_2$CH$_3$) and C(O)(morpholin-4-yl)

In some embodiments, Cy$^{A3}$ is piperidinyl, pyridyl, morpholinyl, cyclohexyl, or tetrahydropyranyl; each optionally substituted with 1, 2, 3 or 4 groups independently selected from CH$_3$, CH$_2$CH$_3$, CN, OH, CH$_2$CH$_2$OH, CH$_2$CH$_2$OCH$_3$, C(O)CH$_3$, C(O)CH$_2$OH, C(O)CH(OH)CH$_3$, S(O)$_2$CH$_3$, C(O)OCH$_3$, C(O)N(CH$_3$)$_2$, C(O)NHCH$_3$, C(O)N(CH$_2$CH$_3$)$_2$, and C(O)N(CH$_3$)(CH$_2$CH$_3$).

In some embodiments, A$^1$ is a bond, A$^2$ is Cy$^{A2}$, A$^3$ is —Y—, R$^A$ is C$_{3-6}$ cycloalkyl (e.g., cyclopropyl), —Y— is C(O), and Cy$^{A2}$ is 4-7 membered heterocycloalkyl (e.g., piperidinyl).

In some embodiments, R$^1$ is

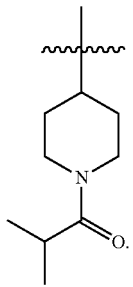

In some embodiments, $R^1$ is

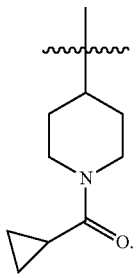

In some embodiments, $R^1$ is

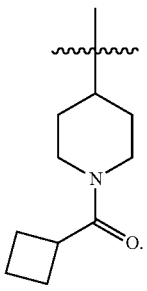 [SMILES: *C1CCN(C(=O)C2CCC2)CC1]

In some embodiments, $R^1$ is

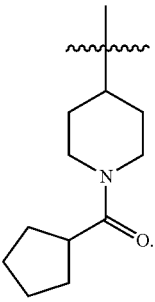 [SMILES: *C1CCN(C(=O)C2CCCC2)CC1]

In some embodiments, $R^1$ is

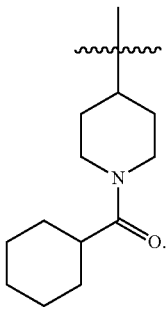 [SMILES: *C1CCN(C(=O)C2CCCCC2)CC1]

In some embodiments, $R^2$ is H, halo, $C_{1-4}$ alkyl, $C_{1-4}$ haloalkyl, $C_{1-4}$ alkoxy, or $C_{1-4}$ haloalkoxy. In some embodiments, $R^2$ is H or $C_{1-4}$ alkyl. In some embodiments, $R^2$ is H.

In some embodiments, $R^3$ is H.

In preferred embodiments, $Cy^B$ forms a hydrogen bond with the NH of the amide group.

For example, if the $Cy^B$ group has an oxo group, the $Cy^B$ can form a hydrogen bond through the carbonyl group with the NH of the amide group. Similarly, $Cy^B$ can be substituted with an electron donating substituent capable of forming a hydrogen bond with the NH of the amide group. Below are illustrative examples wherein W is an electron donating group such as halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}OR^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$:

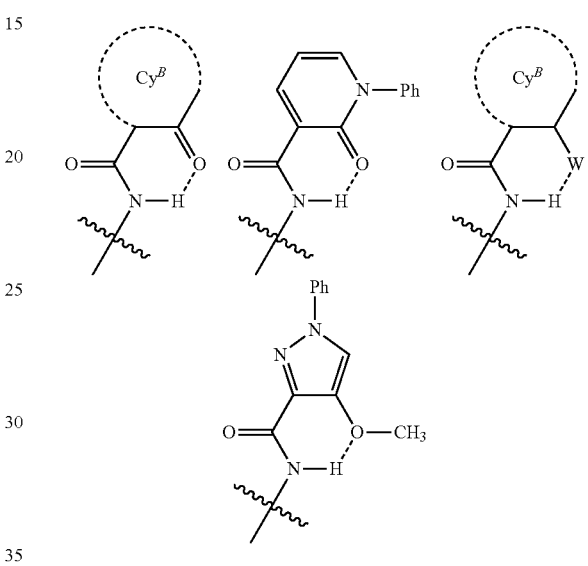

In some embodiments, $Cy^B$ is $C_{3-10}$ cycloalkyl or 4-10 membered heterocycloalkyl; wherein at least one ring-forming carbon atom of $C_{3-10}$ cycloalkyl and 4-10 membered heterocycloalkyl is substituted by oxo to form a carbonyl group; wherein the 4-10 membered heterocycloalkyl has at least one ring-forming carbon atom and 1, 2, 3, or 4 ring-forming heteroatoms independently selected from N, O, and S; wherein the N and S are optionally oxidized; and wherein the $C_{3-10}$ cycloalkyl and 4-10 membered heterocycloalkyl are each optionally substituted with 1, 2, 3 or 4 substituents independently selected from $R^B$; or $Cy^B$ is 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein: (a) at least one ring-forming carbon atom of the 5-10 membered heteroaryl is substituted by oxo to form a carbonyl group; or (b) the 5-10 membered heteroaryl is substituted by halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}OR^{d2}$, $NR^{c2}C(O)R^{b2}$, $NR^{c2}C(O)OR^{a2}$, $NR^{c2}C(O)NR^{c2}R^{d2}$ $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; and wherein the 5-10 membered heteroaryl is further optionally substituted with 1, 2, 3 or 4 substituents independently selected from $R^B$.

In some embodiments, $Cy^B$ is $C_{3-10}$ cycloalkyl or 4-10 membered heterocycloalkyl; wherein at least one ring-forming carbon atom of $C_{3-10}$ cycloalkyl and 4-10 membered heterocycloalkyl is substituted by oxo to form a carbonyl group; wherein the 4-10 membered heterocycloalkyl has at least one ring-forming carbon atom and 1, 2, 3, or 4 ring-forming heteroatoms independently selected from N, O, and S; wherein the N and S are optionally oxidized; and wherein the $C_{3-10}$ cycloalkyl and 4-10 membered heterocycloalkyl are each optionally substituted with 1, 2, 3 or 4 substituents independently selected from $R^B$.

In some embodiments, $Cy^B$ is 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein: (a) at least one ring-forming carbon atom of the 5-10 membered heteroaryl is substituted by oxo to form a carbonyl group; or (b) the 5-10 membered heteroaryl is substituted by halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}OR^{d2}$, $NR^{c2}C(O)R^{b2}$, $NR^{c2}C(O)OR^{a2}$ $NR^{c2}C(O)NR^{c2}R^{d2}$ $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; and wherein the 5-10 membered heteroaryl is further optionally substituted with 1, 2, 3 or 4 substituents independently selected from $R^B$.

In some embodiments, $Cy^B$ is 4-10 membered heterocycloalkyl; wherein at least one ring-forming carbon atom of 4-10 membered heterocycloalkyl is substituted by oxo to form a carbonyl group; wherein the 4-10 membered heterocycloalkyl has at least one ring-forming carbon atom and 1, 2, 3, or 4 ring-forming heteroatoms independently selected from N, O, and S; and wherein the 4-10 membered heterocycloalkyl is optionally substituted with 1, 2 or 3 substituents independently selected from $R^B$; or $Cy^B$ is 5-6 membered heteroaryl, having at least one ring-forming carbon atom which is substituted by oxo to form a carbonyl group and 1 or 2 ring-forming heteroatoms independently selected from N, O, and S; wherein the N and S are optionally oxidized; wherein the 5-6 membered heteroaryl is further optionally substituted with 1, 2, or 3 substituents independently selected from $R^B$.

In some embodiments, $Cy^B$ is 4-10 membered heterocycloalkyl; wherein at least one ring-forming carbon atom of 4-10 membered heterocycloalkyl is substituted by oxo to form a carbonyl group; wherein the 4-10 membered heterocycloalkyl has at least one ring-forming carbon atom and 1, 2, 3, or 4 ring-forming heteroatoms independently selected from N, O, and S; and wherein the 4-10 membered heterocycloalkyl is optionally substituted with 1, 2 or 3 substituents independently selected from $R^B$.

In some embodiments, $Cy^B$ is 5-10 membered heteroaryl, having at least one ring-forming carbon atom which is substituted by oxo to form a carbonyl group and 1 or 2 ring-forming heteroatoms independently selected from N, O, and S; wherein the N and S are optionally oxidized; wherein the 5-6 membered heteroaryl is further optionally substituted with 1, 2, or 3 substituents independently selected from $R^B$.

In some embodiments, $Cy^B$ is 4-10 membered heterocycloalkyl or 5-10 membered heteroaryl wherein one ring-forming carbon atom at the ortho position is substituted by oxo to form a carbonyl group. The ortho position refers to the ring-forming carbon atom directly adjacent to the ring-forming atom connecting the $Cy^B$ group to the —C(=O)NH—$Cy^C$-linker.

In some embodiments, $Cy^B$ is

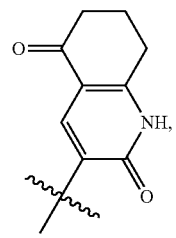

$Cy^B$-1

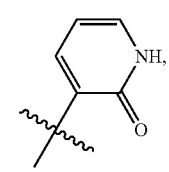

$Cy^B$-2

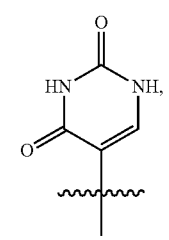

$Cy^B$-3

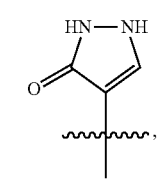

$Cy^B$-4

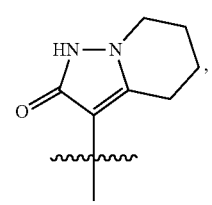

$Cy^B$-5

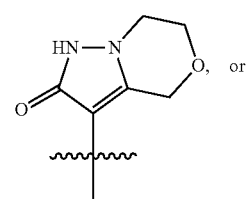

$Cy^B$-6, or

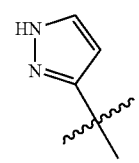

$Cy^B$-7 wherein $Cy^B$-1, $Cy^B$-2, $Cy^B$-3, $Cy^B$-4, $Cy^B$-5, $Cy^B$-6, and $Cy^B$-7 are each optionally substituted with 1, 2 or 3 independently selected $R^B$ groups.

In some embodiments, Cy$^B$ is

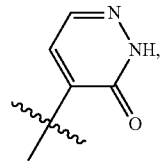
Cy$^B$-8

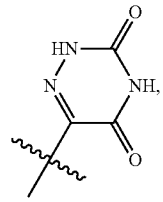
Cy$^B$-9

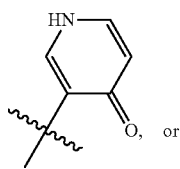
Cy$^B$-10

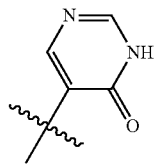
Cy$^B$-11 wherein Cy$^B$-8, Cy$^B$-9, Cy$^B$-10, Cy$^B$-4, and Cy$^B$-11 are each optionally substituted with 1, 2 or 3 independently selected R$^B$ groups.

In some embodiments, Cy$^B$ is

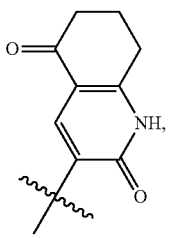
Cy$^B$-1

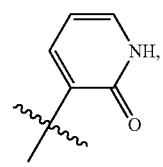
Cy$^B$-2

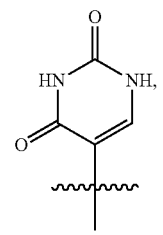
Cy$^B$-3

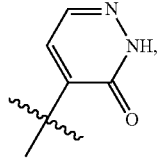
Cy$^B$-8

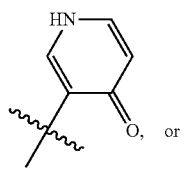
Cy$^B$-9

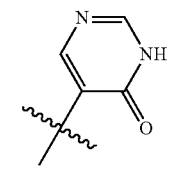
Cy$^B$-10 or

Cy$^B$-11 wherein Cy$^B$-1, Cy$^B$-2, Cy$^B$-3, Cy$^B$-8, Cy$^B$-9, Cy$^B$-10, Cy$^B$-4, and Cy$^B$-11 are each optionally substituted with 1, 2 or 3 independently selected R$^B$ groups.

In some embodiments, Cy$^B$ is Cy$^B$-1 optionally substituted with 1, 2 or 3 independently selected R$^B$ groups. In some embodiments, Cy$^B$ is Cy$^B$-2 optionally substituted with 1, 2 or 3 independently selected R$^B$ groups. In some embodiments, Cy$^B$ is Cy$^B$-3 optionally substituted with 1, 2 or 3 independently selected R$^B$ groups. In some embodiments, Cy$^B$ is Cy$^B$-4 optionally substituted with 1, 2 or 3 independently selected R$^B$ groups. In some embodiments, Cy$^B$ is Cy$^B$-5 optionally substituted with 1, 2 or 3 independently selected R$^B$ groups. In some embodiments, Cy$^B$ is Cy$^B$-6 optionally substituted with 1, 2 or 3 independently selected R$^B$ groups. In some embodiments, Cy$^B$ is Cy$^B$-7 optionally substituted with 1, 2 or 3 independently selected R$^B$ groups.

In some embodiments, Cy$^B$ is

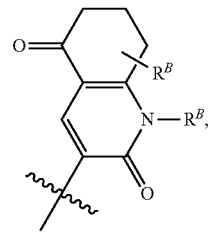
Cy$^B$-1a

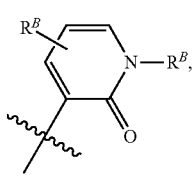
Cy$^B$-2a

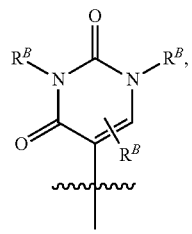
Cy$^B$-3a

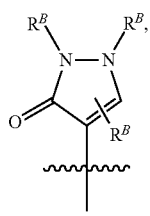
Cy$^B$-4a

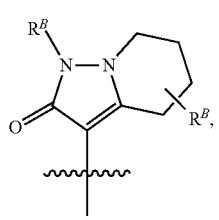
Cy$^B$-5a

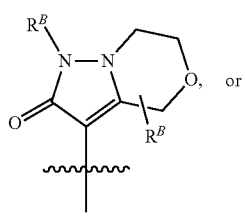
Cy$^B$-6a, or

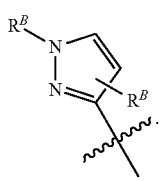
Cy$^B$-7a.

In some embodiments, Cy$^B$ is Cy$^B$-1a. In some embodiments, Cy$^B$ is Cy$^B$-2a. In some embodiments, Cy$^B$ is Cy$^B$-3a. In some embodiments, Cy$^B$ is Cy$^B$-4a. In some embodiments, Cy$^B$ is Cy$^B$-5a. In some embodiments, Cy$^B$ is Cy$^B$-6a. In some embodiments, Cy$^B$ is Cy$^B$-7a.

In some embodiments, Cy$^B$ is C$_{3-10}$ cycloalkyl optionally substituted with 1, 2 or 3 independently selected R$^B$ groups. In some embodiments, Cy$^B$ is cyclopropyl.

In some embodiments, Cy$^B$ is cyclopropyl,

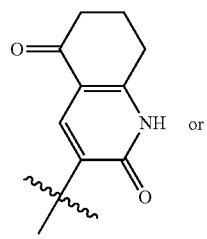
Cy$^B$-1 or

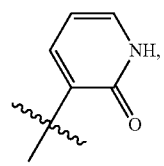
Cy$^B$-2 wherein the cyclopropyl, Cy$^B$-1 and Cy$^B$-2 are each optionally substituted with 1, 2 or 3 independently selected R$^B$ groups.

In some embodiments, Cy$^B$ is

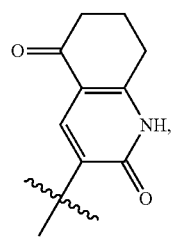
Cy$^B$-1

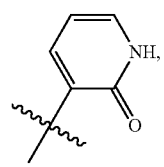
Cy$^B$-2

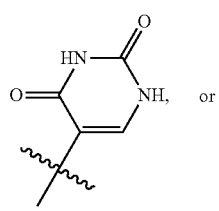
Cy$^B$-3, or

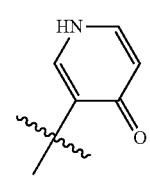
Cy$^B$-10 wherein Cy$^B$-1, Cy$^B$-2, Cy$^B$-3, and Cy$^B$-10 are each optionally substituted with 1, 2 or 3 substituents independently selected from R$^B$.

In some embodiments, Cy$^B$ is

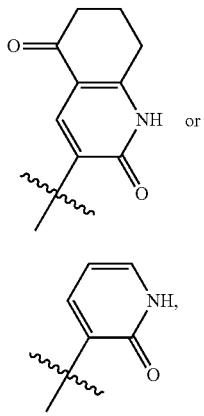

Cy$^B$-1

Cy$^B$-2 wherein Cy$^B$-1 and Cy$^B$-2 are each optionally substituted with 1, 2 or 3 independently selected R$^B$ groups.

In some embodiments, Cy$^B$ is

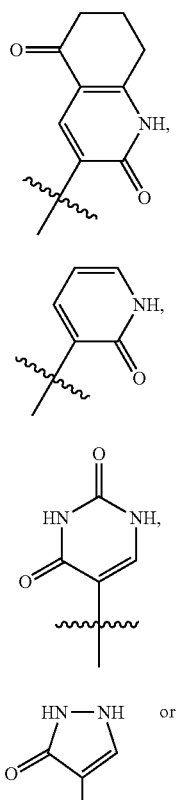

Cy$^B$-1

Cy$^B$-2

Cy$^B$-3

Cy$^B$-4 or

Cy$^B$-5 wherein Cy$^B$-1, Cy$^B$-2, Cy$^B$-3, Cy$^B$-4 and Cy$^B$-5 are each optionally substituted with 1, 2 or 3 independently selected R$^B$ groups.

In some embodiments, Cy$^B$ is

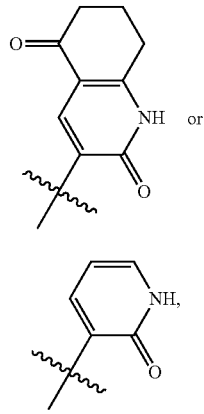

Cy$^B$-1

Cy$^B$-2 wherein Cy$^B$-1 and Cy$^B$-2 are each optionally substituted with 1, 2 or 3 substituents independently selected from R$^B$.

In some embodiments, Cy$^B$ is

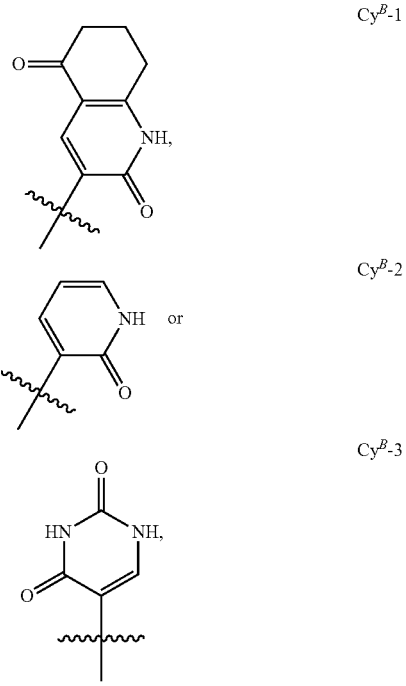

Cy$^B$-1

Cy$^B$-2 or

Cy$^B$-3 wherein Cy$^B$-1, Cy$^B$-2 and Cy$^B$-3 are each optionally substituted with 1, 2 or 3 independently selected R$^B$ groups.

In some embodiments, Cy$^B$ is

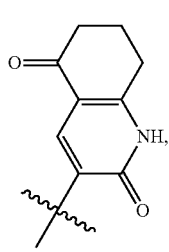

Cy$^B$-1 wherein Cy$^B$-1 is optionally substituted with 1, 2 or 3 independently selected R$^B$ groups. In some embodiments, Cy$^B$ is

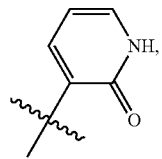
Cy$^B$-2 wherein Cy$^B$-2 is optionally substituted with 1, 2 or 3 independently selected R$^B$ groups. In some embodiments, Cy$^B$ is

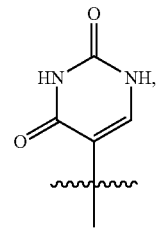
Cy$^B$-3 wherein Cy$^B$-3 is optionally substituted with 1, 2 or 3 independently selected R$^B$ groups. In some embodiments, Cy$^B$ is

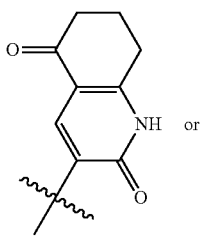
Cy$^B$-1

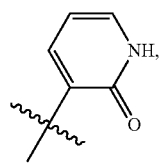
Cy$^B$-2 wherein Cy$^B$-1 and Cy$^B$-2 are each optionally substituted with 1, 2 or 3 substituents independently selected from R$^B$;

each R$^B$ is independently methyl, ethyl, isopropyl, sec-butyl, or phenyl, each of which is optionally substituted by 1 or 2 substituents independently selected from R$^{12}$;

each R$^{12}$ is independently selected from halo, phenyl, and OR$^{a4}$; wherein said phenyl is optionally substituted by 1 or 2 substituents independently selected from R$^g$ group;

each R$^{a4}$ is H or C$_{1-3}$ alkyl; and each R$^g$ is independently selected from halo.

In some embodiments, Cy$^B$ is

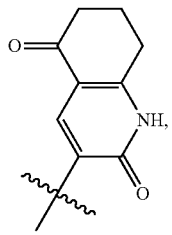
Cy$^B$-1

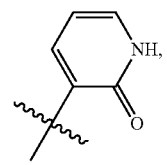
Cy$^B$-2

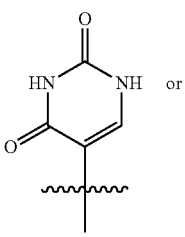
Cy$^B$-3 or

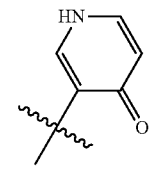
Cy$^B$-10 wherein Cy$^B$-1, Cy$^B$-2, Cy$^B$-3, and Cy$^B$-10 are each optionally substituted with 1, 2 or 3 substituents independently selected from R$^B$;

each R$^B$ is independently methyl, ethyl, isopropyl, sec-butyl, 2-pyridinyl, or phenyl, each of which is optionally substituted by 1 or 2 substituents independently selected from R$^{12}$;

each R$^{12}$ is independently selected from C$_{1-6}$ alkyl, halo, phenyl, and OR$^{a4}$; wherein said C$_{1-6}$ alkyl and phenyl are each optionally substituted by 1 or 2 substituents independently selected from R$^g$ group;

each R$^{a4}$ is H or C$_{1-3}$ alkyl; and each R$^g$ is independently selected from halo.

In some embodiments, Cy$^B$ is

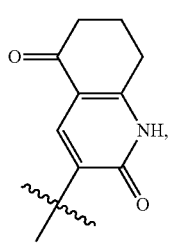
Cy$^B$-1

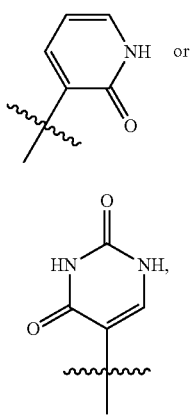
Cy$^B$-2

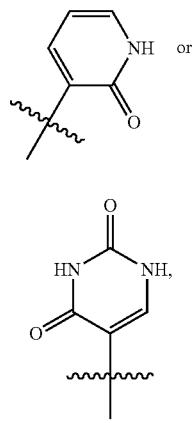
Cy$^B$-2

Cy$^B$-3

Cy$^B$-3 wherein Cy$^B$-1, Cy$^B$-2 and Cy$^B$-3 are each optionally substituted with 1, 2 or 3 substituents independently selected from R$^B$;
each R$^B$ is independently methyl, ethyl, isopropyl, sec-butyl, or phenyl, each of which is optionally substituted by 1 or 2 substituents independently selected from R$^{12}$;
each R$^{12}$ is independently selected from halo, phenyl, and OR$^{a4}$; wherein said phenyl is optionally substituted by 1 or 2 substituents independently selected from R$^g$ group;
each R$^{a4}$ is H or C$_{1-3}$ alkyl; and
each R$^g$ is independently selected from halo.

In some embodiments, Cy$^B$ is wherein Cy$^B$-1, Cy$^B$-2, and Cy$^B$-3 are each optionally substituted with 1, 2 or 3 groups independently selected from unsubstituted phenyl, 4-fluoro-phenyl, 3-fluorophenyl, 2-fluorophenyl, 2-pyridinyl, CH$_2$(phenyl), CH(CH$_2$OH)phenyl, CH$_3$, CH$_2$CH$_3$, CH(CH$_3$)$_2$, CH(CH$_2$OH)CH$_2$CH$_3$, CH(CH$_2$OH)CH$_3$, CH$_2$CH$_2$OH, OCH$_2$CH$_3$ and OCH$_3$ In some embodiments, Cy$^B$ is

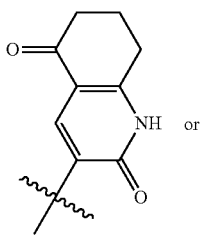
Cy$^B$-1

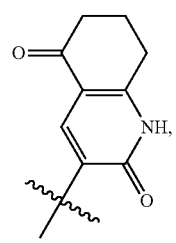
Cy$^B$-1

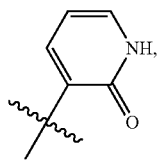
Cy$^B$-2

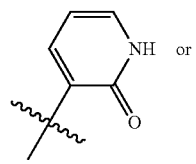
Cy$^B$-2 wherein Cy$^B$-1 and Cy$^B$-2 are each optionally substituted with 1, 2 or 3 groups independently selected from unsubstituted phenyl, 4-fluoro-phenyl, CH$_2$(phenyl), CH(CH$_2$OH)phenyl, CH$_3$, CH$_2$CH$_3$, CH(CH$_2$OH)CH$_2$CH$_3$, CH(CH$_2$OH)CH$_3$, CH$_2$CH$_2$OH, OCH$_2$CH$_3$ and OCH$_3$.

In some embodiments, Cy$^B$ is

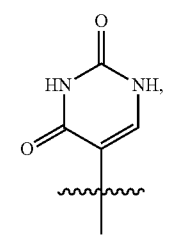
Cy$^B$-3

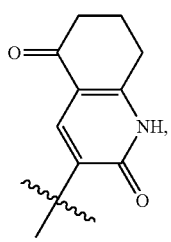
Cy$^B$-1 wherein Cy$^B$-1, Cy$^B$-2 and Cy$^B$-3 are each optionally substituted with 1, 2 or 3 substituents independently selected from unsubstituted phenyl, 4-fluoro-phenyl, 3-fluoro-phenyl, 2-fluoro-phenyl, CH$_2$(phenyl), CH(CH$_2$OH)phenyl, CH$_3$, CH$_2$CH$_3$, CH(CH$_3$)$_2$, CH(CH$_2$OH)CH$_2$CH$_3$, CH(CH$_2$OH)CH$_3$, CH$_2$CH$_2$OH, OCH$_2$CH$_3$ and OCH$_3$.

In some embodiments, $Cy^B$ is

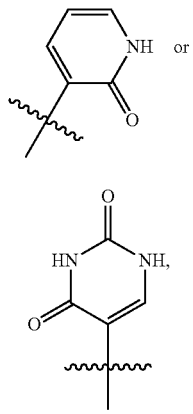

wherein $Cy^B$-2 and $Cy^B$-3 are each optionally substituted 1, 2 or 3 groups independently selected from unsubstituted phenyl, $CH(CH_3)_2$, and 2-pyridinyl.

In some embodiments, $Cy^B$ is

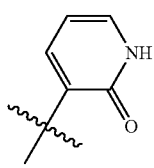

wherein $Cy^B$-2 is optionally substituted 1, 2 or 3 groups independently selected from unsubstituted phenyl, $CH(CH_3)_2$, and 2-pyridinyl.

In some embodiments, $Cy^B$ is

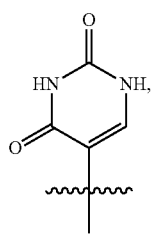

wherein $Cy^B$-3 is optionally substituted 1, 2 or 3 groups independently selected from unsubstituted phenyl, $CH(CH_3)_2$, and 2-pyridinyl.

In some embodiments, $Cy^B$ is

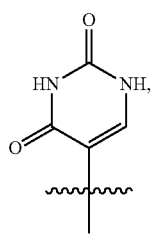

wherein $Cy^B$-3 is substituted with unsubstituted phenyl and $CH(CH_3)_2$.

In some embodiments, $Cy^B$ is

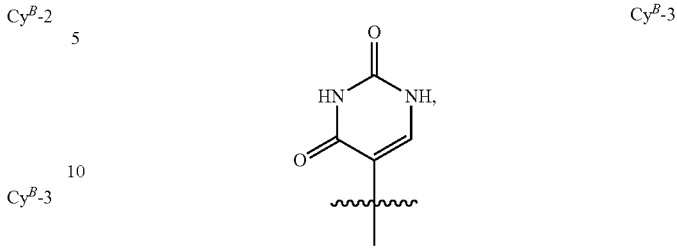

wherein $Cy^B$-3 is substituted with pyridinyl (e.g., 2-pyridinyl, 3-pyridinyl, and 4-pyridinyl) and $CH(CH_3)_2$.

In some embodiments, each $R^B$ is independently selected from halo, $C_{1-6}$ alkyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, CN, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, and $NR^{c2}C(O)OR^{a2}$; wherein said $C_{1-6}$ alkyl, $C_{2-6}$ alkynyl, $C_{3-6}$ cycloalkyl, phenyl, 5-6 membered heteroaryl, and 4-7 membered heterocycloalkyl are each optionally substituted with 1, 2, 3, or 4 substituents independently selected from $R^{12}$.

In some embodiments, each $R^B$ is independently unsubstituted phenyl, 4-fluoro-phenyl, 3-fluorophenyl, 2-fluorophenyl, $CH_2$(phenyl), $CH(CH_2OH)$phenyl, Br, Cl, CN, $CH_3$, $CHF_2$, $CH_2CH_3$, $CH_2OCH_3$, $CH_2OCH_2CH_3$, $CH(CH_3)_2$, $CH(CH_2OH)CH_2CH_3$, $CH(CH_2OH)CH_3$, $CH_2CH_2OH$, $CH_2CH(OH)(CH_3)$, $OCH_3$, $OCH_2CH_3$, $C(O)NH_2$, $C(O)CH_3$, 2,5-difluorophenyl, 3-pyridinyl, 2-pyridinyl, 1-methyl-1H-pyrazol-4-yl, 1-methyl-1H-pyrazol-3-yl, 1-methyl-1H-pyrazol-5-yl, 1,4-dimethyl-1H-pyrazol-3-yl, 1,5-dimethyl-1H-pyrazol-3-yl, 2-methylthiazol-5-yl, cyclohexyl, 3-cyanophenyl, 5-methylisoxazol-3-yl, 5-fluoropyridin-3-yl, 5-fluoropyridin-2-yl, 3-cyanophenyl, $CH_2CN$, thiazol-4-yl, 6-methylpyridin-3-yl, 2-methylpyridin-3-yl, 6-methylpyridin-2-yl, pyrimidin-2-yl, morpholin-4-yl, cyclopropyl, oxazol-2-yl, $CCCH(OH)(CH_3)$, or $C(O)NH(4$-fluoro-phenyl).

In some embodiments, each $R^B$ is independently unsubstituted phenyl, 4-fluoro-phenyl, 3-fluorophenyl, 2-fluorophenyl, $CH_2$(phenyl), $CH(CH_2OH)$phenyl, Br, CN, $CH_3$, $CH_2CH_3$, $CH(CH_3)_2$, $CH(CH_2OH)CH_2CH_3$, $CH(CH_2OH)CH_3$, $CH_2CH_2OH$, $CH_2CH(OH)(CH_3)$, $OCH_3$, $OCH_2CH_3$, $C(O)NH_2$, $C(O)CH_3$, 2,5-difluorophenyl, 3-pyridinyl, 2-pyridinyl, 1-methyl-1H-pyrazol-4-yl, 1-methyl-1H-pyrazol-3-yl, 1-methyl-1H-pyrazol-5-yl, 2-methylthiazol-5-yl, cyclohexyl, 3-cyanophenyl, 5-methylisoxazol-3-yl, 5-fluoropyridin-3-yl, 3-cyanophenyl, $CH_2CN$, thiazol-4-yl, 6-methylpyridin-3-yl, pyrimidin-2-yl, morpholin-4-yl, cyclopropyl, oxazol-2-yl, $CCCH(OH)(CH_3)$, or $C(O)NH(4$-fluoro-phenyl).

In some embodiments, each $R^B$ is independently unsubstituted phenyl, 4-fluoro-phenyl, 3-fluorophenyl, 2-fluorophenyl, 2-pyridinyl, $CH_2$(phenyl), $CH(CH_2OH)$phenyl, $CH_3$, $CH_2CH_3$, $CH(CH_3)_2$, $CH(CH_2OH)CH_2CH_3$, $CH(CH_2OH)CH_3$, $CH_2CH_2OH$, $OCH_3$, $OCH_2CH_3$, or $C(O)NH(4$-fluoro-phenyl).

In some embodiments, each $R^B$ is independently unsubstituted phenyl, 4-fluoro-phenyl, $CH_2$(phenyl), $CH(CH_2OH)$phenyl, $CH_3$, $CH_2CH_3$, $CH(CH_2OH)CH_2CH_3$, $CH(CH_2OH)CH_3$, $CH_2CH_2OH$, $OCH_3$, $OCH_2CH_3$, or $C(O)NH(4$-fluoro-phenyl).

In some embodiments, each $R^B$ is independently unsubstituted phenyl, 4-fluoro-phenyl, 3-fluoro-phenyl, 2-fluorophenyl, CH₂(phenyl), CH(CH₂OH)phenyl, CH₃, CH₂CH₃, CH(CH₃)₂, CH(CH₂OH)CH₂CH₃, CH(CH₂OH)CH₃, CH₂CH₂OH, OCH₃, OCH₂CH₃, or C(O)NH(4-fluoro-phenyl).

In some embodiments, each $R^B$ is independently unsubstituted phenyl or 4-fluoro-phenyl, 3-fluoro-phenyl, 2-fluoro-phenyl, 2-pyridinyl, CH₃, CH₂CH₃ or CH(CH₃)₂. In some embodiments, each $R^B$ is independently unsubstituted phenyl or 4-fluoro-phenyl, 3-fluoro-phenyl, 2-fluoro-phenyl, CH₃, CH₂CH₃ or CH(CH₃)₂. In some embodiments, each $R^B$ is unsubstituted phenyl, CH(CH₃)₂, or 2-pyridinyl. In some embodiments, each $R^B$ is independently unsubstituted phenyl or 4-fluoro-phenyl. In some embodiments, each $R^B$ is unsubstituted phenyl. In some embodiments, each $R^B$ is 4-fluoro-phenyl. In some embodiments, each $R^B$ is pyridinyl (e.g., 2-pyridinyl). In some embodiments, each $R^B$ is independently unsubstituted phenyl or CH(CH₃)₂. In some embodiments, each $R^B$ is independently unsubstituted phenyl or CH₂CH₃. In some embodiments, each $R^B$ is independently 4-fluoro-phenyl or CH(CH₃)₂. In some embodiments, each $R^B$ is independently 4-fluoro-phenyl or CH₂CH₃. In some embodiments, each $R^B$ is independently 3-fluoro-phenyl or CH(CH₃)₂. In some embodiments, each $R^B$ is independently 3-fluoro-phenyl or CH₂CH₃. In some embodiments, each $R^B$ is independently 2-fluoro-phenyl or CH(CH₃)₂. In some embodiments, each $R^B$ is independently 2-fluoro-phenyl or CH₂CH₃.

In some embodiments, $Cy^C$ is phenylene optionally substituted by 1, 2, 3, or 4 substituents independently selected from $R^C$.

In some embodiments, $Cy^C$ is

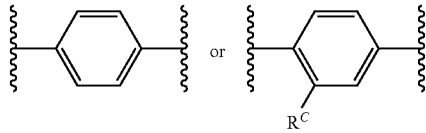

wherein the $R^C$ group on the phenylene ring is ortho to the pyrrolo[2,1-f][1,2,4]triazine ring in Formula I.

In some embodiments, each $R^C$ is independently selected from OH, halo, C₁₋₄ alkyl, and C₁₋₃ haloalkyl. In some embodiments, each $R^C$ is independently halo or C₁₋₄ alkyl. In some embodiments, each $R^C$ is independently F, Cl, or methyl. In some embodiments, each $R^C$ is F.

In some embodiments, $Cy^C$ is

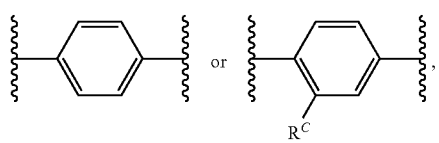

wherein $R^C$ is F, Cl, or methyl, wherein the phenyl ring is attached to the pyrrolo[2,1-f][1,2,4]triazine ring at left site of attachment.

In some embodiments, $Cy^C$ is

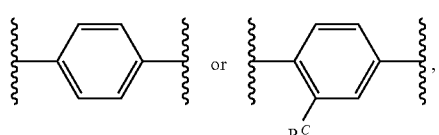

wherein $R^C$ is F, wherein the phenyl ring is attached to the pyrrolo[2,1-f][1,2,4]triazine ring at left site of attachment.

In some embodiments, $R^1$ is

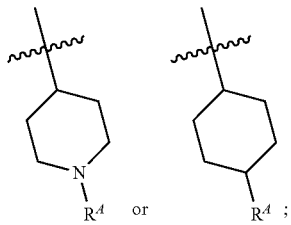

$R^A$ is CH₃, CH₂CH₃, CN, OH, CH₂CH₂OH, CH₂CH₂OCH₃, C(O)CH₃, C(O)CH(CH₃)₂, C(O)(cyclopropyl), C(O)CH₂CH₃, C(O)CH₂OH, C(O)CH(OH)CH₃, SO₂CH₃, C(O)OCH₃, C(O)N(CH₃)₂, C(O)NHCH₃, C(O)N(CH₂CH₃)₂, C(O)N(CH₃)(CH₂CH₃), or C(O)(morpholin-4-yl);

$Cy^B$ is

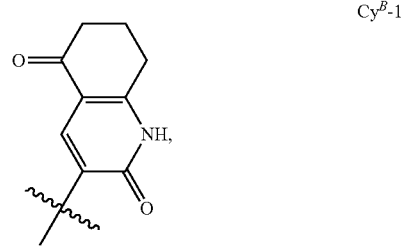

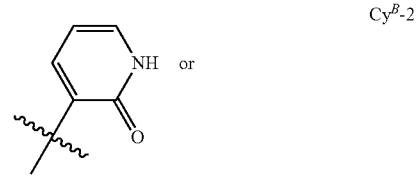

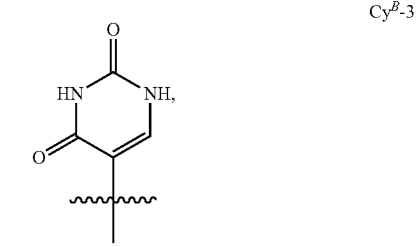

wherein $Cy^B$-1, $Cy^B$-2, and $Cy^B$-3 are each optionally substituted with 1 or 2 substituents independently selected from $R^B$;

each $R^B$ is independently unsubstituted phenyl, 4-F-phenyl, 3-F-phenyl, 2-F-phenyl, 2-pyridinyl, CH₂(phenyl), CH(phenyl)CH₂OH, methyl, ethyl, isopropyl, CH(CH₂OH)CH₂CH₃, CH(CH₂OH)CH₃, CH₂CH₂OH or OCH₂CH₃;

$Cy^C$ is phenylene optionally substituted with 1 $R^C$ group; and $R^C$ is F, Cl or Br.

In some embodiments, $R^1$ is

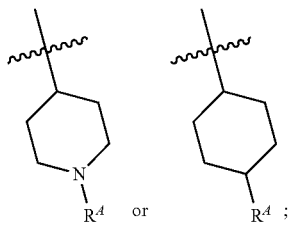

$R^A$ is $CH_3$, $CH_2CH_3$, CN, OH, $CH_2CH_2OH$, $CH_2CH_2OCH_3$, $C(O)CH_3$, $C(O)CH_2OH$, $C(O)CH(OH)CH_3$, $SO_2CH_3$, $C(O)OCH_3$, $C(O)N(CH_3)_2$, $C(O)NHCH_3$, $C(O)N(CH_2CH_3)_2$ or $C(O)N(CH_3)(CH_2CH_3)$;

$Cy^B$ is

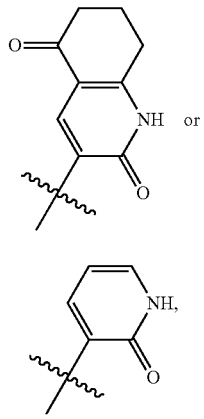

Cy$^B$-1

Cy$^B$-2 wherein Cy$^B$-1 and Cy$^B$-2 are each optionally substituted with 1 or 2 substituents independently selected from $R^B$;

each $R^B$ is independently unsubstituted phenyl, 4-F-phenyl, $CH_2$(phenyl), CH(phenyl)$CH_2OH$, methyl, ethyl, $CH(CH_2OH)CH_2CH_3$, $CH(CH_2OH)CH_3$, $CH_2CH_2OH$ or $OCH_2CH_3$;

Cy$^C$ is phenylene optionally substituted with 1 $R^C$ group; and $R^C$ is F, Cl or Br.

In some embodiments, $R^1$ is

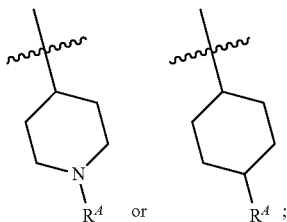

$R^A$ or $R^A$;

$R^A$ is $CH_3$, $CH_2CH_3$, CN, OH, $CH_2CH_2OH$, $CH_2CH_2OCH_3$, $C(O)CH_3$, $C(O)CH(CH_3)_2$, $C(O)CH_2CH_3$, $C(O)CH_2OH$, $C(O)CH(OH)CH_3$, $SO_2CH_3$, $C(O)OCH_3$, $C(O)N(CH_3)_2$, $C(O)NHCH_3$, $C(O)N(CH_2CH_3)_2$, $C(O)N(CH_3)(CH_2CH_3)$, or $C(O)$(morpholin-4-yl);

Cy$^B$ is

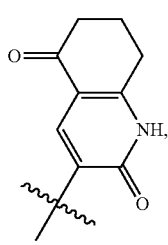

Cy$^B$-1

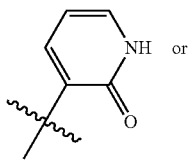

Cy$^B$-2 or

Cy$^B$-3

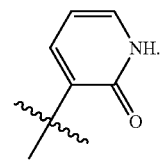 [SMILES: *c1ccc[nH]c1=O]

wherein Cy$^B$-1, Cy$^B$-2, and Cy$^B$-3 are each optionally substituted with 1 or 2 substituents independently selected from $R^B$;

each $R^B$ is independently unsubstituted phenyl, 4-F-phenyl, 3-F-phenyl, 2-F-phenyl, $CH_2$(phenyl), CH(phenyl)$CH_2OH$, methyl, ethyl, isopropyl, $CH(CH_2OH)CH_2CH_3$, $CH(CH_2OH)CH_3$, $CH_2CH_2OH$ or $OCH_2CH_3$;

Cy$^C$ is phenylene optionally substituted with 1 $R^C$ group; and $R^C$ is F, Cl or Br.

In some embodiments, the heteroaryl group of e.g., Cy$^A$, and Cy$^B$ is optionally substituted with an oxo to form a carbonyl. For example, the 5-10 membered heteroaryl group of Cy$^B$ can be substituted with an oxo to form a carbonyl which includes groups such as 2-pyridone e.g., Heteroaryl group can also include substituted pyridone (e.g., substituted 2-pyridone) such as

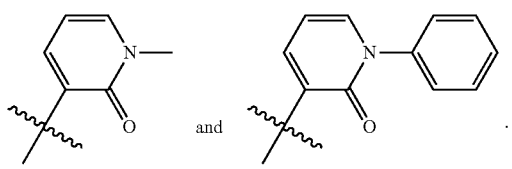

and

In some embodiments: (1) $A^1$, $A^2$, and $A^3$ are each a bond and $R^A$ is $C_{1-6}$ alkyl or (2) $A^1$ and $A^2$ are each a bond, $A^3$ is Cy$^{A3}$, and each $R^A$ is independently selected from $C_{1-6}$ alkyl, CN, $OR^{a1}$, $C(O)R^{b1}$, $C(O)NR^{c1}R^{d1}$, $C(O)OR^{a1}$, and $S(O)_2R^{b1}$; wherein said $C_{1-6}$ alkyl is optionally substituted with a $R^{11}$ group, provided that if $R^A$ is attached to a nitrogen atom, then $R^A$ is not CN or $OR^{a1}$;

each $R^{a1}$, $R^{d1}$, and $R^{d1}$ are independently H or $C_{1-4}$ alkyl;

each $R^{b1}$ is independently $C_{1-4}$ alkyl;

each $R^{11}$ is independently $OR^{a3}$;

$R^2$ is H;

$R^3$ is H;

Cy$^B$ is a 7,8-dihydroquinoline-2,5(1H,6H)-dione or 2-pyridone ring, which is optionally substituted with 1 or 2 independently selected R$^B$ groups;

each R$^B$ is independently methyl, ethyl, isopropyl, sec-butyl, or phenyl, each of which is optionally substituted by 1 or 2 independently selected R$^{12}$ groups;

each R$^{12}$ is independently selected from halo, phenyl, and OR$^{a4}$; wherein said phenyl is optionally substituted by 1 or 2 independently selected R$^g$ group; and each R$^g$ is independently halo;

each R$^{a4}$ is independently H or C$_{1-4}$ alkyl;

Cy$^C$ is phenylene optionally substituted by 1 R$^C$ group; and each R$^C$ is independently halo or C$_{1-4}$ alkyl.

In some embodiments: (1) A$^1$, A$^2$, and A$^3$ are each a bond and R$^A$ is methyl or ethyl; or (2) A$^1$ and A$^2$ are each a bond, A$^3$-R$^A$ is selected from, R$^A$, and R$^A$;

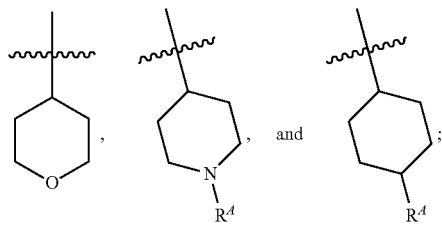

each R$^A$ is independently selected from C$_{1-3}$ alkyl, CN, OH, methylcarbonyl, methoxycarbonyl, N,N-dimethylaminocarbonyl, and methylsulfonyl, wherein said C$_{1-3}$ alkyl is optionally substituted with a OH or OCH$_3$ group, provided that if R$^A$ is attached to a nitrogen atom, then R$^A$ is not CN or OH;

R$^2$ is H;

R$^3$ is H;

Cy$^B$ is a 7,8-dihydroquinoline-2,5(1H,6H)-dione or 2-pyridone ring, which is optionally substituted with a R$^B$ group;

each R$^B$ is independently methyl, ethyl, isopropyl, sec-butyl, or phenyl, each of which is optionally substituted by 1 or 2 independently selected R$^{12}$ groups;

each R$^{12}$ is independently selected from halo, phenyl, and OH; wherein said phenyl is optionally substituted by 1 or 2 independently selected R$^g$ group;

each R$^g$ is F; and

Cy$^C$ is

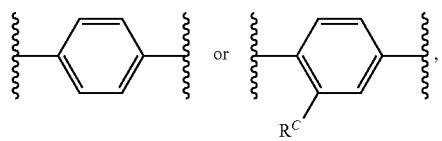

wherein R$^C$ is F, wherein the phenyl ring is attached to the pyrrolo[2,1-f][1,2,4]triazine ring at left site of attachment.

In some embodiments: A$^1$ and A$^2$ are each a bond, A$^3$-R$^A$ is, R$^A$

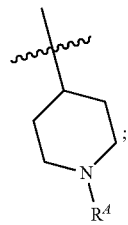

each R$^A$ is independently selected from C$_{1-3}$ alkyl, methylcarbonyl, ethylcarbonyl, isopropylcarbonyl, N,N-dimethylaminocarbonyl, N,N-diethylaminocarbonyl, N,N-(methyl)(ethyl)aminocarbonyl and C(O)[morpholin-4-yl];

R$^2$ is H;

R$^3$ is H;

Cy$^B$ is a 7,8-dihydroquinoline-2,5(1H,6H)-dione or 2,4-dioxo-1,2,3,4-tetrahydropyrimidine ring, which is optionally substituted by 1 or 2 independently selected R$^B$ groups;

each R$^B$ is independently methyl, ethyl, isopropyl, sec-butyl, or phenyl, each of which is optionally substituted by 1 or 2 independently selected R$^{12}$ groups;

each R$^{12}$ is independently selected from halo; and

Cy$^C$ is unsubstituted phenylene.

In some embodiments, the present disclosure provides compounds having Formula (IIa):

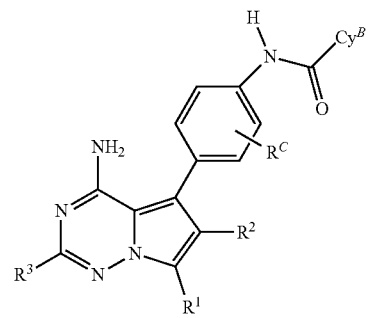

or a pharmaceutically acceptable salt thereof, wherein the variables of Formula (IIa) are as defined in Formula (I) or any embodiments of compounds of Formula (I) as described herein In some embodiments, the present disclosure provides compounds having Formula (IIa1) or Formula (IIa2):

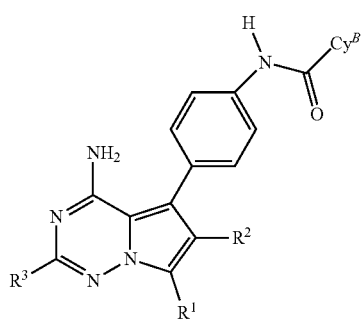

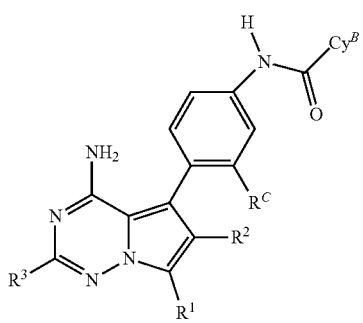

or a pharmaceutically acceptable salt thereof, wherein the variables of Formula (IIa1) and Formula (IIa2) are as defined in Formula (I) or any embodiments of compounds of Formula (I) as described herein In some embodiments, the present disclosure provides compounds having Formula (IIb1) or Formula (IIb2):

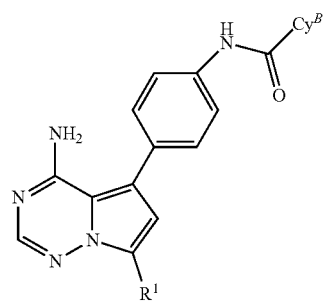

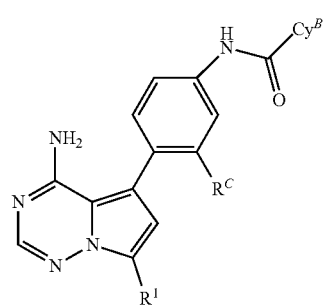

or a pharmaceutically acceptable salt thereof, wherein the variables of Formula (IIb1) and Formula (IIb2) are as defined in Formula (I) or any embodiments of compounds of Formula (I) as described herein In some embodiments, the present disclosure provides compounds having Formula (IIc1) or Formula (IIc2):

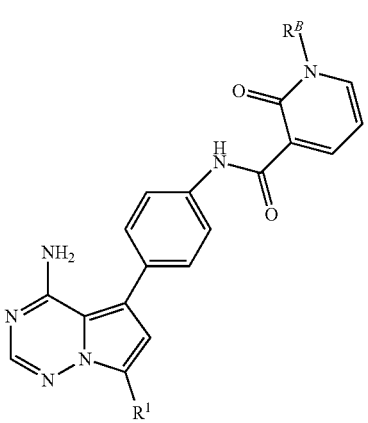

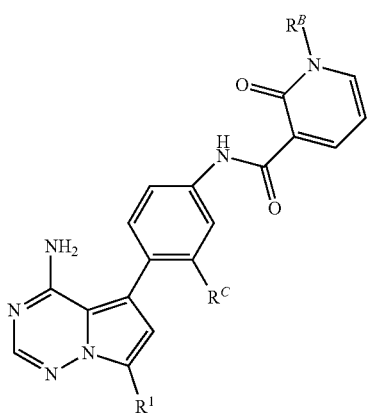

or a pharmaceutically acceptable salt thereof, wherein the variables of Formula (IIc1) and Formula (IIc2) are as defined in Formula (I) or any embodiments of compounds of Formula (I) as described herein In some embodiments, the present disclosure provides compounds having Formula (IId1) or Formula (IId2):

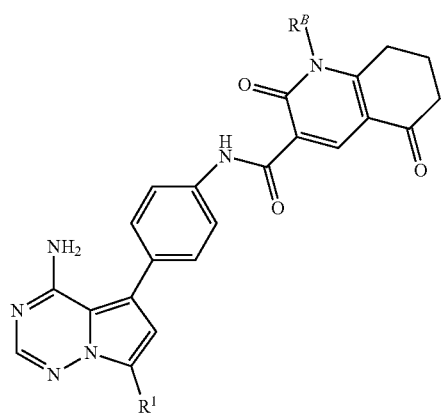

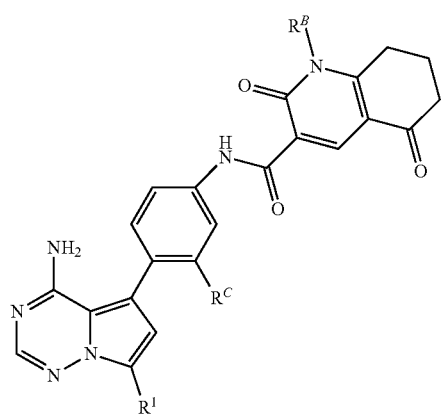

or a pharmaceutically acceptable salt thereof, wherein the variables of Formula (IId1) and Formula (IId2) are as defined in Formula (I) or any embodiments of compounds of Formula (I) as described herein.

In some embodiments, the present disclosure provides compounds having Formula (IIe1):

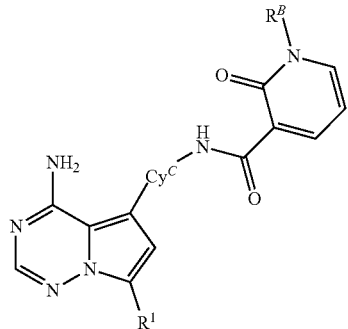

IIe1 or a pharmaceutically acceptable salt thereof, wherein the variables of Formula (IIe1) are as defined in Formula (I) or any embodiments of compounds of Formula (I) as described herein In some embodiments, the present disclosure provides compounds having Formula (IIf1) or Formula (IIf2):

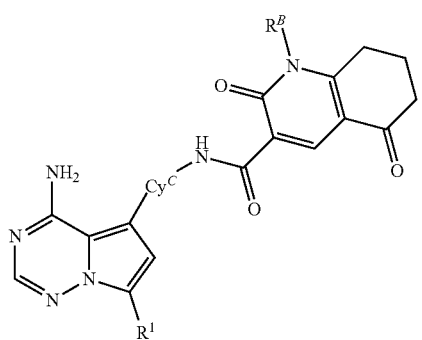

IIf1 or a pharmaceutically acceptable salt thereof, wherein the variables of Formula (IIf1) are as defined in Formula (I) or any embodiments of compounds of Formula (I) as described herein.

In some embodiments, the present disclosure provides compounds having Formula (IIg1) or Formula (IIg2):

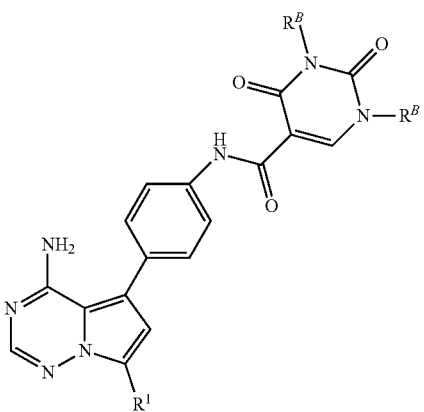

IIg1

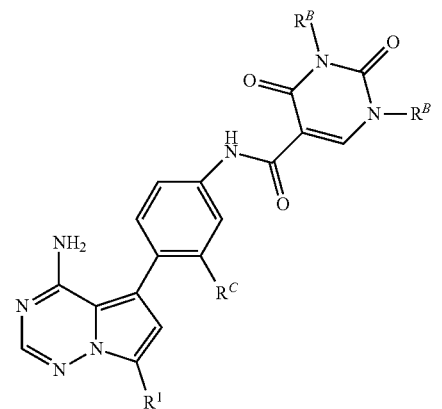

IIg2 or a pharmaceutically acceptable salt thereof, wherein the variables of Formula (IIg1) and Formula (IIg2) are as defined in Formula (I) or any embodiments of compounds of Formula (I) as described herein.

In some embodiments, the present disclosure provides compounds having Formula (IIg3), Formula (IIg4), Formula (IIg5):

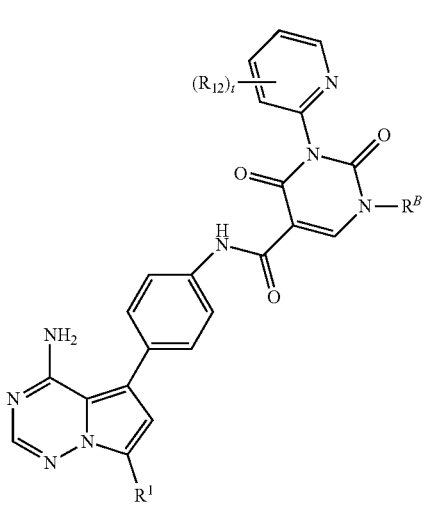

IIg3

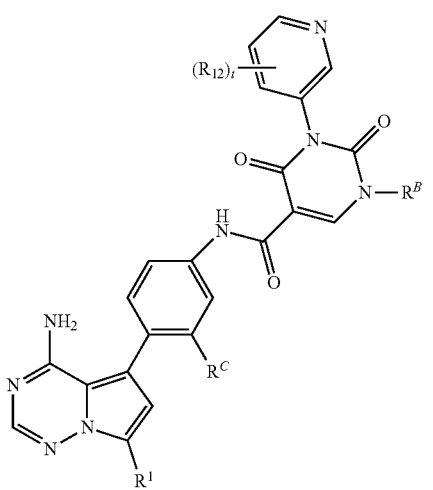

IIg4

-continued

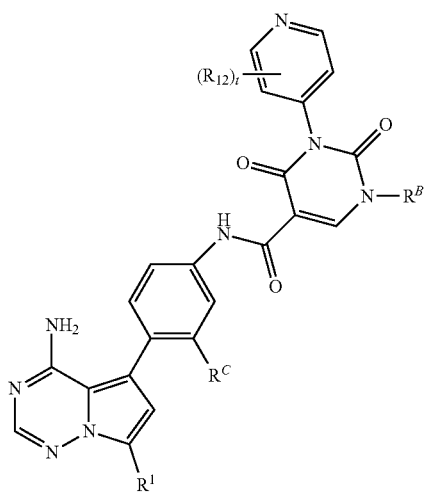

IIg5 or a pharmaceutically acceptable salt thereof, wherein the variables of Formula (IIg3), Formula (IIg4), and Formula (IIg5) are as defined in Formula (I) or any embodiments of compounds of Formula (I) as described herein, and t is 0, 1, 2, 3, or 4.

In some embodiments, the present disclosure provides compounds having Formula (IIh1):

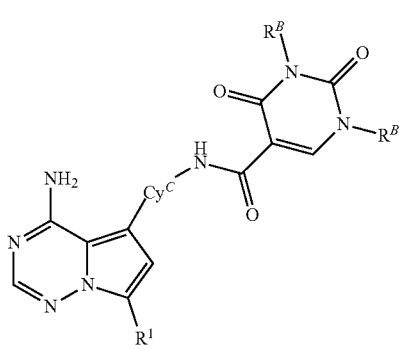

IIh1 or a pharmaceutically acceptable salt thereof, wherein the variables of Formula (IIh1) are as defined in Formula (I) or any embodiments of compounds of Formula (I) as described herein.

In some embodiments, the present disclosure provides compounds having Formula (IIi1):

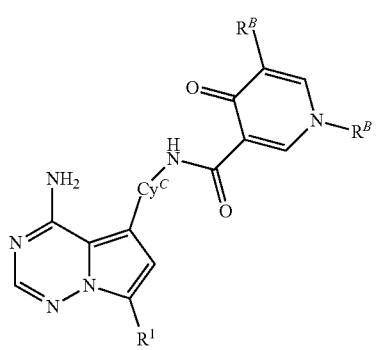

IIi1 or a pharmaceutically acceptable salt thereof, wherein the variables of Formula (IIi1) are as defined in Formula (I) or any embodiments of compounds of Formula (I) as described herein.

In some embodiments, the present disclosure provides compounds having Formula (IIIa), Formula (IVa), Formula (Va), Formula (VIa), Formula (VIIa), or Formula (VIIIa):

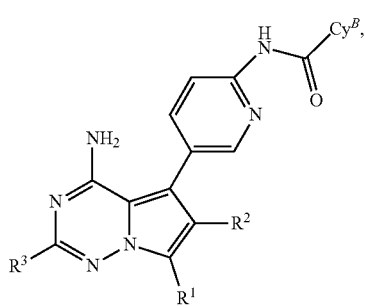

IIIa

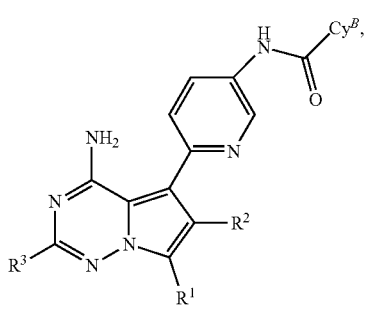

IVa

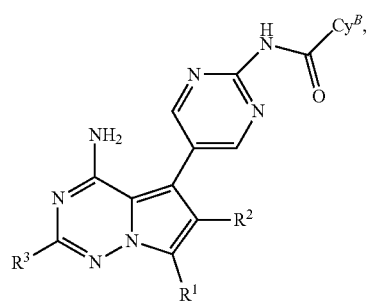

Va

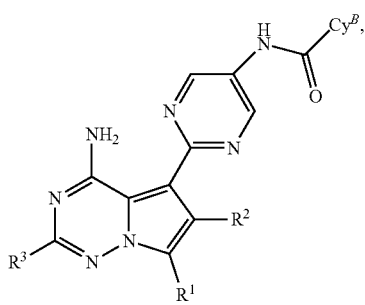

VIa

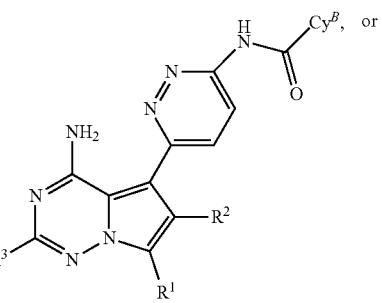

VIIa

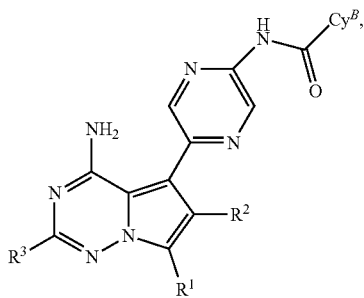

VIIIa or a pharmaceutically acceptable salt thereof, wherein the variables of Formula (IIIa), Formula (IVa), Formula (Va), Formula (VIa), Formula (VIIa), and Formula (VIIIa) are as defined in Formula (I) or any embodiments of compounds of Formula (I) as described herein.

In some embodiments, the present disclosure provides compounds having Formula (IIIb), Formula (IVb), Formula (Vb), Formula (VIb), Formula (VIIb), or Formula (VIIIb):

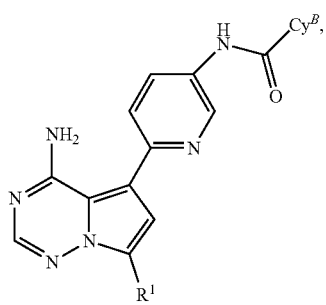

IIIb

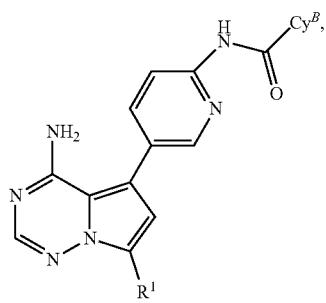

IVb

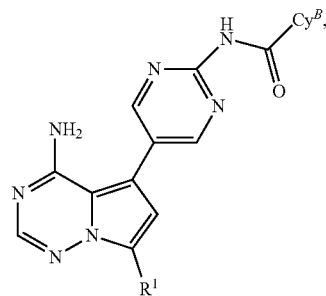

Vb

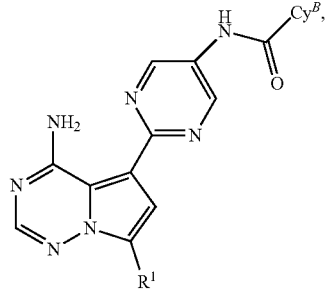

VIb

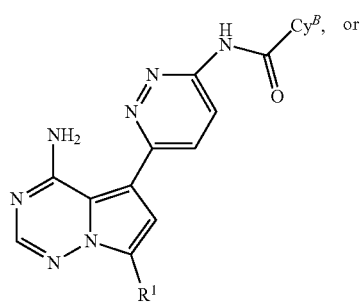

VIIb

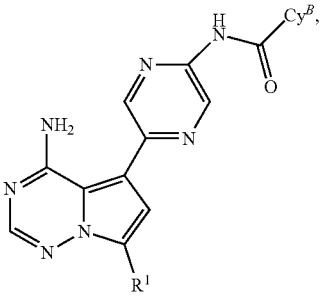

VIIIb or a pharmaceutically acceptable salt thereof, wherein the variables of Formula (IIIb), Formula (IVb), Formula (Vb), Formula (VIb), Formula (VIIb), and Formula (VIIIb) are as defined in Formula (I) or any embodiments of compounds of Formula (I) as described herein.

In some embodiments:

$R^1$ is $A^1$-$A^2$-$A^3$-$R^4$;

$R^2$ is H, halo, CN, $C_{1-4}$ alkyl, $C_{1-4}$ haloalkyl, $C_{1-4}$ alkoxy, $C_{1-4}$ haloalkoxy, cyano-$C_{1-3}$ alkyl or $C_{1-6}$ alkoxyalkyl;

$R^3$ is H, halo, CN, $C_{1-6}$ alkyl, $C_{1-6}$ haloalkyl, $OR^a$, $SR^a$, $C(O)NR^cR^d$, $NR^cR^d$, $NR^cC(O)R^b$, $NR^cS(O)_2R^b$ or $S(O)_2R^b$; wherein said $C_{1-6}$ alkyl and $C_{1-6}$ haloalkyl are optionally substituted with 1, 2 or 3 substituents independently selected from halo, CN, $OR^a$, $SR^a$, $C(O)NR^cR^d$, $NR^cR^d$ $NR^cC(O)R^{b1}$, $NR^cS(O)_2R^b$, $S(O)_2R^b$, $NR^cC(O)OR^a$, $NR^cC(O)NR^cR^d$, $NR^cS(O)_2NR^cR^d$ and $Cy^{R3}$;

$A^1$ is selected from a bond, $Cy^{A1}$, —Y—, —$C_{1-3}$ alkylene-, —$C_{1-3}$ alkylene-Y—, —Y—$C_{1-3}$ alkylene-, and —$C_{1-2}$ alkylene-Y—$C_{1-2}$ alkylene-; wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino;

$A^2$ is selected from a bond, $Cy^{A2}$, —Y—, —$C_{1-3}$ alkylene-, —$C_{1-3}$ alkylene-Y—, —Y—$C_{1-3}$ alkylene-, and —$C_{1-2}$ alkylene-Y—$C_{1-2}$ alkylene-; wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino;

$A^3$ is selected from a bond, $Cy^{A3}$, —Y—, —$C_{1-3}$ alkylene-, —$C_{1-3}$ alkylene-Y—, —Y—$C_{1-3}$ alkylene-, and —$C_{1-2}$ alkylene-Y—$C_{1-2}$ alkylene-; wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino;

$R^A$ is H, $C_{1-6}$ alkyl, $C_{1-6}$ haloalkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^cOR^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, or $S(O)_2NR^{c1}R^{d1}$; wherein said $C_{1-6}$ alkyl or $C_{1-6}$ haloalkyl is optionally substituted with 1, 2, 3 or 4 substituents independently selected from $R^{11}$;

Y is O, S, S(O), $S(O)_2$, C(O), $C(O)NR^f$, $NR^fC(O)$, $NR^fC(O)NR^f$, $NR^fS(O)_2NR^f$, $S(O)_2NR^f$, $NR^fS(O)_2$, or $NR^f$;

each $R^f$ is independently selected from H and $C_{1-3}$ alkyl;

$Cy^{A1}$ is $C_{3-7}$ cycloalkyl, phenyl, 5-6 membered heteroaryl, or 4-7 membered heterocycloalkyl; wherein each 5-6 membered heteroaryl and 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of $C_{3-7}$ cycloalkyl and 4-7 membered heterocycloalkyl is optionally substituted by oxo to form a carbonyl group; and wherein the $C_{3-7}$ cycloalkyl, phenyl, 5-6 membered heteroaryl, and 4-7 membered heterocycloalkyl are each optionally substituted with 1, 2, 3 or 4 substituents independently selected from $R^{A1}$;

each $R^{A1}$ is independently selected from OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$Cy^{A2}$ is $C_{3-7}$ cycloalkyl, phenyl, 5-6 membered heteroaryl, or 4-7 membered heterocycloalkyl; wherein each 5-6 membered heteroaryl and 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of $C_{3-7}$ cycloalkyl and 4-7 membered heterocycloalkyl is optionally substituted by oxo to form a carbonyl group; and wherein the $C_{3-7}$ cycloalkyl, phenyl, 5-6 membered heteroaryl, and 4-7 membered heterocycloalkyl are each optionally substituted with 1, 2, 3 or 4 substituents independently selected from $R^{A2}$;

each $R^{A2}$ is independently selected from OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$Cy^{A3}$ is $C_{3-7}$ cycloalkyl, phenyl, 5-6 membered heteroaryl, or 4-7 membered heterocycloalkyl; wherein each 5-6 membered heteroaryl and 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of $C_{3-7}$ cycloalkyl and 4-7 membered heterocycloalkyl is optionally substituted by oxo to form a carbonyl group; and wherein the $C_{3-7}$ cycloalkyl, phenyl, 5-6 membered heteroaryl, and 4-7 membered heterocycloalkyl are each optionally substituted with 1, 2, 3 or 4 substituents independently selected from $R^{A3}$;

each $R^{A3}$ is independently selected from OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$Cy^{R3}$ is $C_{3-7}$ cycloalkyl, phenyl, 5-6 membered heteroaryl, or 4-7 membered heterocycloalkyl; wherein each 5-6 membered heteroaryl and 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of $C_{3-7}$ cycloalkyl and 4-7 membered heterocycloalkyl is optionally substituted by oxo to form a carbonyl group; and wherein the $C_{3-7}$ cycloalkyl, phenyl, 5-6 membered heteroaryl, and 4-7 membered heterocycloalkyl are each optionally substituted with 1, 2, 3 or 4 substituents independently selected from $R^g$;

$Cy^C$ is phenylene or 5-6 membered heteroarylene; wherein the 5-6 membered heteroarylene has at least one ring-forming carbon atom and 1 or 2 ring-forming heteroatoms independently selected from N, O, and S; and wherein the phenylene and 5-6 membered heteroarylene are each optionally substituted by 1, 2, 3, or 4 substituents independently selected from $R^C$;

each $R^C$ is independently selected from OH, CN, halo, $C_{1-4}$ alkyl, $C_{1-3}$ haloalkyl, $C_{1-4}$ alkoxy, $C_{1-3}$ haloalkoxy, cyano-$C_{1-3}$ alkyl, HO—$C_{1-3}$ alkyl, amino, $C_{1-4}$ alkylamino, di($C_{1-4}$ alkyl)amino, $C_{1-4}$ alkylsulfinyl, $C_{1-4}$ alkylsulfonyl, carbamyl, $C_{1-4}$ alkylcarbamyl, di($C_{1-4}$ alkyl)carbamyl, carboxy, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, and di($C_{1-4}$ alkyl)aminosulfonyl;

$Cy^B$ is $C_{3-10}$ cycloalkyl or 4-10 membered heterocycloalkyl; wherein at least one ring-forming carbon atom of $C_{3-10}$ cycloalkyl and 4-10 membered heterocycloalkyl is substituted by oxo to form a carbonyl group; wherein the 4-10 membered heterocycloalkyl has at least one ring-forming carbon atom and 1, 2, 3, or 4 ring-forming heteroatoms independently selected from N, O, and S; wherein the N and S are optionally oxidized; and wherein the $C_{3-10}$ cycloalkyl and 4-10 membered heterocycloalkyl are each optionally substituted with 1, 2, 3 or 4 substituents independently selected from $R^B$; or $Cy^B$ is 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein: (a) at least one ring-forming carbon atom of the 5-10 membered heteroaryl is substituted by oxo to form a carbonyl group; or (b) the 5-10 membered heteroaryl is substituted by halo, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$OR$^{d2}$, NR$^{c2}$C(O)R$^{b2}$, NR$^{c2}$C(O)OR$^{a2}$, NR$^{c2}$C(O)NR$^{c2}$R$^{d2}$ NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$; and wherein the 5-10 membered heteroaryl is further optionally substituted with 1, 2, 3 or 4 substituents independently selected from R$^B$;

each R$^B$ is independently selected from halo, C$_{1-6}$ alkyl, C$_{1-6}$ haloalkyl, C$_{3-6}$ cycloalkyl, phenyl, 5-6 membered heteroaryl, 4-7 membered heterocycloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$OR$^{d2}$, NR$^{c2}$C(O)R$^{b2}$, NR$^{c2}$C(O)OR$^{a2}$, NR$^{c2}$C(O)NR$^{c2}$R$^{d2}$ NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$; wherein said C$_{1-6}$ alkyl, C$_{3-6}$ cycloalkyl, phenyl, 5-6 membered heteroaryl, and 4-7 membered heterocycloalkyl are each optionally substituted with 1, 2, 3, or 4 substituents independently selected from R$^{12}$;

each R$^{11}$ is independently selected from CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$ OR$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$;

each R$^{12}$ is independently selected from halo, CN, NO$_2$, C$_{1-6}$ alkyl, C$_{1-6}$ haloalkyl, C$_{3-6}$ cycloalkyl, phenyl, 5-6 membered heteroaryl, 4-7 membered heterocycloalkyl, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$OR$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$; wherein said C$_{1-6}$ alkyl, C$_{3-6}$ cycloalkyl, phenyl, 5-6 membered heteroaryl, and 4-7 membered heterocycloalkyl are each optionally substituted with 1, 2, 3, or 4 substituents independently selected from R$^g$;

R$^a$ is selected from H, C$_{1-6}$ alkyl, and C$_{1-6}$ haloalkyl;

R$^b$ is selected from C$_{1-6}$ alkyl and C$_{1-6}$ haloalkyl;

R$^c$ and R$^d$ are each independently selected from H, C$_{1-6}$ alkyl, C$_{1-6}$ haloalkyl, C$_{3-6}$ cycloalkyl, phenyl, 5-6 membered heteroaryl, 4-6 membered heterocycloalkyl, C$_{3-6}$ cycloalkyl-C$_{1-3}$ alkylene, phenyl-C$_{1-3}$ alkylene, 5-6 membered heteroaryl-C$_{1-3}$ alkylene, and 4-6 membered heterocycloalkyl-C$_{1-3}$ alkylene; wherein said C$_{1-6}$ alkyl, C$_{1-6}$ haloalkyl, C$_{3-6}$ cycloalkyl, phenyl, 5-6 membered heteroaryl, 4-6 membered heterocycloalkyl, C$_{3-6}$ cycloalkyl-C$_{1-3}$ alkylene, phenyl-C$_{1-3}$ alkylene, 5-6 membered heteroaryl-C$_{1-3}$ alkylene, and 4-6 membered heterocycloalkyl-C$_{1-3}$ alkylene are each optionally substituted with 1, 2 or 3 substituents independently selected from R$^g$;

R$^{a1}$, R$^{c1}$ and R$^{d1}$ are each independently selected from H, C$_{1-6}$ alkyl, and C$_{1-6}$ haloalkyl; wherein said C$_{1-6}$ alkyl is optionally substituted with 1, 2, 3, or 4 substituents independently selected from R$^g$; or alternatively, R$^{c1}$ and R$^{d1}$ attached to the same N atom, together with the N atom to which they are attached, form a 4-, 5-, 6- or 7-membered heterocycloalkyl group optionally substituted with 1, 2 or 3 substituents independently selected from R$^g$;

R$^{b1}$ is selected from C$_{1-6}$ alkyl and C$_{1-6}$ haloalkyl, each of which is optionally substituted with 1, 2, 3, or 4 substituents independently selected from R$^g$;

R$^{e1}$ is selected from H, CN, C$_{1-6}$ alkyl, C$_{1-6}$ haloalkyl, C$_{1-6}$ alkylthio, C$_{1-6}$ alkylsulfonyl, C$_{1-6}$ alkylcarbonyl, C$_{1-6}$ alkylaminosulfonyl, carbamyl, C$_{1-6}$ alkylcarbamyl, di(C$_{1-6}$ alkyl)carbamyl, aminosulfonyl, C$_{1-6}$ alkylaminosulfonyl, and di(C$_{1-6}$ alkyl)aminosulfonyl;

each R$^{a2}$, R$^{c2}$, and R$^{d2}$ is independently selected from H, C$_{1-6}$ alkyl, C$_{1-6}$ haloalkyl, C$_{3-6}$ cycloalkyl, phenyl, 5-6 membered heteroaryl, and 4-7 membered heterocycloalkyl; wherein said C$_{1-6}$ alkyl, C$_{3-6}$ cycloalkyl, phenyl, 5-6 membered heteroaryl, and 4-7 membered heterocycloalkyl are each optionally substituted with 1, 2, 3, or 4 substituents independently selected from R$^{12}$; or alternatively, any R$^{c2}$ and R$^{d2}$ attached to the same N atom, together with the N atom to which they are attached, form a 4-, 5-, 6- or 7-membered heterocycloalkyl group optionally substituted with 1, 2 or 3 substituents independently selected from R$^{12}$;

each R$^{b2}$ is independently selected from C$_{1-6}$ alkyl, C$_{1-6}$ haloalkyl, C$_{3-6}$ cycloalkyl, phenyl, 5-6 membered heteroaryl, and 4-7 membered heterocycloalkyl, each of which is optionally substituted with 1, 2, 3, or 4 substituents independently selected from R$^{12}$;

each R$^{a3}$, R$^{c3}$ and R$^{d3}$ is independently selected from H, C$_{1-6}$ alkyl, C$_{1-6}$ haloalkyl, C$_{3-6}$ cycloalkyl, phenyl, 5-6 membered heteroaryl, 4-7 membered heterocycloalkyl, C$_{3-6}$ cycloalkyl-C$_{1-4}$ alkylene, phenyl-C$_{1-4}$ alkylene, 5-6 membered heteroaryl-C$_{1-4}$ alkylene, and 4-7 membered heterocycloalkyl-C$_{1-4}$ alkylene; wherein said C$_{1-6}$ alkyl, C$_{3-6}$ cycloalkyl, phenyl, 5-6 membered heteroaryl, 4-7 membered heterocycloalkyl, C$_{3-6}$ cycloalkyl-C$_{1-4}$ alkylene, phenyl-C$_{1-4}$ alkylene, 5-6 membered heteroaryl-C$_{1-4}$ alkylene, and 4-7 membered heterocycloalkyl-C$_{1-4}$ alkylene are each optionally substituted with 1, 2, 3, or 4 substituents independently selected from R$^g$; or alternatively, any R$^{c3}$ and R$^{d3}$ attached to the same N atom, together with the N atom to which they are attached, form a 4-, 5-, 6- or 7-membered heterocycloalkyl group optionally substituted with 1, 2 or 3 substituents independently selected from R$^g$;

each R$^{b3}$ is independently selected from C$_{1-6}$ alkyl, C$_{1-6}$ haloalkyl, C$_{3-6}$ cycloalkyl, phenyl, 5-6 membered heteroaryl, 4-7 membered heterocycloalkyl, C$_{3-6}$ cycloalkyl-C$_{1-4}$ alkylene, phenyl-C$_{1-4}$ alkylene, 5-6 membered heteroaryl-C$_{1-4}$ alkylene, and 4-7 membered heterocycloalkyl-C$_{1-4}$ alkylene, each of which is optionally substituted with 1, 2, 3, or 4 substituents independently selected from R$^g$;

each R$^{a4}$, R$^{c4}$ and R$^{d4}$, is independently selected from H, C$_{1-6}$ alkyl, and C$_{1-6}$ haloalkyl; wherein said C$_{1-6}$ alkyl is optionally substituted with 1, 2, 3, or 4 substituents independently selected from R$^g$; or alternatively, any R$^{c4}$ and R$^{d4}$ attached to the same N atom, together with the N atom to which they are attached, form a 4-, 5-, 6- or 7-membered heterocycloalkyl group optionally substituted with 1, 2 or 3 substituents independently selected from R$^g$;

each R$^{b4}$ is independently selected from C$_{1-6}$ alkyl and C$_{1-6}$ haloalkyl, each of which is optionally substituted with 1, 2, 3, or 4 substituents independently selected from R$^g$; and each R$^g$ is independently selected from OH, NO$_2$, CN, halo, C$_{1-6}$ alkyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, H$_2$N—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;
provided that:
1) $A^1$-$A^2$-$A^3$ is not Y—Y when one of $A^1$, $A^2$ or $A^3$ is a bond, or Y—Y—Y; and
2) when $A^3$ is —Y— or —$C_{1-3}$ alkylene-Y— then $R^4$ is H, $C_{1-6}$ alkyl, or $C_{1-6}$ haloalkyl, wherein said $C_{1-6}$ alkyl or $C_{1-6}$ haloalkyl is optionally substituted with 1, 2, 3 or 4 substituents independently selected from $R^{11}$.

In some embodiments:
$R^1$ is $A^1$-$A^2$-$A^3$-$R^4$;
$R^2$ is H, halo, CN, $C_{1-4}$ alkyl, or $C_{1-4}$ haloalkyl;
$R^3$ is H, halo, CN, $C_{1-6}$ alkyl, or $C_{1-6}$ haloalkyl;
$A^1$ is selected from a bond, $Cy^{41}$, —Y—, —$C_{1-3}$ alkylene-, —$C_{1-3}$ alkylene-Y—, and —Y—$C_{1-3}$ alkylene-;
$A^2$ is selected from a bond, $Cy^{42}$, —Y—, —$C_{1-3}$ alkylene-, —$C_{1-3}$ alkylene-Y—, and —Y—$C_{1-3}$ alkylene-;
$A^3$ is selected from a bond, $Cy^{43}$, —Y—, —$C_{1-3}$ alkylene-, —$C_{1-3}$ alkylene-Y—, and —Y—$C_{1-3}$ alkylene-;
$R^4$ is H, $C_{1-6}$ alkyl, $C_{1-6}$ haloalkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $S(O)R^{b1}$, $S(O)NR^{c1}R^{d1}$, $S(O)_2R^b$, or $S(O)_2NR^{c1}R^{d1}$; wherein said $C_{1-6}$ alkyl or $C_{1-6}$ haloalkyl is optionally substituted with 1, 2, 3 or 4 substituents independently selected from $R^{11}$;
Y is O, S, S(O), $S(O)_2$, or C(O);
$Cy^{41}$ is $C_{3-7}$ cycloalkyl, phenyl, 5-6 membered heteroaryl, or 4-7 membered heterocycloalkyl; wherein each 5-6 membered heteroaryl and 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of $C_{3-7}$ cycloalkyl and 4-7 membered heterocycloalkyl is optionally substituted by oxo to form a carbonyl group; and wherein the $C_{3-7}$ cycloalkyl, phenyl, 5-6 membered heteroaryl, and 4-7 membered heterocycloalkyl are each optionally substituted with 1, 2, 3 or 4 substituents independently selected from $R^{41}$;
each $R^{41}$ is independently selected from OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;
$Cy^{42}$ is $C_{3-7}$ cycloalkyl, phenyl, 5-6 membered heteroaryl, or 4-7 membered heterocycloalkyl; wherein each 5-6 membered heteroaryl and 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of $C_{3-7}$ cycloalkyl and 4-7 membered heterocycloalkyl is optionally substituted by oxo to form a carbonyl group; and wherein the $C_{3-7}$ cycloalkyl, phenyl, 5-6 membered heteroaryl, and 4-7 membered heterocycloalkyl are each optionally substituted with 1, 2, 3 or 4 substituents independently selected from $R^{42}$;
each $R^{42}$ is independently selected from OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;
$Cy^{43}$ is $C_{3-7}$ cycloalkyl, phenyl, 5-6 membered heteroaryl, or 4-7 membered heterocycloalkyl; wherein each 5-6 membered heteroaryl and 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of $C_{3-7}$ cycloalkyl and 4-7 membered heterocycloalkyl is optionally substituted by oxo to form a carbonyl group; and wherein the $C_{3-7}$ cycloalkyl, phenyl, 5-6 membered heteroaryl, and 4-7 membered heterocycloalkyl are each optionally substituted with 1, 2, 3 or 4 substituents independently selected from $R^{43}$;
each $R^{43}$ is independently selected from OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;
$Cy^C$ is phenylene or 5-6 membered heteroarylene; wherein the 5-6 membered heteroarylene has at least one ring-forming carbon atom and 1 or 2 ring-forming heteroatoms independently selected from N, O, and S; and wherein the phenylene and 5-6 membered heteroarylene are each optionally substituted by 1, 2, 3, or 4 substituents independently selected from $R^C$;
each $R^C$ is independently selected from OH, CN, halo, $C_{1-4}$ alkyl, $C_{1-3}$ haloalkyl, $C_{1-4}$ alkoxy, $C_{1-3}$ haloalkoxy, cyano-$C_{1-3}$ alkyl, HO—$C_{1-3}$ alkyl, amino, $C_{1-4}$ alkylamino, di($C_{1-4}$ alkyl)amino, $C_{1-4}$ alkylsulfinyl, $C_{1-4}$ alkylsulfonyl, carbamyl, $C_{1-4}$ alkylcarbamyl, di($C_{1-4}$ alkyl)carbamyl, carboxy, $C_{1-4}$ alkylcarbonyl, $C_{1-4}$ alkoxycarbonyl, $C_{1-4}$ carbonylamino, $C_{1-4}$ alkylsulfonylamino, aminosulfonyl, $C_{1-4}$ alkylaminosulfonyl, and di($C_{1-4}$ alkyl)aminosulfonyl;
$Cy^B$ is $C_{3-10}$ cycloalkyl or 4-10 membered heterocycloalkyl; wherein at least one ring-forming carbon atom of $C_{3-10}$ cycloalkyl and 4-10 membered heterocycloalkyl is substituted by oxo to form a carbonyl group; wherein the 4-10 membered heterocycloalkyl has at least one ring-forming carbon atom and 1, 2, 3, or 4 ring-forming heteroatoms independently selected from N, O, and S; wherein the N and S are optionally oxidized; and wherein the $C_{3-10}$ cycloalkyl and 4-10 membered heterocycloalkyl are each optionally substituted with 1, 2, 3 or 4 substituents independently selected from $R^B$; or
$Cy^B$ is 6-10 membered aryl or 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein: (a) at least one ring-forming carbon atom of the 5-10 membered heteroaryl is substituted by oxo to form a carbonyl group; or (b) the 6-10 membered aryl or 5-10 membered heteroaryl is substituted by halo, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$OR$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$; and wherein the 6-10 membered aryl or 5-10 membered heteroaryl is further optionally substituted with 1, 2, 3 or 4 substituents independently selected from R$^B$;

each R$^B$ is independently selected from halo, C$_{1-6}$ alkyl, C$_{1-6}$ haloalkyl, C$_{3-6}$ cycloalkyl, phenyl, 5-6 membered heteroaryl, 4-7 membered heterocycloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$ NR$^{c2}$OR$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$; wherein said C$_{1-6}$ alkyl, C$_{3-6}$ cycloalkyl, phenyl, 5-6 membered heteroaryl, and 4-7 membered heterocycloalkyl are each optionally substituted with 1, 2, 3, or 4 substituents independently selected from R$^{12}$;

each R$^{11}$ is independently selected from CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$OR$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$;

each R$^{12}$ is independently selected from halo, CN, NO$_2$, C$_{1-6}$ alkyl, C$_{1-6}$ haloalkyl, C$_{3-6}$ cycloalkyl, phenyl, 5-6 membered heteroaryl, 4-7 membered heterocycloalkyl, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$OR$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$; wherein said C$_{1-6}$ alkyl, C$_{3-6}$ cycloalkyl, phenyl, 5-6 membered heteroaryl, and 4-7 membered heterocycloalkyl are each optionally substituted with 1, 2, 3, or 4 substituents independently selected from R$^g$;

R$^{a1}$, R$^{c1}$ and R$^{d1}$ are each independently selected from H, C$_{1-6}$ alkyl, and C$_{1-6}$ haloalkyl; wherein said C$_{1-6}$ alkyl is optionally substituted with 1, 2, 3, or 4 substituents independently selected from R$^g$; or alternatively, R$^{c1}$ and R$^{d1}$ attached to the same N atom, together with the N atom to which they are attached, form a 4-, 5-, 6- or 7-membered heterocycloalkyl group optionally substituted with 1, 2 or 3 substituents independently selected from R$^g$;

R$^{b1}$ is selected from C$_{1-6}$ alkyl and C$_{1-6}$ haloalkyl, each of which is optionally substituted with 1, 2, 3, or 4 substituents independently selected from R$^g$;

each R$^{a2}$, R$^{c2}$, and R$^{d2}$ is independently selected from H, C$_{1-6}$ alkyl, C$_{1-6}$ haloalkyl, C$_{3-6}$ cycloalkyl, phenyl, 5-6 membered heteroaryl, and 4-7 membered heterocycloalkyl; wherein said C$_{1-6}$ alkyl, C$_{3-6}$ cycloalkyl, phenyl, 5-6 membered heteroaryl, and 4-7 membered heterocycloalkyl are each optionally substituted with 1, 2, 3, or 4 substituents independently selected from R$^{12}$; or alternatively, any R$^{c2}$ and R$^{d2}$ attached to the same N atom, together with the N atom to which they are attached, form a 4-, 5-, 6- or 7-membered heterocycloalkyl group optionally substituted with 1, 2 or 3 substituents independently selected from R$^{12}$;

each R$^{b2}$ is independently selected from C$_{1-6}$ alkyl, C$_{1-6}$ haloalkyl, C$_{3-6}$ cycloalkyl, phenyl, 5-6 membered heteroaryl, and 4-7 membered heterocycloalkyl, each of which is optionally substituted with 1, 2, 3, or 4 substituents independently selected from R$^{12}$;

each R$^{a3}$, R$^{c3}$ and R$^{d3}$ is independently selected from H, C$_{1-6}$ alkyl, C$_{1-6}$ haloalkyl, C$_{3-6}$ cycloalkyl, phenyl, 5-6 membered heteroaryl, 4-7 membered heterocycloalkyl, C$_{3-6}$ cycloalkyl-C$_{1-4}$ alkylene, phenyl-C$_{1-4}$ alkylene, 5-6 membered heteroaryl-C$_{1-4}$ alkylene, and 4-7 membered heterocycloalkyl-C$_{1-4}$ alkylene; wherein said C$_{1-6}$ alkyl, C$_{3-6}$ cycloalkyl, phenyl, 5-6 membered heteroaryl, 4-7 membered heterocycloalkyl, C$_{3-6}$ cycloalkyl-C$_{1-4}$ alkylene, phenyl-C$_{1-4}$ alkylene, 5-6 membered heteroaryl-C$_{1-4}$ alkylene, and 4-7 membered heterocycloalkyl-C$_{1-4}$ alkylene are each optionally substituted with 1, 2, 3, or 4 substituents independently selected from R$^g$; or alternatively, any R$^{c3}$ and R$^{d3}$ attached to the same N atom, together with the N atom to which they are attached, form a 4-, 5-, 6- or 7-membered heterocycloalkyl group optionally substituted with 1, 2 or 3 substituents independently selected from R$^g$;

each R$^{b3}$ is independently selected from C$_{1-6}$ alkyl, C$_{1-6}$ haloalkyl, C$_{3-6}$ cycloalkyl, phenyl, 5-6 membered heteroaryl, 4-7 membered heterocycloalkyl, C$_{3-6}$ cycloalkyl-C$_{1-4}$ alkylene, phenyl-C$_{1-4}$ alkylene, 5-6 membered heteroaryl-C$_{1-4}$ alkylene, and 4-7 membered heterocycloalkyl-C$_{1-4}$ alkylene, each of which is optionally substituted with 1, 2, 3, or 4 substituents independently selected from R$^g$;

each R$^{a4}$, R$^{c4}$ and R$^{d4}$, is independently selected from H, C$_{1-6}$ alkyl, and C$_{1-6}$ haloalkyl; wherein said C$_{1-6}$ alkyl is optionally substituted with 1, 2, 3, or 4 substituents independently selected from R$^g$; or alternatively, any R$^{c4}$ and R$^{d4}$ attached to the same N atom, together with the N atom to which they are attached, form a 4-, 5-, 6- or 7-membered heterocycloalkyl group optionally substituted with 1, 2 or 3 substituents independently selected from R$^g$;

each R$^{b4}$ is independently selected from C$_{1-6}$ alkyl and C$_{1-6}$ haloalkyl, each of which is optionally substituted with 1, 2, 3, or 4 substituents independently selected from R$^g$; and each R$^g$ is independently selected from OH, NO$_2$, CN, halo, C$_{1-6}$ alkyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, H$_2$N—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

provided that:
1) A$^1$-A$^2$-A$^3$ is not Y—Y when one of A$^1$, A$^2$ or A$^3$ is a bond, or Y—Y—Y; and
2) when A$^3$ is —Y— or —C$_{1-3}$ alkylene-Y— then R$^A$ is H, C$_{1-6}$ alkyl, or C$_{1-6}$ haloalkyl, wherein said C$_{1-6}$ alkyl or C$_{1-6}$ haloalkyl is optionally substituted with 1, 2, 3 or 4 substituents independently selected from R$^{11}$.

In some embodiments:
R$^1$ is A$^1$-A$^2$-A$^3$-R$^A$;
R$^2$ is H, halo or C$_{1-4}$ alkyl;
R$^3$ is H, halo or C$_{1-6}$ alkyl;
A$^1$ is selected from a bond, —Y—, and —C$_{1-3}$ alkylene-;
A$^2$ is selected from a bond, —Y—, and —C$_{1-3}$ alkylene-;
A$^3$ is selected from a bond, Cy$^{A3}$, —Y—, and —C$_{1-3}$ alkylene-;
R$^A$ is H, C$_{1-6}$ alkyl, C$_{1-6}$ haloalkyl, halo, CN, OR$^{a1}$, SR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, S(O)R$^{b1}$, S(O)NR$^{c1}$R$^{d1}$, S(O)$_2$R$^{b1}$, or S(O)$_2$NR$^{c1}$R$^{d1}$;
wherein said C$_{1-6}$ alkyl or C$_{1-6}$ haloalkyl is optionally substituted with 1, 2, 3 or 4 substituents independently selected from R$^{11}$;

Y is O, S, S(O), S(O)$_2$, or C(O);

Cy$^{A3}$ is C$_{3-7}$ cycloalkyl, phenyl, 5-6 membered heteroaryl, or 4-7 membered heterocycloalkyl; wherein each 5-6 membered heteroaryl and 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of C$_{3-7}$ cycloalkyl and 4-7 membered heterocycloalkyl is optionally substituted by oxo to form a carbonyl group; and wherein the C$_{3-7}$ cycloalkyl, phenyl, 5-6 membered heteroaryl, and 4-7 membered heterocycloalkyl are each optionally substituted with 1, 2, 3 or 4 substituents independently selected from R$^{A3}$;

each R$^{A3}$ is independently selected from OH, CN, halo, C$_{1-6}$ alkyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, H$_2$N—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, and C$_{1-6}$ alkoxycarbonyl;

Cy$^C$ is phenylene, wherein the phenylene is optionally substituted by 1, 2, 3, or 4 substituents independently selected from R$^C$;

each R$^C$ is independently selected from OH, CN, halo, C$_{1-4}$ alkyl, C$_{1-3}$ haloalkyl, C$_{1-4}$ alkoxy, C$_{1-3}$ haloalkoxy, cyano-C$_{1-3}$ alkyl, HO—C$_{1-3}$ alkyl, amino, C$_{1-4}$ alkylamino, and di(C$_{1-4}$ alkyl)amino;

Cy$^B$ is C$_{3-10}$ cycloalkyl or 4-10 membered heterocycloalkyl; wherein at least one ring-forming carbon atom of C$_{3-10}$ cycloalkyl and 4-10 membered heterocycloalkyl is substituted by oxo to form a carbonyl group; wherein the 4-10 membered heterocycloalkyl has at least one ring-forming carbon atom and 1, 2, 3, or 4 ring-forming heteroatoms independently selected from N, O, and S; wherein the N and S are optionally oxidized; and wherein the C$_{3-10}$ cycloalkyl and 4-10 membered heterocycloalkyl are each optionally substituted with 1, 2, 3 or 4 substituents independently selected from R$^B$; or Cy$^B$ is 6-10 membered aryl or 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein at least one ring-forming carbon atom of the 5-10 membered heteroaryl is substituted by oxo to form a carbonyl group; and wherein the 6-10 membered aryl or 5-10 membered heteroaryl is further optionally substituted with 1, 2, 3 or 4 substituents independently selected from R$^B$;

each R$^B$ is independently selected from halo, C$_{1-6}$ alkyl, C$_{1-6}$ haloalkyl, C$_{3-6}$ cycloalkyl, phenyl, 5-6 membered heteroaryl, 4-7 membered heterocycloalkyl, CN, NO$_2$, OR$^{a2}$, SR$^{a2}$, C(O)R$^{b2}$, C(O)NR$^{c2}$R$^{d2}$, C(O)OR$^{a2}$, NR$^{c2}$R$^{d2}$, NR$^{c2}$C(O)R$^{b2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$; wherein said C$_{1-6}$ alkyl, C$_{3-6}$ cycloalkyl, phenyl, 5-6 membered heteroaryl, and 4-7 membered heterocycloalkyl are each optionally substituted with 1, 2, 3, or 4 substituents independently selected from R$^{12}$;

each R$^{11}$ is independently selected from CN, OR$^{a3}$, SR$^{a3}$, C(O)R$^{b3}$, C(O)NR$^{c3}$R$^{d3}$, C(O)OR$^{a3}$, NR$^{c3}$R$^{d3}$ NR$^{c3}$C(O)R$^{b3}$, NR$^{c3}$C(O)OR$^{a3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$;

each R$^{12}$ is independently selected from halo, CN, C$_{1-6}$ alkyl, C$_{1-6}$ haloalkyl, C$_{3-6}$ cycloalkyl, phenyl, 5-6 membered heteroaryl, 4-7 membered heterocycloalkyl, OR$^{a4}$, SR$^{a4}$, C(O)R$^{b4}$, C(O)NR$^{c4}$R$^{d4}$, C(O)OR$^{a4}$, NR$^{c4}$R$^{d4}$, NR$^{c4}$C(O)R$^{b4}$, NR$^{c4}$C(O)OR$^{a4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$; wherein said C$_{1-6}$ alkyl, C$_{3-6}$ cycloalkyl, phenyl, 5-6 membered heteroaryl, and 4-7 membered heterocycloalkyl are each optionally substituted with 1, 2, 3, or 4 substituents independently selected from R$^g$;

R$^{a1}$, R$^{c1}$ and R$^{d1}$ are each independently selected from H, C$_{1-6}$ alkyl, and C$_{1-6}$ haloalkyl; wherein said C$_{1-6}$ alkyl is optionally substituted with 1, 2, 3, or 4 substituents independently selected from R$^g$;

R$^{b1}$ is selected from C$_{1-6}$ alkyl and C$_{1-6}$ haloalkyl, each of which is optionally substituted with 1, 2, 3, or 4 substituents independently selected from R$^g$;

each R$^{a2}$, R$^{c2}$, and R$^{d2}$ is independently selected from H, C$_{1-6}$ alkyl, C$_{1-6}$ haloalkyl, C$_{3-6}$ cycloalkyl, phenyl, 5-6 membered heteroaryl, and 4-7 membered heterocycloalkyl; wherein said C$_{1-6}$ alkyl, C$_{3-6}$ cycloalkyl, phenyl, 5-6 membered heteroaryl, and 4-7 membered heterocycloalkyl are each optionally substituted with 1, 2, 3, or 4 substituents independently selected from R$^{12}$;

each R$^{b2}$ is independently selected from C$_{1-6}$ alkyl, C$_{1-6}$ haloalkyl, C$_{3-6}$ cycloalkyl, phenyl, 5-6 membered heteroaryl, and 4-7 membered heterocycloalkyl, each of which is optionally substituted with 1, 2, 3, or 4 substituents independently selected from R$^{12}$;

each R$^{a3}$, R$^{c3}$ and R$^{d3}$ is independently selected from H, C$_{1-6}$ alkyl, C$_{1-6}$ haloalkyl, C$_{3-6}$ cycloalkyl, phenyl, 5-6 membered heteroaryl, 4-7 membered heterocycloalkyl, C$_{3-6}$ cycloalkyl-C$_{1-4}$ alkylene, phenyl-C$_{1-4}$ alkylene, 5-6 membered heteroaryl-C$_{1-4}$ alkylene, and 4-7 membered heterocycloalkyl-C$_{1-4}$ alkylene; wherein said C$_{1-6}$ alkyl, C$_{3-6}$ cycloalkyl, phenyl, 5-6 membered heteroaryl, 4-7 membered heterocycloalkyl, C$_{3-6}$ cycloalkyl-C$_{1-4}$ alkylene, phenyl-C$_{1-4}$ alkylene, 5-6 membered heteroaryl-C$_{1-4}$ alkylene, and 4-7 membered heterocycloalkyl-C$_{1-4}$ alkylene are each optionally substituted with 1, 2, 3, or 4 substituents independently selected from R$^g$;

each R$^{b3}$ is independently selected from C$_{1-6}$ alkyl, C$_{1-6}$ haloalkyl, C$_{3-6}$ cycloalkyl, phenyl, 5-6 membered heteroaryl, 4-7 membered heterocycloalkyl, C$_{3-6}$ cycloalkyl-C$_{1-4}$ alkylene, phenyl-C$_{1-4}$ alkylene, 5-6 membered heteroaryl-C$_{1-4}$ alkylene, and 4-7 membered heterocycloalkyl-C$_{1-4}$ alkylene, each of which is optionally substituted with 1, 2, 3, or 4 substituents independently selected from R$^g$;

each R$^{a4}$, R$^{c4}$ and R$^{d4}$, is independently selected from H, C$_{1-6}$ alkyl, and C$_{1-6}$ haloalkyl; wherein said C$_{1-6}$ alkyl is optionally substituted with 1, 2, 3, or 4 substituents independently selected from R$^g$;

each R$^{b4}$ is independently selected from C$_{1-6}$ alkyl and C$_{1-6}$ haloalkyl, each of which is optionally substituted with 1, 2, 3, or 4 substituents independently selected from R$^g$; and each R$^g$ is independently selected from OH, NO$_2$, CN, halo, C$_{1-6}$ alkyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, H$_2$N—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

provided that:
1) A$^1$-A$^2$-A$^3$ is not Y—Y when one of A$^1$, A$^2$ or A$^3$ is a bond, or Y—Y—Y; and 2) when $A^3$ is —Y— or —$C_{1-3}$ alkylene-Y— then $R^4$ is H, $C_{1-6}$ alkyl, or $C_{1-6}$ haloalkyl, wherein said $C_{1-6}$ alkyl or $C_{1-6}$ haloalkyl is optionally substituted with 1, 2, 3 or 4 substituents independently selected from $R^1$.

In some embodiments:

$R^1$ is $A^1$-$A^2$-$A^3$-$R^4$;

$R^2$ is H or $C_{1-4}$ alkyl;

$R^3$ is H or $C_{1-6}$ alkyl;

$A^1$ is selected from a bond and —$C_{1-3}$ alkylene-;

$A^2$ is selected from a bond and —$C_{1-3}$ alkylene-;

$A^3$ is selected from a bond, $Cy^{A3}$, and —$C_{1-3}$ alkylene-;

$R^4$ is H, $C_{1-6}$ alkyl, CN, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $S(O)R^{b1}$, $S(O)NR^{c1}R^{d1}$, $S(O)_2R^{b1}$, or $S(O)_2NR^{c1}R^{d1}$; wherein said $C_{1-6}$ alkyl is optionally substituted with 1, 2, 3 or 4 substituents independently selected from $R^1$;

$Cy^{A3}$ is $C_{3-7}$ cycloalkyl, phenyl, 5-6 membered heteroaryl, or 4-7 membered heterocycloalkyl; wherein each 5-6 membered heteroaryl and 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of $C_{3-7}$ cycloalkyl and 4-7 membered heterocycloalkyl is optionally substituted by oxo to form a carbonyl group; and wherein the $C_{3-7}$ cycloalkyl, phenyl, 5-6 membered heteroaryl, and 4-7 membered heterocycloalkyl are each optionally substituted with 1, 2, 3 or 4 substituents independently selected from $R^{A3}$;

each $R^{A3}$ is independently selected from OH, CN, halo, $C_{1-6}$ alkyl, $C_{1-6}$ haloalkyl, and $C_{1-6}$ alkoxy;

$Cy^C$ is phenylene, wherein the phenylene is optionally substituted by 1, 2, 3, or 4 substituents independently selected from $R^C$;

each $R^C$ is independently selected from OH, CN, halo, $C_{1-4}$ alkyl, $C_{1-3}$ haloalkyl, $C_{1-4}$ alkoxy, and $C_{1-3}$ haloalkoxy;

$Cy^B$ is $C_{3-10}$ cycloalkyl or 4-10 membered heterocycloalkyl; wherein at least one ring-forming carbon atom of $C_{3-10}$ cycloalkyl and 4-10 membered heterocycloalkyl is substituted by oxo to form a carbonyl group; wherein the 4-10 membered heterocycloalkyl has at least one ring-forming carbon atom and 1, 2, 3, or 4 ring-forming heteroatoms independently selected from N, O, and S; wherein the N and S are optionally oxidized; and wherein the $C_{3-10}$ cycloalkyl and 4-10 membered heterocycloalkyl are each optionally substituted with 1, 2, 3 or 4 substituents independently selected from $R^B$; or $Cy^B$ is 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein at least one ring-forming carbon atom of the 5-10 membered heteroaryl is substituted by oxo to form a carbonyl group; and wherein the 5-10 membered heteroaryl is further optionally substituted with 1, 2, 3 or 4 substituents independently selected from $R^B$;

each $R^B$ is independently selected from halo, $C_{1-6}$ alkyl, $C_{1-6}$ haloalkyl, phenyl, $OR^{a2}$, $SR^{a2}$, $C(O)R^{b2}$, $C(O)NR^{c2}R^{d2}$, and $C(O)OR^{a2}$; wherein said $C_{1-6}$ alkyl and phenyl are each optionally substituted with 1, 2, 3, or 4 substituents independently selected from $R^{12}$;

each $R^{11}$ is independently selected from CN or $OR^{a3}$;

each $R^{12}$ is independently selected from halo, CN, $C_{1-6}$ alkyl, $C_{1-6}$ haloalkyl, phenyl, $OR^{a4}$, $C(O)R^{b4}$, $C(O)NR^{c4}R^{d4}$, and $C(O)OR^{a4}$; wherein said $C_{1-6}$ alkyl, $C_{3-6}$ cycloalkyl, phenyl, 5-6 membered heteroaryl, and 4-7 membered heterocycloalkyl are each optionally substituted with 1, 2, 3 or 4 substituents independently selected from $R^g$;

$R^{a1}$, $R^{c1}$ and $R^{d1}$ are each independently selected from H, $C_{1-6}$ alkyl, and $C_{1-6}$ haloalkyl; wherein said $C_{1-6}$ alkyl is optionally substituted with 1, 2, 3, or 4 substituents independently selected from $R^g$;

$R^{b1}$ is selected from $C_{1-6}$ alkyl and $C_{1-6}$ haloalkyl, each of which is optionally substituted with 1, 2, 3, or 4 substituents independently selected from $R^g$;

each $R^{a2}$, $R^{c2}$, and $R^{d2}$ is independently selected from H, $C_{1-6}$ alkyl, $C_{1-6}$ haloalkyl, and phenyl; wherein said $C_{1-6}$ alkyl and phenyl are each optionally substituted with 1, 2, 3, or 4 substituents independently selected from $R^{12}$;

each $R^{b2}$ is independently selected from $C_{1-6}$ alkyl, $C_{1-6}$ haloalkyl, $C_{3-6}$ cycloalkyl, and phenyl, each of which is optionally substituted with 1, 2, 3, or 4 substituents independently selected from $R^{12}$;

each $R^{a3}$ is independently selected from H, $C_{1-6}$ alkyl, $C_{1-6}$ haloalkyl, phenyl, phenyl-$C_{1-4}$ alkylene; wherein said $C_{1-6}$ alkyl, phenyl, and phenyl-$C_{1-4}$ alkylene are each optionally substituted with 1, 2, 3, or 4 substituents independently selected from $R^g$;

each $R^{a4}$, $R^{c4}$ and $R^{d4}$, is independently selected from H, $C_{1-6}$ alkyl, and $C_{1-6}$ haloalkyl; wherein said $C_{1-6}$ alkyl is optionally substituted with 1, 2, 3, or 4 substituents independently selected from $R^g$;

each $R^{b4}$ is independently selected from $C_{1-6}$ alkyl and $C_{1-6}$ haloalkyl, each of which is optionally substituted with 1, 2, 3, or 4 substituents independently selected from $R^g$; and each $R^g$ is independently selected from OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, $H_2N$—$C_{1-3}$ alkyl, amino, $C_{1-6}$ alkylamino, and di($C_{1-6}$ alkyl)amino.

In some embodiments:

$R^1$ is $A^1$-$A^2$-$A^3$-$R^4$, (1) wherein said $A^1$, $A^2$, and $A^3$ are each a bond, and $R^4$ is $C_{1-6}$ alkyl or $C(O)NR^{c1}R^{d1}$, (2) wherein said $A^1$ is a bond, $A^2$ is a bond or —$C_{1-3}$ alkylene-, $A^3$ is $Cy^{A3}$, and $R^4$ is $C_{1-6}$ alkyl, CN, $OR^{a1}$, $NR^{c1}R^{d1}$, $C(O)R^{b1}$, $C(O)NR^{c1}R^{d1}$, $C(O)OR^{a1}$, or $S(O)_2R^{b1}$; wherein said $C_{1-6}$ alkyl of $R^4$ is optionally substituted with 1, 2, 3, or 4 substituents independently selected from $R^{11}$, or (3) wherein $A^1$ is $Cy^{A1}$, $A^2$ is a bond or $C(O)$, $A^3$ is $Cy^{A3}$, and $R^4$ is H;

$R^2$ is H;

$R^3$ is H;

$Cy^{A1}$ is $C_{3-7}$ cycloalkyl or 4-7 membered heterocycloalkyl; wherein the 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of $C_{3-7}$ cycloalkyl and 4-7 membered heterocycloalkyl is optionally substituted by oxo to form a carbonyl group;

$Cy^{A3}$ is $C_{3-7}$ cycloalkyl, 6 membered heteroaryl, or 4-7 membered heterocycloalkyl; wherein each 6 membered heteroaryl and 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of $C_{3-7}$ cycloalkyl and 4-7 membered heterocycloalkyl is optionally substituted by oxo to form a carbonyl group; and wherein the $C_{3-7}$ cycloalkyl, 6 membered heteroaryl, and 4-7 membered heterocycloalkyl are each optionally substituted with 1, 2, 3 or 4 $C_{1-6}$ alkyl;

$Cy^B$ is $C_{3-10}$ cycloalkyl or 4-10 membered heterocycloalkyl; wherein at least one ring-forming carbon atom of $C_{3-10}$ cycloalkyl and 4-10 membered heterocycloalkyl is substituted by oxo to form a carbonyl group; wherein the 4-10 membered heterocycloalkyl has at least one ring-forming carbon atom and 1, 2, 3, or 4 ring-forming heteroatoms independently selected from N, O, and S; and wherein the $C_{3-10}$ cycloalkyl and 4-10 membered heterocycloalkyl are each optionally substituted with 1 or 2 substituents independently selected from $R^B$; or $Cy^B$ is 5-10 membered heteroaryl, having one ring-forming carbon atom which is substituted with oxo to form a carbonyl group and 1, 2, 3, or 4 ring-forming heteroatoms independently selected from N, O, and S; wherein the N and S are optionally oxidized; wherein the 5-10 membered heteroaryl is further optionally substituted with 1, 2, 3 or 4 substituents independently selected from $R^B$;

each $R^B$ is independently selected from $C_{1-6}$ alkyl, $C_{2-6}$ alkynyl, CN, halo, phenyl, 5-6 membered heteroaryl, $C_{3-7}$ cycloalkyl, 4-7 membered heterocycloalkyl, $OR^{a2}$, $C(O)R^{b2}$, and $C(O)NR^{c2}R^{d2}$; wherein said $C_{1-6}$ alkyl, $C_{2-6}$ alkynyl, phenyl, 5-6 membered heteroaryl, $C_{3-7}$ cycloalkyl, and 4-7 membered heterocycloalkyl are each optionally substituted with 1, 2, 3, or 4 substituents independently selected from $R^{12}$;

$Cy^C$ is phenylene optionally substituted by 1, 2, 3, or 4 substituents independently selected from $R^C$;

each $R^C$ is independently selected from halo and $C_{1-4}$ alkyl;

each $R^{11}$ is independently $OR^{a3}$ or $C(O)NR^{c3}R^{d3}$;

each $R^{12}$ is independently selected from halo, $C_{1-6}$ alkyl, CN, phenyl, and $OR^{a4}$;

each $R^{a1}$, $R^{c1}$, and $R^{d1}$ is independently selected from H and $C_{1-6}$ alkyl;

each $R^{b1}$ is independently selected from $C_{1-6}$ alkyl;

each $R^{a3}$, $R^{c3}$, $R^{d3}$ and $R^{a4}$ is independently selected from H and $C_{1-6}$ alkyl; and each $R^{a2}$, $R^{b2}$, $R^{c2}$, and $R^{d2}$ is independently selected from H, $C_{1-6}$ alkyl, and phenyl; wherein said $C_{1-6}$ alkyl and phenyl are each optionally substituted with 1, 2, 3, or 4 substituents independently selected from $R^{12}$.

In some embodiments: $R^1$ is $A^1$-$A^2$-$A^3$-$R^4$, (1) wherein said $A^1$, $A^2$, and $A^3$ are each a bond, and $R^4$ is $C_{1-6}$ alkyl, or (2) wherein said $A^1$ is a bond, $A^2$ is a bond or —$C_{1-3}$ alkylene-, $A^3$ is $Cy^{A3}$, and $R^4$ is $C_{1-6}$ alkyl, CN, $OR^{a1}$, $NR^{c1}R^{d1}$, $C(O)R^{b1}$, $C(O)NR^{c1}R^{d1}$, $C(O)OR^{a1}$, or $S(O)_2R^b$; wherein said $C_{1-6}$ alkyl of $R^4$ is optionally substituted with 1, 2, 3, or 4 substituents independently selected from $R^1$;

$R^2$ is H;

$R^3$ is H;

$Cy^{A3}$ is $C_{3-7}$ cycloalkyl, 6 membered heteroaryl, or 4-7 membered heterocycloalkyl; wherein each 6 membered heteroaryl and 4-7 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of $C_{3-7}$ cycloalkyl and 4-7 membered heterocycloalkyl is optionally substituted by oxo to form a carbonyl group;

$Cy^B$ is $C_{3-10}$ cycloalkyl or 4-10 membered heterocycloalkyl; wherein at least one ring-forming carbon atom of $C_{3-10}$ cycloalkyl and 4-10 membered heterocycloalkyl is substituted by oxo to form a carbonyl group; wherein the 4-10 membered heterocycloalkyl has at least one ring-forming carbon atom and 1, 2, 3, or 4 ring-forming heteroatoms independently selected from N, O, and S; and wherein the $C_{3-10}$ cycloalkyl and 4-10 membered heterocycloalkyl are each optionally substituted with 1 or 2 substituents independently selected from $R^B$; or $Cy^B$ is 5-10 membered heteroaryl, having one ring-forming carbon atom which is substituted with oxo to form a carbonyl group and 1, 2, 3, or 4 ring-forming heteroatoms independently selected from N, O, and S; wherein the N and S are optionally oxidized; wherein the 5-10 membered heteroaryl is further optionally substituted with 1, 2, 3 or 4 substituents independently selected from $R^B$;

each $R^B$ is independently selected from $C_{1-6}$ alkyl, phenyl, $OR^{a2}$, and $C(O)NR^{c2}R^{d2}$; wherein said $C_{1-6}$ alkyl and phenyl optionally substituted with 1, 2, 3, or 4 substituents independently selected from $R^{12}$;

$Cy^C$ is phenylene optionally substituted by 1, 2, 3, or 4 substituents independently selected from $R^C$;

each $R^C$ is independently selected from halo and $C_{1-4}$ alkyl;

each $R^{11}$ is independently $OR^{a3}$;

each $R^{12}$ is independently selected from halo, phenyl, and $OR^{a4}$;

each $R^{a1}$, $R^{c1}$, and $R^{d1}$ is independently selected from H and $C_{1-6}$ alkyl;

each $R^{b1}$ is independently selected from $C_{1-6}$ alkyl;

each $R^{a3}$ and $R^{a4}$ is independently selected from H and $C_{1-6}$ alkyl; and each $R^{a2}$, $R^{c2}$, and $R^{d2}$ is independently selected from H, $C_{1-6}$ alkyl, and phenyl; wherein said $C_{1-6}$ alkyl and phenyl are each optionally substituted with 1, 2, 3, or 4 substituents independently selected from $R^{12}$.

In some embodiments: $R^1$ is $A^1$-$A^2$-$A^3$-$R^4$, (1) wherein said $A^1$, $A^2$, and $A^3$ are each a bond, and $R^4$ is $C_{1-6}$ alkyl, or (2) wherein said $A^1$ and $A^2$ are each a bond, $A^3$ is $Cy^{A3}$, and $R^4$ is $C_{1-6}$ alkyl, CN, $OR^{a1}$, $C(O)R^{b1}$, $C(O)NR^{c1}R^{d1}$, $C(O)OR^{a1}$, or $S(O)_2R^{b1}$; wherein said $C_{1-6}$ alkyl is optionally substituted with 1, 2, 3, or 4 substituents independently selected from $R^1$;

$R^2$ is H;

$R^3$ is H;

$Cy^{A3}$ is $C_{3-7}$ cycloalkyl or 4-7 membered heterocycloalkyl; wherein the 4-7 membered heterocycloalkyl has at least one ring-forming carbon atom and 1, 2, 3, or 4 ring-forming heteroatoms independently selected from N, O, and S; wherein a ring-forming carbon atom of $C_{3-7}$ cycloalkyl and 4-7 membered heterocycloalkyl is optionally substituted by oxo to form a carbonyl group;

$Cy^B$ is 5-10 membered heterocycloalkyl; wherein the 5-10 membered heterocycloalkyl has at least one ring-forming carbon atom and 1, 2, 3, or 4 ring-forming heteroatoms independently selected from N, O, and S; wherein at least one ring-forming carbon atom of 5-10 membered heterocycloalkyl is substituted by oxo to form a carbonyl group; and wherein the 5-10 membered heterocycloalkyl is optionally substituted with 1 or 2 substituents independently selected from $R^B$; or $Cy^B$ is 5-10 membered heteroaryl, having one ring-forming carbon atom which is substituted with oxo to form a carbonyl group and 1, 2, 3, or 4 ring-forming heteroatoms independently selected from N, O, and S; wherein the N and S are optionally oxidized; wherein the 5-10 membered heteroaryl is further optionally substituted with 1, 2, 3 or 4 substituents independently selected from $R^B$;

each $R^B$ is independently selected from $C_{1-6}$ alkyl and phenyl; wherein said $C_{1-6}$ alkyl and phenyl are optionally substituted with 1, 2, 3, or 4 substituents independently selected from $R^{12}$;

$Cy^C$ is phenylene optionally substituted by 1, 2, 3, or 4 substituents independently selected from $R^C$;

each $R^C$ is independently halo;

each $R^{11}$ is independently $OR^{a3}$;

each $R^{12}$ is independently selected from halo, phenyl, and $OR^{a4}$;

each $R^{a1}$, $R^d$, and $R^{d1}$ is independently selected from H and $C_{1-6}$ alkyl;

each $R^{b1}$ is independently selected from $C_{1-6}$ alkyl; and each $R^{a3}$ and $R^{a4}$ is independently selected from H and $C_{1-6}$ alkyl.

In some embodiments: $R^1$ is $A^1$-$A^2$-$A^3$-$R^4$, (1) wherein said $A^1$, $A^2$, and $A^3$ are each a bond, and $R^4$ is $C_{1-6}$ alkyl, or (2) wherein said $A^1$ and $A^2$ are each a bond, $A^3$ is $Cy^{A3}$, and $R^4$ is $C_{1-6}$ alkyl, CN, $OR^{a1}$, $C(O)R^{b1}$, $C(O)NR^{c1}R^{d1}$, $C(O)OR^{a1}$, or $S(O)_2R^{b1}$; wherein said $C_{1-6}$ alkyl is optionally substituted with 1, 2, 3, or 4 substituents independently selected from $R^{11}$;

$R^2$ is H;

$R^3$ is H;

$Cy^{A3}$ is $C_{3-7}$ cycloalkyl or 4-7 membered heterocycloalkyl; wherein the 4-7 membered heterocycloalkyl has at least one ring-forming carbon atom and 1, 2, 3, or 4 ring-forming heteroatoms independently selected from N, O, and S; wherein a ring-forming carbon atom of $C_{3-7}$ cycloalkyl and 4-7 membered heterocycloalkyl is optionally substituted by oxo to form a carbonyl group;

$Cy^B$ is 5-6 membered heteroaryl, having one ring-forming carbon atom which is substituted with oxo to form a carbonyl group and 1 or 2 ring-forming heteroatoms independently selected from N, O, and S; wherein the N and S are optionally oxidized; wherein the 5-6 membered heteroaryl is further optionally substituted with 1 or 2 substituents independently selected from $R^B$;

each $R^B$ is independently selected from $C_{1-6}$ alkyl and phenyl; wherein said $C_{1-6}$ alkyl and phenyl are optionally substituted with 1, 2, 3, or 4 substituents independently selected from $R^{12}$;

$Cy^C$ is phenylene optionally substituted by 1, 2, 3, or 4 substituents independently selected from $R^C$;

each $R^C$ is independently halo;

each $R^{11}$ is independently $OR^{a3}$;

each $R^{12}$ is independently selected from halo, phenyl, and $OR^{a4}$;

each $R^{a1}$, $R^{c1}$, and $R^{d1}$ is independently selected from H and $C_{1-6}$ alkyl;

each $R^{b1}$ is independently selected from $C_{1-6}$ alkyl; and each $R^{a3}$ and $R^{a4}$ is independently selected from H and $C_{1-6}$ alkyl.

In some embodiments: $R^1$ is $A^1$-$A^2$-$A^3$-$R^4$, (1) wherein said $A^1$, $A^2$, and $A^3$ are each a bond, and $R^4$ is $C_{1-6}$ alkyl, or (2) wherein said $A^1$ and $A^2$ are each a bond, $A^3$ is $Cy^{A3}$, and $R^4$ is $C_{1-6}$ alkyl, CN, $OR^{a1}$, $C(O)R^{b1}$, $C(O)NR^{c1}R^{d1}$, $C(O)OR^{a1}$, or $S(O)_2R^{b1}$; wherein said $C_{1-6}$ alkyl is optionally substituted with 1, 2, 3, or 4 substituents independently selected from $R^{11}$;

$R^2$ is H;

$R^3$ is H;

$Cy^{A3}$ is $C_{3-7}$ cycloalkyl or 4-7 membered heterocycloalkyl; wherein the 4-7 membered heterocycloalkyl has at least one ring-forming carbon atom and 1, 2, 3, or 4 ring-forming heteroatoms independently selected from N, O, and S; wherein a ring-forming carbon atom of $C_{3-7}$ cycloalkyl and 4-7 membered heterocycloalkyl is optionally substituted by oxo to form a carbonyl group;

$Cy^B$ is 5-10 membered heterocycloalkyl; wherein the 5-10 membered heterocycloalkyl has at least one ring-forming carbon atom and 1, 2, 3, or 4 ring-forming heteroatoms independently selected from N, O, and S; wherein at least one ring-forming carbon atom of 5-10 membered heterocycloalkyl is substituted by oxo to form a carbonyl group; and wherein the 5-10 membered heterocycloalkyl is optionally substituted with 1 or 2 substituents independently selected from $R^B$; or $Cy^B$ is 5-10 membered heteroaryl, having one ring-forming carbon atom which is substituted with oxo to form a carbonyl group and 1, 2, 3, or 4 ring-forming heteroatoms independently selected from N, O, and S; wherein the N and S are optionally oxidized; wherein the 5-10 membered heteroaryl is further optionally substituted with 1, 2, 3 or 4 substituents independently selected from $R^B$;

each $R^B$ is independently selected from $C_{1-6}$ alkyl and phenyl; wherein said $C_{1-6}$ alkyl and phenyl are optionally substituted with 1, 2, 3, or 4 substituents independently selected from $R^{12}$;

$Cy^C$ is phenylene optionally substituted by 1, 2, 3, or 4 substituents independently selected from $R^C$;

each $R^C$ is independently halo;

each $R^{11}$ is independently $OR^{a3}$;

each $R^{12}$ is independently selected from halo, phenyl, and $OR^{a4}$;

each $R^{a1}$, $R^d$, and $R^{d1}$ is independently selected from H and $C_{1-6}$ alkyl;

alternatively, $R^c$ and $R^{d1}$ attached to the same N atom, together with the N atom to which they are attached, form a 6-membered heterocycloalkyl group;

each $R^{b1}$ is independently selected from $C_{1-6}$ alkyl; and each $R^{a3}$ and $R^{a4}$ is independently selected from H and $C_{1-6}$ alkyl.

In some embodiments: $R^1$ is $A^1$-$A^2$-$A^3$-$R^4$, (1) wherein said $A^1$, $A^2$, and $A^3$ are each a bond, and $R^4$ is $C_{1-6}$ alkyl, or (2) wherein said $A^1$ and $A^2$ are each a bond, $A^3$ is $Cy^{A3}$, and $R^A$ is $C_{1-6}$ alkyl, CN, $OR^{a1}$, $C(O)R^{b1}$, $C(O)NR^{c1}R^{d1}$, $C(O)OR^{a1}$, or $S(O)_2R^{b1}$; wherein said $C_{1-6}$ alkyl is optionally substituted with 1, 2, 3, or 4 substituents independently selected from $R^1$;

$R^2$ is H;

$R^3$ is H;

$Cy^{A3}$ is $C_{3-7}$ cycloalkyl or 4-7 membered heterocycloalkyl; wherein the 4-7 membered heterocycloalkyl has at least one ring-forming carbon atom and 1, 2, 3, or 4 ring-forming heteroatoms independently selected from N, O, and S; wherein a ring-forming carbon atom of $C_{3-7}$ cycloalkyl and 4-7 membered heterocycloalkyl is optionally substituted by oxo to form a carbonyl group;

$Cy^B$ is 5-6 membered heteroaryl, having one ring-forming carbon atom which is substituted with oxo to form a carbonyl group and 1 or 2 ring-forming heteroatoms independently selected from N, O, and S; wherein the N and S are optionally oxidized; wherein the 5-6 membered heteroaryl is further optionally substituted with 1 or 2 substituents independently selected from $R^B$;

each $R^B$ is independently selected from $C_{1-6}$ alkyl and phenyl; wherein said $C_{1-6}$ alkyl and phenyl are optionally substituted with 1, 2, 3, or 4 substituents independently selected from $R^{12}$;

$Cy^C$ is phenylene optionally substituted by 1, 2, 3, or 4 substituents independently selected from $R^C$;

each $R^C$ is independently halo;

each $R^{11}$ is independently $OR^{a3}$;

each $R^{12}$ is independently selected from halo, phenyl, and $OR^{a4}$;

each $R^{a1}$, $R^{c1}$, and $R^{d1}$ is independently selected from H and $C_{1-6}$ alkyl;

alternatively, $R^c$ and $R^{d1}$ attached to the same N atom, together with the N atom to which they are attached, form a 6-membered heterocycloalkyl group;

each $R^{b1}$ is independently selected from $C_{1-6}$ alkyl; and each $R^{a3}$ and $R^{a4}$ is independently selected from H and $C_{1-6}$ alkyl.

In some embodiments: $R^1$ is $A^1$-$A^2$-$A^3$-$R^A$, (1) wherein said $A^1$, $A^2$, and $A^3$ are each a bond, and $R^A$ is $C_{1-6}$ alkyl, or (2) wherein said $A^1$ and $A^2$ are each a bond, $A^3$ is $Cy^{A3}$, and $R^A$ is $C_{1-6}$ alkyl, CN, $OR^{a1}$, $C(O)R^{b1}$, $C(O)NR^{c1}R^{d1}$, $C(O)OR^{a1}$, or $S(O)_2R^{b1}$; wherein said $C_{1-6}$ alkyl is optionally substituted with 1, 2, 3, or 4 substituents independently selected from $R^1$;

$R^2$ is H;

$R^3$ is H;

$Cy^{A3}$ is $C_{3-7}$ cycloalkyl or 4-7 membered heterocycloalkyl; wherein the 4-7 membered heterocycloalkyl has at least one ring-forming carbon atom and 1, 2, 3, or 4 ring-forming heteroatoms independently selected from N, O, and S; wherein a ring-forming carbon atom of $C_{3-7}$ cycloalkyl and 4-7 membered heterocycloalkyl is optionally substituted by oxo to form a carbonyl group;

$Cy^B$ is 5-10 membered heterocycloalkyl; wherein the 5-10 membered heterocycloalkyl has at least one ring-forming carbon atom and 1, 2, 3, or 4 ring-forming heteroatoms independently selected from N, O, and S; wherein at least one ring-forming carbon atom of 5-10 membered heterocycloalkyl is substituted by oxo to form a carbonyl group; and wherein the 5-10 membered heterocycloalkyl is optionally substituted with 1 or 2 substituents independently selected from $R^B$; wherein each $R^B$ is independently selected from $C_{1-6}$ alkyl and phenyl; wherein said $C_{1-6}$ alkyl and phenyl are optionally substituted with 1, 2, 3, or 4 substituents independently selected from $R^{12}$;

$Cy^C$ is phenylene optionally substituted by 1, 2, 3, or 4 substituents independently selected from $R^C$;

each $R^C$ is independently halo;

each $R^{11}$ is independently $OR^{a3}$;

each $R^{12}$ is independently selected from halo, phenyl, and $OR^{a4}$;

each $R^{a1}$, $R^{c1}$, and $R^{d1}$ is independently selected from H and $C_{1-6}$ alkyl;

alternatively, $R^{c1}$ and $R^{d1}$ attached to the same N atom, together with the N atom to which they are attached, form a 6-membered heterocycloalkyl group;

each $R^{b1}$ is independently selected from $C_{1-6}$ alkyl; and each $R^{a3}$ and $R^{a4}$ is independently selected from H and $C_{1-6}$ alkyl.

In some embodiments: $R^1$ is $A^1$-$A^2$-$A^3$-$R^A$, (1) wherein said $A^1$, $A^2$, and $A^3$ are each a bond, and $R^A$ is $C(O)NR^{c1}R^{d1}$ or $C_{1-6}$ alkyl; or (2) wherein said $A^1$ is a bond, $A^2$ is a bond or —$C_{1-3}$ alkylene-, $A^3$ is $Cy^{A3}$, and $R^A$ is H, $C_{1-6}$ alkyl, CN, $OR^{a1}$, $C(O)R^{b1}$, $C(O)NR^{c1}R^{d1}$, $NR^{c1}R^{d1}$, $C(O)OR^{a1}$, or $S(O)_2R^{b1}$; wherein said $C_{1-6}$ alkyl is optionally substituted with 1, 2, 3, or 4 substituents independently selected from $R^{11}$; (3) wherein $A^1$ is $Cy^{A1}$, $A^2$ is Y, Y is C(O), $A^3$ is $Cy^{A3}$, and $R^A$ is H; or (4) wherein $A^1$ is a bond, $A^2$ is $Cy^{A2}$, $A^3$ is $Cy^{A3}$, wherein $R^A$ is $C_{1-6}$ alkyl;

$R^2$ is H;

$R^3$ is H;

$Cy^{A3}$ is 5-6 membered heteroaryl, $C_{3-7}$ cycloalkyl or 4-7 membered heterocycloalkyl; wherein the 4-7 membered heterocycloalkyl has at least one ring-forming carbon atom and 1, 2, 3, or 4 ring-forming heteroatoms independently selected from N, O, and S; wherein a ring-forming carbon atom of $C_{3-7}$ cycloalkyl and 4-7 membered heterocycloalkyl is optionally substituted by oxo to form a carbonyl group;

$Cy^B$ is 5-10 membered heterocycloalkyl; wherein the 5-10 membered heterocycloalkyl has at least one ring-forming carbon atom and 1, 2, 3, or 4 ring-forming heteroatoms independently selected from N, O, and S; wherein at least one ring-forming carbon atom of 5-10 membered heterocycloalkyl is substituted by oxo to form a carbonyl group; and wherein the 5-10 membered heterocycloalkyl is optionally substituted with 1 or 2 substituents independently selected from $R^B$;

each $R^B$ is independently selected from halo, CN, $C_{1-6}$ alkyl, $C_{2-6}$ alkynyl, $C_{3-6}$ cycloalkyl, 5-6 membered heteroaryl, 4-7 membered heterocycloalkyl, phenyl, $OR^{a2}$, $C(O)R^{b2}$, $C(O)NR^{c2}R^{d2}$, wherein said $C_{1-6}$ alkyl, $C_{2-6}$ alkynyl, $C_{3-6}$ cycloalkyl, 5-6 membered heteroaryl, 4-7 membered heterocycloalkyl, and phenyl are optionally substituted with 1, 2, 3, or 4 substituents independently selected from $R^{12}$;

$Cy^C$ is phenylene optionally substituted by 1, 2, 3, or 4 substituents independently selected from $R^C$;

each $R^C$ is independently halo;

each $R^{11}$ is independently $OR^{a3}$ or $C(O)NR^{c3}R^{d3}$;

each $R^{12}$ is independently selected from halo, CN, $C_{1-6}$ alkyl, and $OR^{a4}$;

each $R^{a1}$, $R^{c1}$, and $R^{d1}$ is independently selected from H and $C_{1-6}$ alkyl;

alternatively, $R^c$ and $R^{d1}$ attached to the same N atom, together with the N atom to which they are attached, form a 6-membered heterocycloalkyl group;

each $R^{b1}$ is independently selected from $C_{1-6}$ alkyl; and each $R^{a3}$ and $R^{a4}$ is independently selected from H and $C_{1-6}$ alkyl.

In some embodiments, $Cy^B$ is

Cy$^B$-1
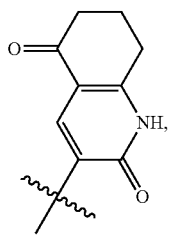

Cy$^B$-2
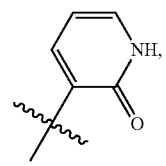

Cy$^B$-3
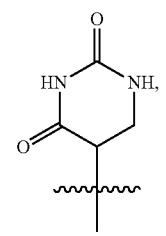

Cy$^B$-8
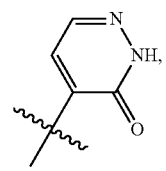

Cy$^B$-9
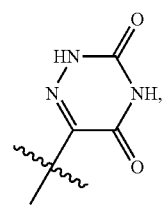

Cy$^B$-10
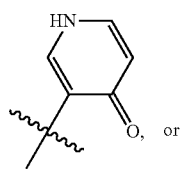, or

Cy$^B$-11
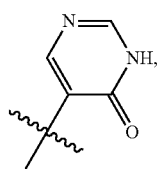

wherein $Cy^B$-1, $Cy^B$-2, $Cy^B$-3, $Cy^B$-8, $Cy^B$-9, $Cy^B$-10, $Cy^B$-4, and $Cy^B$-11 are each optionally substituted with 1, 2 or 3 independently selected $R^B$ groups;

$R^1$ is $A^1$-$A^2$-$A^3$-$R^4$, (1) wherein said $A^1$, $A^2$, and $A^3$ are each a bond, and $R^4$ is $C(O)NR^{c1}R^{d1}$ or $C_{1-6}$ alkyl; or (2) wherein said $A^1$ is a bond, $A^2$ is a bond or —$C_{1-3}$ alkylene-, $A^3$ is $Cy^{A3}$, and $R^4$ is H, $C_{1-6}$ alkyl, CN, $OR^{a1}$, $C(O)R^{b1}$, $C(O)NR^{c1}R^{d1}$, $NR^{c1}R^{d1}$, $C(O)OR^{a1}$, or $S(O)_2R^{b1}$; wherein said $C_{1-6}$ alkyl is optionally substituted with 1, 2, 3, or 4 substituents independently selected from $R^{11}$; (3) wherein $A^1$ is $Cy^{A1}$, $A^2$ is Y, Y is C(O), $A^3$ is $Cy^{A3}$, and $R^4$ is H; or (4) wherein $A^1$ is a bond, $A^2$ is $Cy^{A2}$, $A^3$ is $Cy^{A3}$, wherein $R^4$ is $C_{1-6}$ alkyl;

$R^2$ is H;

$R^3$ is H;

$Cy^{A3}$ is 5-6 membered heteroaryl, $C_{3-7}$ cycloalkyl or 4-7 membered heterocycloalkyl; wherein the 4-7 membered heterocycloalkyl has at least one ring-forming carbon atom and 1, 2, 3, or 4 ring-forming heteroatoms independently selected from N, O, and S; wherein a ring-forming carbon atom of $C_{3-7}$ cycloalkyl and 4-7 membered heterocycloalkyl is optionally substituted by oxo to form a carbonyl group;

each $R^B$ is independently selected from halo, CN, $C_{1-6}$ alkyl, $C_{2-6}$ alkynyl, $C_{3-6}$ cycloalkyl, 5-6 membered heteroaryl, 4-7 membered heterocycloalkyl, phenyl, $OR^{a2}$, $C(O)R^{b2}$, $C(O)NR^{c2}R^{d2}$, wherein said $C_{1-6}$ alkyl, $C_{2-6}$ alkynyl, $C_{3-6}$ cycloalkyl, 5-6 membered heteroaryl, 4-7 membered heterocycloalkyl, and phenyl are optionally substituted with 1, 2, 3, or 4 substituents independently selected from $R^{12}$;

$Cy^C$ is phenylene optionally substituted by 1, 2, 3, or 4 substituents independently selected from $R^C$;

each $R^C$ is independently halo;

each $R^{11}$ is independently $OR^{a3}$ or $C(O)NR^{c3}R^{d3}$;

each $R^{12}$ is independently selected from halo, CN, $C_{1-6}$ alkyl, and $OR^{a4}$;

each $R^{a1}$, $R^{c1}$, and $R^{d1}$ is independently selected from H and $C_{1-6}$ alkyl;

alternatively, $R^{c1}$ and $R^{d1}$ attached to the same N atom, together with the N atom to which they are attached, form a 6-membered heterocycloalkyl group;

each $R^{b1}$ is independently selected from $C_{1-6}$ alkyl; and each $R^{a3}$ and $R^{a4}$ is independently selected from H and $C_{1-6}$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds provided herein are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At certain places, the definitions or embodiments refer to specific rings (e.g., an azetidine ring, a pyridine ring, etc.). Unless otherwise indicated, these rings can be attached any ring member provided that the valency of the atom is not exceeded. For example, an azetidine ring may be attached at any position of the ring, whereas an azetidin-3-yl ring is attached at the 3-position.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds provided herein in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

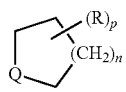

then it is to be understood that substituent R can occur p number of times on the ring, and R can be a different moiety at each occurrence. It is to be understood that each R group may replace any hydrogen atom attached to a ring atom, including one or both of the $(CH_2)_n$ hydrogen atoms. Further, in the above example, should the variable Q be defined to include hydrogens, such as when Q is said to be $CH_2$, NH, etc., any floating substituent such as R in the above example, can replace a hydrogen of the Q variable as well as a hydrogen in any other non-variable component of the ring.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1,-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "$C_{n-m}$ alkoxycarbonyl" refers to a group of formula —C(O)O— alkyl, wherein the alkyl group has n to m carbon atoms. In some embodiments, the alkyl group has 1 to 6, 1 to 4, or 1 to 3 carbon atoms. Examples of alkoxycarbonyl groups include, but are not limited to, methoxycarbonyl, ethoxycarbonyl, propoxycarbonyl (e.g., n-propoxycarbonyl and isopropoxycarbonyl), butoxycarbonyl (e.g., n-butoxycarbonyl and tert-butoxycarbonyl), and the like.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms. Examples of alkylcarbonyl groups include, but are not limited to, methylcarbonyl, ethylcarbonyl, propylcarbonyl (e.g., n-propylcarbonyl and isopropylcarbonyl), butylcarbonyl (e.g., n-butylcarbonyl and tert-butylcarbonyl), and the like.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms.

In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "amino" refers to a group of formula —NH$_2$.

As used herein, the term "carbamyl" to a group of formula —C(O)NH$_2$.

As used herein, the term "carbonyl", employed alone or in combination with other terms, refers to a —C(=O)— group, which may also be written as C(O).

As used herein, the term "carboxy" refers to a —C(O)OH group.

As used herein, the term "cyano-$C_{1-3}$ alkyl" refers to a group of formula —($C_{1-3}$ alkylene)-CN.

As used herein, the term "HO—$C_{1-3}$ alkyl" refers to a group of formula —($C_{1-3}$ alkylene)-OH.

As used herein, the term "HO—C1-3 alkyl" refers to a group of formula —(C1-3 alkylene)-OH.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, "halo" refers to F, Cl, Br, or I. In some embodiments, halo is F, Cl, or Br. In some embodiments, halo is F or Cl.

As used herein, "$C_{n-m}$ haloalkoxy" refers to a group of formula —O-haloalkyl having n to m carbon atoms. An example haloalkoxy group is OCF$_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons ($C_{3-10}$).

In some embodiments, the cycloalkyl is a $C_{3-10}$ monocyclic or bicyclic cycloalkyl. In some embodiments, the cycloalkyl is a $C_{3-7}$ monocyclic cycloalkyl. In some embodiments, the cycloalkyl is a $C_{3-10}$ monocyclic or bicyclic non-aromatic carbocycle, which optionally has ring members which have oxo (=O) or sulfido (=S) substitution and which optionally has a phenyl or 5-6 membered aromatic heterocycle fused to the non-aromatic portion of the ring structure, wherein the heterocycle has 1-3 ring members independently selected from N, S, or O. In some embodiments, the cycloalkyl is a $C_{3-7}$ monocyclic non-aromatic carbocycle, which optionally has ring members which have oxo (=O) or sulfido (=S) substitution and which optionally has a phenyl or 5-6 membered aromatic heterocycle fused to the non-aromatic portion of the ring structure, wherein the heterocycle has 1-3 ring members independently selected from N, S, or O.

In some embodiments, the cycloalkyl is a $C_{3-7}$ monocyclic cycloalkyl. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, or cyclohexyl.

As used herein, the term "aryl," employed alone or in combination with other terms, refers to an aromatic hydrocarbon group, which may be monocyclic or polycyclic (e.g., having 2, 3 or 4 fused rings). Examples of aryl rings include, but are not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl or naphthyl. In some embodiments, the aryl group is phenyl.

As used herein, the term "phenylene", refers to a divalent phenyl linking group. In some embodiments, the phenylene is optionally substituted as described herein.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In one embodiment the heteroaryl group is a 5 to 10 membered heteroaryl group. In another embodiment the heteroaryl group is a 5 to 6 membered heteroaryl group. In certain embodiments, the heteroaryl group is a monocyclic or bicyclic aromatic ring system having 5 to 10 ring-forming atoms, wherein 1 to 4 ring-forming atoms are heteroatoms independently selected from N, O, and S, wherein the N and S as ring members are each optionally oxidized, the carbon ring members may be optionally replaced by carbonyl. In another preferred embodiment, the heteroaryl group is a monocyclic aromatic ring system having 5 to 6 ring-forming atoms, wherein 1 to 4 ring-forming atoms are heteroatoms independently selected from N, O, and S, wherein the N and S as ring members are each optionally oxidized, the carbon ring members may be optionally replaced by carbonyl.

In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl, pyridone, uracil and pyridazinyl. In some embodiments, pyridone is substituted e.g., 1-methylpyridin-2(1H)-one and 1-phenylpyridin-2(1H)-one. In some embodiments, uracil is substituted with, e.g., phenyl, isopropyl, and pyridinyl. In some embodiments, uracil is substituted with phenyl and isopropyl, e.g., 1-isopropyl-2,4-dioxo-3-phenyl-1,2,3,4-tetrahydropyrimidine. In some embodiments, uracil is substituted with pyridinyl and isopropyl, e.g., 1-isopropyl-2,4-dioxo-3-(pyridin-2-yl)-1,2,3,4-tetrahydropyrimidine.

As used herein, the term "heteroarylene", refers to a divalent heteroaryl linking group. In some embodiments, the heteroarylene is optionally substituted as described herein.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group is a morpholine ring, pyrrolidine ring, piperazine ring, piperidine ring, dihydropyran ring, tetrahydropyran ring, tetrahydropyridine, azetidine ring, or tetrahydrofuran ring. In certain embodiments, the heterocycloalkyl group is a monocyclic or bicyclic non-aromatic ring or ring system having 4 to 10 ring-forming atoms, wherein 1 to 4 ring-forming atoms are heteroatoms independently selected from N, O, and S, wherein the N and S as ring members are each optionally oxidized, the carbon ring members may be optionally replaced by carbonyl, and the heterocycloalkyl group can be optionally fused to a 5-6 membered heteroaryl or phenyl ring, wherein the 5-6 membered heteroaryl ring may have 1-3 heteroatom ring members independently selected from N, S, and O. In another embodiment, the heterocycloalkyl group is a monocyclic non-aromatic ring or ring system having 4 to 6 ring-forming atoms, wherein 1 to 2 ring-forming atoms are heteroatoms independently selected from N, O, and S, wherein the N and S as ring members are each optionally oxidized, the carbon ring members may be optionally replaced by carbonyl, and the heterocycloalkyl group can be optionally fused to a 5-6 membered heteroaryl or phenyl ring, wherein the 5-6 membered heteroaryl ring may have 1-3 heteroatom ring members independently selected from N, S, and O. In some embodiments, a 10-membered heterocycloalkyl group is 7,8-dihydroquinoline-2,5(1H,6H)-dione. In some embodiments, a 6-membered heterocycloalkyl group is piperidinyl, piperazinyl, or tetrahydropyranyl.

In some embodiments, the aryl group (e.g., phenyl), heteroaryl group, heterocycloalkyl group, or cycloalkyl group as used herein (e.g., in variables $Cy^{A1}$, $Cy^{A2}$, $Cy^{A3}$, $Cy^C$ etc.) can be a terminal group or an internal group (e.g., a divalent linker). In some embodiments, the terms aryl, heteroaryl, heterocycloalkyl, and cycloalkyl and their corresponding arylene, heteroarylene, heterocycloalkylene and cycloalkylene terms are used interchangeably. A skilled artisan would readily recognize whether such a group is a terminal substituent or a linker based on the structure, the substituents described herein, and the context in which such a term appears. For example, even though the disclosure may list phenyl in the definition of variables such as $Cy^{A2}$, depending on the substitution pattern, the disclosure also covers phenylene groups.

As used herein, "$C_{n-m}$ cycloalkyl-$C_{o-p}$ alkylene" refers to a group of formula-alkylene-cycloalkyl, wherein the cycloalkyl group has n to m ring members and the alkylene group has o to p carbon atoms.

As used herein, "$C_{n-m}$ heterocycloalkyl-$C_{o-p}$ alkylene" refers to a group of formula-alkylene-heterocycloalkyl, wherein the heterocycloalkyl group has n to m ring members and the alkylene group has o to p carbon atoms.

As used herein, "phenyl-$C_{o-p}$ alkylene" refers to a group of formula-alkylene-phenyl, wherein the alkylene group has o to p carbon atoms.

As used herein, "$C_{n-m}$ aryl-$C_{o-p}$ alkylene" refers to a group of formula-alkylene-aryl, wherein the aryl group has n to m ring members and the alkylene group has o to p carbon atoms.

As used herein, "$C_{n-m}$ heteroaryl-$C_{o-p}$ alkylene" refers to a group of formula-alkylene-heteroaryl, wherein the heteroaryl group has n to m ring members and the alkylene group has o to p carbon atoms.

As used herein, the term "oxo" refers to an oxygen atom as a divalent substituent, forming a carbonyl group when attached to a carbon (e.g., C=O), or attached to a heteroatom forming a sulfoxide or sulfone group.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as □-camphorsulfonic acid.

Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein.

Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

The following abbreviations may be used herein: AcOH (acetic acid); $Ac_2O$ (acetic anhydride); aq. (aqueous); atm. (atmosphere(s)); Boc (t-butoxycarbonyl); br (broad); Cbz (carboxybenzyl); calc. (calculated); d (doublet); dd (doublet of doublets); DCM (dichloromethane); DEAD (diethyl azodicarboxylate); DIAD (N,N'-diisopropyl azidodicarboxylate); DIPEA (N,N-diisopropylethylamine); DMF (N,N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography-mass spectrometry); m (multiplet); M (molar); mCPBA (3-chloroperoxybenzoic acid); $MgSO_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); $NaHCO_3$ (sodium bicarbonate); NaOH (sodium hydroxide); $Na_2SO_4$ (sodium sulfate); $NH_4Cl$ (ammonium chloride); $NH_4OH$ (ammonium hydroxide); nM (nanomolar); NMR (nuclear magnetic resonance spectroscopy); OTf (trifluoromethanesulfonate); Pd (palladium); Ph (phenyl); pM (picomolar); PMB (para-methoxybenzyl), $POCl_3$ (phosphoryl chloride); RP-HPLC (reverse phase high performance liquid chromatography); s (singlet); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); μg (microgram(s)); μL (microliter(s)); μM (micromolar); wt % (weight percent).

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the TAM kinases with a compound of the disclosure includes the administration of a compound of the present disclosure to an individual or patient, such as a human, having TAM, as well as, for example, introducing a compound of the disclosure into a sample containing a cellular or purified preparation containing the TAM kinases.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease; for example, inhibiting a disease, condition or disorder in an individual who is experiencing or displaying the pathology or symptomotology of the disease, condition or disorder (i.e., arresting further development of the pathology and/or symptomotology), or 2) ameliorating the disease; for example, ameliorating a disease, condition or disorder in an individual who is experiencing or displaying the pathology or symptomotology of the disease, condition or disorder (i.e., reversing the pathology and/or symptomotology).

As used herein the term "preventing" or "prevention" refers to preventing the disease; for example, preventing a disease, condition or disorder in an individual who may be predisposed to the disease, condition or disorder but does not yet experience or display the pathology or symptomotology of the disease.

Synthesis

Compounds provided herein, including salts thereof, can be prepared using known organic synthesis techniques and according to various possible synthetic routes.

The reactions for preparing compounds provided herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds provided herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry, or by chromatography such as high performance liquid chromatography (HPLC) or thin layer chromatography.

The expressions, "ambient temperature", "room temperature", and "r.t.", as used herein, are understood in the art, and refer generally to a temperature, e.g. a reaction temperature, that is about the temperature of the room in which the reaction is carried out, for example, a temperature from about 20° C. to about 30° C.

Compounds as disclosed herein can be prepared by one skilled in the art according to preparatory routes known in the literature and according to various possible synthetic routes. Example synthetic methods for preparing compounds of the present application are provided in Scheme 1 below.

The reactions for preparing compounds provided herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds provided herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry, or by chromatography such as high performance liquid chromatography (HPLC) or thin layer chromatography.

The expressions, "ambient temperature", "room temperature", and "r.t.", as used herein, are understood in the art, and refer generally to a temperature, e.g. a reaction temperature, that is about the temperature of the room in which the reaction is carried out, for example, a temperature from about 20° C. to about 30° C.

Compounds as disclosed herein can be prepared by one skilled in the art according to preparatory routes known in the literature. A compound of Formula I can be prepared according to Scheme 1. Compounds (i) can be prepared by standard Suzuki coupling of bromides (i-a) with boronic esters or acids (i-b), wherein $R^1$ contains the alkenylene functionality. Catalytic hydrogenation of the $R^1$ functional group using Pd on carbon or another suitable catalyst can then provide compounds (ii) wherein $R^1$ contains the alkylene functionality. Selective bromination of compound (ii) using, e.g., NBS, yields bromides (iii) which are then directly treated with boronic esters or acids (iv) under, e.g., standard Suzuki coupling conditions, to afford compounds of Formula I. Alternatively, compounds of Formula I can be prepared through Suzuki coupling of bromides (iii) with boronic esters or acids (v) followed by reaction of the resultant amines (vi) with carboxylic acids (vii), and a suitable coupling reagent such as HATU or BOP.

Scheme 1

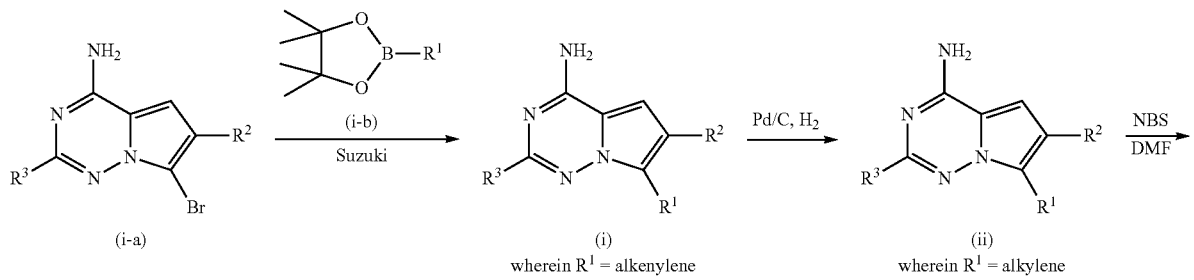

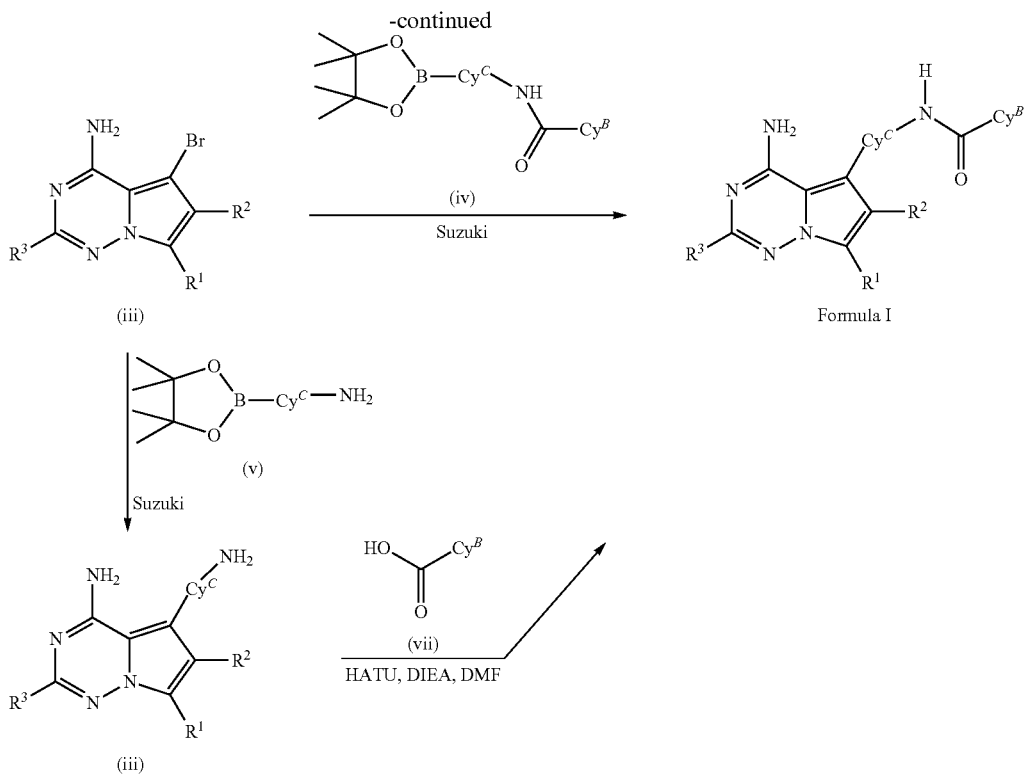

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of TAM kinases as described below.

Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Haque, A. Combs, J. Combi. Chem., 5, 670 (2003); and "Preparative LC-MS Purification: Improved Compound Specific Method Optimization", K. Blom, B. Glass, R. Sparks, A. Combs, J. Combi. Chem., 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 μm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, J. Comb. Chem., 6, 874-883 (2004)]. Typically, the flow rate used with the 30×100 mm column was 60 mL/minute.

pH=10 purifications: Waters XBridge $C_{18}$ 5 μm particle size, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, J. Comb. Chem., 6, 874-883 (2004)]. Typically, the flow rate used with 30×100 mm column was 60 mL/minute.

TAM Kinases

Receptor tyrosine kinases (RTKs) are cell surface proteins that transmit signals from the extracellular environment to the cell cytoplasm and nucleus to regulate cellular events such as survival, growth, proliferation, differentiation, adhesion and migration. All RTKs contain an extracellular ligand binding domain and a cytoplasmic protein tyrosine kinase domain. Ligand binding leads to the dimerization of RTKs, which triggers the activation of the cytoplasmic kinase and initiates downstream signal transduction pathways. RTKs can be classified into distinct subfamilies based on their sequence similarity. The TAM subfamily consists of three RTKs including TYRO3, AXL and MER (Graham et al., 2014, Nature reviews Cancer 14, 769-785; and Linger et al., 2008, Oncogene 32, 3420-3431). TAM kinases are characterized by an extracellular ligand binding domain consisting of two immunoglobulin-like domains and two fibronectin type III domains. Two ligands, growth arrest specific 6 (GAS6) and protein S (ProS), have been identified for TAM kinases. GAS6 can bind to and activate all three TAM kinases, while ProS is a ligand for MER and TYRO3 (Graham et al., 2014, Nature reviews Cancer 14, 769-785).

TAM kinases are over-expressed in many cancers and play important roles in tumor initiation and maintenance; therefore, TAM inhibition represents an attractive approach for targeting another class of oncogenic RTKs (Graham et al., 2014, Nature reviews Cancer 14, 769-785; and Linger et al., 2008, Oncogene 32, 3420-3431).

Axl was originally identified as a transforming gene from DNA of patients with chronic myelogenous leukemia (O'Bryan et al., 1991, Molecular and cellular biology 11, 5016-5031). GAS6 binds to Axl and induces subsequent auto-phosphorylation and activation of Axl tyrosine kinase. Axl activates several downstream signaling pathways including PI3K-Akt, Raf-MAPK, PLC-PKC (Feneyrolles et al., 2014, Molecular cancer therapeutics 13, 2141-2148; Linger et al., 2008, Oncogene 32, 3420-3431). AXL is over-expressed or amplified in a variety of malignancies including lung cancer, prostate cancer, colon cancer, breast cancer, melanoma, and renal cell carcinoma (Linger et al., 2008, Oncogene 32, 3420-3431). Over-expression of AXL is correlated with poor prognosis (Linger et al., 2008, Oncogene 32, 3420-3431). As a result, AXL activation promotes cancer cell survival, proliferation, angiogenesis, metastasis, and resistance to chemotherapy and targeted therapies. AXL knockdown or AXL antibody can inhibit the migration of breast cancer and NSCLC cancer in vitro, and blocked tumor growth in xenograft tumor models (Li et al., 2009, Oncogene 28, 3442-3455). In pancreatic cancer cells, inhibition of AXL decreased cell proliferation and survival (Koorstra et al., 2009, Cancer biology & therapy 8, 618-626). In prostate cancer, AXL inhibition decreased cell migration, invasion, and proliferation (Tai et al., 2008, Oncogene 27, 4044-4055). In addition, AXL over-expression or amplification is a major mechanism for resistance to EGFR inhibitors by lung cancer cells, and AXL inhibition can reverse the resistance (Zhang et al., 2012, Nature genetics 44, 852-860).

Mer was originally identified as a phospho-protein from a lymphoblastoid expression library (Graham et al., 1995, Oncogene 10, 2349-2359). Both GAS6 and ProS can bind to Mer and induce the phosphorylation and activation of Mer kinase (Lew et al., 2014. eLife, 3:e03385). Like Axl, Mer activation also conveys downstream signaling pathways including PI3K-Akt and Raf-MAPK (Linger et al., 2008, Oncogene 32, 3420-3431). MER is over-expressed in many cancers including multiple myeloma, gastric, prostate, breast, melanoma and rhabdomyosarcoma (Linger et al., 2008, Oncogene 32, 3420-3431). MER knockdown inhibits multiple myeloma cell growth in vitro and in xenograft models (Waizenegger et al., 2014, Leukemia, 1-9). In acute myeloid leukemia, MER knockdown induced apoptosis, decreased colony formation, and increased survival in a mouse model (Lee-Sherick et al., 2013, Oncogene 32, 5359-5368). MER inhibition increased apoptosis, decreased colony formation, increased chemo-sensitivity, and decreased tumor growth in NSCLC (Linger et al., 2013, Oncogene 32, 3420-3431). Similar effects are observed for MER knockdown in melanoma (Schlegel et al., 2013) and glioblastoma (Wang et al., 2013, Oncogene 32, 872-882).

Tyro3 was originally identified through a PCR-based cloning study (Lai and Lemke, 1991, Neuron 6, 691-704). Both ligands, GAS6 and ProS, can bind to and activate Tyro3. TYRO3 also plays a role in cancer growth and proliferation. TYRO3 is over-expressed in melanoma cells, and knockdown of TYRO3 induces apoptosis in these cells (Demarest et al., 2013, Biochemistry 52, 3102-3118).

In addition to their role as transforming oncogenes, TAM kinases have emerged as potential immune-oncology targets. The durable clinical responses to immune checkpoint blockade observed in cancer patients clearly indicate that the immune system plays a critical role in tumor initiation and maintenance. Genetic mutations from cancer cells can provide a diverse set of antigens that the immune cells can use to distinguish tumor cells from their normal counterpart. However, cancer cells have evolved multiple mechanisms to evade host immune surveillance. In fact, one hallmark of human cancer is its ability to avoid immune destruction. Cancer cells can induce an immune-suppressive microenvironment by promoting the formation of M2 tumor associated macrophages, myeloid derived suppressor cells (MDSC), and regulatory T cells. Cancer cells can also produce high levels of immune checkpoint proteins such as PD-L1 to induce T cell anergy or exhaustion. It is now clear that tumors co-opt certain immune-checkpoint pathways as a major mechanism of immune resistance (Pardoll, 2012, Cancer 12, 252-264). Antagonizing these negative regulators of T-cell function with antibodies has shown striking efficacy in clinical trials of a number of malignancies including advanced melanoma, non-small cell lung and bladder cancer. While these therapies have shown encouraging results, not all patients mount an anti-tumor response suggesting that other immune-suppressive pathways may also be important.

TAM kinases have been shown to function as checkpoints for immune activation in the tumor milieu. All TAM kinases are expressed in NK cells, and TAM kinases inhibit the anti-tumor activity of NK cells. LDC1267, a small molecule TAM inhibitor, activates NK cells, and blocks metastasis in tumor models with different histologies (Paolino et al., 2014, Nature 507, 508-512). In addition, MER kinase promotes the activity of tumor associated macrophages through the increased secretion of immune suppressive cytokines such as IL10 and IL4, and decreased production of immune activating cytokines such as IL12 (Cook et al., 2013, The Journal of clinical investigation 123, 3231-3242). MER inhibition has been shown to reverse this effect. As a result, MER knockout mice are resistant to PyVmT tumor formation (Cook et al., 2013, The Journal of clinical investigation 123, 3231-3242). The role of TAM kinases in the immune response is also supported by knockout mouse studies. TAM triple knockout mice (TKO) are viable. However, these mice displayed signs of autoimmune disease including enlarged spleen and lymph nodes, autoantibody production, swollen footpad and joints, skin lesions, and systemic lupus erythematosus (Lu and Lemke, 2001, Science 293, 306-311). This is consistent with the knockout phenotype for approved immune-oncology targets such as CTLA4 and PD-1. Both CTLA-4 and PD-1 knockout mice showed signs of autoimmune disease, and these mice die within a few weeks after birth (Chambers et al., 1997, Immunity 7, 885-895; and Nishimura et al., 2001, Science 291, 319-322).

TAM inhibition will have not only direct activity against neoplastic cells, but also activate the anti-cancer immune response. Thus TAM inhibitors represent an attractive approach for the treatment of cancer as single agents. In addition, TAM inhibitors may be combined with other targeted therapies, chemotherapies, radiation, or immunotherapeutic agents to achieve maximal efficacy in the clinic.

Methods of Use

Compounds of the present disclosure can modulate or inhibit the activity of TAM kinases. For example, the compounds of the disclosure can be used to inhibit activity of a TAM kinase in a cell or in an individual or patient in need of inhibition of the kinases by administering an inhibiting amount of a compound of the disclosure to the cell, individual, or patient.

In some embodiments, the compounds of the disclosure are selective for the TAM kinases over one or more of other kinases. In some embodiments, the compounds of the disclosure are selective for the TAM kinases over other kinases. In some embodiments, the selectivity is 2-fold or more, 3-fold or more, 5-fold or more, 10-fold or more, 25-fold or more, 50-fold or more, or 100-fold or more.

The compounds of the invention can inhibit one or more of AXL, MER and TYRO3. In some embodiments the compounds are selective for one TAM kinase over another. "Selective" means that the compound binds to or inhibits a TAM kinase with greater affinity or potency, respectively, compared to a reference enzyme, such as another TAM kinase. For example, the compounds can be selective for AXL over MER and TYRO3, selective for MER over AXL and TYRO3, or selective for AXL and MER over TYRO3. In some embodiments, the compounds inhibit all of the TAM family members (e.g., AXL, MER and TYRO3). In some embodiments, the compounds can be selective for AXL and MER over TYRO3 and other kinases. In some embodiments, provided herein is a method for inhibiting AXL and MER kinase, which comprises contacting the AXL and MER kinase with a compound provided herein, or a pharmaceutically acceptable salt thereof.

As TAM kinases inhibitors, the compounds of the disclosure are useful in the treatment of various diseases associated with abnormal expression or activity of the TAM kinases. Compounds which inhibit TAM kinases will be useful in providing a means of preventing the growth or inducing apoptosis in tumors, particularly by inhibiting angiogenesis. It is therefore anticipated that the compounds will prove useful in treating or preventing proliferative disorders such as cancers. In particular, tumours with activating mutants of receptor tyrosine kinases or upregulation of receptor tyrosine kinases may be particularly sensitive to the inhibitors.

In certain embodiments, the disclosure provides a method for treating a disease or disorder mediated by TAM kinases in a patient in need thereof, comprising the step of administering to said patient a compound provided herein, or a pharmaceutically acceptable composition thereof.

For example, the compounds of the disclosure are useful in the treatment of cancer. Example cancers include bladder cancer, breast cancer, cervical cancer, colorectal cancer, cancer of the small intestine, colon cancer, rectal cancer, cancer of the anus, endometrial cancer, gastric cancer, head and neck cancer (e.g., cancers of the larynx, hypopharynx, nasopharynx, oropharynx, lips, and mouth), kidney cancer, liver cancer (e.g., hepatocellular carcinoma, cholangiocellular carcinoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, esophageal cancer, gall bladder cancer, pancreatic cancer (e.g. exocrine pancreatic carcinoma), stomach cancer, thyroid cancer, parathyroid cancer, skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors).

Other cancers treatable with the compounds of the disclosure include bone cancer, intraocular cancers, gynecological cancers, cancer of the endocrine system, cancer of the adrenal gland, sarcoma of soft tissue, cancer of the urethra, cancer of the penis, pituitary cancer, triple-negative breast cancer (TNBC) and environmentally induced cancers including those induced by asbestos.

Further example cancers include hematopoietic malignancies such as leukemia or lymphoma, multiple myeloma, chronic lymphocytic lymphoma, adult T cell leukemia, B-cell lymphoma, cutaneous T-cell lymphoma, acute myelogenous leukemia, Hodgkin's or non-Hodgkin's lymphoma, myeloproliferative neoplasms (e.g., polycythemia vera, essential thrombocythemia, and primary myelofibrosis), Waldenstrom's Macroglubulinemia, hairy cell lymphoma, chronic myelogenic lymphoma, acute lymphoblastic lymphoma, AIDS-related lymphomas, and Burkitt's lymphoma.

Other cancers treatable with the compounds of the disclosure include tumors of the eye, glioblastoma, melanoma, rhabdosarcoma, lymphosarcoma, and osteosarcoma.

Compounds of the disclosure can also be useful in the inhibition of tumor metastisis.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), small lymphocytic lymphoma (SLL), chronic myelogenous leukemia (CML), diffuse large B-cell lymphoma (DLBCL), mantle cell lymphoma (MCL), marginal zone lymphoma (MZL), Non-Hodgkin lymphoma (including relapsed or refractory NHL), follicular lymphoma (FL), Hodgkin lymphoma, lymphoblastic lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL), multiple myeloma, cutaneous T-cell lymphoma, peripheral T-cell lymphoma, Waldenstrom's Macroglubulinemia, hairy cell lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), colorectal cancer and bile duct cancer.

Exemplary genitourinary tract cancers include cancers of the kidney (adenocarcinoma, Wilm's tumor [nephroblastoma], renal cell carcinoma), bladder and urethra (squamous cell carcinoma, transitional cell carcinoma, adenocarcinoma, urothelial carcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma, Lhermitte-Duclos disease, neoplasm of the central nervous system (CNS), primary CNS lymphoma and spinal axis tumor.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers.

In some embodiments, the present disclosure provides a method for treating hepatocellular carcinoma in a patient in need thereof, comprising the step of administering to said patient a compound of Formula (I) or a compound as disclosed herein, or a pharmaceutically acceptable salt thereof, or a composition comprising a compound of Formula (I) or a compound as disclosed herein.

In some embodiments, the present disclosure provides a method for treating Rhabdomyosarcoma, esophageal cancer, breast cancer, or cancer of a head or neck, in a patient in need thereof, comprising the step of administering to said patient a compound Formula (I) or a compound as disclosed herein, or a pharmaceutically acceptable salt thereof, or a composition comprising a compound of Formula (I) or a compound as disclosed herein.

In some embodiments, the present disclosure provides a method of treating cancer, wherein the cancer is selected from hepatocellular cancer, breast cancer, bladder cancer, colorectal cancer, melanoma, mesothelioma, lung cancer, prostate cancer, pancreatic cancer, testicular cancer, thyroid cancer, squamous cell carcinoma, glioblastoma, neuroblastoma, uterine cancer, and rhabdosarcoma.

Targeting TAM receptor tyrosine kinases can provide a therapeutic approach to treat viral diseases (T Shibata, et. al. *The Journal of Immunology*, 2014, 192, 3569-3581). The present disclosure provides a method for treating infections such as viral infections. The method includes administering to a patient in need thereof, a therapeutically effective amount of a compound of Formula (I) or any of the formulas as described herein, a compound as recited in any of the claims and described herein, a salt thereof. Examples of viruses causing infections treatable by methods of the present disclosure include, but are not limit to, human immunodeficiency virus, human papillomavirus, influenza, hepatitis A, B, C or D viruses, adenovirus, poxvirus, herpes simplex viruses, human cytomegalovirus, severe acute respiratory syndrome virus, ebola virus, Marburg virus and measles virus. In some embodiments, viruses causing infections treatable by methods of the present disclosure include, but are not limit to, hepatitis (A, B, or C), herpes virus (e.g., VZV, HSV-1, HAV-6, HSV-II, and CMV, Epstein Barr virus), adenovirus, influenza virus, flaviviruses (for example: West Nile, dengue, tick-borne encephalitis, yellow fever, Zika), echovirus, rhinovirus, coxsackie virus, cornovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

In some embodiments, the present disclosure provides a method for treating thrombus formation (J. M. E. M. Cosemans et. al. *J. of Thrombosis and Haemostasis* 2010, 8, 1797-1808 and A. Angelillo-Scherrer et. al. *J. Clin. Invest.* 2008, 118, 583-596).

Combination Therapy

One or more additional pharmaceutical agents or treatment methods such as, for example, anti-viral agents, chemotherapeutics or other anti-cancer agents, immune enhancers, immunosuppressants, radiation, anti-tumor and antiviral vaccines, cytokine therapy (e.g., IL2, GM-CSF, etc.), and/or tyrosine kinase inhibitors can be used in combination with the compounds of Formula (I) or a compound as described herein for treatment of TAM-associated diseases, disorders or conditions. The agents can be combined with the present compounds in a single dosage form, or the agents can be administered simultaneously or sequentially as separate dosage forms.

Suitable antiviral agents contemplated for use in combination with the compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddl); zalcitabine (ddC); stavudine (d4T); lamivudine (3TC); abacavir (1592U89); adefovir dipivoxil [bis (POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene);

DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with the compounds of the present application for the treatment of cancer include chemotherapeutic agents, targeted cancer therapies, immunotherapies or radiation therapy. Compounds of this application may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds of the present disclosure. These include anti-androgens including but not limited to flutamide, bicalutamide, and nilutamide, luteinizing hormone-releasing hormone (LHRH) analogs including leuprolide, oserelin, triptorelin, and histrelin, LHRH antagonists (e.g. degarelix), androgen receptor blockers (e.g. enzalutamide) and agents that inhibit androgen production (e.g. abiraterone).

Compounds of the present disclosure may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, PDGFR, FGFR1, FGFR2, FGFR3, FGFR4, TrkA, TrkB, TrkC, ROS, c-Kit, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with TAM inhibitors. These include onartumzumab, tivantnib, and INC-280. Agents against FGFRs include but not limited to AZD4547, BAY1187982, ARQ087, BGJ398, BIBF1120, TKI258, lucitanib, dovitinib, TAS-120, JNJ-42756493, and Debio1347. Agents against Trks include but not limited to LOXO-101 and RXDX-101. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with TAM inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds of the present disclosure include inhibitors of the PI3K-AKT-mTOR pathway, inhibitors of the Raf-MAPK pathway, inhibitors of JAK-STAT pathway, inhibitors of Pim kinases, and inhibitors of protein chaperones and cell cycle progression.

Agents against the PI3 kinase include but are not limited to pilaralisib, idelalisib, buparlisib, and IPI-549. In some embodiments, the PI3K inhibitor is selective for PI3K alpha, PI3K beta, PI3K gamma or PI3K delta. Inhibitors of mTOR such as rapamycin, sirolimus, temsirolimus, and everolimus may be combined with TAM kinases inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), PARP (e.g., olaparib), and proteasomes (e.g., bortezomib, carfilzomib) can also be combined with compounds of the present disclosure. In some embodiments, the JAK inhibitor is selective for JAK1 over JAK2 and JAK3. Agents against Pim kinases include but not limited to LGH447, INCB053914, and SGI-1776.

Other suitable agents for use in combination with the compounds of the present disclosure include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with the compounds of the present disclosure include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds provided herein may also be combined with immunotherapy drugs, including cytokines such as interferon alpha, interleukin 2, and tumor necrosis factor (TNF) inhibitors.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, *vinca* alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-β, etc.).

Other anti-cancer agents include CSF1R inhibitors (PLX3397, LY3022855, etc.) and CSF1R antibodies (IMC-CS4, RG7155, etc.).

Other anti-cancer agents include BET inhibitors (INCB054329, OTX015, CPI-0610, etc.), LSD1 inhibitors (GSK2979552, INCB059872, etc), HDAC inhibitors (panobinostat, vorinostat, etc), DNA methyl transferase inhibitors (azacitidine and decitabine), and other epigenetic modulators.

Other anti-cancer agents include Bcl2 inhibitor ABT-199, and other Bcl-2 family protein inhibitors.

Other anti-cancer agents include TGF beta receptor kinase inhibitor such as LY2157299.

Other anti-cancer agents include BTK inhibitor such as ibrutinib.

Other anti-cancer agents include beta catenin pathway inhibitors, notch pathway inhibitors and hedgehog pathway inhibitors.

Other anti-cancer agents include inhibitors of kinases associated cell proliferative disorder. These kinases include but not limited to Aurora-A, CDK1, CDK2, CDK3, CDK5, CDK7, CDK8, CDK9, ephrin receptor kinases, CHK1, CHK2, SRC, Yes, Fyn, Lck, Fer, Fes, Syk, Itk, Bmx, GSK3, JNK, PAK1, PAK2, PAK3, PAK4, PDK1, PKA, PKC, Rsk and SGK.

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

One or more additional immune checkpoint inhibitors can be used in combination with a compound as described herein for treatment of TAM-associated diseases, disorders or conditions. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, CD96, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, CD96, TIGIT, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab, pembrolizumab, or PDR001. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A (atezolizumab) or MEDI4736 (durvalumab).

In some embodiments, the inhibitor of an immune checkpoint molecule is an inhibitor of CTLA-4, e.g., an anti-CTLA-4 antibody. In some embodiments, the anti-CTLA-4 antibody is ipilimumab or tremelimumab.

In some embodiments, the inhibitor of an immune checkpoint molecule is an inhibitor of LAG3, e.g., an anti-LAG3 antibody. In some embodiments, the anti-LAG3 antibody is BMS-986016 or LAG525.

In some embodiments, the inhibitor of an immune checkpoint molecule is an inhibitor of GITR, e.g., an anti-GITR antibody. In some embodiments, the anti-GITR antibody is TRX518, MK-4166, INCAGN01876 or MK-1248.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562, INCAGN01949, GSK2831781, GSK-3174998, MOXR-0916, PF-04518600 or LAG525. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

Compounds of the present disclosure can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

The compounds of the present disclosure can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

The compounds of the present disclosure can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of the present disclosure can be combined with dendritic cells immunization to activate potent anti-tumor responses.

The compounds of the present disclosure can be used in combination with bispecific macrocyclic peptides that target Fc alpha or Fc gamma receptor-expressing effectors cells to tumor cells. The compounds of the present disclosure can also be combined with macrocyclic peptides that activate host immune responsiveness.

The compounds of the present disclosure can be used in combination with arginase inhibitors, for example CB-1158.

The compounds of the present disclosure can be used in combination with bone marrow transplant for the treatment of a variety of tumors of hematopoietic origin.

The compounds of the present disclosure can be used as anticoagulant as single agent or in combination with other anticoagulants including but not limited to apixaban, dabigatran, edoxaban, fondaparinex, heparin, rivaroxaban, and warfarin.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds provided herein can be administered in the form of pharmaceutical compositions which refers to a combination of a compound provided herein, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This application also includes pharmaceutical compositions which contain, as the active ingredient, one or more of the compounds provided herein in combination with one or more pharmaceutically acceptable carriers. In making the compositions of the present disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the present disclosure can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present disclosure. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present disclosure can vary according to, for example, the particular use for which the treatment is made, the manner of administration of the compound, the health and condition of the patient, and the judgment of the prescribing physician. The proportion or concentration of a compound provided herein in a pharmaceutical composition can vary depending upon a number of factors including dosage, chemical characteristics (e.g., hydrophobicity), and the route of administration. For example, the compounds provided herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds provided herein can also be formulated in combination with one or more additional active ingredients which can include any pharmaceutical agent such as antiviral agents, vaccines, antibodies, immune enhancers, immune suppressants, anti-inflammatory agents and the like.

Labeled Compounds and Assay Methods

Another aspect of the present disclosure relates to fluorescent dye, spin label, heavy metal or radio-labeled compounds provided herein that would be useful not only in imaging but also in assays, both in vitro and in vivo, for localizing and quantitating the TAM kinases in tissue samples, including human, and for identifying TAM kinases ligands by inhibition binding of a labeled compound. Accordingly, the present disclosure includes TAM kinases assays that contain such labeled compounds.

The present disclosure further includes isotopically-labeled compounds of the invention. An "isotopically" or "radio-labeled" compound is a compound provided herein where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}$H (also written as D for deuterium), $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro TAM kinases labeling and competition assays, compounds that incorporate $^{3}$H, $^{14}$C, $^{82}$Br, $^{125}$I, $^{131}$I, or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^{3}$H, $^{14}$C, $^{125}$I, $^{35}$S and $^{82}$Br.

Synthetic methods for incorporating radio-isotopes into organic compounds are applicable to compounds provided herein and are well known in the art.

A radio-labeled compound provided herein can be used in a screening assay to identify/evaluate compounds. In general terms, a newly synthesized or identified compound (i.e., test compound) can be evaluated for its ability to reduce binding of the radio-labeled compound of the application to the TAM kinases. Accordingly, the ability of a test compound to compete with the radio-labeled compound for binding to the TAM kinases directly correlates to its binding affinity.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7 or 8 deuterium atoms. Synthetic methods for including isotopes into organic compounds are known in the art.

Kits

The present disclosure also includes pharmaceutical kits useful, for example, in the treatment or prevention of TAM-associated diseases or disorders, obesity, diabetes and other diseases referred to herein which include one or more containers containing a pharmaceutical composition comprising a therapeutically effective amount of a compound provided herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of TAM kinases as described below.

Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 μm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge $C_{18}$ 5 μm particle size, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

EXAMPLES

Example 1. N-[4-(4-Amino-7-ethylpyrrolo[2,1-f][1,2,4]triazin-5-yl)phenyl]-1-(4-fluorophenyl)-2,5-dioxo-1,2,5,6,7,8-hexahydroquinoline-3-carboxamide

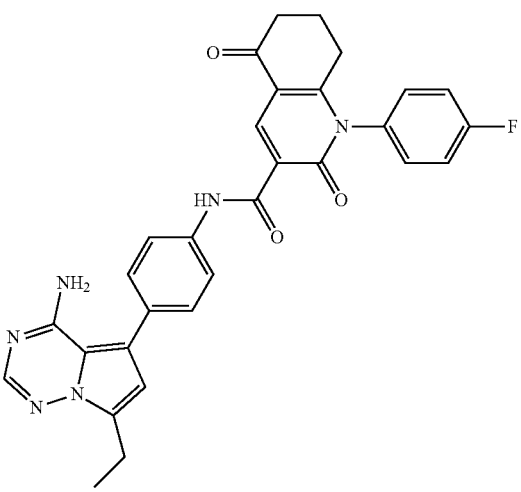 [SMILES: CCc1cc(-c2ccc(NC(=O)c3cc4c(n(-c5ccc(F)cc5)c3=O)CCCC4=O)cc2)c2c(N)ncnn12]

Step 1: N-[(2,6-Dioxocycloexylidene)methyl]urea

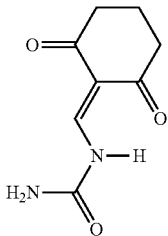

To a mixture of 1,3-cyclohexanedione (from Aldrich, 500 mg, 4.46 mmol) and urea (268 mg, 4.46 mmol) dissolved in N,N-dimethylformamide (1.73 mL at 50° C.), was added ethyl orthoformate (1.11 mL, 6.69 mmol) and acetic acid (8.9 mL). The reaction mixture was heated in a sealed tube at 90° C. for 3 h. The reaction mixture was cooled, concentrated under vacuum, and left at rt for crystallization. The resulting precipitate was filtered by vacuum and the cake was washed with cold sec-BuOH to give the desired product as off-white powders (536 mg, 66%). LCMS calcd for $C_8H_{11}N_2O_3(M+H)^+$: m/z=183.1. Found: 183.1.

Step 2: Methyl 2,5-dioxo-5,6,7,8-tetrahydro-2H-chromene-3-carboxylate

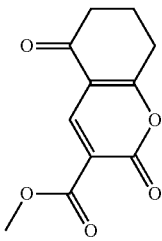 [SMILES: COC(=O)c1cc2c(oc1=O)CCCC2=O]

N-[(2,6-Dioxocyclohexylidene)methyl]urea (50 mg, 0.27 mmol) was dissolved in dry N,N-dimethylformamide (0.54 mL), followed by the addition of acetic acid, cyanomethyl ester (35.4 mg, 0.36 mmol) and potassium tert-butoxide (61.6 mg, 0.55 mmol) with stirring. The reaction mixture was heated at 100° C. for 1 h. After filtration and removal of the solvent, an oily residue was obtained as the desired product (70 mg). The crude product was used directly in the next step without further purification. LCMS calcd for $C_{11}H_{11}O_5(M+H)^+$: m/z=223.1. Found: 223.1.

Step 3: Methyl 1-(4-fluorophenyl)-2,5-dioxo-1,2,5,6,7,8-hexahydroquinoline-3-carboxylate

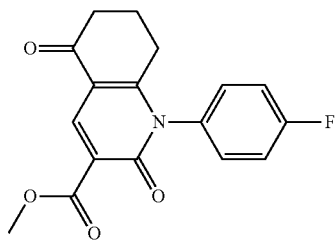 [SMILES: COC(=O)c1cc2c(n(-c3ccc(F)cc3)c1=O)CCCC2=O]

To a solution of methyl 2,5-dioxo-5,6,7,8-tetrahydro-2H-chromene-3-carboxylate (30 mg, 0.14 mmol) in tetrahydrofuran (0.4 mL) and N,N-dimethylformamide (0.1 mL) at rt was added p-fluoroaniline (15 mg, 0.14 mmol). The reaction mixture was stirred at rt for 3 h, followed by the addition of N-(3-dimethylaminopropyl)-N'-ethylcarbodiimide hydrochloride (34 mg, 0.18 mmol) and 4-dimethylaminopyridine (4.1 mg, 0.034 mmol) at rt. The reaction mixture was stirred at rt for additional 20 h. After filtration, the crude was purified by prep LC-MS (pH=2 method; Waters SunFire PrepC18 5 μm OBD™ column, 30×100 mm, 60 mL/min, eluting with a gradient of MeCN and water with 0.1% TFA) to give the desired product (12 mg, 28%). LCMS calcd for $C_{17}H_{15}FNO_4$ $(M+H)^+$: m/z=316.1. Found: 316.1.

Step 4: 1-(4-Fluorophenyl)-2,5-dioxo-1,2,5,6,7,8-hexahydroquinoline-3-carboxylic Acid

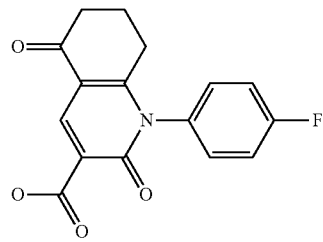 [SMILES: O=C1CCCc2c1cc(C(=O)O)c(=O)n2-c1ccc(F)cc1]

To a solution of methyl 1-(4-fluorophenyl)-2,5-dioxo-1,2,5,6,7,8-hexahydroquinoline-3-carboxylate (5.0 mg, 0.016 mmol) in methanol (0.10 mL) was added 1.0 M sodium hydroxide in water (0.15 mL). The reaction mixture was stirred at rt for 30 min, and the crude was neutralized with HCl (1N), diluted with EtOAc. The EtOAc layer was separated, and the aqueous layer was washed with EtOAc twice. The combined organic layers were dried, concentrated under vacuum to give the desired acid product as off-white powders. LCMS calcd for $C_{16}H_{13}FNO_4$ $(M+H)^+$: m/z=302.1. Found: 302.2.

Step 5: 7-Vinylpyrrolo[2,1-f][1,2,4]triazin-4-amine

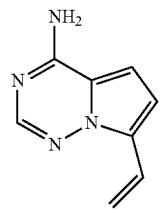

In a sealed flask a mixture of 4,4,5,5-tetramethyl-2-vinyl-1,3,2-dioxaborolane (from Aldrich, 1.52 g, 9.86 mmol), 7-bromopyrrolo[2,1-f][1,2,4]triazin-4-amine (from J & W Pharm Lab, 1.50 g, 7.04 mmol) and N,N-diisopropylethylamine (3.7 mL, 21 mmol) in 1,4-dioxane (20 mL) and water (0.97 mL) was stirred and flushed with $N_2$ for 5 min before bis(tri-t-butylphosphine)palladium (540 mg, 1.0 mmol) was added. The reaction mixture was sealed and heated at 110° C. in an oil bath for 60 min, filtered through a pad of celite and concentrated. The crude was purified by Biotage silica gel column chromatography (40 g column, 0 to 100% EtOAc in hexanes) to give the desired product as white powders (541 mg, 48%). LCMS calcd for $C_8H_9N_4$ $(M+H)^+$: m/z=161.1. Found: 161.1.

Step 6: 7-Ethylpyrrolo[2,1-f][1,2,4]triazin-4-amine

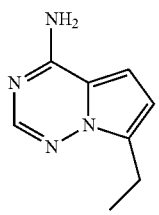

To a solution of 7-vinylpyrrolo[2,1-f][1,2,4]triazin-4-amine (1.00 g, 6.24 mmol) in methanol (30 mL) was added a mixture of palladium (1.33 g) (5% Pd on carbon). The reaction mixture was placed on hydrogen Parr shaker at 25 psi for 2 h. After filtration through a celite pad, the filtrate was concentrated under vacuum to give the desired product as off-white powders. LCMS calcd for $C_8H_{11}N_4(M+H)^+$: m/z=163.1. Found: 163.1.

Step 7: 5-Bromo-7-ethylpyrrolo[2,1-f][1,2,4]triazin-4-amine

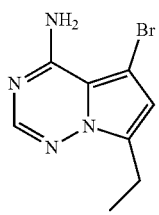

To a solution of 7-ethylpyrrolo[2,1-f][1,2,4]triazin-4-amine (600 mg, 3.7 mmol) in N,N-dimethylformamide (16 mL) was added N-bromosuccinimide (395 mg, 2.22 mmol). The resulting mixture was stirred at rt for 30 min, diluted with EtOAc and filtered. The filtrate was washed with saturated NaHCO$_3$, water, dried over Na$_2$SO$_4$, filtered and concentrated under vacuum to give the desired product as tan solid. LCMS calcd for $C_8H_{10}BrN_4$ $(M+H)^+$: m/z=241.0, 243.0. Found: 241.0, 243.0.

Step 8: 5-(4-Aminophenyl)-7-ethylpyrrolo[2,1-f][1,2,4]triazin-4-amine

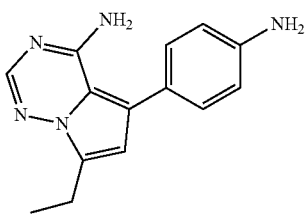 [SMILES: CCc1cc(-c2ccc(N)cc2)c2c(N)ncnn12]

In a sealed tube a mixture of 5-bromo-7-ethylpyrrolo[2,1-f][1,2,4]triazin-4-amine (200 mg, 0.83 mmol), 4-(4,4,5,5-tetramethyl-1,3,2-dioxaborolan-2-yl)aniline (from Aldrich, 236 mg, 1.08 mmol) and N,N-diisopropylethylamine (0.43 mL, 2.5 mmol) in 1,4-dioxane (3.24 mL) and water (0.30 mL) was stirred and flushed with N$_2$ for 5 min before bis(tri-t-butylphosphine)palladium (130 mg, 0.25 mmol) was added. The reaction mixture was sealed and heated at 110° C. in an oil bath for 1 h. After filtration, the crude was diluted with MeOH and purified by prep LC-MS (pH=10 method; XBridge™ PrepC18 5 μm OBD™ column, 30×100 mm, 60 mL/min, eluting with a gradient of MeCN and water with 0.15% NH$_4$OH) to give the desired product as light brown powders (88 mg, 42%). LCMS calcd for $C_{14}H_{16}N_5$ $(M+H)^+$: m/z=254.1. Found: 254.1.

Step 9: N-[4-(4-Amino-7-ethylpyrrolo[2,1-f][1,2,4]triazin-5-yl)phenyl]-1-(4-fluorophenyl)-2,5-dioxo-1,2,5,6,7,8-hexahydroquinoline-3-carboxamide 5-(4-Aminophenyl)-7-ethylpyrrolo[2,1-f][1,2,4]triazin-4-amine (3.2 mg, 0.013 mmol), 1-(4-fluorophenyl)-2,5-dioxo-1,2,5,6,7,8-hexahydroquinoline-3-carboxylic acid (4.6 mg, 0.015 mmol) (prepared in Example 1, step 4), N,N,N',N'-tetramethyl-O-(7-azabenzotriazol-1-yl)uronium hexafluorophosphate (12 mg, 0.032 mmol) in N,N-dimethylformamide (0.10 mL) and N,N-diisopropylethylamine (5.0 mg, 0.04 mmol) were mixed together and stirred at rt for 20 min. The mixture was filtered, concentrated and purified by prep LC-MS (pH=10 method; XBridge™ PrepC18 5 μm OBD™ column, 30×100 mm, 60 mL/min, eluting with a gradient of MeCN and water with 0.15% NH$_4$OH) to give the desired product as white powders (1.6 mg, 20%). LCMS calcd for $C_{30}H_{26}FN_6O_3(M+H)^+$: m/z=537.2. Found: 537.2.

Example 2. N-[4-(4-Amino-7-ethylpyrrolo[2,1-f][1,2,4]triazin-5-yl)phenyl]-1-[(1R)-2-hydroxy-1-phenylethyl]-2-oxo-1,2-dihydropyridine-3-carboxamide

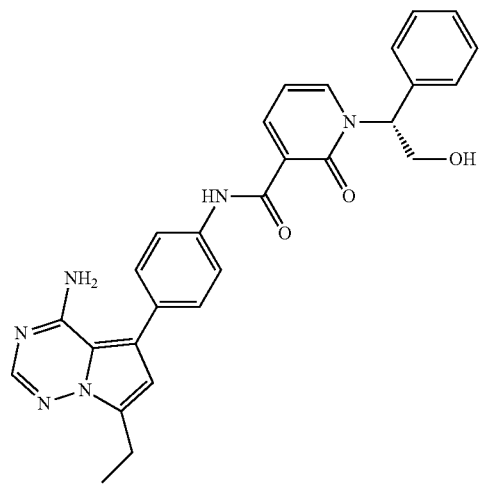 [SMILES: CCc1cc(-c2ccc(NC(=O)c3cccn([C@@H](CO)c4ccccc4)c3=O)cc2)c2c(N)ncnn12]

Step 1: 1-[(1R)-2-Hydroxy-1-phenylethyl]-2-oxo-1,2-dihydropyridine-3-carboxylic Acid

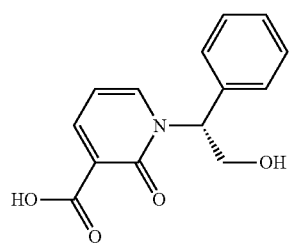 [SMILES: O=C(O)c1cccn([C@@H](CO)c2ccccc2)c1=O]

Dimethyl [(2E)-3-methoxyprop-2-en-1-ylidene]malonate (from Acros Organics, 0.20 g, 1.00 mmol) was taken up in methanol (1.8 mL), combined with (2R)-2-amino-2-phenylethanol (0.14 g, 1.00 mmol) and N,N-diisopropylethylamine (0.55 mL, 3.2 mmol). The reaction mixture was sealed and stirred for 2 h at 130° C. Then the reaction mixture was combined with 2.0 M sodium hydroxide in methanol (5.0 mL) and 2.0 M sodium hydroxide in water (5.0 mL) and continuously stirred at rt for 2 h. The crude was neutralized with HCl (3N), extracted with EtOAcx3. The combined organic layers were dried, filtered and concentrated under vacuum to give the desired product as light brown gum. LCMS calcd for $C_{14}H_{14}NO_4$ $(M+H)^+$: m/z=260.1. Found: 260.1.

Step 2: N-[4-(4-Amino-7-ethylpyrrolo[2,1-f][1,2,4]triazin-5-yl)phenyl]-1-[(1R)-2-hydroxy-1-phenylethyl]-2-oxo-1,2-dihydropyridine-3-carboxamide 5-(4-aminophenyl)-7-ethylpyrrolo[2,1-f][1,2,4]triazin-4-amine (3.0 mg, 0.012 mmol) (prepared in Example HF1, step 8), 1-[(1R)-2-hydroxy-1-phenylethyl]-2-oxo-1,2-dihydropyridine-3-carboxylic acid (3.6 mg, 0.014 mmol), N,N,N',N'-tetramethyl-O-(7-azabenzotriazol-1-yl)uronium hexafluorophosphate (11.2 mg, 0.03 mmol) in N,N-dimethylformamide (0.10 mL) and N,N-diisopropylethylamine (4.6 mg, 0.035 mmol) were mixed together and stirred at rt for 60 min. The reaction mixture was filtered, concentrated and purified by prep LC-MS (pH=10 method; XBridge™ PrepC18 5 μm OBD™ column, 30×100 mm, 60 mL/min, eluting with a gradient of MeCN and water with 0.15% $NH_4OH$) to give the desired product as white powders (2.0 mg, 34%). LCMS calcd for $C_{28}H_{27}N_6O_3$ $(M+H)^+$: m/z=495.2. Found: 495.2.

Example 3. N-[4-(4-Amino-7-ethylpyrrolo[2,1-f][1,2,4]triazin-5-yl)phenyl]-1-[(1R)-2-hydroxy-1-methylethyl]-2-oxo-1,2-dihydropyridine-3-carboxamide Dimethyl [(2E)-3-methoxyprop-2-en-1-ylidene]malonate (from Acros Organics, 200 mg, 1.00 mmol) was taken up in methanol (1.82 mL), combined with (R)-(−)-2-amino-1-propanol (from Aldrich, 75.0 mg, 1.00 mmol) and N,N-diisopropylethylamine (0.55 mL, 3.2 mmol). The reaction mixture was sealed and stirred for 2 h at 130° C. Then the reaction mixture was combined with 2.0 M sodium hydroxide in methanol (5.0 mL) and 2.0 M sodium hydroxide in water (5.0 mL) and continuously stirred at rt for 2 h. The reaction mixture was acidified with 5.0 mL of HCl (3 N), concentrated under vacuum to remove solvents. The residue was washed with THF and EtOAc, dried, filtered and concentrated under vacuum to give the desired product as off-white powders. LCMS calcd for $C_9H_{12}NO_4$ $(M+H)^+$: m/z=198.1. Found: 198.1.

Step 2: N-[4-(4-Amino-7-ethylpyrrolo[2,1-f][1,2,4]triazin-5-yl)phenyl]-1-[(1R)-2-hydroxy-1-methylethyl]-2-oxo-1,2-dihydropyridine-3-carboxamide 5-(4-Aminophenyl)-7-ethylpyrrolo[2,1-f][1,2,4]triazin-4-amine (5.0 mg, 0.020 mmol) (prepared in Example HF1, step 8), 1-[(1R)-2-hydroxy-1-methylethyl]-2-oxo-1,2-dihydropyridine-3-carboxylic acid (4.7 mg, 0.024 mmol), N,N,N',N'-tetramethyl-O-(7-azabenzotriazol-1-yl)uronium hexafluorophosphate (18.8 mg, 0.05 mmol) in N,N-dimethylformamide (0.1 mL) and N,N-diisopropylethylamine (7.7 mg, 0.06 mmol) were mixed together and stirred at rt for 30 min. The mixture was filtered, concentrated and purified by prep LC-MS (pH=10 method; XBridge™ PrepC18 5 μm OBD™ column, 30×100 mm, 60 mL/min, eluting with a gradient of MeCN and water with 0.15% $NH_4OH$) to give the desired product as white powders (2.0 mg, 23%). LCMS calcd for $C_{23}H_{25}N_6O_3$ $(M+H)^+$: m/z=433.2. Found: 433.2.

Example 4. N-[4-(4-Amino-7-ethylpyrrolo[2,1-f][1,2,4]triazin-5-yl)phenyl]-1-[(1R)-1-(hydroxymethyl)propyl]-2-oxo-1,2-dihydropyridine-3-carboxamide

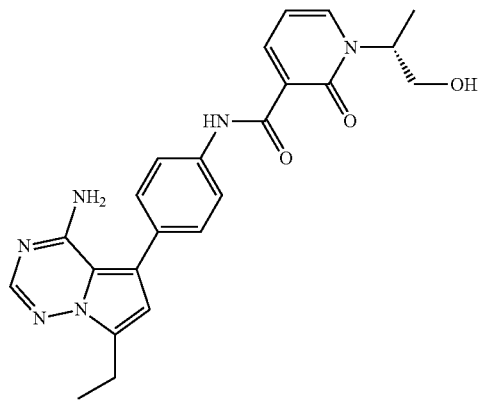 [SMILES: CCc1cc(-c2ccc(NC(=O)c3cccn([C@H](C)CO)c3=O)cc2)c2c(N)ncnn12]

Step 1: 1-[(1R)-2-Hydroxy-1-methylethyl]-2-oxo-1,2-dihydropyridine-3-carboxylic Acid

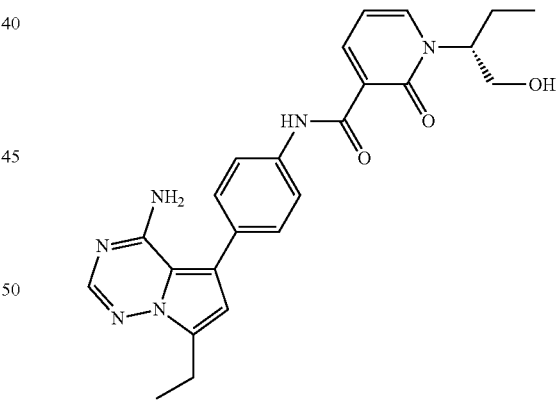

Step 1: 1-[(1R)-1-(Hydroxymethyl)propyl]-2-oxo-1,2-dihydropyridine-3-carboxylic Acid

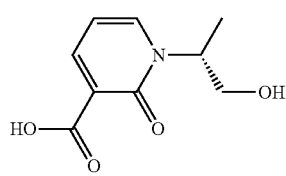

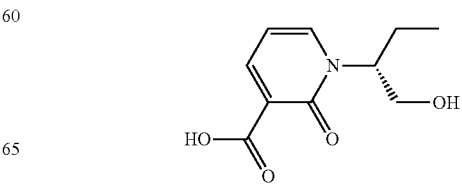

Dimethyl [(2E)-3-methoxyprop-2-en-1-ylidene]malonate (from Acros Organics, 200 mg, 1.00 mmol) was taken up in methanol (1.82 mL), combined with (2R)-2-aminobutan-1-ol (89.0 mg, 1.00 mmol) and N,N-diisopropylethylamine (0.55 mL, 3.2 mmol). The reaction mixture was sealed and stirred for 2 h at 130° C. Then the reaction mixture was combined with 2.0 M sodium hydroxide in methanol (5.0 mL) and 2.0 M sodium hydroxide in water (5.0 mL) and continuously stirred at rt for 1 h. The reaction mixture was acidified with 5.0 mL of HCl (3 N), concentrated under vacuum to remove solvents. The residue was washed with THF and EtOAc, dried, filtered and concentrated under vacuum to give the desired product as off-white powders. LCMS calcd for $C_{10}H_{14}NO_4$ $(M+H)^+$: m/z=212.1. Found: 212.1.

Step 2: N-[4-(4-Amino-7-ethylpyrrolo[2,1-f][1,2,4]triazin-5-yl)phenyl]-1-[(1R)-1-(hydroxymethyl)propyl]-2-oxo-1,2-dihydropyridine-3-carboxamide 5-(4-Aminophenyl)-7-ethylpyrrolo[2,1-f][1,2,4]triazin-4-amine (5.0 mg, 0.020 mmol) (prepared in Example HF1, step 8), 1-[(1R)-1-(hydroxymethyl)propyl]-2-oxo-1,2-dihydropyridine-3-carboxylic acid (5.0 mg, 0.024 mmol), N,N,N',N'-tetramethyl-O-(7-azabenzotriazol-1-yl)uronium hexafluorophosphate (18.8 mg, 0.049 mmol) in N,N-dimethylformamide (0.1 mL) and N,N-diisopropylethylamine (7.7 mg, 0.06 mmol) were mixed together and stirred at rt for 30 min. The reaction mixture was filtered, concentrated and purified by prep LC-MS (pH=10 method; XBridge™ PrepC18 5 μm OBD™ column, 30×100 mm, 60 mL/min, eluting with a gradient of MeCN and water with 0.15% NH₄OH) to give the desired product as white powders (1.7 mg, 19%). LCMS calcd for $C_{24}H_{27}N_6O_3$ $(M+H)^+$: m/z=447.2. Found: 447.2.

Example 5. N-[4-(4-Amino-7-ethylpyrrolo[2,1-f][1,2,4]triazin-5-yl)phenyl]-1-benzyl-2-oxo-1,2-dihydropyridine-3-carboxamide

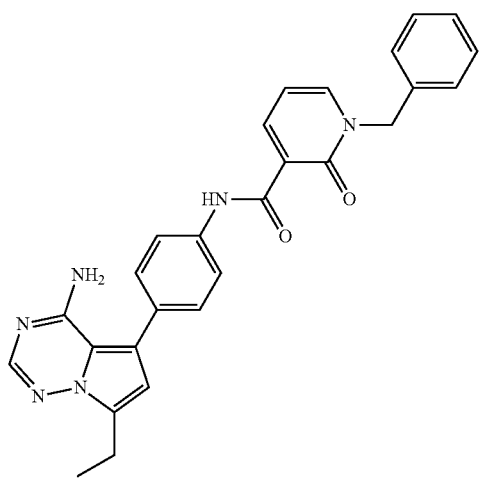 [SMILES: CCc1cc(-c2ccc(NC(=O)c3cccn(Cc4ccccc4)c3=O)cc2)c2c(N)ncnn12]

5-(4-Aminophenyl)-7-ethylpyrrolo[2,1-f][1,2,4]triazin-4-amine (4.6 mg, 0.02 mmol) (prepared in Example 1, step 8), 1-benzyl-2-oxo-1,2-dihydropyridine-3-carboxylic acid (from Aurum Pharmatech, 5 mg, 0.02 mmol), N,N,N',N'-tetramethyl-O-(7-azabenzotriazol-1-yl)uronium hexafluorophosphate (17.3 mg, 0.05 mmol) in N,N-dimethylformamide (0.1 mL) and N,N-diisopropylethylamine (7 mg, 0.05 mmol) were mixed together and stirred at rt for 30 min. The reaction mixture was filtered, concentrated and purified by prep LC-MS (pH=10 method; XBridge™ PrepC18 5 μm OBD™ column, 30×100 mm, 60 mL/min, eluting with a gradient of MeCN and water with 0.15% NH₄OH) to give the desired product as white powders (2.4 mg, 28%). LCMS calcd for $C_{27}H_{25}N_6O_2$ $(M+H)^+$: m/z=465.2. Found: 465.2.

Example 6. N-[4-(4-Amino-7-ethylpyrrolo[2,1-f][1,2,4]triazin-5-yl)phenyl]-1-methyl-2-oxo-1,2-dihydropyridine-3-carboxamide

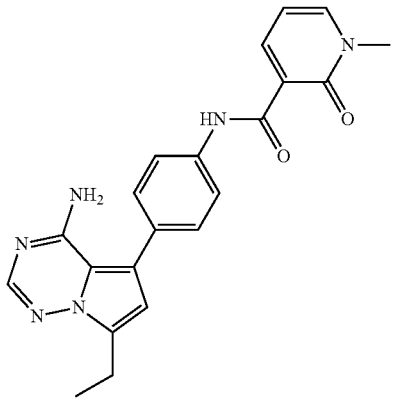 [SMILES: CCc1cc(-c2ccc(NC(=O)c3cccn(C)c3=O)cc2)c2c(N)ncnn12]

5-(4-Aminophenyl)-7-ethylpyrrolo[2,1-f][1,2,4]triazin-4-amine (4 mg, 0.02 mmol) (prepared in Example 1, step 8), 1-methyl-2-oxo-1,2-dihydropyridine-3-carboxylic acid (from Synthonix, 2.9 mg, 0.02 mmol), N,N,N',N'-tetramethyl-O-(7-azabenzotriazol-1-yl)uronium hexafluorophosphate (12 mg, 0.03 mmol) in N,N-dimethylformamide (0.1 mL) and triethylamine (4.8 mg, 0.05 mmol) were mixed together and stirred at rt for 30 min. The reaction mixture was filtered, concentrated and purified by prep LC-MS (pH=10 method; XBridge™ PrepC18 5 μm OBD™ column, 30×100 mm, 60 mL/min, eluting with a gradient of MeCN and water with 0.15% NH₄OH) to give the desired product as white powders (1.6 mg, 26%). LCMS calcd for $C_{21}H_{21}N_6O_2$ $(M+H)^+$: m/z=389.2. Found: 389.2.

Example 7a. N-{4-[4-Amino-7-(cis-4-hydroxycyclohexyl)pyrrolo[2,1-f][1,2,4]triazin-5-yl]phenyl}-2-oxo-1-phenyl-1,2-dihydropyridine-3-carboxamide Example 7b. N-{4-[4-Amino-7-(trans-4-hydroxycyclohexyl)pyrrolo[2,1-f][1,2,4]triazin-5-yl]phenyl}-2-oxo-1-phenyl-1,2-dihydropyridine-3-carboxamide

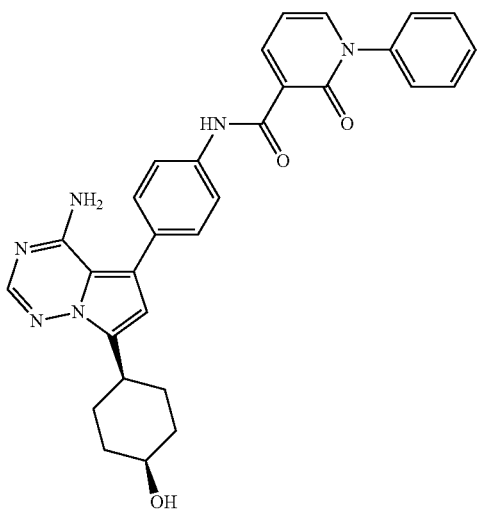

-continued

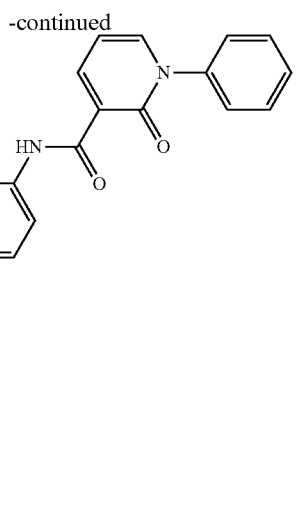

Step 1: Methyl 2-oxo-1-phenyl-1,2-dihydropyridine-3-carboxylate

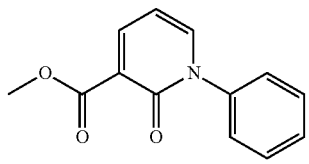 [SMILES: COC(=O)c1cccn(-c2ccccc2)c1=O]

A mixture of methyl 2-oxo-1,2-dihydropyridine-3-carboxylate (from Aldrich, 1.50 g, 9.80 mmol), phenylboronic acid (3.6 g, 29 mmol), activated 4 Å molecular sieves (2.8 g, 12 mmol) and cupric acetate (3.6 g, 20.0 mmol) in methylene chloride (60 mL) was treated with pyridine (2.4 mL, 29 mmol). The reaction mixture was stirred at rt for 60 h, filtered through a celite pad. The filtrate was concentrated under vacuum. The crude product was purified by Biotage silica gel chromatography (0 to 100% ethyl acetate in hexanes) to afford the desired product as white powders (1.26 g, 56%). LCMS calcd for $C_{13}H_{12}NO_3$ $(M+H)^+$: m/z=230.1. Found: 230.1.

Step 2: 2-Oxo-1-phenyl-1,2-dihydropyridine-3-carboxylic Acid

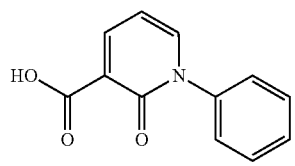 [SMILES: O=C(O)c1cccn(-c2ccccc2)c1=O]

Methyl 2-oxo-1-phenyl-1,2-dihydropyridine-3-carboxylate (800 mg, 3.49 mmol) was dissolved in tetrahydrofuran (7.4 mL) and methanol (3.7 mL). The mixture was then treated with 1.0 M sodium hydroxide in water (14.0 mL), and stirred at rt for 30 min. The reaction mixture was neutralized with HCl (12 M) to pH=6-7. The solvents were removed under vacuum and the product precipitated out. The solid was collected by vacuum filtration, and the cake was washed with water and dried overnight to give the desired acid product as white powders (636 mg, 85%). LCMS calcd for $C_{12}H_{10}NO_3$ $(M+H)^+$: m/z=216.1. Found: 216.1.

Step 3: 2-Oxo-1-phenyl-N-[4-(4,4,5,5-tetramethyl-1,3,2-dioxaborolan-2-yl)phenyl]-1,2-dihydropyridine-3-carboxamide

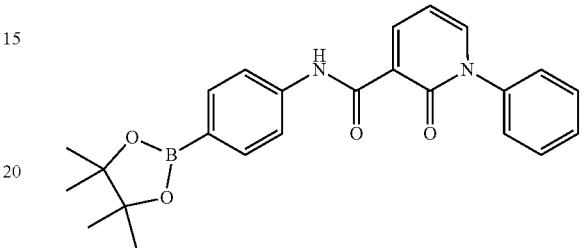

To a mixture of 4-(4,4,5,5-tetramethyl-1,3,2-dioxaborolan-2-yl)aniline (from Aldrich, 214 mg, 0.98 mmol) and 2-oxo-1-phenyl-1,2-dihydropyridine-3-carboxylic acid (200 mg, 0.93 mmol) in N,N-dimethylformamide (4.5 mL) was added triethylamine (194 µL, 1.4 mmol) followed by N,N,N',N'-tetramethyl-O-(7-azabenzotriazol-1-yl)uronium hexafluorophosphate (424 mg, 1.12 mmol). The resulting reaction mixture, which became a mixture of solids quickly, was stirred at rt for 1 h. The solids were filtered and washed with water. Drying by vacuum suction gave the desired product as a white solid (306 mg, 79%). LCMS calcd for $C_{24}H_{26}BN_2O_4(M+H)^+$: m/z=417.2. Found: 417.2.

Step 4: 7-(4-{[tert-Butyl(dimethyl)silyl]oxy}cyclohex-1-en-1-yl)pyrrolo[2,1-f][1,2,4]triazin-4-amine

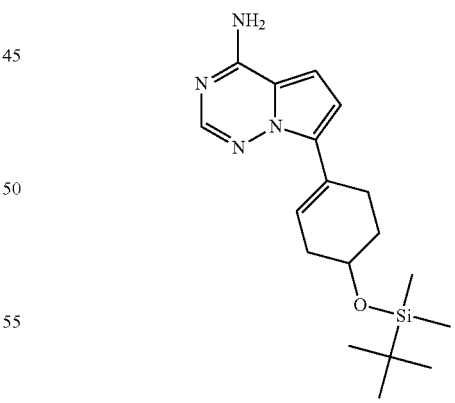

A mixture of tert-butyl(dimethyl) {[4-(4,4,5,5-tetramethyl-1,3,2-dioxaborolan-2-yl)cyclohex-3-en-1-yl]oxy}silane (450 mg, 1.33 mmol), 7-bromopyrrolo[2,1-f][1,2,4]triazin-4-amine (283 mg, 1.33 mmol), sodium carbonate (470 mg, 4.4 mmol), and [1,1'-bis(di-cyclohexylphosphino)ferrocene]dichloropalladium (II) (101 mg, 0.133 mmol) in tert-butyl alcohol (4.0 mL) and water (1.5 mL) was degassed with nitrogen, then stirred and heated at 110° C. for 2 h, then 95° C. overnight. The mixture was diluted with ethyl acetate, washed with saturated NaHCO$_3$, water, dried over Na$_2$SO$_4$, filtered and concentrated. The product was purified by Biotage silica gel chromatography (0 to 50% EtOAc in hexanes) to give the desired product as off-white powders (242.3 mg, 53%). LCMS calcd for C$_{18}$H$_{29}$N$_4$OSi (M+H)$^+$: m/z=345.2. Found: 345.2.

Step 5: 7-(4-{[tert-Butyl(dimethyl)silyl]oxy}cyclohexyl)pyrrolo[2,1-f][1,2,4]triazin-4-amine

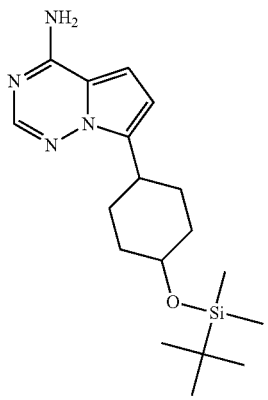 [SMILES: CC(C)(C)[Si](C)(C)OC1CCC(c2ccc3c(N)ncnn23)CC1]

To a solution of 7-(4-{[tert-butyl(dimethyl)silyl]oxy}cyclohex-1-en-1-yl)pyrrolo[2,1-f][1,2,4]triazin-4-amine (230 mg, 0.67 mmol) in methanol (2.8 mL) and tetrahydrofuran (1.4 mL) was added a mixture of palladium (4.6 mg) (10% Pd on carbon). The reaction mixture was vacuumed and placed under a hydrogen balloon for 1 h. After filtration through a celite pad, the filtrate was concentrated under vacuum to give the desired product (161.9 mg, 70%). LCMS calcd for C$_{18}$H$_{31}$N$_4$OSi (M+H)$^+$: m/z=347.2. Found: 347.2.

Step 6: 5-Bromo-7-(4-{[tert-butyl(dimethyl)silyl]oxy}cyclohexyl)pyrrolo[2,1-f][1,2,4]triazin-4-amine

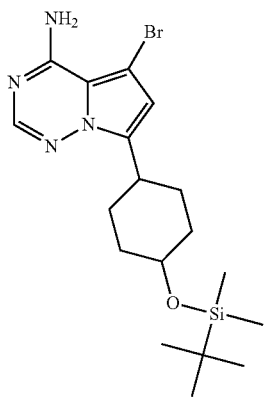 [SMILES: CC(C)(C)[Si](C)(C)OC1CCC(c2cc(Br)c3c(N)ncnn23)CC1]

To a solution of 7-(4-{[tert-butyl(dimethyl)silyl]oxy}cyclohexyl)pyrrolo[2,1-f][1,2,4]triazin-4-amine (80.0 mg, 0.23 mmol) in N,N-dimethylformamide (1.0 mL) was added N-bromosuccinimide (39.0 mg, 0.22 mmol). The resulting mixture was stirred at rt for 10 min. The reaction mixture was diluted with EtOAc, filtered. The filtrate was washed with saturated NaHCO$_3$, water, dried, filtered again and concentrated under vacuum to give the desired product as tan solid. LCMS calcd for C$_{18}$H$_{30}$BrN$_4$OSi (M+H)$^+$: m/z=425.1, 427.1. Found: 425.1, 427.1.

Step 7: N-{4-[4-Amino-7-(4-{[tert-butyl(dimethyl)silyl]oxy}cyclohexyl)pyrrolo[2,1-f][1,2,4]triazin-5-yl]phenyl}-2-oxo-1-phenyl-1,2-dihydropyridine-3-carboxamide

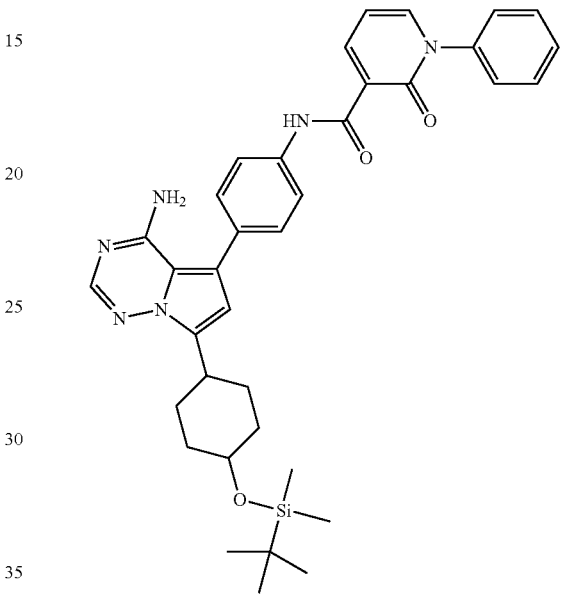

A mixture of 2-oxo-1-phenyl-N-[4-(4,4,5,5-tetramethyl-1,3,2-dioxaborolan-2-yl)phenyl]-1,2-dihydropyridine-3-carboxamide (48.9 mg, 0.12 mmol) (prepared in Example 7, step 3), 5-bromo-7-(4-{[tert-butyl(dimethyl)silyl]oxy}cyclohexyl)pyrrolo[2,1-f][1,2,4]triazin-4-amine (50 mg, 0.12 mmol), sodium carbonate (42 mg, 0.39 mmol), and [1,1'-bis(di-cyclohexylphosphino)ferrocene]dichloropalladium (II) (13.4 mg, 0.018 mmol) in tert-butyl alcohol (0.35 mL) and water (0.13 mL) was degassed with nitrogen, then stirred and heated at 110° C. for 1 h. The mixture was diluted with ethyl acetate, washed with saturated NaHCO$_3$, water, dried over Na$_2$SO$_4$, filtered and concentrated. The crude product was purified by Biotage silica gel chromatography (0 to 100% EtOAc in hexanes) to give the desired product as white powders (34 mg, 46%). LCMS calcd for C$_{36}$H$_{43}$N$_6$O$_3$Si (M+H)$^+$: m/z=635.3. Found: 635.3.

Step 8: N-{4-[4-Amino-7-(4-hydroxycyclohexyl)pyrrolo[2,1-f][1,2,4]triazin-5-yl]phenyl}-2-oxo-1-phenyl-1,2-dihydropyridine-3-carboxamide A solution of N-{4-[4-amino-7-(4-{[tert-butyl(dimethyl)silyl]oxy}cyclohexyl)pyrrolo[2,1-f][1,2,4]triazin-5-yl]phenyl}-2-oxo-1-phenyl-1,2-dihydropyridine-3-carboxamide (34 mg, 0.05 mmol) in tetrahydrofuran (0.2 mL) was treated with 4.0 M hydrogen chloride in dioxane (0.9 mL, 3.6 mmol). The reaction mixture was stirred at rt for 30 min. The crude (trans and cis isomers with a ratio of 1:4) was concentrated under vacuum and purified by prep LC-MS (pH=10 method; XBridge™ PrepC18 5 µm OBD™ column, 30×100 mm, 60 mL/min, eluting with a gradient of MeCN and water with 0.15% NH₄OH) to give the desired cis isomer (9.2 mg, 33%). The minor trans isomer (3.5 mg, 12%) was also isolated. Retention time (RT)=RT=1.189 min for minor trans isomer, first peak off the column; RT=1.216 min for major cis isomer, second peak off the column. LCMS calcd for $C_{30}H_{29}N_6O_3$ (M+H)⁺: m/z=521.2. Found: 521.2. ¹H NMR (500 MHz, dmso) δ 12.06 (s, 1H), 8.62 (dd, J=7.3, 2.2 Hz, 1H), 8.14 (dd, J=6.6, 2.2 Hz, 1H), 7.90 (s, 1H), 7.82 (d, J=8.6 Hz, 2H), 7.66-7.52 (m, 6H), 7.47 (d, J=8.5 Hz, 2H), 6.78-6.72 (m, 2H), 6.55 (s, 1H), 4.38 (d, J=2.9 Hz, 1H), 3.92 (s, 1H), 3.62 (d, J=6.5 Hz, 1H), 3.16 (t, J=11.4 Hz, 1H), 1.99-1.84 (m, 2H), 1.84-1.70 (m, 4H), 1.62 (t, J=12.2 Hz, 1H).

Example 8. N-[4-(4-Amino-7-methylpyrrolo[2,1-f][1,2,4]triazin-5-yl)phenyl]-2-oxo-1-phenyl-1,2-dihydropyridine-3-carboxamide

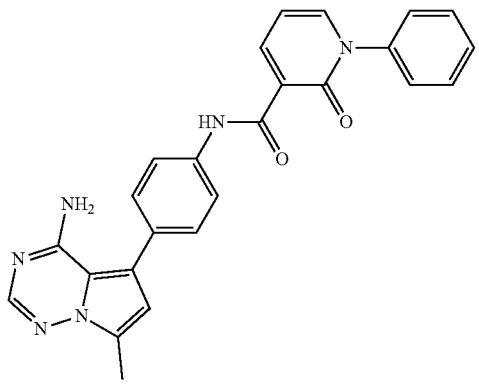 [SMILES: Cc1cc(-c2ccc(NC(=O)c3cccn(-c4ccccc4)c3=O)cc2)c2c(N)ncnn12]

Step 1: 7-Methylpyrrolo[2,1-f][1,2,4]triazin-4-amine

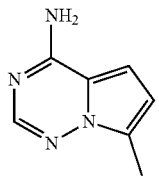

To a solution of 7-bromopyrrolo[2,1-f][1,2,4]triazin-4-amine (from J & W Pharm Lab, 150 mg, 0.70 mmol) in tetrahydrofuran (2.86 mL) under N₂ at rt was added tetrakis(triphenylphosphine)palladium(0) (163 mg, 0.14 mmol). The mixture in a sealed flask was evacuated and refilled with N₂ several times, followed by the addition of 2.0 M dimethylzinc in toluene (5.3 mL, 10 mmol) at rt. The reaction mixture was heated at 90° C. for 4 h. The reaction mixture was quenched with ice-water, extracted with EtOAc. The combined organic layers were dried over Na₂SO₄, filtered, concentrated under vacuum to give the crude, which was purified by prep LC-MS (pH=10 method; XBridge™ PrepC18 5 μm OBD™ column, 30×100 mm, 60 mL/min, eluting with a gradient of MeCN and water with 0.15% NH₄OH) to afford the desired product as white powders (29.2 mg, 28%). LCMS calcd for $C_7H_9N_4$ (M+H)⁺: m/z=149.1. Found: 149.1.

Step 2: 5-Bromo-7-methylpyrrolo[2,1-f][1,2,4]triazin-4-amine

To a solution of 7-methylpyrrolo[2,1-f][1,2,4]triazin-4-amine (29.2 mg, 0.20 mmol) in N,N-dimethylformamide (0.85 mL) was added N-bromosuccinimide (33.3 mg, 0.19 mmol). The resulting mixture was stirred at rt for 15 min and the reaction mixture was diluted with EtOAc, filtered, then washed with saturated NaHCO₃, water, dried, filtered and concentrated under vacuum to give the desired product as off-white powders. LCMS calcd for $C_7H_8BrN_4$ (M+H)⁺: m/z=227.0, 229.0. Found: 227.0, 229.0.

Step 3: N-[4-(4-Amino-7-methylpyrrolo[2,1-f][1,2,4]triazin-5-yl)phenyl]-2-oxo-1-phenyl-1,2-dihydropyridine-3-carboxamide In a sealed tube a mixture of 5-bromo-7-methylpyrrolo[2,1-f][1,2,4]triazin-4-amine (5.6 mg, 0.02 mmol), 2-oxo-1-phenyl-N-[4-(4,4,5,5-tetramethyl-1,3,2-dioxaborolan-2-yl)phenyl]-1,2-dihydropyridine-3-carboxamide (8.0 mg, 0.02 mmol) (prepared in Example 7, step 3) and N,N-diisopropylethylamine (0.01 mL, 0.06 mmol) in 1,4-dioxane (0.14 mL) and water (20 L) was stirred together and flushed with N₂ bubble for 5 min before bis(tri-t-butylphosphine)palladium (4.7 mg, 0.01 mmol) was added. The reaction mixture was sealed and then heated at 110° C. for 1 h. After separation and the aqueous layer extracted with EtOAc, the organic layer was dried, filtered and concentrated under vacuum. The crude was purified by prep LC-MS (pH=10 method; XBridge™ PrepC18 5 μm OBD™ column, 30×100 mm, 60 mL/min, eluting with a gradient of MeCN and water with 0.15% NH₄OH) to give the desired product (2.8 mg, 36%). LCMS calcd for $C_{25}H_{21}N_6O_2$ (M+H)⁺: m/z=437.2. Found: 437.2.

Example 9. N-[4-(4-Amino-7-methylpyrrolo[2,1-f][1,2,4]triazin-5-yl)phenyl]-1-(4-fluorophenyl)-2-oxo-1,2-dihydropyridine-3-carboxamide

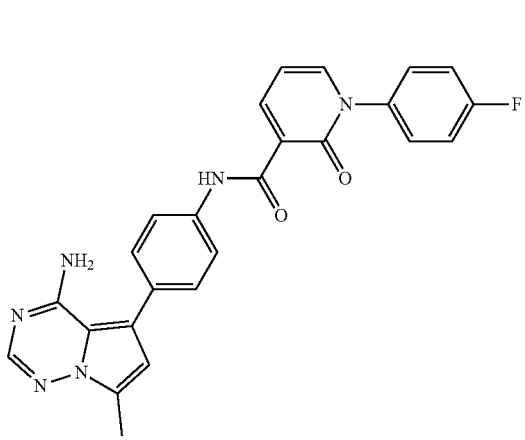 [SMILES: Cc1cc(-c2ccc(NC(=O)c3cccn(-c4ccc(F)cc4)c3=O)cc2)c2c(N)ncnn12]

Step 1: Methyl 1-(4-fluorophenyl)-2-oxo-1,2-dihydropyridine-3-carboxylate

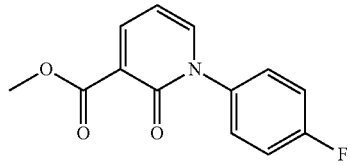 [SMILES: COC(=O)c1cccn(-c2ccc(F)cc2)c1=O]

A mixture of methyl 2-oxo-1,2-dihydropyridine-3-carboxylate (from Aldrich, 1.50 g, 9.8 mmol), 4-fluorophenylboronic acid (from Aldrich, 4.1 g, 29 mmol), activated 4 Å molecular sieves (2.8 g, 12 mmol) and cupric acetate (3.6 g, 20 mmol) in methylene chloride (60 mL) was treated with pyridine (2.4 mL) and then stirred at rt for 18 h. The mixture was filtered through celite and the filtrate was concentrated under vacuum. The crude was purified by Biotage silica gel column chromatography (0 to 100% ethyl acetate in hexanes) to afford the desired product as off-white gum (1.33 g, 55%). LCMS calcd for $C_{13}H_{11}FNO_3$ $(M+H)^+$: m/z=248.1. Found: 248.1.

Step 2: 1-(4-Fluorophenyl)-2-oxo-1,2-dihydropyridine-3-carboxylic Acid

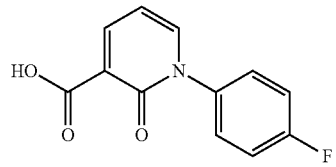 [SMILES: O=C(O)c1cccn(-c2ccc(F)cc2)c1=O]

Methyl 1-(4-fluorophenyl)-2-oxo-1,2-dihydropyridine-3-carboxylate (800 mg, 3.24 mmol) was dissolved in tetrahydrofuran (6.82 mL) and methanol (3.41 mL). The mixture was then treated with 1.0 M sodium hydroxide in water (12.9 mL), and the reaction mixture was stirred at rt for 30 min. The reaction mixture was neutralized with HCl (12 M) to pH=6-7. The solvents were removed under vacuum and the product precipitated out. The solid was collected by vacuum filtration, and the cake was washed with water and dried overnight to give the desired acid product as white powders (540 mg, 72%). LCMS calcd for $C_{12}H_9FNO_3$ $(M+H)^+$: m/z=234.1. Found: 234.1.

Step 3: 1-(4-Fluorophenyl)-2-oxo-N-[4-(4,4,5,5-tetramethyl-1,3,2-dioxaborolan-2-yl)phenyl]-1,2-dihydropyridine-3-carboxamide

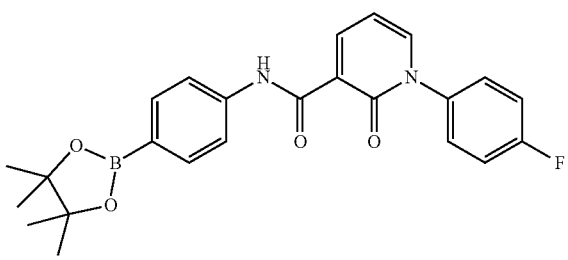 [SMILES: CC1(C)OB(c2ccc(NC(=O)c3cccn(-c4ccc(F)cc4)c3=O)cc2)OC1(C)C]

To a mixture of 4-(4,4,5,5-tetramethyl-1,3,2-dioxaborolan-2-yl)aniline (from Aldrich, 197.3 mg, 0.90 mmol) and 1-(4-fluorophenyl)-2-oxo-1,2-dihydropyridine-3-carboxylic acid (from Aldrich, 200 mg, 0.86 mmol) in N,N-dimethylformamide (4.0 mL) was added triethylamine (180 µL, 1.3 mmol) followed by N,N,N',N'-tetramethyl-O-(7-azabenzotriazol-1-yl)uronium hexafluorophosphate (391 mg, 1.03 mmol). The resulting mixture, which became a mixture of solids quickly, was stirred at rt for 1 h. The solids were filtered and washed with water. Drying by vacuum suction gave the desired product as a white solid (343 mg, 92%). LCMS calcd for $C_{24}H_{25}BFN_2O_4(M+H)^+$: m/z=435.2. Found: 435.2.

Step 4: N-[3-Fluoro-4-(4,4,5,5-tetramethyl-1,3,2-dioxaborolan-2-yl)phenyl]-2-oxo-1-phenyl-1,2-dihydropyridine-3-carboxamide

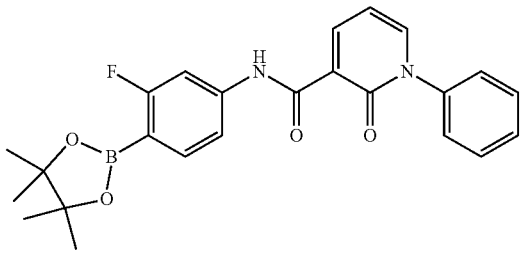 [SMILES: CC1(C)OB(c2ccc(NC(=O)c3cccn(-c4ccccc4)c3=O)cc2F)OC1(C)C]

To a mixture of 3-fluoro-4-(4,4,5,5-tetramethyl-1,3,2-dioxaborolan-2-yl)aniline (from Aldrich, 289.2 mg, 1.22 mmol) and 2-oxo-1-phenyl-1,2-dihydropyridine-3-carboxylic acid (250 mg, 1.16 mmol) (prepared in Example 7, step 2) in N,N-dimethylformamide (5.0 mL) was added triethylamine (243 µL, 1.74 mmol) followed by N,N,N',N'-tetramethyl-O-(7-azabenzotriazol-1-yl)uronium hexafluorophosphate (530 mg, 1.39 mmol). The resulting mixture, which became a mixture of solids quickly, was stirred at rt for 1 h. The solids were filtered and washed with water. Drying by vacuum suction gave the desired product as a white solid (335 mg, 66%). LCMS calcd for $C_{24}H_{25}BFN_2O_4(M+H)^+$: m/z=435.2. Found: 435.2.

Step 5: 1-(4-Fluorophenyl)-N-[3-fluoro-4-(4,4,5,5-tetramethyl-1,3,2-dioxaborolan-2-yl)phenyl]-2-oxo-1,2-dihydropyridine-3-carboxamide

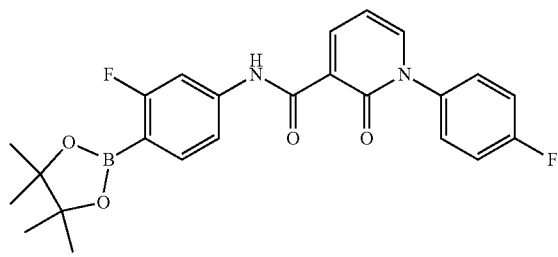 [SMILES: CC1(C)OB(c2ccc(NC(=O)c3cccn(-c4ccc(F)cc4)c3=O)cc2F)OC1(C)C]

To a mixture of 3-fluoro-4-(4,4,5,5-tetramethyl-1,3,2-dioxaborolan-2-yl)aniline (from Aldrich, 213.5 mg, 0.90 mmol) and 1-(4-fluorophenyl)-2-oxo-1,2-dihydropyridine-3-carboxylic acid (200 mg, 0.86 mmol) (prepared in Example 9, step 2) in N,N-dimethylformamide (4.7 mL) was added triethylamine (179 µL, 1.29 mmol) followed by N,N,N',N'-tetramethyl-O-(7-azabenzotriazol-1-yl)uronium hexafluorophosphate (391 mg, 1.03 mmol). The resulting mixture, which became a mixture of solids quickly, was stirred at rt for 1 h. The solids were filtered and washed with water. Drying by vacuum suction gave the desired product as a white solid (305 mg, 79%). LCMS calcd for $C_{24}H_{24}BF_2N_2O_4$ (M+H)$^+$: m/z=453.2. Found: 453.2.

Step 6: N-[4-(4-Amino-7-methylpyrrolo[2,1-f][1,2,4]triazin-5-yl)phenyl]-1-(4-fluorophenyl)-2-oxo-1,2-dihydropyridine-3-carboxamide In a sealed tube a mixture of 5-bromo-7-methylpyrrolo[2,1-f][1,2,4]triazin-4-amine (5 mg, 0.02 mmol) (prepared in Example 8, step 2), 1-(4-fluorophenyl)-2-oxo-N-[4-(4,4,5,5-tetramethyl-1,3,2-dioxaborolan-2-yl)phenyl]-1,2-dihydropyridine-3-carboxamide (8 mg, 0.02 mmol) (prepared in Example 9, step 3) and N,N-diisopropylethylamine (0.01 mL, 0.05 mmol) in 1,4-dioxane (0.13 mL) and water (20 μL) was stirred together and flushed with N$_2$ for 5 min before bis(tri-t-butylphosphine)palladium (4.2 mg, 0.01 mmol) was added. The reaction mixture was sealed and then heated at 110° C. for 1 h. After separation and the aqueous layer extracted with EtOAc, the organic layer was dried, filtered and concentrated under vacuum. The crude was purified by prep LC-MS (pH=10 method; XBridge™ PrepC18 5 μm OBD™ column, 30×100 mm, 60 mL/min, eluting with a gradient of MeCN and water with 0.15% NH$_4$OH) to give the desired product (2.4 mg, 32%). LCMS calcd for $C_{25}H_{20}FN_6O_2$(M+H)$^+$: m/z=455.2. Found: 455.2.

Example 10. N-[4-(4-Amino-7-methylpyrrolo[2,1-f][1,2,4]triazin-5-yl)-3-fluorophenyl]-2-oxo-1-phenyl-1,2-dihydropyridine-3-carboxamide

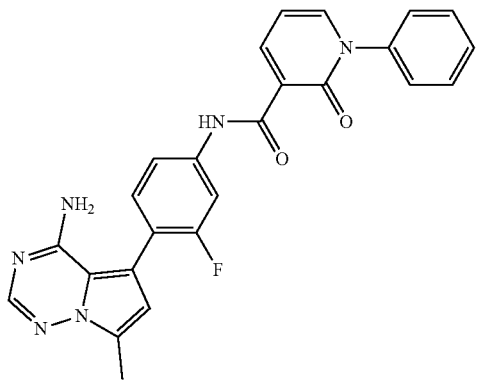 [SMILES: Cc1cc(-c2ccc(NC(=O)c3cccn(-c4ccccc4)c3=O)cc2F)c2c(N)ncnn12]

In a sealed tube a mixture of 5-bromo-7-methylpyrrolo[2,1-f][1,2,4]triazin-4-amine (5 mg, 0.016 mmol) (prepared in Example 8, step 2), N-[3-fluoro-4-(4,4,5,5-tetramethyl-1,3,2-dioxaborolan-2-yl)phenyl]-2-oxo-1-phenyl-1,2-dihydropyridine-3-carboxamide (7.5 mg, 0.017 mmol) (prepared in Example 9, step 4) and N,N-diisopropylethylamine (0.01 mL, 0.049 mmol) in 1,4-dioxane (0.128 mL) and water (20 μL) was stirred together and flushed with N$_2$ for 5 min before bis(tri-t-butylphosphine)palladium (4.2 mg, 0.01 mmol) was added. The reaction mixture was sealed and then heated at 110° C. for 1 h. After separation and the aqueous layer extracted with EtOAc, the organic layer was dried, filtered and concentrated under vacuum. The crude was purified by prep LC-MS (pH=10 method; XBridge™ PrepC18 5 μm OBD™ column, 30×100 mm, 60 mL/min, eluting with a gradient of MeCN and water with 0.15% NH$_4$OH) to give the desired product (1.7 mg, 23%). LCMS calcd for $C_{25}H_{20}FN_6O_2$(M+H)$^+$: m/z=455.2. Found: 455.2.

Example 11. N-[4-(4-Amino-7-methylpyrrolo[2,1-f][1,2,4]triazin-5-yl)-3-fluorophenyl]-1-(4-fluorophenyl)-2-oxo-1,2-dihydropyridine-3-carboxamide

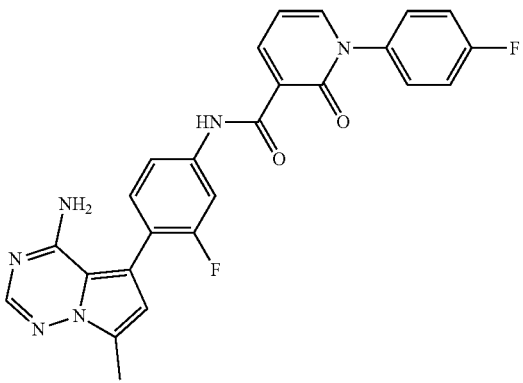 [SMILES: Cc1cc(-c2ccc(NC(=O)c3cccn(-c4ccc(F)cc4)c3=O)cc2F)c2c(N)ncnn12]

In a sealed tube a mixture of 5-bromo-7-methylpyrrolo[2,1-f][1,2,4]triazin-4-amine (3.2 mg, 0.01 mmol) (prepared in Example 8, step 2), 1-(4-fluorophenyl)-N-[3-fluoro-4-(4,4,5,5-tetramethyl-1,3,2-dioxaborolan-2-yl)phenyl]-2-oxo-1,2-dihydropyridine-3-carboxamide (5 mg, 0.01 mmol) (prepared in Example 9, step 5) and N,N-diisopropylethylamine (0.01 mL, 0.04 mmol) in 1,4-dioxane (0.15 mL) and water (20 μL) was stirred together and flushed with N$_2$ for 5 min before bis(tri-t-butylphosphine)palladium (2.7 mg, 0.005 mmol) was added. The reaction mixture was sealed and then heated at 110° C. for 1 h. After separation and the aqueous layer extracted with EtOAc, the organic layer was dried, filtered and concentrated under vacuum. The crude was purified by prep LC-MS (pH=10 method; XBridge™ PrepC18 5 μm OBD™ column, 30×100 mm, 60 mL/min, eluting with a gradient of MeCN and water with 0.15% NH$_4$OH) to give the desired product (2.0 mg, 40%). LCMS calcd for $C_{25}H_{19}F_2N_6O_2$(M+H)$^+$: m/z=473.2. Found: 473.2.

Example 12. N-[4-(4-Amino-7-ethylpyrrolo[2,1-f][1,2,4]triazin-5-yl)-3-fluorophenyl]-2-oxo-1-phenyl-1,2-dihydropyridine-3-carboxamide

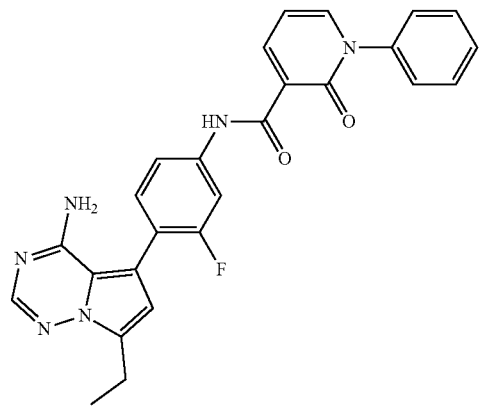 [SMILES: CCc1cc(-c2ccc(NC(=O)c3cccn(-c4ccccc4)c3=O)cc2F)c2c(N)ncnn12]

In a sealed tube a mixture of 5-bromo-7-ethylpyrrolo[2,1-f][1,2,4]triazin-4-amine (6 mg, 0.018 mmol) (prepared in Example 1, step 7), N-[3-fluoro-4-(4,4,5,5-tetramethyl-1,3,2-dioxaborolan-2-yl)phenyl]-2-oxo-1-phenyl-1,2-dihydropyridine-3-carboxamide (8.3 mg, 0.02 mmol) (prepared in Example 9, step 4) and N,N-diisopropylethylamine (0.02 mL, 0.11 mmol) in 1,4-dioxane (0.14 mL) and water (20 µL) was stirred together and flushed with $N_2$ for 5 min before bis(tri-t-butylphosphine)palladium (4.6 mg, 0.01 mmol) was added. The reaction mixture was sealed and then heated at 110° C. for 1 h. After separation and the aqueous layer extracted with EtOAc, the organic layer was dried, filtered and concentrated under vacuum. The crude was purified by prep LC-MS (pH=10 method; XBridge™ PrepC18 5 µm OBD™ column, 30×100 mm, 60 mL/min, eluting with a gradient of MeCN and water with 0.15% $NH_4OH$) to give the desired product (2.4 mg, 28%). LCMS calcd for $C_{26}H_{22}FN_6O_2(M+H)^+$: m/z=469.2. Found: 469.2.

Example 13. N-{4-[4-Amino-7-(tetrahydro-2H-pyran-4-yl)pyrrolo[2,1-f][1,2,4]triazin-5-yl]phenyl}-2-oxo-1-phenyl-1,2-dihydropyridine-3-carboxamide

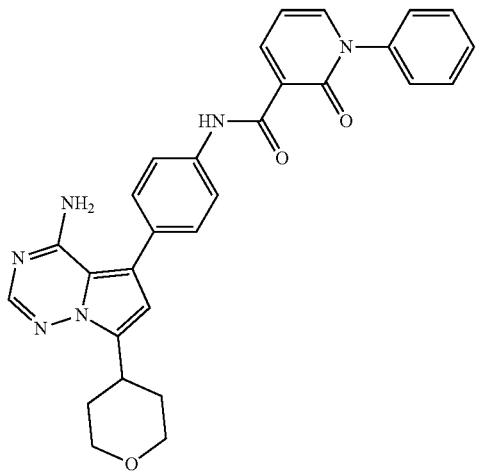 [SMILES: Nc1ncnn2c(C3CCOCC3)cc(-c3ccc(NC(=O)c4cccn(-c5ccccc5)c4=O)cc3)c12]

Step 1: 7-(3,6-Dihydro-2H-pyran-4-yl)pyrrolo[2,1-f][1,2,4]triazin-4-amine

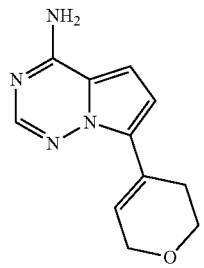 [SMILES: Nc1ncnn2c(C3=CCOCC3)ccc12]

In a sealed flask a mixture of 4-(4,4,5,5-tetramethyl-1,3,2-dioxaborolan-2-yl)-3,6-dihydro-2H-pyran (from Aldrich, 0.64 g, 3.01 mmol), 7-bromopyrrolo[2,1-f][1,2,4]triazin-4-amine (from J & W Pharm Lab, 0.500 g, 2.35 mmol) and N,N-diisopropylethylamine (1.2 mL, 7.0 mmol) in 1,4-dioxane (6 mL) and water (0.32 mL) was stirred together and flushed with $N_2$ for 5 min before bis(tri-t-butylphosphine)palladium (100 mg, 0.24 mmol) was added. The reaction mixture was then sealed and heated at 120° C. for 4 h, filtered through a pad of celite and concentrated. The crude was purified by Biotage silica gel column chromatography (40 g column, 0 to 100% EtOAc in hexanes) to give the desired product as white powders (168.5 mg, 33%). LCMS calcd for $C_{11}H_{13}N_4O$ $(M+H)^+$: m/z=217.1. Found: 217.1.

Step 2: 7-(Tetrahydro-2H-pyran-4-yl)pyrrolo[2,1-f][1,2,4]triazin-4-amine

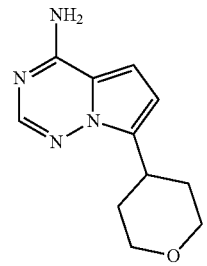 [SMILES: Nc1ncnn2c(C3CCOCC3)ccc12]

To a solution of 7-(3,6-dihydro-2H-pyran-4-yl)pyrrolo[2,1-f][1,2,4]triazin-4-amine (120 mg, 0.55 mmol) in methanol (2.67 mL) and THF (1.3 mL) was added a mixture of palladium (120 mg) (10% Pd on carbon). The reaction mixture was placed under a hydrogen balloon for 2 hours. After filtration through a celite pad, the filtrate was concentrated under vacuum to give the desired product as white powders (90.2 mg, 75%). LCMS calcd for $C_{11}H_{15}N_4O$ $(M+H)^+$: m/z=219.1. Found: 219.1.

Step 3: 5-Bromo-7-(tetrahydro-2H-pyran-4-yl)pyrrolo[2,1-f][1,2,4]triazin-4-amine

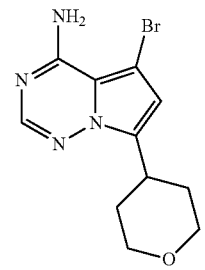 [SMILES: Nc1ncnn2c(C3CCOCC3)cc(Br)c12]

To a solution of 7-(tetrahydro-2H-pyran-4-yl)pyrrolo[2,1-f][1,2,4]triazin-4-amine (50 mg, 0.23 mmol) in N,N-dimethylformamide (0.99 mL) was added N-bromosuccinimide (41 mg, 0.23 mmol). The resulting mixture was stirred at rt for 15 min. The reaction mixture was diluted with EtOAc, filtered. The filtrate was washed with saturated $NaHCO_3$, water, dried, filtered again and concentrated under vacuum to give the desired product as tan solid. LCMS calcd for $C_{11}H_{14}BrN_4O$ $(M+H)^+$: m/z=297.0, 299.0. Found: 297.0, 299.0.

Step 4: N-{4-[4-Amino-7-(tetrahydro-2H-pyran-4-yl)pyrrolo[2,1-f][1,2,4]triazin-5-yl]phenyl}-2-oxo-1-phenyl-1,2-dihydropyridine-3-carboxamide In a sealed tube a mixture of 5-bromo-7-(tetrahydro-2H-pyran-4-yl)pyrrolo[2,1-f][1,2,4]triazin-4-amine (6 mg, 0.02 mmol), 2-oxo-1-phenyl-N-[4-(4,4,5,5-tetramethyl-1,3,2-dioxaborolan-2-yl)phenyl]-1,2-dihydropyridine-3-carboxamide (8.8 mg, 0.02 mmol) (prepared in Example 7, step 3) and N,N-diisopropylethylamine (0.01 mL, 0.06 mmol) in 1,4-dioxane (0.15 mL) and water (20 µL) was stirred together and flushed with $N_2$ or 5 min before bis(tri-t-butylphosphine)palladium (5.2 mg, 0.01 mmol) was added. The reaction mixture was sealed and then heated at 110° C. for 1 h. After separation and the aqueous layer extracted with EtOAc, the organic layer was dried, filtered and concentrated under vacuum. The crude was purified by prep LC-MS (pH=10 method; XBridge™ PrepC18 5 µm OBD™ column, 30×100 mm, 60 mL/min, eluting with a gradient of MeCN and water with 0.15% $NH_4OH$) to give the desired product (3.2 mg, 31%). LCMS calcd for $C_{29}H_{27}N_6O_3$ $(M+H)^+$: m/z=507.2. Found: 507.2.

Example 14. N-{4-[4-Amino-7-(tetrahydro-2H-pyran-4-yl)pyrrolo[2,1-f][1,2,4]triazin-5-yl]phenyl}-1-(4-fluorophenyl)-2-oxo-1,2-dihydropyridine-3-carboxamide

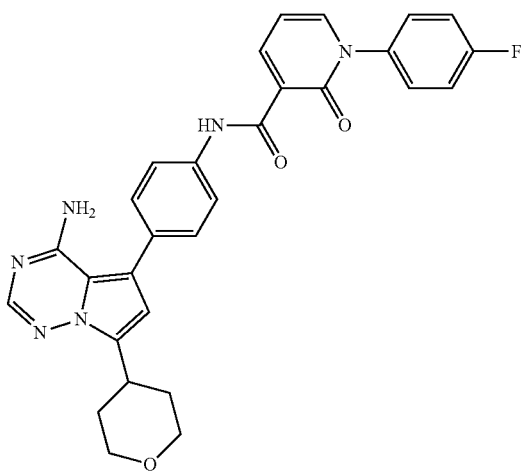 [SMILES: Nc1ncnn2c(C3CCOCC3)cc(-c3ccc(NC(=O)c4cccn(-c5ccc(F)cc5)c4=O)cc3)c12]

In a sealed tube a mixture of 5-bromo-7-(tetrahydro-2H-pyran-4-yl)pyrrolo[2,1-f][1,2,4]triazin-4-amine (6 mg, 0.02 mmol) (prepared in Example 13, step 3), 1-(4-fluorophenyl)-2-oxo-N-[4-(4,4,5,5-tetramethyl-1,3,2-dioxaborolan-2-yl)phenyl]-1,2-dihydropyridine-3-carboxamide (9.2 mg, 0.02 mmol) (prepared in Example 9, step 3) and N,N-diisopropylethylamine (0.01 mL, 0.06 mmol) in 1,4-dioxane (0.15 mL) and water (20 L) was stirred together and flushed with $N_2$ for 5 min before bis(tri-t-butylphosphine)palladium (5.2 mg, 0.01 mmol) was added. The reaction mixture was sealed and then heated at 110° C. for 1 h. After separation and the aqueous layer extracted with EtOAc, the organic layer was dried, filtered and concentrated under vacuum. The crude was purified by prep LC-MS (pH=10 method; XBridge™ PrepC18 5 µm OBD™ column, 30×100 mm, 60 mL/min, eluting with a gradient of MeCN and water with 0.15% $NH_4OH$) to give the desired product (4.8 mg, 45%). LCMS calcd for $C_{29}H_{26}FN_6O_3(M+H)^+$: m/z=525.2. Found: 525.2.

Example 15. N-{4-[4-Amino-7-(tetrahydro-2H-pyran-4-yl)pyrrolo[2,1-f][1,2,4]triazin-5-yl]-3-fluorophenyl}-2-oxo-1-phenyl-1,2-dihydropyridine-3-carboxamide

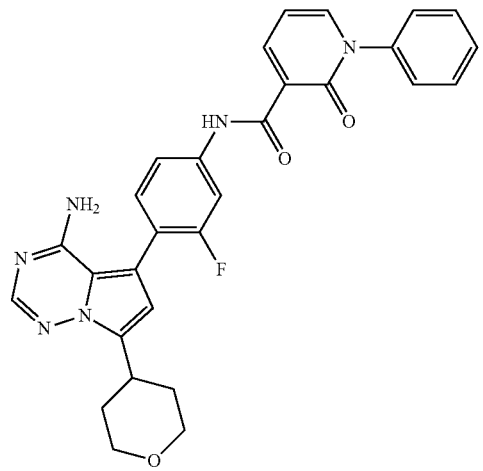 [SMILES: Nc1ncnn2c(C3CCOCC3)cc(-c3ccc(NC(=O)c4cccn(-c5ccccc5)c4=O)cc3F)c12]

In a sealed tube a mixture of 5-bromo-7-(tetrahydro-2H-pyran-4-yl)pyrrolo[2,1-f][1,2,4]triazin-4-amine (5 mg, 0.02 mmol) (prepared in Example 13, step 3), N-[3-fluoro-4-(4,4,5,5-tetramethyl-1,3,2-dioxaborolan-2-yl)phenyl]-2-oxo-1-phenyl-1,2-dihydropyridine-3-carboxamide (7.3 mg, 0.017 mmol) (prepared in Example 9, step 4) and N,N-diisopropylethylamine (0.01 mL, 0.06 mmol) in 1,4-dioxane (0.15 mL) and water (20 L) was stirred together and flushed with $N_2$ for 5 min before bis(tri-t-butylphosphine)palladium (4.3 mg, 0.01 mmol) was added. The reaction mixture was sealed and then heated at 110° C. for 2 h. After separation and the aqueous layer extracted with EtOAc, the organic layer was dried, filtered and concentrated under vacuum. The crude was purified by prep LC-MS (pH=2 method; Waters SunFire PrepC18 5 µm OBD™ column, 30×100 mm, 60 mL/min, eluting with a gradient of MeCN and water with 0.1% TFA) to give the desired product as white powders (6.4 mg, 72%). LCMS calcd for $C_{29}H_{26}FN_6O_3(M+H)^+$: m/z=525.2. Found: 525.2.

Example 16. N-{4-[4-Amino-7-(tetrahydro-2H-pyran-4-yl)pyrrolo[2,1-f][1,2,4]triazin-5-yl]-3-fluorophenyl}-1-(4-fluorophenyl)-2-oxo-1,2-dihydropyridine-3-carboxamide

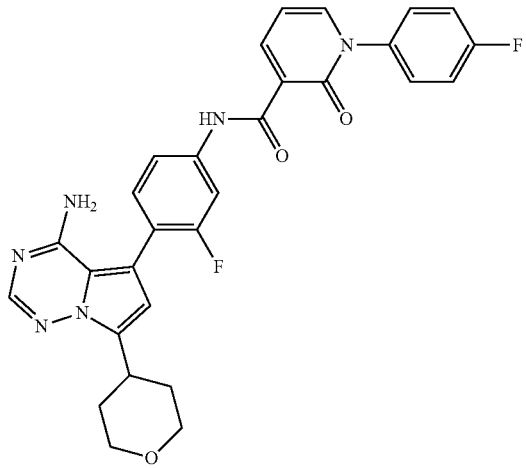 [SMILES: Nc1ncnn2c(C3CCOCC3)cc(-c3ccc(NC(=O)c4cccn(-c5ccc(F)cc5)c4=O)cc3F)c12]

In a sealed tube a mixture of 5-bromo-7-(tetrahydro-2H-pyran-4-yl)pyrrolo[2,1-f][1,2,4]triazin-4-amine (6 mg, 0.02 mmol) (prepared in Example 13, step 3), 1-(4-fluorophenyl)-N-[3-fluoro-4-(4,4,5,5-tetramethyl-1,3,2-dioxaborolan-2-yl)phenyl]-2-oxo-1,2-dihydropyridine-3-carboxamide (9.6 mg, 0.02 mmol) (prepared in Example 9, step 5) and N,N-diisopropylethylamine (0.01 mL, 0.06 mmol) in 1,4-dioxane (0.15 mL) and water (20 µL) was stirred together and flushed with $N_2$ for 5 min before bis(tri-t-butylphosphine)palladium (5.2 mg, 0.01 mmol) was added. The reaction mixture was sealed and then heated at 110° C. for 1 h. After separation and the aqueous layer extracted with EtOAc, the organic layer was dried, filtered and concentrated under vacuum. The crude was purified by prep LC-MS (pH=10 method; XBridge™ PrepC18 5 µm OBD™ column, 30×100 mm, 60 mL/min, eluting with a gradient of MeCN and water with 0.15% $NH_4OH$) to give the desired product (4.4 mg, 40%). LCMS calcd for $C_{29}H_{25}F_2N_6O_3$(M+H)⁺: m/z=543.2. Found: 543.2.

Example 17a. N-{4-[4-Amino-7-(cis-4-hydroxycyclohexyl)pyrrolo[2,1-f][1,2,4]triazin-5-yl]phenyl}-1-(4-fluorophenyl)-2-oxo-1,2-dihydropyridine-3-carboxamide Example 17b. N-{4-[4-Amino-7-(trans-4-hydroxycyclohexyl)pyrrolo[2,1-f][1,2,4]triazin-5-yl]phenyl}-1-(4-fluorophenyl)-2-oxo-1,2-dihydropyridine-3-carboxamide

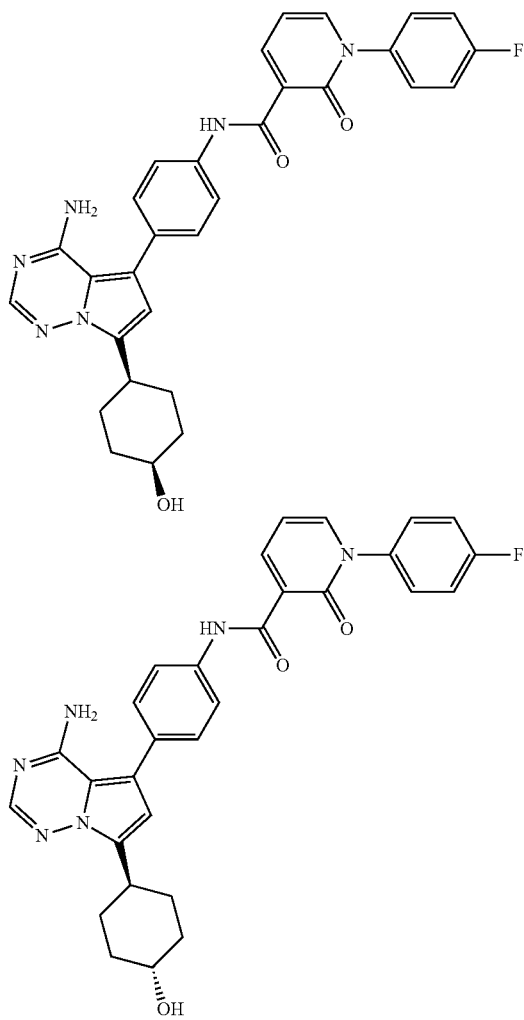

Step 1: N-{4-[4-Amino-7-(4-{[tert-butyl(dimethyl)silyl]oxy}cyclohexyl)pyrrolo[2,1-f][1,2,4]triazin-5-yl]phenyl}-1-(4-fluorophenyl)-2-oxo-1,2-dihydropyridine-3-carboxamide

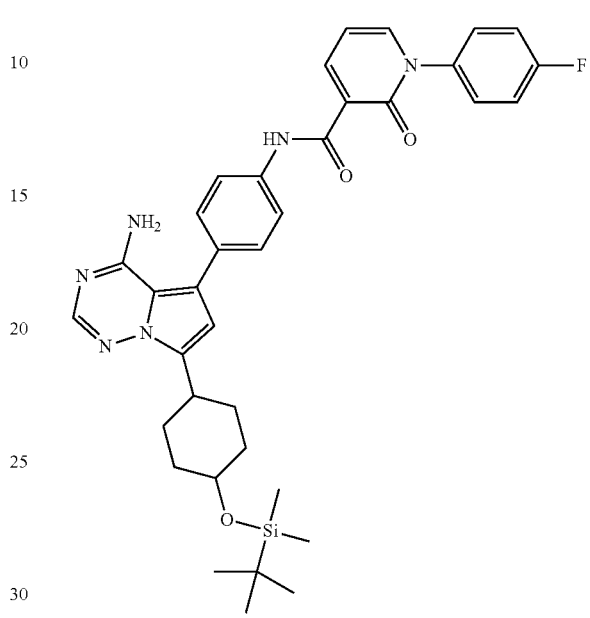

In a sealed tube a mixture of 5-bromo-7-(4-{[tert-butyl(dimethyl)silyl]oxy}cyclohexyl)pyrrolo[2,1-f][1,2,4]triazin-4-amine (5 mg, 0.012 mmol) (prepared in Example 7, step 6), 1-(4-fluorophenyl)-2-oxo-N-[4-(4,4,5,5-tetramethyl-1,3,2-dioxaborolan-2-yl)phenyl]-1,2-dihydropyridine-3-carboxamide (5.4 mg, 0.012 mmol) (prepared in Example 9, step 3) and N,N-diisopropylethylamine (0.012 mL, 0.07 mmol) in 1,4-dioxane (0.15 mL) and water (20 µL) was stirred together and flushed with $N_2$ for 5 min before bis(tri-t-butylphosphine)palladium (3 mg, 0.006 mmol) was added. The reaction mixture was sealed and then heated at 110° C. for 1 h. After separation and the aqueous layer extracted with EtOAc, the organic layer was dried, filtered and concentrated under vacuum. The crude was used directly in the next step. LCMS calcd for $C_{36}H_{42}FN_6O_3Si$ (M+H)⁺: m/z=653.3. Found: 653.3.

Step 2: N-{4-[4-Amino-7-(4-hydroxycyclohexyl)pyrrolo[2,1-f][1,2,4]triazin-5-yl]phenyl}-1-(4-fluorophenyl)-2-oxo-1,2-dihydropyridine-3-carboxamide A solution of N-{4-[4-amino-7-(4-{[tert-butyl(dimethyl)silyl]oxy}cyclohexyl)pyrrolo[2,1-f][1,2,4]triazin-5-yl]phenyl}-1-(4-fluorophenyl)-2-oxo-1,2-dihydropyridine-3-carboxamide (7.7 mg, 0.012 mmol) in methanol (0.05 mL) was treated with 4.0 M hydrogen chloride in dioxane (0.20 mL). The reaction mixture was stirred at rt for 20 min. The crude was concentrated under vacuum and purified by prep LC-MS (pH=10 method; XBridge™ PrepC18 5 µm OBD™ column, 30×100 mm, 60 mL/min, eluting with a gradient of MeCN and water with 0.15% NH₄OH) to give the desired product (cis isomer) as white powders (2.8 mg, 44%). RT=2.047 min for the major cis isomer, second peak off the column. The trans isomer is the minor product and is the first peak off the column. The trans isomer was not isolated. LCMS calcd for $C_{30}H_{28}FN_6O_3(M+H)^+$: m/z=539.2. Found: 539.2.

Example 18a. N-{4-[4-Amino-7-(cis-4-hydroxycyclohexyl)pyrrolo[2,1-f][1,2,4]triazin-5-yl]-3-fluorophenyl}-2-oxo-1-phenyl-1,2-dihydropyridine-3-carboxamide Example 18b. N-{4-[4-Amino-7-(trans-4-hydroxycyclohexyl)pyrrolo[2,1-f][1,2,4]triazin-5-yl]-3-fluorophenyl}-2-oxo-1-phenyl-1,2-dihydropyridine-3-carboxamide

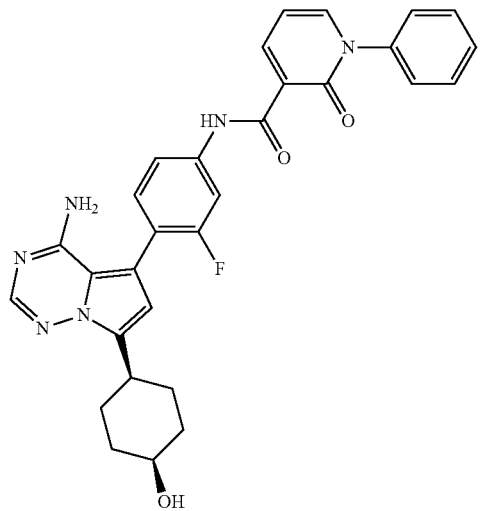

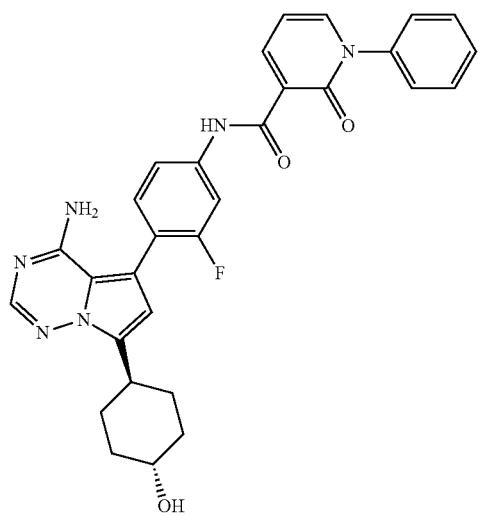

Step 1: N-{4-[4-Amino-7-(4-{[tert-butyl(dimethyl)silyl]oxy}cyclohexyl)pyrrolo[2,1-f][1,2,4]triazin-5-yl]-3-fluorophenyl}-2-oxo-1-phenyl-1,2-dihydropyridine-3-carboxamide

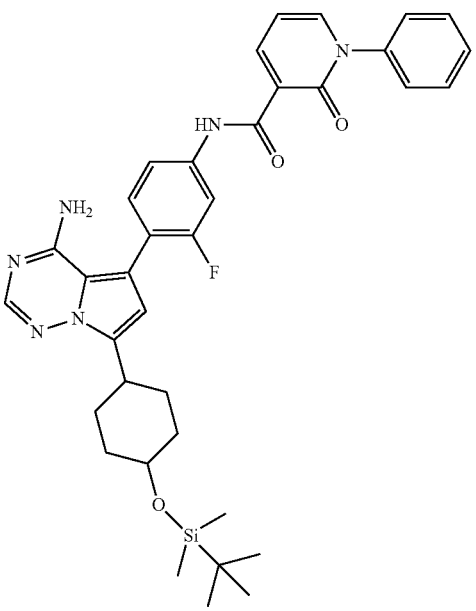 [SMILES: CC(C)(C)[Si](C)(C)OC1CCC(c2cc(-c3ccc(NC(=O)c4cccn(-c5ccccc5)c4=O)cc3F)c3c(N)ncnn23)CC1]

In a sealed tube a mixture of 5-bromo-7-(4-{[tert-butyl(dimethyl)silyl]oxy}cyclohexyl)pyrrolo[2,1-f][1,2,4]triazin-4-amine (6 mg, 0.014 mmol) (prepared in Example 7, step 6), N-[3-fluoro-4-(4,4,5,5-tetramethyl-1,3,2-dioxaborolan-2-yl)phenyl]-2-oxo-1-phenyl-1,2-dihydropyridine-3-carboxamide (6.1 mg, 0.014 mmol) (prepared in Example 9, step 4) and N,N-diisopropylethylamine (0.014 mL, 0.08 mmol) in 1,4-dioxane (0.15 mL) and water (20 µL) was stirred together and flushed with N₂ for 5 min before bis(tri-t-butylphosphine)palladium (3.6 mg, 0.007 mmol) was added. The reaction mixture was sealed and then heated at 110° C. for 40 min. After separation and the aqueous layer extracted with EtOAc, the organic layer was dried, filtered and concentrated under vacuum. The crude was directly used in the next step. LCMS calcd for $C_{36}H_{42}FN_6O_3Si$ $(M+H)^+$: m/z=653.3. Found: 653.3.

Step 2: N-{4-[4-Amino-7-(4-hydroxycyclohexyl)pyrrolo[2,1-f][1,2,4]triazin-5-yl]-3-fluorophenyl}-2-oxo-1-phenyl-1,2-dihydropyridine-3-carboxamide A solution of N-{4-[4-amino-7-(4-{[tert-butyl(dimethyl)silyl]oxy}cyclohexyl)pyrrolo[2,1-f][1,2,4]triazin-5-yl]-3-fluorophenyl}-2-oxo-1-phenyl-1,2-dihydropyridine-3-carboxamide (9.2 mg, 0.014 mmol) in methanol (0.06 mL) was treated with 4.0 M hydrogen chloride in dioxane (0.24 mL). The reaction mixture was stirred at rt for 30 min. The crude was concentrated under vacuum and purified by prep LC-MS (pH=2 method; Waters SunFire PrepC18 5 μm OBD™ column, 30×100 mm, 60 mL/min, eluting with a gradient of MeCN and water with 0.1% TFA) to give the desired product (cis isomer) as white powders. RT=1.208 min for the cis isomer, second peak off the column. LCMS calcd for $C_{30}H_{28}FN_6O_3(M+H)^+$: m/z=539.2. Found: 539.2.

Example 19a. N-{4-[4-Amino-7-(cis-4-hydroxycyclohexyl)pyrrolo[2,1-f][1,2,4]triazin-5-yl]-3-fluorophenyl}-1-(4-fluorophenyl)-2-oxo-1,2-dihydropyridine-3-carboxamide Example 19b. N-{4-[4-Amino-7-(trans-4-hydroxycyclohexyl)pyrrolo[2,1-f][1,2,4]triazin-5-yl]-3-fluorophenyl}-1-(4-fluorophenyl)-2-oxo-1,2-dihydropyridine-3-carboxamide

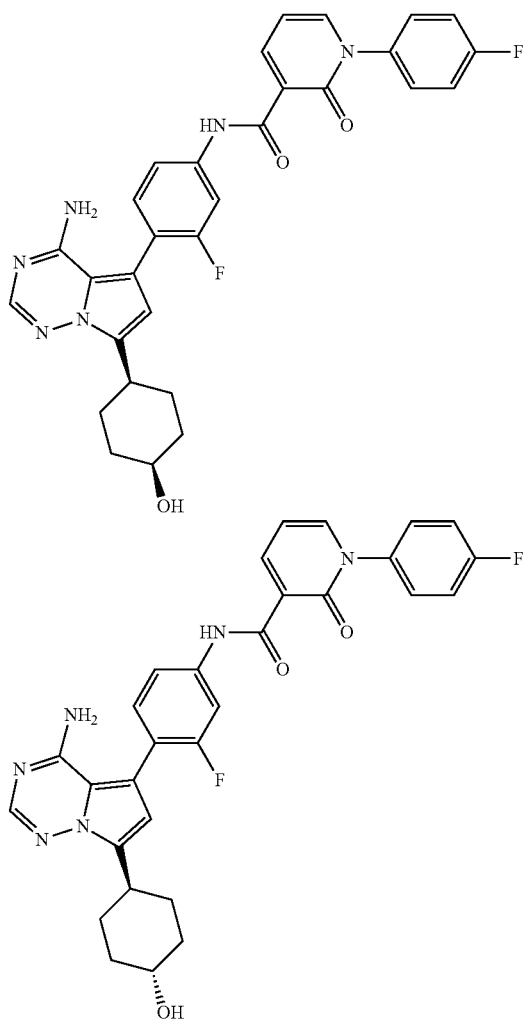

Step 1: N-{4-[4-Amino-7-(4-{[tert-butyl(dimethyl)silyl]oxy}cyclohexyl)pyrrolo[2,1-f][1,2,4]triazin-5-yl]-3-fluorophenyl}-1-(4-fluorophenyl)-2-oxo-1,2-dihydropyridine-3-carboxamide

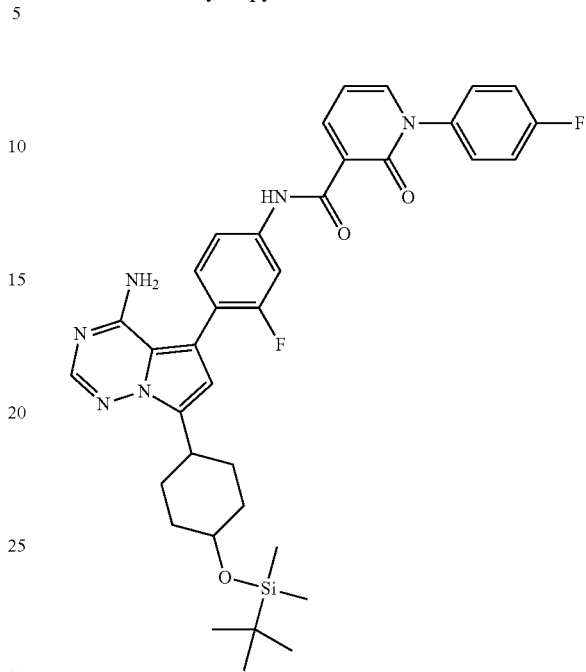

In a sealed tube a mixture of 5-bromo-7-(4-{[tert-butyl(dimethyl)silyl]oxy}cyclohexyl)pyrrolo[2,1-f][1,2,4]triazin-4-amine (5 mg, 0.012 mmol) (prepared in Example 7, step 6), 1-(4-fluorophenyl)-N-[3-fluoro-4-(4,4,5,5-tetramethyl-1,3,2-dioxaborolan-2-yl)phenyl]-2-oxo-1,2-dihydropyridine-3-carboxamide (5.6 mg, 0.012 mmol) (prepared in Example 9, step 5) and N,N-diisopropylethylamine (0.012 mL, 0.07 mmol) in 1,4-dioxane (0.15 mL) and water (20 μL) was stirred together and flushed with $N_2$ for 5 min before bis(tri-t-butylphosphine)palladium (3 mg, 0.006 mmol) was added. The reaction mixture was sealed and then heated at 100° C. for 1 h. After separation and the aqueous layer extracted with EtOAc, the organic layer was dried, filtered and concentrated under vacuum. The crude was used directly in the next step. LCMS calcd for $C_{36}H_{41}F_2N_6O_3Si$ $(M+H)^+$: m/z=671.3. Found: 671.3.

Step 2: N-{4-[4-Amino-7-(4-hydroxycyclohexyl)pyrrolo[2,1-f][1,2,4]triazin-5-yl]-3-fluorophenyl}-1-(4-fluorophenyl)-2-oxo-1,2-dihydropyridine-3-carboxamide A solution of N-{4-[4-amino-7-(4-{[tert-butyl(dimethyl)silyl]oxy}cyclohexyl)pyrrolo[2,1-f][1,2,4]triazin-5-yl]-3-fluorophenyl}-1-(4-fluorophenyl)-2-oxo-1,2-dihydropyridine-3-carboxamide (7.9 mg, 0.012 mmol) in methanol (0.05 mL) was treated with 4.0 M hydrogen chloride in dioxane (0.2 mL). The reaction mixture was stirred at rt for 30 min. The crude was concentrated under vacuum and purified by prep LC-MS (pH=10 method; XBridge™ PrepC18 5 μm OBD™ column, 30×100 mm, 60 mL/min, eluting with a gradient of MeCN and water with 0.15% $NH_4OH$) to give the desired product (cis isomer) as white powders (1.8 mg, 27%). RT=2.114 min for the major cis isomer, second peak off the column. The trans isomer was not isolated, which is the first peak off the column. LCMS calcd for $C_{30}H_{27}F_2N_6O_3(M+H)^+$: m/z=557.2. Found: 557.2.

Example 20. N-{4-[4-Amino-7-(1-methylpiperidin-4-yl)pyrrolo[2,1-f][1,2,4]triazin-5-yl]phenyl}-2-oxo-1-phenyl-1,2-dihydropyridine-3-carboxamide

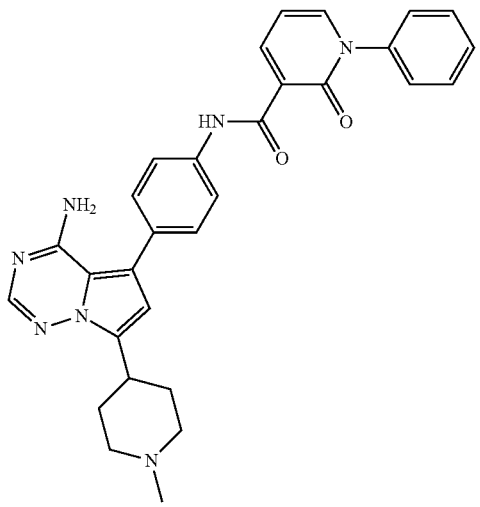 [SMILES: CN1CCC(c2cc(-c3ccc(NC(=O)c4cccn(-c5ccccc5)c4=O)cc3)c3c(N)ncnn23)CC1]

Step 1: 7-(1-Methyl-1,2,3,6-tetrahydropyridin-4-yl)pyrrolo[2,1-f][1,2,4]triazin-4-amine

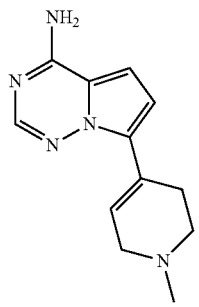 [SMILES: CN1CC=C(c2ccc3c(N)ncnn23)CC1]

The mixture of 7-bromopyrrolo[2,1-f][1,2,4]triazin-4-amine (from J & W Pharm Lab, 208 mg, 0.97 mmol), 1-methyl-4-(4,4,5,5-tetramethyl-1,3,2-dioxaborolan-2-yl)-1,2,3,6-tetrahydropyridine (from Aldrich, 250 mg, 1.12 mmol), potassium phosphate (0.61 g, 2.9 mmol) in 1,4-dioxane (3.4 mL) and water (1.1 mL) was degassed, refilled with nitrogen, followed by addition of dicyclohexyl(2',4',6'-triisopropylbiphenyl-2-yl)phosphine-(2'-aminobiphenyl-2-yl)(chloro)palladium (1:1) (110 mg, 0.14 mmol). The reaction mixture was degassed again, refilled with nitrogen and was then sealed and heated at 80° C. for 1 h. The reaction mixture was allowed to cool to rt, diluted with ethyl acetate, washed with brine, dried over sodium sulfate, filtered, and concentrated under vacuum to give the crude product, which was used directly in the next step. LCMS calcd for $C_{12}H_{16}N_5(M+H)^+$: m/z=230.1. Found: 230.1.

Step 2: 7-(1-Methylpiperidin-4-yl)pyrrolo[2,1-f][1,2,4]triazin-4-amine

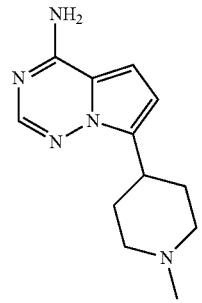 [SMILES: CN1CCC(c2ccc3c(N)ncnn23)CC1]

To a solution of 7-(1-methyl-1,2,3,6-tetrahydropyridin-4-yl)pyrrolo[2,1-f][1,2,4]triazin-4-amine (134 mg, 0.26 mmol) in methanol (1.26 mL) and THF (0.5 mL) was added a mixture of palladium (150 mg, 0.14 mmol) (10% Pd on carbon). The reaction mixture was placed under a hydrogen balloon for 4 hours. After filtration through a celite pad, the filtrate was concentrated under vacuum to give the crude. The crude was further purified by prep LC-MS (pH=10 method; XBridge™ PrepC18 5 μm OBD™ column, 30×100 mm, 60 mL/min, eluting with a gradient of MeCN and water with 0.15% NH$_4$OH) to give the desired product as white powders (22 mg, 36%). LCMS calcd for $C_{12}H_{18}N_5(M+H)^+$: m/z=232.2. Found: 232.2.

Step 3: 5-Bromo-7-(1-methylpiperidin-4-yl)pyrrolo[2,1-f][1,2,4]triazin-4-amine

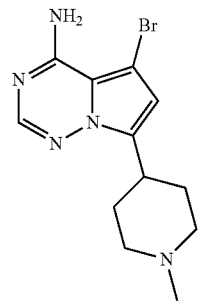 [SMILES: CN1CCC(c2cc(Br)c3c(N)ncnn23)CC1]

To a solution of 7-(1-methylpiperidin-4-yl)pyrrolo[2,1-f][1,2,4]triazin-4-amine (16.5 mg, 0.07 mmol) in N,N-dimethylformamide (0.31 mL) and tetrahydrofuran (0.20 mL) was added N-bromosuccinimide (10.2 mg, 0.06 mmol). The resulting mixture was stirred at rt for 10 min. The reaction mixture was diluted with EtOAc, filtered. The filtrate was washed with saturated NaHCO$_3$, water, dried, filtered and concentrated under vacuum to give the desired product as tan solid. LCMS calcd for $C_{12}H_{17}BrN_5$ (M+H)$^+$: m/z=310.1, 312.1. Found: 310.1, 312.1.

Step 4: N-{4-[4-Amino-7-(1-methylpiperidin-4-yl)pyrrolo[2,1-f][1,2,4]triazin-5-yl]phenyl}-2-oxo-1-phenyl-1,2-dihydropyridine-3-carboxamide In a sealed tube a mixture of 5-bromo-7-(1-methylpiperidin-4-yl)pyrrolo[2,1-f][1,2,4]triazin-4-amine (4 mg, 0.013 mmol), 2-oxo-1-phenyl-N-[4-(4,4,5,5-tetramethyl-1,3,2-dioxaborolan-2-yl)phenyl]-1,2-dihydropyridine-3-carboxamide (5.6 mg, 0.014 mmol) (prepared in Example 7, step 3) and N,N-diisopropylethylamine (0.012 mL, 0.078 mmol) in 1,4-dioxane (0.15 m) and water (20 μL) was stirred together and flushed with N₂ for 5 min before bis(tri-t-butylphosphine)palladium (3.3 mg, 0.006 mmol) was added. The reaction mixture was sealed and then heated at 110° C. for 40 min. After separation and the aqueous layer extracted with EtOAc, the organic layer was dried, filtered and concentrated under vacuum. The crude was purified by prep LC-MS (pH=10 method; XBridge™ PrepC18 5 μm OBD™ column, 30×100 mm, 60 mL/min, eluting with a gradient of MeCN and water with 0.15% NH₄OH) to give the desired product (4.0 mg, 60%). LCMS calcd for $C_{30}H_{30}N_7O_2$ (M+H)⁺: m/z=520.2. Found: 520.2.

Example 21. N-{4-[4-Amino-7-(1-methylpiperidin-4-yl)pyrrolo[2,1-f][1,2,4]triazin-5-yl]phenyl}-1-(4-fluorophenyl)-2-oxo-1,2-dihydropyridine-3-carboxamide

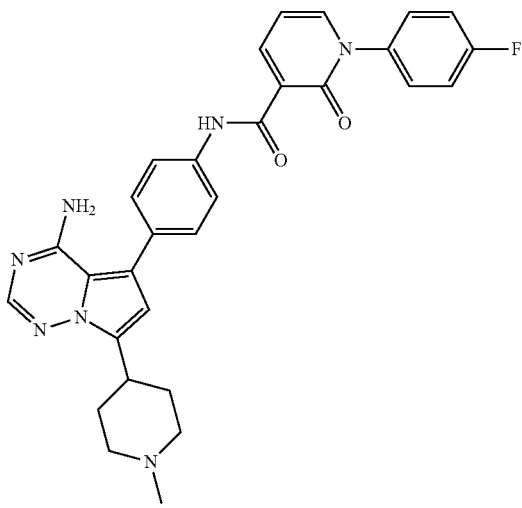 [SMILES: CN1CCC(c2cc(-c3ccc(NC(=O)c4cccn(-c5ccc(F)cc5)c4=O)cc3)c3c(N)ncnn23)CC1]

In a sealed tube a mixture of 5-bromo-7-(1-methylpiperidin-4-yl)pyrrolo[2,1-f][1,2,4]triazin-4-amine (4 mg, 0.013 mmol) (prepared in Example 20, step 3), 1-(4-fluorophenyl)-2-oxo-N-[4-(4,4,5,5-tetramethyl-1,3,2-dioxaborolan-2-yl)phenyl]-1,2-dihydropyridine-3-carboxamide (5.9 mg, 0.014 mmol) (prepared in Example 9, step 3) and N,N-diisopropylethylamine (0.014 mL, 0.04 mmol) in 1,4-dioxane (0.15 mL) and water (20 L) was stirred together and flushed with N₂ for 5 min before bis(tri-t-butylphosphine)palladium (3.3 mg, 0.006 mmol) was added. The reaction mixture was sealed and then heated at 110° C. for 1 h. After separation and the aqueous layer extracted with EtOAc, the organic layer was dried, filtered and concentrated under vacuum. The crude was purified by prep LC-MS (pH=10 method; XBridge™ PrepC18 5 μm OBD™ column, 30×100 mm, 60 mL/min, eluting with a gradient of MeCN and water with 0.15% NH₄OH) to give the desired product (2.1 mg, 30%). LCMS calcd for $C_{30}H_{29}FN_7O_2$(M+H)⁺: m/z=538.2. Found: 538.2.

Example 22. N-{4-[4-Amino-7-(1-methylpiperidin-4-yl)pyrrolo[2,1-f][1,2,4]triazin-5-yl]-3-fluorophenyl}-2-oxo-1-phenyl-1,2-dihydropyridine-3-carboxamide

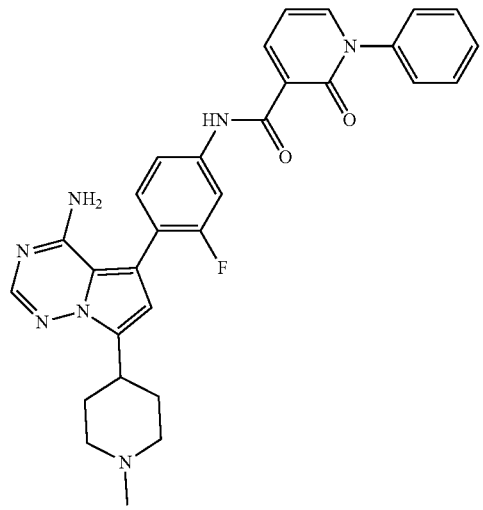 [SMILES: CN1CCC(c2cc(-c3ccc(NC(=O)c4cccn(-c5ccccc5)c4=O)cc3F)c3c(N)ncnn23)CC1]

In a sealed tube a mixture of 5-bromo-7-(1-methylpiperidin-4-yl)pyrrolo[2,1-f][1,2,4]triazin-4-amine (3 mg, 0.01 mmol) (prepared in Example 20, step 3), N-[3-fluoro-4-(4,4,5,5-tetramethyl-1,3,2-dioxaborolan-2-yl)phenyl]-2-oxo-1-phenyl-1,2-dihydropyridine-3-carboxamide (4.2 mg, 0.01 mmol) (prepared in Example 9, step 4) and N,N-diisopropylethylamine (0.01 mL, 0.03 mmol) in 1,4-dioxane (0.15 mL) and water (20 L) was stirred together and flushed with N₂ for 5 min before bis(tri-t-butylphosphine)palladium (2.5 mg, 0.005 mmol) was added. The reaction mixture was sealed and then heated at 110° C. for 40 min. After separation and the aqueous layer extracted with EtOAc, the organic layer was dried, filtered and concentrated under vacuum. The crude was purified by prep LC-MS (pH=2 method; Waters SunFire PrepC18 5 μm OBD™ column, 30×100 mm, 60 mL/min, eluting with a gradient of MeCN and water with 0.1% TFA) to give the desired product. LCMS calcd for $C_{30}H_{29}FN_7O_2$(M+H)⁺: m/z=538.2. Found: 538.2.

Example 23. N-{4-[4-Amino-7-(1-methylpiperidin-4-yl)pyrrolo[2,1-f][1,2,4]triazin-5-yl]-3-fluorophenyl}-1-(4-fluorophenyl)-2-oxo-1,2-dihydropyridine-3-carboxamide

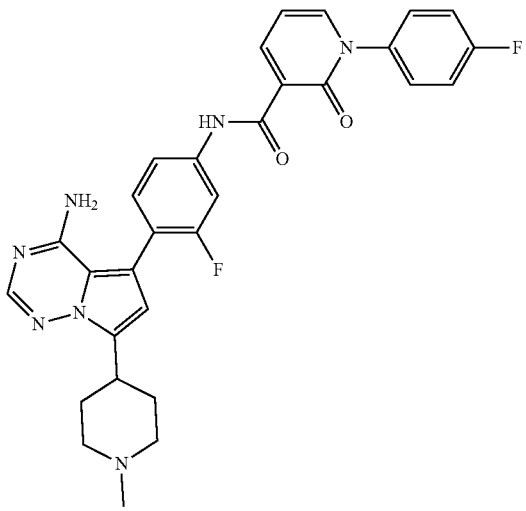 [SMILES: CN1CCC(c2cc(-c3ccc(NC(=O)c4cccn(-c5ccc(F)cc5)c4=O)cc3F)c3c(N)ncnn23)CC1]

In a sealed tube a mixture of 5-bromo-7-(1-methylpiperidin-4-yl)pyrrolo[2,1-f][1,2,4]triazin-4-amine (4 mg, 0.013 mmol) (prepared in Example 20, step 3), 1-(4-fluorophenyl)-N-[3-fluoro-4-(4,4,5,5-tetramethyl-1,3,2-dioxaborolan-2-yl)phenyl]-2-oxo-1,2-dihydropyridine-3-carboxamide (5.8 mg, 0.013 mmol) (prepared in Example 9, step 5) and N,N-diisopropylethylamine (0.014 mL, 0.08 mmol) in 1,4-dioxane (0.15 mL) and water (20 L) was stirred together and flushed with N$_2$ for 5 min before bis(tri-t-butylphosphine)palladium (3.3 mg, 0.006 mmol) was added. The reaction mixture was sealed and then heated at 110° C. for 40 min. After separation and the aqueous layer extracted with EtOAc, the organic layer was dried, filtered and concentrated under vacuum. The crude was purified by prep LC-MS (pH=10 method; XBridge™ PrepC18 5 μm OBD™ column, 30×100 mm, 60 mL/min, eluting with a gradient of MeCN and water with 0.15% NH$_4$OH) to give the desired product (2.5 mg, 35%). LCMS calcd for C$_{30}$H$_{28}$F$_2$N$_7$O$_2$(M+H)$^+$: m/z=556.3. Found: 556.3.

Example 24. N-{4-[7-(1-Acetylpiperidin-4-yl)-4-aminopyrrolo[2,1-f][1,2,4]triazin-5-yl]phenyl}-2-oxo-1-phenyl-1,2-dihydropyridine-3-carboxamide

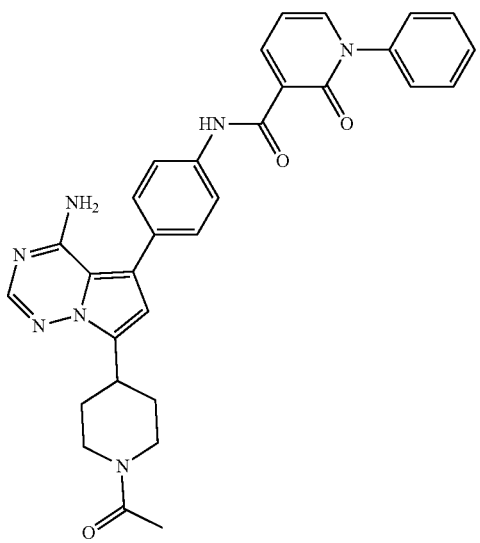 [SMILES: CC(=O)N1CCC(c2cc(-c3ccc(NC(=O)c4cccn(-c5ccccc5)c4=O)cc3)c3c(N)ncnn23)CC1]

Step 1: 7-(1-Acetyl-1,2,3,6-tetrahydropyridin-4-yl)pyrrolo[2,1-f][1,2,4]triazin-4-amine

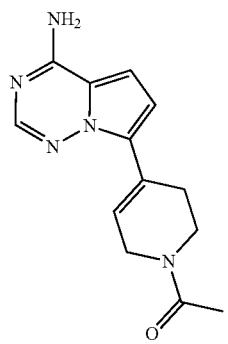 [SMILES: CC(=O)N1CC=C(c2ccc3c(N)ncnn23)CC1]

A mixture of 1-acetyl-4-(4,4,5,5-tetramethyl-1,3,2-dioxaborolan-2-yl)-1,2,3,6-tetrahydropyridine (from Combi-Blocks, 500 mg, 1.99 mmol), 7-bromopyrrolo[2,1-f][1,2,4]triazin-4-amine (from J & W Pharm Lab, 424 mg, 1.99 mmol), sodium carbonate (700 mg, 6.6 mmol), and [1,1'-bis(di-cyclohexylphosphino)ferrocene]dichloropalladium (II) (199 mg, 0.26 mmol) in tert-butyl alcohol (6.0 mL) and water (2.2 mL) was degassed with nitrogen, then stirred and heated at 110° C. for 2 h. The mixture was diluted with ethyl acetate, washed with saturated NaHCO$_3$, water, dried over Na$_2$SO$_4$, filtered and concentrated. The product was purified by Biotage silica gel chromatography (20 g column, 0 to 30% MeOH in EtOAc) to give the desired product as brown solid (317 mg, 62%). LCMS calcd for C$_{13}$H$_{16}$N$_5$O (M+H)$^+$: m/z=258.1. Found: 258.1.

Step 2: 7-(1-Acetylpiperidin-4-yl)pyrrolo[2,1-f][1,2,4]triazin-4-amine

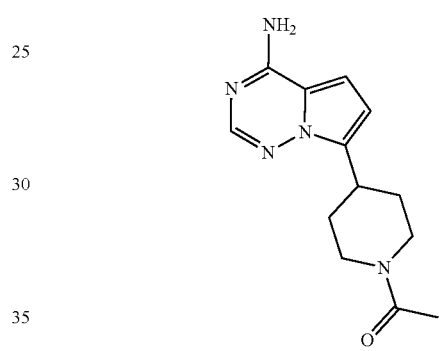

To a cloudy solution of 7-(1-acetyl-1,2,3,6-tetrahydropyridin-4-yl)pyrrolo[2,1-f][1,2,4]triazin-4-amine (305 mg, 1.19 mmol) in methanol (4.9 mL) and tetrahydrofuran (2.4 mL) was added a mixture of palladium (610 mg) (10% Pd on carbon). The reaction mixture was placed under a hydrogen balloon for 18 h, and filtered through a celite pad. The filtrate was concentrated under vacuum to give the desired product as light brown powders (187 mg, 61%). LCMS calcd for C$_{13}$H$_{18}$N$_5$O (M+H)$^+$: m/z=260.1. Found: 260.1.

Step 3: 7-(1-Acetylpiperidin-4-yl)-5-bromopyrrolo[2,1-f][1,2,4]triazin-4-amine

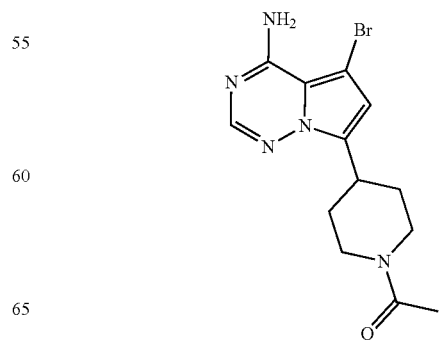

To a solution of 7-(1-acetylpiperidin-4-yl)pyrrolo[2,1-f][1,2,4]triazin-4-amine (178 mg, 0.69 mmol) in N,N-dimethylformamide (3.0 mL) was added N-bromosuccinimide (116 mg, 0.65 mmol). The resulting mixture was stirred at rt for 15 min. The reaction mixture was diluted with EtOAc, and filtered. The filtrate was washed with saturated NaHCO$_3$, water, dried, filtered and concentrated under vacuum to give the desired product as tan solid. LCMS calcd for C$_{13}$H$_{17}$BrN$_5$O (M+H)$^+$: m/z=338.1, 340.1. Found: 338.1, 340.1.

Step 4: N-{4-[7-(1-Acetylpiperidin-4-yl)-4-aminopyrrolo[2,1-f][1,2,4]triazin-5-yl]phenyl}-2-oxo-1-phenyl-1,2-dihydropyridine-3-carboxamide In a sealed tube a mixture of 7-(1-acetylpiperidin-4-yl)-5-bromopyrrolo[2,1-f][1,2,4]triazin-4-amine (6 mg, 0.02 mmol), 2-oxo-1-phenyl-N-[4-(4,4,5,5-tetramethyl-1,3,2-dioxaborolan-2-yl)phenyl]-1,2-dihydropyridine-3-carboxamide (7.8 mg, 0.019 mmol) (prepared in Example 7, step 3) and N,N-diisopropylethylamine (0.018 mL, 0.11 mmol) in 1,4-dioxane (0.15 mL) and water (20 μL) was stirred together and flushed with N$_2$ for 5 min before bis(tri-t-butylphosphine)palladium (4.5 mg, 0.009 mmol) was added. The reaction mixture was sealed and then heated at 110° C. for 1 h. After separation and the aqueous layer extracted with EtOAc, the organic layer was dried, filtered and concentrated under vacuum. The crude was purified by prep LC-MS (pH=10 method; XBridge™ PrepC18 5 μm OBD™ column, 30×100 mm, 60 mL/min, eluting with a gradient of MeCN and water with 0.15% NH$_4$OH) to give the desired product (3.0 mg, 31%) as. LCMS calcd for C$_{31}$H$_{30}$N$_7$O$_3$ (M+H)$^+$: m/z=548.2. Found: 548.2.

Example 25. N-{4-[7-(1-Acetylpiperidin-4-yl)-4-aminopyrrolo[2,1-f][1,2,4]triazin-5-yl]phenyl}-1-(4-fluorophenyl)-2-oxo-1,2-dihydropyridine-3-carboxamide

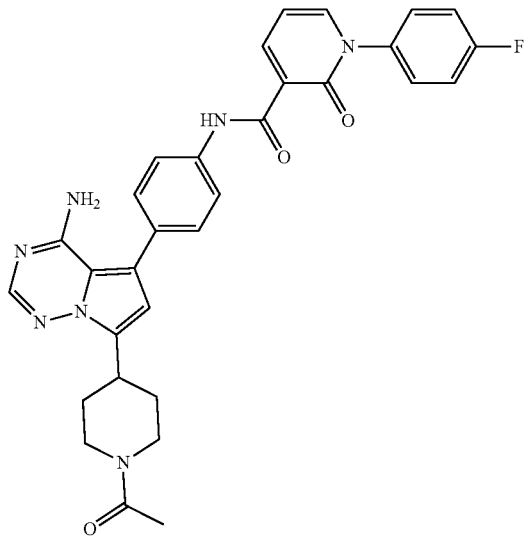 [SMILES: CC(=O)N1CCC(c2cc(-c3ccc(NC(=O)c4cccn(-c5ccc(F)cc5)c4=O)cc3)c3c(N)ncnn23)CC1]

In a sealed tube a mixture of 7-(1-acetylpiperidin-4-yl)-5-bromopyrrolo[2,1-f][1,2,4]triazin-4-amine (6 mg, 0.02 mmol) (prepared in Example 24, step 3), 1-(4-fluorophenyl)-2-oxo-N-[4-(4,4,5,5-tetramethyl-1,3,2-dioxaborolan-2-yl)phenyl]-1,2-dihydropyridine-3-carboxamide (8.1 mg, 0.019 mmol) (prepared in Example 9, step 3) and N,N-diisopropylethylamine (0.018 mL, 0.11 mmol) in 1,4-dioxane (0.15 mL) and water (20 L) was stirred together and flushed with N$_2$ for 5 min before bis(tri-t-butylphosphine)palladium (4.5 mg, 0.009 mmol) was added. The reaction mixture was sealed and then heated at 110° C. for 1 h. After separation and the aqueous layer extracted with EtOAc, the organic layer was dried, filtered and concentrated under vacuum. The crude was purified by prep LC-MS (pH=10 method; XBridge™ PrepC18 5 μm OBD™ column, 30×100 mm, 60 mL/min, eluting with a gradient of MeCN and water with 0.15% NH$_4$OH) to give the desired product (2.9 mg, 29%) as. LCMS calcd for C$_{31}$H$_{29}$FN$_7$O$_3$(M+H)$^+$: m/z=566.2. Found: 566.2.

Example 26. N-{4-[7-(1-Acetylpiperidin-4-yl)-4-aminopyrrolo[2,1-f][1,2,4]triazin-5-yl]-3-fluorophenyl}-2-oxo-1-phenyl-1,2-dihydropyridine-3-carboxamide

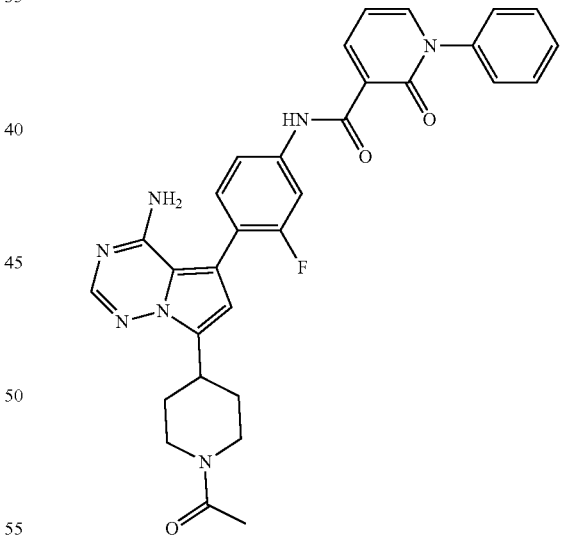

In a sealed tube a mixture of 7-(1-acetylpiperidin-4-yl)-5-bromopyrrolo[2,1-f][1,2,4]triazin-4-amine (6 mg, 0.02 mmol) (prepared in Example 24, step 3), N-[3-fluoro-4-(4,4,5,5-tetramethyl-1,3,2-dioxaborolan-2-yl)phenyl]-2-oxo-1-phenyl-1,2-dihydropyridine-3-carboxamide (8.1 mg, 0.02 mmol) (prepared in Example 9, step 4) and N,N-diisopropylethylamine (0.18 mL, 0.11 mmol) in 1,4-dioxane (0.15 mL) and water (20 μL) was stirred together and flushed with N$_2$ for 5 min before bis(tri-t-butylphosphine)palladium (4.5 mg, 0.01 mmol) was added. The reaction mixture was sealed and then heated at 110° C. for 1 h. After separation and the aqueous layer extracted with EtOAc, the organic layer was dried, filtered and concentrated under vacuum. The crude was purified by prep LC-MS (pH=10 method; XBridge™ PrepC18 5 μm OBD™ column, 30×100 mm, 60 mL/min, eluting with a gradient of MeCN and water with 0.15% NH$_4$OH) to give the desired product (2.4 mg, 24%) as. LCMS calcd for $C_{31}H_{29}FN_7O_3(M+H)^+$: m/z=566.2. Found: 566.2.

Example 27. N-{4-[7-(1-Acetylpiperidin-4-yl)-4-aminopyrrolo[2,1-f][1,2,4]triazin-5-yl]-3-fluorophenyl}-1-(4-fluorophenyl)-2-oxo-1,2-dihydropyridine-3-carboxamide

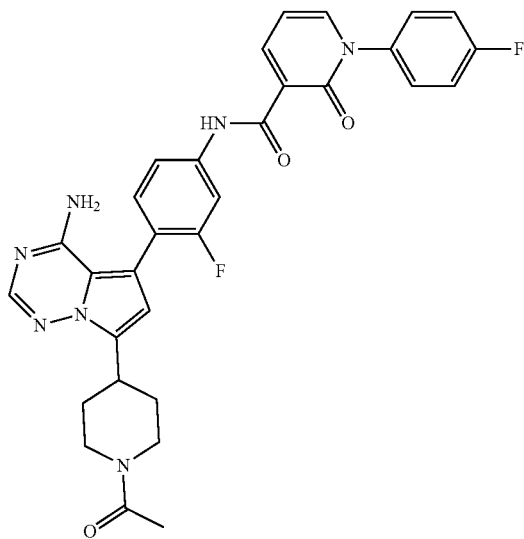 [SMILES: CC(=O)N1CCC(c2cc(-c3ccc(NC(=O)c4cccn(-c5ccc(F)cc5)c4=O)cc3F)c3c(N)ncnn23)CC1]

In a sealed tube a mixture of 7-(1-acetylpiperidin-4-yl)-5-bromopyrrolo[2,1-f][1,2,4]triazin-4-amine (6 mg, 0.02 mmol) (prepared in Example 24, step 3), 1-(4-fluorophenyl)-N-[3-fluoro-4-(4,4,5,5-tetramethyl-1,3,2-dioxaborolan-2-yl)phenyl]-2-oxo-1,2-dihydropyridine-3-carboxamide (8.4 mg, 0.02 mmol) (prepared in Example 9, step 5) and N,N-diisopropylethylamine (0.018 mL, 0.11 mmol) in 1,4-dioxane (0.15 mL) and water (20 L) was stirred together and flushed with N$_2$ for 5 min before bis(tri-t-butylphosphine) palladium (4.5 mg, 0.009 mmol) was added. The reaction mixture was sealed and then heated at 110° C. for 1 h. After separation and the aqueous layer extracted with EtOAc, the organic layer was dried, filtered and concentrated under vacuum. The crude was purified by prep LC-MS (pH=10 method; XBridge™ PrepC18 5 μm OBD™ column, 30×100 mm, 60 mL/min, eluting with a gradient of MeCN and water with 0.15% NH$_4$OH) to give the desired product as off-white powders (2.3 mg, 22%). LCMS calcd for $C_{31}H_{28}F_2N_7O_3$ $(M+H)^+$: m/z=584.2. Found: 584.2.

Example 28a. N-{4-[4-Amino-7-(cis-4-cyanocyclohexyl)pyrrolo[2,1-f][1,2,4]triazin-5-yl]phenyl}-2-oxo-1-phenyl-1,2-dihydropyridine-3-carboxamide Example 28b. N-{4-[4-Amino-7-(trans-4-cyanocyclohexyl)pyrrolo[2,1-f][1,2,4]triazin-5-yl]phenyl}-2-oxo-1-phenyl-1,2-dihydropyridine-3-carboxamide

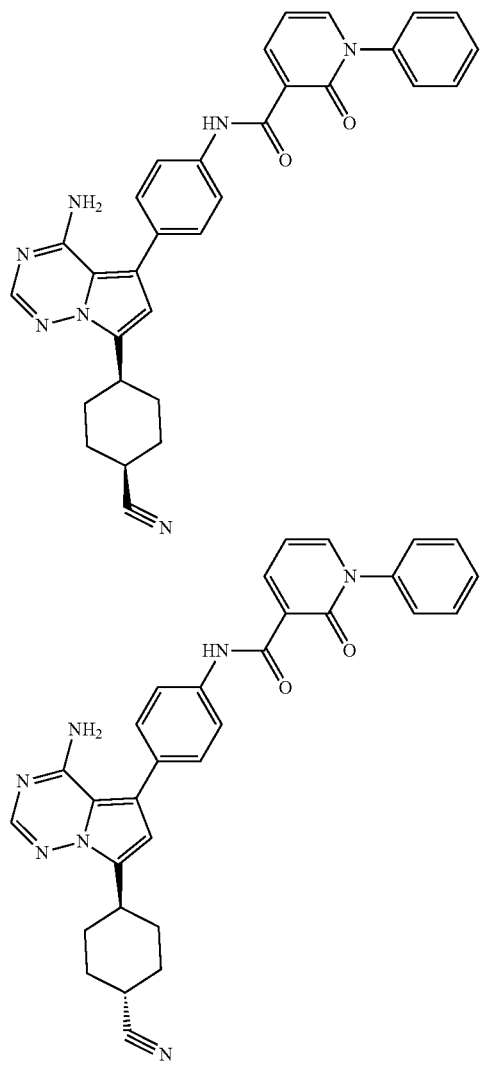

Step 1: 4-(4-Aminopyrrolo[2,1-f][1,2,4]triazin-7-yl)cyclohex-3-ene-1-carbonitrile

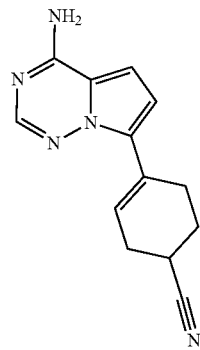 [SMILES: N#CC1CC=C(c2ccc3c(N)ncnn23)CC1]

A mixture of 4-(4,4,5,5-tetramethyl-1,3,2-dioxaborolan-2-yl)cyclohex-3-ene-1-carbonitrile (from Pharma Block, 500 mg, 2.15 mmol), 7-bromopyrrolo[2,1-f][1,2,4]triazin-4-amine (from J & W Pharm Lab, 457 mg, 2.14 mmol), sodium carbonate (760 mg, 7.1 mmol), and [1,1'-bis(dicyclohexylphosphino)ferrocene]dichloropalladium (II) (211 mg, 0.279 mmol) in tert-butyl alcohol (6.4 mL) and water (2.4 mL) was degassed with nitrogen, then stirred and heated at 110° C. for 2 h. The mixture was diluted with ethyl acetate, washed with saturated NaHCO$_3$, water, dried over Na$_2$SO$_4$, filtered and concentrated. The product was purified by Biotage silica gel chromatography (20 g column, 0 to 100% EtOAc in hexanes) to give the desired product as off-white powders (238 mg, 46%). LCMS calcd for C$_{13}$H$_{14}$N$_5$(M+H)$^+$: m/z=240.1. Found: 240.1.

Step 2: 4-(4-Aminopyrrolo[2,1-f][1,2,4]triazin-7-yl)cyclohexanecarbonitrile

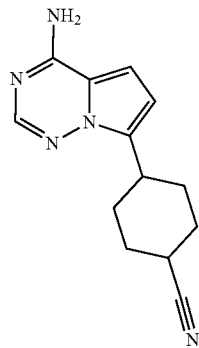 [SMILES: N#CC1CCC(c2ccc3c(N)ncnn23)CC1]

To a solution of 4-(4-aminopyrrolo[2,1-f][1,2,4]triazin-7-yl)cyclohex-3-ene-1-carbonitrile (238 mg, 0.99 mmol) in methanol (4.1 mL) and tetrahydrofuran (2.0 mL) was added a mixture of palladium (512 mg) (10% Pd on carbon). The reaction mixture was placed under a hydrogen balloon for 18 h. After filtration through a celite pad, the filtrate was concentrated under vacuum to give the desired product as clear gum (147.2 mg, 61%). LCMS calcd for C$_{13}$H$_{16}$N$_5$(M+H)$^+$: m/z=242.1. Found: 242.1.

Step 3: 4-(4-Amino-5-bromopyrrolo[2,1-f][1,2,4]triazin-7-yl)cyclohexanecarbonitrile

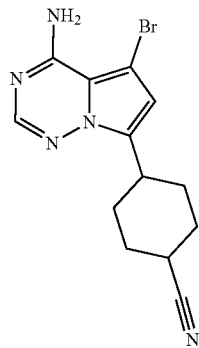 [SMILES: N#CC1CCC(c2cc(Br)c3c(N)ncnn23)CC1]

To a solution of 4-(4-aminopyrrolo[2,1-f][1,2,4]triazin-7-yl)cyclohexanecarbonitrile (137 mg, 0.57 mmol) in N,N-dimethylformamide (2.4 mL) was added N-bromosuccinimide (96 mg, 0.54 mmol). The resulting mixture was stirred at rt for 15 min. The reaction mixture was diluted with EtOAc, and filtered. The filtrate was washed with saturated NaHCO$_3$, water, dried, filtered and concentrated under vacuum to give the desired product as off-white powders (182 mg, 100%). LCMS calcd for C$_{13}$H$_{15}$BrN$_5$ (M+H)$^+$: m/z=320.0, 322.0. Found: 320.0, 322.0.

Step 4: N-{4-[4-Amino-7-(4-cyanocyclohexyl)pyrrolo[2,1-f][1,2,4]triazin-5-yl]phenyl}-2-oxo-1-phenyl-1,2-dihydropyridine-3-carboxamide In a sealed tube a mixture of 4-(4-amino-5-bromopyrrolo[2,1-f][1,2,4]triazin-7-yl)cyclohexanecarbonitrile (9 mg, 0.03 mmol), 2-oxo-1-phenyl-N-[4-(4,4,5,5-tetramethyl-1,3,2-dioxaborolan-2-yl)phenyl]-1,2-dihydropyridine-3-carboxamide (11.7 mg, 0.028 mmol) (prepared in Example 7, step 3) and N,N-diisopropylethylamine (0.015 mL, 0.084 mmol) in 1,4-dioxane (0.11 mL) and water (20 µL) was stirred together and flushed with N$_2$ or 5 min before bis(tri-t-butylphosphine)palladium (7.2 mg, 0.014 mmol) was added. The reaction mixture was sealed and then heated at 110° C. for 1 h. After separation and the aqueous layer extracted with EtOAc, the organic layer was dried, filtered and concentrated under vacuum. The crude was purified by prep LC-MS (pH=10 method; XBridge™ PrepC18 5 µm OBD™ column, 30×100 mm, 60 mL/min, eluting with a gradient of MeCN and water with 0.15% NH$_4$OH) to give the desired cis isomer as off-white powders. RT=1.341 min for the cis isomer, first peak off the column. LCMS calcd for C$_{31}$H$_{28}$N$_7$O$_2$ (M+H)$^+$: m/z=530.2. Found: 530.2.

Example 29a. N-{4-[4-Amino-7-(cis-4-cyanocyclohexyl)pyrrolo[2,1-f][1,2,4]triazin-5-yl]phenyl}-1-(4-fluorophenyl)-2-oxo-1,2-dihydropyridine-3-carboxamide Example 29b. N-{4-[4-Amino-7-(trans-4-cyanocyclohexyl)pyrrolo[2,1-f][1,2,4]triazin-5-yl]phenyl}-1-(4-fluorophenyl)-2-oxo-1,2-dihydropyridine-3-carboxamide

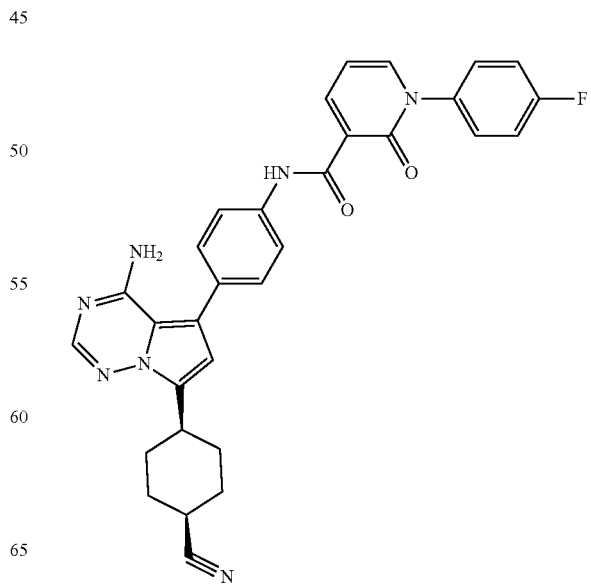

135

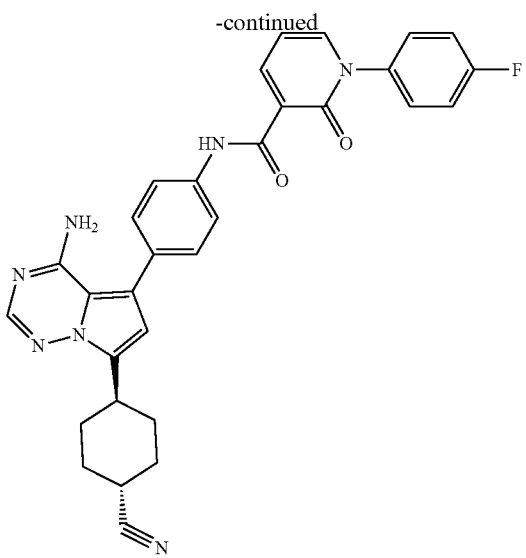

In a sealed tube a mixture of 4-(4-amino-5-bromopyrrolo[2,1-f][1,2,4]triazin-7-yl)cyclohexanecarbonitrile (9 mg, 0.028 mmol) (prepared in Example 28, step 3), 1-(4-fluorophenyl)-2-oxo-N-[4-(4,4,5,5-tetramethyl-1,3,2-dioxaborolan-2-yl)phenyl]-1,2-dihydropyridine-3-carboxamide (13 mg, 0.03 mmol) (prepared in Example 9, step 3) and N,N-diisopropylethylamine (0.015 mL, 0.08 mmol) in 1,4-dioxane (0.11 mL) and water (20 L) was stirred together and flushed with $N_2$ for 5 min before bis(tri-t-butylphosphine)palladium (7.2 mg, 0.014 mmol) was added. The reaction mixture was sealed and then heated at 110° C. for 1 h. After separation and the aqueous layer extracted with EtOAc, the organic layer was dried, filtered and concentrated under vacuum. The crude was purified by prep LC-MS (pH=10 method; XBridge™ PrepC18 5 μm OBD™ column, 30×100 mm, 60 mL/min, eluting with a gradient of MeCN and water with 0.15% $NH_4OH$) to give the desired cis isomer. RT=1.352 min for the cis isomer, first peak off the column. LCMS (M+H)+: found m/z=548.3. LCMS calcd for $C_{31}H_{27}FN_7O_2(M+H)^+$: m/z=548.2. Found: 548.2.

Example 30a. N-{4-[4-Amino-7-(cis-4-cyanocyclohexyl)pyrrolo[2,1-f][1,2,4]triazin-5-yl]-3-fluorophenyl}-2-oxo-1-phenyl-1,2-dihydropyridine-3-carboxamide Example 30b. N-{4-[4-Amino-7-(trans-4-cyanocyclohexyl)pyrrolo[2,1-f][1,2,4]triazin-5-yl]-3-fluorophenyl}-2-oxo-1-phenyl-1,2-dihydropyridine-3-carboxamide

136

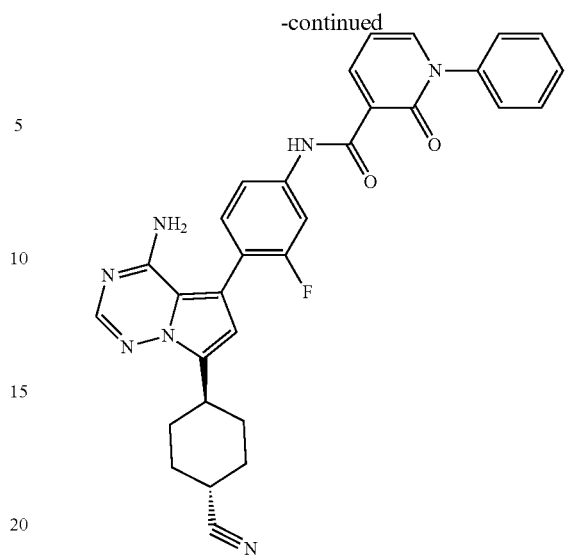

In a sealed tube a mixture of 4-4-amino-5-bromopyrrolo[2,1-f][1,2,4]triazin-7-yl)cyclohexanecarbonitrile (9 mg, 0.028 mmol) (prepared in Example 28, step 3), N-[3-fluoro-4-(4,4,5,5-tetramethyl-1,3,2-dioxaborolan-2-yl)phenyl]-2-oxo-1-phenyl-1,2-dihydropyridine-3-carboxamide (13 mg, 0.03 mmol) (prepared in Example 9, step 4) and N,N-diisopropylethylamine (0.015 mL, 0.084 mmol) in 1,4-dioxane (0.11 mL) and water (20 L) was stirred together and flushed with $N_2$ for 5 min before bis(tri-t-butylphosphine)palladium (7.2 mg, 0.014 mmol) was added. The reaction mixture was sealed and then heated at 110° C. for 1 h. After separation and the aqueous layer extracted with EtOAc, the organic layer was dried, filtered and concentrated under vacuum. The crude was purified by prep LC-MS (pH=10 method; XBridge™ PrepC18 5 μm OBD™ column, 30×100 mm, 60 mL/min, eluting with a gradient of MeCN and water with 0.15% $NH_4OH$) to give the desired cis isomer as white powders. RT=1.332 min for the cis isomer, first peak off the column. LCMS calcd for $C_{31}H_{27}FN_7O_2(M+H)^+$: m/z=548.2. Found: 548.2.

Example 31a. N-{4-[4-Amino-7-(cis-4-cyanocyclohexyl)pyrrolo[2,1-f][1,2,4]triazin-5-yl]-3-fluorophenyl}-1-(4-fluorophenyl)-2-oxo-1,2-dihydropyridine-3-carboxamide Example 31b. N-{4-[4-Amino-7-(trans-4-cyanocyclohexyl)pyrrolo[2,1-f][1,2,4]triazin-5-yl]-3-fluorophenyl}-1-(4-fluorophenyl)-2-oxo-1,2-dihydropyridine-3-carboxamide

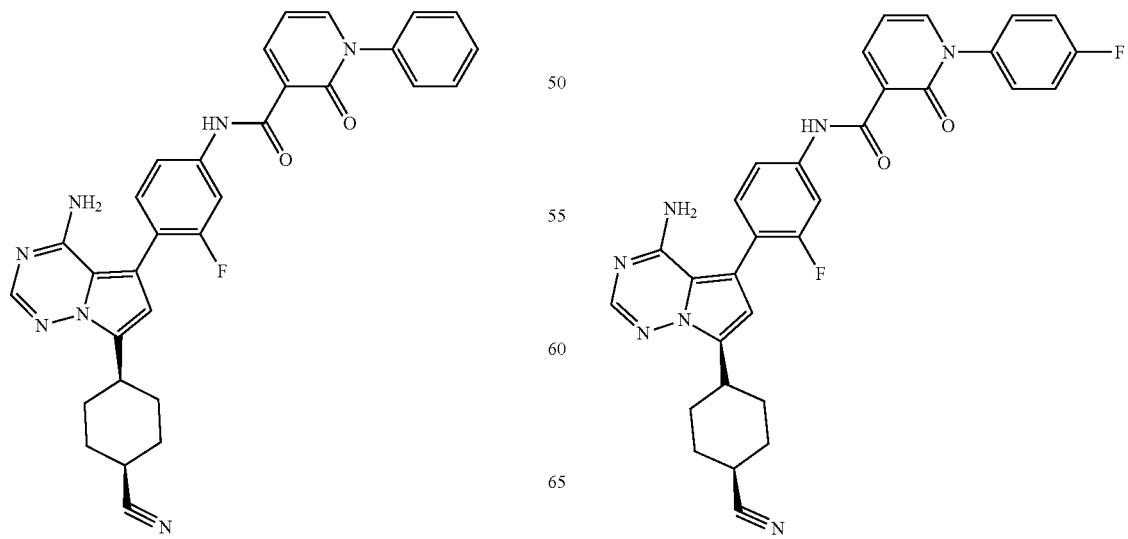

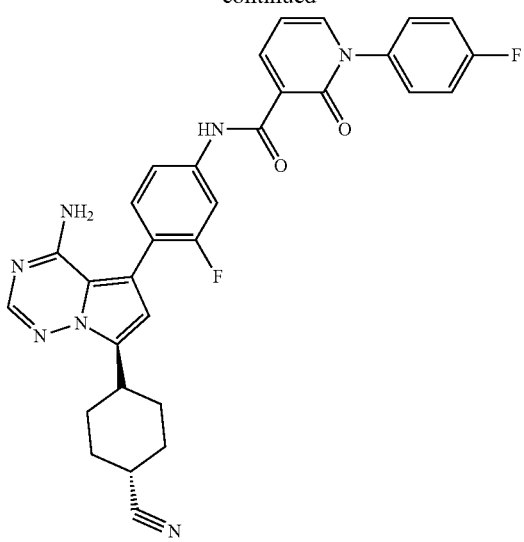

In a sealed tube a mixture of 4-(4-amino-5-bromopyrrolo[2,1-f][1,2,4]triazin-7-yl)cyclohexanecarbonitrile (9 mg, 0.03 mmol) (prepared in Example 28, step 3), 1-(4-fluorophenyl)-N-[3-fluoro-4-(4,4,5,5-tetramethyl-1,3,2-dioxaborolan-2-yl)phenyl]-2-oxo-1,2-dihydropyridine-3-carboxamide (13 mg, 0.03 mmol) (prepared in Example 9, step 5) and N,N-diisopropylethylamine (0.015 mL, 0.084 mmol) in 1,4-dioxane (0.11 mL) and water (20 L) was stirred together and flushed with $N_2$ bubble for 5 min before bis(tri-t-butylphosphine)palladium (7.2 mg, 0.014 mmol) was added. The reaction mixture was sealed and then heated at 110° C. for 1 h. After separation and the aqueous layer extracted with EtOAc, the organic layer was dried, filtered and concentrated under vacuum. The crude was purified by prep LC-MS (pH=10 method; XBridge™ PrepC18 5 μm OBD™ column, 30×100 mm, 60 mL/min, eluting with a gradient of MeCN and water with 0.15% $NH_4OH$) to give the desired cis isomer as white powders. RT=2.666 min for the cis isomer, first peak off the column. LCMS (M+H)+: found m/z=566.3. LCMS calcd for $C_{31}H_{26}F_2N_7O_2$(M+H)+: m/z=566.2. Found: 566.2.

Example 32. N-[4-(4-Amino-7-piperidin-4-ylpyrrolo[2,1-f][1,2,4]triazin-5-yl)phenyl]-2-oxo-1-phenyl-1,2-dihydropyridine-3-carboxamide

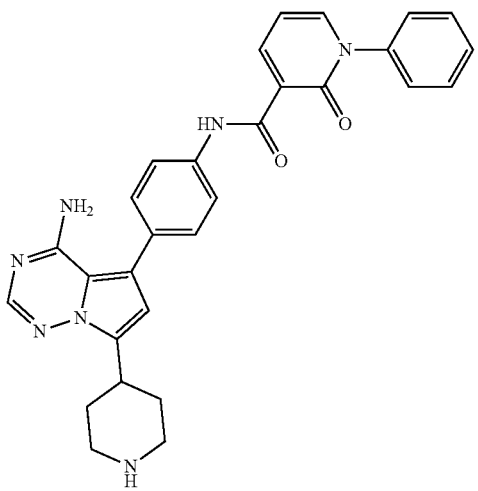 [SMILES: Nc1ncnn2c(C3CCNCC3)cc(-c3ccc(NC(=O)c4cccn(-c5ccccc5)c4=O)cc3)c12]

Step 1: tert-Butyl 4-(4-aminopyrrolo[2,1-f][1,2,4]triazin-7-yl)-3,6-dihydropyridine-1(2H)-carboxylate

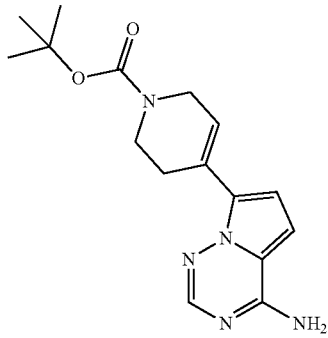 [SMILES: CC(C)(C)OC(=O)N1CC=C(c2ccc3c(N)ncnn23)CC1]

A mixture of tert-butyl 4-(4,4,5,5-tetramethyl-1,3,2-dioxaborolan-2-yl)-3,6-dihydropyridine-1 (2H)-carboxylate (from Aldrich, 0.885 g, 2.86 mmol), 7-bromopyrrolo[2,1-f][1,2,4]triazin-4-amine (from J & W Pharm Lab, 610 mg, 2.86 mmol), sodium carbonate (1.0 g, 9.5 mmol), and [1,1'-bis(di-cyclohexylphosphino)ferrocene]dichloropalladium (II) (217 mg, 0.286 mmol) in tert-butyl alcohol (8.6 mL) and water (3.2 mL) was degassed with nitrogen, then stirred and heated at 110° C. for 2 h. The mixture was diluted with ethyl acetate, washed with saturated $NaHCO_3$, water, dried over $Na_2SO_4$, filtered and concentrated. The crude was purified by Biotage silica gel chromatography (40 g column, 0 to 100% EtOAc in hexanes) to give the desired product as off-white powders (705 mg, 78%). LCMS calcd for $C_{16}H_{22}N_5O_2$ (M+H)+: m/z=316.2. Found: 316.2.

Step 2: tert-Butyl 4-(4-aminopyrrolo[2,1-f][1,2,4]triazin-7-yl)piperidine-1-carboxylate

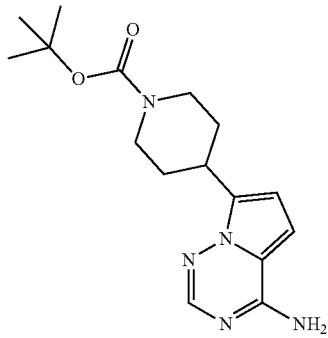 [SMILES: CC(C)(C)OC(=O)N1CCC(c2ccc3c(N)ncnn23)CC1]

To a slightly cloudy solution of tert-butyl 4-(4-aminopyrrolo[2,1-f][1,2,4]triazin-7-yl)-3,6-dihydropyridine-1(2H)-carboxylate (700 mg, 2.22 mmol) in methanol (9.2 mL) and tetrahydrofuran (4.6 mL) was added a mixture of palladium (2.20 g) (10% Pd on carbon). The reaction mixture was placed under a hydrogen balloon for 20 h, and filtered through a celite pad. The filtrate was concentrated under vacuum to give the desired product as light brown powders (455 mg, 65%). LCMS calcd for $C_{16}H_{24}N_5O_2$ (M+H)+: m/z=318.2. Found: 318.2.

Step 3: tert-Butyl 4-(4-amino-5-bromopyrrolo[2,1-f][1,2,4]triazin-7-yl)piperidine-1-carboxylate

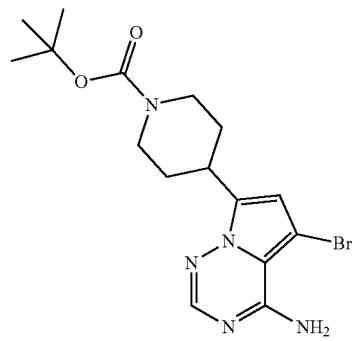 [SMILES: CC(C)(C)OC(=O)N1CCC(c2cc(Br)c3c(N)ncnn23)CC1]

To a solution of tert-butyl 4-(4-aminopyrrolo[2,1-f][1,2,4]triazin-7-yl)piperidine-1-carboxylate (450 mg, 1.42 mmol) in N,N-dimethylformamide (6.1 mL) was added N-bromosuccinimide (240 mg, 1.35 mmol). The resulting mixture was stirred at rt for 10 min. The reaction mixture was diluted with EtOAc, filtered. The filtrate was washed with saturated NaHCO$_3$, water, dried, filtered and concentrated under vacuum to give the desired product as tan solid. LCMS calcd for C$_{16}$H$_{23}$BrN$_5$O$_2$(M+H)$^+$: m/z=396.1, 398.1. Found: 396.1, 398.1.

Step 4: 5-Bromo-7-piperidin-4-ylpyrrolo[2,1-f][1,2,4]triazin-4-amine dihydrochloride

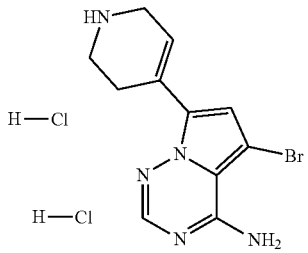 [SMILES: Cl ; Cl ; Nc1ncnn2c(C3=CCNCC3)cc(Br)c12]

tert-Butyl 4-(4-amino-5-bromopyrrolo[2,1-f][1,2,4]triazin-7-yl)piperidine-1-carboxylate (562 mg, 1.42 mmol) was mixed with methanol (3.5 mL) and 4.0 M hydrogen chloride in dioxane (7.1 mL). The mixture was stirred at rt for 1 h. After concentration, the crude product was directly used in the next step as off-white powders. LCMS calcd for C$_{11}$H$_{15}$BrN$_5$ (M+H)$^+$: m/z=296.0, 298.0. Found: 296.0, 298.0.

Step 5: N-[4-(4-Amino-7-piperidin-4-ylpyrrolo[2,1-f][1,2,4]triazin-5-yl)phenyl]-2-oxo-1-phenyl-1,2-dihydropyridine-3-carboxamide In a sealed tube a mixture of 5-bromo-7-piperidin-4-ylpyrrolo[2,1-f][1,2,4]triazin-4-amine dihydrochloride (6.7 mg, 0.013 mmol), 2-oxo-1-phenyl-N-[4-(4,4,5,5-tetramethyl-1,3,2-dioxaborolan-2-yl)phenyl]-1,2-dihydropyridine-3-carboxamide (5.4 mg, 0.013 mmol) (prepared in Example 7, step 3) and N,N-diisopropylethylamine (0.013 mL, 0.077 mmol) in 1,4-dioxane (0.15 mL) and water (20 μL) was stirred together and flushed with N$_2$ for 5 min before bis(tri-t-butylphosphine)palladium (3.3 mg, 0.0064 mmol) was added. The reaction mixture was sealed and then heated at 110° C. for 60 min. After separation and the aqueous layer extracted with EtOAc, the organic layer was dried, filtered and concentrated under vacuum. The crude was purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as off-white powders (4 mg, 61%). LCMS calcd for C$_{29}$H$_{28}$N$_7$O$_2$ (M+H)$^+$: m/z=506.2. Found: 506.2.

Example 33. N-[4-(4-Amino-7-piperidin-4-ylpyrrolo[2,1-f][1,2,4]triazin-5-yl)phenyl]-1-(4-fluorophenyl)-2-oxo-1,2-dihydropyridine-3-carboxamide

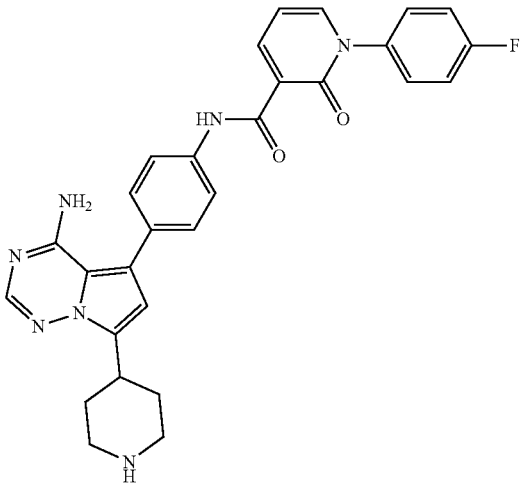 [SMILES: Nc1ncnn2c(C3CCNCC3)cc(-c3ccc(NC(=O)c4cccn(-c5ccc(F)cc5)c4=O)cc3)c12]

In a sealed tube a mixture of 5-bromo-7-piperidin-4-ylpyrrolo[2,1-f][1,2,4]triazin-4-amine dihydrochloride (6.7 mg, 0.013 mmol) (prepared in Example 32, step 4), 1-(4-fluorophenyl)-2-oxo-N-[4-(4,4,5,5-tetramethyl-1,3,2-dioxaborolan-2-yl)phenyl]-1,2-dihydropyridine-3-carboxamide (5.6 mg, 0.013 mmol) (prepared in Example 9, step 3) and N,N-diisopropylethylamine (0.013 mL, 0.08 mmol) in 1,4-dioxane (0.15 mL) and water (20 μL) was stirred together and flushed with N$_2$ for 5 min before bis(tri-t-butylphosphine)palladium (3.3 mg, 0.006 mmol) was added. The reaction mixture was sealed and then heated at 110° C. for 60 min. After separation and the aqueous layer extracted with EtOAc, the organic layer was dried, filtered and concentrated under vacuum. The crude was purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as white powders (4 mg, 59%). LCMS calcd for C$_{29}$H$_{27}$FN$_7$O$_2$(M+H)$^+$: m/z=524.2. Found: 524.2.

141

Example 34. N-[4-(4-Amino-7-piperidin-4-ylpyrrolo[2,1-f][1,2,4]triazin-5-yl)-3-fluorophenyl]-2-oxo-1-phenyl-1,2-dihydropyridine-3-carboxamide

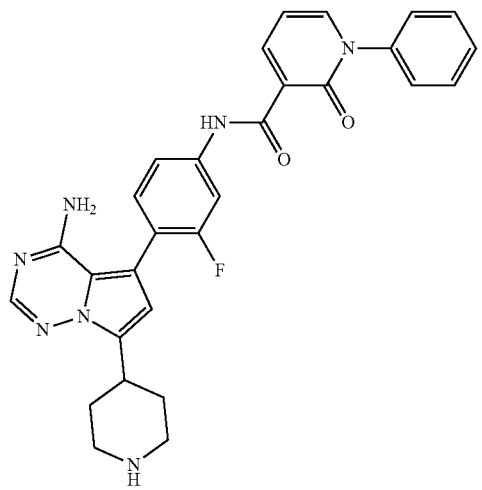 [SMILES: Nc1ncnn2c(C3CCNCC3)cc(-c3ccc(NC(=O)c4cccn(-c5ccccc5)c4=O)cc3F)c12]

In a sealed tube a mixture of 5-bromo-7-piperidin-4-ylpyrrolo[2,1-f][1,2,4]triazin-4-amine dihydrochloride (6.7 mg, 0.013 mmol) (prepared in Example 32, step 4), N-[3-fluoro-4-(4,4,5,5-tetramethyl-1,3,2-dioxaborolan-2-yl)phenyl]-2-oxo-1-phenyl-1,2-dihydropyridine-3-carboxamide (5.6 mg, 0.013 mmol) (prepared in Example 9, step 4) and N,N-diisopropylethylamine (0.0067 mL, 0.039 mmol) in 1,4-dioxane (0.15 mL) and water (20 L) was stirred together and flushed with $N_2$ for 5 min before bis(tri-t-butylphosphine)palladium (3.3 mg, 0.006 mmol) was added. The reaction mixture was sealed and then heated at 110° C. for 60 min. After separation and the aqueous layer extracted with EtOAc, the organic layer was dried, filtered and concentrated under vacuum. The crude was purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as off-white powders (3.2 mg, 47%). LCMS calcd for $C_{29}H_{27}FN_7O_2(M+H)^+$: m/z=524.2. Found: 524.2.

Example 35. N-[4-(4-Amino-7-piperidin-4-ylpyrrolo[2,1-f][1,2,4]triazin-5-yl)-3-fluorophenyl]-1-(4-fluorophenyl)-2-oxo-1,2-dihydropyridine-3-carboxamide

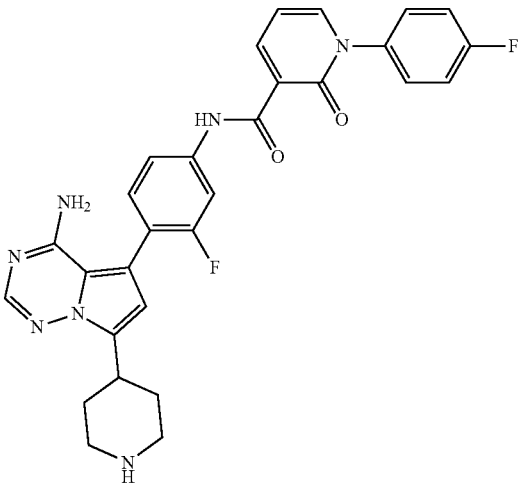 [SMILES: Nc1ncnn2c(C3CCNCC3)cc(-c3ccc(NC(=O)c4cccn(-c5ccc(F)cc5)c4=O)cc3F)c12]

In a sealed tube a mixture of 5-bromo-7-piperidin-4-ylpyrrolo[2,1-f][1,2,4]triazin-4-amine dihydrochloride (6.7 mg, 0.013 mmol) (prepared in Example 32, step 4), 1-(4-fluorophenyl)-N-[3-fluoro-4-(4,4,5,5-tetramethyl-1,3,2-di-

142 oxaborolan-2-yl)phenyl]-2-oxo-1,2-dihydropyridine-3-carboxamide (5.8 mg, 0.013 mmol) (prepared in Example 9, step 5) and N,N-diisopropylethylamine (0.014 mL, 0.077 mmol) in 1,4-dioxane (0.15 mL) and water (20 L) was stirred together and flushed with $N_2$ for 5 min before bis(tri-t-butylphosphine)palladium (3.3 mg, 0.006 mmol) was added. The reaction mixture was sealed and then heated at 110° C. for 60 min. After separation and the aqueous layer extracted with EtOAc, the organic layer was dried, filtered and concentrated under vacuum. The crude was purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as white powders (3.6 mg, 52%). LCMS calcd for $C_{29}H_{26}F_2N_7O_2(M+H)^+$: m/z=542.2. Found: 542.2.

Example 36. Methyl 4-[4-amino-5-(4-{[(2-oxo-1-phenyl-1,2-dihydropyridin-3-yl)carbonyl]amino}phenyl)pyrrolo[2,1-f][1,2,4]triazin-7-yl]piperidine-1-carboxylate

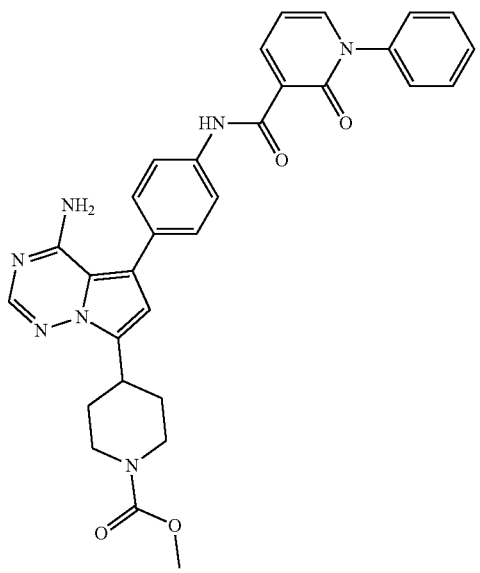 [SMILES: COC(=O)N1CCC(c2cc(-c3ccc(NC(=O)c4cccn(-c5ccccc5)c4=O)cc3)c3c(N)ncnn23)CC1]

Step 1: Methyl 4-(4-amino-5-bromopyrrolo[2,1-f][1,2,4]triazin-7-yl)piperidine-1-carboxylate $NH_2Br$

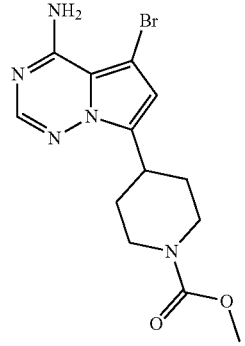 [SMILES: COC(=O)N1CCC(c2cc(Br)c3c(N)ncnn23)CC1]

To a mixture of 5-bromo-7-piperidin-4-ylpyrrolo[2,1-f][1,2,4]triazin-4-amine dihydrochloride (56 mg, 0.11 mmol)

(prepared in Example 32, step 4) in tetrahydrofuran (0.6 mL) was added 1.0 M sodium bicarbonate in water (0.65 mL, 0.65 mmol), followed by the slow addition of methyl chloroformate (42 μL, 0.54 mmol) at 0° C. After stirred at rt for 10 min, the resultant mixture was filtered, extracted with EtOAc, dried, filtered and concentrated to dryness under reduced pressure. The resulting crude was used directly in the next step as light yellow powders (52.6 mg). LCMS calcd for $C_{13}H_{17}BrN_5O_2(M+H)^+$: m/z=354.0, 356.0. Found: 354.0, 356.0.

Step 2: Methyl 4-[4-amino-5-(4-{[(2-oxo-1-phenyl-1,2-dihydropyridin-3-yl) carbonyl]amino}phenyl)pyrrolo[2,1-f][1,2,4]triazin-7-yl]piperidine-1-carboxylate In a sealed tube a mixture of methyl 4-(4-amino-5-bromopyrrolo[2,1-f][1,2,4]triazin-7-yl)piperidine-1-carboxylate (6.8 mg, 0.014 mmol), 2-oxo-1-phenyl-N-[4-(4,4,5,5-tetramethyl-1,3,2-dioxaborolan-2-yl)phenyl]-1,2-dihydropyridine-3-carboxamide (6.2 mg, 0.015 mmol) (prepared in Example 7, step 3) and N,N-diisopropylethylamine (0.0074 mL, 0.042 mmol) in 1,4-dioxane (0.11 mL) and water (20 μL) was stirred together and flushed with $N_2$ for 5 min before bis(tri-t-butylphosphine)palladium (3.6 mg, 0.007 mmol) was added. The reaction mixture was sealed and then heated at 110° C. for 30 min. After separation and the aqueous layer extracted with EtOAc, the organic layer was dried, filtered and concentrated under vacuum. The crude was purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as off-white powders (6.5 mg, 82%). LCMS calcd for $C_{31}H_{30}N_7O_4$ (M+H)⁺: m/z=564.2. Found: 564.2.

Example 37. Methyl 4-{4-amino-5-[4-({[1-(4-fluorophenyl)-2-oxo-1,2-dihydropyridin-3-yl]carbonyl}amino)phenyl]pyrrolo[2,1-f][1,2,4]triazin-7-yl}piperidine-1-carboxylate

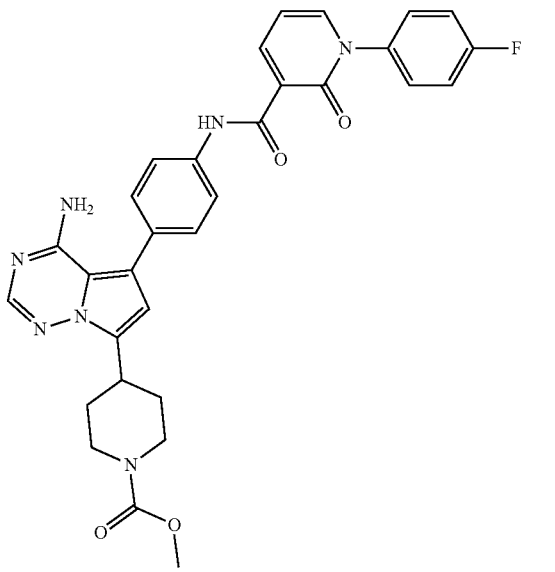 [SMILES: COC(=O)N1CCC(c2cc(-c3ccc(NC(=O)c4cccn(-c5ccc(F)cc5)c4=O)cc3)c3c(N)ncnn23)CC1]

In a sealed tube a mixture of methyl 4-(4-amino-5-bromopyrrolo[2,1-f][1,2,4]triazin-7-yl)piperidine-1-carboxylate (6.8 mg, 0.014 mmol) (prepared in Example 36, step 1), 1-(4-fluorophenyl)-2-oxo-N-[4-(4,4,5,5-tetramethyl-1,3,2-dioxaborolan-2-yl)phenyl]-1,2-dihydropyridine-3-carboxamide (6.4 mg, 0.015 mmol) (prepared in Example 9, step 3) and N,N-diisopropylethylamine (0.0074 mL, 0.042 mmol) in 1,4-dioxane (0.11 mL) and water (20 L) was stirred together and flushed with $N_2$ for 5 min before bis(tri-t-butylphosphine)palladium (3.6 mg, 0.007 mmol) was added. The reaction mixture was sealed and then heated at 110° C. for 30 min. The crude was diluted with MeOH, filtered and purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as off-white powders (5.0 mg, 61%). LC-MS found m/z=582.3. LCMS calcd for $C_{31}H_{29}FN_7O_4(M+H)^+$: m/z=582.2. Found: 582.2.

Example 38. Methyl 4-[4-amino-5-(2-fluoro-4-{[(2-oxo-1-phenyl-1,2-dihydropyridin-3-yl)carbonyl]amino}phenyl)pyrrolo[2,1-f][1,2,4]triazin-7-yl]piperidine-1-carboxylate

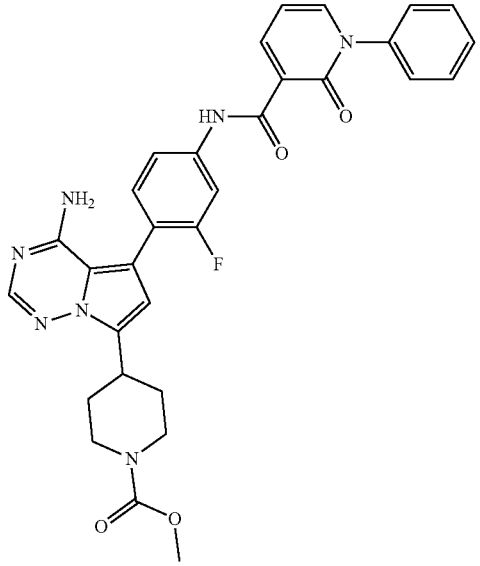 [SMILES: COC(=O)N1CCC(c2cc(-c3ccc(NC(=O)c4cccn(-c5ccccc5)c4=O)cc3F)c3c(N)ncnn23)CC1]

In a sealed tube a mixture of methyl 4-(4-amino-5-bromopyrrolo[2,1-f][1,2,4]triazin-7-yl)piperidine-1-carboxylate (6.8 mg, 0.014 mmol) (prepared in Example 36, step 1), N-[3-fluoro-4-(4,4,5,5-tetramethyl-1,3,2-dioxaborolan-2-yl)phenyl]-2-oxo-1-phenyl-1,2-dihydropyridine-3-carboxamide (6.4 mg, 0.015 mmol) (prepared in Example 9, step 4) and N,N-diisopropylethylamine (0.0074 mL, 0.04 mmol) in 1,4-dioxane (0.11 mL) and water (20 L) was stirred together and flushed with $N_2$ for 5 min before bis(tri-t-butylphosphine)palladium (3.6 mg, 0.007 mmol) was added. The reaction mixture was sealed and then heated at 110° C. for 30 min. The crude was diluted with MeOH, filtered and purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as white powders (6.4 mg, 78%). LCMS calcd for $C_{31}H_{29}FN_7O_4(M+H)^+$: m/z=582.2. Found: 582.2.

Example 39. Methyl 4-{4-amino-5-[2-fluoro-4-({[1-(4-fluorophenyl)-2-oxo-1,2-dihydropyridin-3-yl]carbonyl}amino)phenyl]pyrrolo[2,1-f][1,2,4]triazin-7-yl}piperidine-1-carboxylate

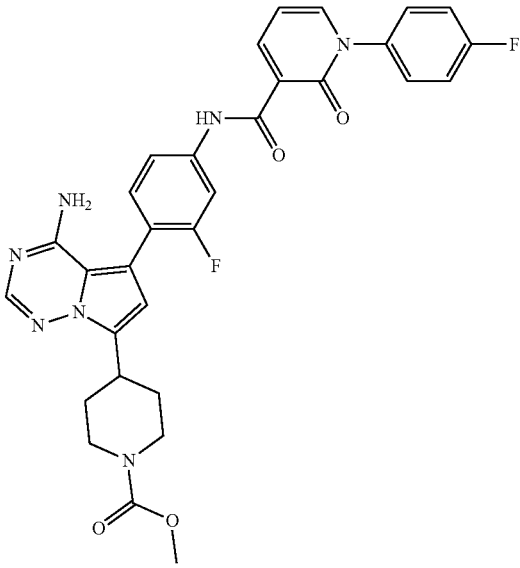 [SMILES: COC(=O)N1CCC(c2cc(-c3ccc(NC(=O)c4cccn(-c5ccc(F)cc5)c4=O)cc3F)c3c(N)ncnn23)CC1]

In a sealed tube a mixture of methyl 4-(4-amino-5-bromopyrrolo[2,1-f][1,2,4]triazin-7-yl)piperidine-1-carboxylate (6.8 mg, 0.014 mmol) (prepared in Example 36, step 1), 1-(4-fluorophenyl)-N-[3-fluoro-4-(4,4,5,5-tetramethyl-1,3,2-dioxaborolan-2-yl)phenyl]-2-oxo-1,2-dihydropyridine-3-carboxamide (6.7 mg, 0.015 mmol) (prepared in Example 9, step 5) and N,N-diisopropylethylamine (0.0074 mL, 0.042 mmol) in 1,4-dioxane (0.11 mL) and water (20 L) was stirred together and flushed with $N_2$ for 5 min before bis(tri-t-butylphosphine)palladium (3.6 mg, 0.007 mmol) was added. The reaction mixture was sealed and then heated at 110° C. for 30 min. The crude was diluted with MeOH, filtered and purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as white powders (4.9 mg, 58%). LCMS calcd for $C_{31}H_{28}F_2N_7O_4(M+H)^+$: m/z=600.2. Found: 600.2.

Example 40. N-(4-{4-Amino-7-[1-(methylsulfonyl)piperidin-4-yl]pyrrolo[2,1-f][1,2,4]triazin-5-yl}phenyl)-2-oxo-1-phenyl-1,2-dihydropyridine-3-carboxamide

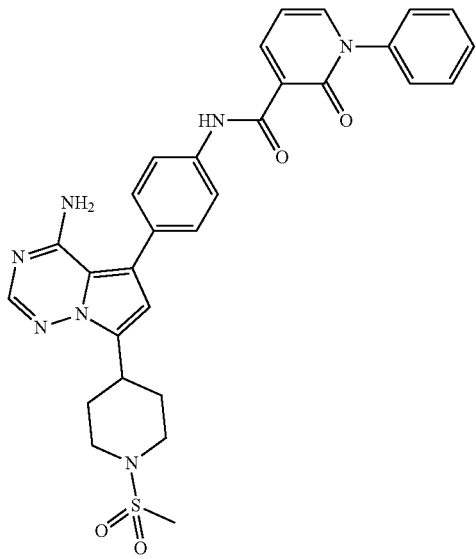 [SMILES: CS(=O)(=O)N1CCC(c2cc(-c3ccc(NC(=O)c4cccn(-c5ccccc5)c4=O)cc3)c3c(N)ncnn23)CC1]

Step 1: 5-Bromo-7-[1-(methylsulfonyl)piperidin-4-yl]pyrrolo[2,1-f][1,2,4]triazin-4-amine

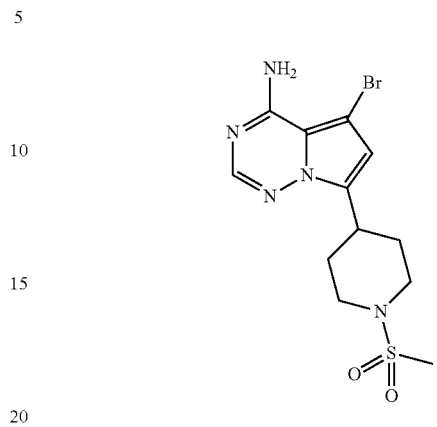

To a mixture of 5-bromo-7-piperidin-4-ylpyrrolo[2,1-f][1,2,4]triazin-4-amine dihydrochloride (56 mg, 0.11 mmol) (prepared in Example 32, step 4) in tetrahydrofuran (0.6 mL) was added 1.0 M sodium bicarbonate in water (0.65 mL), followed by the slow addition of methanesulfonyl chloride (13 μL, 0.16 mmol) at 0° C. After stirred at rt for 10 min, the resultant mixture was filtered, extracted with EtOAc, dried, filtered and concentrated to dryness under reduced pressure. The resulting crude was used directly in the next step as light yellow powders (36.5 mg, 90%). LCMS calcd for $C_{12}H_{17}BrN_5O_2S$ $(M+H)^+$: m/z=374.0, 376.0. Found: 374.0, 376.0.

Step 2: N-(4-{4-Amino-7-[1-(methylsulfonyl)piperidin-4-yl]pyrrolo[2,1-f][1,2,4]triazin-5-yl}phenyl)-2-oxo-1-phenyl-1,2-dihydropyridine-3-carboxamide In a sealed tube a mixture of 5-bromo-7-[1-(methylsulfonyl)piperidin-4-yl]pyrrolo[2,1-f][1,2,4]triazin-4-amine (5 mg, 0.01 mmol), 2-oxo-1-phenyl-N-[4-(4,4,5,5-tetramethyl-1,3,2-dioxaborolan-2-yl)phenyl]-1,2-dihydropyridine-3-carboxamide (5.8 mg, 0.014 mmol) (prepared in Example 7, step 3) and N,N-diisopropylethylamine (0.01 mL, 0.06 mmol) in 1,4-dioxane (0.15 mL) and water (20 μL) was stirred together and flushed with $N_2$ for 5 min before bis(tri-t-butylphosphine)palladium (3.4 mg, 0.0067 mmol) was added. The reaction mixture was sealed and then heated at 110° C. for 30 min. The crude was diluted with MeOH, filtered and purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as white powders (5.4 mg, 69%). LCMS calcd for $C_{30}H_{30}N_7O_4S$ $(M+H)^+$: m/z=584.2. Found: 584.2.

Example 41. N-(4-{4-Amino-7-[1-(methylsulfonyl)piperidin-4-yl]pyrrolo[2,1-f][1,2,4]triazin-5-yl}phenyl)-1-(4-fluorophenyl)-2-oxo-1,2-dihydropyridine-3-carboxamide

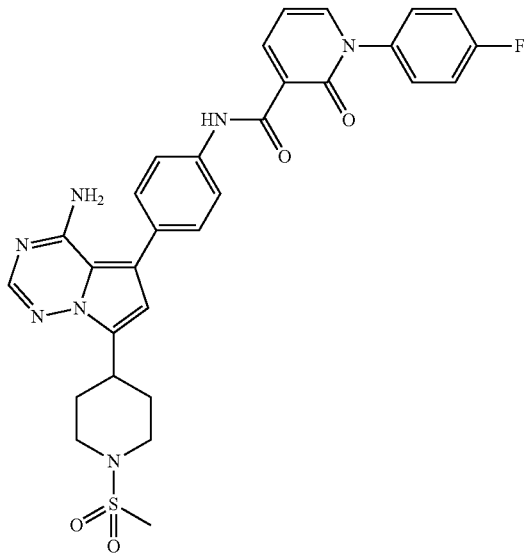 [SMILES: CS(=O)(=O)N1CCC(c2cc(-c3ccc(NC(=O)c4cccn(-c5ccc(F)cc5)c4=O)cc3)c3c(N)ncnn23)CC1]

In a sealed tube a mixture of 5-bromo-7-[1-(methylsulfonyl)piperidin-4-yl]pyrrolo[2,1-f][1,2,4]triazin-4-amine (5 mg, 0.013 mmol) (prepared in Example 40, step 1), 1-(4-fluorophenyl)-2-oxo-N-[4-(4,4,5,5-tetramethyl-1,3,2-dioxaborolan-2-yl)phenyl]-1,2-dihydropyridine-3-carboxamide (6.1 mg, 0.014 mmol) (prepared in Example 9, step 3) and N,N-diisopropylethylamine (0.01 mL, 0.06 mmol) in 1,4-dioxane (0.15 mL) and water (20 μL) was stirred together and flushed with $N_2$ for 5 min before bis(tri-t-butylphosphine)palladium (3.4 mg, 0.0067 mmol) was added. The reaction mixture was sealed and then heated at 110° C. for 30 min. The crude was diluted with MeOH, filtered and purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as white powders (6.2 mg, 77%). LCMS calcd for $C_{30}H_{29}FN_7O_4S$ $(M+H)^+$: m/z=602.2. Found: 602.2.

Example 42. N-(4-{4-Amino-7-[1-(methylsulfonyl)piperidin-4-yl]pyrrolo[2,1-f][1,2,4]triazin-5-yl)}-3-fluorophenyl)-2-oxo-1-phenyl-1,2-dihydropyridine-3-carboxamide

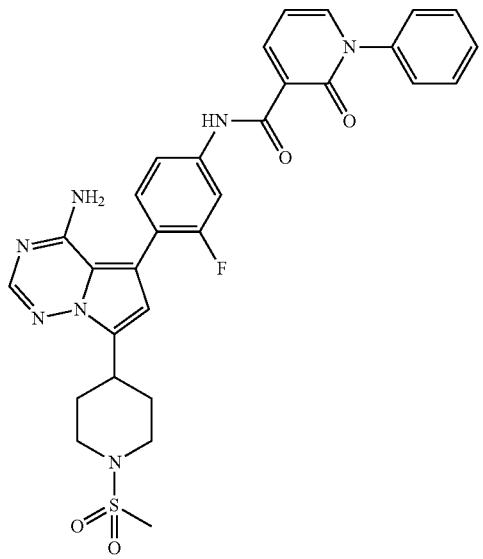 [SMILES: CS(=O)(=O)N1CCC(c2cc(-c3ccc(NC(=O)c4cccn(-c5ccccc5)c4=O)cc3F)c3c(N)ncnn23)CC1]

In a sealed tube a mixture of 5-bromo-7-[1-(methylsulfonyl)piperidin-4-yl]pyrrolo[2,1-f][1,2,4]triazin-4-amine (5 mg, 0.013 mmol) (prepared in Example 40, step 1), N-[3-fluoro-4-(4,4,5,5-tetramethyl-1,3,2-dioxaborolan-2-yl)phenyl]-2-oxo-1-phenyl-1,2-dihydropyridine-3-carboxamide (6.1 mg, 0.014 mmol) (prepared in Example 9, step 4) and N,N-diisopropylethylamine (0.01 mL, 0.06 mmol) in 1,4-dioxane (0.15 mL) and water (20 L) was stirred together and flushed with $N_2$ for 5 min before bis(tri-t-butylphosphine)palladium (3.4 mg, 0.0067 mmol) was added. The reaction mixture was sealed and then heated at 110° C. for 30 min. The crude was diluted with MeOH, filtered and purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as white powders (3.8 mg, 47%). LCMS calcd for $C_{30}H_{29}FN_7O_4S$ $(M+H)^+$: m/z=602.2. Found: 602.2.

Example 43. N-(4-{4-Amino-7-[1-(methylsulfonyl)piperidin-4-yl]pyrrolo[2,1-f][1,2,4]triazin-5-yl)}-3-fluorophenyl)-1-(4-fluorophenyl)-2-oxo-1,2-dihydropyridine-3-carboxamide

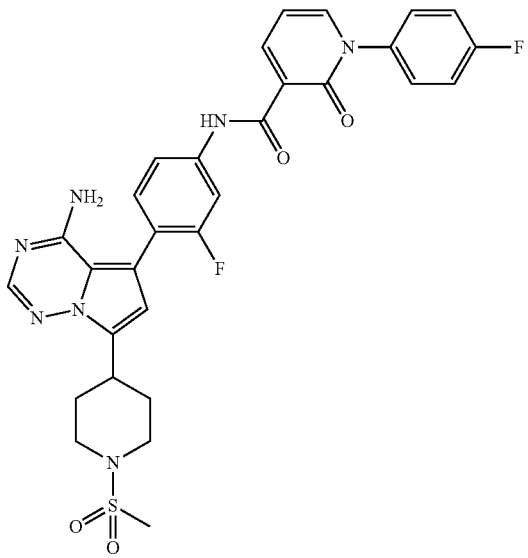 [SMILES: CS(=O)(=O)N1CCC(c2cc(-c3ccc(NC(=O)c4cccn(-c5ccc(F)cc5)c4=O)cc3F)c3c(N)ncnn23)CC1]

In a sealed tube a mixture of 5-bromo-7-[1-(methylsulfonyl)piperidin-4-yl]pyrrolo[2,1-f][1,2,4]triazin-4-amine (5.3 mg, 0.014 mmol) (prepared in Example 40, step 1), 1-(4-fluorophenyl)-N-[3-fluoro-4-(4,4,5,5-tetramethyl-1,3,2-dioxaborolan-2-yl)phenyl]-2-oxo-1,2-dihydropyridine-3-carboxamide (6.7 mg, 0.015 mmol) (prepared in Example 9, step 5) and N,N-diisopropylethylamine (0.01 mL, 0.05 mmol) in 1,4-dioxane (0.15 mL) and water (20 L) was stirred together and flushed with $N_2$ for 5 min before bis(tri-t-butylphosphine)palladium (3.6 mg, 0.007 mmol) was added. The reaction mixture was sealed and then heated at 110° C. for 30 min. The crude was diluted with MeOH, filtered and purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as white powders (3.2 mg, 36%). LCMS calcd for $C_{30}H_{28}F_2N_7O_4S$ $(M+H)^+$: m/z=620.2. Found: 620.2.

149

Example 44. N-[4-(4-Amino-7-{1-[(dimethylamino)carbonyl]piperidin-4-yl}pyrrolo[2,1-f][1,2,4]triazin-5-yl)phenyl]-2-oxo-1-phenyl-1,2-dihydropyridine-3-carboxamide

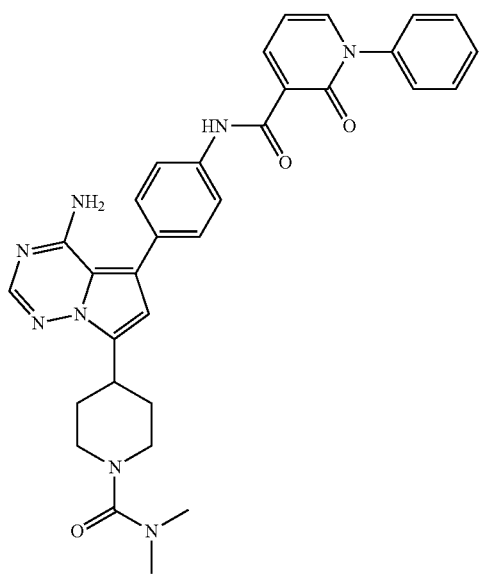 [SMILES: CN(C)C(=O)N1CCC(c2cc(-c3ccc(NC(=O)c4cccn(-c5ccccc5)c4=O)cc3)c3c(N)ncnn23)CC1]

Step 1: 4-(4-Amino-5-bromopyrrolo[2,1-f][1,2,4]triazin-7-yl)-N,N-dimethylpiperidine-1-carboxamide

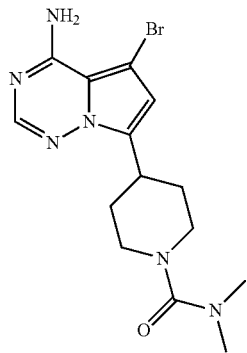 [SMILES: CN(C)C(=O)N1CCC(c2cc(Br)c3c(N)ncnn23)CC1]

To a mixture of 5-bromo-7-piperidin-4-ylpyrrolo[2,1-f][1,2,4]triazin-4-amine dihydrochloride (56 mg, 0.11 mmol) (prepared in Example 32, step 4) in tetrahydrofuran (0.6 mL) was added 1.0 M sodium bicarbonate in water (0.65 mL, 0.65 mmol), followed by the slow addition of N,N-dimethylcarbamoyl chloride (140 mg, 1.3 mmol) at 0° C. After stirred at rt for 80 min, the resultant mixture was filtered, extracted with EtOAc, dried, filtered and concentrated to dryness under reduced pressure. The resulting crude was used directly in the next step as light yellow powders (59.8 mg). LCMS calcd for $C_{14}H_{20}BrN_6O$ (M+H)$^+$: m/z=367.1, 369.1. Found: 367.1, 369.1.

150

Step 2: N-[4-(4-Amino-7-{1-[(dimethylamino)carbonyl]piperidin-4-yl}pyrrolo[2,1-f][1,2,4]triazin-5-yl)phenyl]-2-oxo-1-phenyl-1,2-dihydropyridine-3-carboxamide In a sealed tube a mixture of 4-(4-amino-5-bromopyrrolo[2,1-f][1,2,4]triazin-7-yl)-N,N-dimethylpiperidine-1-carboxamide (3.8 mg, 0.007 mmol), 2-oxo-1-phenyl-N-[4-(4,4,5,5-tetramethyl-1,3,2-dioxaborolan-2-yl)phenyl]-1,2-dihydropyridine-3-carboxamide (3.1 mg, 0.0074 mmol) (prepared in Example 7, step 3) and N,N-diisopropylethylamine (0.004 mL, 0.02 mmol) in 1,4-dioxane (0.1 mL) and water (15 µL) was stirred together and flushed with $N_2$ for 5 min before bis(tri-t-butylphosphine)palladium (1.8 mg, 0.004 mmol) was added. The reaction mixture was sealed and then heated at 110° C. for 50 min. After separation and the aqueous layer extracted with EtOAc, the organic layer was dried, filtered and concentrated under vacuum. The crude was purified by prep LC-MS (pH=2 method; Waters SunFire PrepC18 5 µm OBD™ column, 30×100 mm, 60 mL/min, eluting with a gradient of MeCN and water with 0.1% TFA) to give the desired product as white powders (2 mg, 49%). LCMS calcd for $C_{32}H_{33}N_8O_3$ (M+H)$^+$: m/z=577.3. Found: 577.3.

Example 45. N-[4-(4-Amino-7-{1-[(dimethylamino)carbonyl]piperidin-4-yl}pyrrolo[2,1-f][1,2,4]triazin-5-yl)phenyl]-1-(4-fluorophenyl)-2-oxo-1,2-dihydropyridine-3-carboxamide

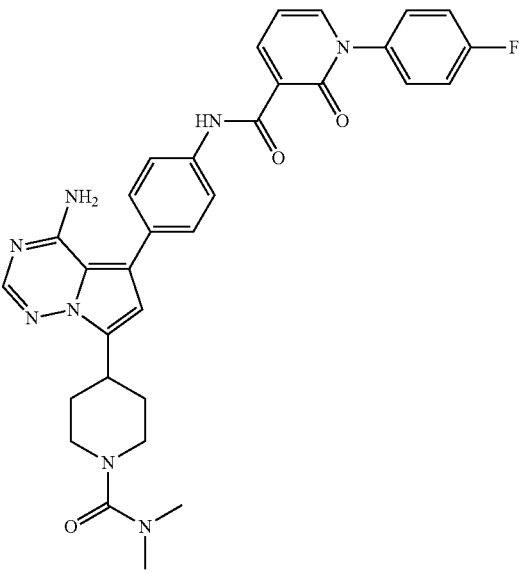 [SMILES: CN(C)C(=O)N1CCC(c2cc(-c3ccc(NC(=O)c4cccn(-c5ccc(F)cc5)c4=O)cc3)c3c(N)ncnn23)CC1]

In a sealed tube a mixture of 4-(4-amino-5-bromopyrrolo[2,1-f][1,2,4]triazin-7-yl)-N,N-dimethylpiperidine-1-carboxamide (3.8 mg, 0.007 mmol) (prepared in Example 44, step 1), 1-(4-fluorophenyl)-2-oxo-N-[4-(4,4,5,5-tetramethyl-1,3,2-dioxaborolan-2-yl)phenyl]-1,2-dihydropyridine-3-carboxamide (3.2 mg, 0.0074 mmol) (prepared in Example 9, step 3) and N,N-diisopropylethylamine (0.006 mL, 0.03 mmol) in 1,4-dioxane (0.11 mL) and water (10 L) was stirred together and flushed with $N_2$ for 5 min before bis(tri-t-butylphosphine)palladium (1.8 mg, 0.004 mmol) was added. The reaction mixture was sealed and then heated at 110° C. for 50 min. The crude was diluted with MeOH, filtered and purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as white powders (2.3 mg, 55%). LCMS calcd for $C_{32}H_{32}FN_8O_3(M+H)^+$: m/z=595.3. Found: 595.3.

Example 46. N-[4-(4-Amino-7-{1-[(dimethylamino)carbonyl]piperidin-4-yl}pyrrolo[2,1-f][1,2,4]triazin-5-yl)-3-fluorophenyl]-2-oxo-1-phenyl-1,2-dihydropyridine-3-carboxamide

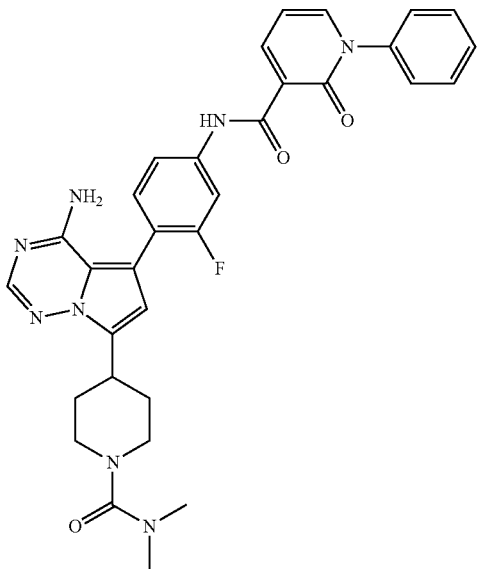 [SMILES: CN(C)C(=O)N1CCC(c2cc(-c3ccc(NC(=O)c4cccn(-c5ccccc5)c4=O)cc3F)c3c(N)ncnn23)CC1]

In a sealed tube a mixture of 4-(4-amino-5-bromopyrrolo[2,1-f][1,2,4]triazin-7-yl)-N,N-dimethylpiperidine-1-carboxamide (3.8 mg, 0.007 mmol) (prepared in Example 44, step 1), N-[3-fluoro-4-(4,4,5,5-tetramethyl-1,3,2-dioxaborolan-2-yl)phenyl]-2-oxo-1-phenyl-1,2-dihydropyridine-3-carboxamide (3.2 mg, 0.0074 mmol) (prepared in Example 9, step 4) and N,N-diisopropylethylamine (0.006 mL, 0.03 mmol) in 1,4-dioxane (0.11 mL) and water (10 L) was stirred together and flushed with $N_2$ for 5 min before bis(tri-t-butylphosphine)palladium (1.8 mg, 0.004 mmol) was added. The reaction mixture was sealed and then heated at 110° C. for 50 min. The crude was diluted with MeOH, filtered and purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as white powders (3.8 mg, 91%). LCMS calcd for $C_{32}H_{32}FN_8O_3(M+H)^+$: m/z=595.3. Found: 595.3.

Example 47. N-[4-(4-Amino-7-{1-[(dimethylamino)carbonyl]piperidin-4-yl}pyrrolo[2,1-f][1,2,4]triazin-5-yl)-3-fluorophenyl]-1-(4-fluorophenyl)-2-oxo-1,2-dihydropyridine-3-carboxamide

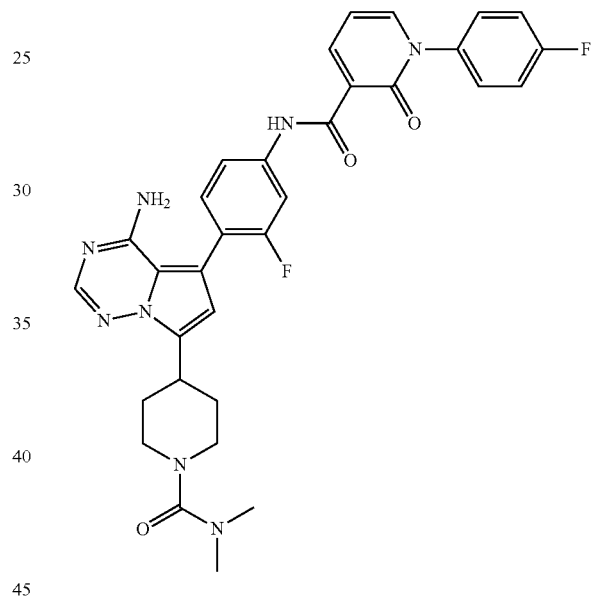

In a sealed tube a mixture of 4-(4-amino-5-bromopyrrolo[2,1-f][1,2,4]triazin-7-yl)-N,N-dimethylpiperidine-1-carboxamide (3.8 mg, 0.007 mmol) (prepared in Example 44, step 1), 1-(4-fluorophenyl)-N-[3-fluoro-4-(4,4,5,5-tetramethyl-1,3,2-dioxaborolan-2-yl)phenyl]-2-oxo-1,2-dihydropyridine-3-carboxamide (3.3 mg, 0.0074 mmol) (prepared in Example 9, step 5) and N,N-diisopropylethylamine (0.006 mL, 0.03 mmol) in 1,4-dioxane (0.11 mL) and water (15 L) was stirred together and flushed with $N_2$ for 5 min before bis(tri-t-butylphosphine)palladium (1.8 mg, 0.004 mmol) was added. The reaction mixture was sealed and then heated at 110° C. for 50 min. The crude was diluted with MeOH, filtered and purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as white powders (2.4 mg, 56%). LCMS calcd for $C_{32}H_{31}F_2N_8O_3(M+H)^+$: m/z=613.2. Found: 613.2.

Example 48. N-(4-{4-Amino-7-[1-(2-methoxyethyl)piperidin-4-yl]pyrrolo[2,1-f][1,2,4]triazin-5-yl}phenyl)-2-oxo-1-phenyl-1,2-dihydropyridine-3-carboxamide

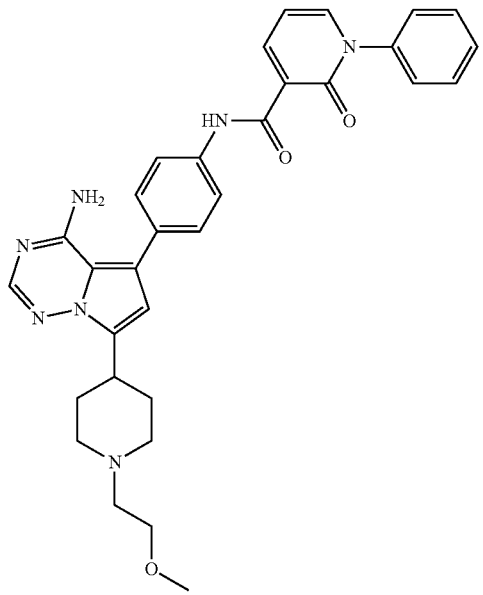 [SMILES: COCCN1CCC(c2cc(-c3ccc(NC(=O)c4cccn(-c5ccccc5)c4=O)cc3)c3c(N)ncnn23)CC1]

Step 1: 5-Bromo-7-[1-(2-methoxyethyl)piperidin-4-yl]pyrrolo[2,1-f][1,2,4]triazin-4-amine

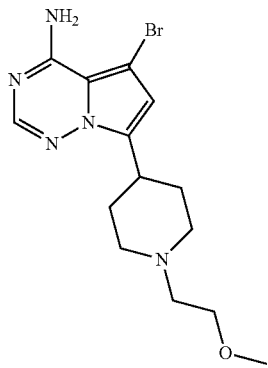 [SMILES: COCCN1CCC(c2cc(Br)c3c(N)ncnn23)CC1]

To a mixture of 5-bromo-7-piperidin-4-ylpyrrolo[2,1-f][1,2,4]triazin-4-amine dihydrochloride (56 mg, 0.11 mmol) (prepared in Example 32, step 4) in ethanol (0.5 mL) was added potassium carbonate (90 mg, 0.65 mmol), triethylamine (91 µL, 0.65 mmol) and potassium iodide (27 mg, 0.16 mmol), followed by ethane, 1-bromo-2-methoxy (75.4 mg, 0.54 mmol). The reaction mixture was sealed and refluxed in an oil bath at 110° C. for 1 h. After cooling, the mixture was filtered, and the cake was washed with EtOH. The filtrate was concentrated under reduced pressure to give the desired product as off-white powders. LCMS calcd for $C_{14}H_{21}BrN_5O$ (M+H)$^+$: m/z=354.1, 356.1. Found: 354.1, 356.1.

Step 2: N-(4-{4-Amino-7-[1-(2-methoxyethyl)piperidin-4-yl]pyrrolo[2,1-f][1,2,4]triazin-5-yl}phenyl)-2-oxo-1-phenyl-1,2-dihydropyridine-3-carboxamide In a sealed tube a mixture of 5-bromo-7-[1-(2-methoxyethyl)piperidin-4-yl]pyrrolo[2,1-f][1,2,4]triazin-4-amine (7.6 mg, 0.01 mmol), 2-oxo-1-phenyl-N-[4-(4,4,5,5-tetramethyl-1,3,2-dioxaborolan-2-yl)phenyl]-1,2-dihydropyridine-3-carboxamide (3.7 mg, 0.01 mmol) (prepared in Example 7, step 3) and N,N-diisopropylethylamine (0.006 mL, 0.03 mmol) in 1,4-dioxane (0.1 mL) and water (10 µL) was stirred together and flushed with $N_2$ for 5 min before bis(tri-t-butylphosphine)palladium (2.2 mg, 0.004 mmol) was added. The reaction mixture was sealed and then heated at 110° C. for 40 min. After separation and the aqueous layer extracted with EtOAc, the organic layer was dried, filtered and concentrated under vacuum. The crude was purified by prep LC-MS (pH=2 method; Waters SunFire PrepC18 5 µm OBD™ column, 30×100 mm, 60 mL/min, eluting with a gradient of MeCN and water with 0.1% TFA) to give the desired product as white powders (4 mg, 84%). LCMS calcd for $C_{32}H_{34}N_7O_3$ (M+H)$^+$: m/z=564.3. Found: 564.3.

Example 49. N-(4-{4-Amino-7-[1-(2-methoxyethyl)piperidin-4-yl]pyrrolo[2,1-f][1,2,4]triazin-5-yl}phenyl)-1-(4-fluorophenyl)-2-oxo-1,2-dihydropyridine-3-carboxamide

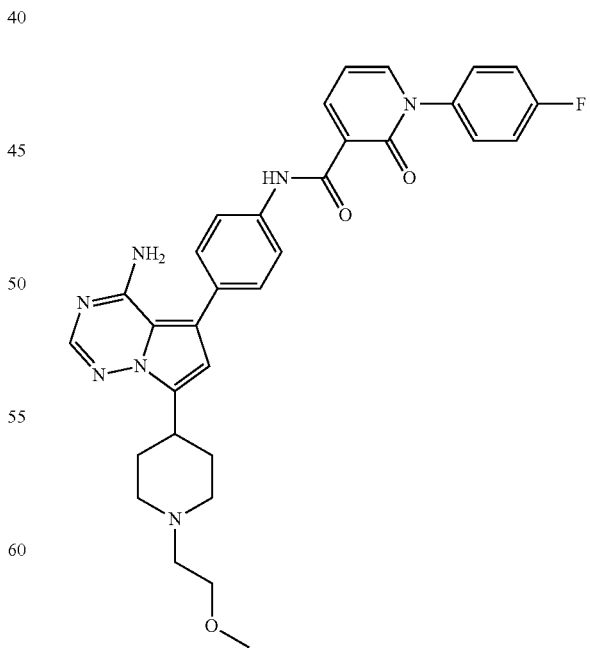

In a sealed tube a mixture of 5-bromo-7-[1-(2-methoxyethyl)piperidin-4-yl]pyrrolo[2,1-f][1,2,4]triazin-4-amine (7.6 mg, 0.0085 mmol) (prepared in Example 48, step 1), 1-(4-fluorophenyl)-2-oxo-N-[4-(4,4,5,5-tetramethyl-1,3,2-dioxaborolan-2-yl)phenyl]-1,2-dihydropyridine-3-carboxamide (3.9 mg, 0.01 mmol) (prepared in Example 9, step 3) and N,N-diisopropylethylamine (0.007 mL, 0.04 mmol) in 1,4-dioxane (0.1 mL) and water (10 L) was stirred together and flushed with $N_2$ for 5 min before bis(tri-t-butylphosphine)palladium (2.2 mg, 0.004 mmol) was added. The reaction mixture was sealed and then heated at 110° C. for 40 min. After separation and the aqueous layer extracted with EtOAc, the organic layer was dried, filtered and concentrated under vacuum. The crude was purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as off-white powders (3.2 mg, 65%). LCMS calcd for $C_{32}H_{33}FN_7O_3(M+H)^+$: m/z=582.3. Found: 582.3.

Example 50. N-(4-{4-Amino-7-[1-(2-methoxyethyl)piperidin-4-yl]pyrrolo[2,1-f][1,2,4]triazin-5-yl}-3-fluorophenyl)-2-oxo-1-phenyl-1,2-dihydropyridine-3-carboxamide

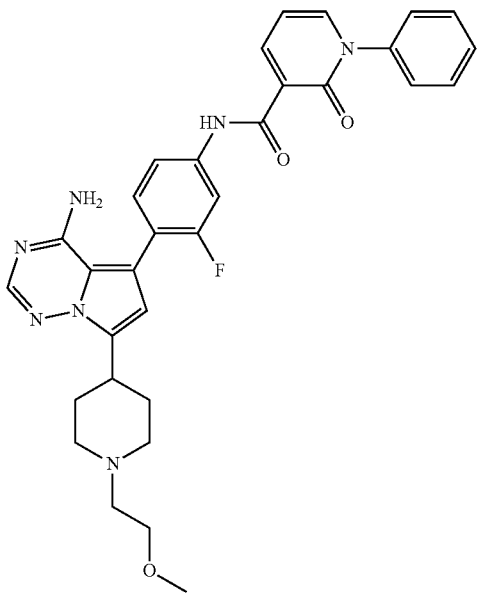 [SMILES: COCCN1CCC(c2cc(-c3ccc(NC(=O)c4cccn(-c5ccccc5)c4=O)cc3F)c3c(N)ncnn23)CC1]

In a sealed tube a mixture of 5-bromo-7-[1-(2-methoxyethyl)piperidin-4-yl]pyrrolo[2,1-f][1,2,4]triazin-4-amine (7.6 mg, 0.0085 mmol) (prepared in Example 48, step 1), N-[3-fluoro-4-(4,4,5,5-tetramethyl-1,3,2-dioxaborolan-2-yl)phenyl]-2-oxo-1-phenyl-1,2-dihydropyridine-3-carboxamide (3.9 mg, 0.01 mmol) (prepared in Example 9, step 4) and N,N-diisopropylethylamine (0.007 mL, 0.03 mmol) in 1,4-dioxane (0.12 mL) and water (15 L) was stirred together and flushed with $N_2$ for 5 min before bis(tri-t-butylphosphine)palladium (2.2 mg, 0.004 mmol) was added. The reaction mixture was sealed and then heated at 110° C. for 40 min. After separation and the aqueous layer extracted with EtOAc, the organic layer was dried, filtered and concentrated under vacuum. The crude was purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as off-white powders (3.9 mg, 79%). LCMS calcd for $C_{32}H_{33}FN_7O_3(M+H)^+$: m/z=582.3. Found: 582.3.

Example 51. N-(4-{4-Amino-7-[1-(2-methoxyethyl)piperidin-4-yl]pyrrolo[2,1-f][1,2,4]triazin-5-yl}-3-fluorophenyl)-1-(4-fluorophenyl)-2-oxo-1,2-dihydropyridine-3-carboxamide

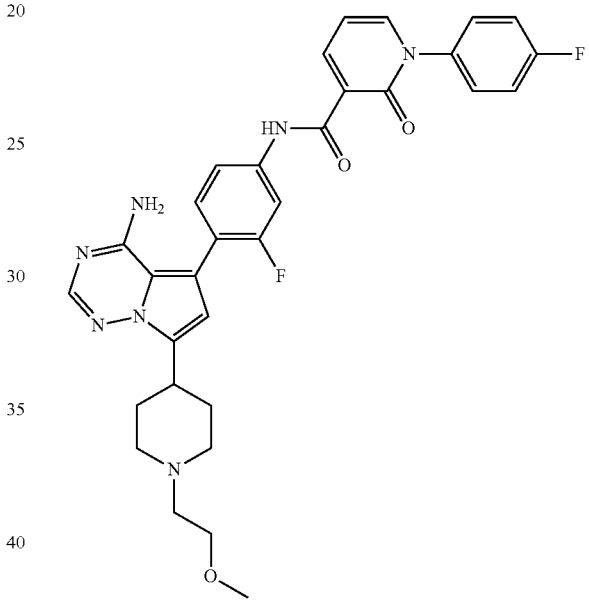

In a sealed tube a mixture of 5-bromo-7-[1-(2-methoxyethyl)piperidin-4-yl]pyrrolo[2,1-f][1,2,4]triazin-4-amine (7.6 mg, 0.0085 mmol) (prepared in Example 48, step 1), 1-(4-fluorophenyl)-N-[3-fluoro-4-(4,4,5,5-tetramethyl-1,3,2-dioxaborolan-2-yl)phenyl]-2-oxo-1,2-dihydropyridine-3-carboxamide (4.0 mg, 0.01 mmol) (prepared in Example 9, step 5) and N,N-diisopropylethylamine (0.007 mL, 0.04 mmol) in 1,4-dioxane (0.15 mL) and water (15 μL) was stirred together and flushed with $N_2$ for 5 min before bis(tri-t-butylphosphine)palladium (2.2 mg, 0.004 mmol) was added. The reaction mixture was sealed and then heated at 110° C. for 40 min. After separation and the aqueous layer extracted with EtOAc, the organic layer was dried, filtered and concentrated under vacuum. The crude was purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as white powders (3.5 mg, 69%). LCMS calcd for $C_{32}H_{32}F_2N_7O_3(M+H)^+$: m/z=600.3. Found: 600.3.

Example 52. N-(4-{4-Amino-7-[1-(2-hydroxyethyl)piperidin-4-yl]pyrrolo[2,1-f][1,2,4]triazin-5-yl}phenyl)-2-oxo-1-phenyl-1,2-dihydropyridine-3-carboxamide

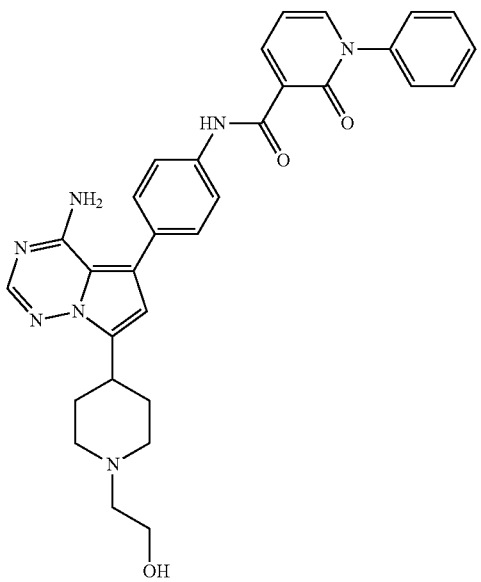 [SMILES: Nc1ncnn2c(C3CCN(CCO)CC3)cc(-c3ccc(NC(=O)c4cccn(-c5ccccc5)c4=O)cc3)c12]

Step 1: 2-[4-(4-Amino-5-bromopyrrolo[2,1-f][1,2,4]triazin-7-yl)piperidin-1-yl]ethanol

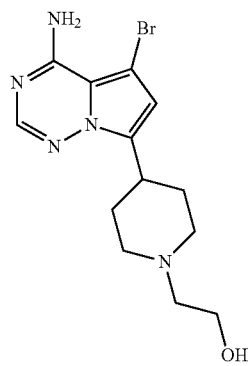 [SMILES: Nc1ncnn2c(C3CCN(CCO)CC3)cc(Br)c12]

To a mixture of 5-bromo-7-piperidin-4-ylpyrrolo[2,1-f][1,2,4]triazin-4-amine dihydrochloride (56 mg, 0.11 mmol) in ethanol (0.5 mL) (prepared in Example 32, step 4) was added potassium carbonate (90 mg, 0.65 mmol), triethylamine (91 µL, 0.65 mmol) and potassium iodide (27 mg, 0.16 mmol), followed by 2-bromoethanol (67.8 mg, 0.54 mmol). The reaction mixture was sealed and refluxed in an oil bath at 110° C. for 1 h. After cooling, the mixture was filtered, and the cake was washed with THF and EtOH. The filtrate was concentrated under reduced pressure to give the desired product as off-white powders. LCMS calcd for $C_{12}H_{19}BrN_5O$ (M+H)$^+$: m/z=340.1, 342.1. Found: 340.1, 342.1.

Step 2: N-(4-{4-Amino-7-[1-(2-hydroxyethyl)piperidin-4-yl]pyrrolo[2,1-f][1,2,4]triazin-5-yl}phenyl)-2-oxo-1-phenyl-1,2-dihydropyridine-3-carboxamide In a sealed tube a mixture of 2-[4-(4-amino-5-bromopyrrolo[2,1-f][1,2,4]triazin-7-yl)piperidin-1-yl]ethanol (13 mg, 0.009 mmol), 2-oxo-1-phenyl-N-[4-(4,4,5,5-tetramethyl-1,3,2-dioxaborolan-2-yl)phenyl]-1,2-dihydropyridine-3-carboxamide (3.7 mg, 0.01 mmol) (prepared in Example 7, step 3) and N,N-diisopropylethylamine (0.007 mL, 0.04 mmol) in 1,4-dioxane (0.15 mL) and water (15 µL) was stirred together and flushed with N$_2$ for 5 min before bis(tri-t-butylphosphine)palladium (2.2 mg, 0.004 mmol) was added. The reaction mixture was sealed and then heated at 110° C. for 20 min. After separation and the aqueous layer extracted with EtOAc, the organic layer was dried, filtered and concentrated under vacuum. The crude was purified by prep LC-MS (pH=2 method; Waters SunFire PrepC18 5 µm OBD™ column, 30×100 mm, 60 mL/min, eluting with a gradient of MeCN and water with 0.1% TFA) to give the desired product as off-white powders (2.3 mg, 49%). LCMS calcd for $C_{31}H_{32}N_7O_3$ (M+H)$^+$: m/z=550.3. Found: 550.3.

Example 53. N-(4-{4-Amino-7-[1-(2-hydroxyethyl)piperidin-4-yl]pyrrolo[2,1-f][1,2,4]triazin-5-yl}phenyl)-1-(4-fluorophenyl)-2-oxo-1,2-dihydropyridine-3-carboxamide

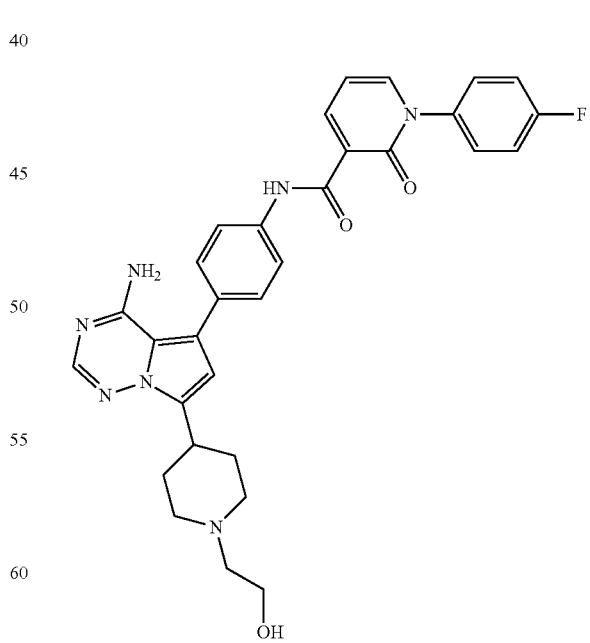

In a sealed tube a mixture of 2-[4-(4-amino-5-bromopyrrolo[2,1-f][1,2,4]triazin-7-yl)piperidin-1-yl]ethanol (13 mg, 0.009 mmol) (prepared in Example 52, step 1), 1-(4- fluorophenyl)-2-oxo-N-[4-(4,4,5,5-tetramethyl-1,3,2-dioxaborolan-2-yl)phenyl]-1,2-dihydropyridine-3-carboxamide (3.9 mg, 0.01 mmol) (prepared in Example 9, step 3) and N,N-diisopropylethylamine (0.007 mL, 0.04 mmol) in 1,4-dioxane (0.15 mL) and water (15 L) was stirred together and flushed with $N_2$ for 5 min before bis(tri-t-butylphosphine) palladium (2.2 mg, 0.0042 mmol) was added. The reaction mixture was sealed and then heated at 110° C. for 20 min. After separation and the aqueous layer extracted with EtOAc, the organic layer was dried, filtered and concentrated under vacuum. The crude was purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as off-white powders (2.3 mg, 48%). LCMS calcd for $C_{31}H_{31}FN_7O_3(M+H)^+$: m/z=568.2. Found: 568.2.

Example 54. N-(4-{4-Amino-7-[1-(2-hydroxyethyl) piperidin-4-yl]pyrrolo[2,1-f][1,2,4]triazin-5-yl)}-3-fluorophenyl)-2-oxo-1-phenyl-1,2-dihydropyridine-3-carboxamide

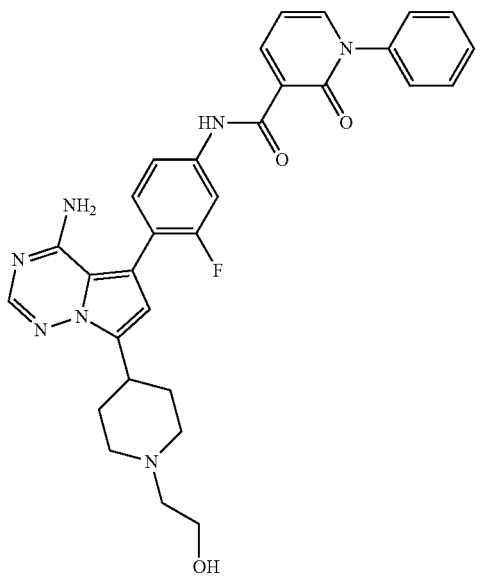 [SMILES: Nc1ncnn2c(C3CCN(CCO)CC3)cc(-c3ccc(NC(=O)c4cccn(-c5ccccc5)c4=O)cc3F)c12]

In a sealed tube a mixture of 2-[4-(4-amino-5-bromopyrrolo[2,1-f][1,2,4]triazin-7-yl)piperidin-1-yl]ethanol (13 mg, 0.009 mmol) (prepared in Example 52, step 1), N-[3-fluoro-4-(4,4,5,5-tetramethyl-1,3,2-dioxaborolan-2-yl)phenyl]-2-oxo-1-phenyl-1,2-dihydropyridine-3-carboxamide (3.9 mg, 0.01 mmol) (prepared in Example 9, step 4) and N,N-diisopropylethylamine (0.007 mL, 0.04 mmol) in 1,4-dioxane (0.15 mL) and water (15 L) was stirred together and flushed with $N_2$ for 5 min before bis(tri-t-butylphosphine) palladium (2.2 mg, 0.0042 mmol) was added. The reaction mixture was sealed and then heated at 110° C. for 20 min. After separation and the aqueous layer extracted with EtOAc, the organic layer was dried, filtered and concentrated under vacuum. The crude was purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as off-white powders (2.7 mg, 56%). LCMS calcd for $C_{31}H_{31}FN_7O_3(M+H)^+$: m/z=568.2. Found: 568.2.

Example 55. N-(4-{4-Amino-7-[1-(2-hydroxyethyl) piperidin-4-yl]pyrrolo[2,1-f][1,2,4]triazin-5-yl)}-3-fluorophenyl)-1-(4-fluorophenyl)-2-oxo-1,2-dihydropyridine-3-carboxamide

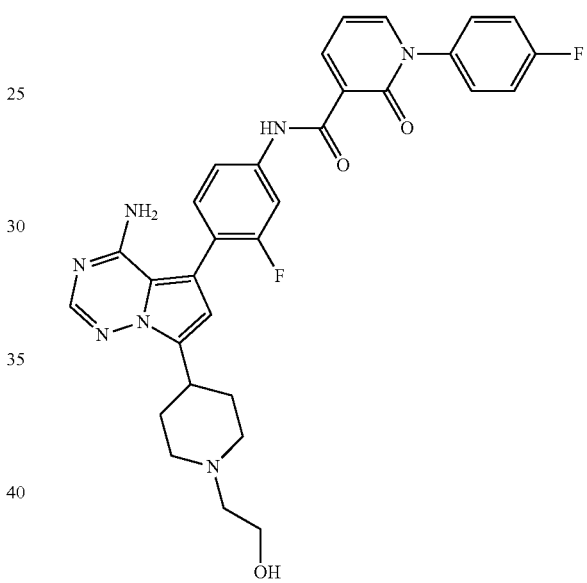

In a sealed tube a mixture of 2-[4-(4-amino-5-bromopyrrolo[2,1-][1,2,4]triazin-7-yl)piperidin-1-yl]ethanol (13 mg, 0.009 mmol) (prepared in Example 52, step 1), 1-(4-fluorophenyl)-N-[3-fluoro-4-(4,4,5,5-tetramethyl-1,3,2-dioxaborolan-2-yl)phenyl]-2-oxo-1,2-dihydropyridine-3-carboxamide (4.0 mg, 0.01 mmol) (prepared in Example 9, step 5) and N,N-diisopropylethylamine (0.007 mL, 0.04 mmol) in 1,4-dioxane (0.15 mL) and water (15 L) was stirred together and flushed with $N_2$ for 5 min before bis(tri-t-butylphosphine)palladium (2.2 mg, 0.004 mmol) was added. The reaction mixture was sealed and then heated at 110° C. for 20 min. After separation and the aqueous layer extracted with EtOAc, the organic layer was dried, filtered and concentrated under vacuum. The crude was purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as off-white powders (2.2 mg, 44%). LCMS calcd for $C_{31}H_{30}F_2N_7O_3(M+H)^+$: m/z=586.2. Found: 586.2.

Example 56. N-{4-[4-Amino-7-(1-{[ethyl(methyl)amino]carbonyl}piperidin-4-yl)pyrrolo[2,1-f][1,2,4]triazin-5-yl]phenyl}-1-(4-fluorophenyl)-2-oxo-1,2-dihydropyridine-3-carboxamide

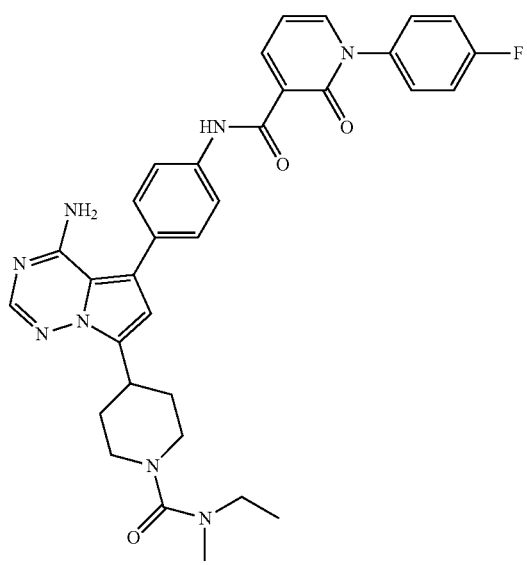 [SMILES: CCN(C)C(=O)N1CCC(c2cc(-c3ccc(NC(=O)c4cccn(-c5ccc(F)cc5)c4=O)cc3)c3c(N)ncnn23)CC1]

Step 1: 4-(4-Amino-5-bromopyrrolo[2,1-f][1,2,4]triazin-7-yl)-N-ethyl-N-methylpiperidine-1-carboxamide

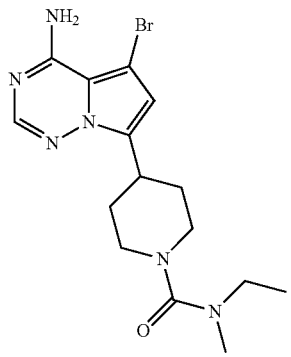 [SMILES: CCN(C)C(=O)N1CCC(c2cc(Br)c3c(N)ncnn23)CC1]

To a mixture of 5-bromo-7-piperidin-4-ylpyrrolo[2,1-f][1,2,4]triazin-4-amine dihydrochloride (20 mg, 0.04 mmol) (prepared in Example 32, step 4) in tetrahydrofuran (0.2 mL) was added 1.0 M sodium bicarbonate in water (0.23 mL, 0.23 mmol), followed by the slow addition of ethyl(methyl)carbamic chloride (56.5 mg, 0.46 mmol) at 0 Celsius. After stirred at rt for 15 min, the resultant mixture was filtered, extracted with EtOAc, dried, filtered and concentrated to dryness under reduced pressure. The resulting crude was used directly in the next step as off-white powders (18.1 mg). LCMS calcd for $C_{15}H_{22}BrN_6O$ (M+H)$^+$: m/z=381.1, 383.1. Found: 381.0, 383.0.

Step 2: N-{4-[4-Amino-7-(1-{[ethyl(methyl)amino]carbonyl}piperidin-4-yl)pyrrolo[2,1-f][1,2,4]triazin-5-yl]phenyl}-1-(4-fluorophenyl)-2-oxo-1,2-dihydropyridine-3-carboxamide In a sealed tube a mixture of 4-(4-amino-5-bromopyrrolo[2,1-f][1,2,4]triazin-7-yl)-N-ethyl-N-methylpiperidine-1-carboxamide (3.3 mg, 0.007 mmol), 1-(4-fluorophenyl)-2-oxo-N-[4-(4,4,5,5-tetramethyl-1,3,2-dioxaborolan-2-yl)phenyl]-1,2-dihydropyridine-3-carboxamide (3.2 mg, 0.007 mmol) (prepared in Example 9, step 3) and N,N-diisopropylethylamine (0.004 mL, 0.02 mmol) in 1,4-dioxane (0.1 mL) and water (14 µL) was stirred together before bis(tri-t-butylphosphine)palladium (1.8 mg, 0.004 mmol) was added. The reaction mixture was sealed and then heated at 110 Celsius for 50 min. The crude was diluted with MeOH, filtered and purified by prep LC-MS (pH=2 method; Waters SunFire PrepC18 5 µm OBD™ column, 30×100 mm, 60 mL/min, eluting with a gradient of MeCN and water with 0.1% TFA) to give the desired product as white powders (2.9 mg, 68%). LCMS calcd for $C_{33}H_{34}FN_8O_3$(M+H)$^+$: m/z=609.3. Found: 609.3.

Example 57. N-{4-[4-Amino-7-(1-{[ethyl(methyl)amino]carbonyl}piperidin-4-yl)pyrrolo[2,1-f][1,2,4]triazin-5-yl]phenyl}-1-(4-fluorophenyl)-2,5-dioxo-1,2,5,6,7,8-hexahydroquinoline-3-carboxamide

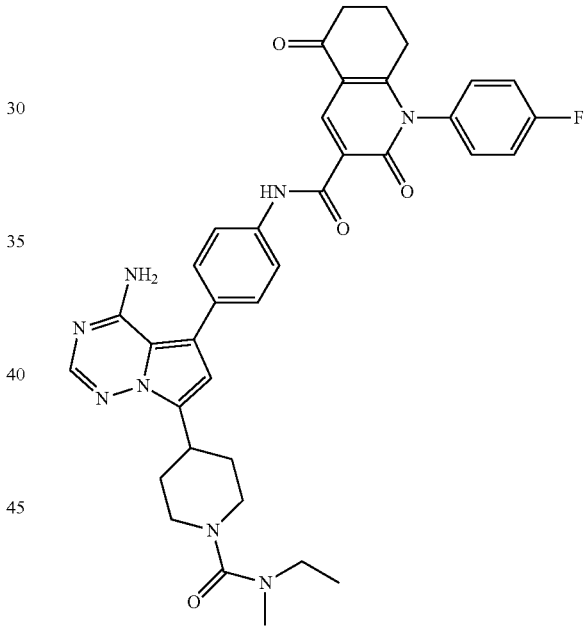

Step 1: 1-(4-Fluorophenyl)-2,5-dioxo-N-[4-(4,4,5,5-tetramethyl-1,3,2-dioxaborolan-2-yl)phenyl]-1,2,5,6,7,8-hexahydroquinoline-3-carboxamide

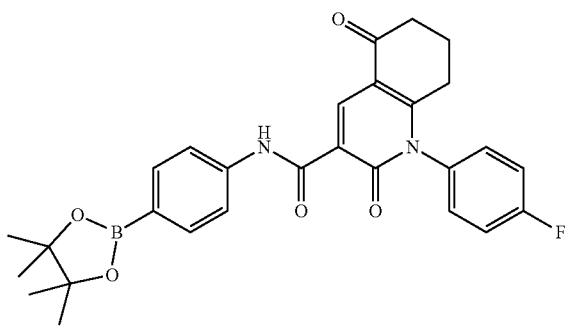 [SMILES: CC1(C)OB(c2ccc(NC(=O)c3cc4c(n(-c5ccc(F)cc5)c3=O)CCCC4=O)cc2)OC1(C)C]

To a mixture of 4-(4,4,5,5-tetramethyl-1,3,2-dioxaborolan-2-yl)aniline (76.4 mg, 0.35 mmol) and 1-(4-fluorophenyl)-2,5-dioxo-1,2,5,6,7,8-hexahydroquinoline-3-carboxylic acid (100.0 mg, 0.33 mmol) (prepared in Example 1, step 4) in N,N-dimethylformamide (1.5 mL) was added triethylamine (69 µL, 0.5 mmol) followed by N,N,N',N'-tetramethyl-O-(7-azabenzotriazol-1-yl)uronium hexafluorophosphate (151 mg, 0.40 mmol). The resulting mixture, which became a mixture of solids quickly, was stirred at rt for 60 min. The precipitate was filtered and washed with water and dry under vacuum to provide the desired product as white powders (186 mg). LCMS calcd for $C_{28}H_{29}BFN_2O_5(M+H)^+$: m/z=503.1. Found: 503.1.

Step 2: N-{4-[4-Amino-7-(1-{[ethyl(methyl)amino]carbonyl}piperidin-4-yl)pyrrolo[2,1-f][1,2,4]triazin-5-yl]phenyl}-1-(4-fluorophenyl)-2,5-dioxo-1,2,5,6,7,8-hexahydroquinoline-3-carboxamide In a sealed tube a mixture of 4-(4-amino-5-bromopyrrolo[2,1-f][1,2,4]triazin-7-yl)-N-ethyl-N-methylpiperidine-1-carboxamide (3.3 mg, 0.007 mmol) (prepared in Example 56, step 1), 1-(4-fluorophenyl)-2,5-dioxo-N-[4-(4,4,5,5-tetramethyl-1,3,2-dioxaborolan-2-yl)phenyl]-1,2,5,6,7,8-hexahydroquinoline-3-carboxamide (3.7 mg, 0.007 mmol) and N,N-diisopropylethylamine (0.008 mL, 0.04 mmol) in 1,4-dioxane (0.10 mL) and water (14 L) was stirred together before bis(tri-t-butylphosphine)palladium (1.8 mg, 0.004 mmol) was added. The reaction mixture was sealed and then heated at 110 Celsius for 50 min. The crude was diluted with MeOH, filtered and purified by prep LC-MS (pH=2 method; Waters SunFire PrepC18 5 µm OBD™ column, 30×100 mm, 60 mL/min, eluting with a gradient of MeCN and water with 0.1% TFA) to give the desired product as white powders (3.8 mg, 80%). LCMS calcd for $C_{37}H_{38}FN_8O_4(M+H)^+$: m/z=677.3. Found: 677.3.

Example 58. N-{4-[4-Amino-7-(1-{[ethyl(methyl)amino]carbonyl}piperidin-4-yl)pyrrolo[2,1-f][1,2,4]triazin-5-yl]-3-fluorophenyl}-1-(4-fluorophenyl)-2,5-dioxo-1,2,5,6,7,8-hexahydroquinoline-3-carboxamide

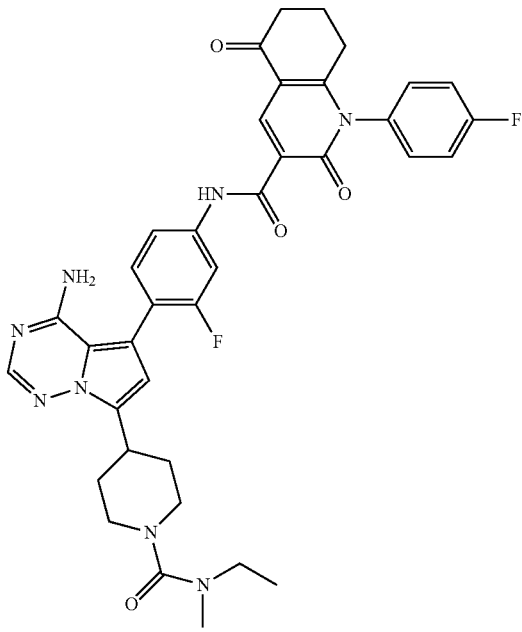 [SMILES: CCN(C)C(=O)N1CCC(c2cc(-c3ccc(NC(=O)c4cc5c(n(-c6ccc(F)cc6)c4=O)CCCC5=O)cc3F)c3c(N)ncnn23)CC1]

Step 1: 1-(4-Fluorophenyl)-N-[3-fluoro-4-(4,4,5,5-tetramethyl-1,3,2-dioxaborolan-2-yl)phenyl]-2,5-dioxo-1,2,5,6,7,8-hexahydroquinoline-3-carboxamide

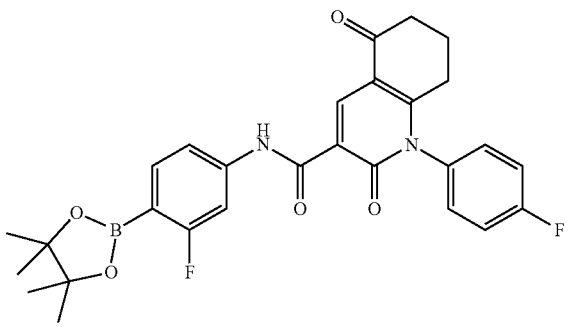 [SMILES: CC1(C)OB(c2ccc(NC(=O)c3cc4c(n(-c5ccc(F)cc5)c3=O)CCCC4=O)cc2F)OC1(C)C]

To a mixture of 2-fluoro-4-(4,4,5,5-tetramethyl-1,3,2-dioxaborolan-2-yl)aniline (82.6 mg, 0.35 mmol) (from Combi-Block) and 1-(4-fluorophenyl)-2,5-dioxo-1,2,5,6,7,8-hexahydroquinoline-3-carboxylic acid (100.0 mg, 0.33 mmol) (prepared in Example 1, step 4) in N,N-dimethylformamide (1.5 mL) was added triethylamine (69 µL, 0.5 mmol) followed by N,N,N',N'-tetramethyl-O-(7-azabenzotriazol-1-yl)uronium hexafluorophosphate (151 mg, 0.40 mmol). The resulting mixture was stirred at rt for 2 h. The reaction mixture was concentrated under vacuum to remove most solvents, and precipitated out. The precipitate was filtered and washed with water. The cake was dried overnight by vacuum suction to give the desired product as off-white powders (156.5 mg, 91%). LCMS calcd for $C_{28}H_{28}BF_2N_2O_5$ $(M+H)^+$: m/z=521.1. Found: 521.1.

Step 2: N-{4-[4-Amino-7-(1-{[ethyl(methyl)amino]carbonyl}piperidin-4-yl)pyrrolo[2,1-f][1,2,4]triazin-5-yl]-3-fluorophenyl}-1-(4-fluorophenyl)-2,5-dioxo-1,2,5,6,7,8-hexahydroquinoline-3-carboxamide In a sealed tube a mixture of 4-(4-amino-5-bromopyrrolo[2,1-f][1,2,4]triazin-7-yl)-N-ethyl-N-methylpiperidine-1-carboxamide (3.3 mg, 0.007 mmol) (prepared in Example 56, step 1), 1-(4-fluorophenyl)-N-[3-fluoro-4-(4,4,5,5-tetramethyl-1,3,2-dioxaborolan-2-yl)phenyl]-2,5-dioxo-1,2,5,6,7,8-hexahydroquinoline-3-carboxamide (3.8 mg, 0.0074 mmol) and N,N-diisopropylethylamine (0.004 mL, 0.02 mmol) in 1,4-dioxane (0.1 mL) and water (14 L) was stirred together before bis(tri-t-butylphosphine)palladium (1.8 mg, 0.004 mmol) was added. The reaction mixture was sealed and then heated at 110 Celsius for 50 min. The crude was diluted with MeOH, filtered and purified by prep LC-MS (pH=2 method; Waters SunFire PrepC18 5 µm OBD™ column, 30×100 mm, 60 mL/min, eluting with a gradient of MeCN and water with 0.1% TFA) to give the desired product as white powders (1.9 mg, 39%). LCMS calcd for $C_{37}H_{37}F_2N_8O_4(M+H)^+$: m/z=695.3. Found: 695.3.

165

Example 59. N-(4-{4-Amino-7-[1-(2-hydroxyethyl) piperidin-4-yl]pyrrolo[2,1-f][1,2,4]triazin-5-yl}phenyl)-1-(4-fluorophenyl)-2,5-dioxo-1,2,5,6,7,8-hexahydroquinoline-3-carboxamide

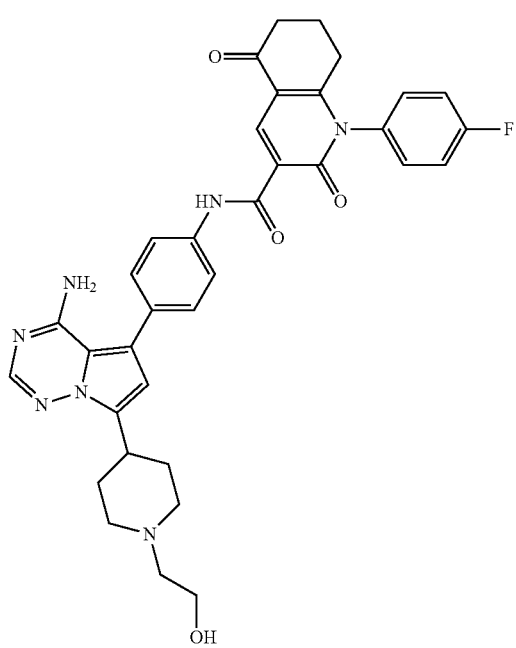 [SMILES: Nc1ncnn2c(C3CCN(CCO)CC3)cc(-c3ccc(NC(=O)c4cc5c(n(-c6ccc(F)cc6)c4=O)CCCC5=O)cc3)c12]

In a sealed tube a mixture of 2-[4-(4-amino-5-bromopyrrolo[2,1-f][1,2,4]triazin-7-yl)piperidin-1-yl]ethanol (10 mg, 0.007 mmol) (prepared in Example 52, step 1), 1-(4-fluorophenyl)-2,5-dioxo-N-[4-(4,4,5,5-tetramethyl-1,3,2-dioxaborolan-2-yl)phenyl]-1,2,5,6,7,8-hexahydroquinoline-3-carboxamide (3.7 mg, 0.0074 mmol) (prepared in Example 57, step 1) and N,N-diisopropylethylamine (0.004 mL, 0.02 mmol) in 1,4-dioxane (0.1 mL) and water (14) was stirred together before bis(tri-t-butylphosphine)palladium (1.8 mg, 0.004 mmol) was added. The reaction mixture was sealed and then heated at 110 Celsius for 50 min. The crude was diluted with MeOH, filtered and purified by prep LC-MS (pH=2 method; Waters SunFire PrepC18 5 μm OBD™ column, 30×100 mm, 60 mL/min, eluting with a gradient of MeCN and water with 0.1% TFA) to give the desired product as white powders (2.1 mg, 47%). LCMS calcd for $C_{35}H_{35}FN_7O_4$ (M+H)$^+$: m/z=636.3. Found: 636.3.

166

Example 60. N-(4-{4-Amino-7-[1-(2-hydroxyethyl) piperidin-4-yl]pyrrolo[2,1-f][1,2,4]triazin-5-yl}-3-fluorophenyl)-1-(4-fluorophenyl)-2,5-dioxo-1,2,5,6,7,8-hexahydroquinoline-3-carboxamide

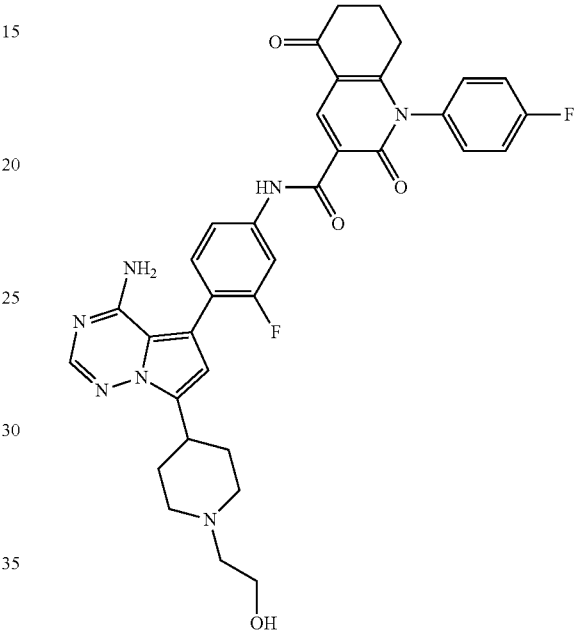

In a sealed tube a mixture of 2-[4-(4-amino-5-bromopyrrolo[2,1-f][1,2,4]triazin-7-yl)piperidin-1-yl]ethanol (10 mg, 0.007 mmol) (prepared in Example 52, step 1), 1-(4-fluorophenyl)-N-[3-fluoro-4-(4,4,5,5-tetramethyl-1,3,2-dioxaborolan-2-yl)phenyl]-2,5-dioxo-1,2,5,6,7,8-hexahydroquinoline-3-carboxamide (3.8 mg, 0.0074 mmol) (prepared in Example 58, step 1) and N,N-diisopropylethylamine (0.004 mL, 0.02 mmol) in 1,4-dioxane (0.1 mL) and water (14 μL) was stirred together before bis(tri-t-butylphosphine) palladium (1.8 mg, 0.004 mmol) was added. The reaction mixture was sealed and then heated at 110 Celsius for 50 min. The crude was diluted with MeOH, filtered and purified by prep LC-MS (pH=2 method; Waters SunFire PrepC18 5 m OBD™ column, 30×100 mm, 60 mL/min, eluting with a gradient of MeCN and water with 0.1% TFA) to give the desired product as white powders (2.4 mg, 52%). LCMS calcd for $C_{35}H_{34}F_2N_7O_4$(M+H)$^+$: m/z=654.3. Found: 654.3.

Example 61. N-(4-(4-Amino-7-(1-(dimethylcarbamoyl)piperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide

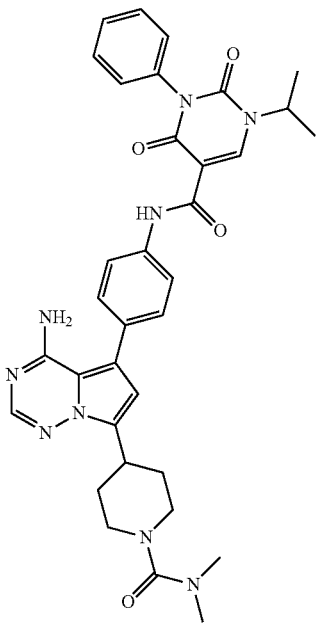 [SMILES: CC(C)n1cc(C(=O)Nc2ccc(-c3cc(C4CCN(C(=O)N(C)C)CC4)n4ncnc(N)c34)cc2)c(=O)n(-c2ccccc2)c1=O]

Step 1: Diethyl 2-((3-phenylureido)methylene)malonate

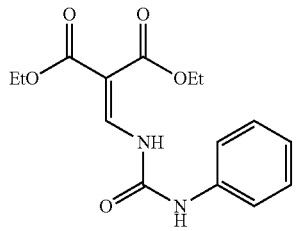 [SMILES: CCOC(=O)C(=CNC(=O)Nc1ccccc1)C(=O)OCC]

To a mixture of diethyl (aminomethylene)malonate (6.0 g, 32 mmol) and phenyl isocyanate (3.8 mL, 35 mmol) in 1,2-dichloroethane (20 mL) at rt was added N,N-diisopropylethylamine (7.2 mL, 42 mmol). The reaction mixture was then stirred at 70° C. overnight, cooled to rt, added Et$_2$O (50 mL), and stirred for another 30 min. The resulting solid was collected by filtration, washed with ether, and dried to give the product as a white solid (4.88 g, 50%). LCMS calcd for $C_{15}H_{19}N_2O_5$ (M+H)$^+$: m/z=307.1. Found: 307.2.

Step 2: Ethyl 2,4-dioxo-3-phenyl-1,2,3,4-tetrahydropyrimidine-5-carboxylate

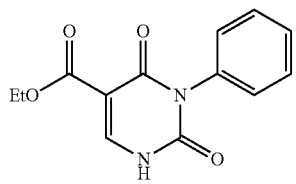 [SMILES: CCOC(=O)c1c[nH]c(=O)n(-c2ccccc2)c1=O]

A mixture of diethyl 2-((3-phenylureido)methylene)malonate from previous step (4.88 g, 15.9 mmol) and 2.5 M NaOEt in EtOH (13 mL, 32 mmol) in EtOH (20 mL) was stirred at rt for 1 h. The resulting mixture was diluted with EtOAc, washed/acidified with 1 N citric acid, washed with water, brine, dried over Na$_2$SO$_4$, and concentrated to provide the crude product as a white solid, which was used directly in the next step (4.1 g, 99%). LCMS calcd for $C_{13}H_{13}N_2O_4$ (M+H)$^+$: m/z=261.1. Found: 261.1.

Step 3: ethyl 1-isopropyl-2,4-dioxo-3-phenyl-1,2,3,4-tetrahydropyrimidine-5-carboxylate

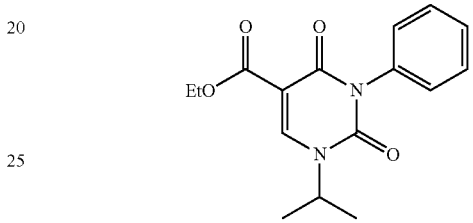

A mixture of ethyl 2,4-dioxo-3-phenyl-1,2,3,4-tetrahydropyrimidine-5-carboxylate from previous step (1.50 g, 5.76 mmol), isopropyl iodide (1.2 mL, 12 mmol), and Cs$_2$CO$_3$ (5.6 g, 17 mmol) in DMF (20 mL) was stirred at 50° C. for 5 h. The reaction mixture was then cooled to rt, diluted with EtOAc, washed with water, brine, dried over Na$_2$SO$_4$, and concentrated to provide the crude product, which was used directly in the next step. LCMS calcd for $C_{16}H_{19}N_2O_4$ (M+H)$^+$: m/z=303.1. Found: 303.1.

Step 4: 1-Isopropyl-2,4-dioxo-3-phenyl-1,2,3,4-tetrahydropyrimidine-5-carboxylic Acid

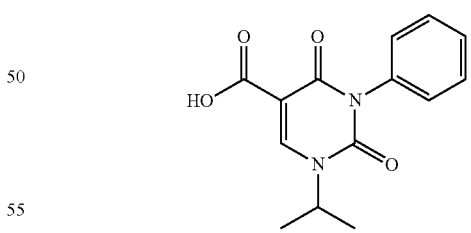

A mixture of ethyl 1-isopropyl-2,4-dioxo-3-phenyl-1,2,3,4-tetrahydropyrimidine-5-carboxylate from previous step (1.70 g, 5.62 mmol) in 4.0 M HCl in 1,4-dioxane (9.8 mL, 39 mmol) and water (2.1 mL) was stirred at 60° C. for 4 h, cooled to rt, and added water. The resulting solid was then collected by filtration (washed with water) to give the product as a white solid (1.1 g, 71%). LCMS calcd for $C_{14}H_{15}N_2O_4$ (M+H)$^+$: m/z=275.1. Found: 275.1.

Step 5: 1-Isopropyl-2,4-dioxo-3-phenyl-N-(4-(4,4,5, 5-tetramethyl-1,3,2-dioxaborolan-2-yl)phenyl)-1,2,3, 4-tetrahydropyrimidine-5-carboxamide

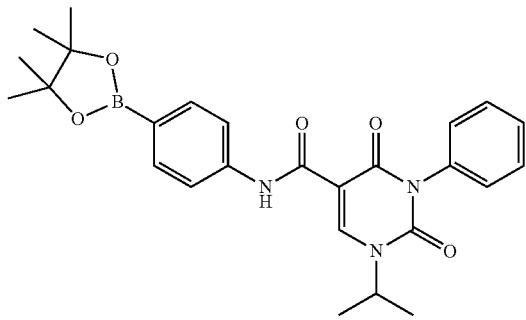 [SMILES: CC(C)n1cc(C(=O)Nc2ccc(B3OC(C)(C)C(C)(C)O3)cc2)c(=O)n(-c2ccccc2)c1=O]

To a mixture of 1-isopropyl-2,4-dioxo-3-phenyl-1,2,3,4-tetrahydropyrimidine-5-carboxylic acid from previous step (400 mg, 1 mmol) and 4-(4,4,5,5-tetramethyl-1,3,2-dioxaborolan-2-yl)aniline (320 mg, 1.46 mmol) in DMF (8 mL) at rt was added Et$_3$N (305 μL, 2.19 mmol), followed by HATU (665 mg, 1.75 mmol). The resulting mixture was stirred at rt for 2 h and added water. The resulting solid was collected by filtration, washed with water, and dried to give the product as a slightly yellow solid (642 mg, 92%). LCMS calcd for C$_{26}$H$_{31}$BN$_3$O$_5$(M+H)$^+$: m/z=476.2. Found: 476.2.

Step 6: tert-Butyl 4-[4-amino-5-(4-{[(1-isopropyl-2, 4-dioxo-3-phenyl-1,2,3,4-tetrahydropyrimidin-5-yl) carbonyl]amino}phenyl)pyrrolo[2,1-f][1,2,4]triazin-7-yl]piperidine-1-carboxylate

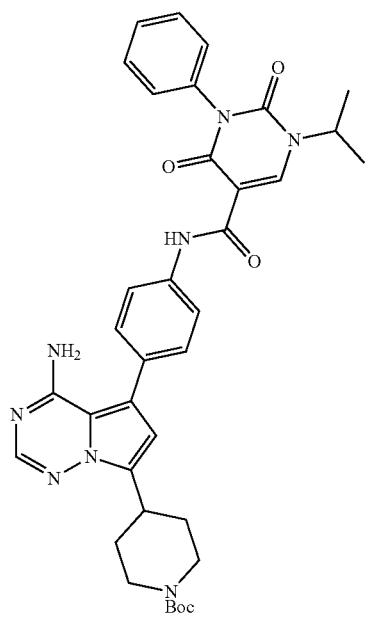 [SMILES: CC(C)n1cc(C(=O)Nc2ccc(-c3cc(C4CCN(C(=O)OC(C)(C)C)CC4)n4ncnc(N)c34)cc2)c(=O)n(-c2ccccc2)c1=O]

A mixture of 1-isopropyl-2,4-dioxo-3-phenyl-N-[4-(4,4, 5,5-tetramethyl-1,3,2-dioxaborolan-2-yl)phenyl]-1,2,3,4-tetrahydropyrimidine-5-carboxamide from previous step (642 mg, 1.35 mmol), tert-butyl 4-(4-amino-5-bromopyrrolo [2,1-f][1,2,4]triazin-7-yl)piperidine-1-carboxylate (535 mg, 1.35 mmol) (from example 32, step 3), XPhos Pd G2 (110 mg, 0.14 mmol), and Na$_2$CO$_3$ (290 mg, 2.7 mmol) in 1,4-Dioxane (10 mL) and water (2.5 mL) was purged with nitrogen, and stirred at 70° C. for 2 h. The reaction mixture was then cooled to rt, diluted with EtOAc, washed with water, brine, dried over Na$_2$SO$_4$, concentrated, and purified via column chromatography (0% to 12% MeOH in DCM) to give the crude product as a yellow solid, which was used directly in the next step (898 mg, 100%). LCMS calcd for C$_{36}$H$_{41}$N$_8$O$_5$ (M+H)$^+$: m/z=665.3. Found: 665.3.

Step 7: N-(4-(4-Amino-7-(piperidin-4-yl)pyrrolo[1, 2-f][1,2,4]triazin-5-yl)phenyl)-1-isopropyl-2,4-dioxo-3-phenyl-1,2,3,4-tetrahydropyrimidine-5-carboxamide

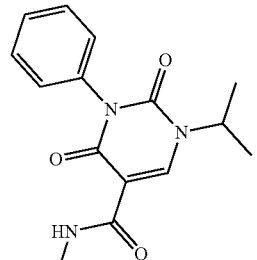
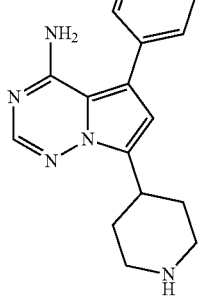

To a solution of tert-butyl 4-[4-amino-5-(4-{[(1-isopropyl-2,4-dioxo-3-phenyl-1,2,3,4-tetrahydropyrimidin-5-yl) carbonyl]amino}phenyl)pyrrolo[2,1-f][1,2,4]triazin-7-yl]piperidine-1-carboxylate from previous step (898 mg, 1.35 mmol) in CH$_2$Cl$_2$ (10 mL) at rt was added 4.0 M HCl in 1,4-dioxane (3.4 mL, 14 mmol). The reaction mixture was stirred at rt for 2 h, diluted with Et$_2$O, and the resulting solid was collected by filtration to give the product as a yellow solid (~2HCl salt) (702 mg, 81%). LCMS calcd for C$_{31}$H$_{33}$N$_8$O$_3$ (M+H)$^+$: m/z=565.3. Found: 565.3.

Step 8: N-(4-(4-Amino-7-(1-(dimethylcarbamoyl) piperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide To a solution of N-[4-(4-amino-7-piperidin-4-ylpyrrolo[2,1-f][1,2,4]triazin-5-yl)phenyl]-1-isopropyl-2,4-dioxo-3-phenyl-1,2,3,4-tetrahydropyrimidine-5-carboxamide (~2 HCl salt) from previous step (150 mg, 0.24 mmol) in CH$_2$Cl$_2$ (5.0 mL) at rt was added Et$_3$N (200 μL, 1.4 mmol), followed by N,N-dimethylcarbamoyl chloride (65 μL, 0.70 mmol). The reaction mixture was stirred at rt for 3 h, diluted with CH$_2$Cl$_2$ (5.0 mL), washed with water, dried over Na$_2$SO$_4$, and concentrated. The resulting residue was dissolved in MeCN (5% water, 0.5% TFA), and purified via pH 2 preparative LC/MS (MeCN/water with TFA) to give the product as a white solid (TFA salt). LCMS calcd for C$_{34}$H$_{38}$N$_9$O$_4$ (M+H)$^+$: m/z=636.3. Found: 636.3. $^1$H NMR (600 MHz, DMSO) δ 11.01 (s, 1H), 8.67 (s, 1H), 8.10 (s, 1H), 7.80 (d, J=8.7 Hz, 2H), 7.52 (td, J=6.9, 1.6 Hz, 2H), 7.49-7.43 (m, 3H), 7.40-7.33 (m, 2H), 6.75 (s, 1H), 4.78 (hept, J=6.7 Hz, 1H), 3.66 (d, J=13.1 Hz, 2H), 3.31 (tt, J=11.8, 3.5 Hz, 1H), 2.86 (t, J=11.7 Hz, 2H), 2.75 (s, 6H), 1.97 (d, J=10.7 Hz, 2H), 1.67 (qd, J=12.6, 3.8 Hz, 2H), 1.43 (d, J=6.8 Hz, 6H).

Example 62. N-(4-(4-Amino-7-(1-(ethyl(methyl)carbamoyl)piperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide

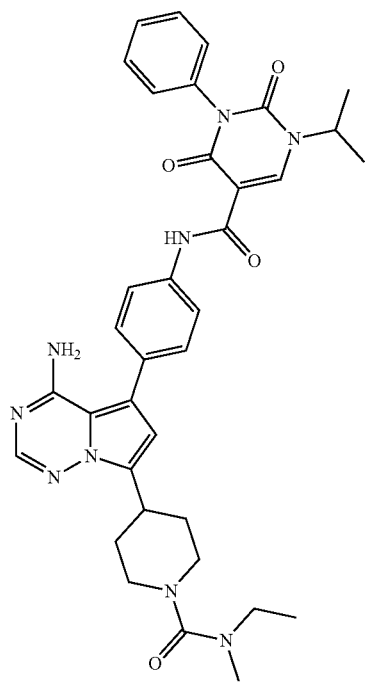 [SMILES: CCN(C)C(=O)N1CCC(c2cc(-c3ccc(NC(=O)c4cn(C(C)C)c(=O)n(-c5ccccc5)c4=O)cc3)c3c(N)ncnn23)CC1]

To a solution of N-[4-(4-amino-7-piperidin-4-ylpyrrolo[2,1-f][1,2,4]triazin-5-yl)phenyl]-1-isopropyl-2,4-dioxo-3-phenyl-1,2,3,4-tetrahydropyrimidine-5-carboxamide (~2 HCl salt) (from example 61, step 7) (150 mg, 0.24 mmol) in CH$_2$Cl$_2$ (5.0 mL) at rt was added Et$_3$N (200 μL, 1.4 mmol), followed by ethyl(methyl)carbamic chloride (86 mg, 0.70 mmol). The reaction mixture was stirred at rt overnight, diluted with CH$_2$Cl$_2$ (5.0 mL), washed with water, dried over Na$_2$SO$_4$, and concentrated. The resulting residue was dissolved in MeCN (5% water, 0.5% TFA), and purified via pH 2 preparative LC/MS (MeCN/water with TFA) to give the product as a white solid (TFA salt). LCMS calcd for C$_{35}$H$_{40}$N$_9$O$_4$ (M+H)$^+$: m/z=650.3. Found: 650.3. $^1$H NMR (600 MHz, DMSO) δ 11.00 (s, 1H), 8.67 (s, 1H), 8.09 (s, 1H), 7.79 (d, J=8.7 Hz, 2H), 7.56-7.50 (m, 2H), 7.50-7.43 (m, 3H), 7.40-7.34 (m, 2H), 6.74 (s, 1H), 4.78 (p, J=6.8 Hz, 1H), 3.63 (d, J=13.0 Hz, 2H), 3.30 (tt, J=11.8, 3.5 Hz, 1H), 3.12 (q, J=7.1 Hz, 2H), 2.85 (t, J=11.8 Hz, 2H), 2.74 (s, 3H), 1.97 (d, J=10.8 Hz, 2H), 1.67 (qd, J=12.6, 3.7 Hz, 2H), 1.43 (d, J=6.8 Hz, 6H), 1.06 (t, J=7.1 Hz, 3H).

Example 63. N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide

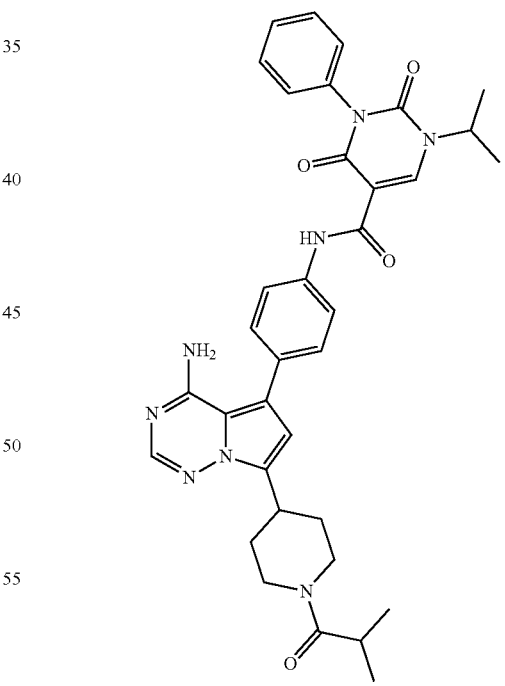

To a solution of N-[4-(4-amino-7-piperidin-4-ylpyrrolo[2,1-f][1,2,4]triazin-5-yl)phenyl]-1-isopropyl-2,4-dioxo-3-phenyl-1,2,3,4-tetrahydropyrimidine-5-carboxamide (~2HCl salt) (from example 61, step 7) (150 mg, 0.24 mmol) in CH$_2$Cl$_2$ (5.0 mL) at rt was added Et$_3$N (200 μL, 1.4 mmol), followed by isobutyryl chloride (30 μL, 0.28 mmol).

The reaction mixture was stirred at rt for 15 min, diluted with CH$_2$Cl$_2$ (5.0 mL), washed with water, dried over Na$_2$SO$_4$, and concentrated. The resulting residue was dissolved in MeCN (5% water, 0.5% TFA), and purified via pH 2 preparative LC/MS (MeCN/water with TFA) to give the product as a white solid (TFA salt). LCMS calcd for C$_{35}$H$_{39}$N$_8$O$_4$ (M+H)$^+$: m/z=635.3. Found: 635.3. $^1$H NMR (600 MHz, DMSO) δ 11.00 (s, 1H), 8.67 (s, 1H), 8.07 (s, 1H), 7.79 (d, J=8.7 Hz, 2H), 7.54-7.50 (m, 2H), 7.49-7.43 (m, 3H), 7.39-7.34 (m, 2H), 6.72 (s, 1H), 4.78 (p, J=6.8 Hz, 1H), 4.54 (d, J=12.4 Hz, 1H), 4.06 (d, J=12.6 Hz, 1H), 3.41 (tt, J=11.8, 3.6 Hz, 1H), 3.20 (t, J=12.5 Hz, 1H), 2.90 (p, J=6.7 Hz, 1H), 2.69 (t, J=12.0 Hz, 1H), 2.03 (dd, J=31.6, 11.8 Hz, 2H), 1.67-1.59 (m, 1H), 1.55-1.47 (m, 1H), 1.43 (d, J=6.8 Hz, 6H), 1.05-0.97 (m, 6H).

was added to the mixture. The reaction mixture was then stirred at rt for 15 min, added water (2.25 mL), concentrated, dissolved in MeCN (5% water, 0.5% TFA), and purified via pH 2 preparative LC/MS (MeCN/water with TFA) to give the product as a white solid (TFA salt). LCMS calcd for C$_{32}$H$_{35}$N$_8$O$_3$ (M+H)$^+$: m/z=579.3. Found: 579.3. $^1$H NMR (600 MHz, DMSO) δ 10.99 (s, 1H), 8.67 (s, 1H), 7.99 (s, 1H), 7.79 (d, J=8.7 Hz, 2H), 7.55-7.50 (m, 2H), 7.49-7.42 (m, 3H), 7.38-7.34 (m, 2H), 6.63 (s, 1H), 4.79 (p, J=6.8 Hz, 1H), 3.54 (d, J=11.3 Hz, 2H), 3.41-3.34 (m, 1H), 3.21-3.12 (m, 2H), 2.82 (d, J=4.6 Hz, 3H), 2.27 (d, J=13.9 Hz, 2H), 1.93-1.84 (m, 2H), 1.43 (d, J=6.8 Hz, 6H).

Example 64. N-(4-(4-Amino-7-(1-methylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide Example 65. N-(4-(4-Amino-7-(1-(dimethylcarbamoyl)piperidin-4-yl)pyrrolo[1,2-f][1,2,4]triazin-5-yl)phenyl)-3-(4-fluorophenyl)-1-isopropyl-2,4-dioxo-1,2,3,4-tetrahydropyrimidine-5-carboxamide

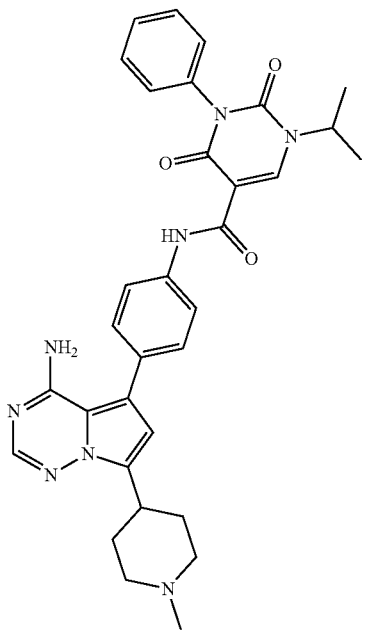 [SMILES: CC(C)n1cc(C(=O)Nc2ccc(-c3cc(C4CCN(C)CC4)n4ncnc(N)c34)cc2)c(=O)n(-c2ccccc2)c1=O]

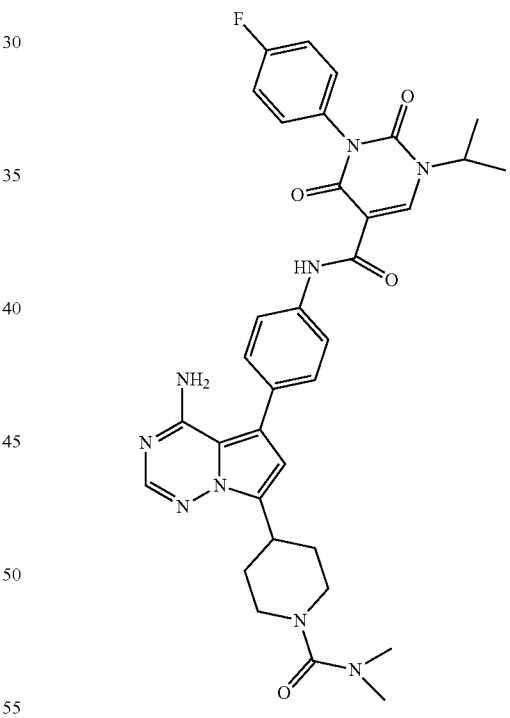

To a mixture of N-[4-(4-amino-7-piperidin-4-ylpyrrolo[2,1-f][1,2,4]triazin-5-yl)phenyl]-1-isopropyl-2,4-dioxo-3-phenyl-1,2,3,4-tetrahydropyrimidine-5-carboxamide (~2HCl salt) (from example 61, step 7) (150 mg, 0.24 mmol) in CH$_2$Cl$_2$ (10 mL) at rt was added N,N-diisopropylethylamine (82 μL, 0.47 mmol). The resulting mixture was stirred at rt for 15 min, and formaldehyde in water (24 μL, 37 wt %, 0.30 mmol) was added to the mixture. The resulting mixture was stirred for 15 min and NaBH(OAc)$_3$ (75 mg, 0.35 mmol)

This compound was prepared following a synthetic sequence analogous to that for example 61. LCMS calcd for C$_{34}$H$_{37}$FN$_9$O$_4$(M+H)$^+$: m/z=654.3. Found: 654.3. $^1$H NMR (600 MHz, DMSO) δ 10.98 (s, 1H), 8.67 (s, 1H), 8.08 (s, 1H), 7.83-7.75 (m, 2H), 7.48-7.45 (m, 2H), 7.45-7.41 (m, 2H), 7.38-7.32 (m, 2H), 6.73 (s, 1H), 4.81-4.75 (m, 1H), 3.66 (d, J=13.1 Hz, 2H), 3.34-3.27 (m, 1H), 2.86 (t, J=11.7 Hz, 2H), 2.75 (s, 6H), 1.97 (d, J=10.7 Hz, 2H), 1.71-1.63 (m, 2H), 1.43 (d, J=6.8 Hz, 6H).

Example 66. N-(4-(4-Amino-7-(1-(ethyl(methyl)carbamoyl)piperidin-4-yl)pyrrolo[1,2-f][1,2,4]triazin-5-yl)phenyl)-3-(4-fluorophenyl)-1-isopropyl-2,4-dioxo-1,2,3,4-tetrahydropyrimidine-5-carboxamide Example 67. N-(4-(4-Amino-7-(1-(dimethylcarbamoyl)piperidin-4-yl)pyrrolo[1,2-f][1,2,4]triazin-5-yl)phenyl)-1-ethyl-3-(4-fluorophenyl)-2,4-dioxo-1,2,3,4-tetrahydropyrimidine-5-carboxamide

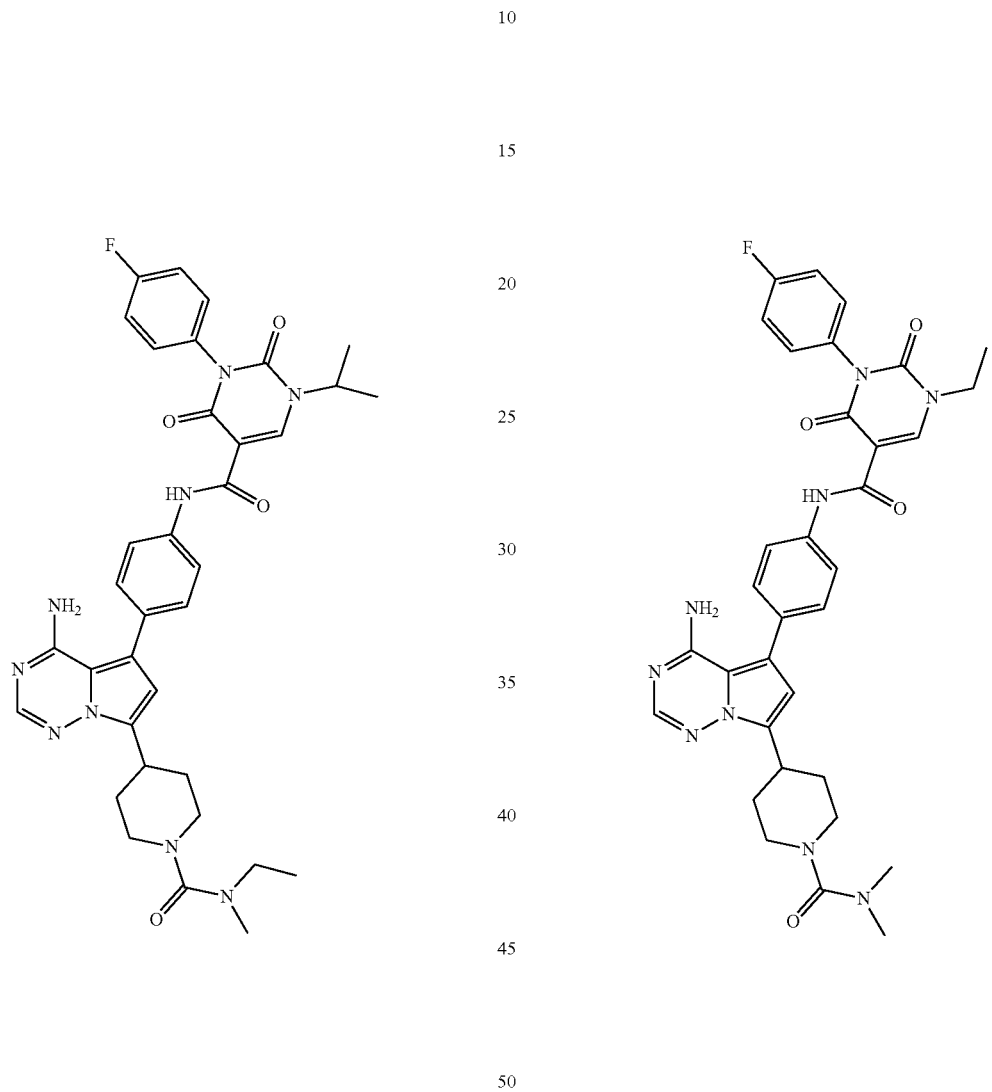

This compound was prepared following a synthetic sequence analogous to that for example 62. LCMS calcd for $C_{35}H_{39}FN_9O_4(M+H)^+$: m/z=668.3. Found: 668.2. H NMR (600 MHz, DMSO) δ 10.98 (s, 1H), 8.67 (s, 1H), 8.07 (s, 1H), 7.83-7.76 (m, 2H), 7.50-7.41 (m, 4H), 7.39-7.33 (m, 2H), 6.73 (s, 1H), 4.82-4.73 (m, 1H), 3.63 (d, J=13.1 Hz, 2H), 3.34-3.25 (m, 1H), 3.12 (q, J=7.1 Hz, 2H), 2.85 (t, J=11.7 Hz, 2H), 2.74 (s, 3H), 1.98 (d, J=10.6 Hz, 2H), 1.73-1.61 (m, 2H), 1.43 (d, J=6.8 Hz, 6H), 1.06 (t, J=7.1 Hz, 3H).

This compound was prepared following a synthetic sequence analogous to that for example 61. LCMS calcd for $C_{33}H_{35}FN_9O_4(M+H)^+$: m/z=640.3. Found: 640.3. $^1$H NMR (600 MHz, DMSO) δ 10.97 (s, 1H), 8.87 (s, 1H), 8.09 (s, 1H), 7.82-7.76 (m, 2H), 7.48-7.40 (m, 4H), 7.38-7.33 (m, 2H), 6.74 (s, 1H), 4.02 (q, J=7.1 Hz, 2H), 3.66 (d, J=13.1 Hz, 2H), 3.34-3.27 (m, 1H), 2.86 (t, J=11.7 Hz, 2H), 2.75 (s, 6H), 1.97 (d, J=10.6 Hz, 2H), 1.71-1.62 (m, 2H), 1.30 (t, J=7.1 Hz, 3H).

177

Example 68. N-(4-(4-Amino-7-(1-(morpholine-4-carbonyl)piperidin-4-yl)pyrrolo[1,2-f][1,2,4]triazin-5-yl)phenyl)-1-ethyl-3-(4-fluorophenyl)-2,4-dioxo-1,2,3,4-tetrahydropyrimidine-5-carboxamide

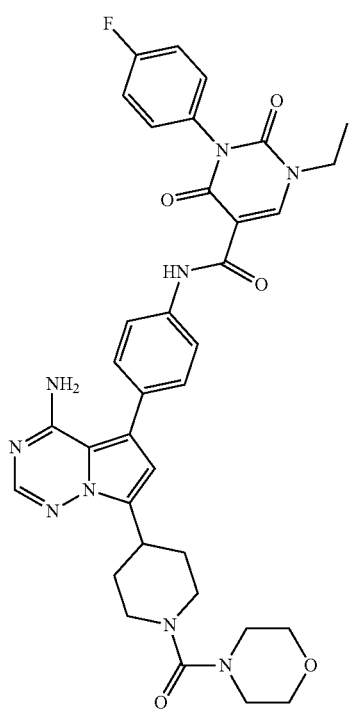 [SMILES: CCn1cc(C(=O)Nc2ccc(-c3cc(C4CCN(C(=O)N5CCOCC5)CC4)n4ncnc(N)c34)cc2)c(=O)n(-c2ccc(F)cc2)c1=O]

This compound was prepared following a synthetic sequence analogous to that for example 61. LCMS calcd for $C_{35}H_{37}FN_9O_5(M+H)^+$: m/z=682.3. Found: 682.3. $^1$H NMR (600 MHz, DMSO) δ 10.97 (s, 1H), 8.86 (s, 1H), 8.08 (s, 1H), 7.82-7.76 (m, 2H), 7.48-7.39 (m, 4H), 7.39-7.31 (m, 2H), 6.72 (s, 1H), 4.02 (q, J=7.1 Hz, 2H), 3.72 (d, J=13.1 Hz, 2H), 3.59-3.54 (m, 4H), 3.37-3.28 (m, 1H), 3.16-3.11 (m, 4H), 2.92 (t, J=11.8 Hz, 2H), 1.98 (d, J=10.7 Hz, 2H), 1.71-1.61 (m, 2H), 1.30 (t, J=7.1 Hz, 3H).

178

Example 69. N-(4-(4-Amino-7-(1-(ethyl(methyl)carbamoyl)piperidin-4-yl)pyrrolo[1,2-f][1,2,4]triazin-5-yl)phenyl)-3-(2-fluorophenyl)-1-isopropyl-2,4-dioxo-1,2,3,4-tetrahydropyrimidine-5-carboxamide

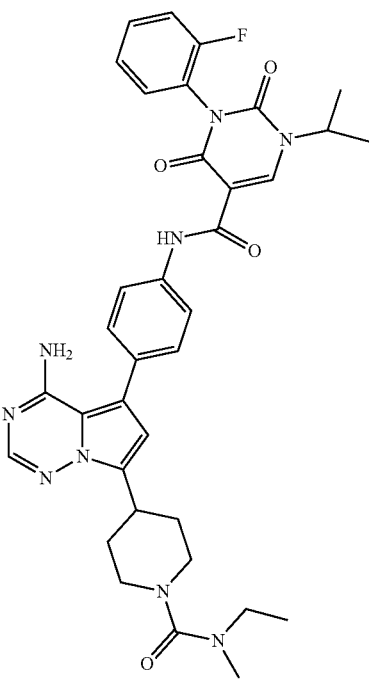 [SMILES: CCN(C)C(=O)N1CCC(c2cc(-c3ccc(NC(=O)c4cn(C(C)C)c(=O)n(-c5ccccc5F)c4=O)cc3)c3c(N)ncnn23)CC1]

This compound was prepared following a synthetic sequence analogous to that for example 62. LCMS calcd for $C_{35}H_{39}FN_9O_4(M+H)^+$: m/z=668.3. Found: 668.3. $^1$H NMR (600 MHz, DMSO) δ 10.83 (s, 1H), 8.72 (s, 1H), 8.07 (s, 1H), 7.82-7.77 (m, 2H), 7.59-7.51 (m, 2H), 7.49-7.35 (m, 4H), 6.73 (s, 1H), 4.81-4.73 (m, 1H), 3.63 (d, J=13.1 Hz, 2H), 3.34-3.26 (m, 1H), 3.12 (q, J=7.1 Hz, 2H), 2.85 (t, J=11.7 Hz, 2H), 2.74 (s, 3H), 1.98 (d, J=10.6 Hz, 2H), 1.67 (qd, J=12.6, 3.7 Hz, 2H), 1.44 (d, J=6.8 Hz, 6H), 1.06 (t, J=7.1 Hz, 3H).

Example 70. N-(4-(4-Amino-7-(1-(dimethylcarbamoyl)piperidin-4-yl)pyrrolo[1,2-f][1,2,4]triazin-5-yl)phenyl)-3-(3-fluorophenyl)-1-isopropyl-2,4-dioxo-1,2,3,4-tetrahydropyrimidine-5-carboxamide

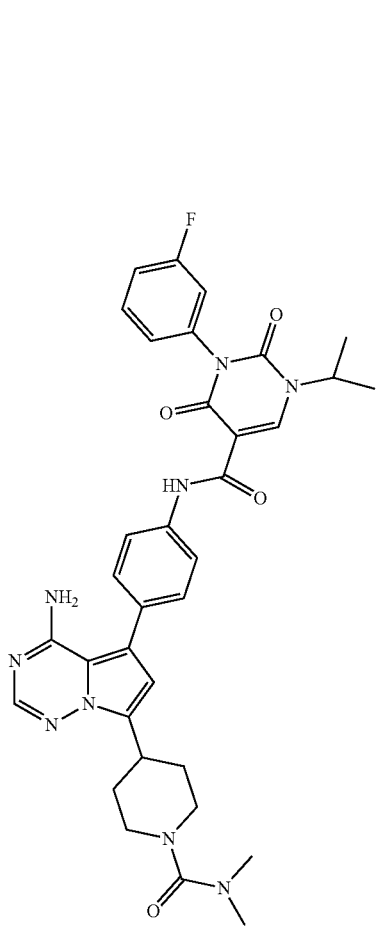 [SMILES: CC(C)C(=O)N1CCC(c2cc(-c3ccc(NC(=O)c4cn(C(C)C)c(=O)n(-c5cccc(F)c5)c4=O)cc3)c3c(N)ncnn23)CC1]

This compound was prepared following a synthetic sequence analogous to that for example 61. LCMS calcd for $C_{34}H_{37}FN_9O_4(M+H)^+$: m/z=654.3. Found: 654.2. $^1$H NMR (400 MHz, DMSO) δ 10.94 (s, 1H), 8.68 (s, 1H), 8.08 (s, 1H), 7.80 (d, J=8.6 Hz, 2H), 7.63-7.52 (m, 1H), 7.47 (d, J=8.6 Hz, 2H), 7.38-7.29 (m, 2H), 7.25 (d, J=8.2 Hz, 1H), 6.74 (s, 1H), 4.78 (p, J=6.8 Hz, 1H), 3.66 (d, J=13.0 Hz, 2H), 3.37-3.20 (m, 1H), 2.87 (q, J=11.3, 10.6 Hz, 2H), 2.75 (s, 6H), 1.97 (d, J=10.8 Hz, 2H), 1.75-1.59 (m, 2H), 1.43 (d, J=6.8 Hz, 6H).

Example 71. N-(4-(4-Amino-7-(1-isobutyrylpiperidin-4-yl)pyrrolo[1,2-][1,2,4]triazin-5-yl)phenyl)-3-(3-fluorophenyl)-1-isopropyl-2,4-dioxo-1,2,3,4-tetrahydropyrimidine-5-carboxamide

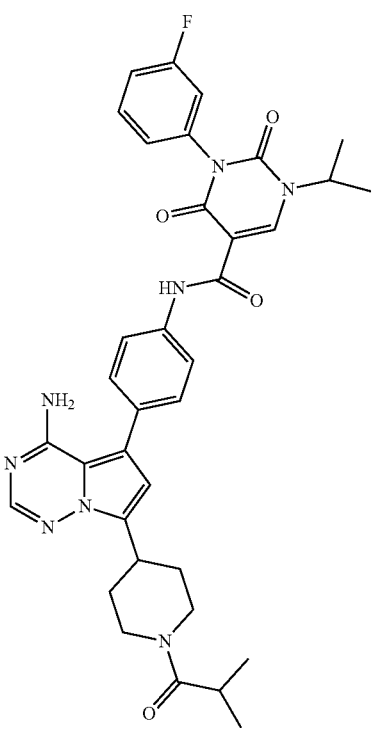

This compound was prepared following a synthetic sequence analogous to that for example 63. LCMS calcd for $C_{35}H_{38}FN_8O_4(M+H)^+$: m/z=653.3. Found: 653.3. $^1$H NMR (600 MHz, DMSO) δ 10.94 (s, 1H), 8.68 (s, 1H), 8.06 (s, 1H), 7.82-7.76 (m, 2H), 7.61-7.53 (m, 1H), 7.47-7.43 (m, 2H), 7.36-7.30 (m, 2H), 7.27-7.22 (m, 1H), 6.72 (s, 1H), 4.78 (p, J=6.8 Hz, 1H), 4.54 (d, J=12.2 Hz, 1H), 4.07 (d, J=12.8 Hz, 1H), 3.45-3.37 (m, 1H), 3.20 (q, J=10.7, 8.7 Hz, 1H), 2.90 (dq, J=13.5, 6.7 Hz, 1H), 2.69 (t, J=12.1 Hz, 1H), 2.03 (dd, J=31.3, 11.9 Hz, 2H), 1.67-1.47 (m, 2H), 1.43 (d, J=6.8 Hz, 6H), 1.04-0.98 (m, 6H).

Example 72. N-(4-(4-Amino-7-(1-(dimethylcarbamoyl)piperidin-4-yl)pyrrolo[1,2-f][1,2,4]triazin-5-yl)phenyl)-1-ethyl-3-(3-fluorophenyl)-2,4-dioxo-1,2,3,4-tetrahydropyrimidine-5-carboxamide

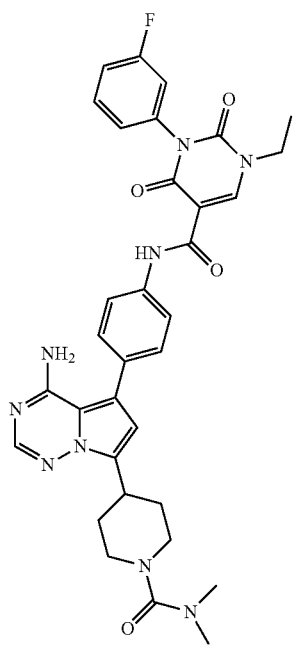 [SMILES: CCn1cc(C(=O)Nc2ccc(-c3cc(C4CCN(C(=O)N(C)C)CC4)n4ncnc(N)c34)cc2)c(=O)n(-c2cccc(F)c2)c1=O]

This compound was prepared following a synthetic sequence analogous to that for example 61. LCMS calcd for $C_{33}H_{35}FN_9O_4(M+H)^+$: m/z=640.3. Found: 640.3. $^1$H NMR (600 MHz, DMSO) δ 10.94 (s, 1H), 8.88 (s, 1H), 8.07 (s, 1H), 7.83-7.75 (m, 2H), 7.57 (ddd, J=9.0, 7.9, 6.4 Hz, 1H), 7.49-7.43 (m, 2H), 7.36-7.31 (m, 2H), 7.25 (ddd, J=7.9, 1.7, 1.0 Hz, 1H), 6.73 (s, 1H), 4.02 (q, J=7.1 Hz, 2H), 3.66 (d, J=13.1 Hz, 2H), 3.34-3.26 (m, 1H), 2.86 (t, J=11.7 Hz, 2H), 2.75 (s, 6H), 1.97 (d, J=10.7 Hz, 2H), 1.72-1.61 (m, 2H), 1.30 (t, J=7.1 Hz, 3H).

Example 73. N-(4-(4-Amino-7-(1-isobutyrylpiperidin-4-yl)pyrrolo[1,2-][1,2,4]triazin-5-yl)phenyl)-1-ethyl-3-(3-fluorophenyl)-2,4-dioxo-1,2,3,4-tetrahydropyrimidine-5-carboxamide

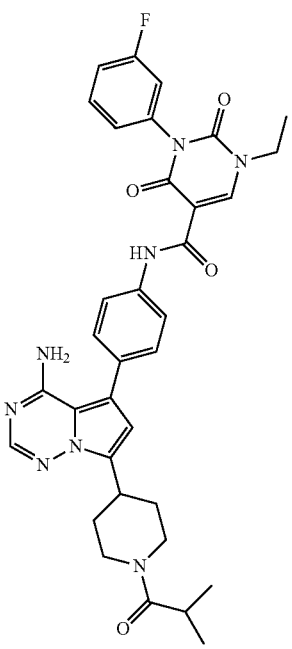 [SMILES: CCn1cc(C(=O)Nc2ccc(-c3cc(C4CCN(C(=O)C(C)C)CC4)n4ncnc(N)c34)cc2)c(=O)n(-c2cccc(F)c2)c1=O]

This compound was prepared following a synthetic sequence analogous to that for example 63. LCMS calcd for $C_{34}H_{36}FN_8O_4(M+H)^+$: m/z=639.3. Found: 639.2. $^1$H NMR (600 MHz, DMSO) δ 10.94 (s, 1H), 8.88 (s, 1H), 8.10 (s, 1H), 7.84-7.73 (m, 2H), 7.60-7.52 (m, 1H), 7.49-7.43 (m, 2H), 7.38-7.30 (m, 2H), 7.25 (ddd, J=7.9, 1.6, 1.0 Hz, 1H), 6.75 (s, 1H), 4.54 (d, J=12.4 Hz, 1H), 4.11-3.97 (m, 3H), 3.41 (tt, J=11.8, 3.6 Hz, 1H), 3.20 (t, J=12.3 Hz, 1H), 2.94-2.85 (m, 1H), 2.69 (t, J=12.0 Hz, 1H), 2.03 (dd, J=31.1, 12.1 Hz, 2H), 1.69-1.45 (m, 2H), 1.30 (t, J=7.1 Hz, 3H), 1.07-0.96 (m, 6H).

Example 74. N-(4-(4-Amino-7-(1-isobutyrylpiperidin-4-yl)pyrrolo[1,2-][1,2,4]triazin-5-yl)phenyl)-2,5-dioxo-1-phenyl-1,2,5,6,7,8-hexahydroquinoline-3-carboxamide

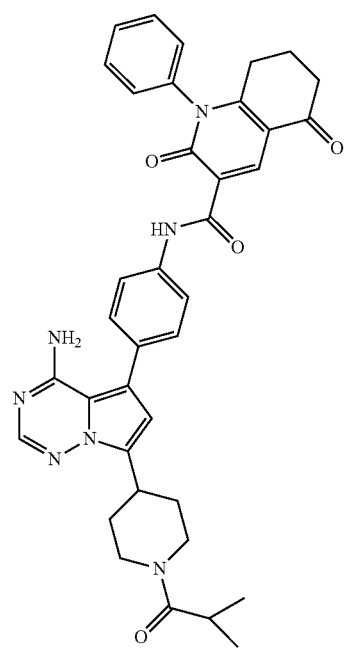 [SMILES: CC(C)C(=O)N1CCC(c2cc(-c3ccc(NC(=O)c4cc5c(n(-c6ccccc6)c4=O)CCCC5=O)cc3)c3c(N)ncnn23)CC1]

This compound was prepared following a synthetic sequence analogous to that for example 57. LCMS calcd for $C_{37}H_{38}N_7O_4$ (M+H)$^+$: m/z=644.3. Found: 644.3. $^1$H NMR (600 MHz, DMSO) δ 11.56 (s, 1H), 8.95 (s, 1H), 7.99 (s, 1H), 7.87-7.77 (m, 2H), 7.69-7.61 (m, 2H), 7.60-7.56 (m, 1H), 7.50-7.39 (m, 4H), 6.66 (s, 1H), 4.54 (d, J=11.9 Hz, 1H), 4.06 (d, J=13.0 Hz, 1H), 3.44-3.36 (m, 1H), 3.25-3.14 (m, 1H), 2.95-2.86 (m, 1H), 2.73-2.65 (m, 1H), 2.57-2.48 (m, 4H), 2.11-1.94 (m, 4H), 1.62 (d, J=8.8 Hz, 1H), 1.50 (d, J=8.9 Hz, 1H), 1.01 (dd, J=9.9, 6.9 Hz, 6H).

Example 75. N-(4-(4-Amino-7-(1-isobutyrylpiperidin-4-yl)pyrrolo[1,2-f][1,2,4]triazin-5-yl)-3-fluorophenyl)-1-isopropyl-2,4-dioxo-3-phenyl-1,2,3,4-tetrahydropyrimidine-5-carboxamide

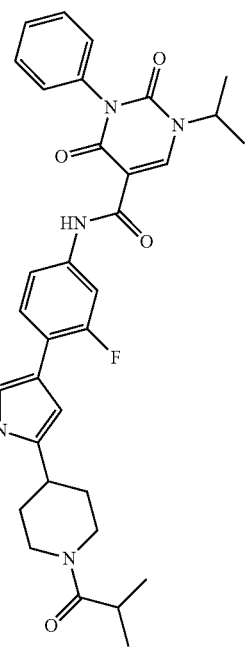

This compound was prepared following a synthetic sequence analogous to that for example 63, using 3-fluoro-4-(4,4,5,5-tetramethyl-1,3,2-dioxaborolan-2-yl)aniline instead of 4-(4,4,5,5-tetramethyl-1,3,2-dioxaborolan-2-yl)aniline. This compound was purified via pH 2 preparative LC/MS (MeCN/water with TFA) to give the product as a white solid (TFA salt). LCMS calcd for $C_{35}H_{38}FN_8O_4$(M+H)$^+$: m/z=653.3. Found: 653.3. $^1$H NMR (400 MHz, DMSO) δ 11.10 (s, 1H), 8.68 (s, 1H), 8.05 (s, 1H), 7.89 (dd, J=12.4, 2.0 Hz, 1H), 7.52 (dd, J=8.1, 6.6 Hz, 2H), 7.49-7.43 (m, 2H), 7.41-7.32 (m, 3H), 6.68 (s, 1H), 4.82-4.75 (m, 1H), 4.54 (d, J=13.2 Hz, 1H), 4.06 (d, J=13.0 Hz, 1H), 3.45-3.37 (m, 1H), 3.20 (t, J=12.2 Hz, 1H), 2.90 (p, J=6.7 Hz, 1H), 2.72-2.62 (m, 1H), 2.12-1.93 (m, 2H), 1.69-1.47 (m, 2H), 1.43 (d, J=6.8 Hz, 6H), 1.01 (broad s, 6H).

Example 76. N-(4-(4-Amino-7-(1-isobutyrylpiperidin-4-yl)pyrrolo[1,2-f][1,2,4]triazin-5-yl)phenyl)-3-(2,5-difluorophenyl)-1-isopropyl-2,4-dioxo-1,2,3,4-tetrahydropyrimidine-5-carboxamide

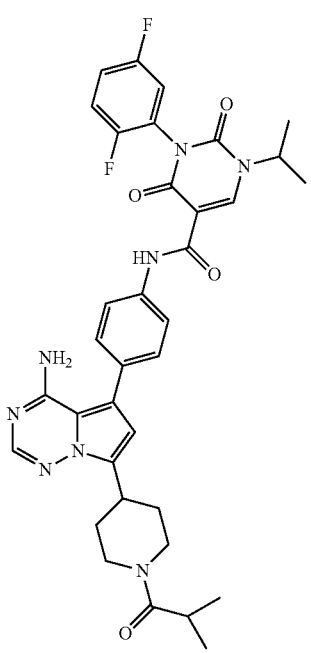 [SMILES: CC(C)C(=O)N1CCC(c2cc(-c3ccc(NC(=O)c4cn(C(C)C)c(=O)n(-c5cc(F)ccc5F)c4=O)cc3)c3c(N)ncnn23)CC1]

This compound was prepared following a synthetic sequence analogous to that for example 63, using 1,4-difluoro-2-isocyanatobenzene instead of isocyanatobenzene. This compound was purified via pH 2 preparative LC/MS (MeCN/water with TFA) to give the product as TFA salt. LCMS calcd for $C_{35}H_{37}F_2N_8O_4(M+H)^+$: m/z=671.3. Found: 671.2. $^1$H NMR (400 MHz, DMSO) δ 10.76 (s, 1H), 8.73 (s, 1H), 8.04 (s, 1H), 7.81 (d, J=8.6 Hz, 2H), 7.59-7.49 (m, 2H), 7.47 (d, J=8.6 Hz, 3H), 6.71 (s, 1H), 4.79 (p, J=6.8 Hz, 1H), 4.55 (d, J=12.1 Hz, 1H), 4.08 (d, J=12.4 Hz, 1H), 3.42 (t, J=11.8 Hz, 1H), 3.26-3.15 (m, 1H), 2.91 (p, J=6.7 Hz, 1H), 2.75-2.64 (m, 1H), 2.11-1.96 (m, 2H), 1.58 (m, J=10.6 Hz, 2H), 1.45 (dd, J=6.7, 3.1 Hz, 6H), 1.03 (d, J=5.5 Hz, 6H).

Example 77. N-(4-(4-Amino-7-(1-isobutyrylpiperidin-4-yl)pyrrolo[1,2-f][1,2,4]triazin-5-yl)-3-methylphenyl)-1-isopropyl-2,4-dioxo-3-phenyl-1,2,3,4-tetrahydropyrimidine-5-carboxamide

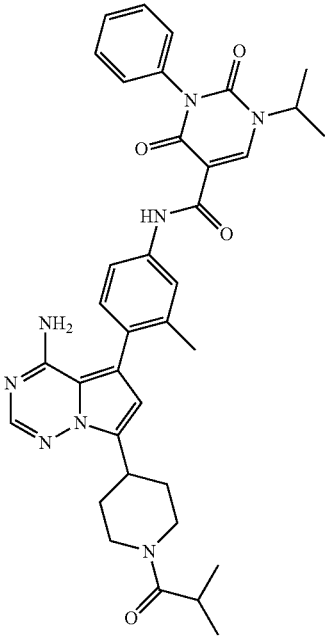 [SMILES: Cc1cc(NC(=O)c2cn(C(C)C)c(=O)n(-c3ccccc3)c2=O)ccc1-c1cc(C2CCN(C(=O)C(C)C)CC2)n2ncnc(N)c12]

This compound was prepared following a synthetic sequence analogous to that for example 63, using 3-methyl-4-(4,4,5,5-tetramethyl-1,3,2-dioxaborolan-2-yl)aniline instead of 4-(4,4,5,5-tetramethyl-1,3,2-dioxaborolan-2-yl)aniline. This compound was purified via pH 2 preparative LC/MS (MeCN/water with TFA) to give the product as a white solid (TFA salt). LCMS calcd for $C_{36}H_{41}N_8O_4$ $(M+H)^+$: m/z=649.3. Found: 649.3.

Example 78. N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-3-yl)-1,2,3,4-tetrahydropyrimidine-5-carboxamide

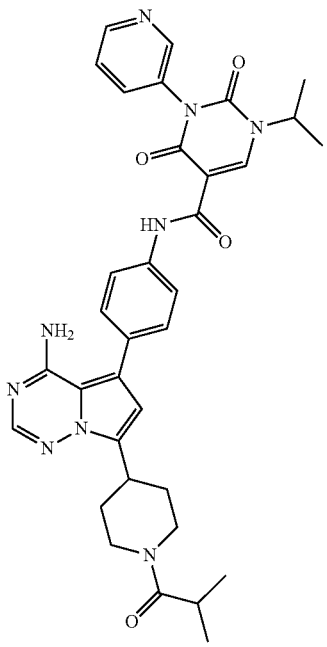 [SMILES: CC(C)C(=O)N1CCC(c2cc(-c3ccc(NC(=O)c4cn(C(C)C)c(=O)n(-c5cccnc5)c4=O)cc3)c3c(N)ncnn23)CC1]

This compound was prepared following a synthetic sequence analogous to that for example 63, using 3-isocyanatopyridine instead of isocyanatobenzene. This compound was purified via pH 2 preparative LC/MS (MeCN/water with TFA) to give the product as a white solid (TFA salt). LCMS calcd for $C_{34}H_{38}N_9O_4$ $(M+H)^+$: m/z=636.3. Found: 636.3. $^1$H NMR (500 MHz, DMSO) δ 10.89 (s, 1H), 8.70 (s, 1H), 8.67 (dd, J=4.8, 1.4 Hz, 1H), 8.60 (d, J=2.2 Hz, 1H), 8.09 (s, 1H), 7.92-7.86 (m, 1H), 7.80 (d, J=8.7 Hz, 2H), 7.61 (dd, J=7.9, 4.6 Hz, 1H), 7.46 (d, J=8.6 Hz, 2H), 6.75 (s, 1H), 4.83-4.76 (m, 1H), 4.54 (d, J=11.9 Hz, 1H), 4.07 (d, J=12.0 Hz, 1H), 3.46-3.36 (m, 1H), 3.20 (t, J=12.6 Hz, 1H), 2.90 (p, J=6.7 Hz, 1H), 2.69 (t, J=11.7 Hz, 1H), 2.10-1.95 (m, 2H), 1.69-1.48 (m, 2H), 1.44 (d, J=6.8 Hz, 6H), 1.01 (t, J=6.8 Hz, 6H).

Example 79. (R)—N-(4-(4-Amino-7-(1-(2-hydroxypropanoyl)piperidin-4-yl)pyrrolo[1,2-f][1,2,4]triazin-5-yl)phenyl)-1-ethyl-3-(4-fluorophenyl)-2,4-dioxo-1,2,3,4-tetrahydropyrimidine-5-carboxamide

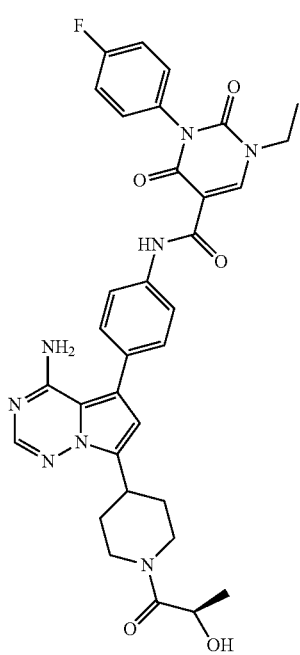 [SMILES: CCn1cc(C(=O)Nc2ccc(-c3cc(C4CCN(C(=O)[C@@H](C)O)CC4)n4ncnc(N)c34)cc2)c(=O)n(-c2ccc(F)cc2)c1=O]

Step 1: N-(4-(4-Amino-7-(piperidin-4-yl)pyrrolo[1,2-f][1,2,4]triazin-5-yl)phenyl)-1-ethyl-3-(4-fluorophenyl)-2,4-dioxo-1,2,3,4-tetrahydropyrimidine-5-carboxamide

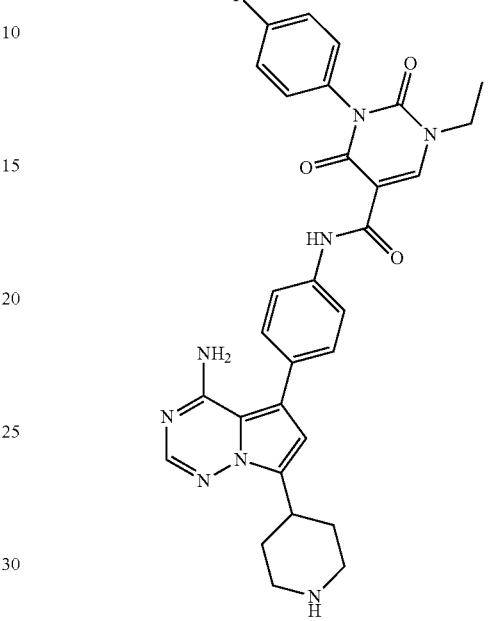

This compound was prepared following a synthetic sequence analogous to that for example 61, from step 1 to step 7, using 1-fluoro-4-isocyanatobenzene instead of isocyanatobenzene, and using ethyl iodide instead of isopropyl iodide. LCMS calcd for $C_{30}H_{30}FN_8O_3$ $(M+H)^+$: m/z=569.2. Found: 569.3.

Step 2: (R)—N-(4-(4-Amino-7-(1-(2-hydroxypropanoyl)piperidin-4-yl)pyrrolo[1,2-f][1,2,4]triazin-5-yl)phenyl)-1-ethyl-3-(4-fluorophenyl)-2,4-dioxo-1,2,3,4-tetrahydropyrimidine-5-carboxamide To a mixture of N-[4-(4-amino-7-piperidin-4-ylpyrrolo[2,1-f][1,2,4]triazin-5-yl)phenyl]-1-ethyl-3-(4-fluorophenyl)-2,4-dioxo-1,2,3,4-tetrahydropyrimidine-5-carboxamide (~2 HCl) (50.0 mg, 0.088 mmol) and (R)-2-hydroxypropanoic acid (16 mg, 0.18 mmol) in DMF (3 mL) was added HATU (70 mg, 0.18 mmol), followed by Et$_3$N (61 pM, 0.44 mmol). The reaction mixture was stirred at rt for 1 h, diluted with MeCN (with 5% water, 0.5% TFA), and purified via pH 2 preparative LC/MS (MeCN/water with TFA) to give the product as a white solid (TFA salt). LCMS calcd for $C_{33}H_{34}FN_8O_5$ $(M+H)^+$: m/z=641.3. Found: 641.3. $^1$H NMR (500 MHz, DMSO) δ 10.95 (s, 1H), 8.85 (s, 1H), 8.05 (s, 1H), 7.78 (d, J=8.6 Hz, 2H), 7.48-7.38 (m, 4H), 7.37-7.30 (m, 2H), 6.69 (d, J=11.8 Hz, 1H), 4.53-4.40 (m, 1H), 4.10 (d, J=11.4 Hz, 1H), 4.01 (q, J=7.1 Hz, 2H), 3.46-3.37 (m, 2H), 3.17 (m, 1H), 2.75 (m, 1H), 2.02 (d, J=10.9 Hz, 2H), 1.50 (m, 2H), 1.29 (t, J=7.1 Hz, 3H), 1.18 (d, J=6.3 Hz, 3H).

Example 80. N-(4-(4-Amino-7-(1-(cyclopropanecarbonyl)piperidin-4-yl)pyrrolo[1,2-f][1,2,4]triazin-5-yl)phenyl)-1-(2-hydroxypropyl)-2,4-dioxo-3-phenyl-1,2,3,4-tetrahydropyrimidine-5-carboxamide

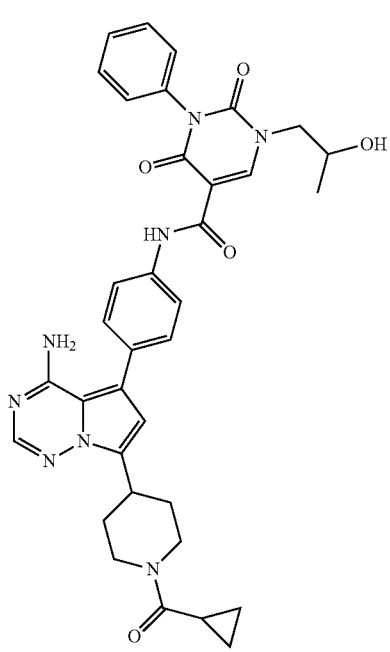 [SMILES: CC(O)Cn1cc(C(=O)Nc2ccc(-c3cc(C4CCN(C(=O)C5CC5)CC4)n4ncnc(N)c34)cc2)c(=O)n(-c2ccccc2)c1=O]

Step 1: Ethyl 1-(2-(tert-butyldimethylsilyloxy)propyl)-2,4-dioxo-3-phenyl-1,2,3,4-tetrahydropyrimidine-5-carboxylate

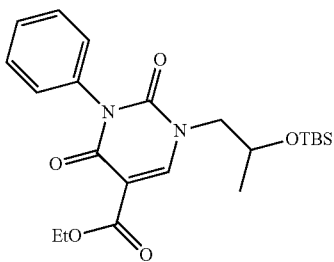 [SMILES: CCOC(=O)c1cn(CC(C)O[Si](C)(C)C(C)(C)C)c(=O)n(-c2ccccc2)c1=O]

A mixture of ethyl 2,4-dioxo-3-phenyl-1,2,3,4-tetrahydropyrimidine-5-carboxylate (150 mg, 0.58 mmol) (from example 61, step 2), ((1-bromopropan-2-yl)oxy)(tert-butyl)dimethylsilane (292 mg, 1.15 mmol), and CsCO$_3$ (563 mg, 1.73 mmol) in DMF (5 mL) was stirred at 100° C. for 5 h. The reaction mixture was then cooled to rt, diluted with EtOAc, washed with water, brine, dried over Na$_2$SO$_4$, and concentrated to afford the crude product, which was used directly in the next step. LCMS calcd for $C_{22}H_{33}N_2O_5Si$ (M+H)$^+$: m/z=433.2. Found: 433.2.

Step 2: 1-(2-Hydroxypropyl)-2,4-dioxo-3-phenyl-1,2,3,4-tetrahydropyrimidine-5-carboxylic Acid

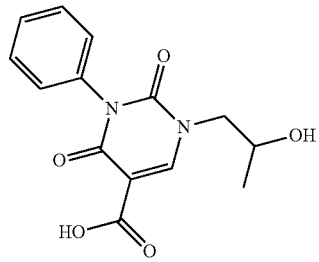 [SMILES: CC(O)Cn1cc(C(=O)O)c(=O)n(-c2ccccc2)c1=O]

A mixture of ethyl 1-(2-((tert-butyldimethylsilyl)oxy)propyl)-2,4-dioxo-3-phenyl-1,2,3,4-tetrahydropyrimidine-5-carboxylate (249 mg, 0.58 mmol) in 4 M HCl in 1,4-dioxane (1.44 mL, 5.76 mmol) and water (0.50 mL) was stirred at 70° C. for 3 h, cooled to rt, and concentrated. The resulting material was then purified via pH 2 preparative LC/MS (MeCN/water with TFA) to afford the product as a yellow oil, which was used directly in the next step. LCMS calcd for $C_{14}H_{15}N_2O_5$ (M+H)$^+$: m/z=291.1. Found: 291.0.

Step 3: N-(4-(4-Amino-7-(piperidin-4-yl)pyrrolo[1,2-f][1,2,4]triazin-5-yl)phenyl)-1-(2-hydroxypropyl)-2,4-dioxo-3-phenyl-1,2,3,4-tetrahydropyrimidine-5-carboxamide

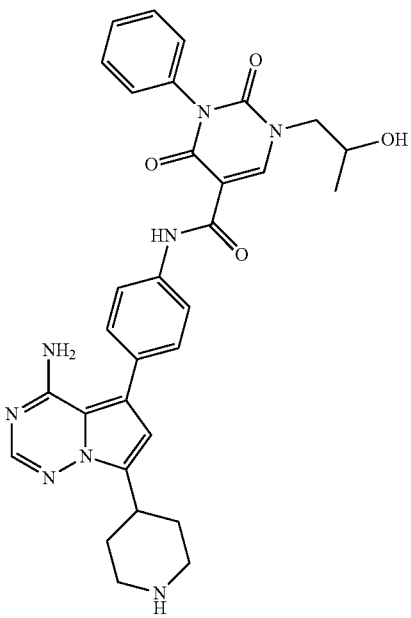 [SMILES: CC(O)Cn1cc(C(=O)Nc2ccc(-c3cc(C4CCNCC4)n4ncnc(N)c34)cc2)c(=O)n(-c2ccccc2)c1=O]

This compound (~2 HCl salt) was prepared following a synthetic sequence analogous to that for example 61 from step 5 to step 7, using 1-(2-hydroxypropyl)-2,4-dioxo-3-phenyl-1,2,3,4-tetrahydropyrimidine-5-carboxylic acid instead of 1-isopropyl-2,4-dioxo-3-phenyl-1,2,3,4-tetrahydropyrimidine-5-carboxylic acid. LCMS calcd for $C_{31}H_{33}N_8O_4$ (M+H)$^+$: m/z=581.3. Found: 581.3.

Step 4: N-(4-(4-Amino-7-(1-(cyclopropanecarbonyl) piperidin-4-yl)pyrrolo[1,2-f][1,2,4]triazin-5-yl)phenyl)-1-(2-hydroxypropyl)-2,4-dioxo-3-phenyl-1,2,3,4-tetrahydropyrimidine-5-carboxamide To a mixture of N-(4-(4-amino-7-(piperidin-4-yl)pyrrolo[2,1-f][1,2,4]triazin-5-yl)phenyl)-1-(2-hydroxypropyl)-2,4-dioxo-3-phenyl-1,2,3,4-tetrahydropyrimidine-5-carboxamide (~2 HCl salt) (25 mg, 0.038 mmol), cyclopropanecarboxylic acid (3.4 µl, 0.042 mmol), and HATU (29 mg, 0.077 mmol) in DMF (1.0 mL) at rt was added Et$_3$N (0.027 mL, 0.191 mmol). The reaction mixture was stirred at rt for 2 h, and the resulting mixture was directly purified via pH 2 preparative LC/MS (MeCN/water with TFA) to give the product as a white solid (a pair of enantiomers) (TFA salt). LCMS calcd for $C_{35}H_{37}N_8O_5$ (M+H)$^+$: m/z=649.3. Found: 649.3.

Example 81. N-(4-(4-Amino-7-(1-(2-(dimethylamino)-2-oxoethyl)piperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide

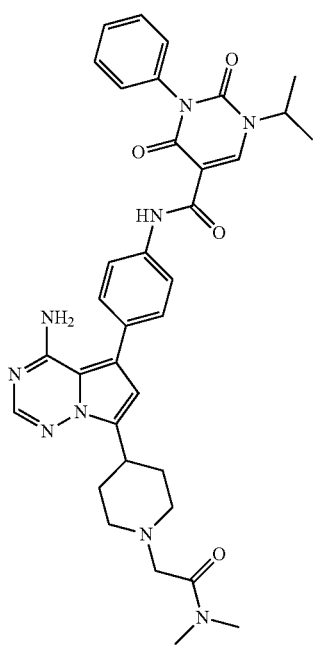 [SMILES: CC(C)n1cc(C(=O)Nc2ccc(-c3cc(C4CCN(CC(=O)N(C)C)CC4)n4ncnc(N)c34)cc2)c(=O)n(-c2ccccc2)c1=O]

A mixture of N-(4-(4-amino-7-(piperidin-4-yl)pyrrolo[2,1-f][1,2,4]triazin-5-yl)phenyl)-1-isopropyl-2,4-dioxo-3-phenyl-1,2,3,4-tetrahydropyrimidine-5-carboxamide (~2 HCl salt) (from example 61, step 7) (180 mg, 0.28 mmol), 2-bromo-N,N-dimethylacetamide (94 mg, 0.57 mmol), and Et$_3$N (0.197 ml, 1.41 mmol) in DMF (2.5 ml) was stirred at rt for 3 h. The reaction mixture was diluted with MeOH, and directly purified via pH 2 preparative LC/MS (MeCN/water with TFA) to give the product as a white solid (TFA salt). LCMS calcd for $C_{35}H_{40}N_9O_4$ (M+H)$^+$: m/z=650.3. Found: 650.3. $^1$H NMR (600 MHz, DMSO) δ 11.00 (s, 1H), 8.67 (s, 1H), 8.03 (s, 1H), 7.80 (d, J=8.5 Hz, 2H), 7.53 (t, J=7.6 Hz, 2H), 7.49-7.39 (m, 3H), 7.37 (d, J=7.3 Hz, 2H), 6.66 (s, 1H), 4.82-4.72 (m, 1H), 4.28 (s, 2H), 3.60 (d, J=11.6 Hz, 2H), 3.47-3.34 (m, 1H), 3.26-3.12 (m, 2H), 2.96 (s, 3H), 2.92 (s, 3H), 2.31-2.22 (m, 2H), 2.12-2.01 (m, 2H), 1.43 (d, J=6.8 Hz, 6H).

Example 82. N-(4-(4-Amino-7-(1-(1-methyl-2-oxopyrrolidin-3-yl)piperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide

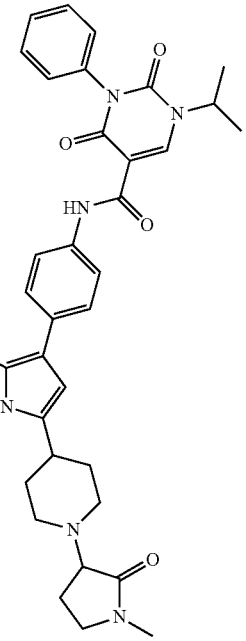

This compound was prepared following a synthetic sequence analogous to that for example 81, using 3-bromo-1-methylpyrrolidin-2-one instead of 2-bromo-N,N-dimethylacetamide, and the reaction mixture was heated at 75° C. for 1 h instead of being stirred at rt for 3 h. This compound was purified via pH 2 preparative LC/MS (MeCN/water with TFA) to give the product as a white solid (a pair of enantiomers) (TFA salt). LCMS calcd for $C_{36}H_{40}N_9O_4$ (M+H)$^+$: m/z=662.3. Found: 662.3.

Example 83. N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide

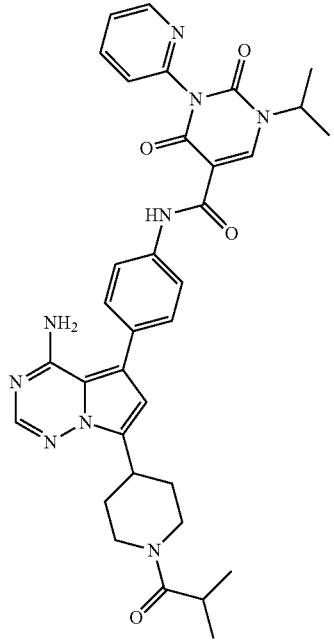 [SMILES: CC(C)C(=O)N1CCC(c2cc(-c3ccc(NC(=O)c4cn(C(C)C)c(=O)n(-c5ccccn5)c4=O)cc3)c3c(N)ncnn23)CC1]

Step 1: 1-(4-(4-Amino-5-bromopyrrolo[1,2-f][1,2,4]triazin-7-yl)piperidin-1-yl)-2-methylpropan-1-one

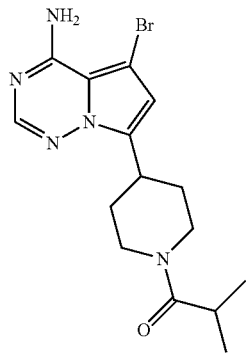 [SMILES: CC(C)C(=O)N1CCC(c2cc(Br)c3c(N)ncnn23)CC1]

To a mixture of 5-bromo-7-(piperidin-4-yl)pyrrolo[2,1-f][1,2,4]triazin-4-amine (~2 HCl) (939 mg, 2.54 mmol) (from example 32, step 4) in $CH_2Cl_2$ (25 ml) at rt was added $Et_3N$ (1.77 ml, 12.7 mmol). The reaction mixture was stirred at rt for 1 h, and added isobutyryl chloride (0.29 ml, 2.80 mmol). The reaction mixture was then stirred at rt for 30 min, concentrated, and the resulting material was purified via column chromatography (0% to 10% MeOH in $CH_2Cl_2$) to give the product as a yellow solid (602 mg, 65%). LCMS calcd for $C_{15}H_{21}BrN_5O$ (M+H)+: m/z=366.1. Found: 366.1.

Step 2: 1-(4-(4-Amino-5-(4-aminophenyl)pyrrolo[1,2-f][1,2,4]triazin-7-yl)piperidin-1-yl)-2-methylpropan-1-one

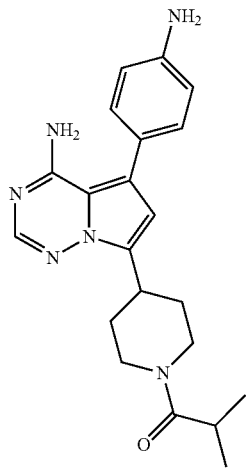 [SMILES: CC(C)C(=O)N1CCC(c2cc(-c3ccc(N)cc3)c3c(N)ncnn23)CC1]

A mixture of 1-(4-(4-amino-5-bromopyrrolo[2,1-f][1,2,4]triazin-7-yl)piperidin-1-yl)-2-methylpropan-1-one (400 mg, 1.09 mmol), 4-(4,4,5,5-tetramethyl-1,3,2-dioxaborolan-2-yl)aniline (251 mg, 1.15 mmol), XPhos Pd G2 (86 mg, 0.11 mmol), and $Na_2CO_3$ (232 mg, 2.18 mmol) in 1,4-dioxane (7.5 ml)/water (1.5 ml) was first purged with $N_2$, and stirred at 85° C. for 3 h. The reaction mixture was then cooled to rt, filtered through a pad of Celite (washed with EtOAc), concentrated, and purified via column chromatography (0% to 10% MeOH in $CH_2Cl_2$) to give the product as a yellow solid (398 mg, 96%). LCMS calcd for $C_{21}H_{27}N_6O$ (M+H)+: m/z=379.2. Found: 379.2.

Step 3: Diethyl 2-((3-pyridin-2-ylureido)methylene)malonate

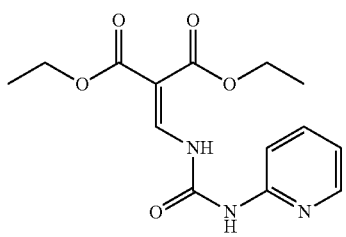 [SMILES: CCOC(=O)C(=CNC(=O)Nc1ccccn1)C(=O)OCC]

To a mixture of diethyl 2-(aminomethylene)malonate (3.0 g, 16.0 mmol) and 2-isocyanatopyridine (2.02 g, 16.8 mmol) in 1,2-dichloroethane (9.0 mL) at rt was added N,N-diisopropylethylamine (3.6 mL, 20.8 mmol). The reaction mixture was then stirred at 70° C. overnight, cooled to rt, and directly purified via column chromatography (0% to 15% MeOH in $CH_2Cl_2$) to give the product (3.18 g, 65%). LCMS calcd for $C_{14}H_{18}N_3O_5$ (M+H)+: m/z=308.1. Found: 308.1.

Step 4: 1-Isopropyl-2,4-dioxo-3-(pyridin-2-yl)-1,2,3,4-tetrahydropyrimidine-5-carboxylic Acid

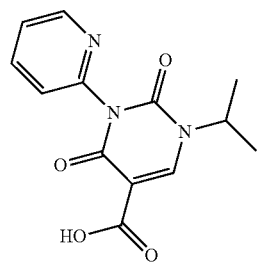 [SMILES: CC(C)n1cc(C(=O)O)c(=O)n(-c2ccccn2)c1=O]

A mixture of diethyl 2-((3-(pyridin-2-yl)ureido)methylene)malonate (3.18 g, 10.4 mmol) and 2.5 M NaOEt in EtOH (6.2 mL, 15.5 mmol) in EtOH (25 mL) was stirred at rt for 3 h. The resulting mixture was diluted with EtOAc, and washed/acidified with 1 N citric acid solution (30 mL). The organic layer was separated, and the aqueous layer was further extracted with 3:1 $CHCl_3$/isopropyl alcohol (30 mL×3). The combined organic layers were dried over $Na_2SO_4$, and concentrated to provide the crude product, ethyl 2,4-dioxo-3-(pyridin-2-yl)-1,2,3,4-tetrahydropyrimidine-5-carboxylate, which was used directly in the next step. LCMS calcd for $C_{12}H_{12}N_3O_4$ (M+H)+: m/z=262.1. Found: 262.2.

A mixture of crude ethyl 2,4-dioxo-3-(pyridin-2-yl)-1,2,3,4-tetrahydropyrimidine-5-carboxylate from previous step, 2-iodopropane (2.06 mL, 20.7 mmol), and $Cs_2CO_3$ (10.1 g, 31.0 mmol) in DMF (35 mL) was stirred at 70° C. for 3 h. The reaction mixture was then cooled to rt, diluted with 3:1 $CHCl_3$/isopropyl alcohol (75 mL), washed with water, brine, dried over $Na_2SO_4$, and concentrated to afford the crude product, ethyl 1-isopropyl-2,4-dioxo-3-(pyridin-2-yl)-1,2,3,4-tetrahydropyrimidine-5-carboxylate, which was used directly in the next step. LCMS calcd for $C_{15}H_{18}N_3O_4$(M+H)+: m/z=304.1. Found: 304.1.

A mixture of crude ethyl 1-isopropyl-2,4-dioxo-3-(pyridin-2-yl)-1,2,3,4-tetrahydropyrimidine-5-carboxylate from previous step in 4 M HCl in 1,4-dioxane (20 mL, 82 mmol)

and water (5.0 mL) was stirred at 80° C. for 5 h, cooled to rt, and concentrated. The resulting material was then purified via column chromatography (0% to 15% MeOH in $CH_2Cl_2$) to give the product as a slightly yellow solid (1.50 g, 47% three steps). LCMS calcd for $C_{13}H_{14}N_3O_4$ $(M+H)^+$: m/z=276.1. Found: 276.1.

Step 5: N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide To a mixture of 1-isopropyl-2,4-dioxo-3-(pyridin-2-yl)-1,2,3,4-tetrahydropyrimidine-5-carboxylic acid (85 mg, 0.31 mmol), 1-(4-(4-amino-5-(4-aminophenyl)pyrrolo[2,1-f][1,2,4]triazin-7-yl)piperidin-1-yl)-2-methylpropan-1-one (129 mg, 0.34 mmol), and HATU (141 mg, 0.37 mmol) in DMF (3.5 mL) at rt was added $Et_3N$ (0.13 mL, 0.93 mmol). The reaction mixture was stirred at rt for 1 h, diluted with $CH_2Cl_2$, and washed with water. The organic layer was separated, dried over $Na_2SO_4$, concentrated, and purified via column chromatography (0% to 10% MeOH in $CH_2Cl_2$) to give the product, which was further purified via pH 2 preparative LC/MS (MeCN/water with TFA) to give the product as a white solid (TFA salt). LCMS calcd for $C_{34}H_{38}N_9O_4$ $(M+H)^+$: m/z=636.3. Found: 636.3. $^1$H NMR (600 MHz, DMSO) δ 10.86 (s, 1H), 8.71 (s, 1H), 8.63 (ddd, J=4.8, 1.8, 0.9 Hz, 1H), 8.10 (s, 1H), 8.06 (td, J=7.7, 1.9 Hz, 1H), 7.80 (d, J=8.7 Hz, 2H), 7.61-7.53 (m, 2H), 7.46 (d, J=8.6 Hz, 2H), 6.76 (s, 1H), 4.77 (p, J=6.8 Hz, 1H), 4.54 (d, J=12.2 Hz, 1H), 4.07 (d, J=13.0 Hz, 1H), 3.41 (tt, J=11.8, 3.5 Hz, 1H), 3.20 (t, J=12.4 Hz, 1H), 2.90 (p, J=6.7 Hz, 1H), 2.69 (t, J=12.1 Hz, 1H), 2.02 (dd, J=30.5, 12.4 Hz, 2H), 1.70-1.48 (m, 2H), 1.44 (d, J=6.8 Hz, 6H), 1.08-0.93 (m, 6H).

Example 84. N-(4-(4-Amino-7-(1,3,5-trimethyl-1H-pyrazol-4-yl)pyrrolo[1,2-f][1,2,4]triazin-5-yl)phenyl)-3-(3-fluorophenyl)-1-isopropyl-2,4-dioxo-1,2,3,4-tetrahydropyrimidine-5-carboxamide

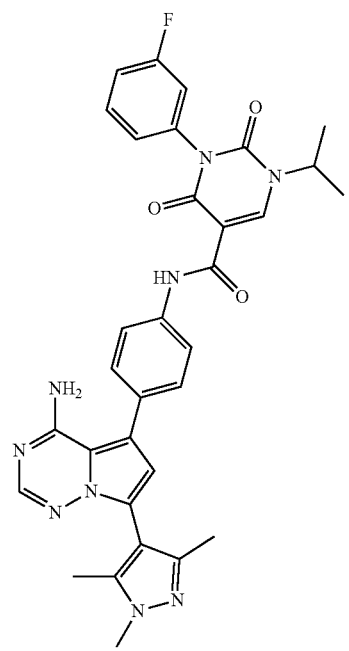 [SMILES: Cc1nn(C)c(C)c1-c1cc(-c2ccc(NC(=O)c3cn(C(C)C)c(=O)n(-c4cccc(F)c4)c3=O)cc2)c2c(N)ncnn12]

Step 1: 7-(3,5-Dimethyl-1H-pyrazol-4-yl)pyrrolo[1,2-f][1,2,4]triazin-4-amine

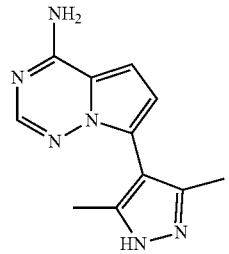 [SMILES: Cc1n[nH]c(C)c1-c1ccc2c(N)ncnn12]

A mixture of 7-bromopyrrolo[2,1-f][1,2,4]triazin-4-amine (0.32 g, 1.50 mmol), 3,5-dimethyl-4-(4,4,5,5-tetramethyl-1,3,2-dioxaborolan-2-yl)-1H-pyrazole (0.425 g, 1.80 mmol), $Na_2CO_3$ (0.318 g, 3.0 mmol), and XPhos Pd G2 (0.118 g, 0.150 mmol) in 1,4-dioxane (6.0 ml)/water (1.0 ml) was vacuumed and refilled with $N_2$ twice and the reaction was stirred at 95° C. overnight. The reaction mixture was then cooled to rt, diluted with EtOAc, washed with water, brine, dried over $Na_2SO_4$, concentrated, and purified via column chromatography (0% to 10% MeOH in $CH_2Cl_2$) to give the crude product as a yellow solid. LCMS calcd for $C_{11}H_{13}N_6(M+H)^+$: m/z=229.1. Found: 229.1.

Step 2: 5-Bromo-7-(3,5-dimethyl-1H-pyrazol-4-yl)pyrrolo[1,2-f][1,2,4]triazin-4-amine

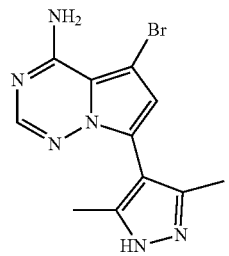 [SMILES: Cc1n[nH]c(C)c1-c1cc(Br)c2c(N)ncnn12]

NBS (0.18 g, 1.0 mmol) was added to a solution of 7-(3,5-dimethyl-1H-pyrazol-4-yl)pyrrolo[2,1-f][1,2,4]triazin-4-amine (0.23 g, 1.0 mmol) in DMSO (1.0 ml)/MeCN (1.0 ml)/water (20 μL) at 0° C. and the mixture was warmed to rt and stirred for 1 h. Water was added to the reaction mixture and the resulting solid was collected by filtration, washed with water, and dried to provide the product. LCMS calcd for $C_{11}H_{12}BrN_6$ $(M+H)^+$: m/z=307.0. Found: 307.0.

Step 3: N-(4-(4-Amino-7-(3,5-dimethyl-1H-pyrazol-4-yl)pyrrolo[1,2-f][1,2,4]triazin-5-yl)phenyl)-3-(3-fluorophenyl)-1-isopropyl-2,4-dioxo-1,2,3,4-tetrahydropyrimidine-5-carboxamide

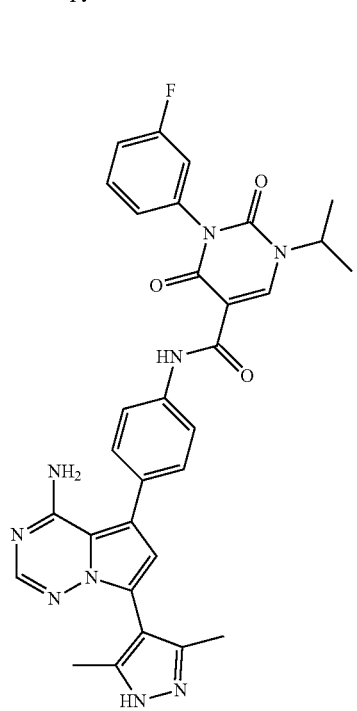

A mixture of 5-bromo-7-(3,5-dimethyl-1H-pyrazol-4-yl)pyrrolo[2,1-f][1,2,4]triazin-4-amine (0.123 g, 0.40 mmol), 3-(3-fluorophenyl)-1-isopropyl-2,4-dioxo-N-(4-(4,4,5,5-tetramethyl-1,3,2-dioxaborolan-2-yl)phenyl)-1,2,3,4-tetrahydropyrimidine-5-carboxamide (0.217 g, 0.440 mmol) (prepared following a synthetic sequence analogous to that for example 61, from step 1 to step 5, using 1-fluoro-3-isocyanatobenzene instead of isocyanatobenzene), $Na_2CO_3$ (0.085 g, 0.80 mmol) and XPhos Pd G2 (0.031 g, 0.040 mmol) in 1,4-dioxane (2.0 ml)/water (0.4 ml) was vacuumed and refilled with $N_2$ twice and the reaction mixture was stirred at 75° C. overnight. The resulting mixture was cooled to rt, diluted with MeCN (with 5% water, 0.5% TFA), filtered, and purified via pH 2 preparative LC/MS (MeCN/water with TFA) to give the product as a white solid (TFA salt). LCMS calcd for $C_{31}H_{29}FN_9O_3(M+H)^+$: m/z=594.2. Found: 594.2.

Step 4: N-(4-(4-Amino-7-(1,3,5-trimethyl-1H-pyrazol-4-yl)pyrrolo[1,2-f][1,2,4]triazin-5-yl)phenyl)-3-(3-fluorophenyl)-1-isopropyl-2,4-dioxo-1,2,3,4-tetrahydropyrimidine-5-carboxamide Methyl iodide (3.2 µl, 0.051 mmol) was added to a mixture of N-(4-(4-amino-7-(3,5-dimethyl-1H-pyrazol-4-yl)pyrrolo[2,1-f][1,2,4]triazin-5-yl)phenyl)-1-isopropyl-2,4-dioxo-1,2,3,4-tetrahydropyrimidine-5-carboxamide (30.0 mg, 0.051 mmol) and $Cs_2CO_3$ (32.9 mg, 0.10 mmol) in DMF (1.0 ml) at rt and the reaction mixture was stirred at rt for 1 h. The reaction mixture was then diluted with MeCN (with 5% water, 0.5% TFA), filtered, and purified via pH 2 preparative LC/MS (MeCN/water with TFA) to give the product as a white solid (TFA salt). LCMS calcd for $C_{32}H_{31}FN_9O_3(M+H)^+$: m/z=608.3. Found: 608.3.

Example 85. N-(4-(4-amino-7-(6-(dimethylcarbamoyl)-4-methylpyridin-3-yl)pyrrolo[1,2-f][1,2,4]triazin-5-yl)phenyl)-1-isopropyl-2,4-dioxo-3-phenyl-1,2,3,4-tetrahydropyrimidine-5-carboxamide

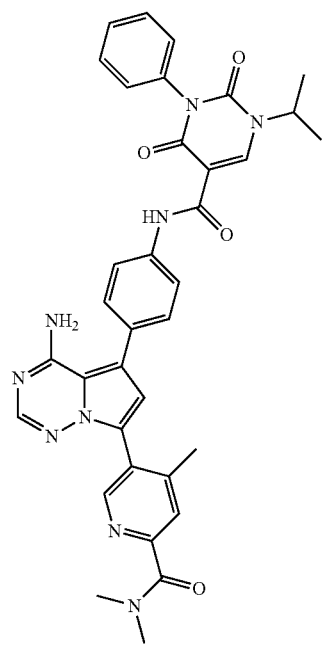 [SMILES: Cc1cc(C(=O)N(C)C)ncc1-c1cc(-c2ccc(NC(=O)c3cn(C(C)C)c(=O)n(-c4ccccc4)c3=O)cc2)c2c(N)ncnn12]

Step 1: 5-(4-Amino-5-bromopyrrolo[1,2-f][1,2,4]triazin-7-yl)-N,N,4-trimethylpicolinamide

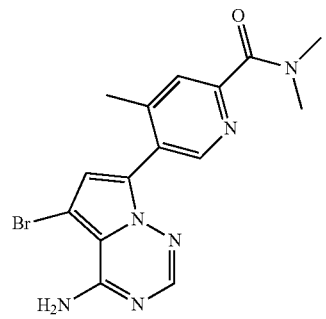 [SMILES: Cc1cc(C(=O)N(C)C)ncc1-c1cc(Br)c2c(N)ncnn12]

This compound was prepared following a synthetic sequence analogous to that for example 84, from step 1 to step 2, using N,N,4-trimethyl-5-(4,4,5,5-tetramethyl-1,3,2-dioxaborolan-2-yl)picolinamide instead of 3,5-dimethyl-4-(4,4,5,5-tetramethyl-1,3,2-dioxaborolan-2-yl)-1H-pyrazole. LCMS calcd for $C_{15}H_{16}BrN_6O$ $(M+H)^+$: m/z=375.1. Found: 375.0.

Step 2: N-(4-(4-Amino-7-(6-(dimethylcarbamoyl)-4-methylpyridin-3-yl)pyrrolo[1,2-f][1,2,4]triazin-5-yl)phenyl)-1-isopropyl-2,4-dioxo-3-phenyl-1,2,3,4-tetrahydropyrimidine-5-carboxamide A mixture of 1-isopropyl-2,4-dioxo-3-phenyl-N-(4-(4,4,5,5-tetramethyl-1,3,2-dioxaborolan-2-yl)phenyl)-1,2,3,4- tetrahydropyrimidine-5-carboxamide (30 mg, 0.063 mmol) (from example 61, step 5), 5-(4-amino-5-bromopyrrolo[2,1-f][1,2,4]triazin-7-yl)-N,N,4-trimethylpicolinamide (26 mg, 0.069 mmol), dicyclohexyl(2',4',6'-triisopropylbiphenyl-2-yl)phosphine-(2'-aminobiphenyl-2-yl)(chloro)palladium (1:1) (XPhos Pd G2) (5.0 mg, 6.3 µmol), and Na$_2$CO$_3$ (13.4 mg, 0.13 mmol) in 1,4-dioxane (1.5 mL)/water (0.3 mL) was purged with N$_2$, and stirred at 70° C. for 2 h. The reaction mixture was cooled to rt, diluted with MeOH, filtered, and purified via pH 2 preparative LC/MS (MeCN/water with TFA) to give the product as a white solid (TFA salt). LCMS calcd for C$_{35}$H$_{34}$N$_9$O$_4$ (M+H)$^+$: m/z=644.3. Found: 644.3.

Example 86. 4-Amino-5-(4-(3-(3-fluorophenyl)-1-isopropyl-2,4-dioxo-1,2,3,4-tetrahydropyrimidine-5-carboxamido)phenyl)-N,N-dimethylpyrrolo[2,1-f][1,2,4]triazine-7-carboxamide

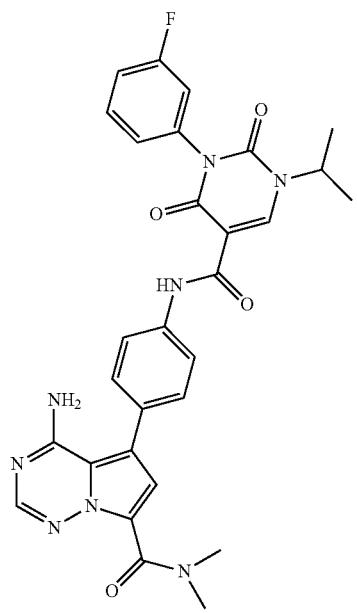 [SMILES: CC(C)n1cc(C(=O)Nc2ccc(-c3cc(C(=O)N(C)C)n4ncnc(N)c34)cc2)c(=O)n(-c2cccc(F)c2)c1=O]

Step 1: 4-Aminopyrrolo[1,2-f][1,2,4]triazine-7-carbonitrile

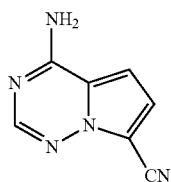 [SMILES: N#Cc1ccc2c(N)ncnn12]

N,N,N',N'-Tetramethylethylenediamine (40 µL, 0.3 mmol), ZnCN (118 mg, 1.0 mmol), Tris(dibenzylideneacetone)dipalladium(0) (37 mg, 0.04 mmol) and (9,9-dimethyl-9H-xanthene-4,5-diyl)bis(diphenylphosphine) (46 mg, 0.080 mmol) was added successively to a solution of 7-bromopyrrolo[2,1-f][1,2,4]triazin-4-amine (210 mg, 1.0 mmol) in DMF (2.0 mL) in a microwave vial. The vial was sealed, degassed three times, and stirred at 160° C. under microwave conditions for 8 min. The reaction mixture was cooled to rt, filtered (washed with CH$_2$Cl$_2$), and concentrated. The resulting material was washed with MeCN, and dried to provide the crude product, which was used directly in the next step. LCMS calcd for C$_7$H$_6$N$_5$ (M+H)$^+$: m/z=160.1. Found: 160.0.

Step 2: 4-Amino-5-bromopyrrolo[1,2-f][1,2,4]triazine-7-carbonitrile

NBS (0.117 g, 0.66 mmol) was added to a solution of 4-aminopyrrolo[2,1-f][1,2,4]triazine-7-carbonitrile (0.10 g, 0.63 mmol) in DMSO (1.0 mL)/MeCN (0.6 mL)/water (0.08 mL) at 0° C. and the reaction mixture was stirred at this temperature for 2 h. Water was added and the resulting solid was collected by filtration, washed with water, and dried to provide the product. LCMS calcd for C$_7$H$_8$BrN$_5$ (M+H)$^+$: m/z=238.0. Found: 238.0.

Step 3: 4-Amino-5-bromopyrrolo[1,2-f][1,2,4]triazine-7-carboxylic Acid

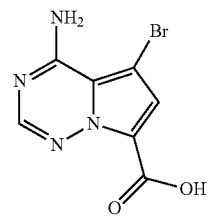 [SMILES: Nc1ncnn2c(C(=O)O)cc(Br)c12]

12 M HCl in water (0.4 mL) was added to a mixture of 4-amino-5-bromopyrrolo[2,1-f][1,2,4]triazine-7-carbonitrile (50 mg, 0.2 mmol) in 1,4-dioxane (0.4 mL). The reaction was stirred at 95° C. for 4 h, cooled to rt, and concentrated to give the crude product, which was used directly in the next step. LCMS calcd for C$_7$H$_6$BrN$_4$O$_2$(M+H)$^+$: m/z=257.0. Found: 257.0.

Step 4: 4-Amino-5-bromo-N,N-dimethylpyrrolo[1,2-f][1,2,4]triazine-7-carboxamide

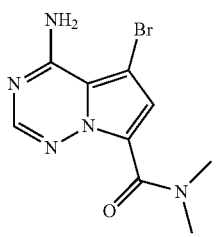 [SMILES: CN(C)C(=O)c1cc(Br)c2c(N)ncnn12]

2 M Dimethylamine in THF (0.38 mL, 0.75 mmol) was added to a mixture of 4-amino-5-bromopyrrolo[2,1-f][1,2, 4]triazine-7-carboxylic acid (25 mg, 0.097 mmol) and BOP (60 mg, 0.14 mmol) in DMF (1.0 mL), followed by Et₃N (50 µL, 0.36 mmol). The reaction mixture was stirred at rt for 3 h, diluted with EtOAc, washed with saturated NaHCO₃ solution, water, brine, dried over Na₂SO₄, and concentrated to give the product, which was used directly in the next step. LCMS calcd for $C_9H_{11}BrN_5O$ (M+H)⁺: m/z=284.0. Found: 284.0.

Step 5: 4-Amino-5-(4-(3-(3-fluorophenyl)-1-isopropyl-2,4-dioxo-1,2,3,4-tetrahydropyrimidine-5-carboxamido)phenyl)-N,N-dimethylpyrrolo[2,1-f][1,2,4]triazine-7-carboxamide A mixture of 3-(3-fluorophenyl)-1-isopropyl-2,4-dioxo-N-[4-(4,4,5,5-tetramethyl-1,3,2-dioxaborolan-2-yl)phenyl]-1,2,3,4-tetrahydropyrimidine-5-carboxamide (0.020 g, 0.040 mmol) (prepared following a synthetic sequence analogous to that for example 61, from step 1 to step 5, using 1-fluoro-3-isocyanatobenzene instead of isocyanatobenzene), 4-amino-5-bromo-N,N-dimethylpyrrolo[2,1-f][1,2,4]triazine-7-carboxamide (0.016 g, 0.057 mmol), Na₂CO₃ (9.0 mg, 0.085 mmol) and XPhos Pd G2 (3.3 mg, 0.0042 mmol) in 1,4-dioxane (1.0 mL)/water (0.1 mL) was vacuumed and refilled with N₂ and stirred at 75° C. for 5 h. The resulting mixture was then cooled to rt, diluted with MeCN (with 5% water, 0.5% TFA), filtered, and purified via pH 2 preparative LC/MS (MeCN/water with TFA) to give the product as a white solid (TFA salt). LCMS calcd for $C_{29}H_{28}FN_8O_4$ (M+H)⁺: m/z=571.2. Found: 571.1.

Example 87. N-(4-(4-Amino-7-(1-isobutyrylpiperidin-4-yl)pyrrolo[2,1-f][1,2,4]triazin-5-yl)phenyl)-1-isopropyl-3-(1-methyl-1H-pyrazol-4-yl)-2,4-dioxo-1,2,3,4-tetrahydropyrimidine-5-carboxamide

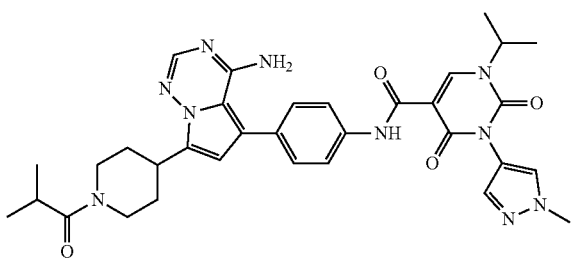

Step 1. Diethyl 2-((3-(1-methyl-1H-pyrazol-4-yl)ureido)methylene)malonate

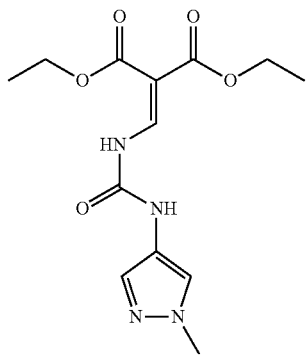 [SMILES: CCOC(=O)C(=CNC(=O)Nc1cnn(C)c1)C(=O)OCC]

A mixture of 1-methyl-1H-pyrazol-4-amine (0.097 g, 1.0 mmol) and 1,1'-carbonyldiimidazole (0.178 g, 1.100 mmol) in DMSO (1 mL) was stirred at rt for 1 h, then diethyl 2-(aminomethylene)malonate (0.187 g, 1.00 mmol) was added to the solution. The reaction mixture was stirred at 80° C. overnight, cooled to rt, and directly purified via column chromatography (0% to 100% EtOAc in hexanes) to afford the product (0.204 g, 66%). LCMS calcd for $C_{13}H_{19}N_4O_5$ (M+H)⁺: m/z=311.1. Found: 311.2.

Step 2. Ethyl 3-(1-methyl-1H-pyrazol-4-yl)-2,4-dioxo-1,2,3,4-tetrahydropyrimidine-5-carboxylate

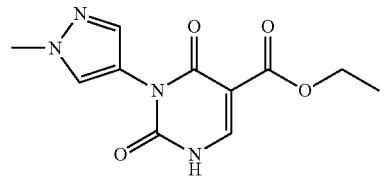 [SMILES: CCOC(=O)c1c[nH]c(=O)n(-c2cnn(C)c2)c1=O]

A mixture of 2.5 M NaOEt in EtOH (0.39 mL, 0.99 mmol) and diethyl 2-((3-(1-methyl-1H-pyrazol-4-yl)ureido)methylene)malonate (0.204 g, 0.66 mmol) in EtOH (2 mL) was stirred at rt for 3 h. The resulting mixture was diluted with CH₂Cl₂, and acidified with 1 N HCl to pH ~7. The organic layer was separated, and the aqueous layer was further extracted with 10% MeOH in CH₂Cl₂. The combined organic layers were dried over Na₂SO₄, and concentrated to provide the crude product (0.172 g, 99%), which was used directly in the next step. LCMS calcd for $C_{11}H_{13}N_4O_4$ (M+H)⁺: m/z=265.1. Found: 265.2.

Step 3. Ethyl 1-isopropyl-3-(1-methyl-1H-pyrazol-4-yl)-2,4-dioxo-1,2,3,4-tetrahydropyrimidine-5-carboxylate

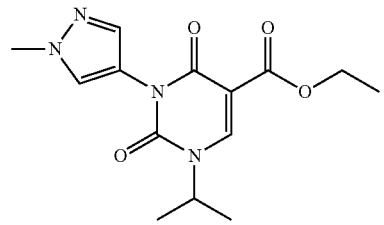 [SMILES: CCOC(=O)c1cn(C(C)C)c(=O)n(-c2cnn(C)c2)c1=O]

A mixture of ethyl 3-(1-methyl-1H-pyrazol-4-yl)-2,4-dioxo-1,2,3,4-tetrahydropyrimidine-5-carboxylate (0.172 g, 0.65 mmol), 2-iodopropane (0.13 mL, 1.30 mmol), and Cs₂CO₃ (0.636 g, 1.95 mmol) in DMF (2 mL) was stirred at 80° C. for 3 h. The reaction mixture was then cooled to rt, and filtered (washed with CH₂Cl₂). The filtrate was diluted with 10% MeOH in CH₂Cl₂, washed with water, brine, dried over Na₂SO₄, and concentrated to afford the crude product (0.195 g, 98%), which was used directly in the next step. LCMS calcd for $C_{14}H_{19}N_4O_4$ (M+H)⁺: m/z=307.1. Found: 307.1.

Step 4. 1-Isopropyl-3-(1-methyl-1H-pyrazol-4-yl)-2,4-dioxo-1,2,3,4-tetrahydropyrimidine-5-carboxylic Acid

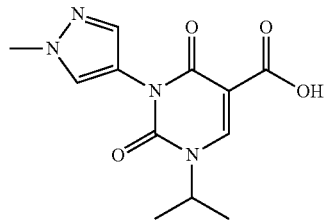 [SMILES: CC(C)n1cc(C(=O)O)c(=O)n(-c2cnn(C)c2)c1=O]

A mixture of ethyl 1-isopropyl-3-(1-methyl-1H-pyrazol-4-yl)-2,4-dioxo-1,2,3,4-tetrahydropyrimidine-5-carboxylate (0.195 g, 0.64 mmol) in 4 M HCl in dioxane (1.27 mL) and water (0.32 mL) was stirred at 80° C. overnight. The reaction mixture was then cooled to rt, diluted with water (3 mL), and neutralized with 1N NaOH solution to pH ~5. The resulting mixture was extracted with 10% MeOH in $CH_2Cl_2$ (3 mL×3), and the combined organic layers were dried over $Na_2SO_4$, and concentrated to afford the crude product (0.172 g, 97%) which was used directly in the next step. LCMS calcd for $C_{12}H_{15}N_4O_4$ $(M+H)^+$: m/z=279.1. Found: 279.1.

Step 5. N-(4-(4-Amino-7-(1-isobutyrylpiperidin-4-yl)pyrrolo[2,1-f][1,2,4]triazin-5-yl)phenyl)-1-isopropyl-3-(1-methyl-1H-pyrazol-4-yl)-2,4-dioxo-1,2,3,4-tetrahydropyrimidine-5-carboxamide To a mixture of 1-isopropyl-3-(1-methyl-1H-pyrazol-4-yl)-2,4-dioxo-1,2,3,4-tetrahydropyrimidine-5-carboxylic acid (0.014 g, 0.050 mmol) and HATU (0.021 g, 0.055 mmol) in DMF (1 mL) was added 1-(4-(4-amino-5-(4-aminophenyl)pyrrolo[2,1-f][1,2,4]triazin-7-yl)piperidin-1-yl)-2-methylpropan-1-one (0.019 g, 0.050 mmol) (from example 83, step 2) and $Et_3N$ (0.021 ml, 0.15 mmol). The mixture was stirred at rt for 2 h., diluted with MeOH, adjusted with TFA to pH ~2, and purified via pH 2 preparative LC/MS (MeCN/water with TFA) to give the product as TFA salt. LCMS calcd for $C_{33}H_{39}N_{10}O_4(M+H)^+$: m/z=639.3. Found: 639.3.

Example 88. N-(4-(4-Amino-7-(1-isobutyrylpiperidin-4-yl)pyrrolo[2,1-f][1,2,4]triazin-5-yl)phenyl)-1-isopropyl-3-(1-methyl-1H-pyrazol-3-yl)-2,4-dioxo-1,2,3,4-tetrahydropyrimidine-5-carboxamide

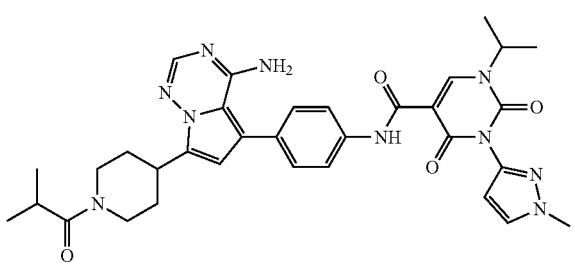 [SMILES: CC(C)C(=O)N1CCC(c2cc(-c3ccc(NC(=O)c4cn(C(C)C)c(=O)n(-c5ccn(C)n5)c4=O)cc3)c3c(N)ncnn23)CC1]

This compound was prepared following a synthetic sequence analogous to that for example 87, using 1-methyl-1H-pyrazol-3-amine instead of 1-methyl-1H-pyrazol-4-amine. This compound was purified via pH 2 preparative LC/MS (MeCN/water with TFA) to give the product as TFA salt. LCMS calcd for $C_{33}H_{39}N_{10}O_4(M+H)^+$: m/z=639.3. Found: 639.3.

Example 89. N-(4-(4-Amino-7-(1-isobutyrylpiperidin-4-yl)pyrrolo[1,2-f][1,2,4]triazin-5-yl)phenyl)-1-isopropyl-3-(2-methylthiazol-5-yl)-2,4-dioxo-1,2,3,4-tetrahydropyrimidine-5-carboxamide

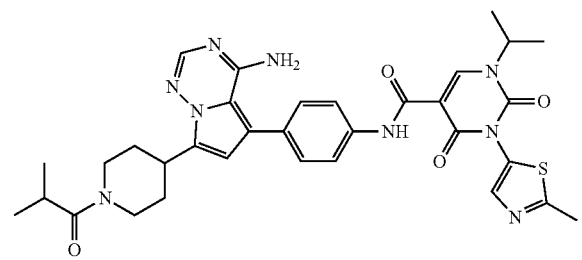 [SMILES: Cc1ncc(-n2c(=O)c(C(=O)Nc3ccc(-c4cc(C5CCN(C(=O)C(C)C)CC5)n5ncnc(N)c45)cc3)cn(C(C)C)c2=O)s1]

This compound was prepared following a synthetic sequence analogous to that for example 87, using 2-methylthiazol-5-amine instead of 1-methyl-1H-pyrazol-4-amine. This compound was purified via pH 2 preparative LC/MS (MeCN/water with TFA) to give the product as TFA salt. LCMS calcd for $C_{33}H_{38}N_9O_4S$ $(M+H)^+$: m/z=656.3. Found: 656.3.

Example 90. N-(4-(4-Amino-7-(1-isobutyrylpiperidin-4-yl)pyrrolo[2,1-f][1,2,4]triazin-5-yl)phenyl)-3-cyclohexyl-1-isopropyl-2,4-dioxo-1,2,3,4-tetrahydropyrimidine-5-carboxamide

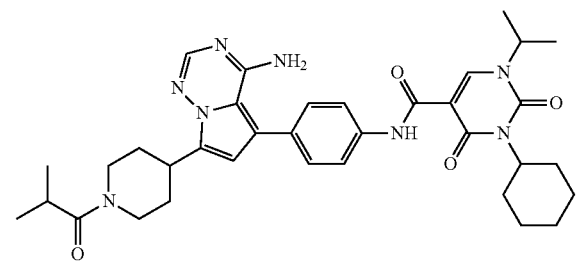 [SMILES: CC(C)C(=O)N1CCC(c2cc(-c3ccc(NC(=O)c4cn(C(C)C)c(=O)n(C5CCCCC5)c4=O)cc3)c3c(N)ncnn23)CC1]

Step 1: 3-Cyclohexyl-1-isopropyl-2,4-dioxo-1,2,3,4-tetrahydropyrimidine-5-carboxylic Acid

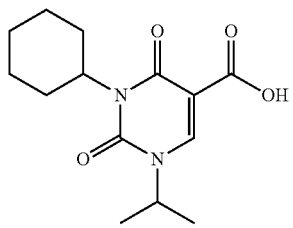 [SMILES: CC(C)n1cc(C(=O)O)c(=O)n(C2CCCCC2)c1=O]

This compound was prepared following a synthetic sequence analogous to that for example 61, step 1 to step 4, using isocyanatocyclohexane instead of isocyanatobenzene. LCMS calcd for $C_{14}H_{21}N_2O_4$ (M+H)⁺: m/z=281.2. Found: 281.1.

Step 2: N-(4-(4-Amino-7-(1-isobutyrylpiperidin-4-yl)pyrrolo[2,1-f][1,2,4]triazin-5-yl)phenyl)-3-cyclohexyl-1-isopropyl-2,4-dioxo-1,2,3,4-tetrahydropyrimidine-5-carboxamide To a mixture of 3-cyclohexyl-1-isopropyl-2,4-dioxo-1,2,3,4-tetrahydropyrimidine-5-carboxylic acid (0.014 g, 0.050 mmol) and HATU (0.021 g, 0.055 mmol) in DMF (1 mL) was added 1-(4-(4-amino-5-(4-aminophenyl)pyrrolo[2,1-f][1,2,4]triazin-7-yl)piperidin-1-yl)-2-methylpropan-1-one (0.019 g, 0.050 mmol) (from example 83, step 2) and Et₃N (0.021 ml, 0.15 mmol). The mixture was stirred at rt for 2 h., diluted with MeOH, adjusted with TFA to pH ~2, and purified via pH 2 preparative LC/MS (MeCN/water with TFA) to give the product as TFA salt. LCMS calcd for $C_{35}H_{45}N_8O_4$ (M+H)⁺: m/z=641.4. Found: 641.3.

Example 91. N-(4-(4-Amino-7-(1-isobutyrylpiperidin-4-yl)pyrrolo[2,1-f][1,2,4]triazin-5-yl)phenyl)-3-(3-cyanophenyl)-1-isopropyl-2,4-dioxo-1,2,3,4-tetrahydropyrimidine-5-carboxamide

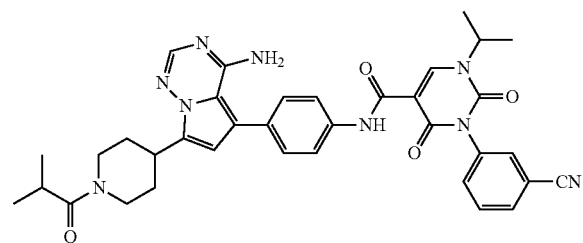 [SMILES: CC(C)C(=O)N1CCC(c2cc(-c3ccc(NC(=O)c4cn(C(C)C)c(=O)n(-c5cccc(C#N)c5)c4=O)cc3)c3c(N)ncnn23)CC1]

Step 1: 3-(3-Bromophenyl)-1-isopropyl-2,4-dioxo-1,2,3,4-tetrahydropyrimidine-5-carboxylic

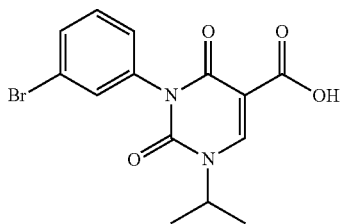 [SMILES: CC(C)n1cc(C(=O)O)c(=O)n(-c2cccc(Br)c2)c1=O]

This compound was prepared following a synthetic sequence analogous to that for example 61, from step 1 to step 4, using 1-bromo-3-isocyanatobenzene instead of isocyanatobenzene. LCMS calcd for $C_{14}H_{14}BrN_2O_4$(M+H)⁺: m/z=353.0. Found: 353.1.

Step 2: N-(4-(4-Amino-7-(1-isobutyrylpiperidin-4-yl)pyrrolo[2,1-f][1,2,4]triazin-5-yl)phenyl)-3-(3-bromophenyl)-1-isopropyl-2,4-dioxo-1,2,3,4-tetrahydropyrimidine-5-carboxamide

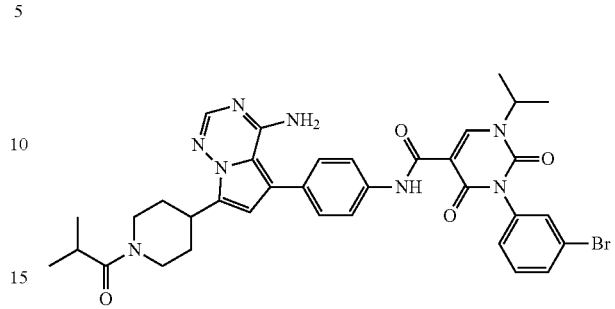

To a mixture of 3-(3-bromophenyl)-1-isopropyl-2,4-dioxo-1,2,3,4-tetrahydropyrimidine-5-carboxylic acid (0.018 g, 0.050 mmol) and HATU (0.021 g, 0.055 mmol) in DMF (1 mL) was added 1-(4-(4-amino-5-(4-aminophenyl)pyrrolo[2,1-f][1,2,4]triazin-7-yl)piperidin-1-yl)-2-methylpropan-1-one (0.019 g, 0.050 mmol) (from example 83, step 2) and Et₃N (0.021 ml, 0.150 mmol). The mixture was stirred at rt for 2 h, and water (4 mL) was added. The resulting solid was collected by filtration, washed with water, and dried to afford the product. LCMS calcd for $C_{35}H_{38}BrN_8O_4$ (M+H)⁺: m/z=713.2. Found: 713.2.

Step 3: N-(4-(4-Amino-7-(1-isobutyrylpiperidin-4-yl)pyrrolo[2,1-f][1,2,4]triazin-5-yl)phenyl)-3-(3-cyanophenyl)-1-isopropyl-2,4-dioxo-1,2,3,4-tetrahydropyrimidine-5-carboxamide A mixture of N-(4-(4-amino-7-(1-isobutyrylpiperidin-4-yl)pyrrolo[2,1-f][1,2,4]triazin-5-yl)phenyl)-3-(3-bromophenyl)-1-isopropyl-2,4-dioxo-1,2,3,4-tetrahydropyrimidine-5-carboxamide (0.036 g, 0.050 mmol), potassium hexacyanoferrate(II) trihydrate (10.5 mg, 0.025 mmol), tBuXPhos Pd G3 (0.32 mg, 0.40 µmol) and KOAc (0.61 mg, 6.3 µmol) in a sealed screw vial was de-gassed and recharged with N₂. 1,4-dioxane (0.50 mL) and water (0.50 mL) was then added. The mixture was re-degassed and charged with N₂ for three cycles. The reaction mixture was then heated at 100° C. for 1 h, cooled to rt, diluted with MeOH, adjusted with TFA to pH ~2, and purified via pH 2 preparative LC/MS (MeCN/water with TFA) to give the product as TFA salt. LCMS calcd for $C_{36}H_{38}N_9O_4$ (M+H)⁺: m/z=660.3. Found: 660.3.

Example 92. N-(4-(4-Amino-7-(1-isobutyrylpiperidin-4-yl)pyrrolo[2,1-f][1,2,4]triazin-5-yl)phenyl)-1-isopropyl-3-(5-methylisoxazol-3-yl)-2,4-dioxo-1,2,3,4-tetrahydropyrimidine-5-carboxamide

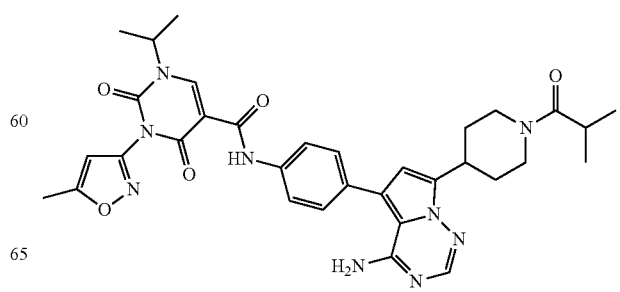

This compound was prepared following a synthetic sequence analogous to that for example 87, using 5-methylisoxazol-3-amine instead of 1-methyl-1H-pyrazol-4-amine. This compound was purified via pH 2 preparative LC/MS (MeCN/water with TFA) to give the product as TFA salt. LCMS calcd for $C_{33}H_{38}N_9O_5$ (M+H)⁺: m/z=640.3. Found: 640.3.

Example 93. N-(4-(4-Amino-7-(4-(dimethylamino)cyclohexyl)pyrrolo[2,1-f][1,2,4]triazin-5-yl)phenyl)-1-isopropyl-2,4-dioxo-3-phenyl-1,2,3,4-tetrahydropyrimidine-5-carboxamide

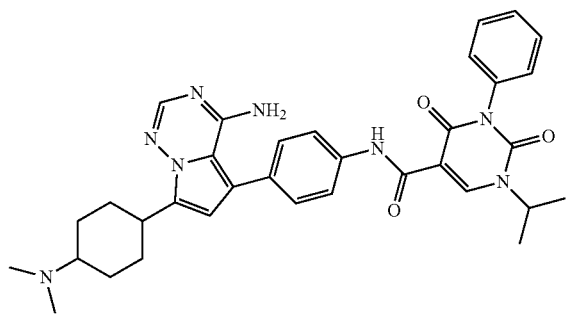 [SMILES: CC(C)n1cc(C(=O)Nc2ccc(-c3cc(C4CCC(N(C)C)CC4)n4ncnc(N)c34)cc2)c(=O)n(-c2ccccc2)c1=O]

Step 1: tert-Butyl (4-(4-aminopyrrolo[2,1-f][1,2,4]triazin-7-yl)cyclohex-3-en-1-yl)carbamate

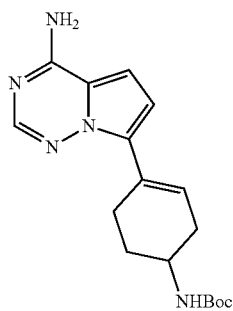 [SMILES: CC(C)(C)OC(=O)NC1CC=C(c2ccc3c(N)ncnn23)CC1]

In a sealed vial, a mixture of 7-bromopyrrolo[2,1-f][1,2,4]triazin-4-amine (300 mg, 1.41 mmol), tert-butyl 4-(4,4,5,5-tetramethyl-1,3,2-dioxaborolan-2-yl)cyclohex-3-enylcarbamate (550 mg, 1.69 mmol), chloro(2-dicyclohexylphosphino-2',4',6'-tri-i-propyl-1,1'-biphenyl)(2'-amino-1,1'-biphenyl-2-yl)palladium(II) (55.4 mg, 0.070 mmol) and potassium phosphate tribasic (0.35 ml, 4.22 mmol) in 1,4-dioxane (10 ml)/water (2.0 ml) was degassed and stirred at 90° C. under $N_2$ for 2.5 h. The reaction mixture was cooled to rt, diluted with EtOAc, and washed with brine. The organic layer was separated, dried over $Na_2SO_4$, concentrated, and purified by column chromatography (0% to 10% MeOH in $CH_2Cl_2$) to give the product (400 mg, 86%). LCMS calcd for $C_{17}H_{24}N_5O_2$ (M+H)⁺: m/z=330.2; Found: 330.1.

Step 2: tert-Butyl (4-(4-aminopyrrolo[2,1-f][1,2,4]triazin-7-yl)cyclohexyl)carbamate

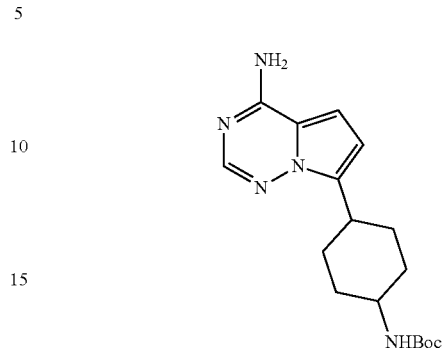

To a mixture of tert-butyl (4-(4-aminopyrrolo[2,1-f][1,2,4]triazin-7-yl)cyclohex-3-en-1-yl)carbamate (460 mg, 1.40 mmol) in MeOH (25 ml) was added 10% Pd/C (297 mg). The resulting mixture was stirred under 1 atm $H_2$ (balloon). After 22 h, more 10% Pd/C (160 mg) was added along with $CH_2Cl_2$ (5 mL). The reaction mixture was then stirred for another 23 h, filtered through Celite (washed with $CH_2Cl_2$), and concentrated to give the crude product (463 mg), which was used directly in the next step. LCMS calcd for $C_{17}H_{26}N_5O_2$ (M+H)⁺: m/z=332.2; Found: 332.2.

Step 3: tert-Butyl (4-(4-amino-5-bromopyrrolo[2,1-f][1,2,4]triazin-7-yl)cyclohexyl)carbamate

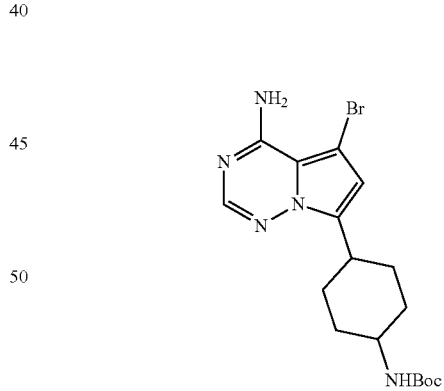

To a solution of tert-butyl (4-(4-aminopyrrolo[2,1-f][1,2,4]triazin-7-yl)cyclohexyl)carbamate (463 mg, 1.40 mmol) in DMF (15 ml) was added NBS (249 mg, 1.40 mmol). The resulting mixture was stirred at rt overnight. Water was then added to the reaction mixture, and the resulting solid was collected by filtration, washed with water, and dried to give the product as a yellow solid (443 mg), which was used directly in the next step. LCMS calcd for $C_{17}H_{25}BrN_5O_2$ (M+H)⁺: m/z=410.1; Found: 410.1.

Step 4: N-(4-(4-Amino-7-(4-aminocyclohexyl)pyrrolo[2,1-f][1,2,4]triazin-5-yl)phenyl)-1-isopropyl-2,4-dioxo-3-phenyl-1,2,3,4-tetrahydropyrimidine-5-carboxamide

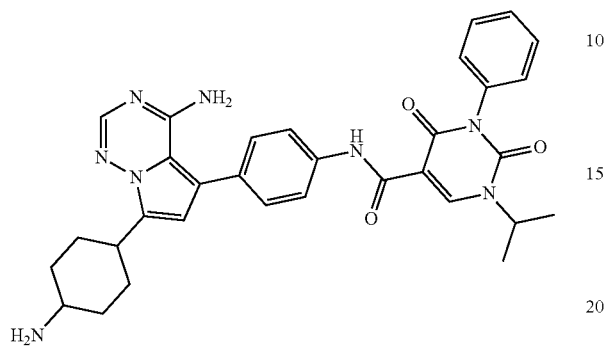

A mixture of tert-butyl (4-(4-amino-5-bromopyrrolo[2,1-f][1,2,4]triazin-7-yl)cyclohexyl)carbamate (27.0 mg, 0.066 mmol), 1-isopropyl-2,4-dioxo-3-phenyl-N-(4-(4,4,5,5-tetramethyl-1,3,2-dioxaborolan-2-yl)phenyl)-1,2,3,4-tetrahydropyrimidine-5-carboxamide (40.7 mg, 0.086 mmol) (from example 61, step 5), chloro(2-dicyclohexylphosphino-2',4',6'-tri-i-propyl-1,1'-biphenyl)(2'-amino-1,1'-biphenyl-2-yl)palladium(II) (2.6 mg, 3.3 μmol) and potassium phosphate tribasic (41.9 mg, 0.197 mmol) in 1,4-dioxane (0.50 mL)/water (0.10 mL) was stirred at 90° C. under $N_2$ for 2 h, cooled to rt, and partitioned between $CH_2Cl_2$ and water. The organic layer was separated and concentrated. To the crude residue was added $CH_2Cl_2$ (400 uL) and TFA (200 μL). The resulting solution was stirred at rt for 1 h, and concentrated. The crude material was purified via pH 2 preparative LC/MS (MeCN/water with TFA) to give the product as TFA salt. LCMS calcd for $C_{32}H_{35}N_8O_3$ (M+H)$^+$: m/z=579.3; Found: 579.2.

Step 5: N-(4-(4-Amino-7-(4-(dimethylamino)cyclohexyl)pyrrolo[2,1-f][1,2,4]triazin-5-yl)phenyl)-1-isopropyl-2,4-dioxo-3-phenyl-1,2,3,4-tetrahydropyrimidine-5-carboxamide To a mixture of N-(4-(4-amino-7-(4-aminocyclohexyl)pyrrolo[2,1-f][1,2,4]triazin-5-yl)phenyl)-1-isopropyl-2,4-dioxo-3-phenyl-1,2,3,4-tetrahydropyrimidine-5-carboxamide (15 mg, 0.022 mmol), formaldehyde in water (37 wt %, 1.6 μL, 0.022 mmol) and Et$_3$N (12 μL, 0.087 mmol) in THF (0.30 ml) was added sodium triacetoxyborohydride (50 mg, 2.05 mmol). The resulting mixture was stirred at rt overnight, filtered, and concentrated. The crude material was purified via pH 2 preparative LC/MS (MeCN/water with TFA) to give the product as TFA salt. LCMS calculated for $C_{34}H_{39}N_8O_3$ (M+H)$^+$: m/z=607.3; Found: 607.3.

Example 94. N-(4-(4-amino-7-(1-(cyclopropanecarbonyl)azetidin-3-yl)pyrrolo[2,1-f][1,2,4]triazin-5-yl)phenyl)-1-isopropyl-2,4-dioxo-3-phenyl-1,2,3,4-tetrahydropyrimidine-5-carboxamide

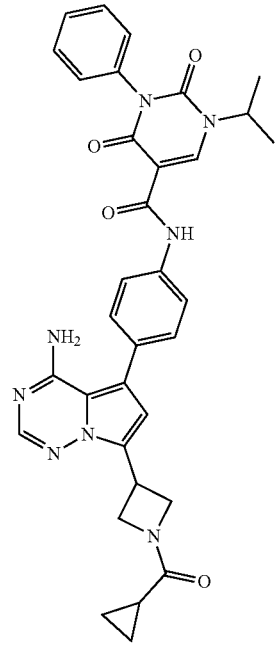 [SMILES: CC(C)n1cc(C(=O)Nc2ccc(-c3cc(C4CN(C(=O)C5CC5)C4)n4ncnc(N)c34)cc2)c(=O)n(-c2ccccc2)c1=O]

Step 1: 7-Iodopyrrolo[1,2-f][1,2,4]triazin-4-amine

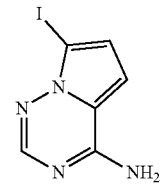

N-Iodosuccinimide (2.5 g, 11 mmol) was added to a solution of pyrrolo[1,2-f][1,2,4]triazin-4-amine (1.5 g, 11 mmol) in DMF (10 mL) at rt and the reaction was stirred for 2 h. The reaction mixture was then diluted with EtOAc, washed with water and concentrated. The resulting solid was washed with water, and dried to give the product. LCMS calcd for $C_6H_6IN_4$ (M+H)$^+$: m/z=261.0. Found: 261.2.

Step 2: tert-Butyl 3-(4-aminopyrrolo[1,2-f][1,2,4]triazin-7-yl)azetidine-1-carboxylate

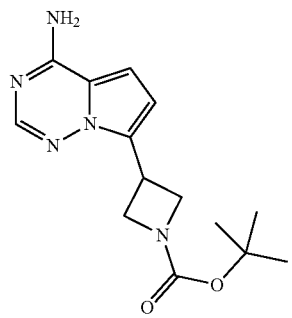 [SMILES: CC(C)(C)OC(=O)N1CC(c2ccc3c(N)ncnn23)C1]

Zinc (0.690 g, 10.5 mmol) was suspended with 1,2-dibromoethane (60 μL, 0.70 mmol) in DMF (20 mL). The resulting mixture was stirred at 70° C. for 10 min and cooled to rt. Chlorotrimethylsilane (89 μL, 0.70 mmol) was added and stirring was continued for 1 h. A solution of tert-butyl 3-iodoazetidine-1-carboxylate (2.5 g, 8.8 mmol) in DMF (10 mL) was then added and the mixture was stirred at 40° C. for 1 h before a mixture of 7-iodopyrrolo[2,1-S][1,2,4]triazin-4-amine (2.4 g, 9.2 mmol), Tris(dibenzylideneacetone)dipalladium(0) (0.80 g, 0.88 mmol) and Tri-(2-furyl)phosphine (0.41 g, 1.8 mmol) in DMF (12 mL) was added. The reaction mixture was then stirred at 75° C. overnight, cooled to rt, and partitioned between EtOAc and saturated NH$_4$Cl solution. The organic layer was separated, washed with water, dried over MgSO$_4$, concentrated and purified via column chromatography (0% to 100% EtOAc in hexanes) to give the product (1.0 g, 39%). LCMS calcd for C$_{14}$H$_{20}$N$_5$O$_2$ (M+H)$^+$: m/z=290.2. Found: 290.2.

Step 3: tert-Butyl 3-(4-amino-5-bromopyrrolo[1,2-f][1,2,4]triazin-7-yl)azetidine-1-carboxylate

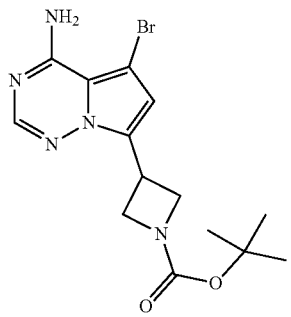 [SMILES: CC(C)(C)OC(=O)N1CC(c2cc(Br)c3c(N)ncnn23)C1]

NBS (0.55 g, 3.1 mmol) was added to a solution of tert-butyl 3-(4-aminopyrrolo[2,1-f][1,2,4]triazin-7-yl)azetidine-1-carboxylate (0.94 g, 3.2 mmol) in DMSO/MeCN/water (7.0 mL/3.0 mL/0.2 mL) at 0° C. and the reaction mixture was stirred at this temperature for 2 h. The resulting mixture was diluted with EtOAc, washed with water, concentrated, and purified via column chromatography (0% to 100% EtOAc in hexanes) to give the desire product (0.35 g, 29%). LCMS calcd for C$_{14}$H$_{19}$BrN$_5$O$_2$(M+H)$^+$: m/z=368.1. Found: 368.0.

Step 4: tert-Butyl 3-(4-amino-5-(4-aminophenyl)pyrrolo[1,2-f][1,2,4]triazin-7-yl)azetidine-1-carboxylate

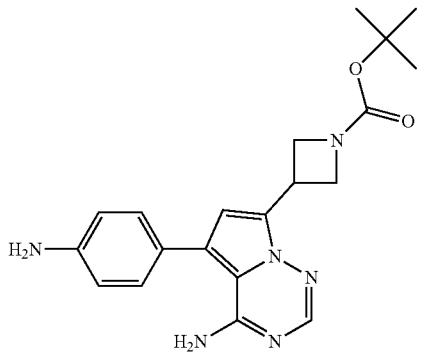 [SMILES: CC(C)(C)OC(=O)N1CC(c2cc(-c3ccc(N)cc3)c3c(N)ncnn23)C1]

A mixture of 4-(4,4,5,5-tetramethyl-1,3,2-dioxaborolan-2-yl)aniline (0.21 g, 0.95 mmol), tert-butyl 3-(4-amino-5-bromopyrrolo[2,1-f][1,2,4]triazin-7-yl)azetidine-1-carboxylate (0.35 g, 0.95 mmol), Cs$_2$CO$_3$ (0.62 g, 1.9 mmol) and dicyclohexyl(2',4',6'-triisopropylbiphenyl-2-yl)phosphine-(2'-aminobiphenyl-2-yl)(chloro)palladium (1:1) (0.075 g, 0.095 mmol) in 1,4-dioxane/water was stirred at 85° C. for 2 h. The reaction mixture was then cooled to rt, and purified via column chromatography (0% to 100% EtOAc in hexanes) to give the product (0.28 g, 77%). LCMS calcd for C$_{20}$H$_{25}$N$_6$O$_2$ (M+H)$^+$: m/z=381.2. Found: 381.3.

Step 5: tert-butyl 3-(4-amino-5-(4-(1-isopropyl-2,4-dioxo-3-phenyl-1,2,3,4-tetrahydropyrimidine-5-carboxamido)phenyl)pyrrolo[2,1-f][1,2,4]triazin-7-yl)azetidine-1-carboxylate

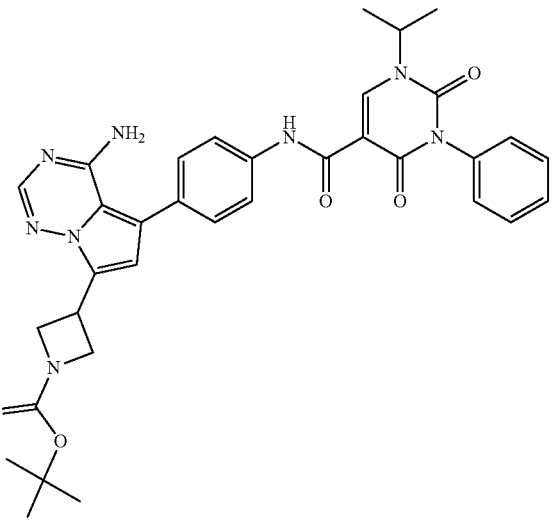

To a mixture of tert-butyl 3-[4-amino-5-(4-aminophenyl)pyrrolo[2,1-f][1,2,4]triazin-7-yl]azetidine-1-carboxylate (140 mg, 0.37 mmol) and 1-isopropyl-2,4-dioxo-3-phenyl-1,2,3,4-tetrahydropyrimidine-5-carboxylic acid (110 mg, 0.40 mmol) (from example 61, step 4) in DMF (3.0 mL) was added Et$_3$N (0.10 mL, 0.74 mmol) followed by HATU (0.17 g, 0.44 mmol). The reaction mixture was stirred at rt for 1 h, quenched with water, and the resulting solid was collected by filtration, and dried to give the product. LCMS calcd for C$_{34}$H$_{37}$N$_8$O$_5$ (M+H)$^+$: m/z=637.3. Found: 637.2.

Step 6: N-(4-(4-Amino-7-(azetidin-3-yl)pyrrolo[1,2-f][1,2,4]triazin-5-yl)phenyl)-1-isopropyl-2,4-dioxo-3-phenyl-1,2,3,4-tetrahydropyrimidine-5-carboxamide

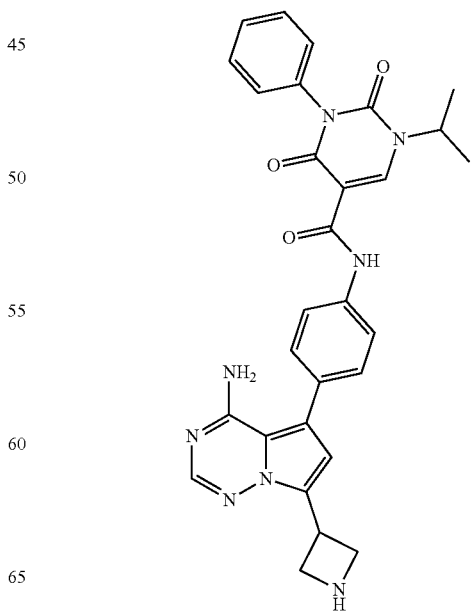

tert-Butyl 3-(4-amino-5-(4-(1-isopropyl-2,4-dioxo-3-phenyl-1,2,3,4-tetrahydropyrimidine-5-carboxamido)phenyl)pyrrolo[1,2-f][1,2,4]triazin-7-yl)azetidine-1-carboxylate (0.25 g, 0.39 mmol) was treated with 4 M HCl in 1,4-dioxane (0.098 mL, 0.39 mmol) in CH$_2$Cl$_2$ (1 mL) at rt for 1 h. The reaction mixture was then concentrated to give the product. LCMS calcd for C$_{29}$H$_{29}$N$_8$O$_3$ (M+H)$^+$: m/z=537.2. Found: 537.2.

Step 7: N-(4-(4-Amino-7-(1-(cyclopropanecarbonyl)azetidin-3-yl)pyrrolo[1,2-f][1,2,4]triazin-5-yl)phenyl)-1-isopropyl-2,4-dioxo-3-phenyl-1,2,3,4-tetrahydropyrimidine-5-carboxamide To a mixture of N-(4-(4-amino-7-(azetidin-3-yl)pyrrolo[2,1-f][1,2,4]triazin-5-yl)phenyl)-1-isopropyl-2,4-dioxo-3-phenyl-1,2,3,4-tetrahydropyrimidine-5-carboxamide (0.0055 g, 10.3 μmol) and Et$_3$N (2.86 μl, 0.020 mmol) in CH$_2$Cl$_2$ (1 ml) was added cyclopropanecarbonyl chloride (1.3 mg, 0.012 mmol). The reaction mixture was stirred at rt for 1 h, concentrated, and purified via pH 2 preparative LC/MS (MeCN/water with TFA) to give the product as TFA salt. LCMS calcd for C$_{33}$H$_{33}$N$_8$O$_4$ (M+H)$^+$: m/z=605.3. Found: 605.2.

Example 95. N-(4-(4-Amino-7-(morpholinomethyl)pyrrolo[1,2-f][1,2,4]triazin-5-yl)phenyl)-1-isopropyl-2,4-dioxo-3-phenyl-1,2,3,4-tetrahydropyrimidine-5-carboxamide

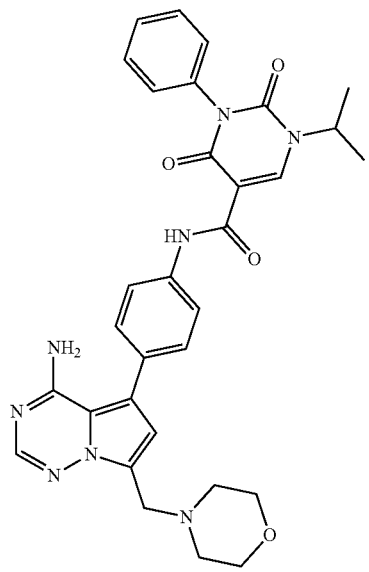 [SMILES: CC(C)n1cc(C(=O)Nc2ccc(-c3cc(CN4CCOCC4)n4ncnc(N)c34)cc2)c(=O)n(-c2ccccc2)c1=O]

Step 1: 4-Aminopyrrolo[1,2-f][1,2,4]triazine-7-carbaldehyde

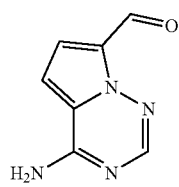

To a solution of pyrrolo[2,1-f][1,2,4]triazin-4-amine (1.0 g, 7.45 mmol) in DMF (15 mL) at 0° C. was added POCl$_3$ (3.47 mL, 37.3 mmol). The reaction mixture was then stirred at 60° C. overnight, cooled to rt, quenched with saturated NaHCO$_3$ solution, and extracted with EtOAc (30 mL×3). The combined organic layers were washed with brine, dried over Na$_2$SO$_4$, concentrated, and purified via column chromatography (0% to 15% MeOH in CH$_2$Cl$_2$) to give the product (200 mg, 16%). LCMS calcd for C$_7$H$_7$N$_4$O (M+H)$^+$: m/z=163.1. Found: 163.1.

Step 2: 4-Amino-5-bromopyrrolo[1,2-f][1,2,4]triazine-7-carbaldehyde

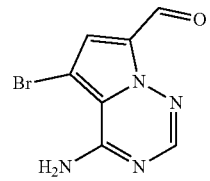 [SMILES: Nc1ncnn2c(C=O)cc(Br)c12]

To a solution of 4-aminopyrrolo[2,1-f][1,2,4]triazine-7-carbaldehyde (200 mg, 1.23 mmol) in THF (6.0 ml) at rt was added 1,3-dibromo-5,5-dimethylhydantoin (212 mg, 0.74 mmol) portionwise. The reaction mixture was then stirred at rt for 1 h, and diluted with water (30 mL)/EtOAc (30 mL). The organic layer was separated, washed with brine, dried over Na$_2$SO$_4$, and concentrated to give the product (127 mg, 43%), which was used directly in the next step. LCMS calcd for C$_7$H$_6$BrN$_4$O (M+H)$^+$: m/z=241.0. Found: 241.0.

Step 3: N-(4-(4-Amino-7-formylpyrrolo[1,2-f][1,2,4]triazin-5-yl)phenyl)-1-isopropyl-2,4-dioxo-3-phenyl-1,2,3,4-tetrahydropyrimidine-5-carboxamide

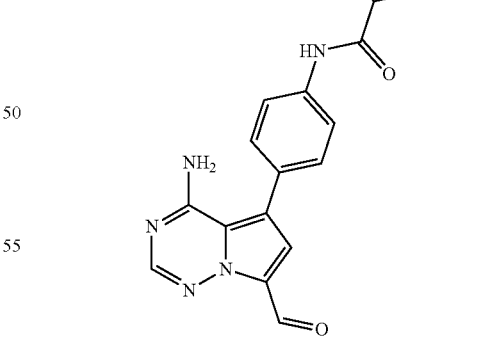

A mixture of 4-amino-5-bromopyrrolo[2,1-f][1,2,4]triazine-7-carbaldehyde (126 mg, 0.52 mmol), 1-isopropyl-2,4-dioxo-3-phenyl-N-(4-(4,4,5,5-tetramethyl-1,3,2-dioxaborolan-2-yl)phenyl)-1,2,3,4-tetrahydropyrimidine-5-carboxamide (248 mg, 0.52 mmol) (from example 61, step 5), chloro(2-dicyclohexylphosphino-2',4',6'-triisopropyl-1,1'-biphenyl)[2-(2'-amino-1,1'-biphenyl)]palladium(II) (XPhos Pd G2) (41 mg, 0.052 mmol), and Na$_2$CO$_3$ (111 mg, 1.04 mmol) in 1,4-dioxane (4.0 mL)/water (1.0 mL) was purged with N₂, and stirred at 70° C. for 2 h. The reaction mixture was then cooled to rt, and diluted with water (30 mL)/EtOAc (30 mL). The organic layer was separated, washed with brine, dried over Na₂SO₄, concentrated, and purified via column chromatography (0% to 15% MeOH in CH₂Cl₂) to give the product (266 mg, 100%). LCMS calcd for $C_{27}H_{24}N_7O_4$ (M+H)⁺: m/z=510.2. Found: 510.2.

Step 4. N-(4-(4-Amino-7-(morpholinomethyl)pyrrolo[1,2-f][1,2,4]triazin-5-yl)phenyl)-1-isopropyl-2,4-dioxo-3-phenyl-1,2,3,4-tetrahydropyrimidine-5-carboxamide To a mixture of N-(4-(4-amino-7-formylpyrrolo[2,1-f][1,2,4]triazin-5-yl)phenyl)-1-isopropyl-2,4-dioxo-3-phenyl-1,2,3,4-tetrahydropyrimidine-5-carboxamide (20 mg, 0.039 mmol), morpholine (0.017 mL, 0.20 mmol), and acetic acid (0.011 mL, 0.20 mmol) in ClCH₂CH₂Cl (1.5 mL) at rt was added sodium triacetoxyborohydride (42 mg, 0.20 mmol). The reaction mixture was then stirred at 50° C. for 15 min, cooled to rt, concentrated, diluted with MeOH, and purified via pH 2 preparative LC/MS (MeCN/water with TFA) to give the product as a white solid (TFA salt). LCMS calcd for $C_{31}H_{33}N_8O_4$ (M+H)⁺: m/z=581.3. Found: 581.3.

Example 96. N-(4-(4-Amino-7-(1-isobutyrylpiperidin-4-yl)pyrrolo[1,2-f][1,2,4]triazin-5-yl)phenyl)-2-isopropyl-3,5-dioxo-4-phenyl-2,3,4,5-tetrahydro-1,2,4-triazine-6-carboxamide

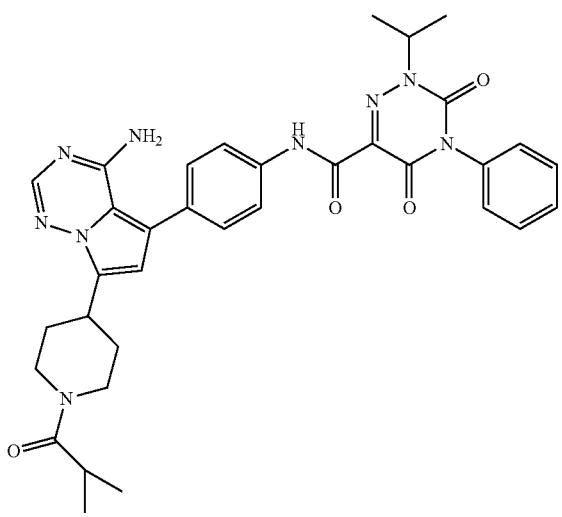 [SMILES: CC(C)C(=O)N1CCC(c2cc(-c3ccc(NC(=O)c4nn(C(C)C)c(=O)n(-c5ccccc5)c4=O)cc3)c3c(N)ncnn23)CC1]

Step 1: N-Phenylhydrazinecarbothioamide

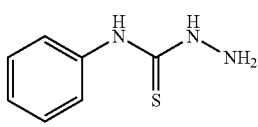 [SMILES: NNC(=S)Nc1ccccc1]

To a stirred solution of hydrazine hydrate (1.7 g, 34 mmol) in isopropyl alcohol (300 mL) at rt was added isothiocyanatobenzene (3.4 mL). The reaction mixture was stirred at rt for 30 min, and the resulting solid was collected by filtration, washed with isopropanol, and dried to give the product (4.8 g). LCMS calcd for $C_7H_{10}N_3S$ (M+H)⁺: m/z=168.1. Found: 168.1.

Step 2: Ethyl 5-oxo-4-phenyl-3-thioxo-2,3,4,5-tetrahydro-1,2,4-triazine-6-carboxylate

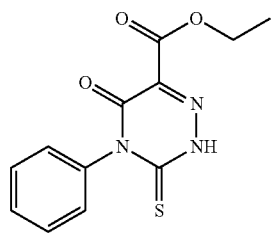 [SMILES: CCOC(=O)c1n[nH]c(=S)n(-c2ccccc2)c1=O]

A mixture of propanedioic acid, oxo-, diethyl ester (5.0 mL, 33 mmol) and N-phenylhydrazinecarbothioamide (5.5 g, 33 mmol) in EtOH (100 mL) was refluxed for 3 days. The reaction mixture was cooled to rt, and the resulting solid was collected by filtration, washed with cold EtOH, and dried to give the product (6 g, 66%). LCMS calcd for $C_{12}H_{12}N_3O_3S$ (M+H)⁺: m/z=278.1. Found: 278.2.

Step 3: Ethyl 3,5-dioxo-4-phenyl-2,3,4,5-tetrahydro-1,2,4-triazine-6-carboxylate

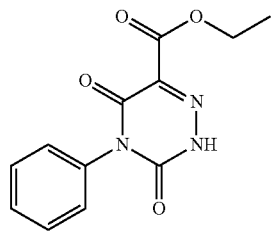 [SMILES: CCOC(=O)c1n[nH]c(=O)n(-c2ccccc2)c1=O]

A mixture of ethyl 5-oxo-4-phenyl-3-thioxo-2,3,4,5-tetrahydro-1,2,4-triazine-6-carboxylate (6.0 g, 22 mmol), H₂O₂ (30 wt % in water, 6.4 mL) and acetic acid (20 mL) in DMF (60 mL) was stirred at rt overnight. The reaction mixture was then diluted with EtOAc, washed with water, brine, dried, and concentrated. The resulting solid was triturated with ether to give the product. LCMS calcd for $C_{12}H_{12}N_3O_4$ (M+H)⁺: m/z=262.1. Found: 262.2.

Step 4: Ethyl 2-isopropyl-3,5-dioxo-4-phenyl-2,3,4,5-tetrahydro-1,2,4-triazine-6-carboxylate

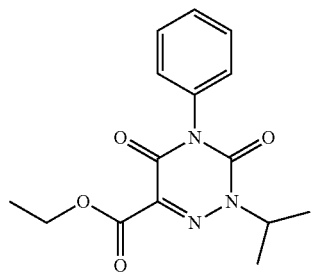 [SMILES: CCOC(=O)c1nn(C(C)C)c(=O)n(-c2ccccc2)c1=O]

Isopropyl iodide (0.46 mL, 4.6 mmol) was added to a mixture of ethyl 3,5-dioxo-4-phenyl-2,3,4,5-tetrahydro-1,2,4-triazine-6-carboxylate (0.6 g, 2 mmol) and $K_2CO_3$ (0.95 g, 6.9 mmol) in DMF (7 mL). The reaction mixture was stirred at 65° C. for 2 h, cooled to rt, diluted with EtOAc, and washed with saturated $NaHCO_3$ solution, water, and brine. The organic layer was separated, dried over $Na_2SO_4$, and concentrated to provide the product. LCMS calcd for $C_{15}H_{18}N_3O_4$ $(M+H)^+$: m/z=304.1. Found: 304.1.

Step 5: 2-Isopropyl-3,5-dioxo-4-phenyl-2,3,4,5-tetrahydro-1,2,4-triazine-6-carboxylic Acid

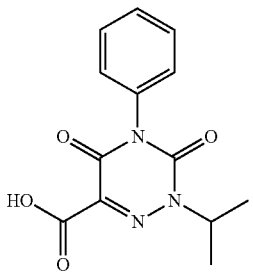 [SMILES: CC(C)n1nc(C(=O)O)c(=O)n(-c2ccccc2)c1=O]

A mixture of ethyl 2-isopropyl-3,5-dioxo-4-phenyl-2,3,4,5-tetrahydro-1,2,4-triazine-6-carboxylate (1.0 g, 3.4 mmol) and water (1.0 mL) in 4 M HCl in 1,4-dioxane (10 mL) was stirred at 70° C. overnight. The reaction mixture was cooled to rt, diluted with water, and extracted with EtOAc. The combined organic layers were dried over $MgSO_4$ and concentrated to provide the desired product. LCMS calcd for $C_{13}H_{14}N_3O_4$ $(M+H)^+$: m/z=276.1. Found: 276.0

Step 6: tert-Butyl 4-[4-amino-5-(4-{[(2-isopropyl-3,5-dioxo-4-phenyl-2,3,4,5-tetrahydro-1,2,4-triazin-6-yl)carbonyl]amino}phenyl)pyrrolo[2,1-f][1,2,4]triazin-7-yl]piperidine-1-carboxylate

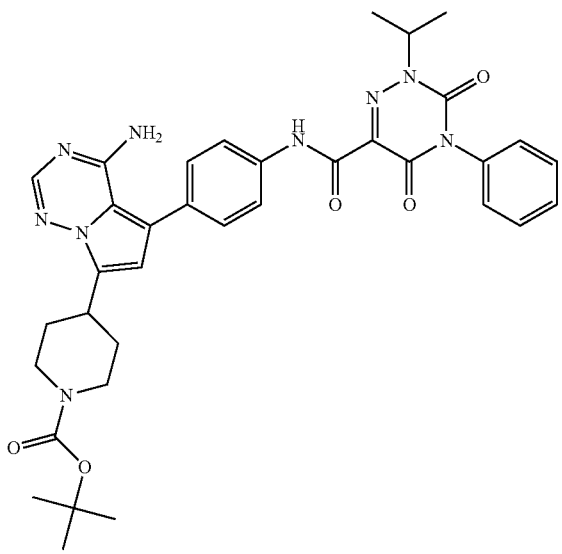 [SMILES: CC(C)n1nc(C(=O)Nc2ccc(-c3cc(C4CCN(C(=O)OC(C)(C)C)CC4)n4ncnc(N)c34)cc2)c(=O)n(-c2ccccc2)c1=O]

To a mixture of tert-butyl 4-[4-amino-5-(4-aminophenyl)pyrrolo[2,1-f][1,2,4]triazin-7-yl]piperidine-1-carboxylate (150 mg, 0.37 mmol) (from example 107, step 4) and 2-isopropyl-3,5-dioxo-4-phenyl-2,3,4,5-tetrahydro-1,2,4-triazine-6-carboxylic acid (101 mg, 0.37 mmol) in DMF (1.7 mL) was added $Et_3N$ (77 µL, 0.55 mmol) followed by HATU (0.168 g, 0.44 mmol). The reaction mixture was stirred at rt for 1 h, quenched with water, and the resulting solid was collected by filtration, and dried to give the product (0.2 g, 80%). LCMS calcd for $C_{35}H_{40}N_9O_5$ $(M+H)^+$: m/z=666.3. Found: 666.2.

Step 7: N-(4-(4-Amino-7-(piperidin-4-yl)pyrrolo[1,2-f][1,2,4]triazin-5-yl)phenyl)-2-isopropyl-3,5-dioxo-4-phenyl-2,3,4,5-tetrahydro-1,2,4-triazine-6-carboxamide

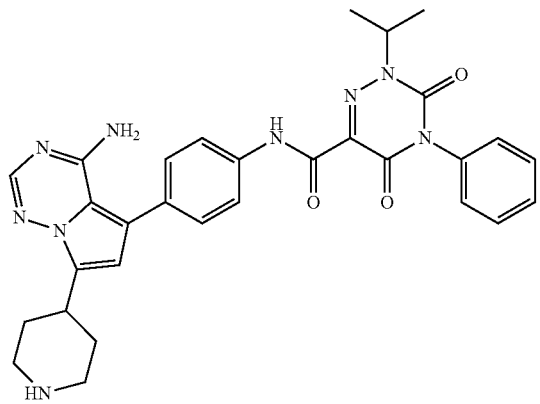 [SMILES: CC(C)n1nc(C(=O)Nc2ccc(-c3cc(C4CCNCC4)n4ncnc(N)c34)cc2)c(=O)n(-c2ccccc2)c1=O]

4 M HCl in 1,4-dioxane (0.71 mL, 2.8 mmol) was added to a mixture of tert-butyl 4-[4-amino-5-(4-{[(2-isopropyl-3,5-dioxo-4-phenyl-2,3,4,5-tetrahydro-1,2,4-triazin-6-yl)carbonyl]amino}phenyl)pyrrolo[2,1-f][1,2,4]triazin-7-yl]piperidine-1-carboxylate (0.20 g, 0.30 mmol) in $CH_2Cl_2$ (0.47 mL). The mixture was stirred at rt for 1 h, and concentrated to give the product (0.17 g, 100%). LCMS calcd for $C_{30}H_{32}N_9O_3$ $(M+H)^+$: m/z=566.3. Found: 566.2.

Step 8: N-(4-(4-Amino-7-(1-isobutyrylpiperidin-4-yl)pyrrolo[1,2-f][1,2,4]triazin-5-yl)phenyl)-2-isopropyl-3,5-dioxo-4-phenyl-2,3,4,5-tetrahydro-1,2,4-triazine-6-carboxamide Isobutyryl chloride (0.0044 g, 0.041 mmol) was added to a solution of N-[4-(4-amino-7-piperidin-4-ylpyrrolo[2,1-f][1,2,4]triazin-5-yl)phenyl]-2-isopropyl-3,5-dioxo-4-phenyl-2,3,4,5-tetrahydro-1,2,4-triazine-6-carboxamide (20 mg, 0.03 mmol) and $Et_3N$ (24 µL, 0.17 mmol) in $CH_2Cl_2$ (1.1 mL). The reaction mixture was stirred at rt for 4 h, and directly purified via pH 2 preparative LC/MS (MeCN/water with TFA) to give the product as TFA salt. LCMS calcd for $C_{34}H_{38}N_9O_4$ $(M+H)^+$: m/z=636.3. Found: 636.3.

219

Example 97. N-(4-(4-Amino-7-(1-isobutyrylpiperidin-4-yl)pyrrolo[2,1-f][1,2,4]triazin-5-yl)phenyl)-1-isopropyl-6-methyl-5-(1-methyl-1H-pyrazol-5-yl)-4-oxo-1,4-dihydropyridine-3-carboxamide

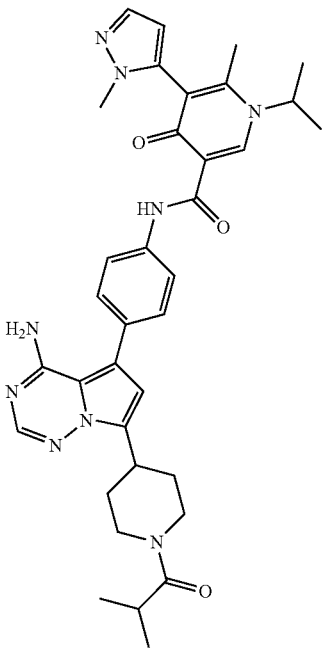 [SMILES: Cc1c(-c2ccnn2C)c(=O)c(C(=O)Nc2ccc(-c3cc(C4CCN(C(=O)C(C)C)CC4)n4ncnc(N)c34)cc2)cn1C(C)C]

Step 1: (E/Z)-3-((Dimethylamnino)methylene)-6-methyl-2H-pyran-2,4(3H)-dione

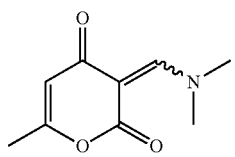

To a solution of 6-methyl-2H-pyran-2,4(3H)-dione (13 g, 103 mmol) in toluene (30 mL) was added N,N-dimethylformamide dimethyl acetal (15 ml, 113 mmol). The resulting solution was stirred at rt for 36 h, and concentrated to give a red solid, which was used directly in the next step. LCMS calcd for $C_9H_{12}NO_3$ (M+H)$^+$: m/z=182.1. Found: 182.1.

Step 2: 1-Isopropyl-6-methyl-4-oxo-1,4-dihydropyridine-3-carboxylic Acid

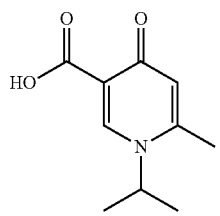

To a 250 mL round-bottomed flask was added (E/Z)-3-((dimethylamino)methylene)-6-methyl-2H-pyran-2,4(3H)-dione (2.0 g, 11.0 mmol), propan-2-amine (1.41 mL, 16.6 mmol) and sodium tert-butoxide (1.57 g, 16.3 mmol) in EtOH (80 mL). The round bottom was equipped with an air condenser and the resulting mixture was stirred at 90° C. for 18 h, cooled to rt, concentrated, and treated with water and $CH_2Cl_2$. The solution was acidified with 4 N HCl solution and upon separation the aqueous layer was extracted with $CH_2Cl_2$. The combined organic layers were washed with water, brine, dried over $Na_2SO_4$, and concentrated to give the crude product, which was used directly in the next step. LCMS calcd for $C_{10}H_{14}NO_3$ (M+H)$^+$: m/z=196.1. Found: 196.1.

Step 3: 5-Bromo-1-isopropyl-6-methyl-4-oxo-1,4-dihydropyridine-3-carboxylic Acid

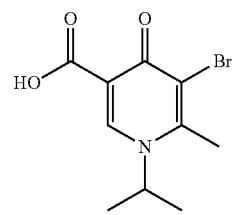

To a solution of 1-isopropyl-6-methyl-4-oxo-1,4-dihydropyridine-3-carboxylic acid (219 mg, 1.12 mmol) in DCE (5 mL) was added NBS (295 mg, 1.66 mmol) and the resulting solution was stirred at rt overnight, diluted with water, and upon separation the aqueous layer was extracted with $CH_2Cl_2$. The combined organic layers were washed with water, brine, dried over $Na_2SO_4$, and concentrated to give the crude product, which was used directly in the next step. LCMS calcd for $C_{10}H_{13}BrNO_3$ (M+H)$^+$: m/z=274.0. Found: 274.0.

Step 4: N-(4-(4-Amino-7-(1-isobutyrylpiperidin-4-yl)pyrrolo[2,1-f][1,2,4]triazin-5-yl)phenyl)-5-bromo-1-isopropyl-6-methyl-4-oxo-1,4-dihydropyridine-3-carboxamide

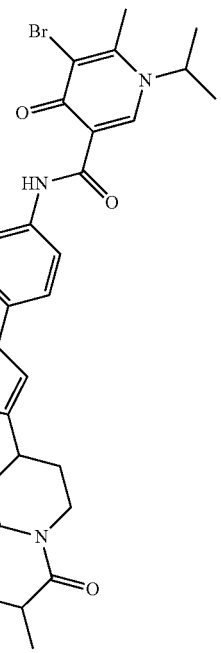

To a solution of 5-bromo-1-isopropyl-6-methyl-4-oxo-1, 4-dihydropyridine-3-carboxylic acid (154 mg, 0.56 mmol) and HATU (256 mg, 0.67 mmol) in DCE (5 mL) was added DIPEA (0.24 mL, 1.41 mmol) and 1-(4-(4-amino-5-(4-aminophenyl)pyrrolo[2,1-f][1,2,4]triazin-7-yl)piperidin-1-yl)-2-methylpropan-1-one (213 mg, 0.56 mmol) (from example 83, step 2). The resulting solution was stirred at rt overnight, and purified via column chromatography (0% to 100% EtOAc in hexanes) to give the product. LCMS calcd for $C_{31}H_{37}BrN_7O_3(M+H)^+$: m/z=634.2. Found: 634.2.

Step 5: N-(4-(4-Amino-7-(1-isobutyrylpiperidin-4-yl)pyrrolo[2,1-f][1,2,4]triazin-5-yl)phenyl)-1-isopropyl-6-methyl-5-(1-methyl-1H-pyrazol-5-yl)-4-oxo-1, 4-dihydropyridine-3-carboxamide A mixture of N-(4-(4-amino-7-(1-isobutyrylpiperidin-4-yl)pyrrolo[2,1-f][1,2,4]triazin-5-yl)phenyl)-5-bromo-1-isopropyl-6-methyl-4-oxo-1,4-dihydropyridine-3-carboxamide (62 mg, 0.098 mmol), (1-methyl-1H-pyrazol-5-yl)boronic acid (61.5 mg, 0.489 mmol), chloro(2-dicyclohexylphosphino-2',4',6'-tri-i-propyl-1,1'-biphenyl)(2'-amino-1,1'-biphenyl-2-yl) palladium(II) (Xphos Pd G2) (11.53 mg, 0.015 mmol), and potassium phosphate tribasic (0.024 ml, 0.29 mmol) in 1,4-dioxane (2.0 ml) and water (0.40 ml) was degassed and purged with $N_2$ several times prior to heating in a sealed vial at 90° C. overnight. After cooling to rt, the mixture was diluted with MeOH, filtered, and purified via pH 2 preparative LC/MS (MeCN/water with TFA) to give the product as TFA salt. LCMS calcd for $C_{35}H_{42}N_9O_3$ $(M+H)^+$: m/z=636.3. Found: 636.4. $^1$H NMR (600 MHz, DMSO) δ 12.87 (s, 1H), 8.73 (s, 1H), 8.06 (s, 1H), 7.82 (d, J=8.7 Hz, 2H), 7.50 (d, J=1.8 Hz, 1H), 7.47 (d, J=8.6 Hz, 2H), 6.73 (s, 1H), 6.21 (d, J=1.8 Hz, 1H), 4.85-4.76 (m, 1H), 4.55 (d, J=12.9 Hz, 1H), 4.08 (d, J=13.1 Hz, 1H), 3.61 (s, 3H), 3.42 (dd, J=11.9, 3.7 Hz, 1H), 3.28-3.16 (m, 1H), 2.98-2.86 (m, 1H), 2.77-2.64 (m, 1H), 2.33 (s, 3H), 2.13-1.96 (m, 2H), 1.71-1.58 (m, 1H), 1.58-1.47 (m, 7H), 1.08-0.97 (m, 6H).

Example 98. N-(4-(4-Amino-7-(1-isobutyrylpiperidin-4-yl)pyrrolo[2,1-f][1,2,4]triazin-5-yl)phenyl)-5'-fluoro-1-isopropyl-2-methyl-4-oxo-1,4-dihydro-[3, 3'-bipyridine]-5-carboxamide

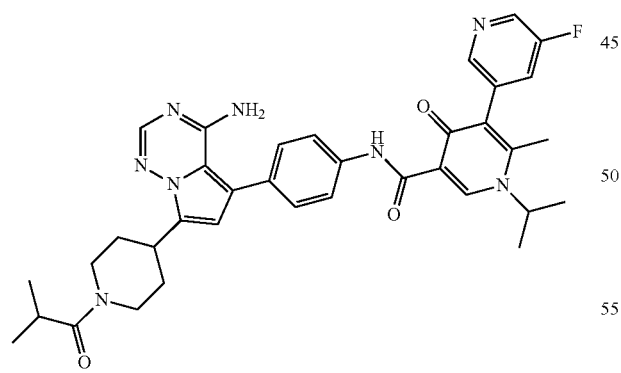 [SMILES: Cc1c(-c2cccc(C#N)c2)c(=O)c(C(=O)Nc2ccc(-c3cc(C4CCN(C(=O)C(C)C)CC4)n4ncnc(N)c34)cc2)cn1C(C)C]

This compound was prepared following a synthetic sequence analogous to that for example 97, using (5-fluoropyridin-3-yl)boronic acid instead of (1-methyl-1H-pyrazol-5-yl)boronic acid. This compound was purified via pH 2 preparative LC/MS (MeCN/water with TFA) to give the product as TFA salt. LCMS calcd for $C_{36}H_{40}FN_8O_3(M+H)^+$: m/z=651.3. Found: 651.3. $^1$H NMR (500 MHz, DMSO) δ 12.86 (s, 1H), 8.74 (s, 1H), 8.61 (d, J=2.8 Hz, 1H), 8.34 (m, 1H), 8.08 (s, 1H), 7.82 (d, J=8.7 Hz, 2H), 7.71 (m, 1H), 7.47 (d, J=8.6 Hz, 2H), 6.75 (s, 1H), 4.83 (m, 1H), 4.56 (m, 1H), 4.09 (m, 1H), 3.42 (m, 1H), 3.21 (m, 1H), 2.91 (m, 1H), 2.70 (m, 1H), 2.34 (s, 3H), 2.02 (m, 2H), 1.64 (m, 1H), 1.53 (m, 7H), 1.02 (m, 6H).

Example 99. N-(4-(4-Amino-7-(1-isobutyrylpiperidin-4-yl)pyrrolo[2,1-f][1,2,4]triazin-5-yl)phenyl)-5-(3-cyanophenyl)-1-isopropyl-6-methyl-4-oxo-1,4-dihydropyridine-3-carboxamide

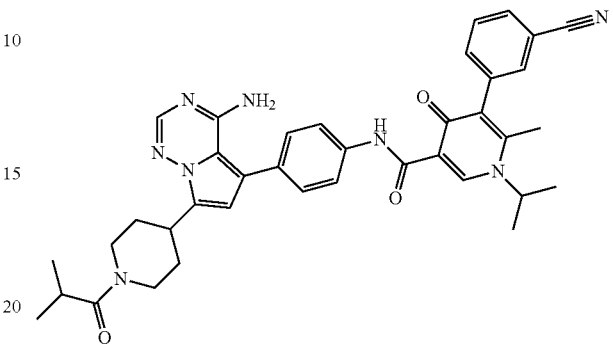

This compound was prepared following a synthetic sequence analogous to that for example 97, using (3-cyanophenyl)boronic acid instead of (1-methyl-1H-pyrazol-5-yl)boronic acid. This compound was purified via pH 2 preparative LC/MS (MeCN/water with TFA) to give the product as TFA salt. LCMS calculated for $C_{38}H_{41}N_8O_3$ $(M+H)^+$: m/z=657.3; Found: 657.3. $^1$H NMR (500 MHz, DMSO) δ 12.91 (s, 1H), 8.73 (s, 1H), 8.08 (s, 1H), 7.87 (m, 1H), 7.82 (d, J=8.7 Hz, 2H), 7.74 (m, 1H), 7.69 (m, 1H), 7.61 (m, 1H), 7.46 (d, J=8.6 Hz, 2H), 6.75 (s, 1H), 4.81 (m, 1H), 4.55 (m, 1H), 4.08 (m, 1H), 3.42 (m, 1H), 3.21 (m, 1H), 2.90 (m, 1H), 2.77-2.61 (m, 1H), 2.30 (s, 3H), 2.13-1.89 (m, 2H), 1.65 (m, 1H), 1.52 (m, 7H), 1.02 (m, 6H).

Example 100. N-(4-(4-Amino-6-bromo-7-(1-isobutyrylpiperidin-4-yl)pyrrolo[1,2-f][1,2,4]triazin-5-yl)phenyl)-4-methoxy-2-oxo-1-phenyl-1,2-dihydropyridine-3-carboxamide

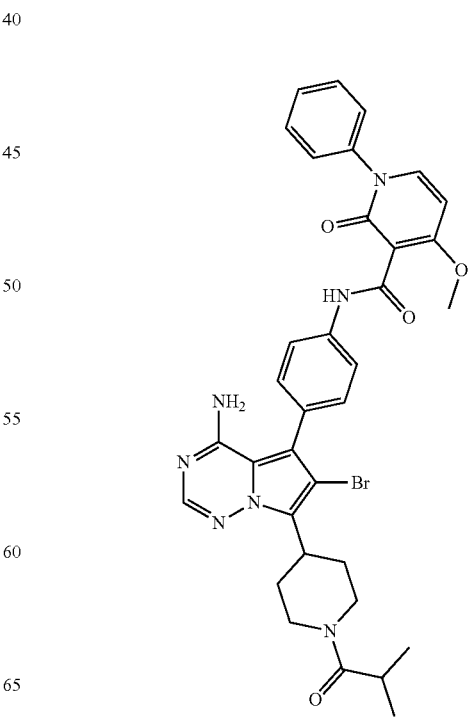

Step 1: 4-Methoxy-2-oxo-1-phenyl-1,2-dihydropyridine-3-carboxylic Acid

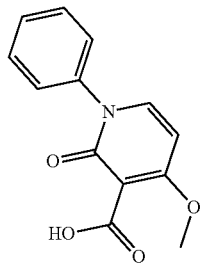 [SMILES: COc1ccn(-c2ccccc2)c(=O)c1C(=O)O]

A mixture of 4-methoxy-2-oxo-1,2-dihydropyridine-3-carboxylic acid (1.40 g, 8.28 mmol) (from Enamine Ltd.), phenylboronic acid (4.04 g, 33.1 mmol), activated 4 Å molecular sieves (2.59 g) and copper (II) acetate (4.51 g, 24.8 mmol) in CH$_2$Cl$_2$ (50 mL) was treated with pyridine (2.68 mL) and stirred at rt for 3 days. The reaction mixture was then diluted with MeOH, filtered, concentrated, and purified via column chromatography (0% to 100% MeOH in EtOAc) to afford the product as a light greenish powder (244 mg, 12%). LCMS calcd for C$_{13}$H$_{12}$NO$_4$ (M+H)$^+$: m/z=246.1. Found: 246.1.

Step 2: N-(4-(4-Amino-7-(1-isobutyrylpiperidin-4-yl)pyrrolo[1,2-f][1,2,4]triazin-5-yl)phenyl)-4-methoxy-2-oxo-1-phenyl-1,2-dihydropyridine-3-carboxamide

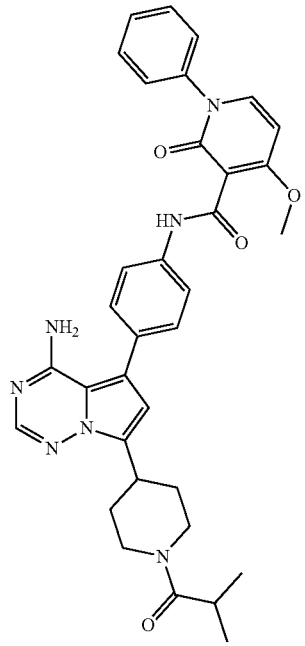 [SMILES: COc1ccn(-c2ccccc2)c(=O)c1C(=O)Nc1ccc(-c2cc(C3CCN(C(=O)C(C)C)CC3)n3ncnc(N)c23)cc1]

To a mixture of 4-methoxy-2-oxo-1-phenyl-1,2-dihydropyridine-3-carboxylic acid (35 mg, 0.14 mmol) and 1-(4-(4-amino-5-(4-aminophenyl)pyrrolo[2,1-f][1,2,4]triazin-7-yl)piperidin-1-yl)-2-methylpropan-1-one (59.4 mg, 0.16 mmol) (from example 83, step 2) in DMF (571 L) was added Et$_3$N (60 μL), followed by HATU (109 mg, 0.29 mmol). The resulting mixture was stirred at rt for 30 min, filtered, and the crude material was purified via column chromatography (0% to 30% MeOH in EtOAc) to give the desired product as a light yellow powder (70 mg, 81%). LCMS calcd for C$_{34}$H$_{36}$N$_7$O$_4$ (M+H)$^+$: m/z=606.3. Found: 606.3.

Step 3: N-(4-(4-Amino-6-bromo-7-(1-isobutyrylpiperidin-4-yl)pyrrolo[1,2-f][1,2,4]triazin-5-yl)phenyl)-4-methoxy-2-oxo-1-phenyl-1,2-dihydropyridine-3-carboxamide To a solution of N-(4-(4-amino-7-(1-isobutyrylpiperidin-4-yl)pyrrolo[2,1-f][1,2,4]triazin-5-yl)phenyl)-4-methoxy-2-oxo-1-phenyl-1,2-dihydropyridine-3-carboxamide (61 mg, 0.10 mmol) in DMF (403 μL) was added NBS (19 mg, 0.11 mmol). The resulting mixture was stirred at rt for 5 min, diluted with EtOAc/THF, filtered, washed with saturated NaHCO$_3$ solution, water, brine, dried over Na$_2$SO$_4$, and concentrated. The crude material was purified via pH 10 preparative LC/MS (MeCN/water with NH$_4$OH) to give the product as an off-white powder. LCMS calcd for C$_{34}$H$_{35}$BrN$_7$O$_4$ (M+H)$^+$: m/z=684.2. Found: 684.2.

Example 101. N-(4-(4-Amino-7-(1-isobutyrylpiperidin-4-yl)pyrrolo[1,2-f][1,2,4]triazin-5-yl)phenyl)-5-bromo-1-(5-fluoropyridin-3-yl)-6-methyl-2-oxo-1,2-dihydropyridine-3-carboxamide

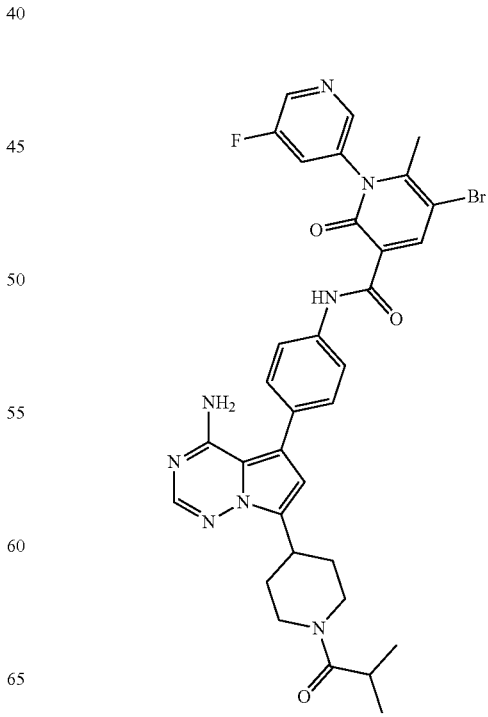

Step 1: 5-Bromo-5'-fluoro-6-methyl-2-oxo-2H-[1,3'-bipyridine]-3-carboxylic Acid

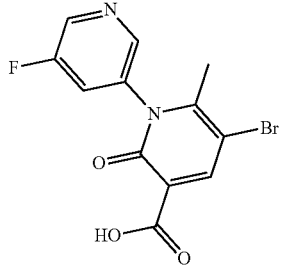 [SMILES: Cc1c(Br)cc(C(=O)O)c(=O)n1-c1cncc(F)c1]

Ethyl 5-bromo-5'-fluoro-6-methyl-2-oxo-2H-[1,3'-bipyridine]-3-carboxylate (1.0 g, 2.82 mmol) (from Affinity Research Chemicals) was dissolved in THF (10 mL) and ethanol (6.7 mL). The mixture was then treated with 1 M NaOH in water (11 mL), and the reaction mixture was stirred at 25° C. for 20 min. The resulting mixture was neutralized with 12 M HCl solution to pH 6-7 and the organic solvents were removed under vacuum. The resulting mixture was extracted with EtOAc. The combined organic layers were dried, and concentrated to give the product as a light brown powder (975 mg). LCMS calcd for $C_{12}H_9BrFN_2O_3(M+H)^+$: m/z=327.0. Found: 327.0.

Step 2: N-(4-(4-Amino-7-(1-isobutyrylpiperidin-4-yl)pyrrolo[2,1-f][1,2,4]triazin-5-yl)phenyl)-5-bromo-5'-fluoro-6-methyl-2-oxo-2H-[1,3'-bipyridine]-3-carboxamide To a mixture of 5-bromo-5'-fluoro-6-methyl-2-oxo-2H-[1,3'-bipyridine]-3-carboxylic acid (38 mg, 0.069 mmol) and 1-(4-(4-amino-5-(4-aminophenyl)pyrrolo[2,1-f][1,2,4]triazin-7-yl)piperidin-1-yl)-2-methylpropan-1-one (25 mg, 0.066 mmol) (from example 83, step 2) in DMF (264 µL) was added Et₃N (28 µL), followed by HATU (50 mg, 0.13 mmol). The resulting mixture was stirred at rt for 20 min, and the crude material was purified via pH 2 preparative LC/MS (MeCN/water with TFA) to give the product as an off-white powder (TFA salt). LCMS calcd for $C_{33}H_{33}BrFN_5O_3$ (M+H)⁺: m/z=687.2. Found: 687.2. ¹H NMR (600 MHz, DMSO) δ 11.64 (s, 1H), 8.84 (d, J=2.6 Hz, 1H), 8.62 (d, J=12.6 Hz, 2H), 8.12 (dt, J=9.2, 2.3 Hz, 1H), 8.06 (s, 1H), 7.82 (d, J=8.6 Hz, 2H), 7.47 (d, J=8.5 Hz, 2H), 6.73 (s, 1H), 4.55 (d, J=12.6 Hz, 1H), 4.07 (d, J=14.0 Hz, 1H), 3.42 (tt, J=12.0, 3.5 Hz, 1H), 3.21 (t, J=12.9 Hz, 1H), 2.91 (dt, J=13.5, 6.7 Hz, 1H), 2.75-2.66 (m, 2H), 2.25 (s, 3H), 2.04 (dd, J=30.5, 13.5 Hz, 2H), 1.72 (m, 1H), 1.60 (m, 1H), 1.52 (d, J=12.1 Hz, 1H), 1.05-0.99 (m, 6H).

Example 102. N-(4-(4-Amino-7-(1-isobutyrylpiperidin-4-yl)pyrrolo[2,1-f][1,2,4]triazin-5-yl)phenyl)-5-(cyanomethyl)-5'-fluoro-6-methyl-2-oxo-2H-[1,3'-bipyridine]-3-carboxamide

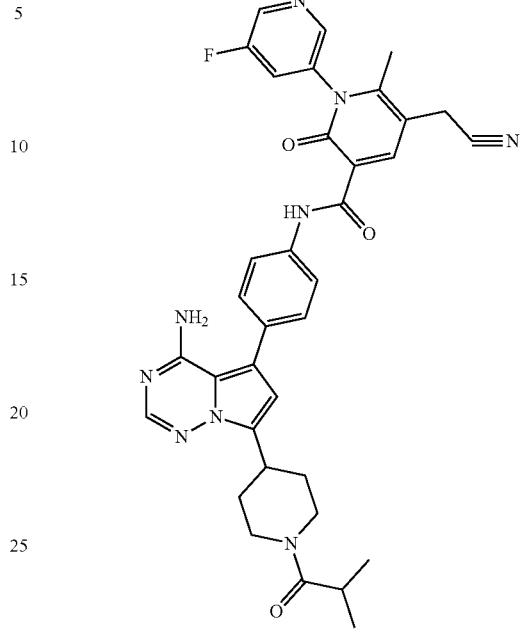

To a stirred mixture of N-(4-(4-amino-7-(1-isobutyrylpiperidin-4-yl)pyrrolo[2,1-f][1,2,4]triazin-5-yl)phenyl)-5-bromo-5'-fluoro-6-methyl-2-oxo-2H-[1,3'-bipyridine]-3-carboxamide (8.0 mg, 0.012 mmol) (from example 101, step 2), isoxazol-4-ylboronic acid (2.0 mg, 0.02 mmol), 1,4-dioxane (200 µL), N-ethyl-N-isopropylpropan-2-amine (4.5 mL) and water (40 µL) was added Pd(tBu₃)₂(3.0 mg, 5.8 µmol). The reaction mixture was then heated at 110° C. for 60 min, cooled to rt, diluted with DMF, and purified via pH 10 preparative LC/MS (MeCN/water with NH₄OH) to give the product as an off-white powder. LCMS calcd for $C_{35}H_{35}FN_9O_3(M+H)^+$: m/z=648.3. Found: 648.3.

Example 103. N-(4-(4-Amino-7-(1-isobutyrylpiperidin-4-yl)pyrrolo[2,1-f][1,2,4]triazin-5-yl)phenyl)-5'-fluoro-6-methyl-2-oxo-5-(thiazol-4-yl)-2H-[1,3'-bipyridine]-3-carboxamide

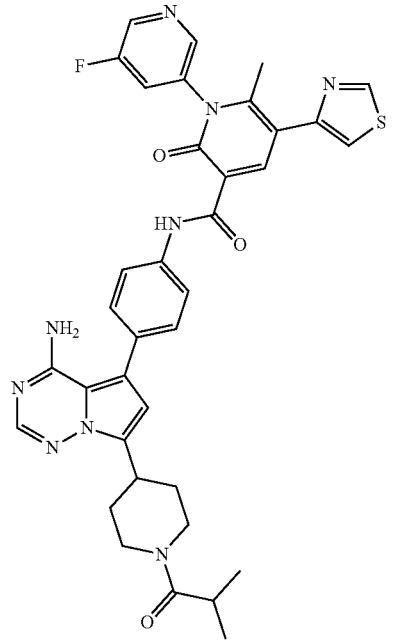 [SMILES: Cc1c(-c2cscn2)cc(C(=O)Nc2ccc(-c3cc(C4CCN(C(=O)C(C)C)CC4)n4ncnc(N)c34)cc2)c(=O)n1-c1cncc(F)c1]

To a mixture of N-(4-(4-amino-7-(1-isobutyrylpiperidin-4-yl)pyrrolo[2,1-f][1,2,4]triazin-5-yl)phenyl)-5-bromo-5'-fluoro-6-methyl-2-oxo-2H-[1,3'-bipyridine]-3-carboxamide (8.0 mg, 0.012 mmol) and Pd(Ph$_3$P)$_4$ (2.7 mg, 2.3 μmol) in toluene (0.30 mL) was added 4-(tributylstannyl)thiazole (8.7 mg, 0.023 mmol). The reaction mixture was sealed in a microwave vial, vacuumed and backfilled with N$_2$ several times, and heated at 120° C. for 20 h. The reaction mixture was cooled to rt, and the crude material was purified via pH 10 preparative LC/MS (MeCN/water with NH$_4$OH) to give the product as an off-white powder. LCMS calcd for C$_{36}$H$_{35}$FN$_9$O$_3$S (M+H)$^+$: m/z=692.3. Found: 692.3.

Example 104. N-(4-(4-Amino-7-(1-isobutyrylpiperidin-4-yl)pyrrolo[2,1-f][1,2,4]triazin-5-yl)phenyl)-6-oxo-1-phenyl-1,6-dihydro-[2,2'-bipyridine]-5-carboxamide

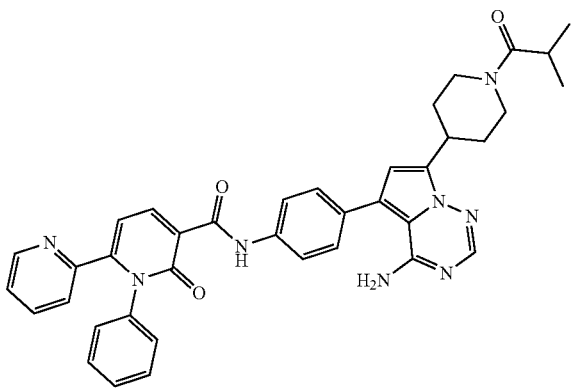 [SMILES: CC(C)C(=O)N1CCC(c2cc(-c3ccc(NC(=O)c4ccc(-c5ccccn5)n(-c5ccccc5)c4=O)cc3)c3c(N)ncnn23)CC1]

Step 1: 6-Oxo-1-phenyl-1,6-dihydro-[2,2'-bipyridine]-5-carbonitrile

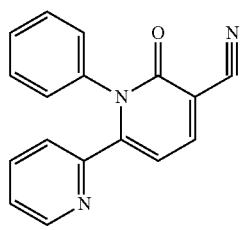 [SMILES: N#Cc1ccc(-c2ccccn2)n(-c2ccccc2)c1=O]

A mixture of 2-cyano-N-phenylacetamide (1.60 g, 10.0 mmol), 3-(dimethylamino)-1-(pyridin-2-yl)prop-2-en-1-one (1.94 g, 11.0 mmol) and 1,4-diazabicyclo[2.2.2]octane (0.98 mL, 10.0 mmol) in EtOH (20 mL) was heated at 90° C. overnight. After cooling to rt, the reaction mixture was concentrated, and partitioned between CH$_2$Cl$_2$ (60 mL) and 2 M HCl solution (20 mL). The organic layer was separated, washed with water, dried over MgSO$_4$, concentrated, and purified via column chromatography (20% to 100% EtOAc in hexanes) to afford the product (1.25 g, 46%). LCMS calcd for C$_{17}$H$_{12}$N$_3$O (M+H)$^+$: m/z=274.1. Found: 274.2.

Step 2: 6-Oxo-1-phenyl-1,6-dihydro-[2,2'-bipyridine]-5-carboxylic Acid

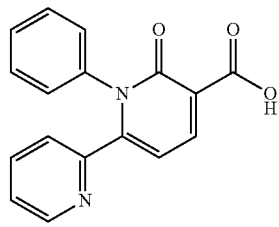 [SMILES: O=C(O)c1ccc(-c2ccccn2)n(-c2ccccc2)c1=O]

6-Oxo-1-phenyl-1,6-dihydro-[2,2'-bipyridine]-5-carbonitrile (0.20 g, 0.73 mmol) in concentrated sulfuric acid (1.5 mL) and water (1.5 mL) was heated at 120° C. for 3 h. After cooling to rt, the reaction mixture was carefully neutralized at 0° C. with 10% NaOH solution to pH ~7. The resulting mixture was extracted with 9:1 CH$_2$Cl$_2$/MeOH (5 mL×3), and the combined organic layers were dried over Na$_2$SO$_4$, and concentrated to give the crude product (0.19 g, 89%), which was used directly in the next step. LCMS calcd for C$_{17}$H$_{13}$N$_2$O$_3$ (M+H)$^+$: m/z=293.1. Found: 293.1.

Step 3: N-(4-(4-Amino-7-(1-isobutyrylpiperidin-4-yl)pyrrolo[2,1-f][1,2,4]triazin-5-yl)phenyl)-6-oxo-1-phenyl-1,6-dihydro-[2,2'-bipyridine]-5-carboxamide To a mixture of 6-oxo-1-phenyl-1,6-dihydro-[2,2'-bipyridine]-5-carboxylic acid (0.015 g, 0.050 mmol) and HATU (0.021 g, 0.055 mmol) in DMF (3 mL) was added 1-(4-(4-amino-5-(4-aminophenyl)pyrrolo[2,1-f][1,2,4]triazin-7-yl)piperidin-1-yl)-2-methylpropan-1-one (0.019 g, 0.0500 mmol) (from example 83, step 2) and Et$_3$N (0.021 ml, 0.15 mmol). The mixture was stirred at rt until completion, diluted with MeOH, adjusted with TFA to pH ~2, and purified via pH 2 preparative LC/MS (MeCN/water with TFA) to give the product as TFA salt. LCMS calcd for C$_{38}$H$_{37}$N$_8$O$_3$ (M+H)$^+$: m/z=653.3. Found: 653.3.

Example 105. N-(4-(4-Amino-7-(1-isobutyrylpiperidin-4-yl)pyrrolo[2,1-f][1,2,4]triazin-5-yl)phenyl)-6'-methyl-6-oxo-1-phenyl-1,6-dihydro-[2,3'-bipyridine]-5-carboxamide

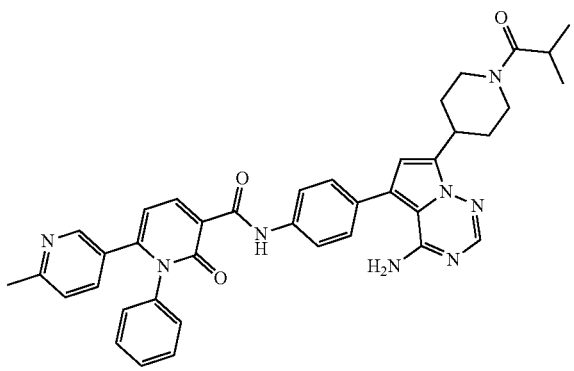 [SMILES: Cc1ccc(-c2ccc(C(=O)Nc3ccc(-c4cc(C5CCN(C(=O)C(C)C)CC5)n5ncnc(N)c45)cc3)c(=O)n2-c2ccccc2)cn1]

Step 1: 3-(Dimethylamino)-1-(6-methylpyridin-3-yl)prop-2-en-1-one

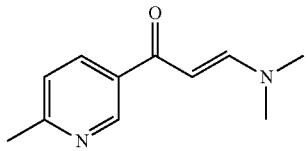

A mixture of 1-(6-methylpyridin-3-yl)ethan-1-one (2.50 g, 18.5 mmol) and 1,1-dimethoxy-N,N-dimethylmethanamine (4.41 g, 37.0 mmol) was heated at 100° C. for 8 h, cooled to rt, and concentrated. The resulting residue was triturated with ether. The solid was then collected by filtration and washed with ether to afford the crude product (2.75 g, 78%). LCMS calcd for $C_{11}H_{15}N_2O$ $(M+H)^+$: m/z=191.1. Found: 191.1.

Step 2: N-(4-(4-Amino-7-(1-isobutyrylpiperidin-4-yl)pyrrolo[2,1-f][1,2,4]triazin-5-yl)phenyl)-6'-methyl-6-oxo-1-phenyl-1,6-dihydro-[2,3'-bipyridine]-5-carboxamide This compound was prepared following a synthetic sequence analogous to those for example 104, from step 1 to step 3, using 3-(dimethylamino)-1-(6-methylpyridin-3-yl)prop-2-en-1-one instead of 3-(dimethylamino)-1-(pyridin-2-yl)prop-2-en-1-one. This compound was purified via pH 2 preparative LC/MS (MeCN/water with TFA) to give the product as TFA salt. LCMS calcd for $C_{39}H_{39}N_8O_3$ $(M+H)^+$: m/z=667.3. Found: 667.3.

Example 106. N-(4-(4-Amino-7-(1-isobutyrylpiperidin-4-yl)pyrrolo[2,1-f][1,2,4]triazin-5-yl)phenyl)-3-methyl-6-oxo-1-phenyl-1,6-dihydro-[2,3'-bipyridine]-5-carboxamide

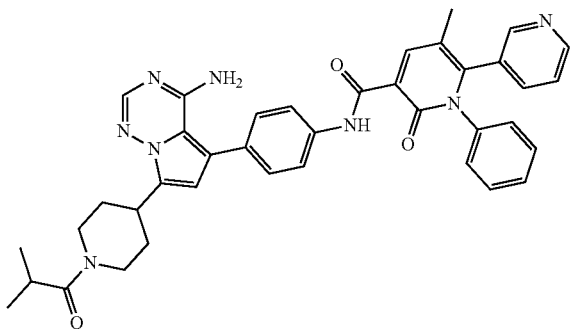 [SMILES: Cc1cc(C(=O)Nc2ccc(-c3cc(C4CCN(C(=O)C(C)C)CC4)n4ncnc(N)c34)cc2)c(=O)n(-c2ccccc2)c1-c1cccnc1]

Step 1: 3-(Dimethylamino)-2-methyl-1-(pyridin-3-yl)prop-2-en-1-one

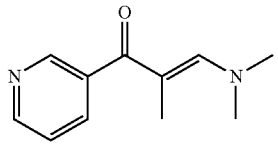

This compound was prepared following a synthetic sequence analogous to those for example 105, step 1, using 1-(pyridin-3-yl)propan-1-one instead of 1-(6-methylpyridin-3-yl)ethan-1-one. LCMS calcd for $C_{11}H_{15}N_2O$ $(M+H)^+$: m/z=191.1. Found: 191.1.

Step 2: N-(4-(4-Amino-7-(1-isobutyrylpiperidin-4-yl)pyrrolo[2,1-f][1,2,4]triazin-5-yl)phenyl)-3-methyl-6-oxo-1-phenyl-1,6-dihydro-[2,3'-bipyridine]-5-carboxamide This compound was prepared following a synthetic sequence analogous to those for example 104, from step 1 to step 3, using 3-(dimethylamino)-2-methyl-1-(pyridin-3-yl)prop-2-en-1-one instead of 3-(dimethylamino)-1-(pyridin-2-yl)prop-2-en-1-one. This compound was purified via pH 2 preparative LC/MS (MeCN/water with TFA) to give the product as TFA salt. LCMS calcd for $C_{39}H_{39}N_8O_3$ $(M+H)^+$: m/z=667.3. Found: 667.3.

Example 107. N-{4-[4-Amino-7-(1-isobutyrylpiperidin-4-yl)pyrrolo[2,1-f][1,2,4]triazin-5-yl]phenyl}-6-methyl-5-(1-methyl-1H-pyrazol-4-yl)-2-oxo-1-phenyl-1,2-dihydropyridine-3-carboxamide

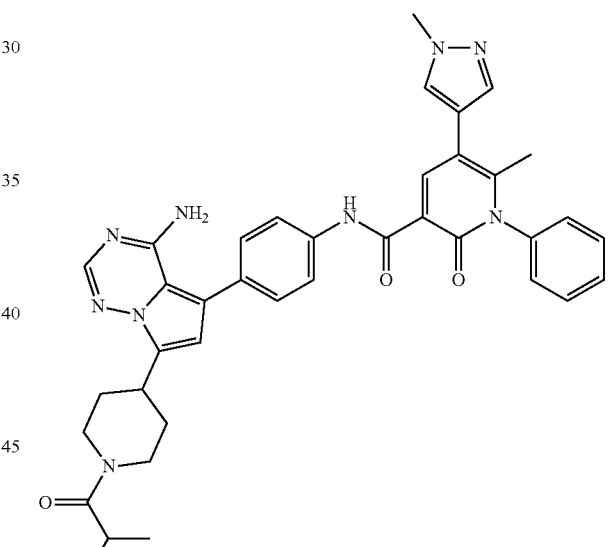

Step 1: 6-Methyl-2-oxo-1-phenyl-1,2-dihydropyridine-3-carbonitrile

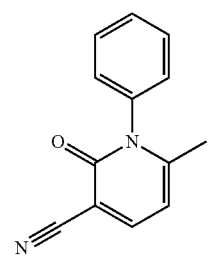 [SMILES: Cc1ccc(C#N)c(=O)n1-c1ccccc1]

To a mixture of 2-cyano-N-phenylacetamide (5.0 g, 31.2 mmol) and 4-methoxy-3-butene-2-one (6.2 g, 62 mmol) in 2-(2-methoxyethoxy)ethanol (75 mL) was added DABCO (3.50 g, 31.2 mmol). The resulting mixture was stirred at 120° C. overnight, cooled to rt, concentrated, and the resulting material was partitioned between CH$_2$Cl$_2$ (300 mL) and 2 M HCl solution (100 mL). The organic layer was separated, washed with water, dried over MgSO$_4$, concentrated, and added EtOAc. The mixture was stirred for 30 min, and the resulting solid was collected by filtration and dried to give the product (3.17 g). The filtrate was concentrated and purified via column chromatography (20% to 90% EtOAc in hexanes) to give an additional 1.58 g of the product as a brown solid (72% combined). LCMS calcd for C$_{13}$H$_{11}$N$_{20}$ (M+H)$^+$: m/z=211.1. Found: 211.1.

Step 2: 6-Methyl-2-oxo-1-phenyl-1,2-dihydropyridine-3-carboxylic Acid

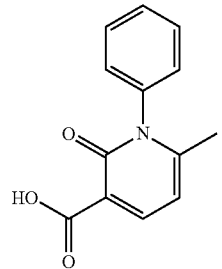 [SMILES: Cc1ccc(C(=O)O)c(=O)n1-c1ccccc1]

A mixture of 6-methyl-2-oxo-1-phenyl-1,2-dihydropyridine-3-carbonitrile (3.17 g, 15.1 mmol) and KOH (3.47 g, 61.8 mmol) in EtOH (34 mL)/water (8.0 mL) was stirred at 90° C. for 46 h. EtOH was evaporated and the resulting mixture was diluted with water and washed with CH$_2$Cl$_2$. The aqueous layer was then acidified with 2 N HCl solution, and extracted with CH$_2$Cl$_2$.

The combined organic layers were dried over MgSO$_4$, and concentrated to give the product (2.2 g, 64%). LCMS calcd for C$_{13}$H$_{12}$NO$_3$ (M+H)$^+$: m/z=230.1. Found: 230.1.

Step 3: 5-Bromo-6-methyl-2-oxo-1-phenyl-1,2-dihydropyridine-3-carboxylic Acid

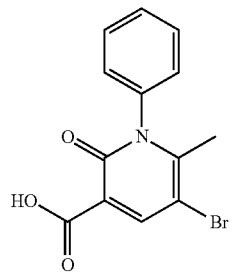 [SMILES: Cc1c(Br)cc(C(=O)O)c(=O)n1-c1ccccc1]

To a solution of 6-methyl-2-oxo-1-phenyl-1,2-dihydropyridine-3-carboxylic acid (2.20 g, 9.6 mmol) in DMF (30 mL) was added NBS (1.70 g, 9.55 mmol). The reaction mixture was stirred at rt for 4 h, added more NBS (300 mg), and stirred overnight. Water (100 mL) was then added to the reaction mixture at 0° C., and stirring continued for 20 min. The resulting solid was collected by filtration, washed with water, and dried to give the product as a tan solid (2.4 g, 81%). LCMS calcd for C$_{13}$H$_{11}$BrNO$_3$ (M+H)$^+$: m/z=308.0. Found: 308.0.

Step 4: tert-Butyl 4-[4-amino-5-(4-aminophenyl)pyrrolo[2,1-f][1,2,4]triazin-7-yl]piperidine-1-carboxylate

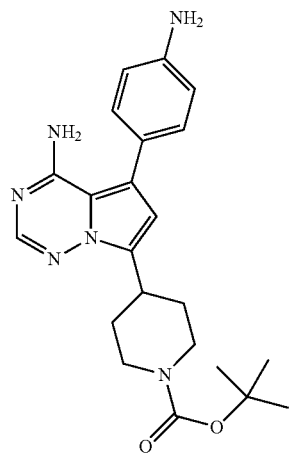 [SMILES: CC(C)(C)OC(=O)N1CCC(c2cc(-c3ccc(N)cc3)c3c(N)ncnn23)CC1]

A mixture of tert-butyl 4-(4-amino-5-bromopyrrolo[2,1-f][1,2,4]triazin-7-yl)piperidine-1-carboxylate (400 mg, 1 mmol) (from example 32, step 3), 4-(4,4,5,5-tetramethyl-1,3,2-dioxaborolan-2-yl)aniline (265 mg, 1.21 mmol), dicyclohexyl(2',4',6'-triisopropylbiphenyl-2-yl)phosphine-(2'-aminobiphenyl-2-yl)(chloro)palladium (1:1) (39.7 mg, 0.051 mmol), and potassium phosphate (643 mg, 3.03 mmol) in 1,4-dioxane (9 mL)/water (1.6 mL) was degassed with N$_2$ and then stirred at 90° C. overnight. The reaction mixture was cooled to rt, diluted with EtOAc, filtered through Celite, concentrated, and purified via column chromatography (10% to 100% EtOAc in hexanes, then 10% MeOH in EtOAc) to give the product (200 mg, 50%). LCMS calcd for C$_{22}$H$_{29}$N$_6$O$_2$ (M+H)$^+$: m/z=409.2. Found: 409.2.

Step 5: tert-Butyl 4-[4-amino-5-(4-{[(5-bromo-6-methyl-2-oxo-1-phenyl-1,2-dihydropyridin-3-yl)carbonyl]amino}phenyl)pyrrolo[2,1-f][1,2,4]triazin-7-yl]piperidine-1-carboxylate

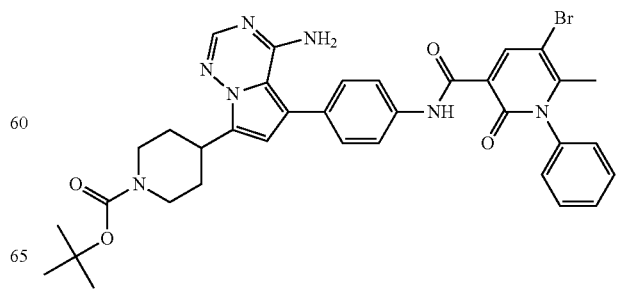

To a mixture of tert-butyl 4-[4-amino-5-(4-aminophenyl)pyrrolo[2,1-f][1,2,4]triazin-7-yl]piperidine-1-carboxylate (100 mg, 0.25 mmol) and 5-bromo-6-methyl-2-oxo-1-phenyl-1,2-dihydropyridine-3-carboxylic acid (75 mg, 0.25 mmol) in DMF (1.5 mL) was added Et$_3$N (51 uL, 0.37 mmol), followed by HATU (112 mg, 0.29 mmol). The resulting mixture was stirred at rt overnight, added water, and extracted with EtOAc. The combined organic layers were dried over Na$_2$SO$_4$, concentrated, and purified via column chromatography (10% to 80% EtOAc in hexanes, then 10% MeOH in EtOAc) to give the product (95 mg, 56%). LCMS calcd for C$_{35}$H$_{37}$BrN$_7$O$_4$ (M+H)$^+$: m/z=698.2. Found: 698.3.

Step 6: tert-Butyl 4-{4-amino-5-[4-({[6-methyl-5-(1-methyl-1H-pyrazol-4-yl)-2-oxo-1-phenyl-1,2-dihydropyridin-3-yl]carbonyl}amino)phenyl]pyrrolo[2,1-f][1,2,4]triazin-7-yl}piperidine-1-carboxylate

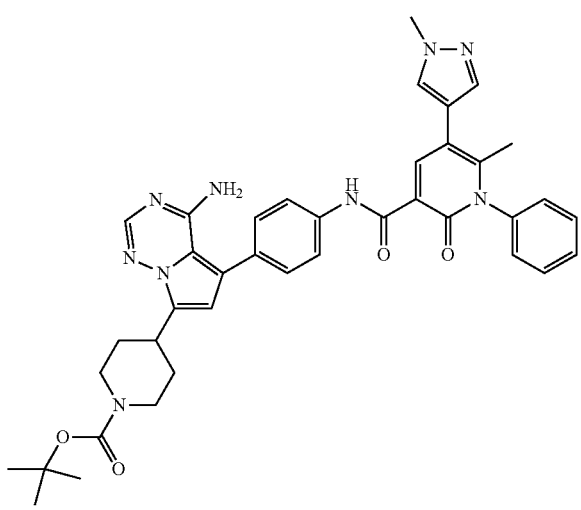 [SMILES: Cc1c(-c2cnn(C)c2)cc(C(=O)Nc2ccc(-c3cc(C4CCN(C(=O)OC(C)(C)C)CC4)n4ncnc(N)c34)cc2)c(=O)n1-c1ccccc1]

A mixture of tert-butyl 4-[4-amino-5-(4-{[(5-bromo-6-methyl-2-oxo-1-phenyl-1,2-dihydropyridin-3-yl)carbonyl]amino}phenyl)pyrrolo[2,1-f][1,2,4]triazin-7-yl]piperidine-1-carboxylate (95 mg, 0.14 mmol), 1-methyl-4-(4,4,5,5-tetramethyl-1,3,2-dioxaborolan-2-yl)-1H-pyrazole (34.0 mg, 0.16 mmol), dicyclohexyl(2',4',6'-triisopropylbiphenyl-2-yl)phosphine-(2'-aminobiphenyl-2-yl)(chloro)palladium (1:1) (5.3 mg, 0.0068 mmol), and potassium phosphate (87 mg, 0.41 mmol) in 1,4-dioxane (1.3 mL)/water (0.30 mL) was degassed with N$_2$ and stirred at 90° C. for 3 h. The resulting mixture was cooled to rt, diluted with CH$_2$Cl$_2$/water, and filtered through Celite. The organic layer was separated, and concentrated to give the crude product (88 mg), which was used directly in the next step. LCMS calcd for C$_{39}$H$_{42}$N$_9$O$_4$ (M+H)$^+$: m/z=700.3. Found: 700.4.

Step 7: N-(4-(4-Amino-7-(piperidin-4-yl)pyrrolo[1,2-f][1,2,4]triazin-5-yl)phenyl)-6-methyl-5-(1-methyl-1H-pyrazol-4-yl)-2-oxo-1-phenyl-1,2-dihydropyridine-3-carboxamide

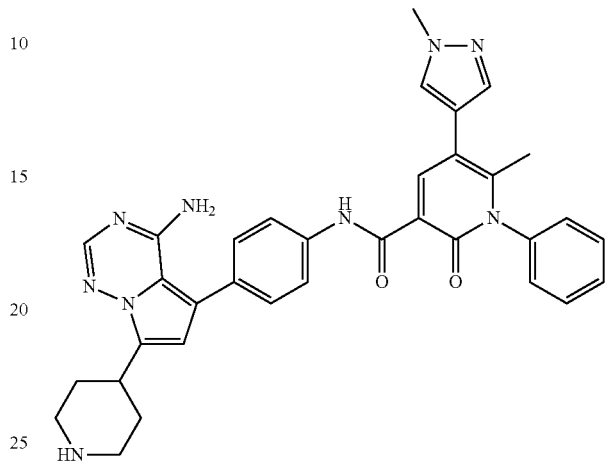

To a solution of tert-butyl 4-{4-amino-5-[4-({[6-methyl-5-(1-methyl-1H-pyrazol-4-yl)-2-oxo-1-phenyl-1,2-dihydropyridin-3-yl]carbonyl}amino)phenyl]pyrrolo[2,1-f][1,2,4]triazin-7-yl}piperidine-1-carboxylate (87 mg, 0.12 mmol) in CH$_2$Cl$_2$ (2 mL) was added TFA (1 mL). The resulting mixture was stirred at rt for 1 h, concentrated, and dried to give the product (90 mg) as TFA salt. LCMS calculated for C$_{34}$H$_{34}$N$_9$O$_2$ (M+H)$^+$: m/z=600.3; Found: 600.2.

Step 8: N-{4-[4-Amino-7-(1-isobutyrylpiperidin-4-yl)pyrrolo[2,1-f][1,2,4]triazin-5-yl]phenyl}-6-methyl-5-(1-methyl-1H-pyrazol-4-yl)-2-oxo-1-phenyl-1,2-dihydropyridine-3-carboxamide To a mixture of N-[4-(4-amino-7-piperidin-4-ylpyrrolo[2,1-f][1,2,4]triazin-5-yl)phenyl]-6-methyl-5-(1-methyl-1H-pyrazol-4-yl)-2-oxo-1-phenyl-1,2-dihydropyridine-3-carboxamide (60 mg, 0.084 mmol) and Et$_3$N (59 uL, 0.42 mmol) in CH$_2$Cl$_2$ (1 mL) was added isobutyryl chloride (12 uL, 0.11 mmol). The resulting mixture was stirred at rt for 90 min, and directly purified via pH 2 preparative LC/MS (MeCN/water with TFA) to give the product as TFA salt. LCMS calculated for C$_{38}$H$_{40}$N$_9$O$_3$ (M+H)$^+$: m/z=670.3; Found: 670.2. $^1$H NMR (600 MHz, DMSO) δ 12.05 (s, 1H), 8.46 (s, 1H), 8.01 (s, 1H), 7.97 (s, 1H), 7.81 (d, J=8.7 Hz, 2H), 7.64-7.59 (m, 3H), 7.57-7.52 (m, 1H), 7.45-7.41 (m, 4H), 6.69 (s, 1H), 4.53 (d, J=12.3 Hz, 1H), 4.05 (d, J=12.9 Hz, 1H), 3.89 (s, 3H), 3.43-3.34 (m, 1H), 3.24-3.15 (m, 1H), 2.89 (hept, J=6.7 Hz, 1H), 2.68 (t, J=12.0 Hz, 1H), 2.09 (s, 3H), 2.02 (dd, J=32.4, 13.2 Hz, 2H), 1.56 (dd, J=72.6, 9.9 Hz, 2H), 1.03-0.97 (m, 6H).

Example 108. N-{4-[4-Amino-7-(1-isobutyrylpiperidin-4-yl)pyrrolo[2,1-f][1,2,4]triazin-5-yl]phenyl}-6-methyl-2-oxo-1-phenyl-5-pyrimidin-2-yl-1,2-dihydropyridine-3-carboxamide

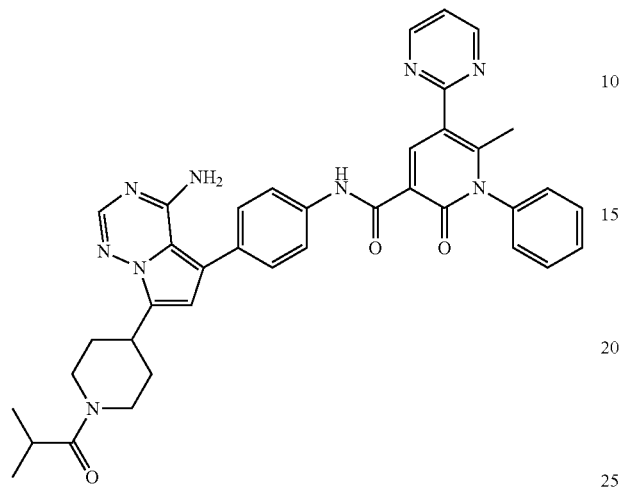

Step 1: Ethyl 5-bromo-6-methyl-2-oxo-1-phenyl-1,2-dihydropyridine-3-carboxylate

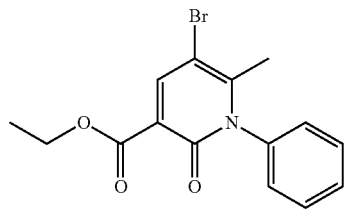 [SMILES: CCOC(=O)c1cc(Br)c(C)n(-c2ccccc2)c1=O]

A mixture of 5-bromo-6-methyl-2-oxo-1-phenyl-1,2-dihydropyridine-3-carboxylic acid (1.0 g, 3.24 mmol) (example 107, step 3) and sulfuric acid (180 uL, 3.4 mmol) in EtOH (60 mL) was refluxed for 3 days, cooled to rt, and concentrated. The resulting residue was dissolved in CH$_2$Cl$_2$, washed with saturated NaHCO$_3$ solution, dried over MgSO4, and concentrated to give the product as a brown solid (1 g). LCMS calcd for C$_{15}$H$_{15}$BrNO$_3$ (M+H)$^+$: m/z=336.0; Found: 336.1.

Step 2: Ethyl 6-methyl-2-oxo-1-phenyl-5-(4,4,5,5-tetramethyl-1,3,2-dioxaborolan-2-yl)-1,2-dihydropyridine-3-carboxylate

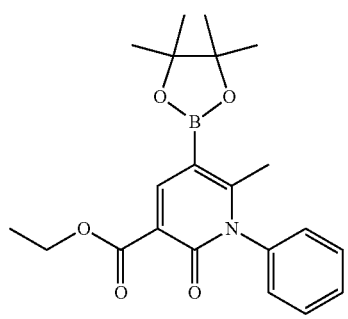 [SMILES: CCOC(=O)c1cc(B2OC(C)(C)C(C)(C)O2)c(C)n(-c2ccccc2)c1=O]

A mixture of ethyl 5-bromo-6-methyl-2-oxo-1-phenyl-1,2-dihydropyridine-3-carboxylate (520 mg, 1.5 mmol), 4,4,5,5,4',4',5',5'-octamethyl-[2,2']bi[[1,3,2]dioxaborolanyl] (786 mg, 3.09 mmol), [1,1'-bis(diphenylphosphino)ferrocene] dichloropalladium (II) (57 mg, 0.077 mmol), and potassium acetate (455 mg, 4.64 mmol) in 1,4-dioxane (13 mL) was degassed with N$_2$ for 5 min, and then stirred at 90° C. for 17 h, cooled to rt, and filtered through a plug of Celite (washed with EtOAc). The filtrate was washed with brine, dried over Na$_2$SO$_4$, and concentrated. The crude material was purified via column chromatography (15% to 65% EtOAc in hexanes) to give the product (168 mg, 28%). LCMS calcd for C$_{21}$H$_{27}$BNO$_5$ (M+H)$^+$: m/z=384.2; Found: 384.2.

Step 3: Ethyl 6-methyl-2-oxo-1-phenyl-5-pyrimidin-2-yl-1,2-dihydropyridine-3-carboxylate

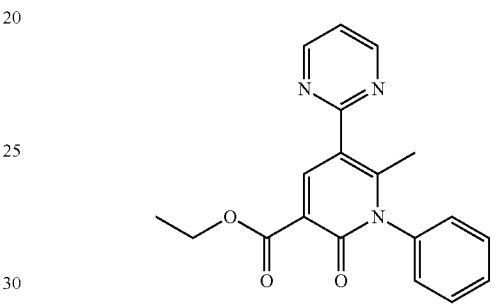

In a sealed microwave vial, a mixture of ethyl 6-methyl-2-oxo-1-phenyl-5-(4,4,5,5-tetramethyl-1,3,2-dioxaborolan-2-yl)-1,2-dihydropyridine-3-carboxylate (168 mg, 0.44 mmol), 2-bromopyrimidine (83.6 mg, 0.53 mmol), dicyclohexyl(2',4',6'-triisopropylbiphenyl-2-yl)phosphine-(2'-aminobiphenyl-2-yl)(chloro)palladium (1:1) (17 mg, 0.022 mmol) and potassium phosphate (279 mg, 1.32 mmol) in 1,4-dioxane (5 mL)/water (1 mL) was stirred at 90° C. for 2.5 h. The reaction mixture was then cooled to rt, diluted with CH$_2$Cl$_2$/water, and filtered through Celite. The organic layer was separated and concentrated to give the crude product (127 mg, 86%), which was used directly in the next step. LCMS calcd for C$_{19}$H$_{18}$N$_3$O$_3$ (M+H)$^+$: m/z=336.1; Found: 336.1.

Step 4: 6-Methyl-2-oxo-1-phenyl-5-pyrimidin-2-yl-1,2-dihydropyridine-3-carboxylic Acid

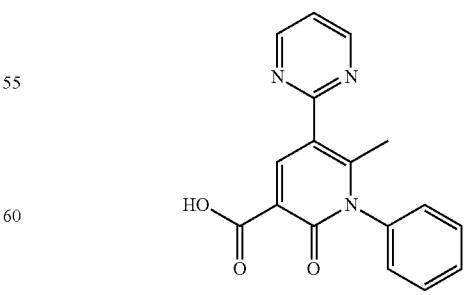

To a solution of ethyl 6-methyl-2-oxo-1-phenyl-5-pyrimidin-2-yl-1,2-dihydropyridine-3-carboxylate (127 mg, 0.38 mmol) in MeOH (2 mL)/water (0.4 mL) was added Lithium hydroxide, monohydrate (79 mg, 1.89 mmol). The resulting mixture was stirred at 40° C. for 3 h, and MeOH was evaporated. This mixture was acidified with 1N HCl solution, and the resulting solid was collected by filtration, washed with water, and dried to give the product (80 mg, 70%). LCMS calcd for $C_{17}H_{14}N_3O_3$ (M+H)$^+$: m/z=308.1; Found: 308.0.

Step 5: 6-Methyl-2-oxo-1-phenyl-5-pyrimidin-2-yl-N-[4-(4,4,5,5-tetramethyl-1,3,2-dioxaborolan-2-yl)phenyl]-1,2-dihydropyridine-3-carboxamide

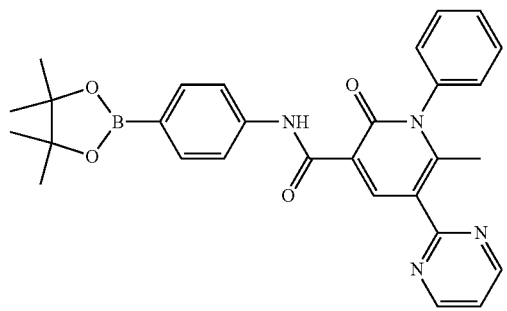 [SMILES: Cc1c(-c2ncccn2)cc(C(=O)Nc2ccc(B3OC(C)(C)C(C)(C)O3)cc2)c(=O)n1-c1ccccc1]

To a mixture of 4-(4,4,5,5-tetramethyl-1,3,2-dioxaborolan-2-yl)aniline (57 mg, 0.26 mmol) and 6-methyl-2-oxo-1-phenyl-5-pyrimidin-2-yl-1,2-dihydropyridine-3-carboxylic acid (80 mg, 0.3 mmol) in DMF (1.6 mL) was added Et$_3$N (54 uL, 0.390 mmol), followed by HATU (119 mg, 0.31 mmol). The resulting mixture was stirred at rt overnight, added water, and the resulting solid was collected by filtration, washed with water, and dried to give the product as a white solid (103 mg, 78%). LCMS calcd for $C_{29}H_{30}BN_4O_4$ (M+H)$^+$: m/z=509.2; Found: 509.2.

Step 6: N-(4-(4-Amino-7-(piperidin-4-yl)pyrrolo[1,2-f][1,2,4]triazin-5-yl)phenyl)-6-methyl-2-oxo-1-phenyl-5-(pyrimidin-2-yl)-1,2-dihydropyridine-3-carboxamide

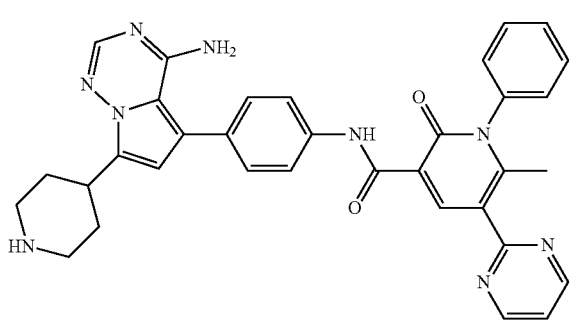 [SMILES: Cc1c(-c2ncccn2)cc(C(=O)Nc2ccc(-c3cc(C4CCNCC4)n4ncnc(N)c34)cc2)c(=O)n1-c1ccccc1]

A mixture of tert-butyl 4-(4-amino-5-bromopyrrolo[2,1-f][1,2,4]triazin-7-yl)piperidine-1-carboxylate (21 mg, 0.053 mmol) (from example 32, step 3), 6-methyl-2-oxo-1-phenyl-5-pyrimidin-2-yl-N-[4-(4,4,5,5-tetramethyl-1,3,2-dioxaborolan-2-yl)phenyl]-1,2-dihydropyridine-3-carboxamide (32 mg, 0.064 mmol), dicyclohexyl(2',4',6'-triisopropylbiphenyl-2-yl)phosphine-(2'-aminobiphenyl-2-yl)(chloro)palladium (1:1) (2.0 mg, 0.0027 mmol), and potassium phosphate (34 mg, 0.16 mmol) in 1,4-dioxane (0.65 mL)/water (0.1 mL) was degassed with N$_2$, and then stirred at 90° C. for 2 h. The reaction mixture was cooled to rt, diluted with CH$_2$Cl$_2$/water, and filtered through Celite. The organic layer was separated, concentrated, and added CH$_2$Cl$_2$ (0.4 mL) and 4 M HCl in 1,4-dioxane (120 uL, 0.48 mmol). The resulting mixture was stirred at rt overnight, and concentrated to give the crude product (30 mg), which was used directly in the next step. LCMS calcd for $C_{34}H_{32}N_9O_2$ (M+H)$^+$: m/z=598.3; Found: 598.2.

Step 7: N-{4-[4-Amino-7-(1-isobutyrylpiperidin-4-yl)pyrrolo[2,1-f][1,2,4]triazin-5-yl]phenyl}-6-methyl-2-oxo-1-phenyl-5-pyrimidin-2-yl-1,2-dihydropyridine-3-carboxamide This compound was prepared following a synthetic sequence analogous to those for example 107, step 8, using N-(4-(4-amino-7-(piperidin-4-yl)pyrrolo[1,2-f][1,2,4]triazin-5-yl)phenyl)-6-methyl-2-oxo-1-phenyl-5-(pyrimidin-2-yl)-1,2-dihydropyridine-3-carboxamide instead of N-[4-(4-amino-7-piperidin-4-ylpyrrolo[2,1-f][1,2,4]triazin-5-yl)phenyl]-6-methyl-5-(1-methyl-1H-pyrazol-4-yl)-2-oxo-1-phenyl-1,2-dihydropyridine-3-carboxamide. This compound was purified via pH 2 preparative LC/MS (MeCN/water with TFA) to give the product as TFA salt. LCMS calculated for $C_{38}H_{38}N_9O_3$ (M+H)$^+$: m/z=668.3; Found: 668.2. $^1$H NMR (600 MHz, DMSO) δ 11.89 (s, 1H), 9.16 (s, 1H), 8.96 (d, J=4.9 Hz, 2H), 8.08 (s, 1H), 7.83 (d, J=8.7 Hz, 2H), 7.63 (t, J=7.7 Hz, 2H), 7.59-7.53 (m, 1H), 7.51-7.44 (m, 5H), 6.74 (s, 1H), 4.53 (d, J=12.3 Hz, 1H), 4.06 (d, J=12.7 Hz, 1H), 3.48-3.33 (m, 1H), 3.19 (t, J=12.4 Hz, 1H), 2.89 (hept, J=6.7 Hz, 1H), 2.68 (t, J=11.9 Hz, 1H), 2.40 (s, 3H), 2.01 (dd, J=30.0, 12.2 Hz, 2H), 1.56 (dd, J=74.3, 9.4 Hz, 2H), 1.00 (d, J=3.9 Hz, 6H).

Example 109. N-{4-[4-Amino-7-(1-methylpiperidin-4-yl)pyrrolo[2,1-f][1,2,4]triazin-5-yl]phenyl)}-6-methyl-2-oxo-1-phenyl-5-pyrimidin-2-yl-1,2-dihydropyridine-3-carboxamide

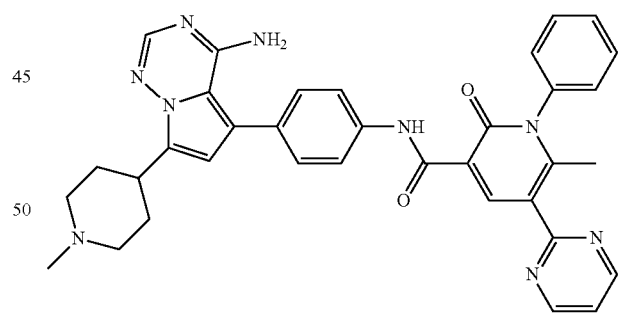

To a mixture of 5-bromo-7-(1-methylpiperidin-4-yl)pyrrolo[2,1-f][1,2,4]triazin-4-amine (from example 20, step 3) (31 mg, 0.10 mmol), 6-methyl-2-oxo-1-phenyl-5-pyrimidin-2-yl-N-[4-(4,4,5,5-tetramethyl-1,3,2-dioxaborolan-2-yl)phenyl]-1,2-dihydropyridine-3-carboxamide (61 mg, 0.12 mmol), dicyclohexyl(2',4',6'-triisopropylbiphenyl-2-yl)phosphine-(2'-aminobiphenyl-2-yl)(chloro)palladium (1:1) (3.9 mg, 0.0050 mmol), and potassium phosphate (64 mg, 0.30 mmol) in 1,4-dioxane (1.2 mL)/water (0.2 mL) was degassed with N$_2$ and then stirred at 90° C. for 3 h. The reaction mixture was cooled to rt, diluted with MeOH, filtered, and purified via pH 2 preparative LC/MS (MeCN/ water with TFA) to give the product as TFA salt. LCMS calcd for $C_{35}H_{34}N_9O_2$ (M+H)$^+$: m/z=612.3; Found: 612.2. $^1$H NMR (600 MHz, DMSO) δ 11.87 (s, 1H), 9.17 (s, 1H), 8.96 (d, J=4.9 Hz, 2H), 7.97 (s, 1H), 7.83 (d, J=8.7 Hz, 2H), 7.63 (t, J=7.7 Hz, 2H), 7.59-7.53 (m, 1H), 7.51-7.47 (m, 3H), 7.44 (d, J=8.6 Hz, 2H), 6.62 (s, 1H), 3.61-3.43 (m, 2H), 3.42-3.32 (m, 1H), 3.16 (q, J=10.4 Hz, 2H), 2.81 (d, J=4.5 Hz, 3H), 2.41 (s, 3H), 2.26 (d, J=14.3 Hz, 2H), 1.93-1.85 (m, 2H).

Example 110. N-{4-[4-Amino-7-(1-isobutyrylpiperidin-4-yl)pyrrolo[2,1-f][1,2,4]triazin-5-yl]phenyl}-6-methyl-5-morpholin-4-yl-2-oxo-1-phenyl-1,2-dihydropyridine-3-carboxamide

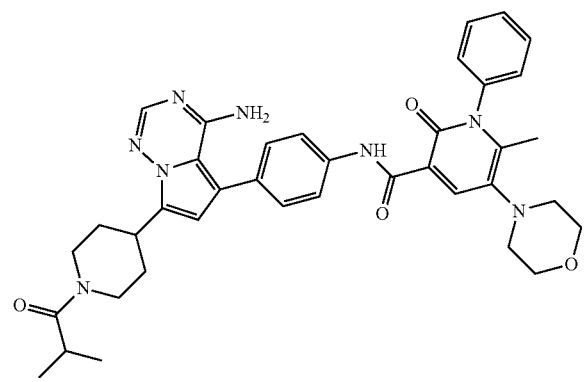 [SMILES: Cc1c(N2CCOCC2)cc(C(=O)Nc2ccc(-c3cc(C4CCN(C(=O)C(C)C)CC4)n4ncnc(N)c34)cc2)c(=O)n1-c1ccccc1]

Step 1: N-[4-(4-Amino-7-piperidin-4-ylpyrrolo[2,1-f][1,2,4]triazin-5-yl)phenyl]-6-methyl-5-morpholin-4-yl-2-oxo-1-phenyl-1,2-dihydropyridine-3-carboxamide

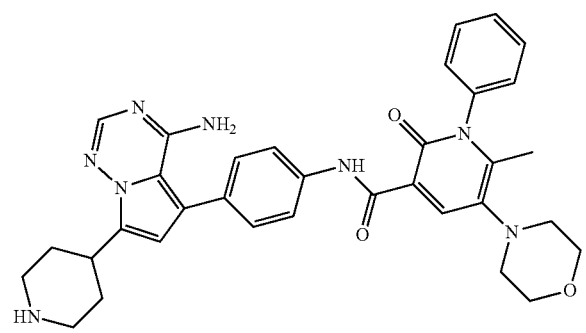 [SMILES: Cc1c(N2CCOCC2)cc(C(=O)Nc2ccc(-c3cc(C4CCNCC4)n4ncnc(N)c34)cc2)c(=O)n1-c1ccccc1]

A mixture of tert-butyl 4-[4-amino-5-(4-{[(5-bromo-6-methyl-2-oxo-1-phenyl-1,2-dihydropyridin-3-yl)carbonyl]amino}phenyl)pyrrolo[2,1-f][1,2,4]triazin-7-yl]piperidine-1-carboxylate (52 mg, 0.074 mmol) (from example 107, step 5) and morpholine (0.10 mL, 1.1 mmol) in DMF (1 mL) was heated at 180° C. under microwave conditions for 60 min, cooled to rt, purified via pH 2 preparative LC/MS (MeCN/water with TFA), and concentrated (de-Boc occurred during this process) to give the product as TFA salt. LCMS calculated for $C_{34}H_{37}N_8O_3$ (M+H)$^+$: m/z=605.3; Found: 605.4.

Step 2: N-{4-[4-Amino-7-(1-isobutyrylpiperidin-4-yl)pyrrolo[2,1-f][1,2,4]triazin-5-yl]phenyl}-6-methyl-5-morpholin-4-yl-2-oxo-1-phenyl-1,2-dihydropyridine-3-carboxamide This compound was prepared following a synthetic sequence analogous to those for example 107, step 8, using N-[4-(4-amino-7-piperidin-4-ylpyrrolo[2,1-f][1,2,4]triazin-5-yl)phenyl]-6-methyl-5-morpholin-4-yl-2-oxo-1-phenyl-1,2-dihydropyridine-3-carboxamide instead of N-(4-(4-amino-7-(piperidin-4-yl)pyrrolo[1,2-f][1,2,4]triazin-5-yl)phenyl)-6-methyl-5-(1-methyl-1H-pyrazol-4-yl)-2-oxo-1-phenyl-1,2-dihydropyridine-3-carboxamide. This compound was purified via pH 2 preparative LC/MS (MeCN/water with TFA) to give the product as TFA salt. LCMS calculated for $C_{38}H_{43}N_8O_4$ (M+H)$^+$: m/z=675.3; Found: 675.3.

Example 111. N-(4-(4-Amino-7-(1-isobutyrylpiperidin-4-yl)pyrrolo[2,1-f][1,2,4]triazin-5-yl)phenyl)-5-cyano-6-methyl-2-oxo-1-phenyl-1,2-dihydropyridine-3-carboxamide

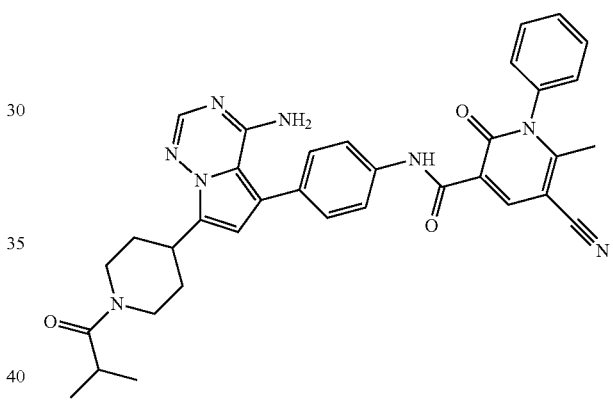

Step 1: Ethyl 5-cyano-6-methyl-2-oxo-1-phenyl-1,2-dihydropyridine-3-carboxylate

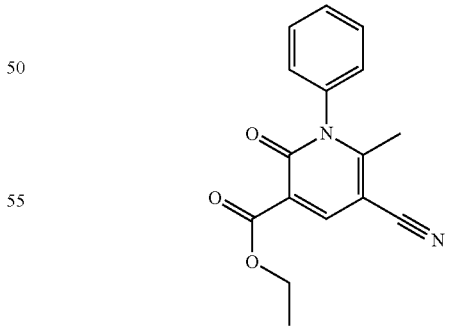

A mixture of ethyl 5-bromo-6-methyl-2-oxo-1-phenyl-1,2-dihydropyridine-3-carboxylate (300 mg, 0.89 mmol) (from example 108, step 1), Pd$_2$(dba)$_3$ (32.7 mg, 0.036 mmol), Xantphos (41 mg, 0.071 mmol), Zinc cyanide (105 mg, 0.89 mmol) and TMEDA (0.040 ml, 0.27 mmol) in DMF (2.5 ml) was degassed with N$_2$, and then stirred at 160° C. under microwave conditions for 10 min. After cooling to rt, the reaction mixture was filtered through Celite (washed with CH₂Cl₂), and concentrated to give the crude product (0.32 g), which was used directly in the next step. LCMS calcd for $C_{16}H_{15}N_2O_3$ (M+H)⁺: m/z=283.1; Found: 283.1.

Step 2: 5-Cyano-6-methyl-2-oxo-1-phenyl-, 2-dihydropyridine-3-carboxylic Acid

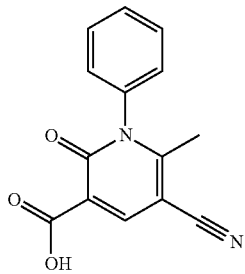 [SMILES: Cc1c(C#N)cc(C(=O)O)c(=O)n1-c1ccccc1]

A mixture of ethyl 5-cyano-6-methyl-2-oxo-1-phenyl-1,2-dihydropyridine-3-carboxylate (250 mg, 0.89 mmol) and lithium hydroxide monohydrate (186 mg, 4.43 mmol) in MeOH (7.0 ml)/water (0.70 ml) was stirred at rt for 5 h, and MeOH was evaporated. Water was added and the resulting mixture was acidified with 1N HCl solution, stirred for another 10 min, filtered, and extracted with CH₂Cl₂. The combined organic layers were dried over MgSO₄, and concentrated to give the product (147 mg, 65%). LCMS calculated for $C_{14}H_{11}N_2O_3$ (M+H)⁺: m/z=255.1; Found: 255.0.

Step 3: tert-butyl 4-(4-amino-5-(4-(5-cyano-6-methyl-2-oxo-1-phenyl-1,2-dihydropyridine-3-carboxamido)phenyl)pyrrolo[2,1-f][1,2,4]triazin-7-yl)piperidine-1-carboxylate

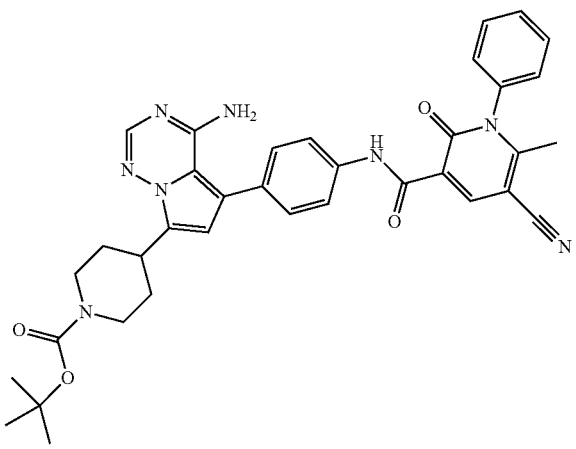 [SMILES: Cc1c(C#N)cc(C(=O)Nc2ccc(-c3cc(C4CCN(C(=O)OC(C)(C)C)CC4)n4ncnc(N)c34)cc2)c(=O)n1-c1ccccc1]

To a solution of tert-butyl 4-(4-amino-5-(4-aminophenyl)pyrrolo[2,1-f][1,2,4]triazin-7-yl)piperidine-1-carboxylate (200 mg, 0.49 mmol) (from example 107, step 4), 5-cyano-6-methyl-2-oxo-1-phenyl-1,2-dihydropyridine-3-carboxylic acid (124 mg, 0.49 mmol), and Et₃N (0.102 mL, 0.73 mmol) in DMF (4 mL) was added HATU (223 mg, 0.59 mmol). The resulting mixture was stirred at rt overnight, added water, and the resulting solid was collected by filtration, washed with water, and dried to give a light yellow solid (307 mg). LCMS calcd for $C_{36}H_{37}N_8O_4$ (M+H)⁺: m/z=645.3; Found: 645.4.

Step 4: N-(4-(4-Amino-7-(piperidin-4-yl)pyrrolo[2,1-f][1,2,4]triazin-5-yl)phenyl)-5-cyano-6-methyl-2-oxo-1-phenyl-1,2-dihydropyridine-3-carboxamide

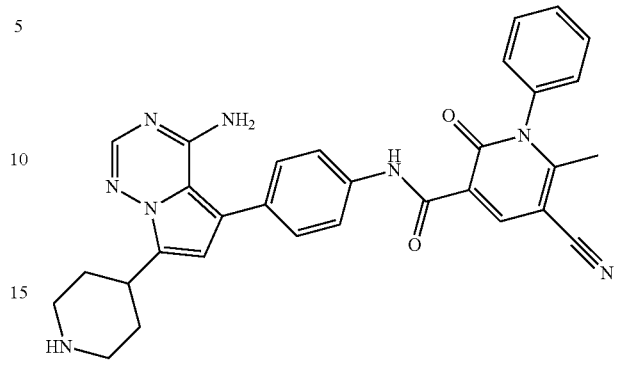

To a solution of tert-butyl 4-(4-amino-5-(4-(5-cyano-6-methyl-2-oxo-1-phenyl-1,2-dihydropyridine-3-carboxamido)phenyl)pyrrolo[1,2-f][1,2,4]triazin-7-yl)piperidine-1-carboxylate (300 mg, 0.47 mmol) in CH₂Cl₂ (4.5 ml) was added 4 M HCl in 1,4-dioxane (0.93 mL, 3.72 mmol). The resulting mixture was stirred at rt for 4 h, added EtOAc, and the resulting solid was collected by filtration, washed with EtOAc, and dried to give the product as a HCl salt (286 mg). LCMS calculated for $C_{31}H_{29}N_8O_2$ (M+H)⁺: m/z=545.2; Found: 545.2.

Step 5: N-(4-(4-Amino-7-(1-isobutyrylpiperidin-4-yl)pyrrolo[2,1-f][1,2,4]triazin-5-yl)phenyl)-5-cyano-6-methyl-2-oxo-1-phenyl-1,2-dihydropyridine-3-carboxamide This compound was prepared following a synthetic sequence analogous to those for example 107, step 8, using N-(4-(4-amino-7-(piperidin-4-yl)pyrrolo[2,1-f][1,2,4]triazin-5-yl)phenyl)-5-cyano-6-methyl-2-oxo-1-phenyl-1,2-dihydropyridine-3-carboxamide instead of N-(4-(4-amino-7-(piperidin-4-yl)pyrrolo[1,2-f][1,2,4]triazin-5-yl)phenyl)-6-methyl-5-(1-methyl-1H-pyrazol-4-yl)-2-oxo-1-phenyl-1,2-dihydropyridine-3-carboxamide. This compound was purified via pH 2 preparative LC/MS (MeCN/water with TFA) to give the product as TFA salt. LCMS calculated for $C_{35}H_{35}N_8O_3$ (M+H)⁺: m/z=615.3; Found: 615.3.

Example 111a. N³-(4-(4-Amino-7-(1-isobutyrylpiperidin-4-yl)pyrrolo[2,1-f][1,2,4]triazin-5-yl)phenyl)-6-methyl-2-oxo-1-phenyl-1,2-dihydropyridine-3,5-dicarboxamide

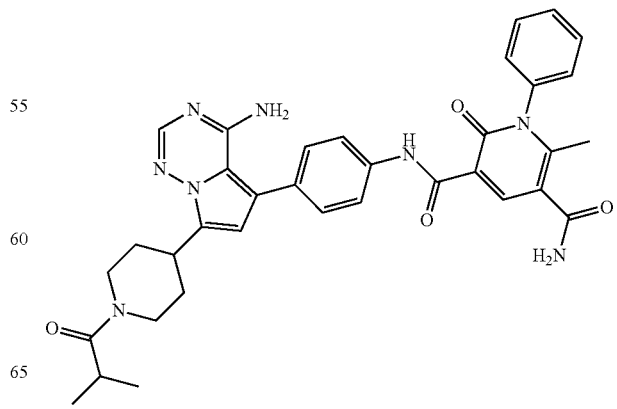

This compound was generated as a by-product from the synthetic sequence described in example 111, due to hydrolysis of the cyano group. This compound was purified via pH 2 preparative LC/MS (MeCN/water with TFA) to give the product as TFA salt. LCMS calculated for $C_{35}H_{37}N_8O_4$ (M+H)$^+$: m/z=633.3; Found: 633.3.

Example 112. 5-Acetyl-N-(4-(4-amino-7-(1-isobutyrylpiperidin-4-yl)pyrrolo[1,2-f][1,2,4]triazin-5-yl)phenyl)-6-methyl-2-oxo-1-phenyl-1,2-dihydropyridine-3-carboxamide

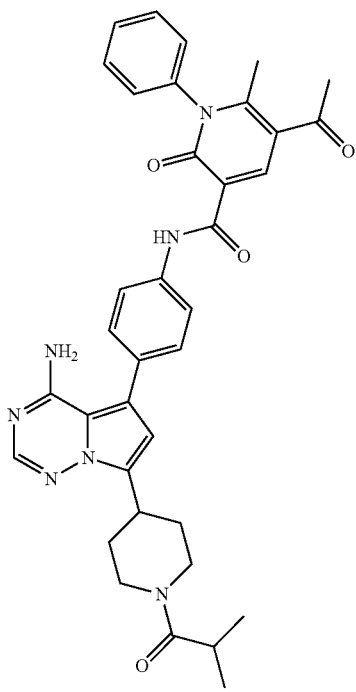 [SMILES: CC(=O)c1cc(C(=O)Nc2ccc(-c3cc(C4CCN(C(=O)C(C)C)CC4)n4ncnc(N)c34)cc2)c(=O)n(-c2ccccc2)c1C]

Step 1: Ethyl 5-acetyl-6-methyl-2-oxo-1-phenyl-1,2-dihydropyridine-3-carboxylate

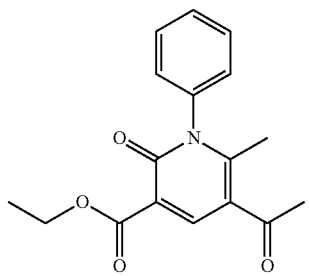 [SMILES: CCOC(=O)c1cc(C(C)=O)c(C)n(-c2ccccc2)c1=O]

A mixture of ethyl 5-bromo-6-methyl-2-oxo-1-phenyl-1,2-dihydropyridine-3-carboxylate (0.46 g, 1.37 mmol) (from example 108, step 1), Palladium(II) acetate (7.7 mg, 0.034 mmol) in 1-butyl-3-methylimidazolium tetrafluoroborate (2.81 mL, 15.1 mmol) was vacuumed and backfilled with N$_2$ three times. To the mixture was added 1-(vinyloxy)butane (0.90 mL, 6.84 mmol) and Et$_3$N (0.23 mL, 1.64 mmol) and the reaction mixture was stirred at 115° C. overnight. The resulting mixture was then cooled to rt, treated with HCl solution (7.07 ml, 11.63 mmol), stirred at rt for 30 min, and extracted with CH$_2$Cl$_2$. The combined organic layers were concentrated, and purified via column chromatography (0% to 100% EtOAc in hexanes) to give the product (0.22 g, 54%). LCMS calcd for $C_{17}H_{18}NO_4$ (M+H)$^+$: m/z=300.1. Found: 300.2.

Step 2: 5-Acetyl-6-methyl-2-oxo-1-phenyl-1,2-dihydropyridine-3-carboxylic Acid

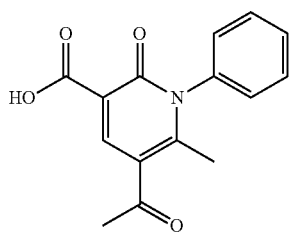 [SMILES: CC(=O)c1cc(C(=O)O)c(=O)n(-c2ccccc2)c1C]

A mixture of ethyl 5-acetyl-6-methyl-2-oxo-1-phenyl-1,2-dihydropyridine-3-carboxylate (0.070 g, 0.23 mmol) in 1 M NaOH solution (1.0 mL) and MeOH (2.0 mL) was stirred at rt for 1 h, and then neutralized with 1 N HCl solution to pH ~5. The resulting solid was collected by filtration, and dried to give the product (0.052 g, 82%). LCMS calcd for $C_{15}H_{14}NO_4$ (M+H)$^+$: m/z=272.1. Found: 272.1.

Step 3: 5-Acetyl-N-(4-(4-amino-7-(1-isobutyrylpiperidin-4-yl)pyrrolo[1,2-f][1,2,4]triazin-5-yl)phenyl)-6-methyl-2-oxo-1-phenyl-1,2-dihydropyridine-3-carboxamide This compound was prepared following a synthetic sequence analogous to that for example 83, step 5, using 5-acetyl-6-methyl-2-oxo-1-phenyl-1,2-dihydropyridine-3-carboxylic acid instead of 1-isopropyl-2,4-dioxo-3-(pyridin-2-yl)-1,2,3,4-tetrahydropyrimidine-5-carboxylic acid. This compound was purified via pH 2 preparative LC/MS (MeCN/water with TFA) to give the product as TFA salt. LCMS calcd for $C_{36}H_{38}N_7O_4$ (M+H)$^+$: m/z=632.3. Found: 632.4. $^1$H NMR (500 MHz, DMSO) δ 11.67 (s, 1H), 8.95 (s, 1H), 8.00 (s, 1H), 7.86-7.78 (m, 2H), 7.66-7.59 (m, 2H), 7.59-7.53 (m, 1H), 7.50-7.37 (m, 4H), 6.67 (s, 1H), 4.57-4.51 (m, 1H), 4.09-4.01 (m, 1H), 3.47-3.36 (m, 1H), 3.27-3.15 (m, 1H), 2.97-2.83 (m, 1H), 2.73-2.66 (m, 1H), 2.63 (s, 3H), 2.31 (s, 3H), 2.09-1.96 (m, 2H), 1.68-1.45 (m, 2H), 1.01 (t, J=6.8 Hz, 6H).

Example 113. N-(4-(4-Amino-7-(1-isobutyrylpiperidin-4-yl)pyrrolo[1,2-f][1,2,4]triazin-5-yl)phenyl)-1-(5-fluoropyridin-3-yl)-2,5-dioxo-1,2,5,6,7,8-hexahydroquinoline-3-carboxamide

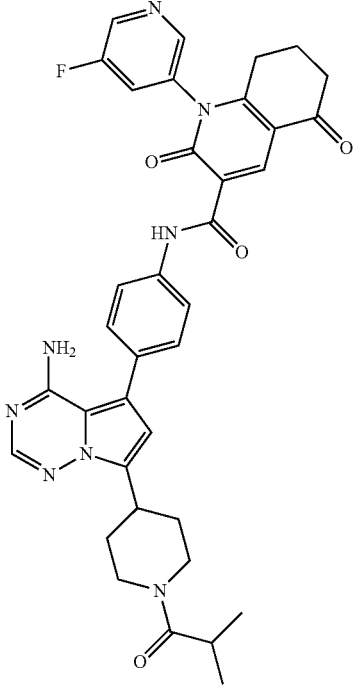 [SMILES: CC(C)C(=O)N1CCC(c2cc(-c3ccc(NC(=O)c4cc5c(n(-c6cncc(F)c6)c4=O)CCCC5=O)cc3)c3c(N)ncnn23)CC1]

Step 1: Ethyl 2,5-dioxo-5,6,7,8-tetrahydro-2H-chromene-3-carboxylate

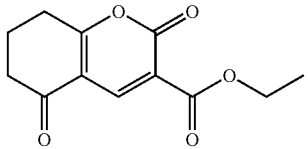 [SMILES: CCOC(=O)c1cc2c(oc1=O)CCCC2=O]

To a mixture of cyclohexane-1,3-dione (1.0 g, 8.9 mmol) in DMF (10 mL) was added 1 M t-BuOK in THF (8.9 mL, 8.9 mmol) at 0° C. The resulting mixture was stirred for 20 min and added ethyl (E)-2-cyano-3-ethoxyacrylate (1.51 g, 8.9 mmol). The reaction mixture was warmed to rt, stirred for 2 h, quenched with 1N HCl solution, and extracted with EtOAc. The combined organic layers were concentrated and purified via column chromatography (0% to 100% EtOAc in hexanes) to give the product. LCMS calcd for $C_{12}H_{13}O_5$ $(M+H)^+$: m/z=237.1. Found: 237.2.

Step 2: 1-(5-Fluoropyridin-3-yl)-2,5-dioxo-1,2,5,6,7,8-hexahydroquinoline-3-carboxylic Acid

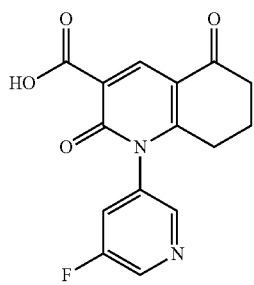 [SMILES: O=C1CCCc2c1cc(C(=O)O)c(=O)n2-c1cncc(F)c1]

A mixture of ethyl 2,5-dioxo-5,6,7,8-tetrahydro-2H-chromene-3-carboxylate (0.28 g, 1.185 mmol) and 5-fluoropyridin-3-amine (0.133 g, 1.19 mmol) in EtOH (3 mL) was stirred at rt overnight, treated with 1 M NaOH solution (2 mL), stirred at rt for 1 h, and purified via pH 2 preparative LC/MS (MeCN/water with TFA) to give the product (0.065 g, 18%). LCMS calcd for $C_{15}H_{12}FN_2O_4(M+H)^+$: m/z=303.1. Found: 303.2.

Step 3: N-(4-(4-Amino-7-(1-isobutyrylpiperidin-4-yl)pyrrolo[1,2-f][1,2,4]triazin-5-yl)phenyl)-1-(5-fluoropyridin-3-yl)-2,5-dioxo-1,2,5,6,7,8-hexahydroquinoline-3-carboxamide This compound was prepared following a synthetic sequence analogous to that for example 83, step 5, using 1-(5-fluoropyridin-3-yl)-2,5-dioxo-1,2,5,6,7,8-hexahydroquinoline-3-carboxylic acid instead of 1-isopropyl-2,4-dioxo-3-(pyridin-2-yl)-1,2,3,4-tetrahydropyrimidine-5-carboxylic acid. This compound was purified via pH 2 preparative LC/MS (MeCN/water with TFA) to give the product as TFA salt. LCMS calcd for $C_{36}H_{36}FN_8O_4(M+H)^+$: m/z=663.3. Found: 663.4. $^1$H NMR (600 MHz, DMSO) δ 11.38 (s, 1H), 8.96 (s, 1H), 8.86 (d, J=2.6 Hz, 1H), 8.68-8.62 (m, 1H), 8.16-8.12 (m, 1H), 8.09 (s, 1H), 7.84 (d, J=8.7 Hz, 2H), 7.47 (d, J=8.6 Hz, 2H), 6.75 (s, 1H), 4.58-4.51 (m, 1H), 4.12-4.03 (m, 1H), 3.46-3.36 (m, 1H), 3.26-3.16 (m, 1H), 2.94-2.85 (m, 1H), 2.75-2.63 (m, 1H), 2.63-2.52 (m, 4H), 2.09-1.95 (m, 4H), 1.69-1.47 (m, 2H), 1.06-0.93 (m, 6H).

Example 114. N-(4-(4-Amino-7-(1-isobutyrylpiperidin-4-yl)pyrrolo[1,2-f][1,2,4]triazin-5-yl)phenyl)-7,7-dimethyl-2,5-dioxo-1-(pyridin-3-yl)-1,2,5,6,7,8-hexahydroquinoline-3-carboxamide

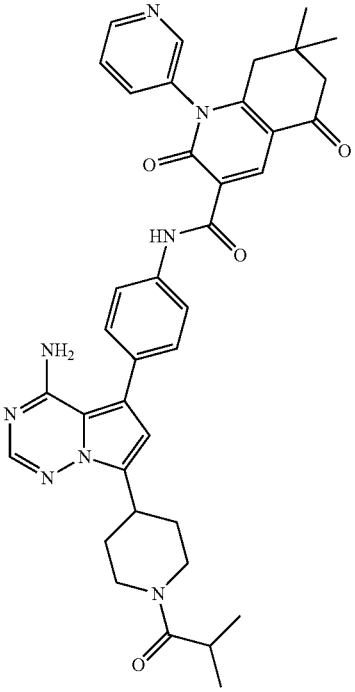 [SMILES: CC(C)C(=O)N1CCC(c2cc(-c3ccc(NC(=O)c4cc5c(n(-c6cccnc6)c4=O)CC(C)(C)CC5=O)cc3)c3c(N)ncnn23)CC1]

Step 1: Ethyl 7,7-dimethyl-2,5-dioxo-5,6,7,8-tetrahydro-2H-chromene-3-carboxylate

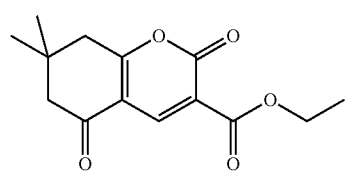 [SMILES: CCOC(=O)c1cc2c(oc1=O)CC(C)(C)CC2=O]

To a mixture of 5,5-dimethylcyclohexane-1,3-dione (2.0 g, 14.3 mmol) in DMF (20 mL) was added 1M t-BuOK in THF (14.3 mL, 14.3 mmol) at 0° C. The resulting mixture was stirred for 20 min, added ethyl (E)-2-cyano-3-ethoxy-acrylate (2.41 g, 14.3 mmol), warmed to rt, and stirred overnight. The reaction mixture was quenched with 1 N HCl solution, extracted with EtOAc, and the combined organic layers were concentrated and purified via column chromatography (0% to 100% EtOAc in hexanes) to give the product (2.8 g, 74%). LCMS calcd for $C_{14}H_{17}O_5(M+H)^+$: m/z=265.1. Found: 265.2.

Step 2: 7,7-Dimethyl-2,5-dioxo-1-(pyridin-3-yl)-1,2,5,6,7,8-hexahydroquinoline-3-carboxylic acid

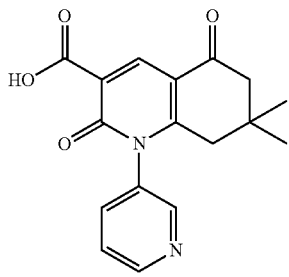 [SMILES: CC1(C)CC(=O)c2cc(C(=O)O)c(=O)n(-c3cccnc3)c2C1]

A mixture of ethyl 7,7-dimethyl-2,5-dioxo-5,6,7,8-tetrahydro-2H-chromene-3-carboxylate (244 mg, 0.92 mmol) and pyridin-3-amine (87 mg, 0.92 mmol) in EtOH (3 mL) was stirred at 60° C. overnight, cooled to rt, and the resulting solid was collected by filtration, and dried to give the product (170 mg, 59%). LCMS calcd for $C_{17}H_{17}N_2O_4$ $(M+H)^+$: m/z=313.1. Found: 313.2.

Step 3: N-(4-(4-Amino-7-(1-isobutyrylpiperidin-4-yl)pyrrolo[1,2-f][1,2,4]triazin-5-yl)phenyl)-7,7-dimethyl-2,5-dioxo-1-(pyridin-3-yl)-1,2,5,6,7,8-hexahydroquinoline-3-carboxamide This compound was prepared following a synthetic sequence analogous to that for example 83, step 5, using 7,7-dimethyl-2,5-dioxo-1-(pyridin-3-yl)-1,2,5,6,7,8-hexahydroquinoline-3-carboxylic acid instead of 1-isopropyl-2,4-dioxo-3-(pyridin-2-yl)-1,2,3,4-tetrahydropyrimidine-5-carboxylic acid. This compound was purified via pH 2 preparative LC/MS (MeCN/water with TFA) to give the product as TFA salt. LCMS calcd for $C_{38}H_{41}N_8O_4$ $(M+H)^+$: m/z=673.3. Found: 673.4. $^1$H NMR (500 MHz, DMSO) δ 11.44 (s, 1H), 8.95 (s, 1H), 8.80 (dd, J=4.8, 1.4 Hz, 1H), 8.70 (d, J=2.4 Hz, 1H), 8.09 (s, 1H), 8.01 (dt, J=8.1, 1.9 Hz, 1H), 7.84 (d, J=8.6 Hz, 2H), 7.73 (dd, J=8.1, 4.8 Hz, 1H), 7.47 (d, J=8.6 Hz, 2H), 6.76 (s, 1H), 4.59-4.49 (m, 1H), 4.12-4.03 (m, 1H), 3.46-3.37 (m, 1H), 3.26-3.15 (m, 1H), 2.96-2.84 (m, 1H), 2.74-2.65 (m, 1H), 2.49-2.42 (m, 4H), 2.11-1.96 (m, 2H), 1.69-1.46 (m, 2H), 1.10-0.89 (m, 12H).

Example 115. N-(4-(4-Amino-7-(1-isobutyrylpiperidin-4-yl)pyrrolo[1,2-f][1,2,4]triazin-5-yl)phenyl)-1-(5-fluoropyridin-3-yl)-6,6-dimethyl-2,5-dioxo-1,2,5,6,7,8-hexahydroquinoline-3-carboxamide

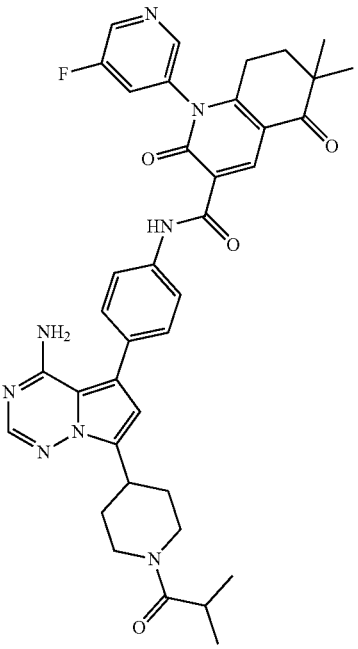 [SMILES: CC(C)C(=O)N1CCC(c2cc(-c3ccc(NC(=O)c4cc5c(n(-c6cncc(F)c6)c4=O)CCC(C)(C)C5=O)cc3)c3c(N)ncnn23)CC1]

Step 1: Ethyl 6,6-dimethyl-2,5-dioxo-5,6,7,8-tetrahydro-2H-chromene-3-carboxylate

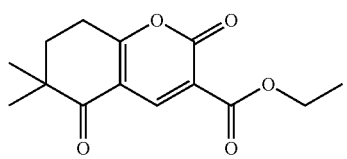 [SMILES: CCOC(=O)c1cc2c(oc1=O)CCC(C)(C)C2=O]

To a mixture of 4,4-dimethylcyclohexane-1,3-dione (1.8 g, 12.8 mmol) in DMF (10 mL) was added 1 M t-BuOK in THF (12.8 mL, 12.8 mmol) at 0° C. The resulting mixture was stirred for 20 min, added ethyl (E)-2-cyano-3-ethoxy-acrylate (2.17 g, 12.8 mmol), warmed to rt, and stirred overnight. The reaction mixture was quenched with 1 N HCl solution, extracted with EtOAc, and the combined organic layers were concentrated and purified via column chromatography (0% to 100% EtOAc in hexanes) to give the product (2.7 g, 80%). LCMS calcd for $C_{14}H_{17}O_5(M+H)^+$: m/z=265.1. Found: 265.2.

Step 2: 1-(5-Fluoropyridin-3-yl)-6,6-dimethyl-2,5-dioxo-1,2,5,6,7,8-hexahydroquinoline-3-carboxylic Acid

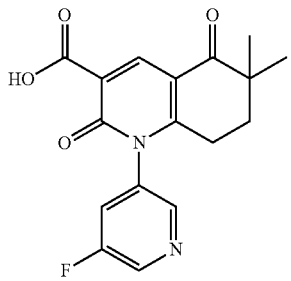 [SMILES: CC1(C)CCc2c(cc(C(=O)O)c(=O)n2-c2cncc(F)c2)C1=O]

A mixture of ethyl 6,6-dimethyl-2,5-dioxo-5,6,7,8-tetrahydro-2H-chromene-3-carboxylate (200 mg, 0.76 mmol) and 5-fluoropyridin-3-amine (85 mg, 0.76 mmol) in EtOH (3 mL) was stirred at 60° C. overnight, cooled to rt, and purified via pH 2 preparative LC/MS (MeCN/water with TFA) to give the product (75 mg, 30%). LCMS calcd for $C_{17}H_{16}FN_2O_4$ $(M+H)^+$: m/z=331.1. Found: 331.2.

Step 3: N-(4-(4-Amino-7-(1-isobutyrylpiperidin-4-yl)pyrrolo[1,2-f][1,2,4]triazin-5-yl)phenyl)-1-(5-fluoropyridin-3-yl)-6,6-dimethyl-2,5-dioxo-1,2,5,6,7,8-hexahydroquinoline-3-carboxamide This compound was prepared following a synthetic sequence analogous to that for example 83, step 5, using 1-(5-fluoropyridin-3-yl)-6,6-dimethyl-2,5-dioxo-1,2,5,6,7,8-hexahydroquinoline-3-carboxylic acid instead of 1-isopropyl-2,4-dioxo-3-(pyridin-2-yl)-1,2,3,4-tetrahydropyrimidine-5-carboxylic acid. This compound was purified via pH 2 preparative LC/MS (MeCN/water with TFA) to give the product as TFA salt. LCMS calcd for $C_{38}H_{40}FN_8O_4$ $(M+H)^+$: m/z=691.3. Found: 691.4.

Example 116. N-{4-[4-Amino-7-(1-isobutyrylpiperidin-4-yl)pyrrolo[2,1-f][1,2,4]triazin-5-yl]phenyl}-6-oxo-1-phenyl-2-pyridin-3-yl-1,6-dihydropyrimidine-5-carboxamide

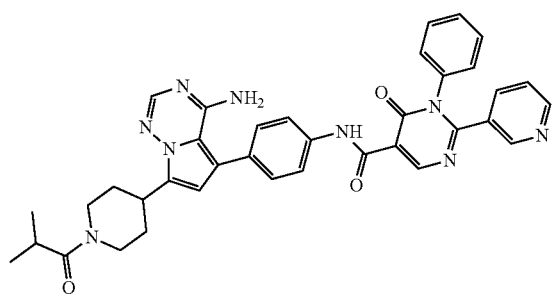 [SMILES: CC(C)C(=O)N1CCC(c2cc(-c3ccc(NC(=O)c4cnc(-c5cccnc5)n(-c5ccccc5)c4=O)cc3)c3c(N)ncnn23)CC1]

Step 1: Sodium [imino(pyridin-3-yl)methyl](phenyl)azanide

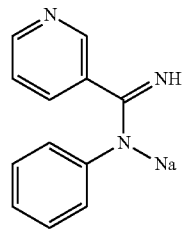

Aniline (931 mg, 10.0 mmol) was added to 1.0 M sodium hexamethyldisilazane in THF (10 mL, 10.0 mmol). The resulting mixture was stirred at rt for 10 min, added 3-pyridinecarbonitrile (1.04 g, 10.0 mmol), stirred at rt for 1 h, and concentrated. The residue was treated with ether, and the resulting solid was collected by filtration, washed with ether and dried to afford the product (2.10 g, 100%), which was used directly in the next step. LCMS calcd for $C_{12}H_{12}N_3$ $(M+2H-Na)^+$: m/z=198.1. Found: 198.1.

Step 2: Ethyl 6-oxo-1-phenyl-2-pyridin-3-yl-1,6-dihydropyrimidine-5-carboxylate

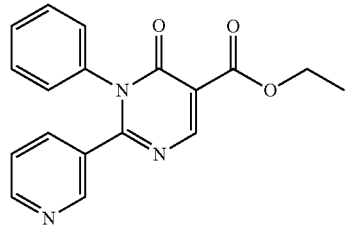 [SMILES: CCOC(=O)c1cnc(-c2cccnc2)n(-c2ccccc2)c1=O]

To a solution of sodium [imino(pyridin-3-yl)methyl](phenyl)azanide (0.219 g, 1.00 mmol) in MeCN (5 mL) was added ammonium chloride (0.054 g, 1.00 mmol), followed by (ethoxymethylene)propanedioic acid, diethyl ester (0.20 mL, 1.00 mmol). The reaction mixture was stirred at 80° C. for 2 h, cooled to rt, and concentrated. The resulting residue was dissolved in EtOAc, and washed with water and brine. The organic layer was separated, dried over MgSO4, concentrated, and purified via column chromatography (0% to 50% EtOAc in hexanes) to afford the product (0.167 g, 52%). LCMS calcd for $C_{18}H_{16}N_3O_3$ $(M+H)^+$: m/z=322.1. Found: 322.2.

Step 3: 6-Oxo-1-phenyl-2-pyridin-3-yl-1,6-dihydropyrimidine-5-carboxylic Acid

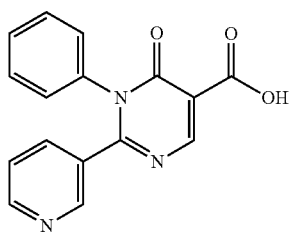 [SMILES: O=C(O)c1cnc(-c2cccnc2)n(-c2ccccc2)c1=O]

A mixture of ethyl 6-oxo-1-phenyl-2-pyridin-3-yl-1,6-dihydropyrimidine-5-carboxylate (133 mg, 0.41 mmol) and lithium iodide (138 mg, 1.03 mmol) in pyridine (2.5 mL) was stirred at 115° C. overnight, cooled to rt, and concentrated. The resulting residue was dissolved in water (2 mL) and extracted with EtOAc (3 mL×2). The aqueous layer was slowly acidified to pH ~4 with 1 N HCl solution, and extracted with 5% MeOH in $CH_2Cl_2$ (3 mL×3). The combined organic layers were washed with brine, dried over $MgSO_4$, and concentrated to give the product (0.103 g, 85%), which was used directly in the next step. LCMS calcd for $C_{16}H_{12}N_3O_3$ $(M+H)^+$: m/z=294.1. Found: 294.1.

Step 4: N-{4-[4-Amino-7-(1-isobutyrylpiperidin-4-yl)pyrrolo[2,1-f][1,2,4]triazin-5-yl]phenyl}-6-oxo-1-phenyl-2-pyridin-3-yl-1,6-dihydropyrimidine-5-carboxamide This compound was prepared following a synthetic sequence analogous to that for example 83, step 5, using 6-oxo-1-phenyl-2-pyridin-3-yl-1,6-dihydropyrimidine-5-carboxylic acid instead of 1-isopropyl-2,4-dioxo-3-(pyridin-2-yl)-1,2,3,4-tetrahydropyrimidine-5-carboxylic acid. This compound was purified via pH 2 preparative LC/MS (MeCN/water with TFA) to give the product as TFA salt. LCMS calcd for $C_{37}H_{36}N_9O_3$ $(M+H)^+$: m/z=654.3. Found: 654.3.

Example 117. N-{4-[4-Amino-7-(1-isobutyrylpiperidin-4-yl)pyrrolo[2,1-f][1,2,4]triazin-5-yl]phenyl}-6-cyclopropyl-3-oxo-2-phenyl-2,3-dihydropyridazine-4-carboxamide

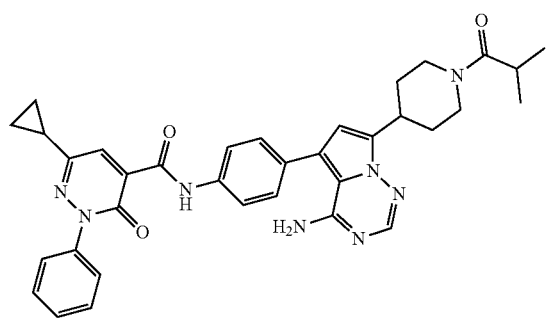 [SMILES: CC(C)C(=O)N1CCC(c2cc(-c3ccc(NC(=O)c4cc(C5CC5)nn(-c5ccccc5)c4=O)cc3)c3c(N)ncnn23)CC1]

Step 1. (2-Cyclopropyl-2-oxoethyl)(triphenyl)phosphonium bromide

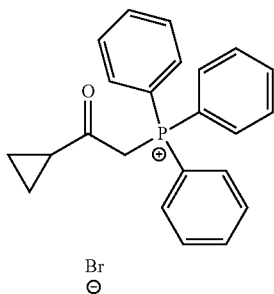 [SMILES: O=C(C[P+](c1ccccc1)(c1ccccc1)c1ccccc1)C1CC1 ; [Br-]]

A solution of 2-bromo-1-cyclopropylethanone (2.44 g, 15.0 mmol) and $PPh_3$ (3.93 g, 15.0 mmol) in THF (60 mL) was stirred at reflux for 1 h, and cooled to rt. The resulting solid was collected by filtration, and washed with ether to afford the product (3.91 g, 61%), which was used directly in the next step. LCMS calcd for $C_{23}H_{22}OP$ (M-Br)+: m/z=345.1. Found: 345.2.

Step 2: 1-Cyclopropyl-2-(triphenylphosphoranylidene)ethanone

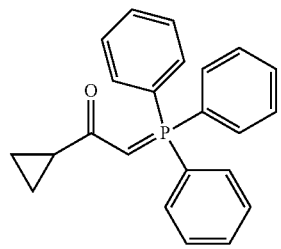 [SMILES: O=C(C=P(c1ccccc1)(c1ccccc1)c1ccccc1)C1CC1]

A mixture of (2-Cyclopropyl-2-oxoethyl)(triphenyl)phosphonium bromide (3.91 g, from previous step) in 1N NaOH solution (40 mL) was stirred overnight, and extracted with $CH_2Cl_2$. The combined organic layers were washed with brine, dried over $MgSO_4$, and concentrated to afford the product (2.60 g, 50%). LCMS calcd for $C_{23}H_{22}OP$ $(M+H)^+$: m/z=345.1. Found: 345.2.

Step 3: 6-Cyclopropyl-3-oxo-2-phenyl-2,3-dihydropyridazine-4-carboxylic Acid

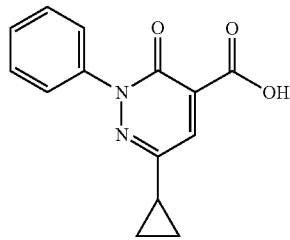 [SMILES: O=C(O)c1cc(C2CC2)nn(-c2ccccc2)c1=O]

To a solution of 1-cyclopropyl-2-(triphenylphosphoranylidene)ethanone (1.72 g, 5.0 mmol) in THF (25 mL) was added diethyl 2-oxomalonate (1.3 g, 7.5 mmol). The resulting mixture was stirred at rt for 30 min, concentrated, and the residue was added to phenylhydrazine hydrochloride (1.08 g, 7.50 mmol) in $EtOH/H_2O$ (1:1, 50 mL). The reaction mixture was stirred at 80° C. overnight. After cooling to rt, the organic solvents were evaporated, and the residue was diluted with $CH_2Cl_2$ (30 mL), and extracted with 1N NaOH solution (5 mL×3). The combined aqueous layers were adjusted with 6 N HCl to pH ~4, and extracted with EtOAc (5 mL×3). The combined organic layers were washed with water and brine, dried over $MgSO_4$, and concentrated to give the product (0.562 g, 44%), which was used directly in the next step. LCMS calcd for $C_{14}H_{13}N_2O_3$ $(M+H)^+$: m/z=257.1. Found: 257.1.

Step 4: N-{4-[4-Amino-7-(1-isobutyrylpiperidin-4-yl)pyrrolo[2,1-f][1,2,4]triazin-5-yl]phenyl}-6-cyclopropyl-3-oxo-2-phenyl-2,3-dihydropyridazine-4-carboxamide This compound was prepared following a synthetic sequence analogous to that for example 83, step 5, using 6-cyclopropyl-3-oxo-2-phenyl-2,3-dihydropyridazine-4-carboxylic acid instead of 1-isopropyl-2,4-dioxo-3-(pyridin-2-yl)-1,2,3,4-tetrahydropyrimidine-5-carboxylic acid. This compound was purified via pH 2 preparative LC/MS (MeCN/water with TFA) to give the product as TFA salt. LCMS calcd for $C_{35}H_{37}N_8O_3$ (M+H)$^+$: m/z=617.3. Found: 617.3.

Example 118. N-(4-(4-Amino-7-(1-isobutyrylpiperidin-4-yl)pyrrolo[2,1-f][1,2,4]triazin-5-yl)phenyl)-5-bromo-6-methyl-2-oxo-2H-[1,2'-bipyridine]-3-carboxamide

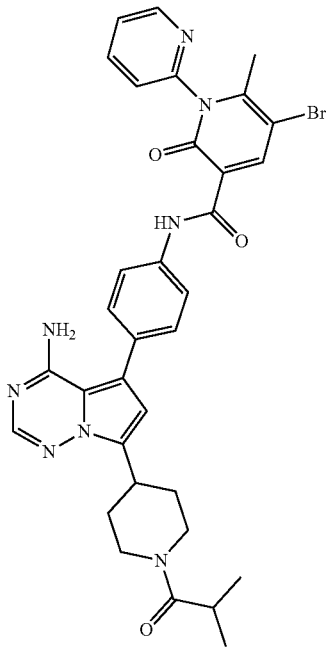 [SMILES: Cc1c(Br)cc(C(=O)Nc2ccc(-c3cc(C4CCN(C(=O)C(C)C)CC4)n4ncnc(N)c34)cc2)c(=O)n1-c1ccccn1]

Step 1: 5-Bromo-6-methyl-2-oxo-2H-[1,2'-bipyridine]-3-carboxylic Acid

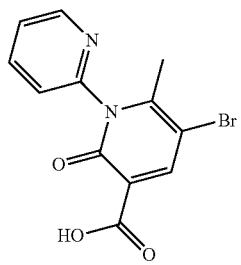 [SMILES: Cc1c(Br)cc(C(=O)O)c(=O)n1-c1ccccn1]

A mixture of ethyl 5-bromo-6-methyl-2-oxo-2H-[1,2'-bipyridine]-3-carboxylate (800 mg, 2.37 mmol) (from Affinity Research Chemicals) in THF (7.9 mL)/MeOH (5.3 mL)/water (2.6 mL) was treated with lithium hydroxide monohydrate (0.33 mL, 11.9 mmol) at 0° C. The reaction mixture was stirred at rt for 60 min, concentrated, and added water. The resulting mixture was neutralized with 12 M HCl solution to pH 6-7, and the resulting solid was collected by filtration, washed with water, and dried to give the product as a light yellow powder (784 mg, 100%). LCMS calcd for $C_{12}H_{10}BrN_2O_3$(M+H)$^+$: m/z=309.0. Found: 309.0.

Step 2: N-(4-(4-Amino-7-(1-isobutyrylpiperidin-4-yl)pyrrolo[2,1-f][1,2,4]triazin-5-yl)phenyl)-5-bromo-6-methyl-2-oxo-2H-[1,2'-bipyridine]-3-carboxamide To a mixture of 5-bromo-6-methyl-2-oxo-2H-[1,2'-bipyridine]-3-carboxylic acid (9.0 mg, 0.03 mmol) and 1-(4-(4-amino-5-(4-aminophenyl)pyrrolo[2,1-f][1,2,4]triazin-7-yl)piperidin-1-yl)-2-methylpropan-1-one (10 mg, 0.03 mmol) (from example 83, step 2) in DMF (528 µl) was added Et$_3$N (11 µl, 0.08 mmol), followed by HATU (20 mg, 0.053 mmol). The resulting mixture was stirred at rt for 20 min, filtered, and the crude was purified via pH 2 preparative LC/MS (MeCN/water with TFA) to give the product as TFA salt. LCMS calcd for $C_{33}H_{34}BrN_8O_3$(M+H)$^+$: m/z=669.2. Found: 669.2. $^1$H NMR (500 MHz, DMSO) δ 11.69 (s, 1H), 8.75-8.67 (m, 2H), 8.60 (s, 1H), 8.17 (td, J=7.8, 1.9 Hz, 1H), 8.05 (s, 1H), 7.81 (d, J=8.7 Hz, 1H), 7.73-7.62 (m, 3H), 7.46 (d, J=8.6 Hz, 1H), 6.72 (s, 1H), 4.55 (d, J=13.6 Hz, 1H), 4.07 (d, J=12.2 Hz, 1H), 3.42 (s, 1H), 3.27-3.16 (m, 1H), 2.91 (p, J=6.7 Hz, 1H), 2.78-2.61 (m, 2H), 2.16 (s, 2H), 2.12-1.95 (m, 2H), 1.58 (dd, J=59.5, 11.1 Hz, 2H), 1.02 (t, J=6.6 Hz, 6H).

Example 119. N-(4-(4-Amino-7-(1-isobutyrylpiperidin-4-yl)pyrrolo[2,1-f][1,2,4]triazin-5-yl)phenyl)-1-cyclopropyl-6-methyl-5-(oxazol-2-yl)-4-oxo-1,4-dihydropyridine-3-carboxamide

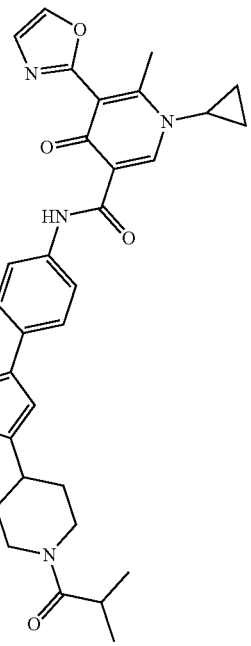

Step 1: 1-Cyclopropyl-6-methyl-4-oxo-1,4-dihydropyridine-3-carboxylic acid

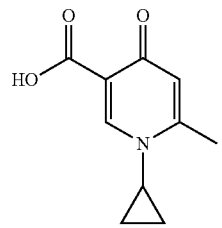

A microwave vial was charged with (E/Z)-3-((dimethylamino)methylene)-6-methyl-2H-pyran-2,4(3H)-dione (1.92 g, 7.95 mmol) (from example 97, step 1), cyclopropanamine (0.83 mL, 11.92 mmol) and t-BuONa (1.13 g, 11.76 mmol) in EtOH (5.0 mL). The resulting mixture was stirred at 90° C. for 18 h, cooled to rt, concentrated, and partitioned between water and $CH_2Cl_2$. The aqueous layer was acidified with 4 N HCl solution and extracted with $CH_2Cl_2$. The combined organic layers were washed with water, brine, dried over $Na_2SO_4$, and concentrated to give the product (1.1 g, 42%). LCMS calcd for $C_{10}H_{12}NO_3$ $(M+H)^+$: m/z=194.1. Found: 194.1.

Step 2: 5-Bromo-1-cyclopropyl-6-methyl-4-oxo-1,4-dihydropyridine-3-carboxylic Acid

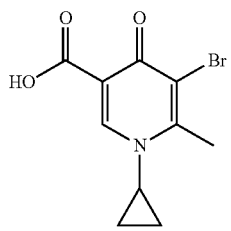

A suspension of 1-cyclopropyl-6-methyl-4-oxo-1,4-dihydropyridine-3-carboxylic acid (0.83 g, 4.30 mmol) in glacial acetic acid (6.0 mL) was treated with $Br_2$ (0.29 mL, 5.58 mmol) and the reaction mixture was stirred at rt for 4 days. Additional $Br_2$ (100 µL) was added and the reaction mixture was stirred overnight, diluted with water, and the resulting solid was collected by filtration, washed with water, and dried to give the product as a beige solid (1.0 g, 86%). LCMS calcd for $C_{10}H_{11}BrNO_3$ $(M+H)^+$: m/z=272.0. Found: 272.0.

Step 3: N-(4-(4-Amino-7-(1-isobutyrylpiperidin-4-yl)pyrrolo[2,1-f][1,2,4]triazin-5-yl)phenyl)-5-bromo-1-cyclopropyl-6-methyl-4-oxo-1,4-dihydropyridine-3-carboxamide

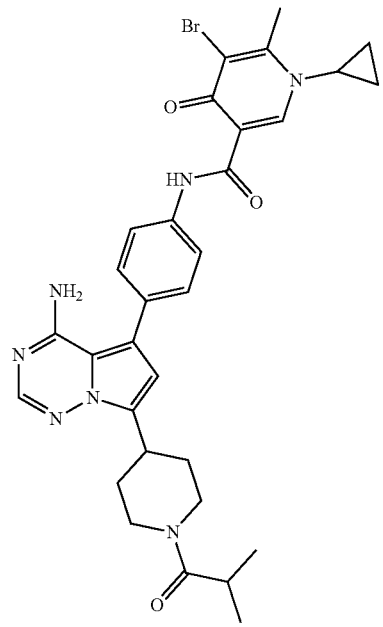 [SMILES: Cc1c(Br)c(=O)c(C(=O)Nc2ccc(-c3cc(C4CCN(C(=O)C(C)C)CC4)n4ncnc(N)c34)cc2)cn1C1CC1]

A mixture of 1-(4-(4-amino-5-(4-aminophenyl)pyrrolo[2,1-f][1,2,4]triazin-7-yl)piperidin-1-yl)-2-methylpropan-1-one (278 mg, 0.74 mmol) (from example 83, step 2), 5-bromo-1-cyclopropyl-6-methyl-4-oxo-1,4-dihydropyridine-3-carboxylic acid (200 mg, 0.74 mmol), HATU (335 mg, 0.88 mmol) and $Et_3N$ (0.21 mL, 1.47 mmol) in DMF (5.0 mL) was stirred at rt for 2 h, and then directly purified via column chromatography to afford the product (252 mg, 54%). LCMS calcd for $C_{31}H_{35}BrN-O_3$ $(M+H)^+$: m/z=632.2. Found: 632.1.

Step 4: N-(4-(4-Amino-7-(1-isobutyrylpiperidin-4-yl)pyrrolo[2,1-f][1,2,4]triazin-5-yl)phenyl)-1-cyclopropyl-6-methyl-5-(oxazol-2-yl)-4-oxo-1,4-dihydropyridine-3-carboxamide To a solution of N-(4-(4-amino-7-(1-isobutyrylpiperidin-4-yl)pyrrolo[2,1-f][1,2,4]triazin-5-yl)phenyl)-5-bromo-1-cyclopropyl-6-methyl-4-oxo-1,4-dihydropyridine-3-carboxamide (20 mg, 0.032 mmol) and 2-(tributylstannyl)oxazole (11 mg, 0.032 mmol) in 1,4-dioxane (2.0 mL) was added $Pd(Ph_3P)_4$ (7.3 mg, 6.3 µmol). The reaction mixture was stirred at reflux overnight, cooled to rt, and the resulting mixture was purified via pH 2 preparative LC/MS (MeCN/water with TFA) to give the product as TFA salt. LCMS calcd for $C_{34}H_{37}N_8O_4$ $(M+H)^+$: m/z=621.3. Found: 621.3.

Example 120. (S)—N-(4-(4-Amino-7-(1-isobutyrylpiperidin-4-yl)pyrrolo[2,1-f][1,2,4]triazin-5-yl)phenyl)-5-(3-hydroxybut-1-yn-1-yl)-2-oxo-1-phenyl-1,2-dihydropyridine-3-carboxamide

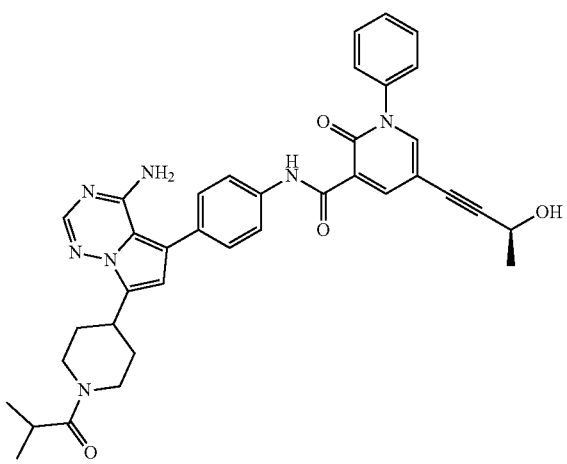 [SMILES: CC(C)C(=O)N1CCC(c2cc(-c3ccc(NC(=O)c4cc(C#C[C@H](C)O)cn(-c5ccccc5)c4=O)cc3)c3c(N)ncnn23)CC1]

Step 1: N-(4-(4-Amino-7-(1-isobutyrylpiperidin-4-yl)pyrrolo[2,1-f][1,2,4]triazin-5-yl)phenyl)-5-bromo-2-oxo-1-phenyl-1,2-dihydropyridine-3-carboxamide

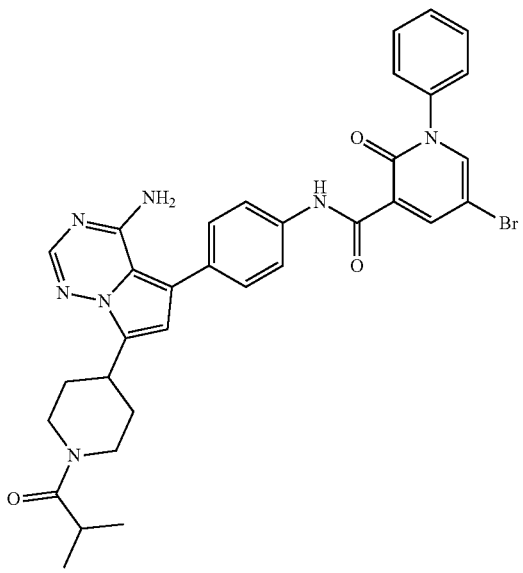 [SMILES: CC(C)C(=O)N1CCC(c2cc(-c3ccc(NC(=O)c4cc(Br)cn(-c5ccccc5)c4=O)cc3)c3c(N)ncnn23)CC1]

A mixture of 1-(4-(4-amino-5-(4-aminophenyl)pyrrolo[2,1-f][1,2,4]triazin-7-yl)piperidin-1-yl)-2-methylpropan-1-one (257 mg, 0.68 mmol) (from example 83, step 2), 5-bromo-2-oxo-1-phenyl-1,2-dihydropyridine-3-carboxylic acid (200 mg, 0.68 mmol), HATU (310 mg, 0.82 mmol) and Et₃N (0.19 mL, 1.36 mmol) in DMF (5.0 mL) was stirred at rt for 2 h. The reaction mixture was then purified via column chromatography to afford the product (310 mg, 70%). LCMS calcd for $C_{33}H_{33}BrN_7O_3$ (M+H)⁺: m/z=654.2. Found: 654.3.

Step 2: (S)—N-(4-(4-Amino-7-(1-isobutyrylpiperidin-4-yl)pyrrolo[2,1-f][1,2,4]triazin-5-yl)phenyl)-5-(3-hydroxybut-1-yn-1-yl)-2-oxo-1-phenyl-1,2-dihydropyridine-3-carboxamide N-(4-(4-amino-7-(1-isobutyrylpiperidin-4-yl)pyrrolo[2,1-f][1,2,4]triazin-5-yl)phenyl)-5-bromo-2-oxo-1-phenyl-1,2-dihydropyridine-3-carboxamide (20 mg, 0.031 mmol) was dissolved in MeCN (10 mL), followed by the addition of (S)-but-3-yn-2-ol (4.7 mg, 0.067 mmol), tris(tert-butyl)phosphine (1.0 mL), Pd(Ph₃P)₄ (3.5 mg, 3.1 μmol), copper (I) iodide (0.36 mg, 1.9 μmol), and Et₃N (0.019 mL, 0.14 mmol). The resulting mixture was stirred at 70° C. for 16 h, cooled to rt, and purified via pH 2 preparative LC/MS (MeCN/water with TFA) to give the product as TFA salt. LCMS calcd for $C_{37}H_{38}N_7O_4$ (M+H)⁺: m/z=644.3. Found: 644.5.

Example 121. N-(4-(4-Amino-7-(1-isobutyrylpiperidin-4-yl)pyrrolo[2,1-f][1,2,4]triazin-5-yl)phenyl)-5'-fluoro-5,6-dimethyl-2-oxo-2H-[1,3'-bipyridine]-3-carboxamide

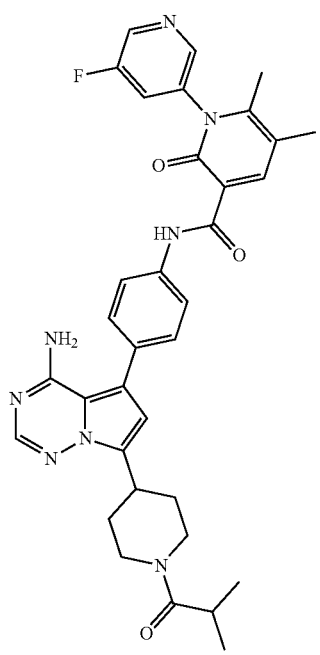 [SMILES: Cc1cc(C(=O)Nc2ccc(-c3cc(C4CCN(C(=O)C(C)C)CC4)n4ncnc(N)c34)cc2)c(=O)n(-c2cncc(F)c2)c1C]

A mixture of N-(4-(4-amino-7-(1-isobutyrylpiperidin-4-yl)pyrrolo[2,1-f][1,2,4]triazin-5-yl)phenyl)-5-bromo-5'-fluoro-6-methyl-2-oxo-2H-[1,3'-bipyridine]-3-carboxamide (8.0 mg, 0.012 mmol) (example 101, step 2) and PdCl$_2$(dppf)-CH$_2$Cl$_2$ adduct (1.0 mg, 1.2 µmol) in 1,4-dioxane (0.50 mL) was sealed in a microwave vial, evacuated and refilled with N$_2$ several times, followed by the addition of 2.0 M dimethylzinc in toluene (0.023 mL, 0.047 mmol). The reaction mixture was heated and stirred at 90° C. for 1 h, cooled to rt, and quenched with ice-water. The crude material was diluted with DMF and purified via pH 10 preparative LC/MS (MeCN/water with NH$_4$OH) to give the desired product as a white solid. LCMS calcd for C$_{34}$H$_{36}$FN$_8$O$_3$ (M+H)$^+$: m/z=623.3. Found: 623.3.

Example 122. N-(4-(4-Amino-7-(1-isobutyrylpiperidin-4-yl)pyrrolo[1,2-f][1,2,4]triazin-5-yl)phenyl)-5-(cyanomethyl)-6-methyl-2-oxo-1-(pyridin-2-yl)-1,2-dihydropyridine-3-carboxamide

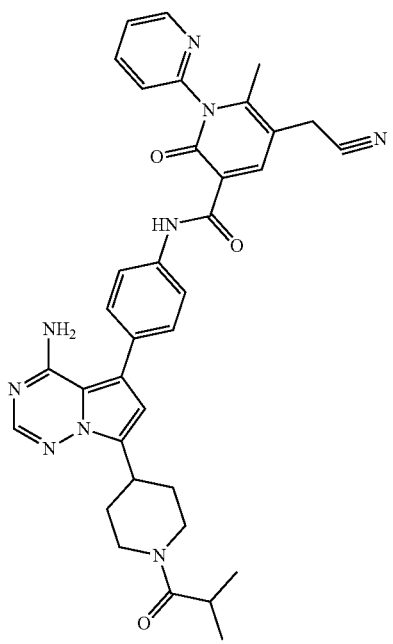 [SMILES: Cc1c(CC#N)cc(C(=O)Nc2ccc(-c3cc(C4CCN(C(=O)C(C)C)CC4)n4ncnc(N)c34)cc2)c(=O)n1-c1ccccn1]

In a sealed tube a mixture of N-(4-(4-amino-7-(1-isobutyrylpiperidin-4-yl)pyrrolo[2,1-S][1,2,4]triazin-5-yl)phenyl)-5-bromo-6-methyl-2-oxo-2H-[1,2'-bipyridine]-3-carboxamide (10 mg, 0.02 mmol) (example 118, step 2), isoxazol-4-ylboronic acid (2.5 mg, 0.02 mmol) in 1,4-dioxane (0.30 mL), N-ethyl-N-isopropylpropan-2-amine (7.7 µL, 0.05 mmol) and water (60 µL) was stirred together before Pd(tBu$_3$)$_2$(3.8 mg, 7.5 µmol) was added. The reaction mixture was sealed and then heated and stirred at 110° C. for 1 h, cooled to rt, diluted with DMF, and purified via pH 10 preparative LC/MS (MeCN/water with NH$_4$OH) to give the desired product as a white solid. LCMS calcd for C$_{35}$H$_{36}$N$_9$O$_3$ (M+H)$^+$: m/z=630.3. Found: 630.3.

Example 123. N-(4-(4-Amino-7-(1-isobutyrylpiperidin-4-yl)pyrrolo[2,1-f][1,2,4]triazin-5-yl)phenyl)-6-methyl-5-(1-methyl-1H-pyrazol-5-yl)-2-oxo-2H-[1,2'-bipyridine]-3-carboxamide

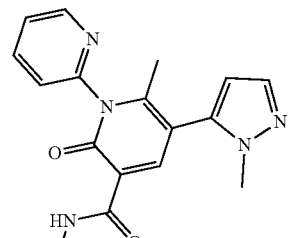

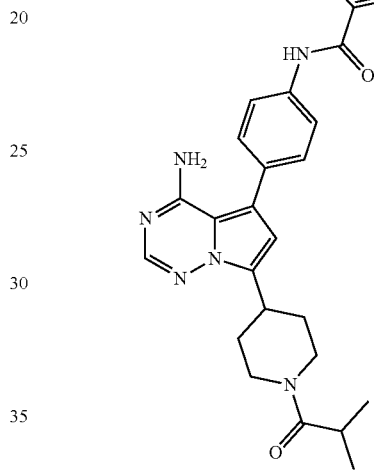

In a sealed tube a mixture of N-(4-(4-amino-7-(1-isobutyrylpiperidin-4-yl)pyrrolo[2,1-S][1,2,4]triazin-5-yl)phenyl)-5-bromo-6-methyl-2-oxo-2H-[1,2'-bipyridine]-3-carboxamide (8.0 mg, 0.012 mmol) (example 118, step 2), (1-methyl-1H-pyrazol-5-yl)boronic acid (2.3 mg, 0.02 mmol), and DIPEA (4.6 mg, 0.036 mmol) in 1,4-dioxane (200 µL) and water (40 µL) was stirred together before Pd(tBu$_3$)$_2$(3.1 mg, 6 µmol) was added. The reaction mixture was sealed and then heated and stirred at 110° C. for 50 min, cooled to rt, diluted with DMF, and purified via pH 10 preparative LC/MS (MeCN/water with NH$_4$OH) to give the desired product as a white solid. LCMS calcd for C$_{37}$H$_{39}$N$_{10}$O$_3$(M+H)$^+$: m/z=671.3. Found: 671.3. $^1$H NMR (500 MHz, DMSO) δ 11.74 (s, 1H), 8.74 (dd, J=4.9, 1.1 Hz, 1H), 8.38 (s, 1H), 8.18 (td, J=7.8, 1.9 Hz, 1H), 7.91 (s, 1H), 7.80 (d, J=8.6 Hz, 2H), 7.76 (d, J=7.9 Hz, 1H), 7.70-7.63 (m, 1H), 7.56 (d, J=1.8 Hz, 1H), 7.43 (d, J=8.6 Hz, 2H), 6.58 (s, 1H), 6.42 (d, J=1.9 Hz, 1H), 4.54 (d, J=11.9 Hz, 1H), 3.74 (s, 3H), 3.61 (s, 1H), 3.40 (t, J=11.9 Hz, 1H), 3.25-3.12 (m, 1H), 2.91 (p, J=6.8 Hz, 1H), 2.75-2.60 (m, 1H), 2.16-1.97 (m, 1H), 1.87 (s, 3H), 1.81-1.73 (m, 1H), 1.51 (d, J=13.9 Hz, 2H), 1.02 (t, J=6.6 Hz, 6H).

Example 124. N-(4-(4-Amino-7-(1-isobutyrylpiperidin-4-yl)pyrrolo[2,1-f][1,2,4]triazin-5-yl)phenyl)-5-chloro-6-methyl-2-oxo-2H-[1,2'-bipyridine]-3-carboxamide

Example 125. N-(4-(4-Amino-7-(1-isobutyrylpiperidin-4-yl)pyrrolo[2,1-f][1,2,4]triazin-5-yl)phenyl)-6-methyl-5-(1-methyl-1H-pyrazol-3-yl)-2-oxo-2H-[1,2'-bipyridine]-3-carboxamide

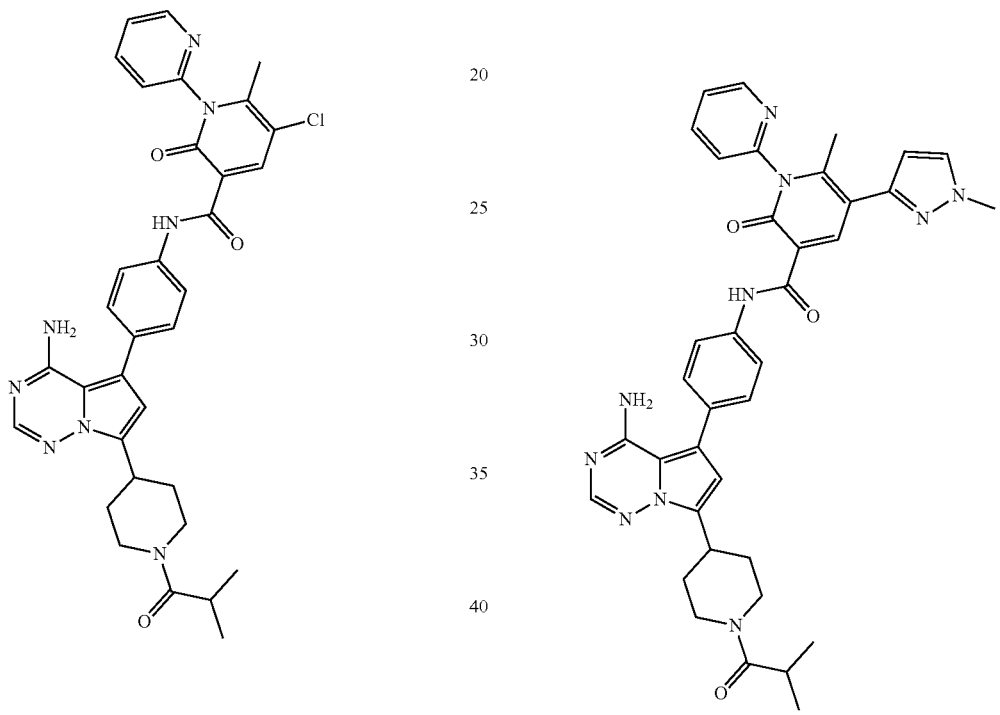

To a microwave vial was added N-(4-(4-amino-7-(1-isobutyrylpiperidin-4-yl)pyrrolo[2,1-S][1,2,4]triazin-5-yl)phenyl)-5-bromo-6-methyl-2-oxo-2H-[1,2'-bipyridine]-3-carboxamide (8.0 mg, 0.01 mmol) (example 118, step 2) and nickel(II) chloride (1.4 mg, 0.02 mmol) in DMF (0.40 mL). The vial was sealed and the reaction mixture was stirred at 180° C. under microwave conditions for 30 min, cooled to rt, and purified via pH 10 preparative LC/MS (MeCN/water with NH$_4$OH) to give the desired product as a white solid. LCMS calcd for C$_{33}$H$_{34}$ClN$_8$O$_3$ (M+H)$^+$: m/z=625.2. Found: 625.2.

This compound was prepared following a synthetic sequence analogous to that for example 123, using 1-methyl-3-(4,4,5,5-tetramethyl-1,3,2-dioxaborolan-2-yl)-1H-pyrazole instead of (1-methyl-1H-pyrazol-5-yl)boronic acid. This compound was purified via pH 10 preparative LC/MS (MeCN/water with NH$_4$OH) to give the desired product as a white solid. LCMS calcd for C$_{37}$H$_{39}$N$_{10}$O$_3$(M+H)$^+$: m/z=671.3. Found: 671.3.

263

Example 126. N-(4-(4-Amino-7-(1-isobutyrylpiperidin-4-yl)pyrrolo[2,1-f][1,2,4]triazin-5-yl)phenyl)-6-methyl-5-(oxazol-2-yl)-2-oxo-2H-[1,2'-bipyridine]-3-carboxamide

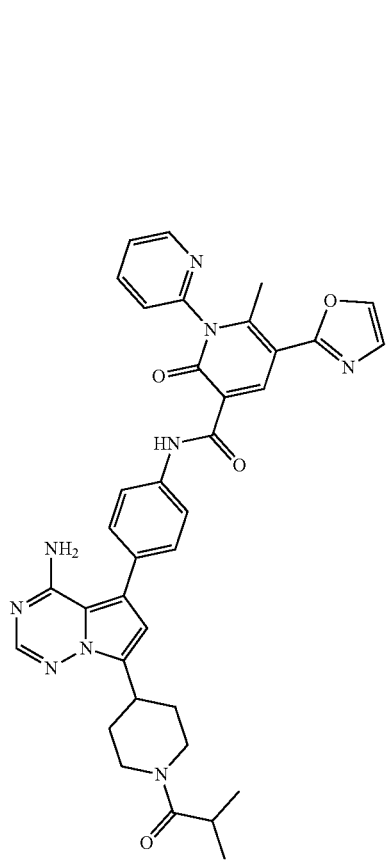 [SMILES: Cc1c(-c2ncco2)cc(C(=O)Nc2ccc(-c3cc(C4CCN(C(=O)C(C)C)CC4)n4ncnc(N)c34)cc2)c(=O)n1-c1ccccn1]

To a mixture of N-(4-(4-amino-7-(1-isobutyrylpiperidin-4-yl)pyrrolo[2,1-f][1,2,4]triazin-5-yl)phenyl)-5-bromo-6-methyl-2-oxo-2H-[1,2'-bipyridine]-3-carboxamide (10 mg, 0.02 mmol) (example 118, step 2), and Pd(Ph$_3$P)$_4$ (3.5 mg, 3.0 µmol) in toluene (0.30 mL) was added 2-(tributylstannyl)oxazole (10.7 mg, 0.03 mmol). The reaction mixture was sealed in a microwave vial, vacuumed and backfilled with N$_2$ several times, and then heated and stirred at 120° C. for 22 h. The reaction mixture was cooled to rt, concentrated, and purified via pH 2 preparative LC/MS (MeCN/water with TFA) to give the product as TFA salt. LCMS calcd for C$_{36}$H$_{36}$N$_9$O$_4$ (M+H)$^+$: m/z=658.3. Found: 658.3.

264

Example 127. N-(4-(4-Amino-7-(1-isobutyrylpiperidin-4-yl)pyrrolo[2,1-f][1,2,4]triazin-5-yl)phenyl)-5-(difluoromethyl)-6-methyl-2-oxo-2H-[1,2'-bipyridine]-3-carboxamide

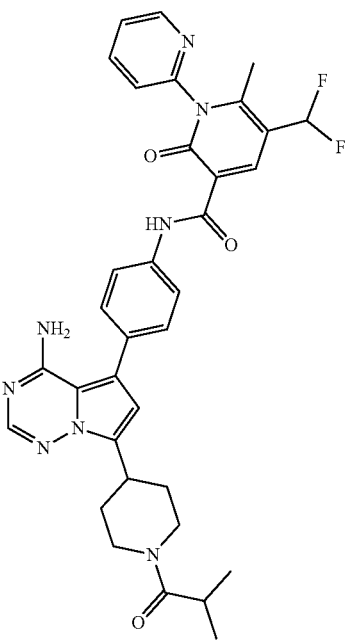 [SMILES: Cc1c(C(F)F)cc(C(=O)Nc2ccc(-c3cc(C4CCN(C(=O)C(C)C)CC4)n4ncnc(N)c34)cc2)c(=O)n1-c1ccccn1]

Step 1: N-(4-(4-Amino-7-(1-isobutyrylpiperidin-4-yl)pyrrolo[2,1-f][1,2,4]triazin-5-yl)phenyl)-6-methyl-2-oxo-5-vinyl-2H-[1,2'-bipyridine]-3-carboxamide

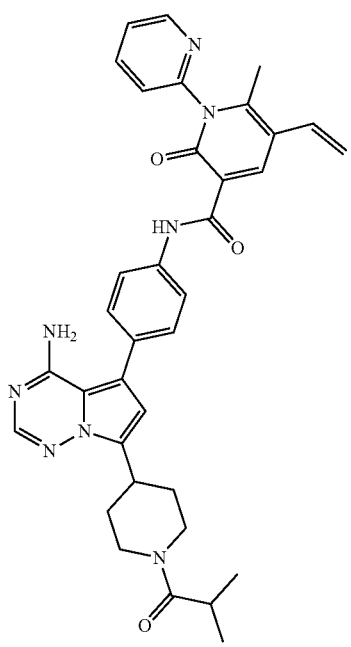 [SMILES: C=Cc1cc(C(=O)Nc2ccc(-c3cc(C4CCN(C(=O)C(C)C)CC4)n4ncnc(N)c34)cc2)c(=O)n(-c2ccccn2)c1C]

A mixture of N-(4-(4-amino-7-(1-isobutyrylpiperidin-4-yl)pyrrolo[2,1-f][1,2,4]triazin-5-yl)phenyl)-5-bromo-6- methyl-2-oxo-2H-[1,2'-bipyridine]-3-carboxamide (40 mg, 0.06 mmol) (example 118, step 2), 4,4,5,5-tetramethyl-2-vinyl-1,3,2-dioxaborolane (13.8 mg, 0.09 mmol), Na$_2$CO$_3$ (20.9 mg, 0.20 mmol), and [1,1'-Bis(di-cyclohexylphosphino)ferrocene]dichloropalladium (II) (4.5 mg, 6.0 µmol) in tert-butyl alcohol (0.19 mL) and water (0.07 mL) was degassed with nitrogen, and then stirred and heated at 115° C. for 2 h. The resulting mixture was cooled to rt, diluted with EtOAc, washed with saturated NaHCO$_3$ solution, water, and brine, dried over Na$_2$SO$_4$, concentrated, and purified via column chromatography (0 to 15% MeOH in EtOAc) to give the desired product as an off-white solid (27.9 mg, 76%). LCMS calcd for C$_{35}$H$_{37}$N$_8$O$_3$ (M+H)$^+$: m/z=617.3. Found: 617.3.

Step 2: N-(4-(4-Amino-7-(1-isobutyrylpiperidin-4-yl)pyrrolo[2,1-f][1,2,4]triazin-5-yl)phenyl)-5-formyl-6-methyl-2-oxo-2H-[1,2'-bipyridine]-3-carboxamide

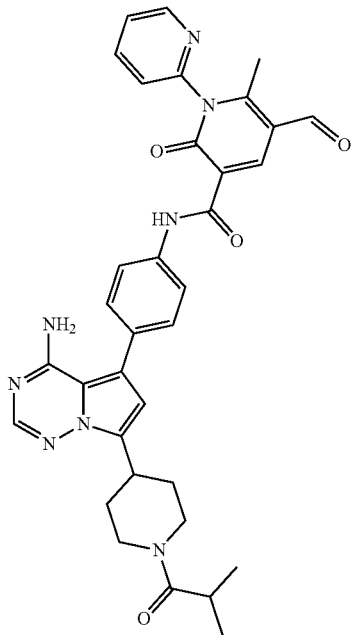 [SMILES: Cc1c(C=O)cc(C(=O)Nc2ccc(-c3cc(C4CCN(C(=O)C(C)C)CC4)n4ncnc(N)c34)cc2)c(=O)n1-c1ccccn1]

To a solution of N-(4-(4-amino-7-(1-isobutyrylpiperidin-4-yl)pyrrolo[2,1-f][1,2,4]triazin-5-yl)phenyl)-6-methyl-2-oxo-5-vinyl-2H-[1,2'-bipyridine]-3-carboxamide (20.0 mg, 0.032 mmol) in THF (0.37 mL) was added OsO$_4$ in water (4 wt. %) (0.06 mL, 9.7 µmol) and sodium periodate (32.6 mg, 0.15 mmol) in water (0.03 mL). The reaction mixture was stirred at 70° C. for 1 h, cooled to rt, filtered through a plug of Celite, rinsed with THF, concentrated, and purified via pH 10 preparative LC/MS (MeCN/water with NH$_4$OH) to give the desired product as a light yellow solid (6.5 mg, 31%). LCMS calcd for C$_{34}$H$_{35}$N$_8$O$_4$ (M+H)$^+$: m/z=619.3. Found: 619.3.

Step 3: N-(4-(4-Amino-7-(1-isobutyrylpiperidin-4-yl)pyrrolo[2,1-f][1,2,4]triazin-5-yl)phenyl)-5-(difluoromethyl)-6-methyl-2-oxo-2H-[1,2'-bipyridine]-3-carboxamide To a solution of N-(4-(4-amino-7-(1-isobutyrylpiperidin-4-yl)pyrrolo[2,1-f][1,2,4]triazin-5-yl)phenyl)-5-formyl-6-methyl-2-oxo-2H-[1,2'-bipyridine]-3-carboxamide (8.0 mg, 0.01 mmol) in THF (0.16 mL) at 0° C. was slowly added (diethylamino)sulfur trifluoride (DAST) (0.034 mL, 0.259 mmol). The resulting reaction mixture was warmed to rt and stirred at rt for 21 h, diluted with DMF, and purified via pH 2 preparative LC/MS (MeCN/water with TFA) to give the product as TFA salt. LCMS calcd for C$_{34}$H$_{35}$F$_2$N$_8$O$_3$(M+H)$^+$: m/z=641.3. Found: 641.3.

Example 128. N-(4-(4-Amino-7-(1-isobutyrylpiperidin-4-yl)pyrrolo[1,2-f][1,2,4]triazin-5-yl)phenyl)-1-isopropyl-4-oxo-5-(pyridin-3-yl)-1,4-dihydropyridine-3-carboxamide

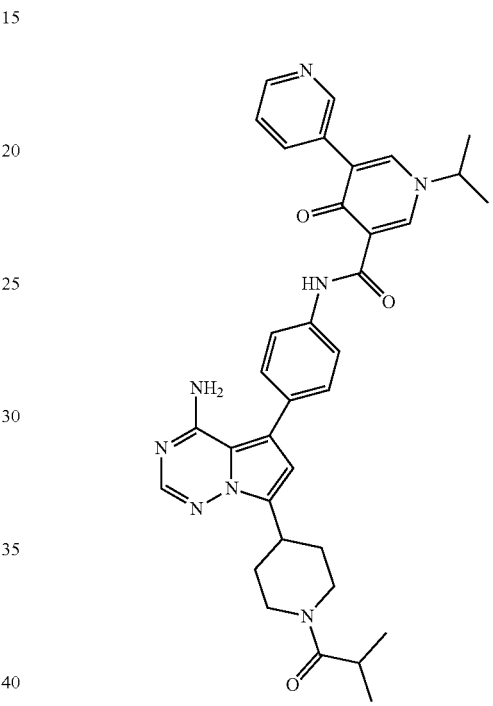

Step 1: Methyl 5-bromo-1-isopropyl-4-oxo-1,4-dihydropyridine-3-carboxylate

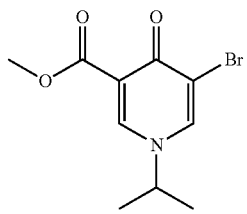

A mixture of methyl 5-bromo-4-oxo-1,4-dihydropyridine-3-carboxylate (151 mg, 0.65 mmol) and Cs$_2$CO$_3$ (420 mg, 1.3 mmol) in DMF (3 mL) was stirred at rt for 15 min and then isopropyl iodide (0.16 mL, 1.6 mmol) was added. The reaction mixture was stirred at rt for 11 days, diluted with EtOAc, filtered through Celite concentrated, and purified via column chromatography (0% to 100% EtOAc in hexanes then 0% to 10% methanol in CH$_2$Cl$_2$) to give the product as an off-white solid (103 mg, 58%). LCMS calcd for C$_{10}$H$_{13}$BrNO$_3$ (M+H)$^+$: m/z=274.0. Found: 274.1.

Step 2: 5-Bromo-1-isopropyl-4-oxo-1,4-dihydropyridine-3-carboxylic Acid

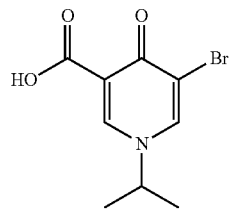

To a solution of methyl 5-bromo-1-isopropyl-4-oxo-1,4-dihydropyridine-3-carboxylate (103 mg, 0.376 mmol) in MeOH (2 mL) was added 3 M NaOH (0.2 mL) and the reaction mixture was stirred at rt for 4 h, acidified with 1 N HCl, diluted with brine, and extracted with EtOAc. The combined organic layers were dried over $Na_2SO_4$, and concentrated to afford the crude product as an off-white solid, which was used directly in the next step (97 mg, 99%). LCMS calcd for $C_9H_{11}BrNO_3$ $(M+H)^+$: m/z=260.0. Found: 260.0.

Step 3: tert-Butyl 4-(4-amino-5-(4-(5-bromo-1-isopropyl-4-oxo-1,4-dihydropyridine-3-carboxamido)phenyl)pyrrolo[1,2-f][1,2,4]triazin-7-yl)piperidine-1-carboxylate

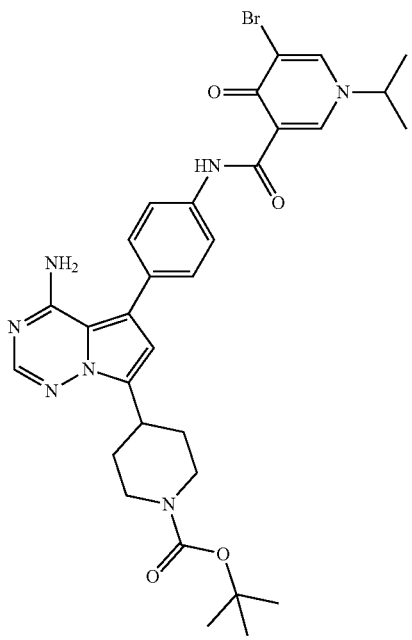 [SMILES: CC(C)n1cc(Br)c(=O)c(C(=O)Nc2ccc(-c3cc(C4CCN(C(=O)OC(C)(C)C)CC4)n4ncnc(N)c34)cc2)c1]

A solution of 5-bromo-1-isopropyl-4-oxo-1,4-dihydropyridine-3-carboxylic acid (83 mg, 0.319 mmol) and HATU (146 mg, 0.383 mmol) in DMF (2 mL) was treated with DIPEA (0.11 mL, 0.638 mmol). This mixture was then added via a cannula to a solution of tert-butyl 4-(4-amino-5-(4-aminophenyl)pyrrolo[1,2-f][1,2,4]triazin-7-yl)piperidine-1-carboxylate (130 mg, 0.319 mmol) (example 107, step 4) in DMF (1 mL). The reaction mixture was stirred at rt for 40 min, diluted with water and extracted twice with EtOAc. The combined organic layers were washed with brine, dried over $Na_2SO_4$, concentrated, and purified via column chromatography (0% to 100% EtOAc in hexanes then 0% to 10% MeOH in $CH_2Cl_2$) to give the product as a yellow solid (208 mg, 100%). LCMS calcd for $C_{31}H_{37}BrN_7O_4$ $(M+H)^+$: m/z=650.2. Found: 650.2.

Step 4: tert-Butyl 4-(4-amino-5-(4-(1-isopropyl-4-oxo-5-(pyridin-3-yl)-1,4-dihydropyridine-3-carboxamido)phenyl)pyrrolo[1,2-f][1,2,4]triazin-7-yl)piperidine-1-carboxylate

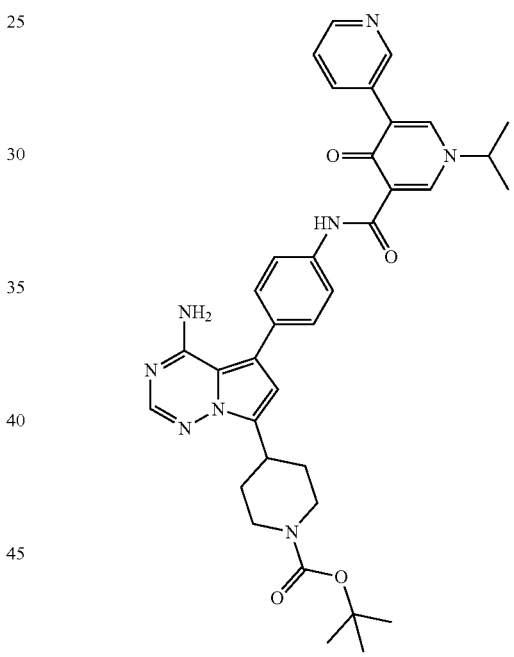

A mixture of tert-butyl 4-(4-amino-5-(4-(5-bromo-1-isopropyl-4-oxo-1,4-dihydropyridine-3-carboxamido)phenyl)pyrrolo[1,2-f][1,2,4]triazin-7-yl)piperidine-1-carboxylate (76 mg, 0.117 mmol), pyridin-3-ylboronic acid (17.2 mg, 0.140 mmol), XPhos-Pd-G2 (9.2 mg, 0.012 mmol) and potassium phosphate tribasic (62 mg, 0.292 mmol), in 1,4-dioxane/water (5:1, 2.4 mL) was degassed with nitrogen, and then heated and stirred at 90° C. for 2 h. The reaction mixture was cooled to rt, diluted with EtOAc, dried over $Na_2SO_4$, filtered through Celite, concentrated, and purified via column chromatography (0% to 100% EtOAc in hexanes then 0% to 10% MeOH in $CH_2Cl_2$) to give the product as an off-white solid (60 mg, 79%). LCMS calcd for $C_{36}H_{41}N_8O_4$ $(M+H)^+$: m/z=649.3. Found: 649.3.

269

Step 5: N-(4-(4-Amino-7-(piperidin-4-yl)pyrrolo[1,2-f][1,2,4]triazin-5-yl)phenyl)-1-isopropyl-4-oxo-5-(pyridin-3-yl)-1,4-dihydropyridine-3-carboxamide

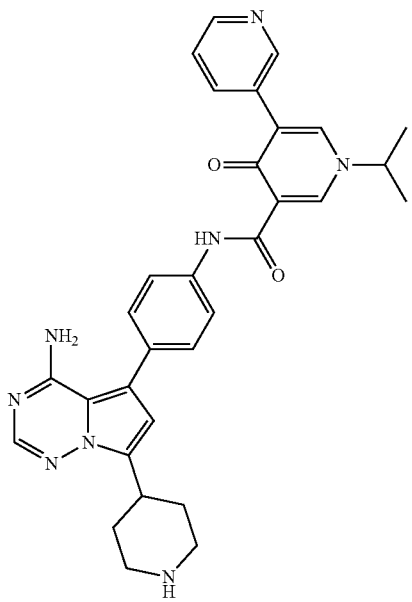 [SMILES: CC(C)n1cc(C(=O)Nc2ccc(-c3cc(C4CCNCC4)n4ncnc(N)c34)cc2)c(=O)c(-c2cccnc2)c1]

A suspension of tert-butyl 4-(4-amino-5-(4-(1-isopropyl-4-oxo-5-(pyridin-3-yl)-1,4-dihydropyridine-3-carboxamido)phenyl)pyrrolo[1,2-f][1,2,4]triazin-7-yl)piperidine-1-carboxylate (60 mg, 0.092 mmol) in $CH_2Cl_2$ (1 mL) was treated with 4 M HCl in 1,4-dioxane (1 mL). The reaction mixture was stirred at rt for 2 h, and concentrated to afford a light yellow solid which was directly used in the next step. LCMS calcd for $C_{31}H_{33}N_8O_2$ (M+H)$^+$: m/z=549.3. Found: 549.3.

Step 6: N-(4-(4-Amino-7-(1-isobutyrylpiperidin-4-yl)pyrrolo[1,2-f][1,2,4]triazin-5-yl)phenyl)-1-isopropyl-4-oxo-5-(pyridin-3-yl)-1,4-dihydropyridine-3-carboxamide A mixture of N-(4-(4-amino-7-(piperidin-4-yl)pyrrolo[1,2-f][1,2,4]triazin-5-yl)phenyl)-1-isopropyl-4-oxo-5-(pyridin-3-yl)-1,4-dihydropyridine-3-carboxamide (20 mg, 0.036 mmol) and $Et_3N$ (0.030 ml, 0.215 mmol) in $CH_2Cl_2$ (1 mL) was treated dropwise with 60 μL of a 10% (v/v) solution of isobutyryl chloride in $CH_2Cl_2$. The reaction mixture was stirred at rt for 40 min, quenched with saturated $NaHCO_3$ solution, and extracted three times with EtOAc. The combined organic layers were dried over $Na_2SO_4$, concentrated, and purified via pH 2 preparative LC/MS (MeCN/water with TFA) to afford the product as an off-white solid (15 mg as TFA salt). LCMS calcd for $C_{35}H_{39}N_8O_3$(M+H)$^+$: m/z=619.3. Found: 619.3.

270

Example 129. N-(4-(4-amino-7-(1-isobutyrylpiperidin-4-yl)pyrrolo[1,2-f][1,2,4]triazin-5-yl)phenyl)-5-(5-fluoropyridin-3-yl)-1-isopropyl-4-oxo-1,4-dihydropyridine-3-carboxamide

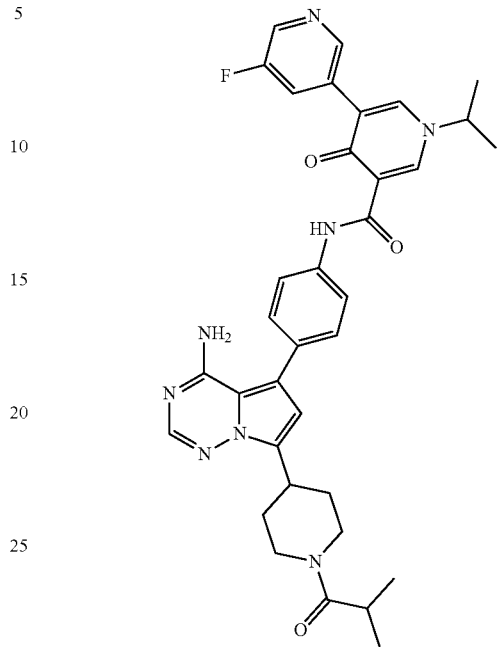

This compound was prepared following a synthetic sequence analogous to that for example 128, using 3-fluoro-5-(4,4,5,5-tetramethyl-1,3,2-dioxaborolan-2-yl)pyridine instead of pyridin-3-ylboronic acid in step 4. This compound was purified via pH 2 preparative LC/MS (MeCN/water with TFA) to give the product as the TFA salt. LCMS calcd for $C_{35}H_{38}FN_8O_3$ (M+H)$^+$: m/z=637.3. Found: 637.3.

Example 130. N-(4-(4-Amino-7-(1-isobutyrylpiperidin-4-yl)pyrrolo[2,1-f][1,2,4]triazin-5-yl)phenyl)-5-bromo-6-methyl-2-oxo-2H-[1,3'-bipyridine]-3-carboxamide

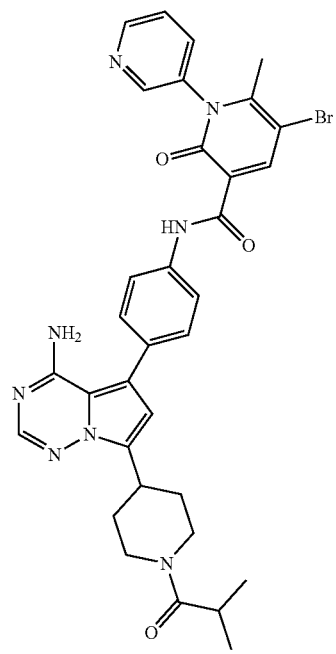 [SMILES: Cc1c(Br)cc(C(=O)Nc2ccc(-c3cc(C4CCN(C(=O)C(C)C)CC4)n4ncnc(N)c34)cc2)c(=O)n1-c1cccnc1]

Step 1: 5-Bromo-6-methyl-2-oxo-2H-[1,3'-bipyridine]-3-carboxylic Acid

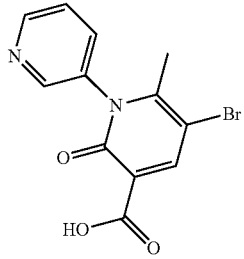 [SMILES: Cc1c(Br)cc(C(=O)O)c(=O)n1-c1cccnc1]

A mixture of ethyl 5-bromo-6-methyl-2-oxo-2H-[1,3'-bipyridine]-3-carboxylate (570 mg, 1.69 mmol) (from Affinity Research Chemicals) and LiOH monohydrate (355 mg, 8.45 mmol) in MeOH (12 mL) and water (2.0 mL) was stirred at rt for 2 h, and MeOH was evaporated. To the residue was added water and the resulting mixture was made slightly acidic by addition of 1 N HCl, which caused a solid to form. The solids were collected by filtration, washed with water, and dried to give the product as a pink solid (333 mg, 64%). LCMS calcd for $Cl_2H_{10}BrN_2O_3$ (M+H)$^+$: m/z=309.0. Found: 309.0.

Step 2: N-(4-(4-Amino-7-(1-isobutyrylpiperidin-4-yl)pyrrolo[2,1-f][1,2,4]triazin-5-yl)phenyl)-5-bromo-6-methyl-2-oxo-2H-[1,3'-bipyridine]-3-carboxamide To a mixture of 1-(4-(4-amino-5-(4-aminophenyl)pyrrolo[2,1-f][1,2,4]triazin-7-yl)piperidin-1-yl)-2-methylpropan-1-one (150 mg, 0.396 mmol) (Example 83, step 2) and 5-bromo-6-methyl-2-oxo-2H-[1,3'-bipyridine]-3-carboxylic acid (123 mg, 0.396 mmol) in DMF (3.0 mL) was added Et$_3$N (0.083 mL, 0.594 mmol), followed by HATU (181 mg, 0.476 mmol). The resulting mixture was stirred at rt for 3 h, added water, and stirred for another 15 min. The resulting solid was collected by filtration, washed with water, and dried to give the product (250 mg, 94%). A portion of this material was further purified via pH 2 preparative LC/MS (MeCN/water with TFA) to give the product as TFA salt. LCMS calcd for $C_{33}H_{34}BrN_8O_3$ (M+H)$^+$: m/z=669.2. Found: 669.2. $^1$H NMR (500 MHz, DMSO) δ 11.70 (s, 1H), 8.75 (dd, J=4.8, 1.5 Hz, 1H), 8.67 (d, J=2.2 Hz, 1H), 8.58 (s, 1H), 8.09 (s, 1H), 7.97 (ddd, J=8.1, 2.4, 1.6 Hz, 1H), 7.81 (d, J=8.7 Hz, 2H), 7.68 (dd, J=7.9, 4.6 Hz, 1H), 7.45 (d, J=8.6 Hz, 2H), 6.75 (s, 1H), 4.53 (d, J=12.8 Hz, 1H), 4.06 (d, J=13.3 Hz, 1H), 3.49-3.32 (m, 1H), 3.19 (t, J=11.8 Hz, 1H), 2.98-2.79 (m, 1H), 2.68 (t, J=11.5 Hz, 1H), 2.19 (s, 3H), 2.11-1.93 (m, 2H), 1.56 (dd, J=59.6, 10.9 Hz, 2H), 1.00 (t, J=6.8 Hz, 6H).

Example 131. N-(4-(4-amino-7-(1-isobutyrylpiperidin-4-yl)pyrrolo[2,1-f][1,2,4]triazin-5-yl)phenyl)-5-chloro-6-methyl-2-oxo-2H-[1,3'-bipyridine]-3-carboxamide

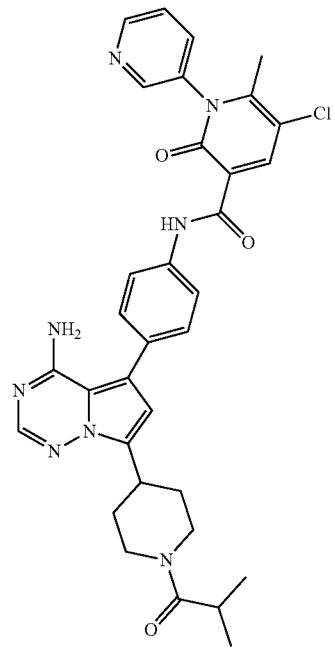

A mixture of N-(4-(4-amino-7-(1-isobutyrylpiperidin-4-yl)pyrrolo[2,1-f][1,2,4]triazin-5-yl)phenyl)-5-bromo-6-methyl-2-oxo-2H-[1,3'-bipyridine]-3-carboxamide (30 mg, 0.045 mmol) (Example 130, step 2) and copper(I) chloride (13.3 mg, 0.134 mmol) in DMF (0.5 mL) was heated and stirred at 170° C. under microwave conditions for 12 min. The reaction mixture was cooled to rt, filtered, and purified via pH 2 preparative LC/MS (MeCN/water with TFA) to give the product as TFA salt. LCMS calcd for $C_{33}H_{34}ClN_8O_3$(M+H)$^+$: m/z=625.2. Found: 625.3. $^1$H NMR (600 MHz, DMSO) δ 11.73 (s, 1H), 8.76 (s, 1H), 8.68 (s, 1H), 8.50 (s, 1H), 8.12 (s, 1H), 7.98 (ddd, J=8.1, 2.4, 1.5 Hz, 1H), 7.82 (d, J=8.7 Hz, 2H), 7.69 (dd, J=8.0, 4.8 Hz, 1H), 7.47 (d, J=8.6 Hz, 2H), 6.77 (s, 1H), 4.53 (d, J=11.8 Hz, 1H), 4.06 (d, J=12.9 Hz, 1H), 3.41 (tt, J=11.8, 3.5 Hz, 1H), 3.20 (t, J=12.7 Hz, 1H), 2.89 (hept, J=6.8 Hz, 1H), 2.68 (t, J=11.9 Hz, 1H), 2.16 (s, 3H), 2.01 (dd, J=29.4, 12.3 Hz, 2H), 1.57 (dd, J=73.5, 9.4 Hz, 2H), 1.01 (d, J=6.9 Hz, 6H).

273

Example 132. N-(4-(4-Amino-7-(1-isobutyrylpiperidin-4-yl)pyrrolo[2,1-f][1,2,4]triazin-5-yl)phenyl)-5,6-dimethyl-2-oxo-2H-[1,3'-bipyridine]-3-carboxamide

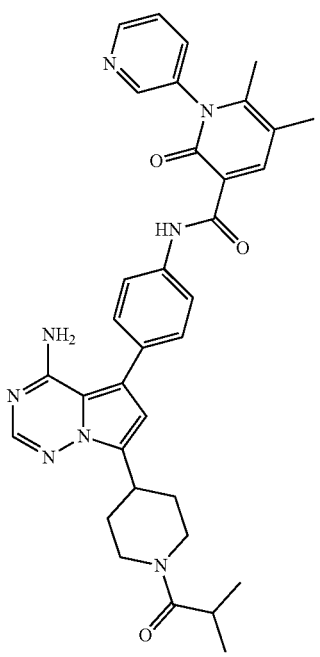 [SMILES: Cc1cc(C(=O)Nc2ccc(-c3cc(C4CCN(C(=O)C(C)C)CC4)n4ncnc(N)c34)cc2)c(=O)n(-c2cccnc2)c1C]

To a mixture of N-(4-(4-amino-7-(1-isobutyrylpiperidin-4-yl)pyrrolo[2,1-f][1,2,4]triazin-5-yl)phenyl)-5-bromo-6-methyl-2-oxo-2H-[1,3'-bipyridine]-3-carboxamide (30 mg, 0.045 mmol) (Example 130, step 2) and PdCl$_2$(dppf)-CH$_2$Cl$_2$ adduct (0.9 mg, 1.1 µmol) in 1,4-dioxane (0.50 mL) was added 2.0 M dimethyl zinc in toluene (0.086 mL, 0.172 mmol) dropwise under an atmosphere of N$_2$. The resulting mixture was stirred at 90° C. overnight, cooled to rt, filtered, and purified via pH 2 preparative LC/MS (MeCN/water with TFA) to give the product as TFA salt. LCMS calcd for C$_{34}$H$_{37}$N$_8$O$_3$ (M+H)$^+$: m/z=605.3. Found: 605.3.

274

Example 133. N-(4-(4-Amino-7-(1-isobutyrylpiperidin-4-yl)pyrrolo[2,1-f][1,2,4]triazin-5-yl)phenyl)-6-methyl-5-(1-methyl-1H-pyrazol-4-yl)-2-oxo-2H-[1,3'-bipyridine]-3-carboxamide

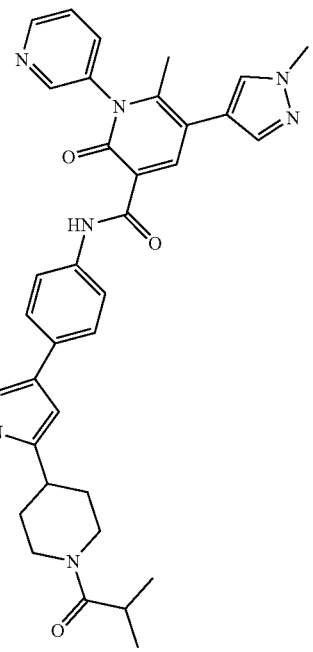

In a sealed vial, a mixture of N-(4-(4-amino-7-(1-isobutyrylpiperidin-4-yl)pyrrolo[2,1-S][1,2,4]triazin-5-yl)phenyl)-5-bromo-6-methyl-2-oxo-2H-[1,3'-bipyridine]-3-carboxamide (20 mg, 0.030 mmol) (Example 130, step 2), 1-methyl-4-(4,4,5,5-tetramethyl-1,3,2-dioxaborolan-2-yl)-1H-pyrazole (12.4 mg, 0.060 mmol), XPhos Pd G2 (2.4 mg, 3.0 µmol) and potassium phosphate tribasic (19.0 mg, 0.090 mmol) in 1,4-dioxane (0.40 mL)/water (0.07 mL) was stirred at 90° C. under N$_2$ overnight. The reaction mixture was then cooled to rt, filtered, and purified via pH 2 preparative LC/MS (MeCN/water with TFA) to give the product as TFA salt. LCMS calcd for C$_{37}$H$_{39}$N$_{10}$O$_3$(M+H)$^+$: m/z=671.3. Found: 671.4.

Example 134. N-(4-(4-Amino-7-(1-isobutyrylpiperidin-4-yl)pyrrolo[2,1-f][1,2,4]triazin-5-yl)phenyl)-6-methyl-5-(1-methyl-1H-pyrazol-5-yl)-2-oxo-2H-[1,3'-bipyridine]-3-carboxamide Example 135. N-(4-(4-Amino-7-(1-isobutyrylpiperidin-4-yl)pyrrolo[2,1-f][1,2,4]triazin-5-yl)phenyl)-6-methyl-5-(1-methyl-1H-pyrazol-3-yl)-2-oxo-2H-[1,3'-bipyridine]-3-carboxamide

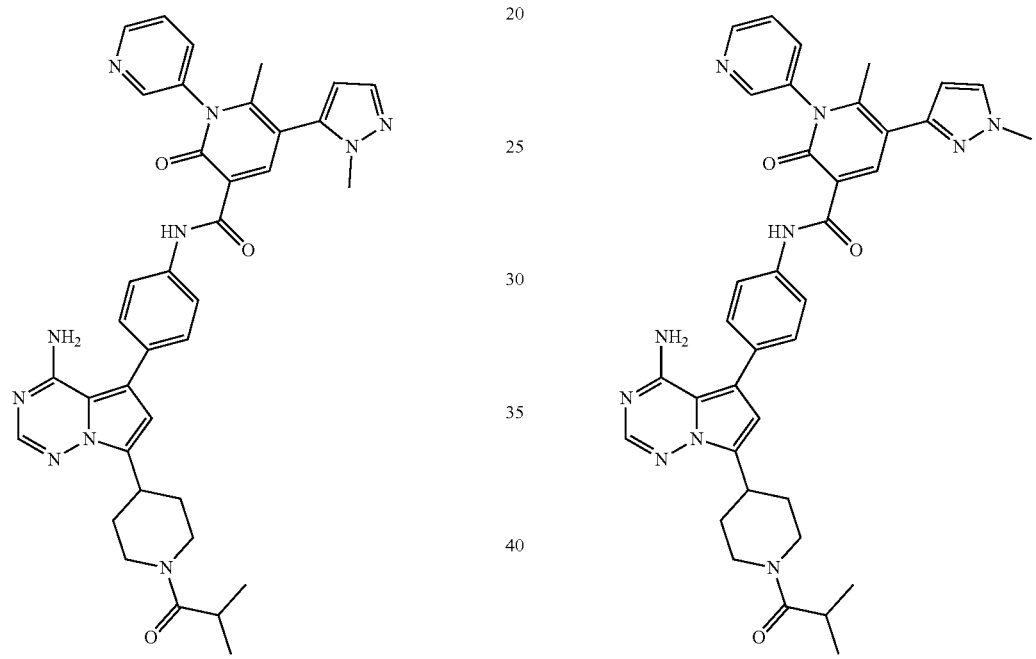

This compound was prepared following a synthetic sequence analogous to that for example 133, using 1-methyl-5-(4,4,5,5-tetramethyl-1,3,2-dioxaborolan-2-yl)-1H-pyrazole instead of 1-methyl-4-(4,4,5,5-tetramethyl-1,3,2-dioxaborolan-2-yl)-1H-pyrazole. This compound was purified via pH 2 preparative LC/MS (MeCN/water with TFA) to give the product as TFA salt. LCMS calcd for $C_{37}H_{39}N_{10}O_3(M+H)^+$: m/z=671.3. Found: 671.4.

This compound was prepared following a synthetic sequence analogous to that for example 133, using 1-methyl-3-(4,4,5,5-tetramethyl-1,3,2-dioxaborolan-2-yl)-1H-pyrazole instead of 1-methyl-4-(4,4,5,5-tetramethyl-1,3,2-dioxaborolan-2-yl)-1H-pyrazole. This compound was purified via pH 2 preparative LC/MS (MeCN/water with TFA) to give the product as TFA salt. LCMS calcd for $C_{37}H_{39}N_{10}O_3(M+H)^+$: m/z=671.3. Found: 671.4.

Example 136. N-(4-(4-Amino-7-(1-isobutyrylpiperidin-4-yl)pyrrolo[2,1-f][1,2,4]triazin-5-yl)phenyl)-5-bromo-6-(methoxymethyl)-2-oxo-1-phenyl-1,2-dihydropyridine-3-carboxamide

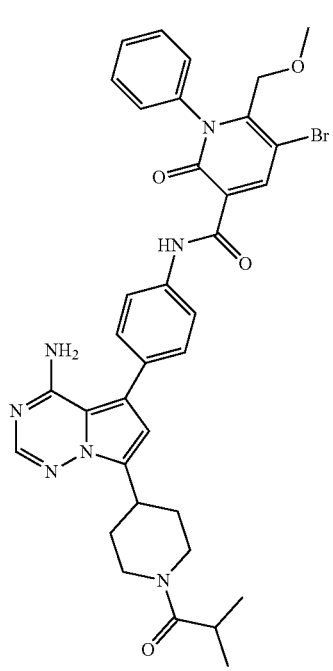 [SMILES: COCc1c(Br)cc(C(=O)Nc2ccc(-c3cc(C4CCN(C(=O)C(C)C)CC4)n4ncnc(N)c34)cc2)c(=O)n1-c1ccccc1]

Step 1: Ethyl 5-bromo-6-(bromomethyl)-2-oxo-1-phenyl-1,2-dihydropyridine-3-carboxylate

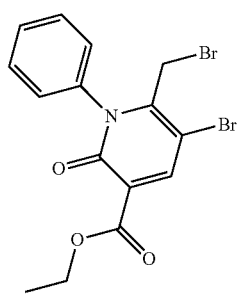 [SMILES: CCOC(=O)c1cc(Br)c(CBr)n(-c2ccccc2)c1=O]

To a mixture of ethyl 5-bromo-6-methyl-2-oxo-1-phenyl-1,2-dihydropyridine-3-carboxylate (310 mg, 0.92 mmol) (from Affinity Research Chemicals) and NBS (197 mg, 1.11 mmol) in carbon tetrachloride (6.0 mL)/chloroform (2.5 mL) was added 2,2'-Azo-bis-isobutyronitrile (15.1 mg, 0.092 mmol). The resulting mixture was stirred at reflux for 6 h, cooled to rt, and concentrated. The resulting material was purified via column chromatography (20% to 70% EtOAc in hexanes) to give the product as a yellow solid (234 mg, 61%). LCMS calcd for $C_{15}H_{14}Br_2NO_3$ $(M+H)^+$: m/z=413.9. Found: 414.0.

Step 2: 5-Bromo-6-(methoxymethyl)-2-oxo-1-phenyl-1,2-dihydropyridine-3-carboxylic Acid

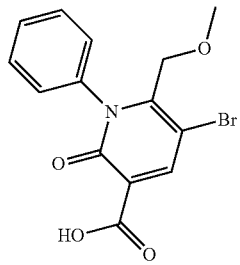 [SMILES: COCc1c(Br)cc(C(=O)O)c(=O)n1-c1ccccc1]

A mixture of ethyl 5-bromo-6-(bromomethyl)-2-oxo-1-phenyl-1,2-dihydropyridine-3-carboxylate (100 mg, 0.24 mmol) and LiOH monohydrate (50.5 mg, 1.21 mmol) in MeOH (4 mL) and water (0.7 mL) was stirred at rt for 1 h, and MeOH was evaporated. To the residue was added water and the resulting mixture was made slightly acidic by addition of 1 N HCl, which caused a solid to form. The solids were collected by filtration, washed with water, and dried to give the product as a yellow solid (79 mg, 97%). LCMS calcd for $C_{14}H_{13}BrNO_4$ $(M+H)^+$: m/z=338.0. Found: 338.0.

Step 3: tert-Butyl 4-(4-amino-5-(4-(5-bromo-6-(methoxymethyl)-2-oxo-1-phenyl-1,2-dihydropyridine-3-carboxamido)phenyl)pyrrolo[1,2-f][1,2,4]triazin-7-yl)piperidine-1-carboxylate

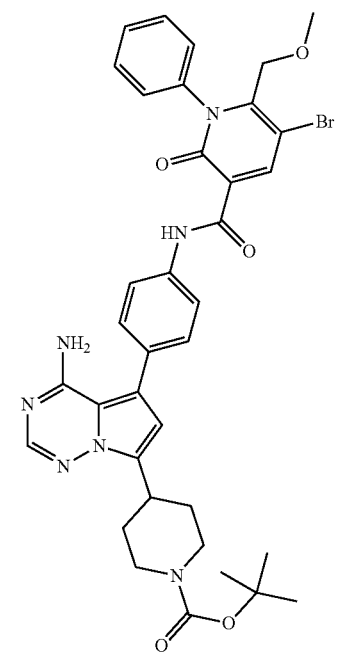 [SMILES: COCc1c(Br)cc(C(=O)Nc2ccc(-c3cc(C4CCN(C(=O)OC(C)(C)C)CC4)n4ncnc(N)c34)cc2)c(=O)n1-c1ccccc1]

To a solution of tert-butyl 4-(4-amino-5-(4-aminophenyl)pyrrolo[2,1-f][1,2,4]triazin-7-yl)piperidine-1-carboxylate (95.0 mg, 0.23 mmol) (Example 107, step 4), 5-bromo-6-(methoxymethyl)-2-oxo-1-phenyl-1,2-dihydropyridine-3-carboxylic acid (79 mg, 0.23 mmol), and Et$_3$N (0.049 mL, 0.349 mmol) in DMF (1.2 mL) was added HATU (106 mg, 0.28 mmol).

The resulting mixture was stirred at rt for 2 h, added water, and stirred for another 10 min. The resulting solid was collected by filtration, washed with water, and dried to give the product as a light yellow solid (156 mg, 92%). LCMS calcd for $C_{36}H_{39}BrN_7O_5(M+H)^+$: m/z=728.2. Found: 728.4.

Step 4: N-(4-(4-Amino-7-(piperidin-4-yl)pyrrolo[2,1-f][1,2,4]triazin-5-yl)phenyl)-5-bromo-6-(methoxymethyl)-2-oxo-1-phenyl-, 2-dihydropyridine-3-carboxamide dihydrochloride

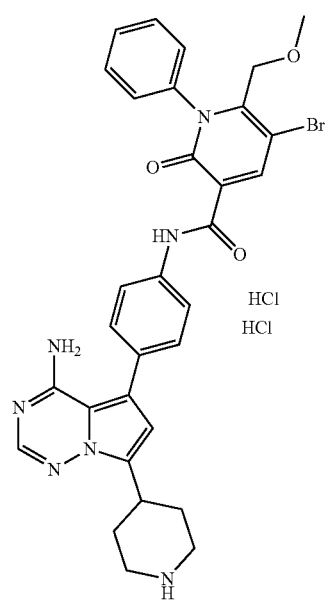 [SMILES: COCc1c(Br)cc(C(=O)Nc2ccc(-c3cc(C4CCNCC4)n4ncnc(N)c34)cc2)c(=O)n1-c1ccccc1 ; Cl ; Cl]

To a solution of tert-butyl 4-(4-amino-5-(4-(5-bromo-6-(methoxymethyl)-2-oxo-1-phenyl-1,2-dihydropyridine-3-carboxamido)phenyl)pyrrolo[2,1-f][1,2,4]triazin-7-yl)piperidine-1-carboxylate (54 mg, 0.074 mmol) in $CH_2Cl_2$ (400 µL) was added 4 N HCl in 1,4-dioxane (148 µL, 0.59 mmol). The resulting mixture was stirred at rt for 2 h, concentrated, and dried to give the product, which was used directly in the next step (50 mg, 96%). LCMS calcd for $C_{31}H_{31}BrN_7O_3$ $(M+H)^+$: m/z=628.2. Found: 628.3.

Step 5: N-(4-(4-Amino-7-(1-isobutyrylpiperidin-4-yl)pyrrolo[2,1-f][1,2,4]triazin-5-yl)phenyl)-5-bromo-6-(methoxymethyl)-2-oxo-1-phenyl-1,2-dihydropyridine-3-carboxamide To a mixture of N-(4-(4-amino-7-(piperidin-4-yl)pyrrolo [2,1-f][1,2,4]triazin-5-yl)phenyl)-5-bromo-6-(methoxymethyl)-2-oxo-1-phenyl-1,2-dihydropyridine-3-carboxamide dihydrochloride (20.0 mg, 0.029 mmol) and $Et_3N$ (0.020 mL, 0.14 mmol) in $CH_2Cl_2$ (0.40 mL) was added isobutyryl chloride (3.1 µL, 0.030 mmol). The resulting mixture was stirred at rt overnight, concentrated, and purified via pH 2 preparative LC/MS (MeCN/water with TFA) to give the product as TFA salt. LCMS calcd for $C_{35}H_{37}BrN_7O_4(M+H)^+$: m/z=698.2. Found: 698.2. $^1$H NMR (500 MHz, DMSO) δ 11.82 (s, 1H), 8.58 (s, 1H), 8.03 (s, 1H), 7.80 (d, J=8.7 Hz, 2H), 7.63-7.53 (m, 3H), 7.45 (d, J=8.6 Hz, 2H), 7.40 (d, J=6.8 Hz, 2H), 6.69 (s, 1H), 4.53 (d, J=12.7 Hz, 1H), 4.14 (s, 2H), 4.05 (d, J=13.8 Hz, 1H), 3.40 (t, J=11.8 Hz, 1H), 3.18 (d, J=12.9 Hz, 1H), 2.99 (s, 3H), 2.94-2.81 (m, 1H), 2.68 (t, J=12.7 Hz, 1H), 2.10-1.95 (m, 2H), 1.56 (dd, J=60.6, 9.7 Hz, 2H), 1.01 (d, J=6.6 Hz, 6H).

Example 137. N-(4-(4-Amino-7-(1-isobutyrylpiperidin-4-yl)pyrrolo[2,1-f][1,2,4]triazin-5-yl)phenyl)-5-cyano-6-(ethoxymethyl)-2-oxo-1-phenyl-1,2-dihydropyridine-3-carboxamide

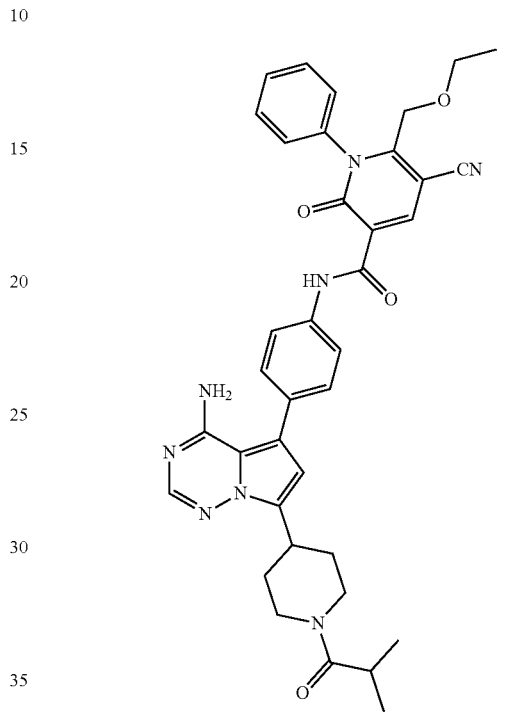

Step 1: 5-Bromo-6-(ethoxymethyl)-2-oxo-1-phenyl-1,2-dihydropyridine-3-carboxylic Acid

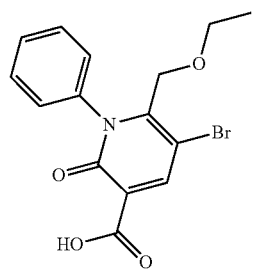 [SMILES: CCOCc1c(Br)cc(C(=O)O)c(=O)n1-c1ccccc1]

A mixture of ethyl 5-bromo-6-(bromomethyl)-2-oxo-1-phenyl-1,2-dihydropyridine-3-carboxylate (40 mg, 0.10 mmol) (Example 136, step 1) and LiOH monohydrate (22 mg, 0.52 mmol) in EtOH (1.2 mL) and water (0.2 mL) was stirred at rt for 2 h, and EtOH was evaporated. To the residue was added water and the resulting mixture was made slightly acidic by addition of 1 N HCl, which caused a solid to form. The solid was collected by filtration, washed with water, and dried to give the product as a yellow solid (25 mg, 69%). LCMS calcd for $C_{15}H_{15}BrNO_4$ $(M+H)^+$: m/z=352.0. Found: 352.0.

Step 2: N-(4-(4-Amino-7-(1-isobutyrylpiperidin-4-yl)pyrrolo[2,1-f][1,2,4]triazin-5-yl)phenyl)-5-bromo-6-(ethoxymethyl)-2-oxo-1-phenyl-1,2-dihydropyridine-3-carboxamide

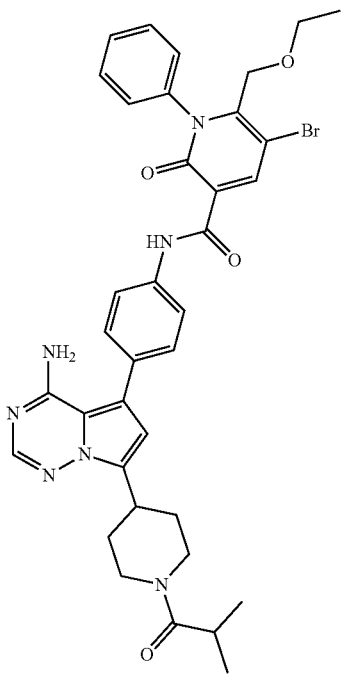 [SMILES: CCOCc1c(Br)cc(C(=O)Nc2ccc(-c3cc(C4CCN(C(=O)C(C)C)CC4)n4ncnc(N)c34)cc2)c(=O)n1-c1ccccc1]

To a mixture of 1-(4-(4-amino-5-(4-aminophenyl)pyrrolo[2,1-f][1,2,4]triazin-7-yl)piperidin-1-yl)-2-methylpropan-1-one (26 mg, 0.069 mmol) (Example 83, step 2) and 5-bromo-6-(ethoxymethyl)-2-oxo-1-phenyl-1,2-dihydropyridine-3-carboxylic acid (24 mg, 0.069 mmol) in DMF (0.40 mL) was added Et₃N (0.014 mL, 0.10 mmol), followed by HATU (31 mg, 0.082 mmol). The resulting mixture was stirred at rt for 90 min, added water, and stirred for another 10 min. The resulting solid was collected by filtration, washed with water, and dried to give the product as a light yellow solid (47 mg, 96%). LCMS calcd for $C_{36}H_{39}BrN_7O_4$ (M+H)⁺: m/z=712.2. Found: 712.2.

Step 3: N-(4-(4-Amino-7-(1-isobutyrylpiperidin-4-yl)pyrrolo[2,1-f][1,2,4]triazin-5-yl)phenyl)-5-cyano-6-(ethoxymethyl)-2-oxo-1-phenyl-1,2-dihydropyridine-3-carboxamide A mixture of N-(4-(4-amino-7-(1-isobutyrylpiperidin-4-yl)pyrrolo[2,1-f][1,2,4]triazin-5-yl)phenyl)-5-bromo-6-(ethoxymethyl)-2-oxo-1-phenyl-1,2-dihydropyridine-3-carboxamide (18.0 mg, 0.025 mmol), Pd(OAc)₂ (0.23 mg, 1.0 µmol), XantPhos (1.2 mg, 2.02 µmol), Zinc cyanide (3.0 mg, 0.025 mmol) and TMEDA (1.1 µL, 7.6 µmol) in DMF (0.50 mL) was degassed with N₂, and then heated and stirred at 160° C. for 10 min under microwave conditions. The reaction mixture was cooled to rt, filtered, and purified via pH 2 preparative LC/MS (MeCN/water with TFA) to give the product as TFA salt. LCMS calcd for $C_{37}H_{39}N_8O_4$ (M+H)⁺: m/z=659.3. Found: 659.3. ¹H NMR (500 MHz, DMSO) δ 11.40 (s, 1H), 8.65 (s, 1H), 8.01 (s, 1H), 7.81 (d, J=8.6 Hz, 2H), 7.68-7.52 (m, 3H), 7.50-7.38 (m, 4H), 6.67 (s, 1H), 4.51 (s, 1H), 4.22 (s, 2H), 4.04 (s, 1H), 3.40 (t, J=11.7 Hz, 1H), 3.31-3.12 (m, 3H), 2.95-2.82 (m, 1H), 2.65 (d, J=26.7 Hz, 1H), 2.12-1.94 (m, 2H), 1.76-1.38 (m, 2H), 1.13-0.88 (m, 9H).

Example 138. N-(4-(4-Amino-7-(1-isobutyrylpiperidin-4-yl)pyrrolo[2,1-f][1,2,4]triazin-5-yl)phenyl)-3-(1,4-dimethyl-1H-pyrazol-3-yl)-1-isopropyl-2,4-dioxo-1,2,3,4-tetrahydropyrimidine-5-carboxamide

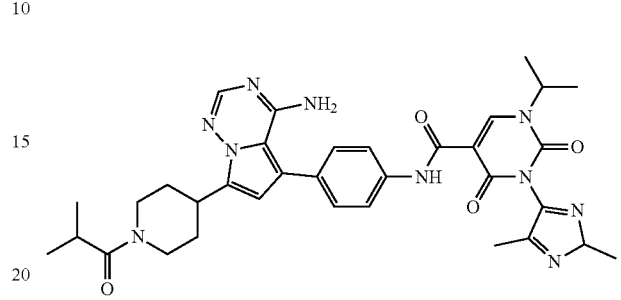

This compound was prepared following a synthetic sequence analogous to that for example 87, using 1,4-dimethyl-1H-pyrazol-3-amine instead of 1-methyl-1H-pyrazol-4-amine. This compound was purified via pH 2 preparative LC/MS (MeCN/water with TFA) to give the product as TFA salt. LCMS calcd for $C_{34}H_{41}N_{10}O_4$(M+H)⁺: m/z=653.3. Found: 653.5.

Example 139. N-(4-(4-Amino-7-(1-isobutyrylpiperidin-4-yl)pyrrolo[2,1-f][1,2,4]triazin-5-yl)phenyl)-1-cyclopropyl-2,4-dioxo-3-phenyl-1,2,3,4-tetrahydropyrimidine-5-carboxamide

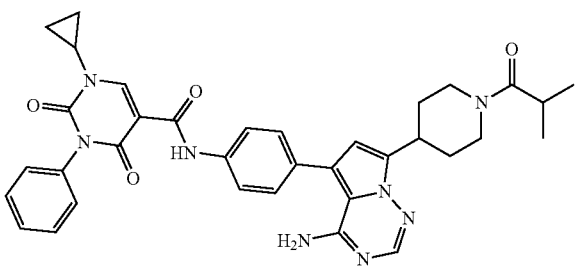 [SMILES: CC(C)C(=O)N1CCC(c2cc(-c3ccc(NC(=O)c4cn(C5CC5)c(=O)n(-c5ccccc5)c4=O)cc3)c3c(N)ncnn23)CC1]

Step 1: Diethyl 2-((cyclopropylamino)methylene)malonate

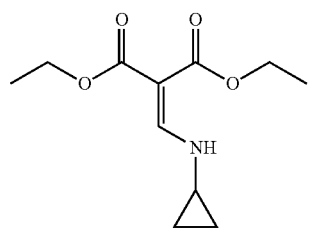 [SMILES: CCOC(=O)C(=CNC1CC1)C(=O)OCC]

To a solution of diethyl 2-(ethoxymethylene)malonate (2.16 g, 10.0 mmol) in MeCN (20 mL) was added cyclopropylamine (0.70 mL, 10.1 mmol). The reaction mixture was stirred at rt overnight, then at 80° C. for 1 h, cooled to rt, and concentrated to give the crude product, which was used directly in the next step. LCMS calcd for $C_{11}H_{18}NO_4$ (M+H)$^+$: m/z=228.1. Found: 228.1.

Step 2: Ethyl 1-cyclopropyl-2,4-dioxo-3-phenyl-1,2,3,4-tetrahydropyrimidine-5-carboxylate

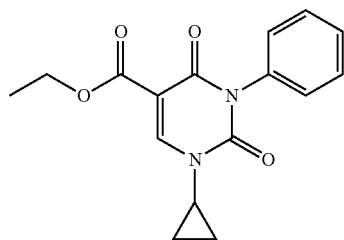 [SMILES: CCOC(=O)c1cn(C2CC2)c(=O)n(-c2ccccc2)c1=O]

A mixture of diethyl 2-((cyclopropylamino)methylene)malonate (0.45 g, 2.00 mmol) and isocyanatobenzene (0.476 g, 4.00 mmol) in pyridine (0.97 mL) was heated and stirred at 170° C. for 3 h, cooled to rt, and purified via column chromatography (0% to 10% MeOH in $CH_2Cl_2$) to give the product (0.336 g, 56%). LCMS calcd for $C_{16}H_{17}N_2O_4$ (M+H)$^+$: m/z=301.1. Found: 301.2.

Step 3: 1-Cyclopropyl-2,4-dioxo-3-phenyl-1,2,3,4-tetrahydropyrimidine-5-carboxylic Acid

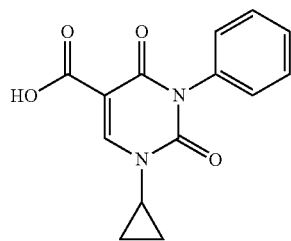 [SMILES: O=C(O)c1cn(C2CC2)c(=O)n(-c2ccccc2)c1=O]

A mixture of ethyl 1-cyclopropyl-2,4-dioxo-3-phenyl-1,2,3,4-tetrahydropyrimidine-5-carboxylate (0.336 g, 1.12 mmol) in 4.0 M HCl in 1,4-dioxane (2.24 mL, 8.95 mmol) and water (0.56 mL) was stirred at 80° C. for 3 h, cooled to rt, and concentrated to afford the crude product, which was used directly in the next step. LCMS calcd for $C_{14}H_{13}N_2O_4$ (M+H)$^+$: m/z=273.1. Found: 273.1.

Step 4: N-(4-(4-Amino-7-(1-isobutyrylpiperidin-4-yl)pyrrolo[2,1-f][1,2,4]triazin-5-yl)phenyl)-1-cyclopropyl-2,4-dioxo-3-phenyl-1,2,3,4-tetrahydropyrimidine-5-carboxamide To a mixture of 1-cyclopropyl-2,4-dioxo-3-phenyl-1,2,3,4-tetrahydropyrimidine-5-carboxylic acid (0.014 g, 0.050 mmol) and HATU (0.021 g, 0.055 mmol) in DMF (1 mL) was added 1-(4-(4-amino-5-(4-aminophenyl)pyrrolo[2,1-f][1,2,4]triazin-7-yl)piperidin-1-yl)-2-methylpropan-1-one (0.019 g, 0.050 mmol) (Example 83, step 2) and Et$_3$N (0.021 mL, 0.150 mmol). The reaction mixture was stirred at rt for 2 h, diluted with MeOH, adjusted with TFA to pH 2, and purified via pH 2 preparative LC/MS (MeCN/water with TFA) to give the product as TFA salt. LCMS calcd for $C_{35}H_{37}N_8O_4$ (M+H)$^+$: m/z=633.3. Found: 633.3.

Example 140. N-(4-(4-Amino-7-(1-isobutyrylpiperidin-4-yl)pyrrolo[2,1-f][1,2,4]triazin-5-yl)phenyl)-1-cyclopropyl-2,4-dioxo-3-(pyridin-3-yl)-1,2,3,4-tetrahydropyrimidine-5-carboxamide

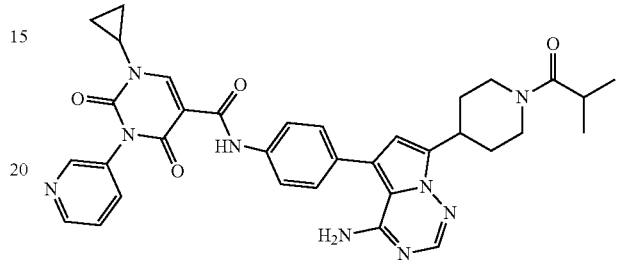

This compound was prepared following a synthetic sequence analogous to that for example 139, using 3-isocyanatopyridine instead of isocyanatobenzene in step 2. This compound was purified via pH 2 preparative LC/MS (MeCN/water with TFA) to give the product as TFA salt. LCMS calcd for $C_{34}H_{36}N_9O_4$ (M+H)$^+$: m/z=634.3. Found: 634.3.

Example 141. N-(4-(4-Amino-7-(1-isobutyrylpiperidin-4-yl)pyrrolo[2,1-f][1,2,4]triazin-5-yl)phenyl)-1'-cyclopropyl-2'-methyl-4'-oxo-1',4'-dihydro-[2,3'-bipyridine]-5'-carboxamide

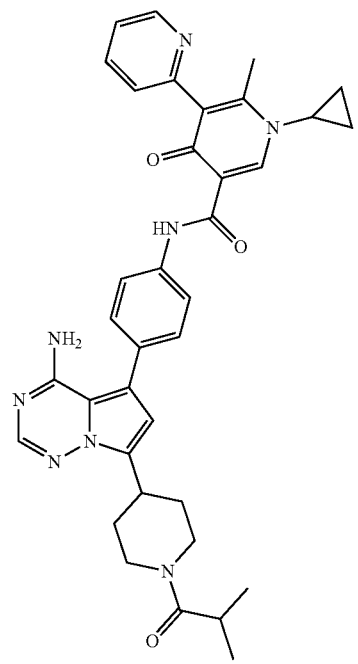 [SMILES: Cc1c(-c2ccccn2)c(=O)c(C(=O)Nc2ccc(-c3cc(C4CCN(C(=O)C(C)C)CC4)n4ncnc(N)c34)cc2)cn1C1CC1]

Step 1: 3-((Dimethylamino)methylene)-6-methyl-2H-pyran-2,4(3H)-dione

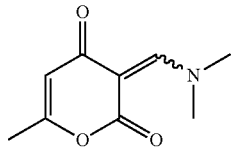

To a solution of 6-methyl-2H-pyran-2,4(3H)-dione (11.5 g, 91 mmol) in toluene (30 mL) was added N,N-dimethylformamide dimethyl acetal (13.1 mL, 98 mmol). The reaction mixture was then stirred overnight, and concentrated to give the crude product, which was used directly in the next step. LCMS calcd for $C_9H_{12}NO_3$ (M+H)$^+$: m/z=182.1. Found: 182.3.

Step 2: 1-Cyclopropyl-6-methyl-4-oxo-1,4-dihydropyridine-3-carboxylic Acid

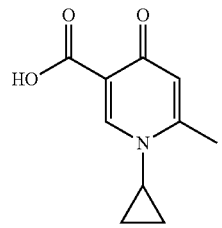

A mixture of 3-((dimethylamino)methylene)-6-methyl-2H-pyran-2,4(3H)-dione (1.92 g, 7.95 mmol), cyclopropanamine (0.83 mL, 11.9 mmol) and sodium tert-butoxide (1.13 g, 11.8 mmol) in EtOH (5.0 mL) was heated and stirred at 90° C. for 18 h, cooled to rt, concentrated, and treated with water and $CH_2Cl_2$. The aqueous solution was acidified with 4 N HCl and extracted with $CH_2Cl_2$. The combined organic layers were washed with water, brine, dried over $Na_2SO_4$, and concentrated to give the desired compound (1.1 g, 42%). LCMS calcd for $C_{10}H_{12}NO_3$ (M+H)$^+$: m/z=194.1. Found: 194.3.

Step 3: 5-Bromo-1-cyclopropyl-6-methyl-4-oxo-1,4-dihydropyridine-3-carboxylic Acid

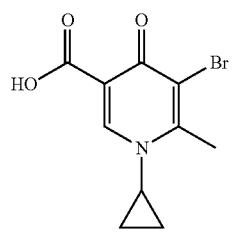

A suspension of 1-cyclopropyl-6-methyl-4-oxo-1,4-dihydropyridine-3-carboxylic acid (0.83 g, 4.30 mmol) in glacial acetic acid (6.0 mL) was treated with $Br_2$ (0.29 mL, 5.58 mmol). The reaction mixture was stirred at rt for 4 days, added additional $Br_2$ (100 µL), and stirred overnight. The reaction mixture was diluted with water, and the resulting solid was collected by filtration, washed with water, and dried to give the product as a beige solid (1.0 g, 86% yield). LCMS calcd for $C_{10}H_{11}BrNO_3$ (M+H)$^+$: m/z=272.0. Found: 272.2.

Step 4: N-(4-(4-Amino-7-(1-isobutyrylpiperidin-4-yl)pyrrolo[2,1-f][1,2,4]triazin-5-yl)phenyl)-5-bromo-1-cyclopropyl-6-methyl-4-oxo-1,4-dihydropyridine-3-carboxamide

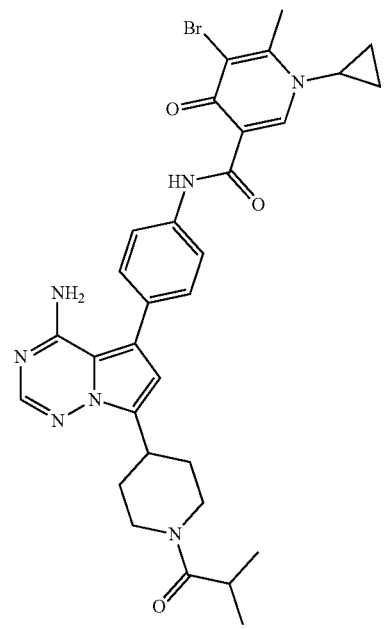 [SMILES: Cc1c(Br)c(=O)c(C(=O)Nc2ccc(-c3cc(C4CCN(C(=O)C(C)C)CC4)n4ncnc(N)c34)cc2)cn1C1CC1]

A mixture of 1-(4-(4-amino-5-(4-aminophenyl)pyrrolo[2,1-f][1,2,4]triazin-7-yl)piperidin-1-yl)-2-methylpropan-1-one (278 mg, 0.735 mmol) (Example 83, step 2), 5-bromo-1-cyclopropyl-6-methyl-4-oxo-1,4-dihydropyridine-3-carboxylic acid (200 mg, 0.735 mmol), HATU (335 mg, 0.882 mmol) and $Et_3N$ (0.21 mL, 1.47 mmol) in DMF (5.0 mL) was stirred at rt for 2 h, and then purified via column chromatography to give the product (252 mg, 54%). LCMS calcd for $C_{31}H_{35}BrN_7O_3$(M+H)$^+$: m/z=632.2. Found: 632.3.

287

Step 5: N-(4-(4-Amino-7-(1-isobutyrylpiperidin-4-yl)pyrrolo[2,1-f][1,2,4]triazin-5-yl)phenyl)-1-1'-cyclopropyl-2'-methyl-4'-oxo-1',4'-dihydro-[2,3'-bipyridine]-5'-carboxamide To a solution of N-(4-(4-amino-7-(1-isobutyrylpiperidin-4-yl)pyrrolo[2,1-f][1,2,4]triazin-5-yl)phenyl)-5-bromo-1-cyclopropyl-6-methyl-4-oxo-1,4-dihydropyridine-3-carboxamide (20.0 mg, 0.032 mmol) and 2-(tributylstannyl)pyridine (11.3 mg, 0.032 mmol) in 1,4-dioxane (2.0 mL) was added Pd(Ph$_3$P)$_4$ (7.3 mg, 6.3 µmol). The reaction mixture was heated and stirred at reflux overnight, cooled to rt, and purified via pH 2 preparative LC/MS (MeCN/water with TFA) to give the product as TFA salt. LCMS calcd for C$_{36}$H$_{39}$N$_8$O$_3$ (M+H)$^+$: m/z=631.3. Found: 631.1. $^1$H NMR (500 MHz, DMSO) δ 13.0-11.8 (m, 1H); 8.95 (m, 1H); 8.71 (s, 1H); 8.45 (m, 1H); 8.25 (s, 1H); 7.95-7.80 (m, 4H); 7.50 (m, 2H); 6.85 (m, 1H); 4.60 (m, 1H); 4.10 (m, 1H); 3.81 (m, 1H); 3.41 (m, 1H); 3.25 (m, 1H); 2.85 (m, 1H); 2.65 (m, 1H); 2.41 (s, 3H); 2.1-1.9 (m, 2H); 1.7-1.4 (m, 2H); 1.3-1.1 (m, 4H); 1.0 (m, 6H).

Example 142. N-(4-(4-Amino-7-(1-isobutyrylpiperidin-4-yl)pyrrolo[2,1-f][1,2,4]triazin-5-yl)phenyl)-1-cyclopropyl-2,2'-dimethyl-4-oxo-1,4-dihydro-[3,3'-bipyridine]-5-carboxamide

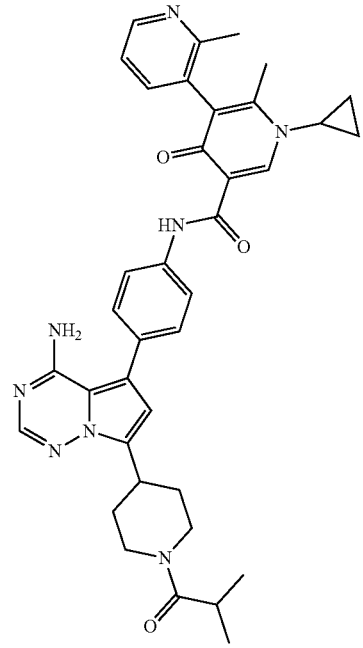 [SMILES: Cc1ncccc1-c1c(C)n(C2CC2)cc(C(=O)Nc2ccc(-c3cc(C4CCN(C(=O)C(C)C)CC4)n4ncnc(N)c34)cc2)c1=O]

To a solution of (2-methylpyridin-3-yl)boronic acid (4.3 mg, 0.032 mmol) and N-(4-(4-amino-7-(1-isobutyrylpiperidin-4-yl)pyrrolo[1,2-f][1,2,4]triazin-5-yl)phenyl)-5-bromo-1-cyclopropyl-6-methyl-4-oxo-1,4-dihydropyridine-3-carboxamide (20.0 mg, 0.032 mmol) (Example 141, step 4) in 1,4-dioxane (2.0 mL) and water (0.2 mL) were added K$_2$CO$_3$ (26.0 mg, 0.188 mmol) and Pd(Ph$_3$P)$_4$ (10.1 mg, 8.7 µmol). The reaction mixture was heated at reflux and stirred for 12 h, cooled to rt, and purified via pH 2 preparative LC/MS (MeCN/water with TFA) to give the product as TFA salt. LCMS calcd for C$_{37}$H$_{41}$N$_8$O$_3$ (M+H)$^+$: m/z=645.3. Found: 645.1.

Example 143. N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyrimidin-2-yl)-1,2,3,4-tetrahydropyrimidine-5-carboxamide

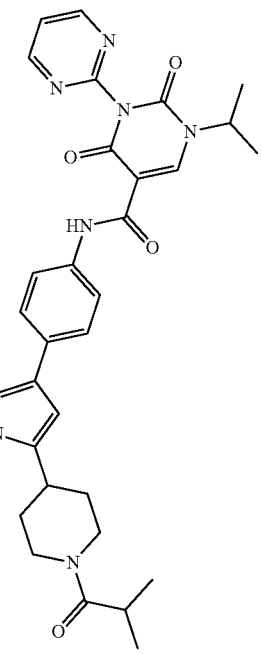

This compound was prepared following a synthetic sequence analogous to that for example 87, using pyrimidin-2-amine instead of 1-methyl-1H-pyrazol-4-amine in step 1. This compound was purified via pH 2 preparative LC/MS (MeCN/water with TFA) to give the product as TFA salt. LCMS calcd for C$_{33}$H$_{37}$N$_{10}$O$_4$(M+H)$^+$: m/z=637.3. Found: 637.3. $^1$H NMR (400 MHz, DMSO) δ 10.68 (s, 1H), 9.08 (d, J=4.9 Hz, 2H), 8.73 (s, 1H), 8.08 (s, 1H), 7.84-7.72 (m, 3H), 7.46 (d, J=8.6 Hz, 2H), 6.75 (s, 1H), 4.76 (p, J=6.7 Hz, 1H), 4.59-4.49 (m, 1H), 4.12-4.01 (m, 1H), 3.49-3.34 (m, 1H), 3.27-3.14 (m, 1H), 2.90 (p, J=6.7 Hz, 1H), 2.76-2.61 (m, 1H), 2.11-1.94 (m, 2H), 1.72-1.49 (m, 2H), 1.45 (d, J=6.8 Hz, 6H), 1.01 (s, 6H).

Example 144. N-(4-(4-Amino-7-(1-isobutyrylpiperidin-4-yl)pyrrolo[1,2-f][1,2,4]triazin-5-yl)phenyl)-1-cyclopropyl-2,4-dioxo-3-(pyridin-2-yl)-1,2,3,4-tetrahydropyrimidine-5-carboxamide Example 145. N-(4-(4-Amino-7-(1-isobutyrylpiperidin-4-yl)pyrrolo[1,2-f][1,2,4]triazin-5-yl)phenyl)-3-(5-fluoropyridin-2-yl)-1-isopropyl-2,4-dioxo-1,2,3,4-tetrahydropyrimidine-5-carboxamide

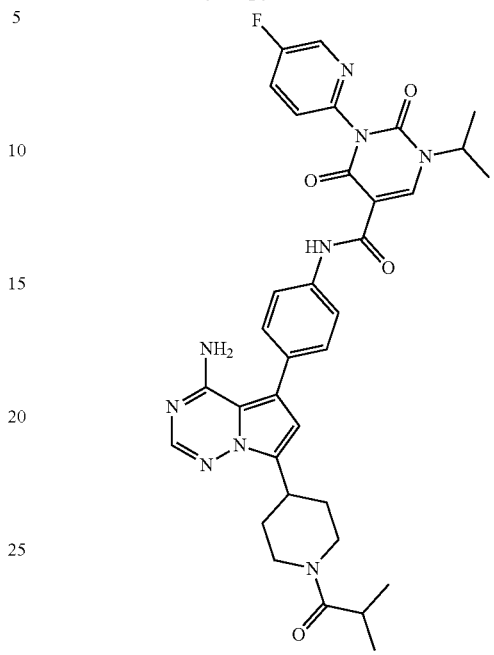

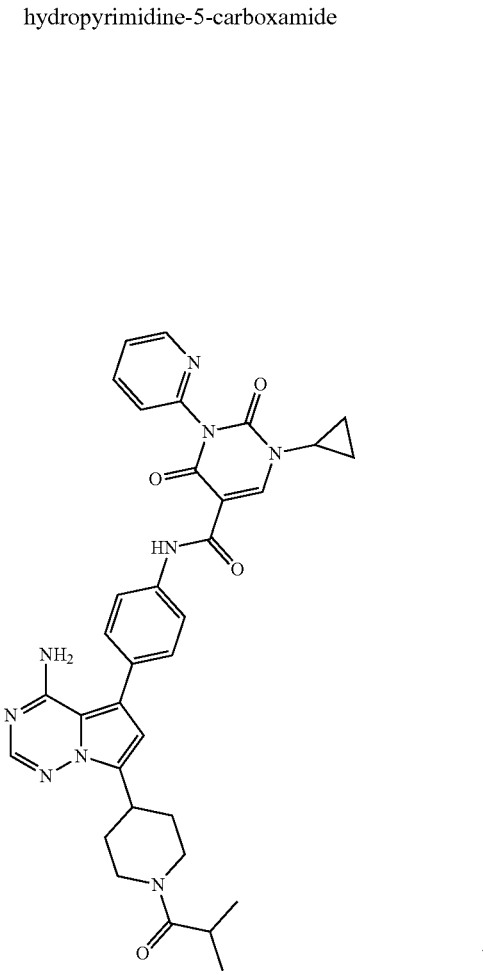

This compound was prepared following a synthetic sequence analogous to that for example 87, using 5-fluoropyridin-2-amine instead of 1-methyl-1H-pyrazol-4-amine in step 1. This compound was purified via pH 2 preparative LC/MS (MeCN/water with TFA) to give the product as TFA salt. LCMS calcd for $C_{34}H_{37}FN_9O_4(M+H)^+$: m/z=654.3. Found: 654.3.

Example 146. N-(4-(4-Amino-7-(1-isobutyrylpiperidin-4-yl)pyrrolo[1,2-f][1,2,4]triazin-5-yl)phenyl)-1-isopropyl-4-oxo-5-(pyridin-2-yl)-1,4-dihydropyridine-3-carboxamide

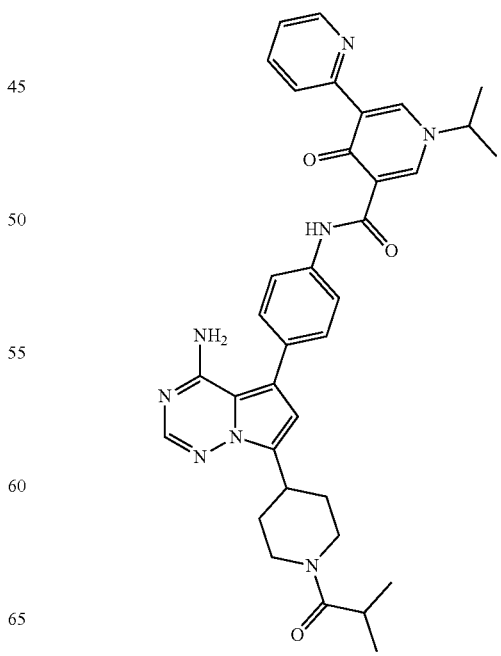

This compound was prepared following a synthetic sequence analogous to that for example 139, using 2-isocyanatopyridine instead of isocyanatobenzene in step 2. This compound was purified via pH 2 preparative LC/MS (MeCN/water with TFA) to give the product as TFA salt. LCMS calcd for $C_{34}H_{36}N_9O_4$ (M+H)$^+$: m/z=634.3. Found: 634.3. $^1$H NMR (600 MHz, DMSO) δ 10.81 (s, 1H), 8.64 (ddd, J=4.9, 1.9, 0.8 Hz, 1H), 8.53 (s, 1H), 8.13-8.00 (m, 2H), 7.83-7.74 (m, 2H), 7.56 (ddd, J=7.5, 4.9, 1.0 Hz, 1H), 7.52 (dt, J=8.0, 0.9 Hz, 1H), 7.49-7.41 (m, 2H), 6.73 (s, 1H), 4.54 (d, J=12.2 Hz, 1H), 4.07 (d, J=12.8 Hz, 1H), 3.41 (tt, J=11.8, 3.6 Hz, 1H), 3.34-3.28 (m, 1H), 3.20 (t, J=12.3 Hz, 1H), 2.90 (p, J=6.7 Hz, 1H), 2.69 (t, J=12.0 Hz, 1H), 2.02 (dd, J=30.8, 12.2 Hz, 2H), 1.67-1.47 (m, 2H), 1.17-0.84 (m, 10H).

Step 1: N-(4-(4-Amino-7-(1-isobutyrylpiperidin-4-yl)pyrrolo[1,2-f][1,2,4]triazin-5-yl)phenyl)-5-bromo-1-isopropyl-4-oxo-1,4-dihydropyridine-3-carboxamide

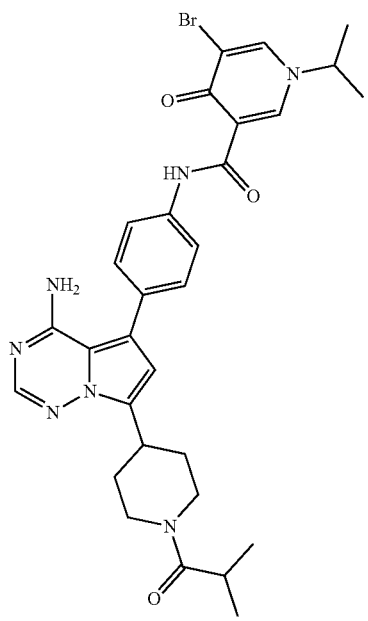 [SMILES: CC(C)C(=O)N1CCC(c2cc(-c3ccc(NC(=O)c4cn(C(C)C)cc(Br)c4=O)cc3)c3c(N)ncnn23)CC1]

To a mixture of 1-(4-(4-amino-5-(4-aminophenyl)pyrrolo[2,1-f][1,2,4]triazin-7-yl)piperidin-1-yl)-2-methylpropan-1-one (200 mg, 0.53 mmol) (example 83, step 2) and 5-bromo-1-isopropyl-4-oxo-1,4-dihydropyridine-3-carboxylic acid (137 mg, 0.53 mmol) (example 128, step 2) in DMF (4.0 mL) was added Et$_3$N (0.11 mL, 0.79 mmol), followed by HATU (241 mg, 0.63 mmol). The resulting mixture was stirred at rt for 3 h, added water, and stirred for another 15 min. The resulting solid was collected by filtration, washed with water, and dried to give the product. LCMS calcd for C$_{30}$H$_{35}$BrN$_7$O$_3$ (M+H)$^+$: m/z=620.2. Found: 620.2.

Step 2: N-(4-(4-Amino-7-(1-isobutyrylpiperidin-4-yl)pyrrolo[1,2-f][1,2,4]triazin-5-yl)phenyl)-1-isopropyl-4-oxo-5-(pyridin-2-yl)-1,4-dihydropyridine-3-carboxamide To a mixture of N-(4-(4-amino-7-(1-isobutyrylpiperidin-4-yl)pyrrolo[2,1-f][1,2,4]triazin-5-yl)phenyl)-5-bromo-1-isopropyl-4-oxo-1,4-dihydropyridine-3-carboxamide (40.0 mg, 0.064 mmol), Pd(PPh$_3$)$_4$(14.9 mg, 0.013 mmol) in toluene (1.2 mL) was added 2-(tributylstannyl)pyridine (0.042 mL, 0.129 mmol). The mixture was purged with N$_2$, and heated and stirred at 120° C. overnight. The reaction mixture was then cooled to rt, diluted with MeOH, filtered and purified via pH 2 preparative LC/MS (MeCN/water with TFA) to give the product as TFA salt. LCMS calcd for C$_{35}$H$_{39}$N$_8$O$_3$ (M+H)$^+$: m/z=619.3. Found: 619.3.

Example 147. N-(4-(4-Amino-7-(1-isobutyrylpiperidin-4-yl)pyrrolo[1,2-f][1,2,4]triazin-5-yl)phenyl)-1-cyclopropyl-6-methyl-4-oxo-5-(pyridin-3-yl)-1,4-dihydropyridine-3-carboxamide

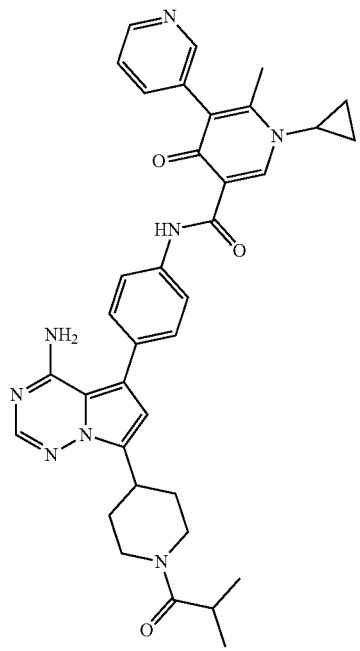 [SMILES: Cc1c(-c2cccnc2)c(=O)c(C(=O)Nc2ccc(-c3cc(C4CCN(C(=O)C(C)C)CC4)n4ncnc(N)c34)cc2)cn1C1CC1]

A mixture of N-(4-(4-amino-7-(1-isobutyrylpiperidin-4-yl)pyrrolo[2,1-f][1,2,4]triazin-5-yl)phenyl)-5-bromo-1-cyclopropyl-6-methyl-4-oxo-1,4-dihydropyridine-3-carboxamide (12.0 mg, 0.019 mmol) (example 141 step 4), pyridin-3-ylboronic acid (2.8 mg, 0.023 mmol), Chloro(2-dicyclohexylphosphino-2',4',6'-tri-i-propyl-1,1'-biphenyl)(2'-amino-1,1'-biphenyl-2-yl) palladium(II) (Xphos Pd G2) (1.5 mg, 1.90 μmol), and potassium phosphate tribasic (8.9 mg, 0.042 mmol) in 1,4-dioxane (0.50 mL) and water (0.10 mL) were degassed with N$_2$, and then heated and stirred at 80° C. for 2 h. The reaction mixture was then cooled to rt, diluted with MeOH, filtered, and purified via pH 2 preparative LC/MS (MeCN/water with TFA) to give the product as TFA salt. LCMS calcd for C$_{36}$H$_{39}$N$_8$O$_3$ (M+H)$^+$: m/z=631.3. Found: 631.3.

Example 148. N-(4-(4-Amino-7-(1-isobutyrylpiperidin-4-yl)pyrrolo[1,2-f][1,2,4]triazin-5-yl)phenyl)-3-(1,5-dimethyl-1H-pyrazol-3-yl)-1-isopropyl-2,4-dioxo-1,2,3,4-tetrahydropyrimidine-5-carboxamide

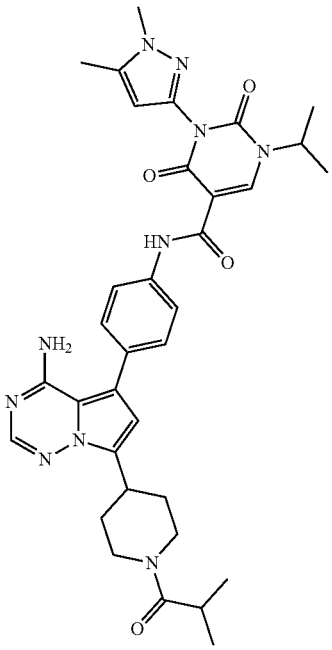 [SMILES: Cc1cc(-n2c(=O)c(C(=O)Nc3ccc(-c4cc(C5CCN(C(=O)C(C)C)CC5)n5ncnc(N)c45)cc3)cn(C(C)C)c2=O)nn1C]

This compound was prepared following a synthetic sequence analogous to that for example 87, using 1,5-dimethyl-1H-pyrazol-3-amine instead of 1-methyl-1H-pyrazol-4-amine in step 1. This compound was purified via pH 2 preparative LC/MS (MeCN/water with TFA) to give the product as TFA salt. LCMS calcd for $C_{34}H_{41}N_{10}O_4$ (M+H)$^+$: m/z=653.3. Found: 653.3.

Example 149. N-(4-(4-Amino-7-(1-isobutyrylpiperidin-4-yl)pyrrolo[1,2-f][1,2,4]triazin-5-yl)phenyl)-1-isopropyl-3-(6-methylpyridin-2-yl)-2,4-dioxo-1,2,3,4-tetrahydropyrimidine-5-carboxamide

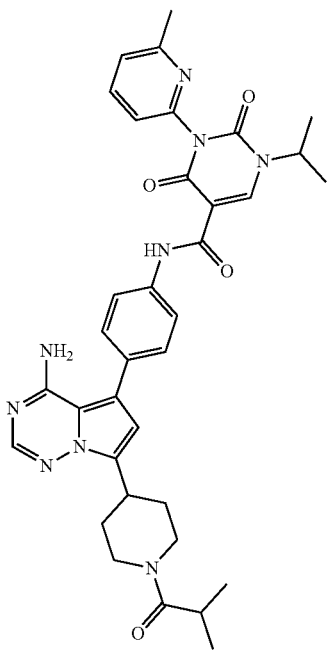 [SMILES: Cc1cccc(-n2c(=O)c(C(=O)Nc3ccc(-c4cc(C5CCN(C(=O)C(C)C)CC5)n5ncnc(N)c45)cc3)cn(C(C)C)c2=O)n1]

This compound was prepared following a synthetic sequence analogous to that for example 87, using 6-methylpyridin-2-amine instead of 1-methyl-1H-pyrazol-4-amine in step 1. This compound was purified via pH 2 preparative LC/MS (MeCN/water with TFA) to give the product as TFA salt. LCMS calcd for $C_{35}H_{40}N_9O_4$ (M+H)$^+$: m/z=650.3. Found: 650.3.

Example A

Axl Autophosphorylation Assay

Autophosphorylation of Axl was carried out by incubating the recombinant Axl protein (Life Technologies, PV4275) in buffer containing 50 mM Tris, pH7.5, 0.2 mg/ml Axl, 5 mM ATP, 20 mM $MgCl_2$ and 2 mM DTT at room temperature for 1 hour.

TAM Enzymatic Assay

The kinase assay buffer contained 50 mM HEPES, pH7.5, 10 mM MgCl2, 1 mM EGTA, 0.01% NP-40 and 2 mM DTT. 0.1 ul test compounds dissolved in DMSO were transferred from compound plates to white 384-well assay plates (Greiner LUMITRAC plates). The final concentration of DMSO was 1.25%. Enzyme solutions of 5.1 nM phosphor-Axl, or 0.0625 nM c-Mer (Carna Biosciences, 08-108), or 0.366 nM Tyro3 (Life Technologies, PR7480A) were prepared in assay buffer. A 1 mM stock solution of peptide substrate Biotin-EQEDEPEGDYFEWLE-amide SEQ ID NO: 1 (Quality Controlled Biochemicals, MA) dissolved in DMSO was diluted to 1 uM in assay buffer containing 2000 uM ATP. 4 ul enzyme solution (or assay buffer for the enzyme blank) was added to the appropriate wells in each plate, and then 4 ul/well substrate solution was added to initiate the reaction. The plate was protected from light and incubated at room temperature for 60 min. The reaction was stopped by adding 4 ul detection solution containing 50 mM Tris-HCl, pH7.8, 150 mM NaCl, 0.05% BSA, 45 mM EDTA, 180 nM SA-APC (Perkin Elmer, CR130-100) and 3 nM Eu-W1024 anti-phosphotyrosine PY20 (Perkin Elmer, AD0067). The plate was incubated for 1 h at room temperature, and HTRF (homogenous time resolved fluorescence) signal was measured on a PHERAstar FS plate reader (BMG labtech). Percentage of inhibition was calculated for each concentration and IC50 value was generated from curve fitting with GraphPad Prism software.

The compounds provided herein were found to be inhibitors of TAM according to the TAM Enzymatic Assay. All the compounds as described herein have been tested. The compounds shown in Table 1 below exhibit an $IC_{50}$ of less than 1 μM against at least one kinase selected from Tyro3, Axl and Mer.

The compounds provided herein were found to be inhibitors of one or more of AXL, MER, and TYRO3. $IC_{50}$ data is provided below in Table 1. The symbol "†" indicates an $IC_{50}$ of ≤5 nM, "††" indicates an $IC_{50}$ of >5 nM but ≤10 nM. "†††" indicates an $IC_{50}$ of >10 nM but ≤100 nM; "††††" indicates an $IC_{50}$ of greater than 100 nM; and na indicates not available.

TABLE 1

| Example | Axl $IC_{50}$ (nM) | Mer $IC_{50}$ (nM) | Tyro3 $IC_{50}$ (nM) |
|---|---|---|---|
| 1 | ††† | ††† | †††† |
| 2 | ††† | ††† | †††† |
| 3 | †††† | †††† | †††† |
| 4 | †††† | †††† | †††† |
| 5 | †††† | †††† | †††† |

TABLE 1-continued

| Example | Axl IC$_{50}$ (nM) | Mer IC$_{50}$ (nM) | Tyro3 IC$_{50}$ (nM) |
|---|---|---|---|
| 7 (cis isomer) | †† | † | †††† |
| 7 (trans isomer) | † | † | ††† |
| 8 | ††† | ††† | †††† |
| 9 | ††† | ††† | ††† |
| 10 | ††† | ††† | †††† |
| 11 | ††† | †† | †††† |
| 12 | ††† | † | †††† |
| 13 | †† | †† | †††† |
| 14 | † | † | ††† |
| 15 | † | † | ††† |
| 16 | † | † | ††† |
| 17 | † | † | ††† |
| 18 | † | † | †† |
| 19 | † | † | † |
| 20 | ††† | †† | †††† |
| 21 | †† | † | ††† |
| 22 | † | † | ††† |
| 23 | † | † | ††† |
| 24 | † | † | ††† |
| 25 | † | † | ††† |
| 26 | † | † | ††† |
| 27 | † | † | ††† |
| 28 | † | † | †††† |
| 29 | † | † | ††† |
| 30 | † | † | ††† |
| 31 | † | † | ††† |
| 32 | † | † | ††† |
| 33 | † | † | ††† |
| 34 | † | † | ††† |
| 35 | † | † | †† |
| 36 | †† | †† | †††† |
| 37 | † | † | ††† |
| 38 | † | † | ††† |
| 39 | † | † | ††† |
| 40 | †† | †† | †††† |
| 41 | † | † | ††† |
| 42 | † | † | ††† |
| 43 | † | † | ††† |
| 44 | † | † | †††† |
| 45 | † | † | ††† |
| 46 | † | † | ††† |
| 47 | † | † | ††† |
| 48 | †† | †† | ††† |
| 49 | † | † | ††† |
| 50 | † | † | ††† |
| 51 | † | † | †† |
| 52 | † | † | ††† |
| 53 | †† | † | ††† |
| 54 | † | † | ††† |
| 55 | † | † | †† |
| 56 | †† | †† | †††† |
| 57 | † | †† | †††† |
| 58 | † | †† | †††† |
| 59 | † | ††† | †††† |
| 60 | † | †† | ††† |
| 61 | † | † | ††† |
| 62 | † | † | ††† |
| 63 | † | † | ††† |
| 64 | † | † | ††† |
| 65 | † | † | ††† |
| 66 | † | †† | ††† |
| 67 | † | † | †††† |
| 68 | † | † | †††† |
| 69 | † | †† | †††† |
| 70 | † | † | ††† |
| 71 | † | †† | ††† |
| 72 | † | †† | †††† |
| 73 | † | †† | †††† |
| 74 | † | † | ††† |
| 75 | † | † | ††† |
| 76 | † | †† | †††† |
| 77 | † | ††† | †††† |
| 78 | † | † | ††† |
| 79 | † | † | ††† |
| 80 | † | †† | †††† |
| 81 | † | † | ††† |
| 82 | † | † | ††† |
| 83 | † | † | ††† |
| 84 | †† | ††† | †††† |
| 85 | † | ††† | †††† |
| 86 | ††† | ††† | †††† |
| 87 | † | † | †††† |
| 88 | † | † | ††† |
| 89 | na | na | na |
| 90 | †† | ††† | †††† |
| 91 | † | ††† | †††† |
| 92 | na | na | na |
| 93 | † | † | † |
| 94 | † | †† | †††† |
| 95 | † | ††† | †††† |
| 96 | † | † | ††† |
| 97 | † | †† | ††† |
| 98 | † | † | ††† |
| 99 | † | † | ††† |
| 100 | ††† | ††† | †††† |
| 101 | † | † | †††† |
| 102 | † | † | ††† |
| 103 | † | † | ††† |
| 104 | † | † | †† |
| 105 | † | †† | ††† |
| 106 | † | † | †††† |
| 107 | † | †† | †††† |
| 108 | † | † | ††† |
| 109 | † | † | †† |
| 110 | † | †† | †††† |
| 111 | † | † | †††† |
| 111a | †† | ††† | †††† |
| 112 | † | † | ††† |
| 113 | † | † | ††† |
| 114 | † | † | ††† |
| 115 | † | ††† | †††† |
| 116 | † | † | ††† |
| 117 | † | †† | †††† |
| 118 | † | † | †††† |
| 119 | † | † | †††† |
| 120 | † | † | †††† |
| 121 | † | † | †††† |
| 122 | † | † | †††† |
| 123 | † | †† | †††† |
| 124 | † | †† | †††† |
| 125 | † | † | †††† |
| 126 | † | † | †††† |
| 127 | † | † | †††† |
| 128 | † | †† | †††† |
| 129 | † | †† | †††† |
| 130 | † | † | †††† |
| 131 | † | † | †††† |
| 132 | † | † | †††† |
| 133 | † | †† | †††† |
| 134 | † | †† | †††† |
| 135 | † | † | †††† |
| 136 | † | † | †††† |
| 137 | † | †† | †††† |
| 138 | † | †† | †††† |
| 139 | † | † | †††† |
| 140 | † | †† | †††† |
| 141 | † | † | †††† |
| 142 | † | †† | †††† |
| 143 | † | †† | †††† |
| 144 | † | †† | †††† |
| 145 | na | na | na |
| 146 | na | na | na |
| 147 | † | † | †††† |
| 148 | † | †† | †††† |
| 149 | † | †† | †††† |

Example B. Generation of BAF3-AXL, BAF3-MER and BAF3-TYRO3 Cells and Cell Proliferation Assay The cytoplasmic domain of AXL, MER, or TYRO3 fused with dimerization sequence and HA tag was cloned into pMSCV vector with puromycin-resistance marker to generate three constructs (pMSCV-AXL, pMSCV-MER and pMSCV-TYRO3). BAF3 cells were transfected with the three constructs individually by electroporation. Single clones that were IL3 independent and puromycin-resistant were selected and characterized. Cells with stable expression of AXL, MER, or TYRO3 were selected and designated BAF3-AXL, BAF3-MER and BAF3-TYRO3 cells.

BAF3, BAF3-AXL, BAF3-MER or BAF3-TYRO3 cells lines were maintained in RPMI1640 with 10% FBS (Gibco/Life Technologies, Carlsbad, Calif.). To measure the effect of test compounds on cell viability, 1000 cells/well were plated into 384 well tissue culture plates in growth medium with a serial dilution of compound or DMSO alone for 48 hours at 37° C. with 5% $CO_2$, cell viability was measured by ATP assay (CellTiter-Glo Assay, Promega) according to the manufacturer's procedure. The data were converted to percent inhibition relative to DMSO control and $IC_{50}$ curves were fitted using GraphPad Prism software.

Example C. BaF3-AXL ELISA and BaF3-MER ELISA

BaF3-AXL or BaF3-MER cells were maintained in culture medium RPMI with 10% FBS and puromycin (1 µg/ml, Gibco/Life Technologies, Carlsbad, Calif.). To measure the effect of test compounds on phosphor-AXL or phosphor-MER, the cells were plated ($5 \times 10^4$ cells/well) in a V-bottom polypropylene plate (Greiner bio-one) in the presence or absence of test compounds diluted in culture medium, and incubated for 1 hour at 37° C. with 5% $CO_2$. The cells were harvested by centrifugation, and lysed in 110 µl of ice cold lysis buffer (Cell Signaling) with protease and phosphatase inhibitors (Halts PI, Thermo Fisher) for 30 min on ice. The cell lysate was stored at −80° C. for ELISA. ELISA plates were prepared by incubating Costar plate with anti-HA antibody (1 µg/ml) for 1 hour at room temperature. The plates were washed and blocked with PBS with 3% BSA. Cell lysate were loaded onto ELISA plate and incubated at 4° C. overnight. The plates were washed and incubated with LANCE Eu-W1024 anti-phospho-tyrosine antibody (PY-20) (Perkin Elmer) in DELFIA assay buffer (Perkin Elmer) for 1 hour, and read on the Pherastar (BMG Labtech). The data was converted to percent inhibition relative to DMSO control and $IC_{50}$ determination was performed by fitting the curve of percent inhibition versus the log of the inhibitor concentration using GraphPad Prism.

Example D. H1299 Phospho-AXL ELISA

H1299 cells (ATCC), human non-small cell lung carcinoma cell line with Axl expression, are maintained in culture medium RPMI with 10% FBS (Gibco/Life Technologies, Carlsbad, Calif.). To measure the effect of test compounds on phosphor-AXL, the cells were plated (30000 cells/well) in 96 well tissue culture plates (Costar) and incubated overnight at 37° C. with 5% $CO_2$. Compounds at an appropriate concentration were added and incubated for 1 hour at 37° C. with 5% $CO_2$. rhGas6 (R&D Systems, 6 µg/ml) were added to each well. Plates were incubated at 37° C. with 5% $CO_2$ for 15 min. Cells were harvested and lysed in 110 µL of ice cold lysis buffer (Cell Signaling) with protease and phosphatase inhibitors (Halts PI, Thermo Fisher). The lysate was incubated for 1 hour on ice and stored at −80° C. for ELISA. ELISA plates were prepared by incubating Costar plate with anti-HA antibody (1 µg/ml) for 1 hour at room temperature. The plates were washed and blocked with PBS with 3% BSA. Cell lysate was loaded onto ELISA plates and incubated at 4° C. overnight. The plates were washed and incubated with LANCE Eu-W1024 anti-phospho-tyrosine antibody (PY-20) (Perkin Elmer) in DELFIA assay buffer (Perkin Elmer) for 1 hour, and read on the Pherastar (BMG Labtech). The data was converted to percent inhibition relative to DMSO control and $IC_{50}$ determination was performed by fitting the curve of percent inhibition versus the log of the inhibitor concentration using GraphPad Prism.

Example E. Whole Blood H1299 Phospho-AXL ELISA

H1299 Cells (ATCC) are maintained in culture medium RPMI with 10% FBS (Gibco/Life Technologies, Carlsbad, Calif.). To measure the effect of test compounds on phospho-AXL in whole blood, the cells are plated (30000 cells/well) in 96 well tissue culture plates (Costar) and incubated overnight at 37° C. with 5% $CO_2$. Blood obtained from normal donors was mixed test compounds for 1 hour. Culture medium was removed from H1299 cells, and blood with compound was added to each well. After 1 hour incubation at 37° C. with 5% $CO_2$, rh-Gas6 (4 µg/ml, R&D Systems) was added to each well. The plate was incubated at 37° C. with 5% $CO_2$ for 15 min. The cells were washed with PBS, and lysed in 110 uL of ice cold lysis buffer (Cell Signaling) with protease and phosphatase inhibitors (Halts PI, Thermo Fisher) for 1 hour on ice. The plate was stored at −80° C. for ELISA. ELISA plates were prepared by incubating Costar plate with anti-HA antibody (1 ug/ml) for 1 hour at room temperature. The plates were washed and blocked with PBS with 3% BSA. Cell lysate were loaded onto ELISA plate and incubated at 4° C. overnight. The plates were washed and incubated with LANCE Eu-W1024 anti-phospho-tyrosine antibody (PY-20) (Perkin Elmer) in DELFIA assay buffer (Perkin Elmer) for 1 hour, and read on the Pherastar (BMG Labtech). The data was converted to percent inhibition relative to DMSO control and $IC_{50}$ determination was performed by fitting the curve of percent inhibition versus the log of the inhibitor concentration using GraphPad Prism.

Example F. G361 Phospho-Akt Cell Insight ELISA

G361 cells (ATCC), human malignant melanoma cell line expressing Mer, are maintained in culture medium RPMI with 10% FBS (Gibco/Life Technologies, Carlsbad, Calif.). To measure the effect of test compounds on MER signaling pathway, the cells were plated at $2 \times 10^4$ cells/well in 100 µL volume in 96 well CellBind surface plates (Corning), and incubated overnight at 37° C. with 5% $CO_2$. 20 µL of test compounds at appropriate concentrations were added to the cells and incubated for 1 hour. rhGas6 (4 µg/ml, R&D Systems) was added to each well, and incubated for 20 min. The cells were fixed by adding 50 uL 4% paraformaldehyde (Electron Microscopy Sciences) in PBS (Corning) for 30 min at room temperature. Plates were washed and incubated with 50 uL 0.2% triton X-100 (Sigma) in PBS for 10 minutes at room temperature. Plates were washed and incubated with 100 uL blocking buffer (0.1% BSA in PBS) for 30 min. Plates are washed and incubated with Phospho-AKT (Ser473) (D9E) rabbit mAb (Cell Signaling) diluted in 0.1% BSA (1:300 dilution) at 4° C. overnight. Plates were washed and incubated with 50 uL Alexaflour 488 F(ab')$^2$ fragment of goat anti-rabbit IgG (H+L) (Molecular Probes, 1:1000 dilution) and Hoechst 33342 (Thermo Fisher, 1:2000 dilution) in PBS at room temperature for 2 hours. Plates were washed with PBS, and read on Cell Insight CX5 (Thermo Fisher).

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula (IIg1) or Formula (IIg2):

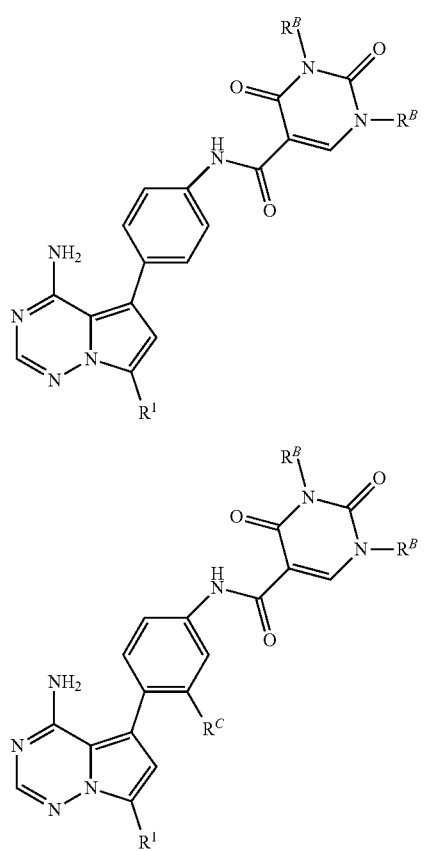

or a pharmaceutically acceptable salt thereof, wherein:

$R^1$ is $Cy^{A3}$-$R^A$;

$R^A$ is H, $C_{1-6}$ alkyl, $C_{1-6}$ haloalkyl, halo, $C_{3-6}$ cycloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}OR^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, or $S(O)_2NR^{c1}R^{d1}$; wherein said $C_{1-6}$ alkyl or $C_{1-6}$ haloalkyl is optionally substituted with 1, 2, 3 or 4 substituents independently selected from $R^{11}$;

$Cy^{A3}$ is piperidinyl optionally substituted with 1, 2, 3 or 4 substituents independently selected from $R^{A3}$;

each $R^{A3}$ is independently selected from OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^B$ is independently selected from halo, $C_{1-6}$ alkyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$ $NR^{c2}OR^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkynyl, $C_{3-6}$ cycloalkyl, phenyl, 5-6 membered heteroaryl, and 4-7 membered heterocycloalkyl are each optionally substituted with 1, 2, 3, or 4 substituents independently selected from $R^{12}$;

each $R^{11}$ is independently selected from CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}OR^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}$ $S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $R^{12}$ is independently selected from halo, CN, $NO_2$, $C_{1-6}$ alkyl, $C_{1-6}$ haloalkyl, $C_{3-6}$ cycloalkyl, phenyl, 5-6 membered heteroaryl, 4-7 membered heterocycloalkyl, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}OR^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{3-6}$ cycloalkyl, phenyl, 5-6 membered heteroaryl, and 4-7 membered heterocycloalkyl are each optionally substituted with 1, 2, 3, or 4 substituents independently selected from $R^g$;

$R^{a1}$, $R^{c1}$ and $R^{d1}$ are each independently selected from H, $C_{1-6}$ alkyl, and $C_{1-6}$ haloalkyl; wherein said $C_{1-6}$ alkyl is optionally substituted with 1, 2, 3, or 4 substituents independently selected from $R^g$; or alternatively, $R^{c1}$ and $R^{d1}$ attached to the same N atom, together with the N atom to which they are attached, form a 4-, 5-, 6- or 7-membered heterocycloalkyl group optionally substituted with 1, 2 or 3 substituents independently selected from $R^g$;

$R^{b1}$ is selected from $C_{1-6}$ alkyl and $C_{1-6}$ haloalkyl, each of which is optionally substituted with 1, 2, 3, or 4 substituents independently selected from $R^g$;

$R^{e1}$ is selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^{a2}$, $R^{c2}$, and $R^{d2}$ is independently selected from H, $C_{1-6}$ alkyl, $C_{1-6}$ haloalkyl, $C_{3-6}$ cycloalkyl, phenyl, 5-6 membered heteroaryl, and 4-7 membered heterocycloalkyl; wherein said $C_{1-6}$ alkyl, $C_{3-6}$ cycloalkyl, phenyl, 5-6 membered heteroaryl, and 4-7 membered heterocycloalkyl are each optionally substituted with 1, 2, 3, or 4 substituents independently selected from $R^{12}$; or alternatively, any $R^{c2}$ and $R^{d2}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b2}$ is independently selected from $C_{1-6}$ alkyl, $C_{1-6}$ haloalkyl, $C_{3-6}$ cycloalkyl, phenyl, 5-6 membered heteroaryl, and 4-7 membered heterocycloalkyl, each of which is optionally substituted with 1, 2, 3, or 4 substituents independently selected from $R^{12}$;

each $R^{a3}$, $R^{c3}$ and $R^{d3}$ is independently selected from H, $C_{1-6}$ alkyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-4}$ alkylene, phenyl-$C_{1-4}$ alkylene, 5-6 membered heteroaryl-$C_{1-4}$ alkylene, and 4-7 membered heterocycloalkyl-$C_{1-4}$ alkylene; wherein said $C_{1-6}$ alkyl, $C_{3-6}$ cycloalkyl, phenyl, 5-6 membered heteroaryl, 4-7 membered heterocycloalkyl, $C_{3-6}$ cycloalkyl-$C_{1-4}$ alkylene, phenyl-$C_{1-4}$ alkylene, 5-6 membered heteroaryl-$C_{1-4}$ alkylene, and 4-7 membered heterocycloalkyl-$C_{1-4}$ alkylene are each optionally substituted with 1, 2, 3, or 4 substituents independently selected from $R^g$; or alternatively, any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b3}$ is independently selected from $C_{1-6}$ alkyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-4}$ alkylene, phenyl-$C_{1-4}$ alkylene, 5-6 membered heteroaryl-$C_{1-4}$ alkylene, and 4-7 membered heterocycloalkyl-$C_{1-4}$ alkylene, each of which is optionally substituted with 1, 2, 3, or 4 substituents independently selected from $R^g$;

each $R^{a4}$, $R^{c4}$ and $R^{d4}$, is independently selected from H, $C_{1-6}$ alkyl, and $C_{1-6}$ haloalkyl; wherein said $C_{1-6}$ alkyl is optionally substituted with 1, 2, 3, or 4 substituents independently selected from $R^g$; or alternatively, any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b4}$ is independently selected from $C_{1-6}$ alkyl and $C_{1-6}$ haloalkyl, each of which is optionally substituted with 1, 2, 3, or 4 substituents independently selected from $R^g$; and each $R^g$ is independently selected from OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The compound of claim 1 or a pharmaceutically acceptable salt thereof, wherein:

$R^A$ is H, $C_{1-6}$ alkyl, $C_{1-6}$ haloalkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}OR^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, or $S(O)_2NR^{c1}R^{d1}$; wherein said $C_{1-6}$ alkyl or $C_{1-6}$ haloalkyl is optionally substituted with 1, 2, 3 or 4 substituents independently selected from $R^{11}$; and each $R^B$ is independently selected from halo, $C_{1-6}$ alkyl, $C_{1-6}$ haloalkyl, $C_{3-6}$ cycloalkyl, phenyl, 5-6 membered heteroaryl, 4-7 membered heterocycloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$ $NR^{c2}OR^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{3-6}$ cycloalkyl, phenyl, 5-6 membered heteroaryl, and 4-7 membered heterocycloalkyl are each optionally substituted with 1, 2, 3, or 4 substituents independently selected from $R^{12}$.

3. The compound of claim 1, or a pharmaceutically acceptable salt thereof, wherein $R^A$ is $C_{1-6}$ alkyl, CN, $OR^{a1}$, $NR^{c1}R^{d1}$, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$ or $S(O)_2NR^{c1}R^{d1}$; wherein said $C_{1-6}$ alkyl is optionally substituted with 1 or 2 substituents independently selected from $R^{11}$, provided that if $R^A$ is attached to a nitrogen atom, then $R^A$ is not CN, $OR^{a1}$, or $NR^{c1}R^{d1}$.

4. The compound of claim 1, or a pharmaceutically acceptable salt thereof, wherein $R^A$ is $C_{1-6}$ alkyl, CN, $OR^{a1}$, $C(O)R^{b1}$, $C(O)NR^{c1}R^{d1}$, $C(O)OR^{a1}$, and $S(O)_2R^{b1}$; wherein said $C_{1-6}$ alkyl is optionally substituted with 1 substituent selected from $R^{11}$, provided that if $R^A$ is attached to a nitrogen atom, then $R^A$ is not CN or $OR^{a1}$.

5. The compound of claim 1, or a pharmaceutically acceptable salt thereof, wherein each $R^{11}$ is independently $OR^{a3}$.

6. The compound of claim 1, or a pharmaceutically acceptable salt thereof, wherein each $R^{11}$ is independently OH or $OCH_3$.

7. The compound of claim 1, or a pharmaceutically acceptable salt thereof, wherein $Cy^{43}$ is optionally substituted with $R^A$ selected from $CH_3$, CN, OH, $CH_2CH_2OH$, $CH_2CH_2OCH_3$, $C(O)CH_3$, $C(O)CH_2CH_3$, $C(O)CH(CH_3)_2$, $C(O)CH_2OH$, $C(O)CH(CH_3)OH$, $S(O)_2CH_3$, $C(O)OCH_3$, $C(O)N(CH_3)_2$, $C(O)NH(CH_3)$, $C(O)N(CH_2CH_3)_2$, $C(O)NH(CH_2CH_3)$, $C(O)N(CH_3)(CH_2CH_3)$, $CH_2C(O)N(CH_3)_2$, $N(CH_3)_2$, and C(O)(morpholin-4-yl).

8. The compound of claim 1, or a pharmaceutically acceptable salt thereof, wherein $Cy^{43}$ is optionally substituted with $R^A$ selected from $CH_3$, CN, OH, $CH_2CH_2OH$, $CH_2CH_2OCH_3$, $C(O)CH_3$, $C(O)CH_2CH_3$, $C(O)CH(CH_3)_2$, $C(O)CH_2OH$, $C(O)CH(CH_3)OH$, $S(O)_2CH_3$, $C(O)OCH_3$, $C(O)N(CH_3)_2$, $C(O)NH(CH_3)$, $C(O)N(CH_2CH_3)_2$, $C(O)NH(CH_2CH_3)$, $C(O)N(CH_3)(CH_2CH_3)$, and C(O)(morpholin-4-yl).

9. The compound of claim 1, or a pharmaceutically acceptable salt thereof, wherein $R^1$ is

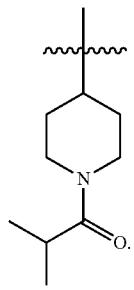 [SMILES: *C1CCN(C(=O)C(C)C)CC1]

10. The compound of claim 1, or a pharmaceutically acceptable salt thereof, wherein each $R^B$ is independently selected from halo, $C_{1-6}$ alkyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, CN, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, and $NR^{c2}C(O)OR^{a2}$; wherein said $C_{1-6}$ alkyl, $C_{2-6}$ alkynyl, $C_{3-6}$ cycloalkyl, phenyl, 5-6 membered heteroaryl, and 4-7 membered heterocycloalkyl are each optionally substituted with 1, 2, 3, or 4 substituents independently selected from $R^{12}$.

11. The compound of claim 1, or a pharmaceutically acceptable salt thereof, wherein each $R^B$ is independently unsubstituted phenyl, 4-fluoro-phenyl, 3-fluorophenyl, 2-fluorophenyl, $CH_2(phenyl)$, $CH(CH_2OH)phenyl$, Br, Cl, CN, $CH_3$, $CHF_2$, $CH_2CH_3$, $CH_2OCH_3$, $CH_2OCH_2CH_3$, $CH(CH_3)_2$, $CH(CH_2OH)CH_2CH_3$, $CH(CH_2OH)CH_3$, $CH_2CH_2OH$, $CH_2CH(OH)(CH_3)$, $OCH_3$, $OCH_2CH_3$, $C(O)NH_2$, $C(O)CH_3$, 2,5-difluorophenyl, 3-pyridinyl, 2-pyridinyl, 1-methyl-1H-pyrazol-4-yl, 1-methyl-1H-pyrazol-3-yl, 1-methyl-1H-pyrazol-5-yl, 1,4-dimethyl-1H-pyrazol-3-yl, 1,5-dimethyl-1H-pyrazol-3-yl, 2-methylthiazol-5-yl, cyclohexyl, 3-cyanophenyl, 5-methylisoxazol-3-yl, 5-fluoropyridin-3-yl, 5-fluoropyridin-2-yl, 3-cyanophenyl, $CH_2CN$, thiazol-4-yl, 6-methylpyridin-3-yl, 2-methylpyridin-3-yl, 6-methylpyridin-2-yl, pyrimidin-2-yl, morpholin-4-yl, cyclopropyl, oxazol-2-yl, $CCCH(OH)(CH_3)$, or C(O)NH(4-fluoro-phenyl).

12. The compound of claim 1, or a pharmaceutically acceptable salt thereof, wherein each $R^B$ is independently unsubstituted phenyl, 4-fluoro-phenyl, 3-fluorophenyl, 2-fluorophenyl, 2-pyridinyl, $CH_2(phenyl)$, $CH(CH_2OH)phenyl$, $CH_3$, $CH_2CH_3$, $CH(CH_3)_2$, $CH(CH_2OH)CH_2CH_3$, $CH(CH_2OH)CH_3$, $CH_2CH_2OH$, $OCH_3$, $OCH_2CH_3$, or C(O)NH(4-fluoro-phenyl).

13. The compound of claim 1, or a pharmaceutically acceptable salt thereof, wherein each $R^C$ is independently F, Cl, or methyl.

14. The compound of claim 1, or a pharmaceutically acceptable salt thereof, wherein each $R^C$ is F.

15. The compound of claim 1, or a pharmaceutically acceptable salt thereof, wherein, $R^1$ is

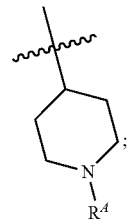

$R^A$ is $CH_3$, $CH_2CH_3$, CN, OH, $CH_2CH_2OH$, $CH_2CH_2OCH_3$, $C(O)CH_3$, $C(O)CH(CH_3)_2$, C(O)(cyclopropyl), $C(O)CH_2CH_3$, $C(O)CH_2OH$, $C(O)CH(OH)CH_3$, $SO_2CH_3$, $C(O)OCH_3$, $C(O)N(CH_3)_2$, $C(O)NHCH_3$, $C(O)N(CH_2CH_3)_2$, $C(O)N(CH_3)(CH_2CH_3)$, or C(O)(morpholin-4-yl);

each $R^B$ is independently unsubstituted phenyl, 4-fluorophenyl, 3-fluorophenyl, 2-fluorophenyl, 2-pyridinyl, $CH_2(phenyl)$, $CH(phenyl)CH_2OH$, methyl, ethyl, isopropyl, $CH(CH_2OH)CH_2CH_3$, $CH(CH_2OH)CH_3$, $CH_2CH_2OH$ or $OCH_2CH_3$; and $R^C$ is F, Cl or Br.

16. The compound of claim 1, wherein the compound is selected from:

N-(4-(4-Amino-7-(1-(dimethylcarbamoyl)piperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide;

N-(4-(4-Amino-7-(1-(ethyl(methyl)carbamoyl)piperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide;

N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide;

N-(4-(4-Amino-7-(1-methylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide;

N-(4-(4-Amino-7-(1-(dimethylcarbamoyl)piperidin-4-yl)pyrrolo[1,2-f][1,2,4]triazin-5-yl)phenyl)-3-(4-fluorophenyl)-1-isopropyl-2,4-dioxo-1,2,3,4-tetrahydropyrimidine-5-carboxamide;

N-(4-(4-Amino-7-(1-(ethyl(methyl)carbamoyl)piperidin-4-yl)pyrrolo[1,2-f][1,2,4]triazin-5-yl)phenyl)-3-(4-fluorophenyl)-1-isopropyl-2,4-dioxo-1,2,3,4-tetrahydropyrimidine-5-carboxamide;

N-(4-(4-Amino-7-(1-(dimethylcarbamoyl)piperidin-4-yl)pyrrolo[1,2-f][1,2,4]triazin-5-yl)phenyl)-1-ethyl-3-(4-fluorophenyl)-2,4-dioxo-1,2,3,4-tetrahydropyrimidine-5-carboxamide;

N-(4-(4-Amino-7-(1-(morpholine-4-carbonyl)piperidin-4-yl)pyrrolo[1,2-f][1,2,4]triazin-5-yl)phenyl)-1-ethyl-3-(4-fluorophenyl)-2,4-dioxo-1,2,3,4-tetrahydropyrimidine-5-carboxamide;

N-(4-(4-Amino-7-(1-(ethyl(methyl)carbamoyl)piperidin-4-yl)pyrrolo[1,2-f][1,2,4]triazin-5-yl)phenyl)-3-(2-fluorophenyl)-1-isopropyl-2,4-dioxo-1,2,3,4-tetrahydropyrimidine-5-carboxamide;

N-(4-(4-Amino-7-(1-(dimethylcarbamoyl)piperidin-4-yl)pyrrolo[1,2-f][1,2,4]triazin-5-yl)phenyl)-3-(3-fluorophenyl)-1-isopropyl-2,4-dioxo-1,2,3,4-tetrahydropyrimidine-5-carboxamide;

N-(4-(4-Amino-7-(1-isobutyrylpiperidin-4-yl)pyrrolo[1,2-f][1,2,4]triazin-5-yl)phenyl)-3-(3-fluorophenyl)-1-isopropyl-2,4-dioxo-1,2,3,4-tetrahydropyrimidine-5-carboxamide;

N-(4-(4-Amino-7-(1-(dimethylcarbamoyl)piperidin-4-yl)pyrrolo[1,2-f][1,2,4]triazin-5-yl)phenyl)-1-ethyl-3-(3-fluorophenyl)-2,4-dioxo-1,2,3,4-tetrahydropyrimidine-5-carboxamide; and N-(4-(4-Amino-7-(1-isobutyrylpiperidin-4-yl)pyrrolo[1,2-f][1,2,4]triazin-5-yl)phenyl)-1-ethyl-3-(3-fluorophenyl)-2,4-dioxo-1,2,3,4-tetrahydropyrimidine-5-carboxamide;

or a pharmaceutically acceptable salt thereof.

17. The compound of claim 1, wherein the compound is selected from:

N-(4-(4-Amino-7-(1-isobutyrylpiperidin-4-yl)pyrrolo[1,2-f][1,2,4]triazin-5-yl)-3-fluorophenyl)-1-isopropyl-2,4-dioxo-3-phenyl-1,2,3,4-tetrahydropyrimidine-5-carboxamide;

N-(4-(4-Amino-7-(1-isobutyrylpiperidin-4-yl)pyrrolo[1,2-f][1,2,4]triazin-5-yl)phenyl)-3-(2,5-difluorophenyl)-1-isopropyl-2,4-dioxo-1,2,3,4-tetrahydropyrimidine-5-carboxamide;

N-(4-(4-Amino-7-(1-isobutyrylpiperidin-4-yl)pyrrolo[1,2-f][1,2,4]triazin-5-yl)-3-methylphenyl)-1-isopropyl-2,4-dioxo-3-phenyl-1,2,3,4-tetrahydropyrimidine-5-carboxamide;

N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-3-yl)-1,2,3,4-tetrahydropyrimidine-5-carboxamide;

(R)—N-(4-(4-Amino-7-(1-(2-hydroxypropanoyl)piperidin-4-yl)pyrrolo[1,2-f][1,2,4]triazin-5-yl)phenyl)-1-ethyl-3-(4-fluorophenyl)-2,4-dioxo-1,2,3,4-tetrahydropyrimidine-5-carboxamide;

N-(4-(4-Amino-7-(1-(2-(dimethylamino)-2-oxoethyl)piperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide;

N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide;

N-(4-(4-Amino-7-(1-isobutyrylpiperidin-4-yl)pyrrolo[2,1-f][1,2,4]triazin-5-yl)phenyl)-1-isopropyl-3-(1-methyl-1H-pyrazol-4-yl)-2,4-dioxo-1,2,3,4-tetrahydropyrimidine-5-carboxamide;

N-(4-(4-Amino-7-(1-isobutyrylpiperidin-4-yl)pyrrolo[2,1-f][1,2,4]triazin-5-yl)phenyl)-1-isopropyl-3-(1-methyl-1H-pyrazol-3-yl)-2,4-dioxo-1,2,3,4-tetrahydropyrimidine-5-carboxamide;

N-(4-(4-Amino-7-(1-isobutyrylpiperidin-4-yl)pyrrolo[1,2-f][1,2,4]triazin-5-yl)phenyl)-1-isopropyl-3-(2-methylthiazol-5-yl)-2,4-dioxo-1,2,3,4-tetrahydropyrimidine-5-carboxamide;

N-(4-(4-Amino-7-(1-isobutyrylpiperidin-4-yl)pyrrolo[2,1-f][1,2,4]triazin-5-yl)phenyl)-3-cyclohexyl-1-isopropyl-2,4-dioxo-1,2,3,4-tetrahydropyrimidine-5-carboxamide;

N-(4-(4-Amino-7-(1-isobutyrylpiperidin-4-yl)pyrrolo[2,1-f][1,2,4]triazin-5-yl)phenyl)-3-(3-cyanophenyl)-1-isopropyl-2,4-dioxo-1,2,3,4-tetrahydropyrimidine-5-carboxamide; and N-(4-(4-Amino-7-(1-isobutyrylpiperidin-4-yl)pyrrolo[2,1-f][1,2,4]triazin-5-yl)phenyl)-1-isopropyl-3-(5-methylisoxazol-3-yl)-2,4-dioxo-1,2,3,4-tetrahydropyrimidine-5-carboxamide;

or a pharmaceutically acceptable salt thereof.

18. The compound of claim 1, wherein the compound is selected from:

N-(4-(4-Amino-7-(1-isobutyrylpiperidin-4-yl)pyrrolo[2,1-f][1,2,4]triazin-5-yl)phenyl)-3-(1,4-dimethyl-1H-pyrazol-3-yl)-1-isopropyl-2,4-dioxo-1,2,3,4-tetrahydropyrimidine-5-carboxamide;

N-(4-(4-Amino-7-(1-isobutyrylpiperidin-4-yl)pyrrolo[2,1-f][1,2,4]triazin-5-yl)phenyl)-1-cyclopropyl-2,4-dioxo-3-phenyl-1,2,3,4-tetrahydropyrimidine-5-carboxamide;

N-(4-(4-Amino-7-(1-isobutyrylpiperidin-4-yl)pyrrolo[2,1-f][1,2,4]triazin-5-yl)phenyl)-1-cyclopropyl-2,4-dioxo-3-(pyridin-3-yl)-1,2,3,4-tetrahydropyrimidine-5-carboxamide;

N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyrimidin-2-yl)-1,2,3,4-tetrahydropyrimidine-5-carboxamide;

N-(4-(4-Amino-7-(1-isobutyrylpiperidin-4-yl)pyrrolo[1,2-f][1,2,4]triazin-5-yl)phenyl)-1-cyclopropyl-2,4-dioxo-3-(pyridin-2-yl)-1,2,3,4-tetrahydropyrimidine-5-carboxamide;

N-(4-(4-Amino-7-(1-isobutyrylpiperidin-4-yl)pyrrolo[1,2-f][1,2,4]triazin-5-yl)phenyl)-3-(5-fluoropyridin-2-yl)-1-isopropyl-2,4-dioxo-1,2,3,4-tetrahydropyrimidine-5-carboxamide;

N-(4-(4-Amino-7-(1-isobutyrylpiperidin-4-yl)pyrrolo[1,2-f][1,2,4]triazin-5-yl)phenyl)-3-(1,5-dimethyl-1H-pyrazol-3-yl)-1-isopropyl-2,4-dioxo-1,2,3,4-tetrahydropyrimidine-5-carboxamide; and N-(4-(4-Amino-7-(1-isobutyrylpiperidin-4-yl)pyrrolo[1,2-f][1,2,4]triazin-5-yl)phenyl)-1-isopropyl-3-(6-methylpyridin-2-yl)-2,4-dioxo-1,2,3,4-tetrahydropyrimidine-5-carboxamide;

or a pharmaceutically acceptable salt thereof.

19. A pharmaceutical composition comprising a compound of claim 1, or a pharmaceutically acceptable salt thereof, and a pharmaceutically acceptable carrier.

20. A method for inhibiting a TAM kinase, said method comprising: contacting the TAM kinase with the compound of claim 1, or a pharmaceutically acceptable salt thereof.

21. A method for inhibiting AXL and MER kinase, said method comprising: contacting the AXL and MER kinase with the compound of claim 1, or a pharmaceutically acceptable salt thereof.

22. A compound, which is N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide, or a pharmaceutically acceptable salt thereof.

23. A pharmaceutical composition comprising the compound of claim 22, or a pharmaceutically acceptable salt thereof, and a pharmaceutically acceptable carrier.

24. A compound, which is N-(4-(4-Amino-7-(1-isobutyrylpiperidin-4-yl)pyrrolo[1,2-f][1,2,4]triazin-5-yl)phenyl)-1-isopropyl-2,4-dioxo-3-phenyl-1,2,3,4-tetrahydropyrimidine-5-carboxamide.

25. A pharmaceutical composition comprising the compound of claim 24 and a pharmaceutically acceptable carrier.

* * * * *

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: synthetic peptide

<400> SEQUENCE: 1

Glu Gln Glu Asp Glu Pro Glu Gly Asp Tyr Phe Glu Trp Leu Glu
1               5                   10                  15
```